United States Patent
Pharkya et al.

(10) Patent No.: US 11,085,015 B2
(45) Date of Patent: *Aug. 10, 2021

(54) MICROORGANISMS AND METHODS FOR PRODUCTION OF 4-HYDROXYBUTYRATE, 1,4-BUTANEDIOL AND RELATED COMPOUNDS

(71) Applicant: Genomatica, Inc., San Diego, CA (US)

(72) Inventors: Priti Pharkya, San Diego, CA (US); Anthony P. Burgard, Bellefonte, PA (US); Stephen J. Van Dien, Encinitas, CA (US); Robin E. Osterhout, San Diego, CA (US); Mark J. Burk, San Diego, CA (US); John D. Trawick, La Mesa, CA (US); Michael P. Kuchinskas, Escondido, CA (US); Brian Steer, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/585,078

(22) Filed: May 2, 2017

(65) Prior Publication Data

US 2017/0362565 A1    Dec. 21, 2017

Related U.S. Application Data

(63) Continuation of application No. 13/908,907, filed on Jun. 3, 2013, now Pat. No. 9,677,045.

(Continued)

(51) Int. Cl.
*C12P 7/42*    (2006.01)
*C12P 7/18*    (2006.01)
(Continued)

(52) U.S. Cl.
CPC .............. *C12N 1/20* (2013.01); *C07C 31/207* (2013.01); *C07C 59/01* (2013.01); *C08G 18/284* (2013.01);
(Continued)

(58) Field of Classification Search
None
See application file for complete search history.

(56) References Cited

U.S. PATENT DOCUMENTS 4,048,196 A    9/1977    Broecker et al.
4,301,077 A    11/1981    Pesa et al.
(Continued)

FOREIGN PATENT DOCUMENTS

EP    1710302 A1    10/2006
GB    1230276        4/1971
(Continued)

OTHER PUBLICATIONS

Abe et al., "Biosynthesis from gluconate of a random copolyester consisting of 3-hydroxybutyrate and medium-chain-length 3-hydroxyalkanoates by *Pseudomonas* sp. 61-3," *Int. J. Biol. Macromol.*, 16(3):115-119 (1994).

(Continued)

*Primary Examiner* — Richard C Ekstrom
(74) *Attorney, Agent, or Firm* — Jones Day

(57) ABSTRACT

The invention provides non-naturally occurring microbial organisms having a 4-hydroxybutyrate pathway and being capable of producing 4-hydroxybutyrate, wherein the microbial organism comprises one or more genetic modifications. The invention additionally provides methods of producing 4-hydroxybutyrate or related products using the microbial organisms.

22 Claims, 92 Drawing Sheets

Specification includes a Sequence Listing.

Related U.S. Application Data

(60) Provisional application No. 61/655,429, filed on Jun. 4, 2012.

(51) Int. Cl.

| | | |
|---|---|---|
| *C12N 1/20* | (2006.01) | |
| *C12N 1/14* | (2006.01) | |
| *C12N 1/16* | (2006.01) | |
| *C12N 9/18* | (2006.01) | |
| *C12N 15/52* | (2006.01) | |
| *C12N 15/63* | (2006.01) | |
| *C07C 31/20* | (2006.01) | |
| *C07C 59/01* | (2006.01) | |
| *C08G 18/28* | (2006.01) | |
| *C08G 18/32* | (2006.01) | |
| *C08G 63/06* | (2006.01) | |
| *C08G 63/16* | (2006.01) | |
| *C08G 63/181* | (2006.01) | |
| *C08G 69/02* | (2006.01) | |

(52) U.S. Cl.
CPC ......... *C08G 18/3206* (2013.01); *C08G 63/06* (2013.01); *C08G 63/16* (2013.01); *C08G 63/181* (2013.01); *C08G 69/02* (2013.01); *C12N 1/14* (2013.01); *C12N 1/16* (2013.01); *C12N 9/18* (2013.01); *C12N 15/52* (2013.01); *C12N 15/63* (2013.01); *C12P 7/18* (2013.01); *C12P 7/42* (2013.01); *C12Y 301/01* (2013.01); *Y02P 20/52* (2015.11)

(56) References Cited

U.S. PATENT DOCUMENTS

| | | |
|---|---|---|
| 4,430,430 A | 2/1984 | Momose et al. |
| 4,652,685 A | 3/1987 | Cawse et al. |
| 4,876,331 A | 10/1989 | Doi |
| 5,164,309 A | 11/1992 | Gottschalk et al. |
| 5,245,023 A | 9/1993 | Peoples et al. |
| 5,250,430 A | 10/1993 | Peoples et al. |
| 5,286,842 A | 2/1994 | Kimura |
| 5,292,860 A | 3/1994 | Shiotani et al. |
| 5,378,616 A | 1/1995 | Tujimoto et al. |
| 5,413,922 A | 5/1995 | Matsuyama et al. |
| 5,461,139 A | 10/1995 | Gonda et al. |
| 5,475,086 A | 12/1995 | Tobin et al. |
| 5,478,952 A | 12/1995 | Schwartz |
| 5,502,273 A | 3/1996 | Bright et al. |
| 5,516,883 A | 5/1996 | Hori et al. |
| 5,534,432 A | 7/1996 | Peoples et al. |
| 5,563,239 A | 10/1996 | Hubbs et al. |
| 5,602,321 A | 2/1997 | John |
| 5,608,146 A | 3/1997 | Frommer et al. |
| 5,610,041 A | 3/1997 | Somerville et al. |
| 5,650,555 A | 7/1997 | Somerville et al. |
| 5,663,063 A | 9/1997 | Peoples et al. |
| 5,674,978 A | 10/1997 | Tobin et al. |
| 5,705,626 A | 1/1998 | Tobin et al. |
| 5,747,311 A | 5/1998 | Jewell |
| 5,750,848 A | 5/1998 | Krüger et al. |
| 5,770,435 A | 6/1998 | Donnelly et al. |
| 5,830,716 A | 11/1998 | Kojima et al. |
| 5,846,740 A | 12/1998 | Tobin et al. |
| 5,849,894 A | 12/1998 | Clemente et al. |
| 5,869,301 A | 2/1999 | Nghiem et al. |
| 5,908,924 A | 6/1999 | Burdette et al. |
| 5,942,660 A | 8/1999 | Gruys et al. |
| 5,958,745 A | 9/1999 | Gruys et al. |
| 5,994,478 A | 11/1999 | Asrar et al. |
| 5,998,366 A | 12/1999 | Tobin et al. |
| 6,010,870 A | 1/2000 | Pelzer et al. |
| 6,011,139 A | 1/2000 | Tobin et al. |
| 6,011,144 A | 1/2000 | Steinbuchel et al. |
| 6,022,729 A | 2/2000 | Steinbuchel et al. |
| 6,080,562 A | 6/2000 | Byrom et al. |
| 6,091,002 A | 7/2000 | Asrar et al. |
| 6,111,658 A | 8/2000 | Tabata |
| 6,117,658 A | 9/2000 | Dennis et al. |
| 6,156,852 A | 12/2000 | Asrar et al. |
| 6,159,738 A | 12/2000 | Donnelly et al. |
| 6,204,341 B1 | 3/2001 | Asrar et al. |
| 6,228,579 B1 | 5/2001 | Zyskind et al. |
| 6,228,623 B1 | 5/2001 | Asrar et al. |
| 6,248,862 B1 | 6/2001 | Asrar et al. |
| 6,277,586 B1 | 8/2001 | Tobin et al. |
| 6,280,986 B1 | 8/2001 | Hespell et al. |
| 6,316,262 B1 | 11/2001 | Huisman et al. |
| 6,329,183 B1 | 12/2001 | Skraly et al. |
| RE37,543 E | 2/2002 | Krüger et al. |
| 6,361,983 B1 | 3/2002 | Ames |
| 6,448,061 B1 | 9/2002 | Pan et al. |
| 6,448,473 B1 | 9/2002 | Mitsky et al. |
| 6,455,267 B1 | 9/2002 | Tobin et al. |
| 6,495,152 B2 | 12/2002 | Steinbuchel et al. |
| 6,515,205 B1 | 2/2003 | Liebergesell et al. |
| 6,576,450 B2 | 6/2003 | Skraly et al. |
| 6,593,116 B1 | 7/2003 | Huisman et al. |
| 6,596,521 B1 | 7/2003 | Chang et al. |
| 6,623,946 B1 | 9/2003 | Möckel et al. |
| 6,682,906 B1 | 1/2004 | Tobin et al. |
| 6,686,310 B1 | 2/2004 | Kourtakis et al. |
| 6,689,589 B2 | 2/2004 | Huisman et al. |
| 6,730,503 B1 | 5/2004 | Asakura et al. |
| 6,759,219 B2 | 7/2004 | Hein et al. |
| 6,770,464 B2 | 8/2004 | Steinbuchel et al. |
| 6,835,820 B2 | 12/2004 | Cannon et al. |
| 6,897,055 B2 | 5/2005 | Möckel et al. |
| 6,913,911 B2 | 7/2005 | Huisman et al. |
| 6,916,637 B2 | 7/2005 | Rieping et al. |
| 7,052,883 B2 | 5/2006 | Rieping et al. |
| 7,067,300 B2 | 6/2006 | Emptage et al. |
| 7,081,357 B2 | 7/2006 | Huisman et al. |
| 7,125,693 B2 | 10/2006 | Davis et al. |
| 7,127,379 B2 | 10/2006 | Palsson et al. |
| 7,132,267 B2 | 11/2006 | Davis et al. |
| 7,135,315 B2 | 11/2006 | Hoshino et al. |
| 7,186,541 B2 | 3/2007 | Gokarn et al. |
| 7,223,567 B2 | 5/2007 | Ka-Yiu et al. |
| 7,229,804 B2 | 6/2007 | Huisman et al. |
| 7,256,021 B2 | 8/2007 | Hermann |
| 7,309,597 B2 | 12/2007 | Liao et al. |
| 7,314,974 B2 | 1/2008 | Cao et al. |
| 7,393,676 B2 | 7/2008 | Gokarn et al. |
| 7,425,433 B2 | 9/2008 | Rosazza et al. |
| 7,504,250 B2 | 3/2009 | Emptage et al. |
| 7,858,350 B2 | 12/2010 | Burk et al. |
| 7,947,483 B2 | 5/2011 | Burgard et al. |
| 8,067,214 B2 | 11/2011 | Burk et al. |
| 8,129,169 B2 | 3/2012 | Van Dien et al. |
| 8,178,327 B2 | 5/2012 | Burk et al. |
| 8,357,520 B2 | 1/2013 | Burk et al. |
| 8,969,054 B2 | 3/2015 | Burk et al. |
| 9,487,803 B2 | 11/2016 | Burk et al. |
| 9,677,045 B2 * | 6/2017 | Pharkya ................ C12N 15/63 |
| 2002/0012939 A1 | 1/2002 | Palsson |
| 2002/0164729 A1 | 11/2002 | Skraly et al. |
| 2002/0168654 A1 | 11/2002 | Maranas et al. |
| 2003/0059792 A1 | 3/2003 | Palsson et al. |
| 2003/0203459 A1 | 10/2003 | Chen et al. |
| 2003/0224363 A1 | 12/2003 | Park et al. |
| 2003/0233218 A1 | 12/2003 | Schilling |
| 2003/0233675 A1 | 12/2003 | Cao et al. |
| 2004/0009466 A1 | 1/2004 | Maranas et al. |
| 2004/0023347 A1 | 2/2004 | Skraly |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0106176 A1 | 6/2004 | Skraly |
| 2004/0152159 A1 | 8/2004 | Causey et al. |
| 2004/0152166 A1 | 8/2004 | Mockel |
| 2005/0042736 A1 | 2/2005 | San et al. |
| 2005/0090645 A1 | 4/2005 | Asakura |

(56) References Cited

U.S. PATENT DOCUMENTS

| | | |
|---|---|---|
| 2005/0164342 A1 | 7/2005 | Tobin |
| 2005/0170480 A1 | 8/2005 | Huisman |
| 2005/0221466 A1 | 10/2005 | Liao et al. |
| 2005/0239179 A1 | 10/2005 | Skraly et al. |
| 2005/0287655 A1 | 12/2005 | Tabata et al. |
| 2006/0041152 A1 | 2/2006 | Cantrell et al. |
| 2006/0046288 A1 | 3/2006 | Ka-Yiu et al. |
| 2006/0084155 A1 | 4/2006 | Huisman et al. |
| 2006/0134760 A1 | 6/2006 | Rieping |
| 2006/0141594 A1 | 6/2006 | San et al. |
| 2006/0199254 A1 | 9/2006 | Rosazza et al. |
| 2007/0072279 A1 | 3/2007 | Meynial-Salles et al. |
| 2007/0087425 A1 | 4/2007 | Ohto |
| 2007/0184539 A1 | 8/2007 | San et al. |
| 2007/0190605 A1 | 8/2007 | Bessler et al. |
| 2007/0259410 A1 | 11/2007 | Donaldson et al. |
| 2007/0292927 A1 | 12/2007 | Donaldson et al. |
| 2008/0120732 A1 | 5/2008 | Elliot |
| 2008/0138870 A1 | 6/2008 | Bramucci et al. |
| 2008/0171371 A1 | 7/2008 | Yukawa et al. |
| 2008/0182308 A1 | 7/2008 | Donaldson et al. |
| 2008/0229451 A1 | 9/2008 | Cao et al. |
| 2008/0261230 A1 | 10/2008 | Liao et al. |
| 2008/0274524 A1 | 11/2008 | Bramucci et al. |
| 2008/0274525 A1 | 11/2008 | Bramucci et al. |
| 2008/0274526 A1 | 11/2008 | Bramucci et al. |
| 2008/0293125 A1 | 11/2008 | Subbian et al. |
| 2009/0023182 A1 | 1/2009 | Schilling |
| 2009/0047719 A1 | 2/2009 | Burgard et al. |
| 2009/0075351 A1 | 3/2009 | Burk et al. |
| 2009/0100536 A1 | 4/2009 | Adams et al. |
| 2009/0111154 A1 | 4/2009 | Liao et al. |
| 2009/0158452 A1 | 6/2009 | Johnson et al. |
| 2009/0246842 A1 | 10/2009 | Hawkins et al. |
| 2009/0253192 A1 | 10/2009 | Emptage et al. |
| 2009/0275096 A1 | 11/2009 | Burgard et al. |
| 2010/0021978 A1 | 1/2010 | Burk et al. |
| 2010/0099925 A1 | 4/2010 | Kharas |
| 2010/0112654 A1 | 5/2010 | Burk et al. |
| 2010/0184171 A1 | 7/2010 | Jantama et al. |
| 2010/0304453 A1 | 12/2010 | Trawick et al. |
| 2010/0330634 A1 | 12/2010 | Park et al. |
| 2011/0014669 A1 | 1/2011 | Madden et al. |
| 2011/0045575 A1 | 2/2011 | Van Dien et al. |
| 2011/0129899 A1 | 6/2011 | Haselbeck et al. |
| 2011/0129904 A1 | 6/2011 | Burgard et al. |
| 2011/0190513 A1 | 8/2011 | Lynch |
| 2011/0217742 A1 | 9/2011 | Sun et al. |
| 2011/0294178 A1 | 12/2011 | Soucaille et al. |
| 2013/0109067 A1 | 5/2013 | Soucaille et al. |
| 2013/0109069 A1 | 5/2013 | Burk et al. |
| 2013/0273623 A1 | 10/2013 | Walther et al. |
| 2014/0120595 A1 | 5/2014 | Lynch |

FOREIGN PATENT DOCUMENTS

| | | |
|---|---|---|
| GB | 1314126 | 4/1973 |
| GB | 1344557 | 1/1974 |
| GB | 1512751 | 6/1978 |
| JP | 62285779 | 12/1987 |
| KR | 1020060011345 A | 2/2006 |
| KR | 100676160 B1 | 1/2007 |
| KR | 100679638 B1 | 1/2007 |
| KR | 1020070021732 A | 2/2007 |
| KR | 1020070096348 A | 10/2007 |
| KR | 10-2009-0025902 | 3/2009 |
| WO | WO 1982/003854 | 11/1982 |
| WO | WO 1991/000917 | 1/1991 |
| WO | WO 1992/019747 | 11/1992 |
| WO | WO 1993/002187 | 2/1993 |
| WO | WO 1993/002194 | 4/1993 |
| WO | WO 1993/006225 | 4/1993 |
| WO | WO 1994/011519 | 5/1994 |
| WO | WO 1994/012014 | 6/1994 |
| WO | WO 1995/011985 | 5/1995 |
| WO | WO 1998/036078 | 8/1998 |
| WO | WO 1999/006532 | 2/1999 |
| WO | WO 1999/014313 | 3/1999 |
| WO | WO 2000/061763 | 10/2000 |
| WO | WO 2002/055995 | 7/2002 |
| WO | WO 2002/061115 | 8/2002 |
| WO | WO 2003/008603 | 1/2003 |
| WO | WO 2003/106998 | 12/2003 |
| WO | WO 2004/018621 | 3/2004 |
| WO | WO 2004/029235 | 4/2004 |
| WO | WO 2005/026338 | 3/2005 |
| WO | WO 2005/052135 | 6/2005 |
| WO | WO 2007/030830 | 3/2007 |
| WO | WO 2007/141208 | 12/2007 |
| WO | WO 2008/018930 | 2/2008 |
| WO | WO 2008/027742 | 6/2008 |
| WO | WO 2008/115840 | 9/2008 |
| WO | WO 2008/131286 | 10/2008 |
| WO | WO 2008/144626 | 11/2008 |
| WO | WO 2009/011974 | 1/2009 |
| WO | WO 2009/023493 | 2/2009 |
| WO | WO 2009/031766 | 3/2009 |
| WO | WO 2009/049274 | 4/2009 |
| WO | WO 2009/094485 | 7/2009 |
| WO | WO 2009/103026 | 8/2009 |
| WO | WO 2009/111513 | 9/2009 |
| WO | WO 2009/131040 | 10/2009 |
| WO | WO 2010/006076 | 1/2010 |
| WO | WO 2010/085731 | 7/2010 |
| WO | WO 2011/100601 | 8/2011 |
| WO | WO 2011/137192 | 11/2011 |
| WO | WO 2012/001003 | 1/2012 |

OTHER PUBLICATIONS

Aberhart et al., "Stereospecific hydrogen loss in the conversion of [2H7]isobutyrate to beta-hydroxyisobutyrate in Pseudomonas putida. The stereochemistry of beta-hydroxyisobutyrate dehydrogenase," *J. Chem. Soc. Perkin1.*, 6:1404-1406 (1979).

Abiko et al., "Localization of NAD-isocitrate dehydrogenase and glutamate dehydrogenase in rice roots: candidates for providing carbon skeletons to NADH-glutamate synthase," *Plant Cell Physiol.*, 46(10):1724-1734 (2005).

Adams et al., "Oxidoreductase-type enzymes and redox proteins involved in fermentative metabolisms of hyperthermophilic Archaea," *Adv. Protein Chem.*, 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.*, 6:785-792 (1999).

Aidoo et al., "Cloning, sequencing and disruption of a gene from *Streptomyces clavuligerus* Involved in clavulanic acid biosynthesis," *Gene*, 147(1):41-46 (1994).

Alber et al., "Malonyl-coenzyme A reductase in the modified 3-hydroxypropionate cycle for autotrophic carbon fixation in archaeal *Metallosphaera* and *Sulfolobus* spp.," *J. Bacteriol.*, 188:8551-8559 (2006).

Alberty, "Biochemical thermodynamics," *Biochim. Biophys. Acta*, 1207:1-11 (1994).

Alhapel et al., "Molecular and functional analysis of nicotinate catabolism in *Eubacterium barkeri*," *Proc. Natl. Acad. Sci. U.S.A.*, 103(33)12341-12346 (2006).

Allen et al., "DNA sequence of the putA gene from *Salmonella typhimurium*: a bifunctional membrane-associated dehydrogenase that binds DNA," *Nucleic Acids Res.*, 21:1676 (1993).

Amarasingham et al., "Regulation of alpha-ketoglutarate dehydrogenase formation in *Escherichia coli*," *J. Biol. Chem.*, 240:3664-3668 (1965).

Amos et al., "Composition of poly-.beta.-hydroxyalkanoate from *Syntrophomonas wottei* grown on unsaturated fatty acid substrates," *Arch. Microbiol.*, 155:103-106 (1991).

Amuro et al., "Isolation and characterization of the two distinct genes for human glutamate dehydrogenase," *Biochem. Biophys. Acta.*, 1049:216-218 (1990).

Andersen et al., "Cloning of the lysA gene from *Mycobacterium tuberculosis*," *Gene*, 124:105-109 (1993).

(56) References Cited

OTHER PUBLICATIONS

Andersen et al., "A gene duplication led to specialized gamma-aminobutyrate and beta-alaine aminotransferase in yeast," *FEBS J.*, 274(7):1804-1817 (2007).
Andre et al., "Nucleotide sequence of the yeast UGA1 gene encoding GABA transaminase," *Nucleic Acids Res.*, 18:3049 (1990).
Aneja et al., "Poly-3-hydroxybutyrate degradation in Rhizobium (Sinorhizobium) meliloti: isolation and characterization of a gene encoding 3-hydroxybutryate dehydrogenase," *J. Bacteriol.*, 181(3):849-857 (1999).
Ansorge et al., "Production of Recombinant L-Leucine Dehydrogenase from Bacillus cereus in Pilot Scale Using the Runaway Replication System *E. coli*[pIET98]," *Biotechnol. Bioeng.*, 68(5):557-562 (2000).
Aoshima et al., "A novel biotin protein required for reductive carboxylation of 2-oxoglutarate by isocitrate dehydrogenase in Hydrogenobacter thermophilus TK-6," *Mol. Microbiol.*, 51(3):791-798 (2004).
Aoshima et al., "A novel oxalosuccinate-forming enzyme involved in the reductive carboxylation of 2-oxoglutarate in Hydrogenobacter thermophilus TK-6," *Mol. Microbiol.*, 62(3):748-759 (2006).
Aragon et al., "A survey of enzymes which generate or use acetoacetyl thioesters in rat liver," *J. Biol. Chem.*, 258(8):4725-4733 (1983).
Arikawa et al., "Soluble fumarate reductase isoenzymes from *Saccharomyces cerevisiae* are required for anaerobic growth," *FEMS Microbiol. Lett.*, 165:111-116 (1998).
Arps et al., "Genetics of Serine Pathway Enzymes in Methylobacterium extorquens AM1: Phosphoenolpyruvate Carboxylase and Malyl Coenzyme A Lyase," *J. Bacteriol.*, 175(12):3776-3783 (1993).
Asano et al., "Crystalline 3-methylaspartase from a facultative anaerobe, *Escherichia coli* strain YG1002," *FEMS Microbiol. Lett.*, 118(3):255-258 (1994).
Asano et al., "Alteration of substrate specificity of aspartase by directed evolution," *Biomol.Eng*, 22:95-101 (2005).
Asaoka et al., "Production of 1,4-butanediol from bacillus which is fermented on sugar substrate, from which production is recovered," *Chiyoda Chem. Eng. Constr. Co.* (Official Publication Date 1987). Database WPI Week 198804 Thomson Scientific, London, GB; AN 1988-025175.
Asuncion et al., "Overexpression, purification, crystallization and data collection of 3-methylaspartase from Clostridium tetanomorphum," *Acta Crystallogr.D. Biol. Crystallogr.*, 57:731-733 (2001).
Asuncion et al., "The Structure of 3-Methylaspartase from Clostridium tetanomorphum Functions via the Common Enolase Chemical Step," *J. Biol. Chem.*, 277(10):8306-8311 (2002).
Atlung et al., "Effects of sigmaS and the transcriptional activator AppY on induction of the *Escherichia coli* hya and cbdAB-appA operons in response to carbon and phosphate starvation," *J. Bacteriol.*, 179:2141-2146 (1997).
Atsumi et al., "Non-fermentative pathways for synthesis of branched-chain higher alcohols as biofuels," *Nature*, 451(7174): 86-89 (2008).
Baba et al., "Construction of *Escherichia coli* K-12 in-frame, single-gene knockout mutants: the Keio collection," *Mol. Syst. Biol.*, 2:2006.0008 (2006).
Baker et al., "Purification and properties of L-erythro-3,5-diaminohexanoate dehydrogenase from Clostridium sticklandii," *Biochemistry*, 13(2):292-299 (1974).
Baker et al., "Purification and properties of L-erythro-3,5-diaminohexanoate dehydrogenase from a lysine-fermenting Clostirdium," *J. Biol. Chem.*, 247(23):7724-7734 (1972).
Barker et al., "Butyryl-CoA:acetoacetate CoA-transferase from a lysine-fermenting Clostridium," *J. Biol. Chem.*, 253(4):1219-1225 (1978).
Barker et al., "Pathway of Lysine Degradation in Fusobacterium nucleatum," *J. Bacteriol.*, 152(1):201-207 (1982).
Barrowman et al., "Immunological comparison of microbial TPP-dependent non-oxidative alpha-keto acid decarboxylase," *FEMS Microbiology Lett.*, 34:57-60 (1986).
Barthelmebs et al., "Expression of *Escherichia coli* of Native and Chimeric Phenolic Acid Decarboxylases with Modified Enzymatic activites and Method for Scrreening recombinant *E. coli* Strains Expressing These Enzymes," *Appl. Environ. Microbiol.*, 67:1063-1069 (2001).
Barton et al., "An integrated biotechnology platform for developing sustainable chemical processes," *J. Ind. Microbiol. Biotech.*, 42(3):349-360 (2014).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.*, 172:7035-7042 (1990).
Baum et al., "A plant glutamate decarboxylase containing a calmodulin binding domain, Cloning, sequence, and functional analysis," *J. Biol. Chem.*, 268:19610-19617 (1993).
Benachenhou-Lahfa et al., "PCR-mediated cloning and sequencing of the gene encoding glutamate dehydrogenase from the archaeon Sulfolobus shilbatae: Identification of putative amino-acid signatures for extremophilic adaptation," *Gene*, 140:17-24 (1994).
Berg et al., "A 3-Hydroxypropionate/4-Hydroxybutyrate Autotrophic Carbon Dioxide Assimilation Pathway in Archaea," *Science*, 318:1782-1786 (2007).
Bergquist et al., "Degenerate oligonucleotide gene shuffling," *Methods Mol. Biol.*, 352:191-204 (2007).
Bergquist et al., "Degenerate oligonucleotide gene shuffling (DOGS) and random drift mutagenesis (RNDN): two complementary techniques for enzyme evolution," *Biomol. Eng.*, 22:63-72 (2005).
Berkovitch et al., "A locking mechanism preventing radical damage in the absence of substrate, as revealed by the x-ray structure of lysine 5,6-aminomutase," *Proc. Natl. Acad. Sci. U.S.A.*, 101:15870-15875 (2004).
Bermejo et al., "Expression of Clostridium acetobutylicum ATCC 824 Genes in *Escherichia coli* for Acetone Production and Acetate Detoxification," *Appl. Environ. Microbiol.*, 64(3):1079-1085 (1998).
Biellmann et al., "Aspartate-beta-semialdehyde dehydrogenase from *Escherichia coli*. Purification and general properties," *Eur. J. Biochem.*, 104(1):53-58 (1980).
Biello, "Turning Bacteria into Plastic Factories," *Scientific American*, 1-2 (2008). (Printed Feb. 17, 2011).
Binstock et al., "Fatty acid oxidation complex from *Escherichia coli*," *Methods Enzymol.*, 71 Pt C:403-411 (1981).
Birrer et al., "Electro-transformation of Clostridium beijerinckii NRRL B-592 with shuttle plasmid pHR106 and recombinant derivatives," *Appl. Microbiol. Biotechnol.*, 41(1):32-38 (1994).
Bisswanger, "Substrate Specificity of the Pyruvate Dehydrogenase Complex from *Escherichi coli*," *J. Biol. Chem.*, 256(2):815-822 (1981).
Blanco et al., "Critical catalytic functional groups in the mechanims of aspartate-β-semialdehyde dehydrogenase," *Acta Crystallogr. D. Biol. Crystallogr.*, 60:1808-1815 (2004).
Blanco et al., "The role of substrate-binding roups in the mechanism of asparte-β-semialdehyde dehydrogenase," *Acta Crystallogr. D. Biol. Crystallog.*, 60:1388-1395 (2004).
Blattner et al., "The complete genome sequence of *Escherichia coli* K-12," *Science*, 277:1453-1462 (1997).
Boles et al., "Characterization of a glucose-repressed pyruvate kinase (Pyk2p) in *Saccharomyces cerevisiae* that is catalytically insensitive to fructose-1,6-bisphosphate," *J. Bacteriol.*, 179:2987-2993 (1997).
Bonnarme et al., "Itaconate biosynthesis in Aspergillus terreus," *J. Bacteriol.*, 177(12):3573-3578 (1995).
Bonner et al., "Purification and Properties of Fatty Acyl Thiesterase I from *Escherichia coli*," *J. Biol. Chem.*, 247(10) 3123-3133 (1972).
Borisov et. al., "Aerobic respiratory chain of *Escherichia coli* is not allowed to work in fully uncoupled mode," *Proc. Natl. Acad. Sci. U.S.A.*, 108:17320-17324 (2011).
Botsford et al., "Accumulation of glutamate by *Salmonella typhimurium* in response to osmotic stress," *Appl. Environ. Microbiol.*, 60:2568-2574 (1994).
Botting et al., "Substrate Specificity of the 3-Methylaspartate Ammonia-Lyase Reaction: Observation of Differential Relative Reaction rates for Substrate-Product Pairs," *Biochemistry*, 27:2953-2955 (1988).

(56) References Cited

OTHER PUBLICATIONS

Bower et al., "Cloning, Sequencing, and Characterization of the Bacillus subtilis Biotin Biosynthetic Operon," *J. Bacteriol.*, 178(14):4122-4130 (1996).

Boynton et al., "Cloning, sequencing, and expression of clustered genes encoding beta-hydroxybutyryl-coenzyme A (CoA) dehydrogenase, crotonase, and butyryl-CoA dehydrogenase from Clostridium acetobutylicum ATCC 824," *J. Bateriol.*, 178(11):3015-3024 (1996).

Bradford et al., "A rapid and sensitive method for the quantitation of microgram quantities of protein utilizing the principle of protein-dye binding," *Anal. Biochem.*, 72:248-254 (1976).

Branden et al., "Introduction to Protein Structure," *Garland Publishing Inc.*, New York, p. 247 (1991).

Brandl et al., "Ability of the phototrophic bacterium Rhodospirillum rubrum to produce various poly (beta-hydroxyalkanoates): potential sources for biodegradable polyesters," *Int. J. Biol. Macromol.*, 11:49-55 (1989).

Branlant et al., "Nucleotide sequence of the *Escherichia coli* gap gene. Differente evolutionay behaviour of the Nad+-binding domain and of the catalytic domain of D-glyceraldehyde-3-phosphate dehydrogenase," *Eur. J. Biochem.*, 150(1):61-66 (1985).

Brasen et al., "Unusual ADP-forming acetyl-coenzyme A synthetases from the mesophilic halophilic euarchaeon Haloarcula marismortui and from the hyperthermophilic crenarchaeon Pyrobaculum aerophilum," *Arch. Microbiol.*, 182:277-287 (2004).

Bravo et al., "Reliable, sensitive, rapid and quantitative enzyme-based assay for gamma-hydroxybutyric acid (GHB)," *J. Forensic Sci.*, 49:379-387 (2004).

Breitkreuz et al., "A novel gamma-hydroxybutyrate dehydrogenase: identification and expression of an *Arabidopsis* cDNA and potential role under oxygen deficiency," *J. Biol. Chem.*, 278:41552-41556 (2003).

Bremer, "Pyruvate Dehydrogenase, Substrate Specificity and Product Inhibition," *Eur. J. Biochem.*, 8:535-540 (1969).

Bridger et al., "The subunits of succinyl-coenzyme. A synthetase—function and assembly," In Krebs' Citric Acid Cycle—Half a Century and Still Turning, *Biochem. Soc. Symp.*, 54:103-111 (1987).

Brosch et al., "Genome plasticity of BCG and impact on vaccine efficacy," *Proc. Natl. Acad. Sci. U.S.A.*, 104(13):5596-5601 (2007).

Bu et al., "Two human glutamate decarboxylases, 65-kDa GAD and 67-kDa GAD, are each encoded by a single gene," *Proc. Natl. Acad. Sci. U.S.A.*, 89(6):2115-2119 (1992).

Bu, et al., "The exon-intron organization of the genes (GAD1 and GAD2) encoding two human glutamate decarboxylases (GAD67 and GAD65) suggests that they derive from a common ancestral GAD," *Genomics*, 21:222-228 (1994).

Buck et al., "Overexpression and site-directed mutagenesis of the succinyl-CoA synthetase of *Escherichia coli* and nucleotide sequence of a gene (g30) that is adjacent to the suc operon," *Biochem. J.*, 260(3):737-747 (1989).

Buck et al., "Primary Structure of the Succinyl-CoA Synthetase of *Escherichia coli*," *Biochemistry*, 24:6245-6252 (1985).

Buck et al., "Cloning and expression of the succinyl-CoA synthetase genes of *Escherichia coli* K12," *J. Gen. Microbiol.*, 132(6):1753-1762 (1986).

Buckel et al., "Glutaconate CoA-Transferase from Acidaminococcus fermentans," *Eur. J. Biochem.*, 118:315-321 (1981).

Bult et al., "Complete genome sequence of the methanogenic archaeon, Methanococcus jannaschii," *Science*, 273:1058-1073 (1996).

Burgard et al., "Probing the Performance Limits of the *Escherichia coli* Metabolic Network Subject to Gene Additions or Deletions," *Biotechnol. Bioeng.*, 74(5):364-375 (2001).

Burgard et al., "Minimal Reaction Sets for *Escherichia coli* Metabolism under Different Growth Requirements and Uptake Environments," *Biotechnol. Prog.*, 17:791-797 (2001).

Burgard et al., "Optknock: a bilevel programming framework for identifying gene knockout strategies for microbial strain optimization," *Biotechnol. Bioeng.*, 84(6):647-657 (2003).

Burke et al, "The Isolation, Characterization, and Sequence of the Pyruvate Kinase Gene of *Saccharomyces cerevisiae*," *J. Biol. Chem.*, 258(4):2193-2201 (1983).

Buu et al., "Functional Characterization and Localization of Acetyl-CoA Hydrolase, Ach1p, in *Saccharomyces cerevisiae*," *J. Biol. Chem.*, 278(19):17203-17209 (2003).

Calhoun et al., "Energetic efficiency of *Escherichia coli*: effects of mutations in components of the aerobic respiratory chain," *J. Bacteriol.*, 175:3020-3025 (1993).

Campbell et al., "A new *Escherichia coli* metabolic competency: growth on fatty acids by a novel anaerobic β-oxidation pathway," *Mol. Microbiol.*, 47(3):793-805 (2003).

Carlier et al., "The assimilation of gamma-butyrolactone in Agrobacterium tumefaciens C58 interferes with the accumulation of the N-acyl-homoserine lactone signal," *Mol. Plant Microbe Interact.*, 17(9):951-957 (2004).

Cary et al., "Cloning and expression of Clostridium acetobutylicum phosphotransbutyrylase and butyrate kinase genes in *Escherichia coli*," *J. Bacteriol.*, 170:4613-4618 (1988).

Cary et al., "Cloning and expression of Clostridium acetobutylicum ATCC 824 acetoacetyl-coenzyme A: acetate/butyrate: coenzyme A-transferase in *Escherichia coli*," *Appl. Environ. Microbiol.*, 56(6):1576-1583 (1990).

Caspi et al., "MetaCyc: a multiorganism database of metabolic pathways and enzymes," *Nucleic Acids Res.*, 34(Database issue):D511-D516 (2006).

Causey et al., "Engineering *Escherichia coli* for efficient conversion of glucose to pyruvate," *Proc. Natl. Acad. Sci. U.S.A.*, 101:2235-2240 (2004).

Cha et al., "Succinic Thiokinase. I. Purification of the Enzyme from Pig Heart," *J. Biol. Chem.*, 239:1961-1967 (1964).

Chandra Raj et al., "Pyruvate decarboxylase: a key enzyme for the oxidative metabolism of lactic acid by Acetobacter pasteruianus," *Arch. Microbiol.*, 176:443-451 (2001).

Chao et al., "The Effects of Wall Population on Coexistence of Bacteria in the Liquid Phase of Chemostat Cultures," *J. Gen. Microbiol.*, 20:1229-1236 (1985).

Chavez et al., "The NADP-glutamate dehydrogenase of the cyanobacterium Synechocystis 6803: cloning, transcriptional analysis and disruption of the gdhA gene," *Plant Mol. Biol.*, 28:173-188 (1995).

Chen et al., "Acetone-Butanol-Isopropanol Production by *Clostridium beijerinckii* (Synonym, Clostridium Butylicum)," *Biotechn. Lett.*, 8(5):371-376 (1986).

Chen et al., "Regulation of the adhE gene, which encodes ethanol dehydrogenase in *Escherichia coli*," *J. Bacteriol.*, 173(24):8009-8013 (1991).

Chen et al., "A novel lysine 2,3-aminomutase encoded by the yodO gene of Bacillus subtilis: characterization and the observation of organic radical intermediates," *Biochem. J.*, 348:539-549 (2000).

Chen et al., "Cloning, Sequencing, Heterologous Expression, Purification, and Characterization of Adenosylcobalamin-dependent D-Ornithine Aminomutase from Clostridium sticklandii," *J. Biol. Chem.*, 276:44744-44750 (2001).

Chicco et al., "Regulation of Gene Expression of Branched-chain Keto Acid Dehydrogenase Complex in Primary Cultured Hepatocytes by Dexamethasone and cAMP Analog," *J. Biol. Chem.*, 269(30):19427-19434 (1994).

Chirpich et al., "Lysine 2,3-Aminomutase. Purification and properties of a pyridoxal phosphate and S-adenosylmethionine-activated enzyme," *J. Biol. Chem.*, 245(7):1778-1789 (1970).

Cho et al., "Critical residues for the coenzyme specificity of NAD+-deptendent 15-hydroxyprtaglandin dehydrogenase," *Arch. Biochem. Biophys.*, 419(2): 139-146 (2003).

Chowdhury et al., "Cloning and Overexpression of the 3-Hydroxyisobutyrate Dehydrogenase Gene from Pseudomonas putida E23," *Biosci. Biotechnol. Biochem.*, 67(2):438-441 (2003).

Chowdhury et al., "3-Hydroxyisobutyrate dehydrogenase from Pseudomonas putida E23: purification and characterization," *Biosci. Biotechnol. Biochem.*, 60(12):2043-2047 (1996).

Christenson et al., "Kinetic analysis of the 4-methylideneimidazole-5-one-containing tyrosine aminomutase in enediyne antitumor antibiotic C-1027 biosynthesis," *Biochemistry*, 42(43):12708-12718 (2003).

(56) References Cited

OTHER PUBLICATIONS

Chu et al., "Enzymatically active truncated cat brain glutamate decarboxylase: expression, purification, and absorption spectrum," *Arch. Biochem. Biophys.*, 313:287-295 (1994).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Clarke et al., "Rational construction of a 2-hydroxyacid dehydrogenase with new substrate specificity," *Biochem. Biophys. Res. Commun.*, 148:15-23 (1987).

Clausen et al., "PAD1 encodes phenylacrylic acid decarboxylase which confers resistance to cinnamic acid in *Saccharomyces cerevisiae*," *Gene*, 142:107-112 (1994).

Cock et al., "A nuclear gene with many introns encoding ammonium-inductible chloroplastic NADP-specific glutamate dehydrogenase(s) in Chlorella sorokiniana," *Plant Mol. Biol.*, 17:1023-1044 (1991).

Coco et al., "DNA shuffling method for generating highly recombined genes and evolved enzymes," *Nat. Biotechnol.*, 19(4):354-359 (2001).

Cogoni et al., "*Saccharomyces cerevisiae* has a single glutamate synthase gene coding for a plant-like high-molecular-weight polypeptide," *J. Bacteriol.*, 177:792-798 (1995).

Colby et al., "Purification and properties of 3-Hydroxybutyryl-Coenzyme A Dehydrogenase from Clostridium beijerinckii (Clostridium butylicum:) NRRL B593," *Appl. Environ. Microbiol.*, 58:3297-3302 (1992).

Cole et al., "Deciphering the biology of *Mycobacterium tuberculosis* from the complete genome sequence," *Nature*, 393:537-544 (1998).

Coleman et al., "Expression of a glutamate decarboxylase homologue is required for normal oxidative stress tolerance in *Saccharomyces cerevisiae*," *J. Biol. Chem.*, 276:244-250 (2001).

Colonna et al., "Synthesis and radiocarbon evidence of terephthalate polyesters completely prepared from renewable resources," *Green Chemistry*, 13:2543-2548 (2011).

Cooper, "Glutamate-γ-aminobutyrate transaminase," *Methods Enzymol.*, 113:80-82 (1985).

Corthesy-Theulaz et al., "Cloning and characterization of Helicobacter pylori succinyl CoA: acetoacetate CoA-transferase, a novel prokaryotic member of the CoA-transferase family," *J. Biol. Chem.*, 272(41):25659-25667 (1997).

Creaghan et al., "Succinate dehydrogenase-dependent nutritional requirement for succinate in mutants of *Escherichia coli* K12," *J. Gen. Microbiol.*, 107(1):1-13 (1978).

Cukalovic et al., "Feasibility of production method for succinic acid derivatives: a marriage of renewable resources and chemical technology," *Biofuels Bioprod. Bioref.*, 2:505-529 (2008).

Cunningham et al., "Transcription and transcript processing in the sdhCDAB-sucABCD operon of *Escherichia coli*," *Microbiology*, 144:2113-2123 (1998).

Currie et al., Nuclear Instruments and Methods in Physics Research B, 172:281-287 (2000).

Darlison et al., "Nucleotide sequence of the sucA gene encoding the 2-oxoglutarate dehydrogenase of *Escherichia coli* K12," *Eur. J. Biochem.*, 141(2):351-359 (1984).

Datsenko et al., "One-step inactivation of chromosomal genes in *Escherichia coli* K-12 using PCR products," *Proc. Natl. Acad. Sci. U.S.A.*, 97(12):6640-6645 (2000).

Davie et al., "Expression and Assembly of a Functional E1 Component (α2β2) of Mammalian Branched-Chain α-Ketoacid Dehydrogenase Complex in *Escherichia coli*," *J. Biol. Chem.*, 267:16601-16606 (1992).

De Biase et al., "Isolation, overexpression, and biochemical characterization of the two isoforms of glutamic acid decarboxylase from *Escherichia coli*," *Protein Expr. Purif.*, 8:430-438 (1996).

De Crecy et al., "Development of a novel continuous culture device for experimental evolution of bacterial populations," *Appl. Microbiol. Biotechnol.*, 77:489-496 (2007).

De La Torre et al., "Identification and functional analysis of prokaryotic-type aspartate aminotransferase: implications for plant amino acid metabolism," *Plant J.*, 46(3):414-425 (2006).

Deana, "Substrate specificity of a dicarboxyl-CoA: dicarboxylic acid coenzyme A transferase from rat liver mitochondria," *Biochem. Int.*, 26(4):767-773 (1992).

Deckert et al., "The complete genome of the hyperthermophilic bacterium Aquifex aeolicus," *Nature*, 392:353-358 (1998).

Diao et al., "Crystal Structure of Butyrate Kinase 2 from Thermotoga maritima, a Member of the ASKHA Superfamily of Phosphotransferases," *J. Bacteriol.*, 191(8):2521-2529 (2009).

Diao et al., "Crystallization of butyrate kinase 2 from Thermotoga maritima medicated by varpor diffusion of acetic acid," *Acta Crystallogr. D. Crystallogr.*, 59:1100-1102 (2003).

Diaz et al., "Gene cloning, heterologous overexpression and optimized refolding of the NAD-glutamate dehydrogenase from haloferax mediterranei," *Extremophiles*, 10(2):105-115 (2006).

Diderichsen et al., "Cloning of aldB, which encodes alpha-acetolactate decarboxylase, an exoenzyme from Bacillus brevis," *J. Bacteriol.*, 172(8):4315-4321 (1990).

Diruggiero et al., "Expression and in vitro assembly of recombinant glutamate dehydrogenase from the hyperthermophilic archaeon Pyrococcus turiosus," *Appl. Environ. Microbiol.*, 61:159-164 (1995).

Doi et al., "Biosynthesis and characterization of poly(3-hydroxybutyrate-co-4-hydroxybutyrate) in Alcaligenes eutrophus," *Int. J. Biol. Macromol.*, 12:106-111 (1990).

Doi et al., "Nuclear Magnetic Resonance Studies on Unusual Bacterial Copolyesters of 3-Hydroxybutyrate and 4-Hydroxybutyrate," *Macromolecules*, 21:2722-2727 (1988).

Doi, "Microbial Synthesis, Physical Properties, and Biodegradability of Polyhydroxyalkanoates," *Macromol. Symp.*, 98:585-599 (1995).

Dombek et al., "Ethanol production during batch fermentation with *Saccharomyces cerevisiae*: changes in glycolytic enzymes and internal pH," *Appl. Environ. Microbiol.*, 53:1286-1291 (1987).

Donnelly et al., "Succinic semialdehyde dehydrogenases of *Escherichia coli*: Their role in the degradation of p-hydroxyphenylacetate and γ-aminobutyrate," *Eur. J. Biochem.*, 113:555-561 (1981).

Donnelly et al., "Two succinic semialdehyde dehydrogenases are induced when *Escherichia coli* K-12 is grown on gamma-aminobutyrate," *J. Bacteriol.*, 145:1425-1427 (1981).

Dover et al., "Genetic analysis of the gamma-aminobutyrate utilization pathway in *Escherichia coli* K-12," *J. Bacteriol.*, 117(2):494-501 (1974).

Doyle et al., "Structural basis for a change in substrate specificity: crystal structure of S113E isocitrate dehydrogenase in a complex with isopropylmalate, Mg2+, and NADP," *Biochemistry*, 40(14):4234-4241 (2001).

Drake, "Acetogenesis, acetogenic bacteria, and the acetyl-CoA "Wood/Ljungdahl" pathway: past and current perspectives," in H.L. Drake (ed.), *Acetogenesis*, pp. 3-60 Chapman and Hall, New York (1994).

Drewke et al., "4-O-Phosphoryl-L-threonine, a substrate of the pdxC(serC) gene product involved in vitamin $B_6$ biosynthesis," *FEBS Lett.*, 390:179-182 (1996).

Duncan et al., "Acetate utilization and butyryl coenzyme A (CoA):acetate-CoA transferase in butyrate-producing bacteria from the human large intestine," *Appl. Environ. Microbiol.*, 68(10):5186-5190 (2002).

Duncan et al., "Purification and properties of NADP-dependent glutamate dehydrogenase from Ruminococcus flavefaciens FD-1," *Appl. Environ. Microbiol.*, 58:4032-4037 (1992).

Dürre et al., "Solventogenic enzymes of Clostridium acetobutylicum: catalytic properties, genetic organization, and transcriptional regulation," *FEMS Microbiol. Rev.*, 17(3):251-262 (1995).

Dykhuizen, "Chemostats used for studying natural selection and adaptive evolution," *Methods Enzymol.*, 613-631 (1993).

Edwards et al., "Systems properties of the Haemophilus influenzae Rd metabolic genotype," *J. Biol. Chem.*, 274(25):17410-17416 (1999).

Edwards et al., "The *Escherichia coli* MG1655 in silico Metabolic Genotype: Its Definition, Characteristics, and Capabilities," *Proc. Natl. Acad. Sci. U.S.A.*, 97(10):5528-5533 (2000).

(56) References Cited

OTHER PUBLICATIONS

Edwards et al., "In Silico Predictions of *Escherichia coli* metabolic capabilities are Consistent with Experimental Data," *Nat. Biotechnol.*, 19(2):125-130 (2001).
Efe et al., "Options for biochemical production of 4-hydroxybutyrate and its lactone as a substitute for petrochemical production," *Biotechnol. Bioeng.*, 99:1392-1406 (2008).
Eggen et al., "The glutamate dehydrogenase-encoding gene of the hyperthermophilic archaeon Pyrococcus furiosus: sequence, transcription and analysis of the deduced amino acid sequence," *Gene*, 132:143-148 (1993).
Enomoto et al., "Cloning and sequencing of the gene encoding the soluble fumarate reductase from *Saccharomyces cerevisiae*," *DNA Res.*, 3:263-267 (1996).
Estevez et al., "X-ray crystallographic and kinetic correlation of a clinically observed human fumarase mutation," *Protein Sci.*, 11:1552-1557 (2002).
Faehnle et al., "A New Branch in the Family: Structure of Aspartate-β-semialdehyde dehydrogenase from Methanococcus jannaschii," *J. Mol. Biol.*, 353:1055-1068 (2005).
Feist et al., "The growing scope of applications of genome-scale metabolic reconstructions using *Escherichia coli*," *Nat. Biotechnol.*, 26(6):659-667 (2008).
Fell et al., "Fat Synthesis in Adipose Tissue. An Examination of Stoichiometric Constraints," *Biochem. J.*, 238(3):781-786 (1986).
Fernandez-Valverde et al., "Purification of Pseudomonas putida Acyl coenzyme a Ligase Active with a Range of Aliphatic and Aromatic Substrates," *Appl. Environ. Microbiol.*, 59:1149-1154 (1993).
Fidler et al., "Polyhydroxyalkanoate production in recombinant *Escherichia coli*," FEMS Microbiology Reviews, 103:231-236 (1992).
Filetici et al., "Sequence of the GLT1 gene from *Saccharomyces cerevisiae* reveals the domain structure of yeast glutamate synthase," *Yeast*, 12:1359-1366 (1996).
Fischer et al., "Metabolic flux profiling of *Escherichi coli* mutants in central carbon metabolism using GC-MS," *Eur. J. Biochem.*, 270(5) 880-891 (2003).
Fishbein et al., "Purification and properties of an enzyme in human blood and rat liver microsomes catalyzing the formation and hydrolysis of gamma-lactones. I. Tissue localization, stoichiometry, specificity, distinction from esterase," *J. Biol. Chem.*, 241(21):4835-4841 (1966).
Fishbein et al., "Purification and properties of an enzyme in human blood and rat liver microsomes catalyzing the formation and hydrolysis of γ-lactones. II. Metal ion effects, kinetics, and equilibra," *J. Biol. Chem.*, 241(21):4842-4847 (1966).
Föllner et al., "Analysis of the PHA granule-associatc proteins GA20 and GA11 in Methylobacterium extorquens and Methylobacterium rhodesianum," *J. Basic Microbiol.*, 37(1):11-21 (1997).
Fong et al., "Metabolic gene-deletion strains of *Escherichia coli* evolve to computationally predicted growth phenotypes," *Nat. Genet.*, 36(10):1056-1058 (2004).
Fong et al., "Description and interpretation of adaptive evolution of *Escherichia coli* K-12 MG1655 by using a genome-scale in silico metabolic model," *J. Bacteriol.*, 185(21):6400-6408 (2003).
Fong et al., "In silico design and adaptive evolution of *Escherichia coli* for production of lactic acid," *Biotechnol. Bioeng.*, 91:643-648 (2005).
Fontaine et al, "A New Type of Glucose Fermentation by *Clostridium thermoaceticum* N.sp.," *J. Bacteriol.*, 43:701-715 (1942).
Fontaine et al., "Molecular characterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.*, 184(3):821-830 (2002).
Ford et al., "Molecular properties of the lys1+ gene and the regulation of alpha-aminoadipate reductase in Schizosaccharomyces pombe," *Curr. Genet.*, 28(2):131-137 (1995).
Forster et al., "Genome-scale reconstruction of the *Saccharomyces cerevisiae* metabolic network," *Genome Res.*, 13(2):244-253 (2003).
Four pages from URL: shigen.nig.ac.jp/ecoli/pec/genes.List.DetailAction.do (Printed Dec. 21, 2009).
Friedrich et al., "The complete stereochemistry of the enzymatic dehydration of 4-hydroxybutyryl coenzyme A to crotonyl coenzyme A," *Angew. Chem. Int. Ed. Engl.*, 47:3254-3257 (2008).
Fries et al., "Reaction Mechanism of the Heteroameric (α2β2) E1 Component of 2-Oxo Acid Dehydrogenase Multienzyme Complexes," *Biochemistry*, 42:6996-7002 (2003).
Fuhrer et al., "Computational prediction and experimental verification of the gene encoding the NAD+/NADP+-dependent succinate semialdehyde dehydrogenase in *Escherichia coli*," *J. Bacteriol.*, 189:8073-8078 (2007).
Fujii et al., "Characterization of L-lysine 6-aminotransferase and its structural gene from Favobacterium lutescens IFO3084," *J. Biochem.*, 128(3):391-397 (2000).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Fujita et al., "Novel Substrate Specificity of designer3-Isopropylmalate Dehydrogenase Derived from thermus thermophilus HB1," *Biosci. Biotechnol. Biochem.*, 5(12):2695-2700 (2001).
Fukao et al., "Succinyl-coA:3-Ketoacid CoA Transferase (SCOT): Cloning of the Human SCOT Gene, Tertiary Structural Modeling of the Human SCOT Monomer, and Characterization of Three Pathogenic Mutations," *Genomics*, 68:144-151 (2000).
Fukuda et al., "Substrate recognition by 2-oxoacid:ferredoxin oxidoreductase from *Sulfolobus* sp. Strain 7," *Biochim. Biophys. Acta*, 1597:74-80 (2002).
Fukuda et al., "Role of a highly conserved YPITP motif in 2-oxoacid:ferredoxin oxidoreductase," *Eur. J. Biochem.*, 268:5639-5646 (2001).
Gallego et al., "A role for glutamate decarboxylase during tomato ripening: the characterisation of a cDNA encoding a putative glutamate decarboxylase with a calmodulin-binding site," *Plant Mol. Biol.*, 27:1143-1151 (1995).
Gay et al., "Cloning Structural Gene sacB, Which codes for Exoenzyme Levansucrase of Bacillus subtilis: Epxresion of the Gene in *Escherichia coli*," *J. Bacteriol.*, 153:1424-1431 (1983).
Gerhardt et al., "Fermentation of 4-aminobutyrate by Clostridium aminobutyricum: cloning of two genes involved in the formation and dehydration of 4-hydroxybutyryl-CoA," *Arch. Microbiol.*, 174:189-199 (2000).
Gerngross et al., "Enzyme-catalyzed synthesis of poly((R)-(-)-3-hydroxybutyrate): formation of macroscopic granules in vitro," *Proc. Natl. Acad. Sci. U.S.A.*, 92:6279-6783 (1995).
Gerngross, et al., "Overexpression and purification of the soluble polyhydroxyalkanoate synthase from Alcalligenes eutrophus: evidence for a required posttranslational modification for catalytic activity," *Biochemistry*, 33:9311-9320 (1994).
Gibbs et al., "Degenerate oligonucleotide gene shuffling (DOGS): a method for enhancing the frequency of recombination with family shuffling," *Gene*, 271:13-20 (2001).
Giesel et al., "On the occurrence of enoate reductase and 2-oxocarboxylate reductase in clostridia and some observations on the amino acid fermentation by Peptostreptococcus anaerobius," *Arch. Microbiol.*, 135(1):51-57 (1983).
Girbal et al., "Regulation of metabolic shifts in Clostridium acetobutylicum ATCC 824," *FEMS Microbiol. Rev.*, 17:287-297 (1995).
Goda et al., "Cloning, Sequencing, and Expression in *Escherichia coli* of the Clostridium tetanomorphum Gene Encoding β-Methylaspartase and Characterization of the Recombinant Protein," *Biochemistry*, 31:10747-10756 (1992).
Gong et al., "Specificity Determinants for the Pyruvate Dehydrogenase Component Reaction Mapped with Mutated and Prosthetic Group Modified Lipoyl Domains," *J. Biol. Chem.*, 275(18):13645-13653 (2000).
Gonzalez et al., "Cloning of a yeast gene coding for the glutamate synthase small subunit (GUS2) by complementation of Sac-

(56) References Cited

OTHER PUBLICATIONS charomyces cerevisiae and Escherichia coli glutamate auxotrophs," Mol. Microbiol., 6:301-308 (1992).
Gonzalez-Pajuelo et al., "Metabolic engineering of Clostridium acetobutylicum for the industrial production of 1,3-propanediol from glycerol," Met. Eng., 7:329-336 (2005).
Goupil et al., "Imbalance of leucine flux in Lactoccus lactis and its use for the isolation of diacetyl-overproducing strains," Appl. Environ. Microbiol., 62(7):2636-2640 (1996).
Goupil-Feuillerat et al., "Transcriptional and translational regulation of alpha-acetolactate decarboxylase of Lactococcus lactis subsp. Lactis," J. Bacteriol., 182(19):5399-5408 (2000).
Green et al., "Catabolism of α-Ketoglutarate by a sucA Mutant of Bradyrhizobium japonicum: Evidence for an Alternative Tricarboxylic Acid Cycle," J. Bacteriol., 182(10):2838-2844 (2000).
Gregerson et al., "Molecular characterization of NADH-dependent glutamate synthase from alfalfa nodules," Plant Cell, 5:215-226 (1993).
Guirard et al., "Purification and properties of ornithine decarboxylase from Lactobacillus sp. 30a," J. Biol. Chem., 255(12):5960-5964 (1980).
Guo et al., "Posttranslational activation, site-directed mutation and phylogenetic analyses of lysine biosynthesis enzymes alpha-aminoadipate reductase Lys1P (AARO and the phosphopantetheinyl transferase Lys7p (PPTase) from Schizosaccharomyces pombe," Yeast, 21(15):1279-1288 (2004).
Guo et al., "Site-directed mutational analysis of the novel catalytic domains of alpha-aminoadipate reductase (Lys2p) from Candida albicans," Mol. Genet. Genomics, 269(2):271-279.
Guzman et al., "Tight regulation, modulation, and high-level expression by vectors containing the arabinose PBAD promoter," J. Bacteriol., 177:4121-4130 (1995).
Hadfield et al., "Active site analysis of the potential antimicrobial target aspartate semialdehyde dehydrogenase," Biochemistry, 40(48):14475-14483 (2001).
Hadfield et al., "Structure of aspartate-beta-semialdehyde dehydrogenase from Escherichia coli, a key enzyme in the aspartate family of amino acid biosynthesis," J. Mol. Biol., 289(4):991-1002 (1999).
Hammer et al., "Purification and characterization of an inducible L-lysine:2-oxoglutarate 6-aminostransferase from Dandida utilis," J. Basic Microbiol., 32:21-27 (1992).
Hanai et al., "Engineered synthetic pathway for isopropanol production in Escherichia coli," Appl. Environ. Microbiol., 73:7814-7818 (2007).
Hansford, "Control of mitochondrial substrate oxidation," Curr. Top. Bioenerg., 10:217-278 (1980).
Hasegawa et al., "Transcriptional regulation of ketone body-utilizing enzyme, acetoacetyl-CoA synthetase, by C/EBPα during adipocyte differentiation," Biochim. Biophys. Acta, 1779:414-419 (2008).
Hashidoko et al., "Cloning of a DNA Fragment Carrying the 4-Hydroxycinnamate Decarboxylase (pofK) Gene from Klebsiella oxtoca, and Its Constitutive Expression in Escherichia coli JM109 Cells," Biosci. Biotech. Biochem., 58(1):217-218 (1994).
Hashimoto et al., "Activation of L-Lysine ε-Dehydrogenase from Agrobacterium tumefaciens by Several Amino Acids and Monocarboxylates," J. Biochem., 106:76-80 (1989).
Hasson et al., "The Crystal Structure of Benzoylformate Decarboxylase at 1.6 Å Resolution: Diversity of Catalytic Residues in thiamin Diphosphate-Dependent Enzymes," Biochemistry, 37:9918-9930 (1998).
Hawes et al., "Mammalian 3-hydroxyisobutyrate dehydrogenase," Methods Enzymol., 324:218-228 (2000).
Hayashi et al., "Purification of NADH-ferricyanide dehydrogenase and NADH-quinone reductase from Escherichia coli membranes and their roles in the respiratory chain," Biochim. Biophys. Acta, 977:62-69 (1989).
Hayden et al., "Glutamate dehydrogenase of Halobacterium salinarum: evidence that the gene sequence currently assigned to the NADP+-dependent enzyme is in fact that of the NAD+-dependent glutamate dehydrogenase," FEMS Microbiol. Lett., 211:37-41 (2002).
Hayes et al., "Combining computational and experimental screening for rapid optimization of protein properties," Proc. Natl. Acad. Sci. U.S.A., 99(25):15926-15931 (2002).
Hein et al., "Biosynthesis of poly(4-hydroxybutyric acid) by recombinant strains of Escherichia coli," FEMS Microbiol. Lett., 153(2):411-418 (1997).
Henne et al., "Construction of environmental DNA libraries in Escherichia coli and screening for the presence of genes conferring utilization of 4-hydroxybutyrate," Appl. Environ. Microbiol., 65(9):3901-3907 (1999).
Hennessy et al., "The reactivity of gamma-hydroxybutyric acid (GHB) and gamma-butyrolactone (GBL) in alcoholic solutions," J. Forensic. Sci., 49(6):1220-1229 (2004). (provided electronically by publisher as pp. 1-10).
Henning et al., "Identification of Novel enzoylformate Decarboxlyases by Growth Selection," App. Environ. Microbiol., 72(12)7510-7517 (2006).
Hermes et al., "Searching sequence space by definably random mutagenesis: Improving the catalytic potency of an enzyme," Proc. Natl. Acad. Sci. U.S.A., 87:696-700 (1990).
Herrmann et al., "Two beta-alanyl-CoA: ammonia lyases in Clostridium propionicum," FEBS J., 272:813-821 (2005).
Hesslinger et al., "Novel keto acid formate-lyase and propionate kinase enzymes are components of an anaerobic pathway in Escherichia coli that degrades L-threonine to propionate," Mol. Microbiol, 27:477-492 (1998).
Hester et al., "Purification of active E1 alpha 2 beta 2 of Pseudomonas putida branched-chain-oxoacid dehydrogenase," Eur. J. Biochem., 233(3):828-836 (1995).
Heydari et al., "Highly Stable L-Lysine 6-Dehydrogenase from the Thermophile Geobacillus stearothemophilus Isolated from a Japanese Hot Spring: Characterization, gene Cloning and Sequencing, and Expression," Appl. Environ. Microbiol., 70:937-942 (2004).
Hezayen et al., "Biochemical and enzymological properties of the polyhydroxybutyrate synthase from the extremely halophilic archaeon strain 56," Arch. Biochem. Biophys., 403(2):284-291 (2002).
Hibbert et al. "Directed evolution of biocatalytic processes," Biomol. Eng., 22:11-19 (2005).
Hijarrubia et al., "Domain Structure characterization of the Multifunctional α-Aminoadipate Reductase from Penicillium chrysogenum by Limited Proteolysis," J. Biol. Chem., 278:8250-8256 (2003).
Hillmer et al., "Solubilization and partial characterization of particulate dehydrogenases from Clostridium kluyveri," Biochim. Biophys. Acta, 334:12-23 (1974).
Hiramitsu et al., "Production of Poly(3-hydroxybutyrate-co-4-hydroxybutyrate) by Alcallgenes latus," Biotechnol Lett., 15:461-464 (1993).
Hirano et al., "Purification and Characterization of the alcohol dehydrogenase with a broad substrate specificity originated from 2-phenylethanol-assimilating Brevibacterium sp. KU 1390," J. Biosci. Bioeng., 100(3):318-322 (2005).
Hiser et al., "ERG10 from Saccharomyces cerevisiae encodes acetoacetyl-CoA thiolase," J. Biol. Chem., 269:31383-31389 (1994).
Hoffmeister et al., "Mitochondrial trans-2-enoyl-CoA reductase of wax ester fermentation from Euglena gracilis defines a new family of enzymes involved in lipid synthesis," J. Biol. Chem., 280:4329-4338 (2005).
Hogan et al., "Improved specificity toward substrates with ositively charged side chains by site-directed mutagenesis of the L-lactate dehydrogenase of Bacillus stearothermophilus," Biochemistry, 34(13):4225-4230 (1995).
Hong et al., "Enhanced Production of Succinic Acid by Metabolically Engineered Escherichia coli with Amplified Activities of Malic Enzyme and Fumarase," Biotechnol. Bioprocess Eng., 9:252-255 (2004).
Hong et al., "The genome sequence of the capnophilic rumen bacterium Mannheimia succiniciproducens," Nat. Biotechnol., 22(10):1275-1281 (2004).
Huang et al., "Identification and Characterization of a Second Butyrate Kinase from Clostridium acetobutylicum ATCC 824," J. Mol. Microbiol. Biotechnol., 2(1):33-38 (2000).

(56) References Cited

OTHER PUBLICATIONS

Huang et al., "Purification and Characterization of a Ferulic Acid Decarboxylase from Pseudomonas fluorescens," *J. Bacteriol.*, 176(19):5912-5918 (1994).
Hughes et al., "Evidence for Isofunctional Enzymes in the Degradation of Phenol, m- and p-Toulate, and p-Cresol via Catechol meta-Cleavage Pathways in Alcaligenes eutrophus," *J. Bacteriol.*, 158:79-83 (1984).
Hugler et al., "Malonyl-coenzyme A reductase from Chloroflexus aurantiacus, a key enzyme of the 3-hydroxypropionate cycle for autotrophic CO(2) fixation," *J. Bacteriol.*, 184:2404-2410 (2002).
Huh et al., "Global analysis of protein localization in budding yeast," *Nature*, 425:686-691 (2003).
Huisman et al., "Ch. 30: Enzyme Evolution for Chemical Process Applications," In R N. Patel (ed.), *Biocatalysis In The Pharmaceutical And Biotechnology Industries*, CRC Press, Boca Raton, FL, p. 717-742 (2007).
Huo et al., "Substrate specificity and identification of functional groups of homoserine kinase from *Escherichia col*," *Biochemistry*, 35(50):16180-16185 (1996).
Ibarra et al., "*Escherichia coli* K-12 undergoes adaptive evolution to achieve in silico predicted optimal growth," *Nature*, 420(6912):186-189 (2002).
Iffland et al., "Directed molecular evolution of cytochrome c peroxidase," *Biochemistry*, 39(25):10790-10798 (2000).
Ikai et al., "Identification and Analysis of a Gene Encoding L-2,4-Diaminobutyrate:2-Ketoglutarate 4-Aminotransferase Invloved in the 1,3-Diaminopropane Production Pathway in Acinetobacter baumanni," *J. Bacteriol.*, 179(16):5118-5125 (1997).
Imai et al., "Measurement of yeast intracellular pH by image processing and the change it undergoes during growth phase," *J. Biotechnol.*, 38:165-172 (1995).
Ingoldsby et al., "The discovery of four distinct glutamate dehydrogenase genes in a strain of Halobacterium salinarum," *Gene*, 349:237-244 (2005).
Ishida et al., "Efficient production of L-Lactic acid by metabolically engineered *Saccharomyces cerevisiae* with a genome-integrated L-lactate dehydrogenase gene." *Appl. Envirom. Microbiol.*, 71:1964-1970 (2005).
Ishige et al., "Wax ester production from n-alkanes by *Acinetobacter* sp. strain M-1: ultrastructure of cellular inclusions and role of acyl coenzyme A reductase," *Appl. Environ. Microbiol.*, 68(3):1192-1195 (2002).
Ismaiel et al., "Purification and characterization of a primary-secondary alcohol dehydrogenase from two strains of Clostridium beijerinckii," *J. Bacteriol.*, 175(16):5097-5105 (1993).
Ismail et al., "Functional genomics by NMR spectroscopy Phenylacetate catabolism in *Escherichia coli*," *Eur. J. Biochem.*, 270:3047-3054 (2003).
Ito et al., "D-3-hydroxybutyrate dehydrogenase from Pseudomonas fragi: molecular cloning of the enzyme gene and crystal structure of the enzyme," *J. Mol. Biol.*, 355(4):722-733 (2006).
Iverson et al., "Structure of the *Escherichia coli* fumarate reductase respiratory complex," *Science*, 284(5422):1961-1966 (1999).
Jeon et al., "Heterologous expression of the alcohol dehydrogenase (adhI) gene from Geobacillus thermoglucosidasius strain M10EXG," *J. Biotechnol.*, 135:127-133 (2008).
Jesudason et al., "Synthetic Poly[(R,S)-.beta.-hydroxyalkanoates] with Butyl and Hexyl Side Chains," *Macromolecules*, 27:2595-2602 (1994).
Jewell et al., "Bioconversion of propionic, valeric and 4-hydroxybutyric acids into the corresponding alcohols by Clostridium acetobutylicum NRRL 527," *Curr. Microbiol.*, 13(4):215-219 (1986).
Jiang et al., "De novo computational design of retro-aldol enzymes," *Science*, 319(5868):1387-1391 (2008).
Johnson et al., "Alteration of a single amino acid changes the substrate specificity of dihydroflavonol 4-reductase," *Plant J.*, 25(3):325-333 (2001).
Johnston et al., "Complete nucleotide sequence of *Saccharomyces cerevisiae* chromosome VIII," *Science*, 265:2077-2082 (1994).

Jones et al., "Construction and characterization of F plasmid-based expression vectors," *Biotechnol. Bioengineer.*, 59:659-665 (1998).
Jones et al., "Acetone-butanol fermentation revisited," *Microbiol. Rev.*, 50(4):484-524 (1986).
Jones et al., "Purification and characterization of D-b-hydroxybutyrate dehydrogenase expressed in *Escherichia coli*," *Biochem. Cell Biol.*, 71(7-8):406-410 (1993).
Kakimoto et al., "β-Aminoisobutyrate-α-ketoglutarate transaminase in relation to β-aminoisobutyric aciduria," *Biochim. Biophys. Acta.*, 156(2):374-380 (1968).
Kaneko et al., "Sequence analysis of the genome of the unicellular cyanobacterium *Synechocystis* sp. strain PCC6803, II. Sequence determination of the entire genome and assignment of potential protein-coding regions," *DNA Res.*, 3:109-136 (1996).
Kapatral et al., "Genome Sequence and Analysis of the Oral Bacterium Fusobacterium nucleatum Strain ATCC 25586," *J. Bacteriol.*, 184(7):2005-2018 (2002).
Karlen et al., "Absolute determination of the activity of two C14 dating standards," *Arkiv Geofysik*, 4:465-471 (1964).
Kato et al., "3-Methylaspartate ammonia-lyase as a marker enzyme of the mesaconate pathway for (S)-glutamate fermentation in Enterobacteriaceae," *Arch. Microbiol.*, 168(6):457-463 (1997).
Kato et al., "Open reading frame 3 of the barotolerant bacterium strain DSS12 is complementary with cydD in *Escherichia coli*: cydD functions are required for cell stability at high pressure," *J. Biochem.*, 120:301-305 (1996).
Kato et al., "Production of a novel copolyester of 3-hydroxybutyric acid with a medium-chain-length 3-hydroxyalkanoic acids by *Pseudomonas* sp. 61-3 from sugars," *Appl. Microbiol. Biotechnol.*, 45:363-370 (1996).
Kazahaya et al, "Aerobic Dissimilation of Glucose by Heterolactic Bacteria," *J. Gen. Appl. Microbiol.*, 18(1):43-55 (1972).
Keng et al., "Specificity of Aspartokinase III from *Escherichia coli* and an Examination of Important Catalytic Residues," *Arch. Biochem. Biophys.*, 335:73-81 (1996).
Kessler et al., "Pyruvate-formate-lyase-deactivase and acetyl-CoA reductase activities of *Escherichia coli* reside on a polymeric protein particle encoded by adhE," *FEBS. Lett.*, 281:59-63 (1991).
Khalameyzer et al., "Screening, Nucleotide Sequence, and Biochemical Characterization of an Esterase from Pseudomonas fluorescens with High Activity towards Lactone," *Applied and Environmental Microbiology*, 65(2):477-482 (1999).
Khan et al., "Molecular properties and enhancement of thermostability by random mutagenesis of glutamate ehydrogenase from Bacillus subtilis," *Biosci. Biotechnol. Biochem.*, 69(10):1861-1870 (2005).
Killenberg-Jabs et al., "Active oligomeric states of pyruvate decarboxylase and their functional characterization," *Eur. J. Biochem.*, 268:1698-1704 (2001).
Kim et al., "Construction of an *Escherichia coli* K-12 Mutant for Homoethanologenic Fermentation of glucose or Xylose without Foreign Genes," *Appl. Environ. Microbiol.*, 73:1766-1771 (2007).
Kim et al., "Dihydrolipoamide Dehydrogenase Mutation Alters the NADH Sensitivity of Pyruvate Dehydrogenase Complex of *Escherichi coli* K-12," *J. Bacteriol.*, 190:3851-3858 (2008).
Kim et al., "Effect of overexpression of Actinobacillus succinogenes phosphoenolpyruvate carboxykinase on succinate production in *Escherichia coli,*" *Appl. Environ. Microbiol.*, 70:1238-1241 (2004).
Kim, "Purification and Propertis of a mine α-Ketoglutarate Transaminase from *Escherichia coli,*" *J. Biol. Chem.*, 239:783-786 (1964).
Kimura et al., "Production of Poly(3-hydroxybutyrate-co-4-hydroxybutyrate) by Pseudomonas acidovorans," *Biotechnol. Lett.*, 14(6):445-450 (1992).
Kinnaird et al., "The complete nucleotide sequence of the Neurospora crassa am (NADP-specific glutamate dehydrogenase) gene," *Gene*, 26:253-260 (1983).
Kino et al., "Synthesis of DL-tryptophan by modified broad specificity amino acid racemase from Pseudomonas putida IFO 12996," *Appl. Microbiol. Biotechnol.*, 73(6):1299-1305 (2007).
Kinoshita, "Purification of two alcohol dehydrogenases from Zymomonas mobilis and their properties," *Appl. Microbiol. Biotechnol.*, 22:249-254 (1985).

(56) References Cited

OTHER PUBLICATIONS

Kirby et al., "Purification and properties of rabbit brain and liver 4-aminobutyrate aminotransferases isolated by monoclonal-antibody Immunoadsorbent chromatography," *Biochem. J.*, 230:481-488 (1985).
Kizer et al., "Application of Functional Genomics to Pathway Optimization for Increased Isoprenoid Production," *Appl. Environ. Microbiol.*, 74(10):3229-3241 (2008).
Klatt et al., "Comparative genomics provides evidence for the 3-hydroxypropionate autotrophic pathway in filamentous anoxygenic phototrophic bacteria and in hot spring microbial mats," *Environ. Microbiol.*, 9(8):2067-2078 (2007).
Klenk et al., "The complete genome sequence of the hyperthermophilic, sulphate-reducing archaeon Archaeoglobus fulgidus," *Nature*, 390:364-370 (1997).
Knapp et al., "Crystal Structure of the Truncated Cubic Core Component of the *Escherichia coli* 2-Oxoglutarate Dehydrogenase Multienzyme Complex," *J. Mol. Biol.*, 289:655-668 (1998).
Knappe et al., "A radical-chemical route to acetyl-CoA: the anaerobically induced pyruvate formate-lyase system of *Escherichia coli*," *FEMS Microbiol. Rev.*, 75:383-398 (1990).
Kobayashi et al., "Frementative Production of 1,4-Butanediol from Sugars by *Bacillus* sp.," *Agric. Biol. Chem.*, 51(6):1689-1690 (1987).
Kobayashi et al., "Physiochemical, Catalytic, and Immunochemical Properties of Fumarases Crystallized Separately from Mitochondrial and Cytosolic Fractions of Rat Liver," *J. Biochem.*, 89:1923-1931 (1981).
Koo et al., "Cloning and characterization of the bifunctional alcohol/acetaldehyde dehydrogenase gene (adhE) in Leuconostoc mesenteroides isolated from kimchi," *Biotechnol. Lett.*, 27(7):505-510 (2005).
Korbert et al., "Crystallization of the NADP+-dependent Glutamate Dehydrogenase from *Escherichia coli*," *J. Mol. Biol.*, 234:1270-1273 (1993).
Korolev et al., "Autotracing of *Escherichia coli* acetate CoA-transferase α-subunit structure using 3.4 Å MAD and 1.9 Å native data," *Acta. Cryst.*, D58:2116-2121 (2002).
Kort et al., "Glutamate dehydrogenase from the hyperthermophilic bacterium Thermotoga maritima: molecular characterization and phylogenetic implications," *Extremophiles*, 1:52-60 (1997).
Kosaka et al., "Characterization of the sol operon in butanol-hyperproducing Clostridium saccharoperbutylacetonicum strain N1-4 and its degeneration mechanism," *Biosci. Biotechnol. Biochem.*, 71:58-68 (2007).
Kosjek et al., "Purification and characterization of a chemotolerant alcohol dehydrogenase applicable to coupled redox reactions," *Biotechnol. Bioeng.*, 86(1):55-62 (2004).
Kreimeyer et al., "Indentification of the Last Unknown Genes in the fermentation Pathway of Lysine," *J. Biol. Chem.*, 282:7191-7197 (2007).
Kretz et al., "Gene site saturation mutagenesis: a comprehensive mutagenesis approach," *Methods Enzymol.*, 388:3-11 (2004).
Krieger et al., "Pyruvate decarboxylase from Kluyveromyces lactis An enzyme with an extraordinary substrate activation behaviour," *Eur. J. Biochem.*, 269:3256-3263 (2002).
Kumamaru et al., "Enhanced degradation of polychlorinated biphenyls by directed evolution of biphenyl dioxgenase," *Nat. Biotechnol.*, 16(7):663-666 (1998).
Kunioka et al., "New bacterial copolyesters produced in Alcaligenes eutrophus from organic acids," *Polym. Commun.*, 29:174-176 (1988).
Kurihara et al., "A Novel Putrescine Utilization Pathway Involves γ-Glutamylated Intermediates of *Escherichia coli* K-12," *J. Biol. Chem.*, 280(6) 4602-4608 (2005).
Kuznetsova et al., "Enzyme genomics: Application of general enzymatic screens to discover new enzymes," *FEMS Microbiol. Rev.*, 29:263-279 (2005).
Kwok et al., "GFP-labelled Rubisco and aspartate aminotransferase are present in plastid stromules and traffic between plastids," *J. Exp. Bot.*, 55(397):595-604 (2004).

Kwon et al., "Brain 4-aminobutyrate aminotransferase. Isolation and sequence of a cDNA encoding the enzyme," *J. Biol. Chem.*, 267:7215-7216 (1992).
Kwon et al., "Influence of gluconeogenic phosphoenolpyruvate carboxykinase (PCK) expression on succinic acid fermentation in *Escherichia coli* under high bicarbonate condition," *J. Microbiol. Biotechnol.*, 16(9):1448-1452 (2006).
Lageveen et al., "Formation of Polyesters by Pseudomonas oleovorans: Effect of Substrates on Formation and Composition of Poly-(R)-3-Hydroxyalkanoates and Poly-(R)-3-Hydroxyalkenoates," *Appl. Environ. Microbiol.*, 54:2924-2932 (1988).
Laivenieks et al., "Cloning sequencing, and overexpression of the Anaerobiospirillum succiniciproducens phosphoenolpyruvate carboxykinase (pckA) gene," *Appl. Environ. Microbiol.*, 63:2273-2280 (1997).
Lam et al., "Metabolic Relationships between Pyridoxine (vitamin B6) and Serine Biosynthesis in *Escherichia coli* K-12," *J. Bacteriol.*, 172(11):6518-6528 (1990).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.*, 395:147-155 (2006).
Lamed et al., "Novel NAP-linked alcohol-aldehyde/ketone oxidoreductase in thermophilic ethanologenic bacteria," *Biochem. J.*, 195:183-190 (1981).
Lebbink et al., "Engineering activity and stability of *Thermotoga maritima* Glutamate Dydrogenase. I. Introduction of a Six-residue Ion-pair Network in the Hinge Region," *J. Mol. Biol.*, 280:287-296 (1998).
Lebbink et al., "Engineering activity and stability of *Thermotoga maritima* glutamate dehydrogenase. II: construction of a 16-residue ion-pair network at the subunit interface," *J. Mol. Biol.*, 289(2):357-369 (1999).
Leduc et al., "The Hotdog Thiesterase EntH (YbdB) Plays a Role in Vivo in Optimal Enterobactin biosynthesis by Interacting with the ArCP Domain of EntB," *J. Bacteriol.*, 189(19):7112-7126 (2007).
Lee et al., "Identification of essential active-site residues in ornithine decarboxylase of Nicotiana glutinosa decarboxylating both L-ornithine and L-lysine," *Biochem. J.*, 360(Pt 3):657-665 (2001).
Lee et al., "Biosynthesis of enantiopure (s)-3-hydroxybutyric acid in metabolically engineered *Escherichia coli*," *Appl. Microbiol. Biotechnol.*, 79(4):633-641 (2008).
Lee et al., "Cloning and Characterization of Mannheimia succiniciproducens MBEL55E Phosphoenolpyruvate Carboxykinase (pckA) Gene," *Biotechnol. Bioprocess Eng.*, 7:95-99 (2002).
Lee et al., "Phylogenetic diversity and the structural basis of substrate specificity in the beta/alpha-barrel fold basic amino acid decarboxylases," *J. Biol. Chem.*, 282(37):27115-27125.
Lee et al., "A new approach to directed gene evolution by recombined extension on truncated templates (RETT)," *J. Molec. Catalysis*, 26:119-129 (2003).
Lee et al., "Biosynthesis of copolyesters consisting of 3-hydroxybutyric acid and medium-chain-length 3-hydroxyalkanoic acids from 1,3-butanediol or from 3-hydroxybutyrate by Pseudomonas sp. A33," *Appl. Microbiol. Biotechnol.*, 42: 901-909 (1995).
Lee et al., "Enhanced biosynthesis of P(3HB-3HV) and P(3HB-4HB) by amplification of the cloned PHB biosynthesis genes in Alcatigenes eutrophus," *Biotechnol. Lett.*, 19:771-774 (1997).
Lemoigne et al., "Fermentation b-Hydroxybutyrique," *Annales des Fermentations*, 5:527-536 (1925).
Lemonnier et al., "Expression of the second lysine decarboxylase gene of *Escherichia coli*," *Microbiology*, 144(Pt 3):751-760 (1998).
Lenski et al., *Proc. Natl. Acad. Sci. U.S.A.*, 91:6808-6814 (1994).
Lepore et al., "The x-ray crystal structure of lysine-2,3-aminomutase from Clostridium subterminale," *Proc. Natl. Acad. Sci. U.S.A.*, 102:13819-13824 (2005).
Li et al., "Effects of Substitution of Tryptophan 412 in the Substrate Activation Pathway of Yeast Pyruvate Decarboxylase," *Biochemistry*, 38:10004-10012 (1999).
Li, "Development of a reporter system for the study of gene expression for solvent production in Clostridium beijerinckii NRRL

(56) References Cited

OTHER PUBLICATIONS

B592 and Clostridium acetobutylicum ATCC 824," Dissertation, Department of Biochemestry, Virginia Polytechnic Institute and State University (Sep. 1998).

Lian et al., "Sterochemical and Isotopic Labeling Studies of 4-Oxalocrotonate Decarboxylase and Vinylpyruvate Hydratase: Analysis and Mechanistic Implications," *J. Am. Chem. Soc.*, 116:10403-10411 (1994).

Liebergesell et al., "Cloning and nucleotide sequences of genes relevant for biosynthesis of poly(3-hydroxybutyric acid) in Chromatium vinosum strain D," *Eur. J. Biochem.*, 209(1):135-150 (1992).

Lin et al., "Fed-batch culture of a metabolically engineered *Escherichia coli* strain designed for high-level succinate production and yield under aerobic conditions," *Biotechnol. Bioeng.*, 90(6):775-779 (2005).

Lin et al., "Functional expression of horseradish peroxidase in *E. coli* by directed evolution," *Biotechnol. Prog.*, 15(3):467-471 (1999).

Lingen et al., "Alteration of the Substrate Specificity of Benzoylformate Decarboxylase from Pseudomonas putida by Directed Evolution," *Chembiochem*, 4:721-726 (2003).

Lingen et al., "Improving the carboligase activity of benzoylformate decarboxylase from Pseudomonas putida by a combination of directed evolution and site-directed mutagenesis," *Protein Eng.*, 15:585-593 (2002).

Link et al., "Methods for generating precise deletions and insertions in the genome of wild-type *Escherichia coli*: application to open reading frame characterization," *J. Bacteriol.*, 179:6228-6237 (1997).

Liu et al., "Exploitation of butyrate kinase and phosphotransbu lase from Clostridium acetobutylicum for the in vitro biosynthesis of poly (hydroxyalkanoic acid)," *Appl. Microbiol. Biotechnol.*, 53(5):545-552 (2000).

Liu et al., "Crystal Structures of Unbound and Aminoxyacetate-Bound *Escheriha coli* Y-Aminobutyrate Aminotransferase," *Biochemistry*, 43:10896-10905 (2004).

Liu et al., "Kinetic and crystallographic analysis of active site mutants of *Escherichia coli* gamma-aminobutyrate aminotransferase," *Biochemistry*, 44:(8):2982-2992 (2005).

Liu et al., "A Novel Genetically Engineered Pathway for Synthesis of Poly(Hydroyalkanoic Acids) in *Escherichia coli*," *Applied and Environmental Microbiology*, 66(2):739-743 (2000).

Ljungdahl et al., "Formate dehydrogenase, a selenium-tungsten enzyme from Clostridium thermoaceticum," *Methods Enzymol.*, 53:360-372 (1978).

Lokanath et al., "Crystal Structure of novel NADP-dependent 3-Hydroxyisobutyrate Dehydrogenase from Thermus thermophilus HB8," *J. Mol Biol.*, 352:905-917 (2005).

Louie et al., "Cloning and characterization of the gamma-glutamyl phosphate reductase gene of Campylobacter jejuni," *Mol. Gen. Genet.*, 240:29-35 (1993).

Louis et al., "Restricted Distribution of the Butyrate Kinase Pathway among Butyrate-Producing Bacteria from the Human Colon," *J. Bacteriol.*, 186(7):2099-2106 (2004).

Low et al., "Mimicking somatic hypermutation affinity maturation of antibodies displayed on baceriophage using a bacterial mutator strain," *J. Mol. Biol.*, 260(3):359-368 (1996).

Lu et al, "Functional analysis and regulation of the divergent spuABCDEFG-spuI operons for polyamine uptake and utilization in Pseudomonas aeruginosa PA01," *J. Bacteriol.*, 184:3765-3773.

Lu et al., "Enhanced production of poly(3-hydroxybutyrate-co-3-hydroxyhexanoate) via manipulating the fatty acid beta-oxidation pathway in *E. coli*," *FEMS Microbiol. Lett.*, 221(1):97-101 (2003).

Lu et al., "Molecular cloning of polyhydroxyalkanoate synthesis operon from Aeromonas hydrophilia and its expression in *Escherichia coli*," *Biotechnol. Prog.*, 20(5):1332-1336 (2004).

Lutke-Eversloh et al., "Biochemical and molecular characterization of a succinate semialdehyde dehydrogenase involved in the catabolism of 4-hydroxybutyric acid in Ralstonia eutropha," *FEMS Microbiol. Lett.*, 181:63-71 (1999).

Lutz et al., "Independent and tight regulation of transcriptional units in *Escherichia coli* via the LacR/O, the TetR/O and AraC/I1-I2 regulatory elements," *Nucleic Acids Res.*, 25:1203-1210 (1997).

Lutz et al., "Creating multiple-crossover DNA libraries independent of sequence identity," *Proc. Natl. Acad. Sci. U.S.A.*, 98(20):11248-11253 (2001).

Lutz et al., "Rapid generation of incremental truncation libraries for protein engineering using aphosphothioate nucleotides," *Nucleic Acids Res.*, 15:29(4):e16 (2001).

Ma et al., "Induced Rebuilding of Aspartase Confromation," *Ann. N. Y. Acad. Sci.*, 672:60-65 (1992).

Mac et al., "Location of the two genes encoding glutaconate coenzyme A-transferase at the beginning of the hydroxyglutarate operon in Acidaminococcus fermentans," *Eur.J.Biochem.*, 226:41-51 (1994).

Mack et al., "Conversion of glutaconate CoA-transferase from Acidaminococcus fermentans into an acyl-CoA hydrolase by site-directed mutagenesis," *FEBS Lett.*, 405:209-212 (1997).

Mahadevan et al., "The effects of alternate optimal solutions in constraint-based genome-scale metabolic models," *Metab. Eng.*, 5(4):264-276 (2003).

Mahadevan et al., "Applications of metabolic modeling to drive bioprocess development for the production of value-added chemicals," *Biotechnol. Bioprocess Eng.*, 10(5):408-417 (2005).

Mahan et al., "Genetic analysis of the proBA genes of *Salmonella typhimurium*: physical and genetic analyses of the cloned proB+ A+ genes of *Escherichia coli* and of a mutant allele that confers proline overproduction and enhanced osmotolerance," *J. Bacteriol.*, 156(3):1249-1262.

Majewski et al., "Simple Constrained-Optimization View of Acete Overflow in *E. coli*," *Biotechnol. Bioeng.*, 35(7):732-738 (1990).

Majumdar et al., "Functional consequences of substitution in the active site (phosphor) histidine residue of *Escherichia coli* succinyl-CoA synthetase," *Biochim. Biophys. Acta.*, 1076:86-90 (1991).

Mandal et al., "Isolation of a glutamate synthase (GOGAT)-negative, pleiotropically N utilization-defective mutant of Azospirillum brasilense: cloning and partial characterization of GOGAT structural gene," *J. Bacteriol.*, 175:8024-8029 (1993).

Manning et al., "Tracer studies of the interconversion of R- and S-methylmalonic semialdehydes in man," *Biochem. J.*, 231:481-484 (1985).

Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.*, 334:459-476 (2003).

Marek et al., "Cloning and expression of the *Escherichia coli* K-12 sad gene," *J. Bacteriol.*, 170(2):991-994 (1988).

Marks et al., "Molecular Cloning and Characterization of (R)-3-Hydroxybutyrate Dehydrogenase from Human Heart," *J. Biol. Chem.*, 267:15459-15463 (1992).

Martin et al., "Engineering a mevalonate pathway in *Escherichia coli* for production of terpenoids," *Nat. Biotechnol.*, 21:796-802 (2003).

Martinez-Blanco et al., "Purification and Biochemical Characterization of Phenylacetyl-CoA Ligase from Pseudomonas putida," *J. Biol. Chem.*, 265(12):7084-7090 (1990).

Mat-Jan et al., "Anaerobic growth defects resulting from gene fusions affecting succinyl-CoA synthetase in *Escherichia coli* K12," *Mol. Gen. Genet.*, 215:276-280 (1989).

Mattevi, "Atomic structure of the cubic core of the pyruvate dehydrogenase multienzyme complex," *Science*, 255:1544-1550 (1992).

Matthies et al., "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.*, 58(5):1435-1439 (1992).

Mavrovouniotis, "Estimation of standard Gibbs energy changes of biotransformations," *J. Biol. Chem.*, 266:14440-14445 (1991).

McKinlay et al., "Prospects for a bio-based succinate industry," *Appl. Microbiol. Biotechnol.*, 76(4):727-740 (2007).

McLaggan et al., "Interdependence of K+ and glutamate accumulation during osmotic adaptation of *Escherichia coli*," *J. Biol. Chem.*, 269:1911-1917 (1994).

McPherson et al., "Complete nucleotide sequence of the *Escherichia coli* gdhA gene," *Nucleic Acids Res.*, 11(15):5257-5266 (1983).

(56) References Cited

OTHER PUBLICATIONS

Melchiorsen et al., "The level of pyruvate-formate lyase controls the shift from homolactic to mixed-acid product formation in Lactoccus lactis," *Appl. Microbiol. Biotechnol.*, 58(3):338-344 (2002).
Meng et al., "Site-Directed Mutagenesis and functional Analysis of the Active-Site Residues of the E2 Component of Bovine Branched-Chain α-Keto Acid Dehydrogenase Complex," *Biochemistry*, 33:12879-12885 (1994).
Menzel et al., "Enzymatic evidence for an involvement of pyruvate dehydrogenase in the anaerobic glycerol metabolism of Klebsiella pneumoniae," *J. Biotechnol.*, 56:135-142 (1997).
Menzel et al., "Kinetic, dynamic, and pathway studies of glycerol metabolism by Klebsiella pneumoniae in anaerobic continuous culsutre: IV. Enzynmes and fluxes of pyruvate metabolism," *Biotechnol. Bioeng.*, 60(5):617-626 (1998).
Mermelstein et al., "Metabolic Engineering of Clostridium acetobutylicum ATCC 824 for Increased Solvent Production by Enhancement of Acetone Formation Enzyme Activities Using a Synthetic Acetone Operon," *Biotechnol. Bioeng.*, 42(9):1053-1060 (1993).
Metz et al., "Purification of a jojoba embryo fatty acyl-coenzyme A reductase and expression of its cDNA in high erucic acid rapeseed," *Plant Physiol.*, 122(3):635-644 (2000).
Metzer et al., "In vivo cloning and characterization of the gabCTDP gene cluster of *Escherichia coli* K-12," *J. Bacteriol.*, 172:3250-3256 (1990).
Metzer et al., "Isolation and properties of *Escherichia coli* K-12 mutants impaired in the utilization of gamma-aminobutyrate," *J. Bacteriol.*, 137(3):1111-1118 (1979).
Miles et al., "Molecular genetic aspects of the citric acid cycle of *Escherichia coli*," *Biochem. Soc. Symp.*, 54:45-65 (1987).
Miller et al., "Cloning and characterization of gdhA, the structural gene for glutamate dehydrogenase of *Salmonella typhimurium*," *J. Bacteriol.*, 157:171-178 (1984).
Misono et al., "Occurrence of L-Lysine E-Dehydrogenase in Agrobacterium tumefaciens," *J. Bacteriol.*, 150(1):398-401 (1982).
Miyamoto et al., "Possible physiological roles of aspartase, NAD- and NADP-requiring glutamate dehydrogenases of Pseudomonas fluorescens," *J. Biochem.*, 112:52-56 (1992).
Miyazaki et al., "α-Aminoadipate aminotransferase from an extremely thermophilic bacterium, Thermus thermophilus," *Microbiology*, 150:2327-2334 (2004).
Mizobata et al., "Purification and Characterization of a thermostable Class II Fumarase from Thermus thermophilus," *Arch. Biochem. Biophys.*, 355:49-55 (1998).
Momany et al., "Crystallographic Structures of a PLP-Dependent Ornithine Decarboxylase from Lactobacillus 30a to 3.0 Å Resolution," *J. Mol. Biol.*, 242:643-655 (1995).
Monnet et al., "Regulation of branched-chain amino acid biosynthesis by alpha-acetolactate decarboxylase in *Streptococcus thermophilus*," *Lett.Appl.Microbiol.*, 36:399-405 (2003).
Moore et al., "Expression and Purification of Aspartate β-Semialdehyde Dehydrogenase from Infectious Microorganisms," *Protein Expr. Purif.*, 25:189-194 (2002).
Morris et al., "Nucleotide sequence of the LYS2 gene of *Saccharomyces cerevisiae*: homology to Bacillus brevis tyrocidine synthetase1," *Gene*, 98:141-145 (1991).
Mountain et al., "The Klebsiella aerogenes glutamate dehydrogenase (gdnA) gene: cloning, high-level expression and hybrid enzyme formation in *Escherichia coli*," *Mol. Gen. Genet.*, 199:141-145 (1985).
Muh et al., "4-Hydroxybutyryl-CoA dehydratase from Clostridium aminobutyricum: characterization of FAD and iron-sulfur clusters involved in an overall non-redox reaction," *Biochemistry*, 35:11710-11718 (1996).
Muh et al., "Mossbauer study of 4-hydroxyburyl-CoA dehydratase—probing the role of an iron-sulfur cluster in an overall non-redox reaction," *Eur. J. Biochem.*, 248:380-384 (1997).
Muller et al., "Nucleotide exchange and excision technology (NExT) DNA shuffling: a robust method for DNA fragmentation and directed evolution," *Nucleic Acids Res.*, 33(13):e117 (2005).
Mullins et al., "A specialized citric acid cycle requiring succinyl-coenzyme A (CoA):acetate CoA-transferase (AarC) confers acetic acid resistance on the acidophile Acetobacter aceti," *J. Bacteriol.*, 190:4933-4940 (2008).
Muratsubaki et al., "One of the fumarate reductase isoenzymes from *Saccharomyces cerevisiae* is encoded by the OSM1 gene," *Arch. Biochem. Biophys.*, 352(2):175-181 (1998).
Musfeldt et al., "Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcus jannaschii," *J. Bacteriol.*, 184(3):636-644 (2002).
Nagasu et al., "Nucleotide Sequence of the GDH gene coding for the NADP-specific glutamate dehydrogenase of *Saccharomyces cerevisiae*," *Gene*, 37:247-253 (1985).
Naggert et al., "Cloning, sequencing, and characterization of *Escherichia coli* thioesterase II," *J. Biol Chem.*, 266(17):11044-11050 (1991).
Najmudin et al., "Purification, crystallization and preliminary X-ray crystallographic studies on acetolactate decarboxylase," *Acta. Crystallogr. D. Biol. Crystallog.*, 59:1073-1075 (2003).
Nakahigashi et al., "Nucleotide sequence of the fadA and fadB genes from *Escherichia coli*," *Nucleic Acids Res.*, 18(16):4937 (1990).
Nakano et al., "Characterization of Anaerobic Fermentative Growth of Bacillus subtilis: Identification of Fermentation End Products and Genes Required for Growth," *J. Bacteriol.*, 179(21):6749-6755 (1997).
Namba et al., "Coenzyme A and Nicotinamide Adenine dinucleotide-deptendent Branched Chain α-Keto Acid Dehydrogenase," *J. Biol. Chem.*, 244:4437-4447 (1969).
Ness et al., "Synthetic shuffling expands functional protein diversity by allowing amino acids to recombine independently," *Nat. Biotechnol.*, 20(12):1251-1255 (2002).
Nexant, "1,4-Butanediol/THF—PERP Program New Report Alert," Nexant ChemSystems PERP Report 02/03-7, p. 1-5 (Jan. 2004).
Niegemann et al., "Molecular organization of the *Escherichia coli* gab cluster: nucleotide sequence of the structural genes gabD and gabP and expression of the GABA permease gene," *Arch. Microbiol.*, 160:454-460 (1993).
Nishizawa et al., "Gene expression and characterization of two 2-oxoacid:ferredoxin oxidoreductases from *Aeropyrum pernix* K1," *FEBS. Lett.*, 579:2319-2322 (2005).
Niu et al., "Benzene-free synthesis of adipic acid," *Biotechnol. Prog.*, 18:201-211 (2002).
Noguchi et al., "The energetic conversion competence of *Escherichia coli* during aerobic respiration studied by 31P NMR using a circulating fermentation system," *J. Biochem.*, 136:509-515 (2004).
Nolling et al., "Genome sequence and comparative analysis of the solvent-producing bacterium Clostridium acetobutylicum," *J. Bacteriol.*, 183(16):4823-4838 (2001).
Nowicki et al., "Recombinant tyrosine aminotransferase from Trypanosoma cruzi: structural characterization and site directed mutagenesis of a broad substrate specificity enzyme," *Biochim. Biophys. Acta*, 1546(2):268-281 (2001).
Ohgami et al., "Expression of acetoacetyl-CoA synthetase, a novel cytosolic ketone utilizing enzyme, in human brain," *Biochem. Pharmacol.*, 65:989-994 (2003).
Ohsugi et al., "Metabolism of L-β-Lysine by a Pseudomonas, Purification and Properties of a Deacetylase-Thiolesterase utilizing 4-Acetamidobutyrl CoA and Related Compounds," *J. Biol. Chem.*, 256:7642-7651 (1981).
Okino et al., "An efficient succinic acid production process in a metabolically engineered Corynebacterium glutamicum strain," *Appl. Microbiol. Biotechnol.*, 81(3):459-464 (2008).
Oku et al., "Biosynthesis of Branched-chain Fatty Acids in Bacillis subtilis," *J. Biol. Chem.*, 263:18386-18396 (1988).
Okuno et al., "2-Aminoadipate-2-oxoglutarate aminotransferase isoenzymes in human liver: a plausible physiological role in lysine and tryptophan metabolism," *Enzyme Protein*, 47(3):136-148 (1993).

(56) References Cited

OTHER PUBLICATIONS

Oliver et al., "Determination of the nucleotide sequence for the glutamate synthase structural genes of *Escherichia coli* K-12," *Gene*, 60:1-11 (1987).
Olivera et al., "Molecular characterization of the phenylacetic acid catabolic pathway in Pseudomonas putida U: the phenylacetyl-CoA catabolon," *Proc. Natl. Acad. Sci. U.S.A.*, 95:6419-6424 (1998).
Onuffer et al., "Redesign of the substrate specificity of *Escherichia coli* aspartate aminotransferase to that of *Escherichia coli* tyrosine aminotransferase by homology modeling and site-directed mutagenesis," *Protein Sci.*, 4:1750-1757 (1995).
O'Reilly et al., "Sequence and analysis of the citrulline biosynthetic operon argC-F from Bacillus subtilis," *Microbiology*, 140:1023-1025 (1994).
Orencio-Trejo et al., "Metabolic regluation analysis of an ethanologenic *Escherichia coli* strain based on RT-PCR and enzymatic activities," *Biotechnol. Biofuels*, 1:8 (2008).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. U.S.A.*, 96(7):3562-3567 (1999).
O'Sullivan, et al., "Purification and characterisation of acetolactate decarboxylase from Leuconostoc lactis NCW1," *FEMS Microbiol. Lett.*, 194(2):245-249 (2001).
Otten et al., "Directed evolution: selecting today's biocatalysts," *Biomol. Eng.*, (22):1-9 (2005).
Palosaari et al., "Purification and properties of the inducible coenzyme A-linked butyraldehyde dehydrogenase from Clostridium acetobutylicum," *J. Bacteriol.*, 170(7):2971-2976 (1988).
Park et al., "Biosynthesis of poly(3-hydroxybutyrate- co-3-hydroxyalkanoates) by metabolically engineered *Escherichia coli* strains," *Appl. Biochem. Biotechnol.*, 113-116:335-346 (2004).
Park et al., "Identification and Characterization of a New Enoyl coenzyme A Hydratase involved in biosynthesis of Medium-Chain-Length Polyhydroxyalkanoates in recombinant *Escherichia coli*," *J. Bacteriol.*, 185(18):5391-5397 (2003).
Park et al., "New FadB homologous enzymes and their use in enhanced biosynthesis of medium-chain-length polyhydroxyalkanoates in FadB mutant *Escherichia coli*," *Biotechnol. Bioeng.*, 86:681-686 (2004).
Park et al., "Regulation of succinate dehydrogenase (sdhCDAB) operon expression ion *Escherichia coli* in response to carbon supply and anaerobiosis: role of ArcA and Fnr," *Mol. Microbiol.*, 15:473-482 (1995).
Park et al., "Aerobic regulation of the sucABCD genes of *Escherichia coli*, which encode alpha-ketoglutarate dehydrogenase and succinyl coenzyme A synthetase: roles of ArcA, Fnr, and the upstream sdhCDAB promoter," *J. Bacteriol.*, 179:4138-4142 (1997).
Park et al., "Isolation and characterization of recombinant mitochondrial 4-aminobutyrate aminotransferase," *J. Biol. Chem.*, 268:7636-7639 (1993).
Parker et al., "Characterization of the Zymomonas mobilis glucose facilitator gene product (glf) in recombinant *Escherichia coli*: examination of transport mechanism, kinetics and the role of glucokinase in glucose transport," *Mol Microbiol.*, 15(5):795-802 (1995).
Parsot et al., "Nucleotide sequence of *Escherichia coli* argB and argC genes: comparison of N-acetylglutamate kinase and N-acetylglutamate-gamma-semialdehyde dehydrogenase with homologous and analogous enzymes," *Gene*, 68(2): 275-283 (1988).
Pauwels et al., "The N-acetylglutamate synthase? N-acetylglutamate kinase metabolon of *Saccharomyces cerevisiae* allows cor-ordinated feedback regulation of the first two steps in arginine biosynthesis," *Eur. J. Biochem.*, 270:1014-1024 (2003).
Paxton et al., "Role of branched-chain 2-oxo acid dehydrogenase and pyruvate dehydrogenase in 2-oxobutyrate metabolism," *Biochem. J.*, 234:295-303 (1986).

Pelanda et al., "Glutamate synthase genes of the diazotroph Azospirillum brasillense. Cloning, sequencing, and analysis of functional domains," *J. Biol. Chem.*, 268:3099-3106 (1993).
Peoples et al., "Fine structural analysis of the Zoogloea ramigera phhA-phhB locus encoding beta-ketothiolase and acetoacetyl-CoA reductase: nucleotide sequence of phbB," *Mol. Microbiol.*, 3:349-357 (1989).
Pereira et al., "Active site mutants of *Escherichia coli* citrate synthase. Effects of mutations on catalytic and allosteric properties," *J. Biol. Chem.*, 269:412-417 (1994).
Peretz et al., "Amino Acid Sequence of Alcohol Dehydrogenase from the Thermophilic Bacterium Thermoanaerobium brockii," *Biochemistry*, 28:6549-6555 (1989).
Peretz et al., "Molecular cloning, nucleotide sequencing, and expression of genes encoding alcohol dehydrogenases from the thermophile Thermoanaerobacter brockii and the mesophile Clostridium beijerinckii," *Anaerobe*, 3:259-270 (1997).
Perez et al., "*Escherichia coli* YqhD exhibits aldehyde reductase activity and protects from the harmful effect of lipid peroxidation-derived aldehydes," *J. Biol. Chem.*, 283(12):7346-7353 (2008).
Perez-Prior et al., "Reactivity of lactones and Ghb formation," *J. Org. Chem.*, 70(2):420-426 (2005).
Petitdemange et al., "Regulation of the NADH and NADPH-ferredoxin oxidoreductases in clostridia of the butyric group," *Biochim. Biophys. Acta.*, 421(2):334-337 (1976).
Phalip et al., "Purification and properties of the alpha-acetolactate decarboxylase from *Lactococcus lactis* subsp. Lactis NCDO 2118," *FEBS Lett.*, 351:95-99 (1994).
Pharkya et al., "Exploring the overproduction of amino acids using the bilevel optimization framework OptKnock," *Biotechnol. Bioeng.*, 84(7):887-899 (2003).
Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.*, 174:177-182 (1988).
Pohl et al., "Remarkably broad substrate tolerance of malonyl-CoA synthetase, an enzyme capable of intracellular synthesis of polyketide precursors," *J. Am. Chem Soc.*, 123(24): 5822-5823 (2001).
Pohlmann et al., "Genome sequence of the bioplastic-producing "Knallgas" bacterium Ralstonia eutropha H16," *Nat. Biotechnol.*, 24(10):1257-1262 (2006).
Poirier et al., "Polyhydroxybutyrate, a Biodegradable Thermoplastic Produced in Transgenic Plants," *Science*, 256:520-523 (1992).
Polovnikova et al., "Structural and Kinetic Analysis of Catalysis by a thiamin diphosphate-Dependent Enzyme, Benzoylformate Decarboxylase," *Biochemistry*, 42:1820-1830 (2003).
Poston, "Assay of leucine 2,3-aminomutase," *Methods Enzymol.*, 166:130-135 (1988).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.*, 175:377-385 (1993).
Presecan et al., "The Bacillus subtillis genome from gerBC (311 degrees) to licR (334 degrees)," *Microbiology*, 143:3313-3328 (1997).
Price et al., "Genome-scale models of microbial cells: evaluating the consequences of constraints," *Nat. Rev. Microbiol.*, 2(11):886-897 (2004).
Pritchard et al., "A general model of error-prone PCR," *J. Theor. Biol.*, 234:497-509 (2005).
Purnell et al., "Modulation of higher-plant NAD(H)-dependent glutamate dehydrogenase activity in transgenic tobacco via alteration of beta subunit levels," *Planta*, 222:167-180 (2005).
Qi et al., "Functional expression of prokaryotic and eukaryotic genes in *Escherichia coli* for conversion of glucose to p-hydroxystyrene," *Metab. Eng.*, 9:268-276 (2007).
Qian et al., "Metabolic engineering of *Escherichia coli* for the production of putrescine: a four carbon diamine," *Biotechnol. Bioeng.*, 104(4)651-662 (2009).
Qiu et al., "Metabolic engineering for the production of copolyesters consisting of 3-hydroxybutyrate and 3-hydroxyhexanoate by Aeromonas hydrophilia," *Macromol. Biosci.*, 4(3):255-261 (2004).

(56) References Cited

OTHER PUBLICATIONS

Radhakrishnan et al., "Applications of metabolic modeling to drive bioprocess development for the production of value-aded chemicals," *Biotechnol. Bioprocess. Eng.*, 10:408-417 (2005).
Rajpal et al., "A general method for greatly improving the affinity of antibodies by using combinatorial libraries," *Proc. Natl. Acad. Sci. U.S.A.*, 102(24):8466-8471 (2005).
Ramon-Maiques et al., "Structure of Acetylglutamate Kinase, a Key Enzyme for Arginine Biosynthesis and a Prototype for the Amino Acid Kinase Enzyme Family, during Catalysis," *Structure*, 10:329-342 (2002).
Ramos et al., "Mutations affecting the enzymes involved in the utilization of 4-aminobutyric. acid as nitrogen source by the yeast *Saccharomyces cerevisiae*," *Eur. J. Biochem.*, 149:401-404 (1985).
Rathinasabapathi, "Propionate, a source of β-alanine, is an inhibitor of β-alanine methylation in Limonium latifolium, Plumbaginaceae," *J. Plant Physiol.*, 159:671-674 (2002).
Read et al., "Annotation of the Yersinia Intermedia ATCC 29909 Genome," retrieved from: UniProt Database Accession No. C4SW2 http://www.uniprot.org/uniprot/C4SZW2 (Dec. 2008).
Recasens et al., "Cysteine Sulfinate Aminotransferase and Aspartate Aminotransferase Isoenzymes of Rat Brain. Purification, Characterization, and Further Evidence for Identity," *Biochemistry*, 19:4583-4589 (1980).
Redenbach et al., "A set of ordered cosmids and a detailed genetic and physical map for the 8 Mb *Streptomyces coelicolor* A3(2) chromosome," *Mol. Microbiol.*, 21:77-96 (1996).
Reed et al., "An expanded genome-scale model of *Escherichia coli* K-12 (iJR904 GSM/GPR)," *Genome. Biol.*, 4(9):R54 (2003).
Reetz et al., "Iterative saturation mutagenesis (ISM) for rapid directed evolution of functional enzymes," *Nat. Protoc.*, 2(4):891-903 (2007).
Reetz et al., "Creation of Enantioselective biocatalysts for Organic Chemistry by In Vitro Evolution," *Agnew. Chem. Int. Ed. Engl.*, 36:2830-2832 (1997).
Reetz et al., "Directed Evolution of an Enantioselective Enzyme through Combinatorial Multiple-Cassette Mutagenesis," *Agnew. Chem. Int. Ed. Engl.*, 40:3589-3591 (2001).
Reetz et al., "Expanding the Range of Substrate Acceptance of Enzymes: Combinatorial Active-site saturation test," *Agnew. Chem.*, 117:4264-4268 (2005).
Reetz et al., "Iterative Saturation Mutagenesis on the Basis of B Factors as a Strategy for Increasing Protein Thermostability," *Agnew. Chem. Int. Ed. Engl.*, 45:7745-7751 (2006).
Reetz et al., "Expanding the range of substrate acceptance of enzymes: combinatorial active-site saturation test," *Agnew. Chem. Int. Ed Engl.*, 44:4192-4196 (2005).
Reidhaar-Olson et al., "Combinatorial cassette mutagenesis as a probe of the informational content of protein sequences," *Science*, 241(4861):53-57 (1988).
Reidhaar-Olson et al., "Random mutagenesis of protein sequences using oligonucleotide cassettes," *Methods Enzymol.*, 208:564-586 (1991).
Reiser et al., "Isolation of mutants of Acinetobacter calcoaceticus deficient in wax ester synthesis and complementation of one mutation with a gene encoding a fatty acyl coenzyme A reductase," *J. Bacteriol.*, 179(9):2969-2975 (1997).
Reitzer, "Ammonia Assimillation and the Biosynthesis of Glutamine, Glutamate, Aspartate, Asparagine, 1-Alanine, and d-Alanine," In Neidhardt (Ed.), *Escherichia coli and Salmonella: Cellular and Molecular Biology*, ASM Press: Washington, DC, p. 391-407 (1996).
Repetto et al., "Structure and Regulation of KGD1, the Structural Gene for Yeast α-Ketoglutarate Dehydrogenase," *Mol. Cell.* 9:2695-2705 (1989).
Resnekov et al., "Organization and regulation of the Bacillus subtilis odhAB operon, which encodes two of the subenzymes of the 2-oxoglutarate dehydrogenase complex," *Mol. Gen. Genet.*, 234(2):285-296 (1992).
Ribeiro et al., "Microbial reduction of α-acetyl-γ-butyrolactone," *Tetrahedron: Asymmetry*, 17(6):984-988 (2006).

Rigden et al., "A cofactor-dependent phosphoglycerate mutase homolog from Bacillus stearothermophilus is actually a broad specificity phosphatase," *Protein Sci.*, 10:1835-1846 (2001).
Riondet et al., "Measurement of the intracellular pH in *Escherichia coli* with the internally conjugated fluorescent probe 5- (and 6) carboxyfluorescein succinimidyl ester," *Biotechnol. Tech.*, 11:735-738 (1997).
Riviere et al., "Acetyl:Succinate CoA-transferase in Procyclic Trypanosoma brucei," *J. Biol Chem.*, 279(44):45337-45346 (2004).
Robinson et al., "Studies on Rat Brain Acyl-Coenzyme a Hydrolase (Short Chain)," *Biochem. Biophys. Res. Commun.*, 71:959-965 (1976).
Roca et al., "Metabolic engineering of ammonium assimilation in xylose-fermenting *Saccharmyces cerevisiae* improves ethanol production," *Appl. Environ. Microbiol.*, 69(8):4732-4736 (2003).
Rodriguez et al., "Characterization of the p-coumaric acid decarboxylase from Lactobacillus plantarum CECT 748(T)," *J. Agric. Food Chem.*, 56(9):3068-3072 (2008).
Rohdich et al., "Enoate reductases of Clostridia. Cloning, sequencing, and expression," *J. Biol. Chem.*, 276(8):5779-5787 (2001).
Romero et al., "Partial purification, characterization and nitrogen regulation of the lysine epsilon-aminotransferase of *Streptomyces clavuligerus*," *J. Ind. Microbiol. Biotechnol.*, 18(4):241-246 (1997).
Rose et al., "The role of the allosteric B site in the fumarase reaction," *Proc. Natl. Acad. Sci. U.S.A.*, 101:3393-3397 (2004).
Rose et al., "Enzymatic phosphorylation of acetate," *J. Biol. Chem.*, 211(2):737-756 (1954).
Roy et al., "Cloning and Characterization of the Gene Encoding Lipamide Dehydrogenase in *Saccharomyces cerevisiae*," *J. Gen. Microbiol.*, 133:925-933 (1987).
Ruldeekulthamrong et al., "Molecular characterization of lysine 6-dehydrogenase from Achromobacter denitrificans," *BMB Rep.*, 41:790-795 (2008).
Sabo et al., "Purification and Physical Properties of Inducible *Escherichia coli* Lysine Decarboxylase," *Biochemistry*, 13(4):662-670 (1974).
Saini et al., "Coutilizing microbes: A comprehensive review," *Biotechnology Advances*, 29(6):949-960 (2011).
Saito et al., "Microbial synthesis and properties of poly(3-hydroxybutyrate-co-4-hydroxybutyrate) in Comamonas acidovorans," *Int. J. Biol. Macromol.*, 16:99-104 (1994).
Saito et al., "Microbial Synthesis and properties of Poly(3-hydroxybutyrate-co-4-hydroxybutyrate)," *Polym. Int.*, 39:169-174 (1996).
Sakakibara et al., "Isolation and characterization of a cDNA that encodes maize glutamate dehydrogenase," *Plant Cell Physiol.*, 36:789-797 (1995).
Salmon et al., "Global gene expression profiling in *Escherichia coli* K12: effects of oxygen availability and ArcA," *J. Biol. Chem.*, 280(15):15084-15096 (2005).
Samsonova et al., "Molecular cloning and characterization of *Escherichia coli* K12 ygjG gene," *BMC Microbiol.*, 3:2 (2003).
Sanchez et al., "Properties and functions of two succinic-semialdehyde dehydrogenases from Pseudomonas putida," *Biochim. Biophys. Acta.*, 953(3):249-257 (1988).
Sanchez et al., "Purification and properties of two succinic semialdehyde dehydrogenases from Klebsiella pneumoniae," *Biochim. Biophys. Acta.*, 990(3):225-231 (1989).
Sariaslani, "Development of a combined biological and chemical process for production of industrial aromatics from renewable resources," *Annu.Rev.Microbiol.*, 61:51-69 (2007).
Sarovich et al., "pPSX: a novel vector for the cloning and heterologous expression of antitumor antibiotic gene clusters," *Plasmid*, 57:306-313 (2007).
Sato et al., "Poly[(R)-3-Hydroxybutyrate] Formation in *Escherichia coli* from Glucose through an Enoyl-CoA Hydratase-Mediated Pathway," *J. Biosci. Bioeng.*, 103(1):38-44 (2007).
Scherf et al., "Purification and properties of 4-hydroxybutyrate coenzyme A transferase from Clostridium aminobutyricum," *Appl. Environ. Microbiol.*, 57(9):2699-2702 (1991).

(56) References Cited

OTHER PUBLICATIONS

Scherf et al., "Purification and properties of an iron-sulfur and FAD-containing 4hydroxybuturyl-CoA dehydratase/vinylacetyl-CoA Δ3-Δ2-isomerase from Clostridium aminobutyricum," *Eur. J. Biochem.*, 215:421-429 (1993).
Scherf et al., "Suffinate-ethanol fermentation in Clostridium kluyveri: purification and characterisation of 4-hydroxybutyryl-CoA dehydratase/vinylacetyl-CoA delta 3-delta 2-isomerase," *Arch. Microbiol.*, 161:239-245 (1994).
Schilling et al., "Combining Pathway Analysis with Flux Balance Analysis for the Comprehensive Study of Metabolic Systems," *Biotechnol. Bioeng.*, 71(4):286-306 (2000-2001).
Schilling et al., "Theory for the Systematic Definition of Metabolic Pathways and Their Use in Interpreting Metabolic Function from a Pathway-Oriented Perspective," *J. Theor. Biol.*, 203(3):229-248 (2000).
Schilling et al., "Toward Metabolic Phenomics: Analysis of Genomic Data Using Flux Balances," *Biotechnol. Prog.*, 15(3):288-295 (1999).
Schneider et al., "The *Escherichia coli* gabDTPC operon: specific γ-aminobutyrate catabolism and nonspecific induction," *J. Bacteriol.*, 184:6976-6986 (2002).
Schulz et al., "Stereopsecific Production of the Herbicide Phosphinothricin (Glufosinate) by Transamination: Isolation and Characterization of a Phosphinothricin-Specific Transaminase from *Escherichia coli*," *Appl. Environ. Microbiol.*, 56:1-6 (1990).
Scott et al., "Soluble γ-Aminobutyric-Glutamic Transaminase from Pseudomonas fluorescens," *J. Biol. Chem.*, 234:932-936 (1959).
Seedorf et al., "The genome of Clostridium kluyveri, a strict anaerobe with unique metabolic features," *Proc. Natl. Acad. Sci. U.S.A.*, 105(6):2128-2133 (2008).
Seffernick et al., "Melamine deaminase and atrazine chlorohydrolase: 98 percent identical but functionally different," *J. Bacteriol.*, 183(3):2405-2410 (2001).
Selifonova et al., "Rapid evolution of novel traits in microorganisms," *Appl. Environ. Microbiol.*, 67(8):3645-3649 (2001).
Sen et al., "Developments in directed evolution for improving enzyme functions," *Appl. Biochem. Biotechnol.*, 143(3):212-223 (2007).
Shafiani et al., "Cloning and characterization of aspartate-β-semialdehyde dehydrogenase from *Mycobacterium tuberculosis* H37 Rv," *J. Appl. Microbiol.*, 98:832-838 (2005).
Shalel-Levanon et al., "Effect of ArcA and FNR on the expression of genes related to the oxygen regulation and the glycolysis pathway in *Eschericiha coli* under microaerobic growth conditions," *Biotechnol. Bioeng.*, 92(2):147-159 (2005).
Shames et al., "Interaction of aspartate and aspartate-derived antimetabolites with the enzymes of the threonine biosynthetic pathway of *Escherichia ecoli*," *J. Biol. Chem.*, 259(24):15331-15339 (1984).
Shao et al., "Random-priming in vitro recombination: an effective tool for directed evolution," *Nucleic Acids Res.*, 26(2):681-683 (1998).
Shi et al., "The structure of L-aspartate ammonia-lyase from *Escherichia coli*," *Biochem.*, 36(30):9136-9144 (1997).
Shigeoka et al., "Characterization and molecular properties of 2-oxoglutarate decarboxylase from Euglena gracilis," *Arch. Biochem. Biophys.*, 288:22-28 (1991).
Shigeoka et al., "The effect of thiamin on the activation of thiamin pyrophosphate-dependent 2-oxoglutarate decarboxylase in Euglena gracilis," *Biochem. J.*, 292 (Pt 2):463-467 (1993).
Shigeoka et al., "Effect of L-glutamate on 2-oxoglutarate decarboxylase in Euglena gracilis," *Biochem. J.*, 282 (Pt 2):319-323 (1992).
Shimomura et al., "3-Hydroxyisobu 1-CoA Hydrolase," *Meth. Enzymol.*, 324:229-240 (2000).
Shimomura et al., "Purification and Partial Characterization of 3-Hydroxyisobutyryl-coenzyme A Hydrolase of Rat Liver," *J. Biol. Chem.*, 269:14248-14253 (1994).

Shingler et al., "Nucleotide Sequence and Functional Analysis of the Complete Phenol/3,4-Dimethylphenol Catabolic Pathway of *Pseudomonas* sp. Strain CF600," *J. Bacteriol.*, 174(3):711-724 (1992).
Shiraki et al., "Fermentative production of (R)-(-)-(3) hydroxybutyrate using 3-hydroxybutyrate dehydrogenase null mutant of Ralstonia eutropha and recombinant *Escherichia coli*," *J. Biosci. Bioeng.*, 102(6):529-534 (2006).
Shukla et al., "Production of D(-)-lactate from sucrose and molasses," *Biotechnol. Lett.*, 26(9):689-693 (2004).
Sieber et al., "Libraries of hybrid proteins from distantly related sequences," *Nat. Biotechnol.*, 19(5):456-460 (2001).
Siegert et al., "Exchanging the substrate specificities of pyruvate decarboxylase from Zymomonas mobilis and benzoylase from *Pseudomonas putida*," *Protein Eng. Des. Sel.*, 18:345-357 (2005).
Simonov et al., "Application of Gas Chromatography and Gas Chromatography-Mass Spectrometry to the Detection of γ-Hydroxybutyric Acid and Its Precursors in Various Materials," *J. Anal. Chem.*, 59:965-971 (2004).
Sinclair et al, "Purification and characterization of the branched chain α-ketoacid dehydrogenase complex from *Saccharomyces cerevisiae*," *Biochem. Mol. Biol. Int.*, 31(5):911-922 (1993).
Sivaraman et al., "Codon choice in genes depends on flanking sequence information—implications for theoretical reverse translation," *Nucleic Acids Res.*, 36(3):e16 (2008).
Sjostrom et al., "Purfication and characterisation of a plasminogen-binding protein from Haemophilus influenzae. Sequence determination reveals identity with aspartase," *Biochim. Biophys. Acta.*, 1324:182-190 (1997).
Skarstedt et al., "*Escherichia coli* Acetate Kinase Mechanism Studied by Net Initial Rate, Equilibriu, and Independent Isotopic Exchange Kinetics," *J. Biol. Chem.*, 251:6775-6783 (1976).
Skinner et al., "An *Escherichia coli* mutant defective in the NAD-dependent succinate semialdehyde dehydrogenase," *Arch. Microbiol.*, 132(3):270-275 (1982).
Smit et al., "Identification, Cloning, and Characterization of a Lactococcus lactis Branched-Chain α-Keto Acid Decarboxylase Involved in Flavor Formation," *Appl. Environ. Microbiol.*, 71:303-311 (2005).
Smith et al., "Fumarate metabolism and the microaerophily of *Campylobacter* species," *Int. J. Biochem. Cell Biol.*, 31:961-975 (1999).
Smith et al., "Purification and characteristics of a gamma-glutamyl kinase involved in *Escherichia coli* proline biosynthesis," *J. Bacteriol.*, 157:545-551 (1984).
Smith et al., "Complete genome sequence of Methanobacterium thermoautotrophicum deltaH: functional analysis and comparative genomics," *J. Bacteriol.*, 179:7135-7155 (1997).
Snedecor et al., "Selection, expression, and nucleotide sequencing of the glutamate dehydrogenase gene of Peptostreptococcus asaccharolyticus," *J. Bacteriol.*, 173:6162-6167 (1991).
Soda et al., "L-Lysine:alpha-ketoglutarate aminotransferase. II. Purification, crystallization, and properties," *Biochemistry*, 7(11):4110-4119 (1968).
Sohling et al., "Molecular analysis of the anaerobic succinate degradation pathway in Clostridium kluyveri.," *J. Bacteriol.*, 178(3):871-880 (1996).
Söhling et al., "Purification and characterization of a Coenzyme-A-dependent succinate-semialdehyde dehydrogenase from Clostridium kluyveri," *Eur. J. Biochem.*, 212:121-127 (1993).
Sokatch et al., "Purification of a Branched-Chain Keto Acid Dehydrogenase from Pseudomonas putida," *J. Bacteriol.*, 647-652 (1981).
Song et al., "Construction of recombinant *Escherichia coli* strains producing poly (4-hydroxybutyric acid) homopolyester from glucose," *Wei Sheng Wu Xue.Bao.*, 45:382-386 (2005). (In Chinese, includes English abstract).
Song et al., "Structure, Function, and Mechanism of the Phenylacetate Pathway Hot Dog-fold Thioesterase Paal," *J. Biol. Chem.*, 281(16):11028-11038 (2006).
Spencer et al., "Transcription analysis of the sucAB, aceEF and lpd genes of *Escherichia coli*," *Mol. Gen. Genetics*, 200:145-154 (1985).

(56) References Cited

OTHER PUBLICATIONS

Spencer et al., "Nucleotide sequence of the sucB gene encoding the dihydrolipoamide succinyltransferase of *Escherichia coli* K12 and homology with the corresponding acetyltransferase," *Eur. J. Biochem.*, 141(2):361-374 (1984).
Stadtman, "The enzymatic synthesis of β-alanyl coenzyme A," *J. Am. Chem. Soc.*, 77:5765-5766 (1955).
Stanley et al., "Expression and stereochemical and isotope effect studies of active 4-oxalocrotonate decarboxylase," *Biochemistry*, 39(12):3514 (2000).
Stanley et al., "Expression and Sterochemical and Isotope Effect Studies of Active 4-Oxalocrotonate Decarboxylase," *Biochemistry*, 39:(4):718-726 (2000).
Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," *Microbiology*, 151(Pt 11):3793-3801 (2005).
Starai et al., "Residue Leu-641 of Acetyl-CoA synthetase is critical for the acetylation of residue Lys-609 by the Protein acetyltransferase enzyme of *Salmonella enterica*," *J. Biol. Chem.*, 280(28):26200-26205 (2005). (Epub May 17, 2005).
Steinbüchel et al., "NAD-linked L(+)-lactate dehydrogenase from the strict aerobe alcaligenes eutrophus. 2. Kinetic properties and inhibition by oxaloacetate," *Eur. J. Biochem.*, 130(2):329-334 (1983).
Steinbuchel et al., "A multifunctional fermentative alcohol dehydrogenase from the strict aerobe Alcaligenes eutrophus: purification and properties," *Eur. J. Biochem.*, 141:555-564 (1984).
Steinbuchel et al., "Physiology and molecular genetics of poly(beta-hydroxy-alkanoic acid) synthesis in Alcaligenes eutrophus," *Mol. Microbiol.*, 5(3):535-542 (1991).
Steinbuchel et al., "Diversity of bacterial polyhydroxyalkanoic acids," *FEMS Microbiol. Lett.*, 128:219-228 (1995).
Steinbuchel et al., "A Pseudomonas strain accumulating polyesters of 3-hydroxybutyric acid and medium-chain-length 3-hydroxyalkanoic acids," *Appl. Microbiol. Biotechnol.*, 37:691-697 (1992).
Stemmer, "DNA Shuffling by random fragmentation and reassembly: in vitro recombination for molecular evolution," *Proc. Natl. Acad. Sci. U.S.A.*, 91(22):10747-10751 (1994).
Stemmer, "Rapid evolution of a protein in vitro by DNA shuffling," *Nature*, 370:389-391 (1994).
Stokell et al., "Probing the roles of key residues in the unique regulatory NADH binding site of type II citrate synthase of *Escherichia coli*," *J. Biol. Chem.*, 278(37):35435-35443 (2003).
Stols et al., "New vectors for co-expression of proteins: Structure of Bacillus subtilis ScoAB obtained by high-throughput protocols," *Protein Expr. Purif.*, 53:396-403 (2007).
Stoyan et al., "Cloning, sequencing and overexpression of the leucine dehydrogenase gene from *Bacillus cereus*," *J. Biotechnol.*, 54:77-80 (1997).
Strauss et al., "Enzymes of a novel autotrophic CO2 fixation pathway in the phototrophic bacterium Chloroflexus aurantiacus, the 3-hydroxypropionate cycle," *Eur. J. Biochem.*, 215:633-643 (1993).
Suda et al., "Purification and properties of alpha-keoadipate reductase, a newly discovered enzyme from human placenta," *Arch. Biochem. Biophys.*, 176(2):610-620 (1976).
Suda et al., "Subcellular Localization and tissue Distribution of α-Ketodaipate Reduction and Oxidation in the Rat," *Biochem. Biophys. Res. Commun.*, 77:586-591 (1977).
Suematsu et al., "Molecular cloning and functional expression of rat liver cytosolic acetyl-CoA hydrolase," *Eur. J. Biochem.*, 268(9):2700-2709 (2001).
Sulzenbacher et al., "Crystal structure of *E.coli* alcohol dehydrogenase YqhD: evidence of a covalently modified NADP coenzyme," *J.Mol. Biol.*, 342(2):489-502 (2004).
Suthers et al., "Metabolic flux elucidation for large-scale models using 13C labeled isotopes," *Metab. Eng.*, 9(5-6):387-405 (2007).

Suzuki et al., "GriC and GriD Constitute a carboxylic acid reductase involved in grixazone biosynthesis in *Streptomyces griseus*," *J. Antibiot.*, 60(6):380-387 (2007).
Suzuki, "Phosphotransacetylase of *Escherichia coli* B, activation by pyruvate and inhibition by NADH and certain nucleotides," *Biochim. Biophys. Acta*, 191(3):559-569 (1969).
Syntichaki et al., "The amino-acid sequence similarity of plant glutamate dehydrogenase to the extremophilic archaeal enzyme conforms to its stress-related function," *Gene.*, 168:87-92 (1996).
Takagi et al., "Isolation of a Versatile Serratia marcescens Mutant as a Host and Molecular Cloning of the Aspartase Gene," *J. Bacteriol.*, 161(1):1-6 (1985).
Takagi et al., "Purification, Crystallization, and Molecular Properties of Aspartase from Pseudomonas fluorescens," *J. Biochem.*, 96:545-552 (1984).
Takahashi et al., "Metabolic Pathways for Cytoxic End Product Formation from Glutamate- and Aspartate-Containing Peptides by Porphyromonas gingivalis," *J. Bacteriol.*, 182(17):4704-4710 (2000).
Takahashi-Abbe et al., "Biochemical and functional properties of a pyruvate formate-lyase (PFL)-activating system in *Streptococcus mutans*," *Oral Microbiol. Immunol.*, 18(5)293-297 (2003).
Takanashi et al., "Characterization of a novel 3-hydroxybutyrate dehydrogenase from Ralstonia pickettii T1," *Antonie van Leeuwnhoek*, 95(3):249-262 (2009).
Takatsuka et al., "Gene cloning and molecular characterization of lysine decarboxylase from Selenomonas ruminantium delineate its evolutionary relationship to ornithine decarboxylases from eukaryotes," *J. Bacteriol.*, 182(23):6732-6741 (2000).
Takatsuka et al., "Identification of the amino acid residues conferring substrate specificity upon selenomonas ruminantium lysine decarboxylase," *Biosci. Biotechnol. Biochem.*, 63(10):1843-1846 (1999).
Takigawa et al., "Probabilistic path ranking based on adjacent pairwise coexpression for metabolic transcripts analysis," *Bioinformatics*, 24(2):250-257 (2008).
Tamaki et al., "Purification, Properties, and Sequencing of Aminisobutyrate Aminotransferases from Rat Liver," *Meth. Enzymol.*, 324:376-389 (2000).
Tanaka et al., "Cloning and characterization of a human orthologue of testis-specific succinyl CoA:3-oxo acid CoA transferase (Scot-t) cDNA," *Mol. Hum. Reprod.*, 8:16-23 (2001.).
Tanaka et al., "Lysine decarboxylase of Vibrio parahaemolyticus: kinetics of transcription and role in acid resistance," *J. Appl. Microbiol.*, 104(5):1283-1293 (2007).
Tang et al., "Identification of a novel pyridoxal 5'-phosphaste binding site in adenosylcobalamin-dependent lysine 5,6-aminomutase from Porphyromonas gingivalis," *Biochemistry*, 41(27):8767-8776 (2002).
Tani et al., "Thermostable NADP(+)-dependent medium-chain alcohol dehydrogenase from *Acinetobacter* sp strain M-1: Purification and characterization and gene expression in *Escherichia coli*," *Appl. Environ. Microbiol.*, 66:5231-5235 (2000).
Teller et al., "The glutamate dehydrogenase gene of Clostridium symbiosum, Cloning by polymerase chain reaction sequence analysis and over-expression in *Escherichia coli*," *Eur. J. Biochem.*, 206:151-159 (1992).
Ter Schure et al., "Pyruvate Decarboxylase Catalyzes Decarboxylation of Branched-Chaing 2-Oxo Acids but Is Not Essential for Fusel Alcohol Production by *Saccharomyces cerevisiae*," *Appl. Environ. Microbiol.*, 64(4):1303-1307 (1998).
Thakur et al., "Changes in the Electroencephalographic and .gamma.-Aminobutyric Acid Transaminsase and Succinic Semialdehyde Dehydrogenase in the Allergen Induced Rat Brain," *Biochem. Int.*, 16:235-243 (1998).
Thauer, "Microbiology. A fifth pathway of carbon fixation," *Science*, 318:1732-1733 (2007).
Tian et al., "Variant tricarboxylic acid cycle in *Mycobacterium tuberculosis*: identification of alpha-ketoglutarate decarboxylase," *Proc Nati Acad Sci U.S.A.*, 102:10670-10675 (2005).
Tobin et al., "Localization of the lysine epsilon-aminotransferase (lat) and delta-(L-alpha-aminoadipyl)-L-cysteinyl-D-Valine synthetase (pcbAB) genes from *Streptomyces clavuligerus* and production of

(56) References Cited

OTHER PUBLICATIONS lysine epsilon-aminotransferase activity in *Escherichia coli*," *J. Bacteriol.*, 173(19):6223-6229 (1991).
Tomb et al., "The complete genome sequence of the gastric pathogen Helicobacter pylori," *Nature*, 388:539-547 (1997).
Toth et al., "The ald gene, encoding a coenzyme A-acylating aldehyde dehydrogenase, distinguishes Clostridium beijerinckii and two other solvent-producing clostridia from Clostridium acetobutylicum," *Appl. Environ. Microbiol.*, 65(11):4973-4980 (1999).
Tretter et al., "Alpha-ketoglutarate dehydrogenase: a target and generator of oxidative stress," *Philos. Trans. R. Soc. Lond B. Biol. Sci.*, 360:2335-2345 (2005).
Tseng et al., "Metabolic engineering of *Escherichia coli* for enhanced production of (R)- and (S)-3-hydroxybutyrate," *Appl. Environ. Microbiol.*, 75(10):3137-3145 (2009).
Tucci et al., "A novel prokaryotic trans-2-enoyl-CoA reductase from the spirochete Treponema denticola," *FEBS Lett.*, 581:1561-1566 (2007).
Twarog et al., "Role of Buyryl Phosphate in the Energy Metabolism of Clostridium Tetanomorphum," *J. Bacteriol.*, 86:112-117 (1963).
Two pages from URL: www.genome.jp/dbget-bin/www_bget?cdf:CD2966 (Printed Dec. 21, 2009).
Two pages from URL: www.genome.jp/dbget-bin/www_bget?cpe:CPE2531 (Printed Dec. 21, 2009).
Two pages from URL: www.genome.jp/dbget-bin/www_bget?ctc:CTC01366 (Printed Dec. 21, 2009).
Two pages from URL: www.genome.jp/dbget-bin/www_bget?cth:Cthe_0423 (Printed Mar. 4, 2010).
Two pages from URL: Openwetware.org/wiki/Synthetic_Biology:BioBricks, Synthetic Biology:BioBricks, portal for information relating to the Resistry of Standard Biological Parts (Printed Dec. 21, 2009).
Tzimagiorgis et al., "Molecular cloning, structure and expression analysis of a full-length mouse brain glutamate dehydrogenase cDNA," *Biochem. Biophys. Acta.*, 1089:250-253 (1991).
Tzimagiorgis et al., "Structure and expression analysis of a member of the human glutamate dehydrogenase (GLUD) gene gamily mapped to chromosome 10p11.2," *Hum. Genet.*, 91:433-438 (1993).
Uchiyama et al., "Identification of the4-Hydroxycinnamate Decarboxylase (PAD) Gene of Klebsiella oxytoca," *Biosci. Biotechnol. Biochem.*, 72:116-123 (2008).
Umeda et al., "Cloning and sequence analysis of the poly(3-hydroxyalkanoic acid)-synthesis genes of Pseudomonas acidophila," *Appl. Biochem. Biotechnol.*, 70-72:341-352 (1998).
Uttaro et al., "Purification and characterisation of a novel isopropanol dehydrogenase from *Phytomonas* sp," *Mol. Biochem. Parasitol.*, 85:213-219 (1997).
Valdes-Hevia et al., "Isolation and characterization of the gene encoding phosphoenolpyruvate carboxykinase from *Saccharomyces cerevisiae*," *FEBS Lett.*, 258(2):313-316 (1989).
Valentin et al., "Indentication of 4-hydroxyhexanoic acid as a new constituent of biosynthetic polyhydroxyalkanoic acids from bacteria," *Appl. Microbiol. Biotechnol.*, 40:710-716 (1994).
Valentin et al., "Identification of 4-hydroxyvaleric acid as a constituent of biosynthetic polyhydroxyalkanoic acids from bacteria," *Appl. Microbiol. Biotechnol.*, 36:507-514 (1992).
Valentin et al., "Identification of 5-hydroxyhexanoic acid, 4-hydroxyaheptanoic acid and 4-hydroxyoctanoic acid as new constituents of bacterial polyhydroxyalkanoic acids," *Appl. Microbiol. Biotechnol.*, 46:261-267 (1996).
Valentin et al., "Metabolic pathway for biosynthesis of poly(3-hydroxybutyrate-co-4-hydroxybutyrate) from 4-hydroxybutyrate by Alcaligenes eutrophus," *Eur. J. Biochem.*, 227(1-2):43-60 (1995).
Valentin et al., "Poly(3-hydroxybutyrate-co-4-hydroxybutyrate) formation from gamma-aminobutyrate and glutamate," *Biotechnol Bioeng.*, 67(3):291-299 (2000).
Valentin et al., "Production of poly(3-hydroxybutyrate-co-4-hydroxybutyrate) in recombinant *Escherichia coli* grown on glucose," *J. Biotechnol.*, 58:33-38 (1997).

Valentine et al., "Purification and role of phosphotransbutyrylase," *J. Biol. Chem.*, 235:1948-1952 (1960).
Valle et al., "Complete nucleotide sequence of the glutamate dehydrogenase gene from *Escherichia coli* K-12," *Gene*, 27:193-199 (1984).
Valle et al., "Nucleotide sequence of the promotor and amino-terminal coding region of the glutamate dehydrogenase structural gene of *Escherichia coli*," *Gene*, 23:199-209 (1983).
Vamecq et al., "The microsomal dicarboxylyl-CoA synthetase," *Biochem. J.*, 230:683-693 (1985).
Van Der Rest et al., "Functions of the membrane-associated and cytoplasmic malate dehydrogenases in the citric acid cycle of *Escherichia coli*," *J. Bacteriol.*, 182(24):6892-6899 (2000).
Van Der Voorhorst et al., "Genetic and biochemcial characterization of a short-chain alcohol dehydrogenase from the hyperthermophilic archaeon Pyrococcus furiosus," *Eur. J. Biochem.*, 268:3062-3068 (2001).
Van Grinsven et al., "Acetate:Succinate CoA-transferase in the Hydrogenosomes of Trichomonas vaginalis," *J. Biol. Chem.*, 283:1411-1418 (2008).
Vanderwinkel et al., "Growth of *Escherichia coli* on Fatty Acids: Requirement for Coenzyme a Transferase Activity," *Biochem. Biophys. Res. Commun.*, 33:902-908 (1968).
Vanrolleghem et al., "Validation of a Metabolic Network for *Saccharomyces cerevisiae* Using Mixed Substrate Studies," *Biotechnol. Prog.*, 12(4):434-448 (1996).
Varma et al., "Metabolic Flux Balancing: Basic Concepts, Scientific and Practical Use," *Biotechnology*, 12:994-998 (1994).
Varma et al., "Stoichiometric flux balance models quantitatively predict growth and metabolic by-product secretion in wild-type *Escherichia coli* W3110," *Appl. Environ. Microbiol.*, 60:3724-3731 (1994).
Vazquez et al., "Phosphotransbutyrylase Expression in Bacillus megaterium," *Curr. Microbiol.*, 42:345-349 (2001).
Venkitasubramanian et al., *Biocatalysis in the Pharmaceutical and Biotechnology Industries*, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol Chem.*, 282:478-485 (2007).
Vernal et al., "Cloning and heterologous expression of a broad specificity aminotransferase of leishmania mexicana promastigotes1," *FEMS Microbiol. Lett.*, 229(2):217-222 (2003).
Vernal et al., "Isolation and partial characterization of a broad specificity aminotransferase from Leishmania mexicana promastigotes," *Mol. Biochem. Parasitol.*, 96(1-2):83-92 (1998).
Vey et al., "Structural basis for glycyl radical formation by pyruvate formate-lyase activating enzyme," *Proc. Natl. Acad. Sci. U.S.A.*, 105(42):16137-16141 (2008).
Viola, "L-aspartase: new tricks from an old enzyme," *Adv. Enzymol. Relat. Areas. Mol. Biol.*, 74:295-341 (2000).
Vita et al., "Disulfide bond-dependent mechanism of protection against oxidative stress in pyruvate-ferredoxin oxidoreductase of anaerobic Desulfovibrio bacteria," *Biochemistry*, 47(3):957-964 (2008).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).
Wakil et al., "Studies on the Fatty Acid Oxidizing System of Animal Tissues," *J. Biol. Chem.*, 207:631-638 (1954).
Walter et al., "Sequence and arrangement of two genes of the butyrate-synthesis pathway of Clostridium acetobutylicum ATCC 824," *Gene*, 134:107-111 (1993).
Walter et al., "Molecular characterization of two Clostridium acetobutylicum ATCC 824 butanol dehydrogenase isozyme genes," *J. Bacteriol.*, 174(22):7149-7158 (1992).
Wang et al., "Molecular cloning and functional identification of a novel phenylacetyl-CoA ligase gene from Penicillium chrysogenum," *Biochem. Biophys. Res. Commun.*, 360(2):453-458 (2007).

(56) References Cited

OTHER PUBLICATIONS

Wang et al., "The primary structure of branched-chain α-oxo acid dehydrogenase from Bacillus subtilis and its similarity to other α-oxo acid dehydrogenases," *Eur. J. Biochem.*, 213:1091-1099 (1993).

Wang et al., "Isolation of poly-3-hydroxybutyrate metabolism genes from complex microbial communities by phenotypic complementation of bacterial mutants," *Appl. Environ. Microbiol.*, 72(1):384-391 (2006).

Wang et al., "Screening microorganisms for utilization of furfural and possible intermediates in its degradative pathway," *Biotechnol. Lett.*, 16(9):977-982 (1994).

Ward et al., "Molecular analysis of the role of two aromatic aminotransferases and a broad-specificity aspartate aminotransferase in the aromatic amino acid metabolism of Pyrococcus furiosus," *Archaea*, 1:133-141 (2002).

Weaver, "Structure of free fumarase C from *Eschericiha coli*," *Acta. Crystallog. D. Biol. Crystallogr.*, 61:1395-1401 (2005).

Weidner et al., "Molecular Characterization of the Genes Encoding Pyruvate Formate-Lyase and Its Activating Enzyme of Clostridium pasteruianum," *J. Bacteriol.*, 178(8):2440-2444 (1996).

Welch et al., "Purification and characterization of the NADH-dependent butanol dehydrogenase from Clostridium acetobutylicum (ATCC 824)," *Arch. Biochem. Biophys.*, 273(2):309-318 (1989).

Werpy et al., "Top Value Added Chemicals from Biomass. Volume I—Results of Screening for Potential Candidates from Sugars and Synthesis Gas," DOE Report (2004).

Westin et al., "The Identification of Succinyl-CoA Thioesterase Suggests a Novel Pathway for Succinate Production in Peroxisomes," *J. Biol. Chem.*, 280(46):38125-38132 (2005).

Wexler et al., "A wide host-range metagenomic library from a waste water treatment plant yields a novel alcohol/aldehyde dehdrogenase," *Environ. Microbiol.*, 7:1917-1926 (2005).

Whalen et al., "Analysis of an avtA::Mu dl(Ap lac) Mutant: Metabolic role of Transaminase C," *J. Bacteriol.*, 150(2):739-746 (1982).

Whalen et al., "Gratuitous Repression of avtA in *Escherichia coli* and *Salmonella typhimurium*," *J. Bacteriol.*, 158(2):571-574 (1984).

Wiesenborn et al., "Coenzyme A Transferase from Clostridium acetobutylicum ATC 824 and Its Role in the Uptake of Acids," *Appl. Environ. Microbiol.*, 55:323-329 (1989).

Wilkie et al., "Recombinant Expression, Purification, and Characterization of Three Isoenzymes of Aspartate Aminotrannsferase from *Arabidopsis thaliana*," *Protein Expr. Purif.*, 12:381-389 (1998).

Wilks et al., "A specific, highly active malate dehydrogenase by redesign of a lactate dehydrogenase framework," *Science*, 242(4885):1541-1544 (1988).

Wilks et al., "Design for a broad substrate specificity keto acid dehydrogenase," *Biochemistry*, 29(37)8587-8591 (1990).

Wilks et al., "Design of a specific phenyllactate dehydrogenase by peptide loop exchange on the Bacillus stearothermophilus lactate dehydrogenase framework," *Biochemistry*, 31(34):7802-7806 (1992).

Willadsen et al., "Assay of 4-hydroxybutyryl-CoA dehydrasate from Clostridium aminobutyricum," *FEMS Microbiol. Lett.*, 70:187-191 (1990).

Williams et al., "Biodegradable plastics from plants," *CHEMTECH*, 26:38-44 (1996).

Willke et al., "Biotechnological production of itaconic acid," *Appl. Microbiol. Biotechnol.*, 56:289-295 (2001).

Winzer et al., "Differential regulation of two thiolase genes from Clostridium acetobutylicum DSM 792," *J. Mol. Microbiol. Biotechnol.*, 2:531-541 (2000).

Witkowski et al., "Conversion of a β-ketoacyl synthase to a malonyl decarboxylase by replacement of the active-site cysteine with glutamine," *Biochemistry*, 38(36):11643-11650 (1999).

Wolff et al., "Purification and characterization of the oxygen-sensitive 4-hydroxybutanoate dehydrogenase from Clostridium kluyveri," *Protein Expr. Purif.*, 6:206-212 (1995).

Wolff et al., "Dehydrogenases involved in the conversion of succinate to 4-hydroxybutanoate by Clostridium kluyven," *Appl. Environ. Microbiol.*, 59:1876-1882 (1993).

Wong et al., "Sequence satruation mutagenesis with tunable mutation frequencies," *Anal. Biochem.*, 341:187-189 (2005).

Wong et al., "Sequence saturation mutagenesis (SeSaM): a novel method for directed evolution," *Nucleic Acids Res.*, 32(3):e26 (2004).

Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3:74-82 (2008).

Wynn et al., "Chaperonins GroEL and GroES Promote Assembly of Heterotramers ($\alpha 2\beta 2$) of Mammalian Mitochondrial Branched-chain α-Keto Acid Decarboxylase in *Escherichia coli*," *J. Biol. Chem.*, 267(18):12400-12403 (1992).

Wynn et al., "Cloning and Expression in *Escherichia coli* of a Mature E1βSubunit of Bovine Mitochondrial Branched-chain α-Keto Acid Dehydrogenase Complex," *J. Biol Chem.*, 267(3):1881-1887 (1992).

Yagi et al., "Aspartate: 2-Oxoglutarate Aminotransferase from Bakers' Yeast: Crystallization and Charactierization," *J. Biochem.*, 92:35-43 (1982).

Yagi et al., "Crystallization and Properties of Aspartate Aminotransferase from *Escherichi coli* B," *FEBS Lett.*, 100(1)81-84 (1979).

Yagi et al., "Glutamate-Aspartate Transaminase from Microorganisms," *Meth. Enzymol.*, 113:83-89 (1985).

Yakunin et al., "Purification and characterization of pyruvate oxidoreductase from the photosynthetic bacterium Rhodobacter capsulatus," *Biochim. Biophys. Acta.*, 1409(1):39-49 (1998).

Yamamoto et al., "Carboxylation reaction catalyzed by 2-oxoglutarate:ferredoxin oxidoreductases from Hydrogenobacter thermophilus," *Extremophiles*, 14:79-85 (2010).

Yamamoto et al., "Purification and properties of NADP-dependent formate dehydrogenase from Clostridium thermoaceticum, a tungsten-selenium-iron protein," *J. Biol. Chem.*, 258(3):1826-1832 (1983).

Yang et al, "Nucleotide Sequence of the fadA Gene. Primary structure of 3-ketoacyl-coenzyme A thiolase from *Escherichia coli* and the structural organization of the fadAB operon," *J. Biol. Chem.*, 265(18):10424-10429 (1990) with correction in *J. Biol. Chem.*, 266(24):16255 (1991).

Yang et al. *J. Biol. Chem.*, 265(18): p. 10424-10429 (1990).

Yang et al., "Aspartate Dehydrogenase, a Novel Enszyme Idnetified from Structural and Functional Studies of TM16343," *J. Biol. Chem.*, 278:8804-8808 (2003).

Yang et al., "Nucleotide sequence of the promoter and fadB gene of the fadBA operon and primary structure of the multifunctional fatty acid oxidation protein from *Escherichia coli*," *Biochemistry*, 30(27):6788-6795 (1991).

Yano et al., "Directed evolution of an aspartate aminotransferase with new substrate specificities," *Proc. Natl. Acad. Sci. U.S.A.*, 95:5511-5515 (1998).

Yarlett et al., "Trichomonas vaginalis: characterization of ornithine decarboxylase," *Biochem. J.*, 293:487-493 (1993).

Yee et al., "Isolation and characterization of a NADP-dependent glutamate dehydrogenase gene from the primitive eucaryote Giardia lamblia," *J. Biol. Chem.*, 267:7539-7544 (1992).

Yim et al., "Metabolic engineering of *Escherichia coli* for direct production of 1,4-butanediol," *Nature Chemical Biology*, 7(7):445-452 (2011).

Yoshida et al., "The structures of L-rhamnose isomerase from Pseudomonas stutzeri in complexs with L-rhamnose and D-allose provide insights into broad substrate specificity," *J. Mol. Biol.*, 365(5): 1505-1516 (2007).

Youngleson et al., "Homology between hydroxybutyryl and hydroxyacyl coenzyme A dehydrogenase enzymes from Clostridium acetobutylicum fermentation and vertebrate fatty acid beta-oxidation pathways," *J. Bacteriol.*, 171(12):6800-6807 (1989).

Yu et al., "sucAB and sucCD are mutually essential genes in *Escherichia coli*," *FEMS Microbiol. Lett.*, 254(2):245-250 (2006).

Yun et al., "The genes for anabolic 2-oxoglutarate: ferredoxin oxidoreductse from hydrogenobacter thermophilus TK-6," *Biochem. Biophys. Res. Commun.*, 282(2):589-594 (2001).

(56) References Cited

OTHER PUBLICATIONS

Yun et al., "Enhancement of lactate and succinate formation in adhE or pta-ackA mutants of NADH dehydrogenase-deficient *Escherichia coli*," *J. Appl. Microbiol.*, 99:1404-1412 (2005).

Yun et al., "ω-Amino acid:pyruvate transaminase from Alcaligenes denitrificans Y2k-2: a new catalyst for kinetic resolution of β-amino acids and amines," *Appl. Environ. Microbiol.*, 70(4):2529-2534 (2004).

Zeiher et al., "Identification and Characterization of Mitochondrial Acetyl-Coenzyme A Hydrolase from *Pisum sativum* L. Seedlings," *Plant Physiol.*, 94:20-27 (1990).

Zhang et al., "2-Oxoacid: Ferredoxin Oxidoreductase from the Thermoacidophilic Archaeon, *Sulfolobus* sp. Strain 7," *J. Biochem.*, 120:587-599 (1996).

Zhang et al., "Directed evolution of a fucosidase from a galactosidase by DNA shuffling and screening," *Proc. Natl. Acad. Sci. U.S.A.*, 94:4504-4509 (1997).

Zhang et al., "Isolation and Properties of a levo-lactonase from Fusarium proliferatum ECD2002: a robust biocatalyst for production of chiral lactones," *App. Microbiol. Biotechnol.*, 75(5):1087-1094 (2007).

Zhang, et al., "Kinetic and mechanistic characterization of the polyhydroxybutyrate synthase from Ralstonia eutropha," *Biomacromolecules*, 1(2):244-251 (2000).

Zhao et al., "Molecular evolution by staggered extension process (StEP) in vitro recombination," *Nat. Biotechnol.*, 16(3):258-261 (1998).

Zhou et al., "Engineering a native homoethanol pathway in *Escherichia coli* B for ethanol production," *Biotechnol. Lett.*, 30:335-342 (2008).

Zhou et al., "The remarkable structural and functional organization of the eukaryotic pyruvate dehydrogenase complexes," *Proc. Natl. Acad. Sci. U.S.A.*, 98:14802-14807 (2001).

Zhou et al., "Functional replacement of the *Escherichia coli* D-(-)-lactate dehydrogenase gene (1dhA) with the L-(+)-lactate dehydrogenase gene (1dhL) from Pediococcus acidilactici," *Appl. Environ. Micro.*, 69:2237-2244 (2003).

Zhuang et al., "The YbgC protein encoded by the ybgC gene of the tol-pal gene cluster of Haemophilus influenzae catalyzes acyl-coenzyme A thioester hydrolysis," *FEBS Lett.*, 516:161-163 (2002).

Kozak, "Initiation of translation in prokaryotes and eukaryotes," *Gene*, 234(2):187-208 (1999).

Sadowski et al., "The sequence-structure relationship and protein function prediction," *Curr. Op. Struct. Biol.*, 19:357-362 (2009).

Tang et al., "Identification of Dehalobacter reductive dehalogenases that catalyse dechlorination of chloroform, 1,1,1-trichloroethane and 1,1-dichloroethane," *Philos. Trans. R. Soc. Lond. B. Biol. Sci.*, 368(20120318):1-10 (2013).

Tsuji et al., "The effects of temperature and pH on the growth of eight enteric and nine glucose non-fermenting species of gram-negative rods," *Microbiol. Immunol.*, 26(1):15-24 (1982).

Zhou et al., "Global analysis of gene transcription regulation in prokaryotes," *Cell. Mol. Life Sci.*, 63:2260-2290 (2006).

Zhu, "The Effects of pH and Temperature on the Growth of *Escherichia coli* DH5a," California State Science Fair, Apr. 2, 2007, Project No. J1440.

U.S. Appl. No. 12/049,256, 20090075351, filed Mar. 14, 2008, Compositions and Methods for the Biosynthesis of 1,4-Butanediol and its Precursors, Patented.

U.S. Appl. No. 12/830,238, filed Jul. 2, 2010, Compositions and Methods for the Biosynthesis of 1,4-Butanediol and its Precursors, Abandoned.

U.S. Appl. No. 13/286,135, 20120094345, filed Oct. 31, 2011, Compositions and Methods for the Biosynthesis of 1,4-Butanediol and its Precursors, Patented.

U.S. Appl. No. 13/348,564, 20120122171, filed Jan. 11, 2012, Compositions and Methods for the Biosynthesis of 1,4-Butanediol and its Precursors, Patented.

U.S. Appl. No. 13/717,350, 20130196397, filed Dec. 17, 2012, Compositions and Methods for the Biosynthesis of 1,4-Butanediol and its Precursors, Patented.

U.S. Appl. No. 14/530,530, 20150267229, filed Oct. 31. 2014, Compositions and Methods for the Biosynthesis of 1,4-Butanediol and its Precursors, Abandoned.

U.S. Appl. No. 14/603,174, 20150368676, filed Jan. 22, 2015, Compositions and Methods for the Biosynthesis of 1,4-Butanediol and its Precursors, Patented.

U.S. Appl. No. 15/270,578, 20170088840, filed Sep. 20, 2016, Compositions and Methods for the Biosynthesis of 1,4-Butanediol and its Precursors, Published.

U.S. Appl. No. 15/056,914, 20170022524, filed Feb. 29, 2016, Compositions and Methods for the Biosynthesis of 1,4-Butanediol and its Precursors, Abandoned.

U.S. Appl. No. 15/925,301, 20190062758, filed Mar. 19, 2018, Compositions and Methods for the Biosynthesis of 1,4-Butanediol and its Precursors, Published.

U.S. Appl. No. 11/891,602, 20090047719, filed Aug. 10, 2007, Compositions and Methods for the Biosynthesis of 1,4-Butanediol and its Precursors, Patented.

U.S. Appl. No. 13/065,303, 20110201071, filed Mar. 18, 2011, Compositions and Methods for the Biosynthesis of 1,4-Butanediol and its Precursors, Patented.

U.S. Appl. No. 13/914,422, 20140030780, filed Jun. 10, 2013, Methods and Organisms for the Growth-Coupled Production of 1,4-Butanediol, Abandoned.

U.S. Appl. No. 15/424,723, 20170240931, filed Feb. 3, 2017, Methods and Organisms for the Growth-Coupled Production of 1,4-Butanediol, Published.

U.S. Appl. No. 12/556,550, 20100112654, filed Sep. 9, 2009, Microorganisms for the Production of 1,4-Butanediol, Patented.

U.S. Appl. No. 12/947,790, 20110159572, filed Nov. 16, 2010, Microorganisms for the Production of 1,4-Butanediol, Patented.

U.S. Appl. No. 13/009,813, 20110281337, filed Jan. 19, 2011, Microorganisms for the Production of 1,4-Butanediol, Patented.

U.S. Appl. No. 13/449,187, 20130109069, filed Apr. 17, 2012, Microorganisms for the Production of 1,4-Butanediol, Patented.

U.S. Appl. No. 13/566,826, 20130071886, filed Aug. 3, 2012, Microorganisms for the Production of 1,4-Butanediol, Abandoned.

U.S. Appl. No. 14/700,096, 20160053287, filed Apr. 29, 2015, Microorganisms for the Production of 1,4-Butanediol, Abandoned.

U.S. Appl. No. 15/682,349, 20180142269, filed Aug. 21 2017, Microorganisms for the Production of 1,4-Butanediol, Published.

U.S. Appl. No. 12/793,623, 20110003355, filed Jun. 3, 2010, Process of Separating Components of a Fermentation Broth, Patented.

U.S. Appl. No. 14/066,598, 20140322777, filed Oct. 29 2013, Process of Separating Components of a Fermentation Broth, Patented.

U.S. Appl. No. 15/975,630, 20190112247, filed May 9, 2018, Process of Separating Components of a Fermentation Broth, Pending.

U.S. Appl. No. 12/794,700, 20110045575, filed Jun. 4, 2010, Microorganisms for the Production of 1,4-Butanediol and the Related Methods, Patented.

U.S. Appl. No. 13/361,799, 20120225463, filed Jan. 30, 2012, Microorganisms for the Production of 1,4-Butanediol and Related Methods, Patented.

U.S. Appl. No. 15/148,759, 20160355846, filed May 6, 2016, Microorganisms for the Production of 1,4-Butanediol and Related Methods, Patented.

U.S. Appl. No. 16/294,753, filed Mar. 6, 2019, Microorganisms for the Production of 1,4-Butanediol and Related Methods, Pending.

U.S. Appl. No. 12/878,980, 20110201068, filed Sep. 9, 2010, Microorganisms for the Co-Production of Isopropanol with Primary Alcohols, Diols and Acids, Patented.

U.S. Appl. No. 14/167,693, 20140377820, filed Jan. 29, 2014, Microorganisms and Methods for the Co-Production of Isopropanol with Primary Alcohols, Diols, and Acids, Abandoned.

U.S. Appl. No. 12/904,130, 20110129899, filed Oct. 13, 2010, Microorganisms for the Production of 1,4-Butanediol, 4-Hydroxybutanal, 4-Hydroxybutyryl-COA, Putrescine, and Related Compounds, and Methods Related Thereto, Patented.

U.S. Appl. No. 13/109,732, 20110229946, filed May 17, 2011, Microorganisms for the Production of 1,4-Butanediol,

(56) References Cited

OTHER PUBLICATIONS

4-Hydroxybutanal, 4-Hydroxybutyryl-COA, Putrescine, and Related Compounds, and Methods Related Thereto, Patented.
U.S. Appl. No. 13/447,094, 20130029381, filed Apr. 13, 2012, Microorganisms for the Production of 1,4-Butanediol, 4-Hydroxybutanal, 4-Hydroxybutyryl-COA, Putrescine, and Related Compounds, and Methods Related Thereto, Abandoned.
U.S. Appl. No. 13/737,866, 20130189751, filed Jan. 9, 2013, Microorganisms for the Production of 1,4-Butanediol, 4-Hydroxybutanal, 4-Hydroxybutyryl-COA, Putrescine, and Related Compounds, and Methods Related Thereto, Abandoned.
U.S. Appl. No. 15/173,427, 20160376614, filed Jun. 3, 2016, Microorganisms for the Production of 1,4-Butanediol, 4-Hydroxybutanal, 4-Hydroxybutyryl-COA, Putrescine, and Related Compounds, and Methods Related Thereto, Abandoned.
U.S. Appl. No. 16/216,865, filed Dec. 11, 2018, Microorganisms for the Production of 1,4-Butanediol, 4-Hydroxybutanal, 4-Hydroxybutyryl-COA, Putrescine, and Related Compounds, and Methods Related Thereto, Pending.
U.S. Appl. No. 13/530,053, 20130034884, filed Jun. 21, 2012, Microorganisms for Producing 1,4-Butanediol and Methods Related Thereto, Abandoned.
U.S. Appl. No. 15/018,736, 20160264978, filed Feb. 8, 2016, Microorganisms for Producing 1,4-Butanediol and Methods Related Thereto, Published.
U.S. Appl. No. 13/908,907, 20140030779, filed Jun. 3, 2013, Microorganisms and Methods for Production of 4-Hydroxybutyrate, 1,4-Butanediol and Related Compounds, Patented.
U.S. Appl. No. 15/585,078, 20170362565, filed May 2, 2017, Microorganisms and Methods for Production of 4-Hydroxybutyrate, 1,4-Butanediol and Related Compounds, Published.
U.S. Appl. No. 14/405,390, 20150148513, filed Dec. 3, 2014, Microorganisms and Methods for Production of 4-Hydroxybutyrate, 1,4-Butanediol and Related Compounds, Published.
U.S. Appl. No. 13/975,678, 20140058056, filed Aug. 26, 2013, Microorganisms and Methods for Enhancing the Availability of Reducing Equivalents in the Presence of Methanol, and for Producing 1,4-Butanediol Related Thereto, Patented.
U.S. Appl. No. 15/488,320, 20180030484, filed Apr. 14, 2017, Microorganisms and Methods for Enhancing the Availability of Reducing Equivalents in the Presence of Methanol, and for Producing 1,4-Butanediol Related Thereto, Published.
U.S. Appl. No. 14/424,404, 20150203875, filed Feb. 26, 2015, Microorganisms and Methods for Enhancing the Availability of Reducing Equivalents in the Presence of Methanol, and for Producing 1,4-Butanediol Related Thereto, Published.
U.S. Appl. No. 14/211,863, 20140275465, filed Mar. 14, 2014, Process and Systems for Obtaining 1,4-Butanediol from Fermentation Broths, Abandoned.
U.S. Appl. No. 15/651,929, 20180065907, filed Jul. 17, 2017, Process and Systems for Obtaining 1,4-Butanediol from Fermentation Broths, Published.
U.S. Appl. No. 15/696,098, 20170362149, filed Sep. 5, 2017, Process and Systems for Obtaining 1,4-Butanediol from Fermentation Broths, Abandoned.
U.S. Appl. No. 16/216,965, filed Dec. 11, 2018, Process and Systems for Obtaining 1,4-Butanediol from Fermentation Broths, Pending.
U.S. Appl. No. 14/776,517, 20160031778, filed Sep. 14, 2015, Process and Systems for Obtaining 1,4-Butanediol from Fermentation Broths, Patented.
U.S. Appl. No. 15/845,398, 20180237367, filed Dec. 18, 2017, Process and Systems for Obtaining 1,4-Butanediol from Fermentation Broths, Published.
U.S. Appl. No. 14/262,461, 20140371417, filed Apr. 25, 2014, Microorganisms and Methods for Production of 4-Hydroxybutyrate, 1,4-Butanediol and Related Compounds, Abandoned.
U.S. Appl. No. 15/191,421, 20170183694, filed Jun. 23, 2016, Microorganisms and Methods for Production of 4-Hydroxybutyrate, 1,4-Butanediol and Related Compounds, Published.
U.S. Appl. No. 13/011,796, 20110201089, filed Jan. 21, 2011, Methods for Increasing Product Yields, Patented.
U.S. Appl. No. 13/011,788, 20110207189, filed Jan. 21, 2011, Methods for Increasing Product Yields, Patented.
U.S. Appl. No. 13/011,818, 20110212507, filed Jan. 21, 2011, Methods for Increasing Product Yields, Patented.
U.S. Appl. No. 13/556,998, filed Jul. 24, 2012, Methods for Increasing Product Yields, Abandoned.
U.S. Appl. No. 14/165,289, filed Jan. 27, 2014, Methods for Increasing Product Yields, Abandoned.
U.S. Appl. No. 13/889,056, 2014001149, filed May 7, 2013, Methods for Increasing Product Yields, Abandoned.
U.S. Appl. No. 14/806,435, 20160145652, filed Jul. 22, 2015, Methods for Increasing Product Yields, Patented.
U.S. Appl. No. 16/137,264, filed Sep. 20, 2018, Methods for Increasing Product Yields, Pending.
U.S. Appl. No. 12/940,021, 20110217742, filed Nov. 4, 2010, Microorganisms and Methods for the Coproduction 1,4-Butanediol and Gamma-Butyrolactone, Patented.
U.S. Appl. No. 13/936,878, 20140162327, filed Jul. 8, 2013, Microorganisms and Methods for the Coproduction 1,4-Butanediol and Gamma-Butyrolactone, Patented.
U.S. Appl. No. 14/954,487, 20160319313, filed Nov. 30, 2015, Microorganisms and Methods for the Coproduction 1,4-Butanediol and Gamma-Butyrolactone, Patented.
U.S. Appl. No. 15/971,878, filed May 4, 2018, Microorganisms and Methods for the Coproduction 1,4-Butanediol and Gamma-Butyrolactone, Pending.
U.S. Appl. No. 12/358,217, 20090191593, filed Jan. 22, 2009, Methods and Organisms for Utilizing Synthesis Gas or Other Gaseous Carbon Sources and Methanol, Patented.
U.S. Appl. No. 12/863,978, 20110195461, filed Apr. 15, 2011, Methods and Organisms for Utilizing Synthesis Gas or Other Gaseous Carbon Sources and Methanol, Patented.
U.S. Appl. No. 12/875,068, 20110003344, filed Sep. 2, 2010, Methods and Organisms for Utilizing Synthesis Gas or Other Gaseous Carbon Sources and Methanol, Patented.
U.S. Appl. No. 13/106,764, 20110223637, filed May 12, 2011, Methods and Organisms for Utilizing Synthesis Gas or Other Gaseous Carbon Sources and Methanol, Patented.
U.S. Appl. No. 13/615,168, 20130071883, filed Sep. 13, 2012, Methods and Organisms for Utilizing Synthesis Gas or Other Gaseous Carbon Sources and Methanol, Patented.
U.S. Appl. No. 14/185,709, 20150024468, filed Feb. 20, 2014, Methods and Organisms for Utilizing Synthesis Gas or Other Gaseous Carbon Sources and Methanol, Patented.
U.S. Appl. No. 14/700,103, 20160053288, filed Apr. 29, 2015, Methods and Organisms for Utilizing Synthesis Gas or Other Gaseous Carbon Sources and Methanol, Abandoned.
U.S. Appl. No. 15/889,788, 20180334690, filed Feb. 6, 2018, Methods and Organisms for Utilizing Synthesis Gas or Other Gaseous Carbon Sources and Methanol, Pending.
U.S. Appl. No. 12/639,977, 20100304453, filed Dec. 16, 2009, Microorganisms and Methods for Conversion of Syngas and Other Carbon Sources to Useful Products, Patented.
U.S. Appl. No. 13/371,278, 20120208249, filed Feb. 10, 2012, Microorganisms and Methods for Conversion of Syngas and Other Carbon Sources to Useful Products, Patented.
U.S. Appl. No. 13/920,927, 20140147900, filed Jun. 18, 2013, Microorganisms and Methods for Conversion of Syngas and Other Carbon Sources to Useful Products, Patented.

* cited by examiner

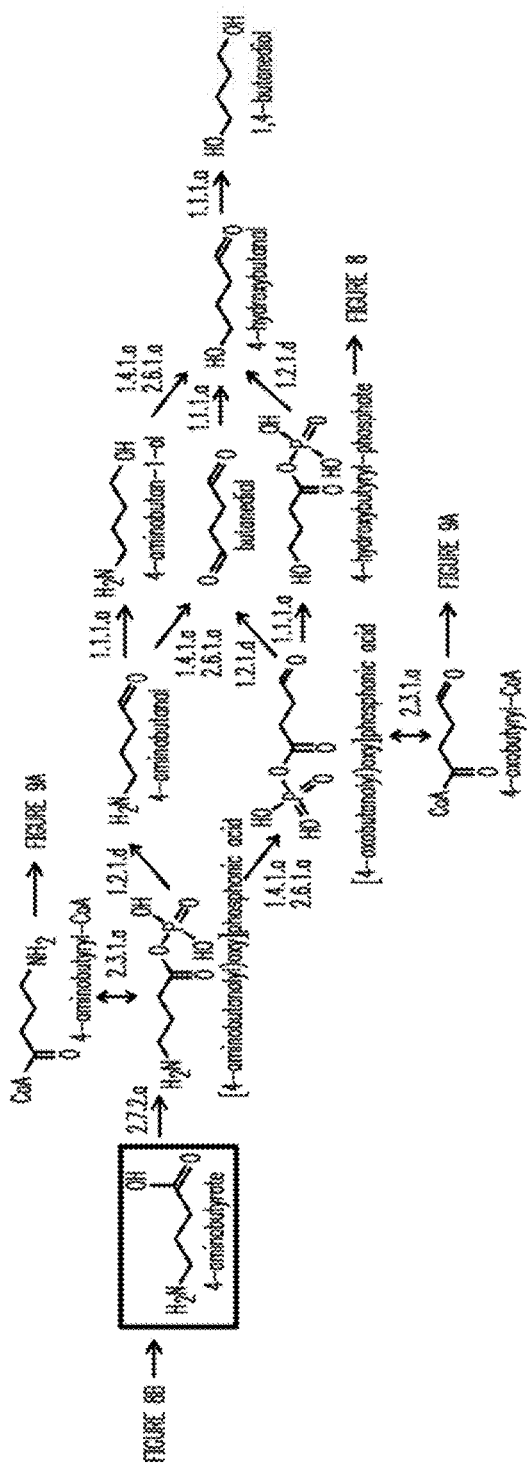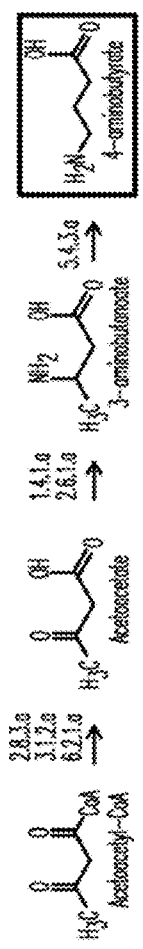
FIG. 9B
FIG. 9C

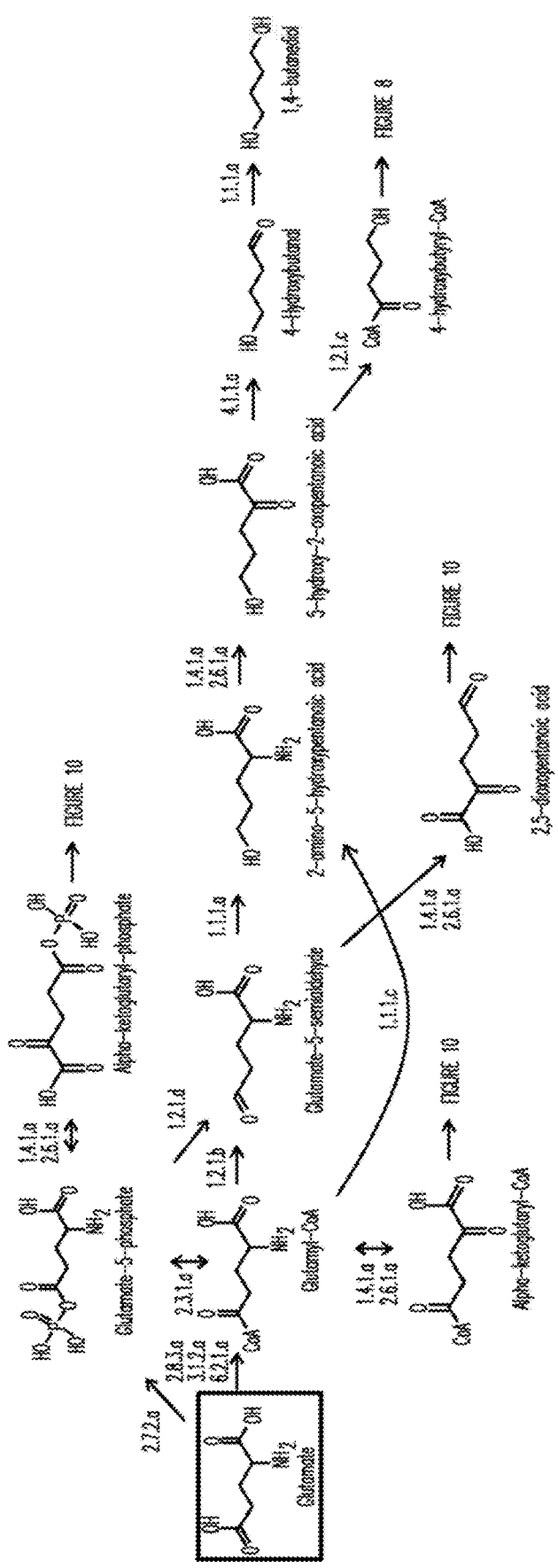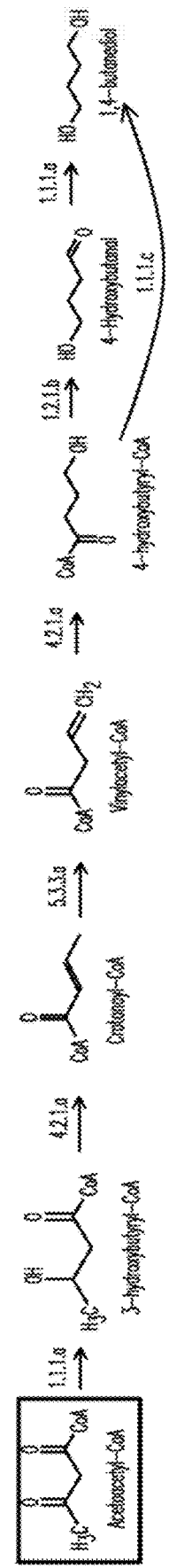
FIG. 11
FIG. 12

A.

ATGAACTTACATGAATATCAGGCAAAACAACTTTTTGCCCGCTATGGCTTACCAGCACCGGTGGGTTATG
CCTGTACTACTCCGCGCGAAGCAGAAGAAGCCGCTTCAAAAATCGGTGCCGGTCCGTGGGTAGTGAAAT
GTCAGGTTCACGCTGGTGGCCGCGGTAAAGCGGGCGGTGTGAAAGTTGTAAACAGCAAAGAAGACATC
CGTGCTTTTGCAGAAAACTGGCTGGGCAAGCGTCTGGTAACGTATCAAACAGATGCCAATGGCCAACCG
GTTAACCAGATTCTGGTTGAAGCAGCGACCGATATCGCTAAAGAGCTGTATCTCGGTGCCGTTGTTGAC
CGTAGTTCCCGTCGTGTGGTCTTTATGGCCTCCACCGAAGGCGGCGTGGAAATCGAAAAAGTGGCGGA
AGAAACTCCGCACCTGATCCATAAAGTTGCGCTTGATCCGCTGACTGGCCCGATGCCGTATCAGGGACG
CGAGCTGGCGTTCAAACTGGGTCTGGAAGGTAAACTGGTTCAGCAGTTCACCAAAATCTTCATGGGCCT
GGCGACCATTTTCCTGGAGCGCGACCTGGCGTTGATCGAAATCAACCCGCTGGTCATCACCAAACAGGG
CGATCTGATTTGCCTCGACGGCAAACTGGGCGCTGACGGCAACGCACTGTTCCGCCAGCCTGATCTGCG
CGAAATGCGTGACCAGTCGCAGGAAGATCCGCGTGAAGCACAGGCTGCACAGTGGGAACTGAACTACG
TTGCGCTGGACGGTAACATCGGTTGTATGGTTAACGGCGCAGGTCTGGCGATGGGTACGATGGACATC
GTTAAACTGCACGGCGGCGAACCGGCTAACTTCCTTGACGTTGGCGGCGGCGCAACCAAAGAACGTGT
AACCGAAGCGTTCAAAATCATCCTCTCTGACGACAAAGTGAAAGCCGTTCTGGTTAACATCTTCGGCGGT
ATCGTTCGTTGCGACCTGATCGCTGACGGTATCATCGGCGCGGTAGCAGAAGTGGGTGTTAACGTACCG
GTCGTGGTACGTCTGGAAGGTAACAACGCCGAACTCGGCGCGAAGAAACTGGCTGACAGCGGCCTGAA
TATTATTGCAGCAAAAGGTCTGACGGATGCAGCTCAGCAGGTTGTTGCCGCAGTGGAGGGGAAATAAT
GTCCATTTTAATCGATAAAAACACCAAGGTTATCTGCCAGGGCTTTACCGGTAGCCAGGGGACTTTCCAC
TCAGAACAGGCCATTGCATACGGCACTAAAATGGTTGGCGGCGTAACCCCAGGTAAAGGCGGCACCAC
CCACCTCGGCCTGCCGGTGTTCAACACCGTGCGTGAAGCCGTTGCTGCCACTGGCGCTACCGCTTCTGTT
ATCTACGTACCAGCACCGTTCTGCAAAGACTCCATTCTGGAAGCCATCGACGCAGGCATCAAACTGATTA
TCACCATCACTGAAGGCATCCCGACGCTGGATATGCTGACCGTGAAAGTGAAGCTGGATGAAGCAGGC
GTTCGTATGATCGGCCCGAACTGCCCAGGCGTTATCACTCCGGGTGAATGCAAAATCGGTATCCAGCCT
GGTCACATTCACAAACCGGGTAAAGTGGGTATCGTTTCCCGTTCCGGTACACTGACCTATGAAGCGGTT
AAACAGACCACGGATTACGGTTTCGGTCAGTCGACCTGTGTCGGTATCGGCGGTGACCCGATCCCGGGC
TCTAACTTTATCGACATTCTCGAAATGTTCGAAAAGATCCGCAGACCGAAGCGATCGTGATGATCGGT
GAGATCGGCGGTAGCGCTGAAGAAGAAGCAGCTGCGTACATCAAAGAGCACGTTACCAAGCCAGTTGT
GGGTTACATCGCTGGTGTGACTGCGCCGAAAGGCAAACGTATGGGCCACGCGGGTGCCATCATTGCCG
GTGGGAAAGGGACTGCGGATGAGAAATTCGCTGCTCTGGAAGCCGCAGGCGTGAAAACCGTTCGCAGC
CTGGCGGATATCGGTGAAGCACTGAAAACTGTTCTGAAATAA

B.

MNLHEYQAKQLFARYGLPAPVGYACTTPREAEEAASKIGAGPWVVKCQVHAGGRGKAGGVKVVNSKEDIR
AFAENWLGKRLVTYQTDANGQPVNQILVEAATDIAKELYLGAVVDRSSRRVVFMASTEGGVEIEKVAEETPH
LIHKVALDPLTGPMPYQGRELAFKLGLEGKLVQQFTKIFMGLATIFLERDLALIEINPLVITKQGDLICLDGKLGA
DGNALFRQPDLREMRDQSQEDPREAQAAQWELNYVALDGNIGCMVNGAGLAMGTMDIVKLHGGEPAN
FLDVGGGATKERVTEAFKIILSDDKVKAVLVNIFGGIVRCDLIADGIIGAVAEVGVNVPVVVRLEGNNAELGAK
KLADSGLNIIAAKGLTDAAQQVVAAVEGK

C.

MSILIDKNTKVICQGFTGSQGTFHSEQAIAYGTKMVGGVTPGKGGTTHLGLPVFNTVREAVAATGATASVIY
VPAPFCKDSILEAIDAGIKLIITITEGIPTLDMLTVKVKLDEAGVRMIGPNCPGVITPGECKIGIQPGHIHKPGKV
GIVSRSGTLTYEAVKQTTDYGFGQSTCVGIGGDPIPGSNFIDILEMFEKDPQTEAIVMIGEIGGSAEEEAAAYIK
EHVTKPVVGYIAGVTAPKGKRMGHAGAIIAGGKGTADEKFAALEAAGVKTVRSLADIGEALKTVLK

ATGGCCAACATAAGTTCACCATTCGGGCAAAACGAATGGCTGGTTGAAGAGATGTACCGCAAGTTCCGC
GACGACCCCTCCTCGGTCGATCCCAGCTGGCACGAGTTCCTGGTTGACTACAGCCCCGAACCCACCTCCC
AACCAGCTGCCGAACCAACCCGGGTTACCTCGCCACTCGTTGCCGAGCGGGCCGCTGCGGCCGCCCCGC
AGGCACCCCCAAGCCGGCCGACACCGCGGCCGCGGGCAACGGCGTGGTCGCCGCACTGGCCGCCAAA
ACTGCCGTTCCCCGCCAGCCGAAGGTGACGAGGTAGCGGTGCTGCGCGGCGCCGCCGCGGCCGTCGT
CAAGAACATGTCCGCGTCGTTGGAGGTGCCGACGGCGACCAGCGTCCGGGCGGTCCCGGCCAAGCTAC
TGATCGACAACCGGATCGTCATCAACAACCAGTTGAAGCGGACCCGCGGCGGCAAGATCTCGTTCACGC
ATTTGCTGGGCTACGCCCTGGTGCAGGCGGTGAAGAAATTCCCGAACATGAACCGGCACTACACCGAA
GTCGACGGCAAGCCCACCGCGGTCACGCCGGCGCACACCAATCTCGGCCTGGCGATCGACCTGCAAGG
CAAGGACGGGAAGCGTTCCCTGGTGGTGGCCGGCATCAAGCGGTGCGAGACCATGCGATTCGCGCAGT
TCGTCACGGCCTACGAAGACATCGTACGCCGGGCCCGCGACGGCAAGCTGACCACTGAAGACTTTGCCG
GCGTGACGATTTCGCTGACCAATCCCGGAACCATCGGCACCGTGCATTCGGTGCCGCGGCTGATGCCCG
GCCAGGGCGCCATCATCGGCGTGGGCGCCATGGAATACCCCGCCGAGTTTCAAGGCGCCAGCGAGGAA
CGCATCGCCGAGCTGGGCATCGGCAAATTGATCACTTTGACCTCCACCTACGACCACCGCATCATCCAGG
GCGCGGAATCGGGCGACTTCCTGCGCACCATCCACGAGTTGCTGCTCTCGGATGGCTTCTGGGACGAGG
TCTTCCGCGAACTGAGCATCCCATATCTGCCGGTGCGCTGGAGCACCGACAACCCCGACTCGATCGTCG
ACAAGAACGCTCGCGTCATGAACTTGATCGCGGCCTACCGCAACCGCGGCCATCTGATGGCCGATACCG
ACCCGCTGCGGTTGGACAAAGCTCGGTTCCGCAGTCACCCCGACCTCGAAGTGCTGACCCACGGCCTGA
CGCTGTGGGATCTCGATCGGGTGTTCAAGGTCGACGGCTTTGCCGGTGCGCAGTACAAGAAACTGCGC
GACGTGCTGGGCTTGCTGCGCGATGCCTACTGCCGCCACATCGGCGTGGAGTACGCCCATATCCTCGAC
CCCGAACAAAAGGAGTGGCTCGAACAACGGGTCGAGACCAAGCACGTCAAACCCACTGTGGCCCAACA
GAAATACATCCTCAGCAAGCTCAACGCCGCCGAGGCCTTTGAAACGTTCCTACAGACCAAGTACGTCGG
CCAGAAGCGGTTCTCGCTGGAAGGCGCCGAAAGCGTGATCCCGATGATGGACGCGGCGATCGACCAGT
GCGCTGAGCACGGCCTCGACGAGGTGGTCATCGGGATGCCGCACCGGGGCCGGCTCAACGTGCTGGCC
AACATCGTCGGCAAGCCGTACTCGCAGATCTTCACCGAGTTCGAGGGCAACCTGAATCCGTCGCAGGCG
CACGGCTCCGGTGACGTCAAGTACCACCTGGGCGCCACCGGGCTGTACCTGCAGATGTTCGGCGACAAC
GACATTCAGGTGTCGCTGACCGCCAACCCGTCGCATCTGGAGGCCGTCGACCCGGTGCTGGAGGGATT
GGTGCGGGCCAAGCAGGATCTGCTCGACCACGGAAGCATCGACAGCGACGGCCAACGGGCGTTCTCGG
TGGTGCCGCTGATGTTGCATGGCGATGCCGCGTTCGCCGGTCAGGGTGTGGTCGCCGAGACGCTGAAC
CTGGCGAATCTGCCGGGCTACCGCGTCGGCGGCACCATCCACATCATCGTCAACAACCAGATCGGCTTC
ACCACCGCGCCCGAGTATTCCAGGTCCAGCGAGTACTGCACCGACGTCGCAAAGATGATCGGGGCACC
GATCTTTCACGTCAACGGCGACGACCCGGAGGCGTGTGTCTGGGTGGCGCGGTTGGCGGTGGACTTCC
GACAACGGTTCAAGAAGGACGTCGTCATCGACATGCTGTGCTACCGCCGCCGCGGGCACAACGAGGGT
GACGACCCGTCGATGACCAACCCCTACATGTACGACGTCGTCGACACCAAGCGCGGGGCCCGCAAAAG
CTACACCGAAGCCCTGATCGGACGTGGCGACATCTCGATGAAGGAGGCCGAGGACGCGCTGCGCGACT
ACCAGGGCCAGCTGGAACGGGTGTTCAACGAAGTGCGCGAGCTGGAGAAGCACGGTGTGCAGCCGAG
CGAGTCGGTCGAGTCCGACCAGATGATTCCCGCGGGGCTGGCCACTGCGGTGGACAAGTCGCTGCTGG
CCCGGATCGGCGATGCGTTCCTCGCCTTGCCGAACGGCTTCACCGCGCACCCGCGAGTCCAACCGGTGC
TGGAGAAGCGCCGGGAGATGGCCTATGAAGGCAAGATCGACTGGGCCTTTGGCGAGCTGCTGGCGCT
GGGCTCGCTGGTGGCCGAAGGCAAGCTGGTGCGCTTGTCGGGGCAGGACAGCCGCCGCGGCACCTTCT
CCCAGCGGCATTCGGTTCTCATCGACCGCCACACTGGCGAGGAGTTCACACCACTGCAGCTGCTGGCGA
CCAACTCCGACGGCAGCCCGACCGGCGGAAAGTTCCTGGTCTACGACTCGCCACTGTCGGAGTACGCCG
CCGTCGGCTTCGAGTACGGCTACACTGTGGGCAATCCGGACGCCGTGGTGCTCTGGGAGGCGCAGTTC

FIG. 15

GGCGACTTCGTCAACGGCGCACAGTCGATCATCGACGAGTTCATCAGCTCCGGTGAGGCCAAGTGGGG
CCAATTGTCCAACGTCGTGCTGCTGTTACCGCACGGGCACGAGGGGCAGGGACCCGACCACACTTCTGC
CCGGATCGAACGCTTCTTGCAGTTGTGGGCGGAAGGTTCGATGACCATCGCGATGCCGTCGACTCCGTC
GAACTACTTCCACCTGCTACGCCGGCATGCCCTGGACGGCATCCAACGCCCGCTGATCGTGTTCACGCCC
AAGTCGATGTTGCGTCACAAGGCCGCCGTCAGCGAAATCAAGGACTTCACCGAGATCAAGTTCCGCTCA
GTGCTGGAGGAACCCACCTATGAGGACGGCATCGGAGACCGCAACAAGGTCAGCCGGATCCTGCTGAC
CAGTGGCAAGCTGTATTACGAGCTGGCCGCCCGCAAGGCCAAGGACAACCGCAATGACCTCGCGATCG
TGCGGCTTGAACAGCTCGCCCCGCTGCCCAGGCGTCGACTGCGTGAAACGCTGGACCGCTACGAGAAC
GTCAAGGAGTTCTTCTGGGTCCAAGAGGAACCGGCCAACCAGGGTGCGTGGCCGCGATTCGGGCTCGA
ACTACCCGAGCTGCTGCCTGACAAGTTGGCCGGGATCAAGCGAATCTCGCGCCGGGCGATGTCAGCCCC
GTCGTCAGGCTCGTCGAAGGTGCACGCCGTCGAACAGCAGGAGATCCTCGACGAGGCGTTCGGCTAA

B.

MANISSPFGQNEWLVEEMYRKFRDDPSSVDPSWHEFLVDYSPEPTSQPAAEPTRVTSPLVAERAAAAAPQA
PPKPADTAAAGNGVVAALAAKTAVPPPAEGDEVAVLRGAAAAVVKNMSASLEVPTATSVRAVPAKLLIDNR
IVINNQLKRTRGGKISFTHLLGYALVQAVKKFPNMNRHYTEVDGKPTAVTPAHTNLGLAIDLQGKDGKRSLV
VAGIKRCETMRFAQFVTAYEDIVRRARDGKLTTEDFAGVTISLTNPGTIGTVHSVPRLMPGQGAIIGVGAME
YPAEFQGASEERIAELGIGKLITLTSTYDHRIIQGAESGDFLRTIHELLLSDGFWDEVFRELSIPYLPVRWSTDNP
DSIVDKNARVMNLIAAYRNRGHLMADTDPLRLDKARFRSHPDLEVLTHGLTLWDLRVFKVDGFAGAQYKK
LRDVLGLLRDAYCRHIGVEYAHILDPEQKEWLEQRVETKHVKPTVAQQKYILSKLNAAEAFETFLQTKYVGQK
RFSLEGAESVIPMMDAAIDQCAEHGLDEVVIGMPHRGRLNVLANIVGKPYSQIFTEFEGNLNPSQAHGSGD
VKYHLGATGLYLQMFGDNDIQVSLTANPSHLEAVDPVLEGLVRAKQDLLDHGSIDSDGQRAFSVVPLMLHG
DAAFAGQGVVAETLNLANLPGYRVGGTIHIIVNNQIGFTTAPEYSRSSEYCTDVAKMIGAPIFHVNGDDPEAC
VWVARLAVDFRQRFKKDVVIDMLCYRRRGHNEGDDPSMTNPYMYDVVDTKRGARKSYTEALIGRGDISM
KEAEDALRDYQGQLERVFNEVRELEKHGVQPSESVESDQMIPAGLATAVDKSLLARIGDAFLALPNGFTAHP
RVQPVLEKRREMAYEGKIDWAFGELLALGSLVAEGKLVRLSGQDSRRGTFSQRHSVLIDRHTGEEFTPLQLLA
TNSDGSPTGGKFLVYDSPLSEYAAVGFEYGYTVGNPDAVVLWEAQFGDFVNGAQSIIDEFISSGEAKWGQLS
NVVLLLPHGHEGQGPDHTSARIERFLQLWAEGSMTIAMPSTPSNYFHLLRRHALDGIQRPLIVFTPKSMLRH
KAAVSEIKDFTEIKFRSVLEEPTYEDGIGDRNKVSRILLTSGKLYYELAARKAKDNRNDLAIVRLEQLAPLPRRRL
RETLDRYENVKEFFWVQEEPANQGAWPRFGLELPELLPDKLAGIKRISRRAMSAPSSGSSKVHAVEQQEILDE
AFG

ATGGAAATCAAAGAAATGGTGAGCCTTGCACGCAAGGCTCAGAAGGAGTATCAAGCTACCCATAACCA
AGAAGCAGTTGACAACATTTGCCGAGCTGCAGCAAAAGTTATTTATGAAAATGCAGCTATTCTGGCTCG
CGAAGCAGTAGACGAAACCGGCATGGGCGTTTACGAACACAAAGTGGCCAAGAATCAAGGCAAATCCA
AAGGTGTTTGGTACAACCTCCACAATAAAAAATCGATTGGTATCCTCAATATAGACGAGCGTACCGGTAT
GATCGAGATTGCAAAGCCTATCGGAGTTGTAGGAGCCGTAACGCCGACGACCAACCCGATCGTTACTCC
GATGAGCAATATCATCTTTGCTCTTAAGACCTGCAATGCCATCATTATTGCCCCCCACCCCAGATCCAAAA
AATGCTCTGCACACGCAGTTCGTCTGATCAAAGAAGCTATCGCTCCGTTCAACGTACCGGAAGGTATGG
TTCAGATCATCGAAGAACCCAGCATCGAGAAGACGCAGGAACTCATGGGCGCCGTAGACGTAGTAGTT
GCTACGGGTGGTATGGGCATGGTGAAGTCTGCATATTCTTCAGGAAAGCCTTCTTTCGGTGTTGGAGCC
GGTAACGTTCAGGTGATCGTGGATAGCAACATCGATTTCGAAGCTGCTGCAGAAAAAATCATCACCGGT
CGTGCTTTCGACAACGGTATCATCTGCTCAGGCGAACAGAGCATCATCTACAACGAGGCTGACAAGGAA
GCAGTTTTCACAGCATTCCGCAACCACGGTGCATATTTCTGTGACGAAGCCGAAGGAGATCGGGCTCGT
GCAGCTATCTTCGAAAATGGAGCCATCGCGAAAGATGTAGTAGGTCAGAGCGTTGCCTTCATTGCCAAG
AAAGCAAACATCAATATCCCCGAGGGTACCCGTATTCTCGTTGTTGAAGCTCGCGGCGTAGGAGCAGAA
GACGTTATCTGTAAGGAAAAGATGTGTCCCGTAATGTGCGCCCTCAGCTACAAGCACTTCGAAGAAGGT
GTAGAAATCGCACGTACGAACCTCGCCAACGAAGGTAACGGCCACACCTGTGCTATCCACTCCAACAAT
CAGGCACACATCATCCTCGCAGGATCAGAGCTGACGGTATCTCGTATCGTAGTGAATGCTCCGAGTGCC
ACTACAGCAGGCGGTCACATCCAAAACGGTCTTGCCGTAACCAATACGCTCGGATGCGGATCATGGGGT
AATAACTCTATCTCCGAGAACTTCACTTACAAGCACCTCCTCAACATTTCACGCATCGCACCGTTGAATTC
AAGCATTCACATCCCCGATGACAAAGAAATCTGGGAACTCTAA

B.

MEIKEMVSLARKAQKEYQATHNQEAVDNICRAAAKVIYENAAILAREAVDETGMGVYEHKVAKNQGKSKG
VWYNLHNKKSIGILNIDERTGMIEIAKPIGVVGAVTPTTNPIVTPMSNIIFALKTCNAIIIAPHPRSKKCSAHAVR
LIKEAIAPFNVPEGMVQIIEEPSIEKTQELMGAVDVVVATGGMGMVKSAYSSGKPSFGVGAGNVQIVDSNI
DFEAAAEKIITGRAFDNGIICSGEQSIIYNEADKEAVFTAFRNHGAYFCDEAEGDRARAAIFENGAIAKDVVGQ
SVAFIAKKANINIPEGTRILVVEARGVGAEDVICKEKMCPVMCALSYKHFEEGVEIARTNLANEGNGHTCAIHS
NNQAHIILAGSELTVSRIVVNAPSATTAGGHIQNGLAVTNTLGCGSWGNNSISENFTYKHLLNISRIAPLNSSI
HIPDDKEIWEL

ATGCAACTTTTCAAACTCAAGAGTGTAACACATCACTTTGACACTTTTGCAGAATTTGCCAAGGAATTCTG
TCTTGGAGAACGCGACTTGGTAATTACCAACGAGTTCATCTATGAACCGTATATGAAGGCATGCCAGCTC
CCCTGCCATTTTGTTATGCAGGAGAAATATGGGCAAGGCGAGCCTTCTGACGAAATGATGAATAACATC
TTGGCAGACATCCGTAATATCCAGTTCGACCGCGTAATCGGTATCGGAGGAGGTACGGTTATTGACATC
TCTAAACTTTTCGTTCTGAAAGGATTAAATGATGTACTCGATGCATTCGACCGCAAAATACCTCTTATCAA
AGAGAAAGAACTGATCATTGTGCCCACAACATGCGGAACGGGTAGCGAGGTGACGAACATTTCTATCG
CAGAAATCAAAAGCCGTCACACCAAAATGGGATTGGCTGACGATGCCATTGTTGCAGACCATGCCATCA
TCATACCTGAACTTCTGAAGAGCTTGCCTTTCCACTTCTACGCATGCAGTGCAATCGATGCTCTTATCCAT
GCCATCGAGTCATACGTATCTCCTAAAGCCAGTCCATATTCTCGTCTGTTCAGTGAGGCGGCTTGGGACA
TTATCCTGGAAGTATTCAAGAAAATCGCCGAACACGGCCCTGAATACCGCTTCGAAAAGCTGGGAGAAA
TGATCATGGCCAGCAACTATGCCGGTATAGCCTTCGGAAATGCAGGAGTAGGAGCCGTCCACGCACTAT
CCTACCCGTTGGGAGGCAACTATCACGTGCCGCATGGAGAAGCAAACTATCAGTTCTTCACAGAGGTAT
TCAAAGTATACCAAAAGAAGAATCCTTTCGGCTATATAGTCGAACTCAACTGGAAGCTCTCCAAGATACT
GAACTGCCAGCCCGAATACGTATATCCGAAGCTGGATGAACTTCTCGGATGCCTTCTTACCAAGAAACCT
TTGCACGAATACGGCATGAAGGACGAAGAGGTAAGAGGCTTTGCGGAATCAGTGCTTAAGACACAGCA
AAGATTGCTCGCCAACAACTACGTAGAGCTTACTGTAGATGAGATCGAAGGTATCTACAGAAGACTCTA
CTAA

B.

MQLFKLKSVTHHFDTFAEFAKEFCLGERDLVITNEFIYEPYMKACQLPCHFVMQEKYGQGEPSDEMMNNIL
ADIRNIQFDRVIGIGGGTVIDISKLFVLKGLNDVLDAFDRKIPLIKEKELIIVPTTCGTGSEVTNISIAEIKSRHTKM
GLADDAIVADHAIIIPELLKSLPFHFYACSAIDALIHAIESYVSPKASPYSRLFSEAAWDIILEVFKKIAEHGPEYRFE
KLGEMIMASNYAGIAFGNAGVGAVHALSYPLGGNYHVPHGEANYQFFTEVFKVYQKKNPFGYIVELNWKLS
KILNCQPEYVYPKLDELLGCLLTKKPLHEYGMKDEEVRGFAESVLKTQQRLLANNYVELTVDEIEGIYRRLY

ATGAAAGACGTATTAGCGGAATATGCCTCCCGAATTGTTTCGGCCGAAGAAGCCGTAAAACATATCAAA
AATGGAGAACGGGTAGCTTTGTCACATGCTGCCGGAGTTCCTCAGAGTTGTGTTGATGCACTGGTACAA
CAGGCCGACCTTTTCCAGAATGTCGAAATTTATCACATGCTTTGTCTCGGCGAAGGAAAATATATGGCAC
CTGAAATGGCCCCTCACTTCCGACACATAACCAATTTTGTAGGTGGTAATTCTCGTAAAGCAGTTGAGGA
AAATAGAGCCGACTTCATTCCGGTATTCTTTTATGAAGTGCCATCAATGATTCGCAAAGACATCCTTCACA
TAGATGTCGCCATCGTTCAGCTTTCAATGCCTGATGAGAATGGTTACTGTAGTTTTGGAGTATCTTGCGA
TTATAGCAAACCGGCAGCAGAAAGCGCTCATTTAGTTATAGGGGAAATCAACCGTCAAATGCCATATGT
ACATGGCGACAACTTGATTCACATATCGAAGTTGGATTACATCGTGATGGCAGACTACCCTATCTATTCT
CTTGCAAAGCCCAAAATCGGAGAAGTAGAAGAAGCTATCGGGCGTAATTGTGCCGAGCTTATTGAAGA
TGGTGCCACACTCCAACTCGGTATCGGCGCGATTCCTGATGCAGCCCTGTTATTCCTCAAGGACAAAAAA
GATCTGGGGATCCATACCGAGATGTTCTCCGATGGTGTTGTCGAATTAGTTCGCAGTGGAGTAATTACA
GGAAAGAAAAAGACACTTCACCCCGGAAAGATGGTCGCAACCTTCTTAATGGGAAGCGAAGACGTATA
TCATTTCATCGACAAAAATCCCGATGTAGAACTTTATCCGGTAGATTACGTCAATGATCCGCGAGTAATC
GCTCAAAATGATAATATGGTCAGCATCAATAGCTGTATCGAAATCGATCTTATGGGACAAGTCGTGTCC
GAATGTATAGGAAGCAAGCAATTCAGCGGAACCGGCGGTCAAGTAGATTATGTTCGTGGAGCAGCATG
GTCTAAAAACGGCAAAAGCATCATGGCAATTCCCTCAACAGCCAAAAACGGTACTGCATCTCGAATTGT
ACCTATAATTGCAGAGGGAGCTGCTGTAACAACCCTCCGCAACGAAGTCGATTACGTTGTAACCGAATA
CGGTATAGCACAACTCAAAGGAAAGAGTTTGCGCCAGCGAGCAGAAGCTCTTATTGCCATAGCCCACCC
GGATTTCAGAGAGGAACTAACGAAACATCTCCGCAAACGTTTCGGATAA

B.

MKDVLAEYASRIVSAEEAVKHIKNGERVALSHAAGVPQSCVDALVQQADLFQNVEIYHMLCLGEGKYMAPE
MAPHFRHITNFVGGNSRKAVEENRADFIPVFFYEVPSMIRKDILHIDVAIVQLSMPDENGYCSFGVSCDYSKP
AAESAHLVIGEINRQMPYVHGDNLIHISKLDYIVMADYPIYSLAKPKIGEVEEAIGRNCAELIEDGATLQLGIGAI
PDAALLFLKDKKDLGIHTEMFSDGVVELVRSGVITGKKKTLHPGKMVATFLMGSEDVYHFIDKNPDVELYPV
DYVNDPRVIAQNDNMVSINSCIEIDLMGQVVSECIGSKQFSGTGGQVDYVRGAAWSKNGKSIMAIPSTAKN
GTASRIVPIIAEGAAVTTLRNEVDYVVTEYGIAQLKGKSLRQRAEALIAIAHPDFREELTKHLRKRFG

ATGATTAAGAGTTTTAATGAAATTATCATGAAGGTAAAGAGCAAAGAAATGAAAAAAGTTGCTGT
TGCTGTAGCACAAGACGAGCCAGTACTTGAAGCAGTAAGAGATGCTAAGAAAAATGGTATTGCAG
ATGCTATTCTTGTTGGAGACCATGACGAAATCGTGTCAATCGCGCTTAAAATAGGAATGGATGTA
AATGATTTTGAAATAGTAAACGAGCCTAACGTTAAGAAAGCTGCTTTAAAAGGCAGTAGAGCTTGT
ATCAACTGGAAAAGCTGATATGGTAATGAAGGGACTTGTAAATACAGCAACTTTCTTAAGATCTG
TATTAAACAAGAAGTTGGACTTAGAACAGGAAAAACTATGTCTCACGTTGCAGTATTTGAAACT
GAGAAATTTGATAGACTATTATTTTTAACAGATGTTGCTTTCAATACTTATCCTGAATTAAAGGA
AAAAATTGATATAGTAAACAATTCAGTTAAGGTTGCACATGCAATAGGAATTGAAAATCCAAAGG
TTGCTCCAATTTGTGCAGTTGAGGTTATAAACCCTAAAATGCCATCAACACTTGATGCAGCAATG
CTTTCAAAAATGAGTGACAGAGGACAAATTAAAGGTTGTGTAGTTGACGGACCTTTAGCACTTGA
TATAGCTTTATCAGAAGAAGCAGCACATCATAAGGGAGTAACAGGAGAAGTTGCTGGAAAAGCTG
ATATCTTCTTAATGCCAAACATAGAAACAGGAAATGTAATGTATAAGACTTTAACATATACAACT
GATTCAAAAAATGGAGGAATCTTAGTTGGAACTTCTGCACCAGTTGTTTTAACTTCAAGAGCTGA
CAGCCATGAAACAAAAATGAACTCTATAGCACTTGCAGCTTTAGTTGCAGGCAATAAATAA

B.

MIKSFNEIIMKVKSKEMKKVAVAVAQDEPVLEAVRDAKKNGIADAILVGDHDEIVSIALKIGMDV
NDFEIVNEPNVKKAALKAVELVSTGKADMVMKGLVNTATFLRSVLNKEVGLRTGKTMSHVAVFET
EKFDRLLFLTDVAFNTYPELKEKIDIVNNSVKVAHAIGIENPKVAPICAVEVINPKMPSTLDAAM
LSKMSDRGQIKGCVVDGPLALDIALSEEAAHHKGVTGEVAGKADIFLMPNIETGNVMYKTLTYTT
DSKNGGILVGTSAPVVLTSRADSHETKMNSIALAALVAGNK

ATGTATAGATTACTAATAATCAATCCTGGCTCGACCTCAACTAAAATTGGTATTTATGACGATGA
AAAAGAGATATTTGAGAAGACTTTAAGACATTCAGCTGAAGAGATAGAAAAATATAACACTATAT
TTGATCAATTTCAATTCAGAAAGAATGTAATTTTAGATGCGTTAAAAGAAGCAAACATAGAAGTA
AGTTCTTTAAATGCTGTAGTTGGAAGAGGCGGACTCTTAAAGCCAATAGTAAGTGGAACTTATGC
AGTAAATCAAAAAATGCTTGAAGACCTTAAAGTAGGAGTTCAAGGTCAGCATGCGTCAAATCTTG
GTGGAATTATTGCAAATGAAATAGCAAAAGAAATAAATGTTCCAGCATACATAGTTGATCCAGTT
GTTGTGGATGAGCTTGATGAAGTTTCAAGAATATCAGGAATGGCTGACATTCCAAGAAAAAGTAT
ATTCCATGCATTAAATCAAAAAGCAGTTGCTAGAAGATATGCAAAAGAAGTTGGAAAAAAATACG
AAGATCTTAATTTAATCGTAGTCCACATGGGTGGAGGTACTTCAGTAGGTACTCATAAAGATGGT
AGAGTAATAGAAGTTAATAATACACTTGATGGAGAAGGTCCATTCTCACCAGAAAGAAGTGGTGG
AGTTCCAATAGGAGATCTTGTAAGATTGTGCTTCAGCAACAAATATACTTATGAAGAAGTAATGA
AAAAGATAAACGGCAAAGGCGGAGTTGTAGTTACTTAAATACTATCGATTTTAAGGCTGTAGTT
GATAAAGCTCTTGAAGGAGATAAGAAATGTGCACTTATATATGAAGCTTTCACATTCCAGGTAGC
AAAAGAGATAGGAAAATGTTCAACCGTTTTAAAAGGAAATGTAGATGCAATAATCTTAACAGGCG
GAATTGCGTACAACGAGCATGTATGTAATGCCATAGAGGATAGAGTAAAATTCATAGCACCTGTA
GTTAGATATGGTGGAGAAGATGAACTTCTTGCACTTGCAGAAGGTGGACTTAGAGTTTTAAGAGG
AGAAGAAAAAGCTAAGGAATACAAATAA

B.

MYRLLIINPGSTSTKIGIYDDEKEIFEKTLRHSAEEIEKYNTIFDQFQFRKNVILDALKEANIEV
SSLNAVVGRGGLLKPIVSGTYAVNQKMLEDLKVGVQGQHASNLGGIIANEIAKEINVPAYIVDPV
VVDELDEVSRISGMADIPRKSIPHALNQKAVARRYAKEVGKKYEDLNLIVVHMGGGTSVGTHKDG
RVIEVNNTLDGEGPFSPERSGGVPIGDLVRLCFSNKYTYEEVMKKINGKGGVVSYLNTIDFKAVV
DKALEGDKKCALIYEAFTFQVAKEIGKCSTVLKGNVDAIILTGGIAYNEHVCNAIEDRVKFIAPV
VRYGGEDELLALAEGGLRVLRGEEKAKEYK

ATGATTAAGAGTTTTAATGAAATTATCATGAAGGTAAAGAGCAAAGAAATGAAAAAAGTTGCTGT
TGCTGTAGCACAAGACGAGCCAGTACTTGAAGCAGTACGCGATGCTAAGAAAAATGGTATTGCAG
ATGCTATTCTTGTTGGCGACCATGACGAAATCGTGTCAATCGCGCTTAAAATAGGCATGGATGTA
AATGATTTTGAAATAGTAAACGAGCCTAACGTTAAGAAAGCTGCTTTAAAGGCAGTAGAGCTGGT
ATCAACTGGAAAAGCTGATATGGTAATGAAGGGACTTGTAAATACAGCAACTTTCTTACGCTCTG
TATTAAACAAAGAAGTTGGACTGAGAACAGGAAAAACTATGTCTCACGTTGCAGTATTTGAAACT
GAGAAATTTGATCGTCTGTTATTTTTAACAGATGTTGCTTTCAATACTTATCCTGAATTAAAGGA
AAAAATTGATATCGTAAACAATTCAGTTAAGGTTGCACATGCAATAGGTATTGAAAATCCAAAGG
TTGCTCCAATTTGTGCAGTTGAGGTTATAAACCCTAAAATGCCATCAACACTTGATGCAGCAATG
CTTTCAAAAATGAGTGACAGAGGACAAATTAAAGGTTGTGTAGTTGACGGACCGTTAGCACTTGA
TATCGCTTTATCAGAAGAAGCAGCACATCATAAGGGCGTAACAGGAGAAGTTGCTGGAAAAGCTG
ATATCTTCTTAATGCCAAACATTGAAACAGGAAATGTAATGTATAAGACTTTAACATATACAACT
GATAGCAAAAATGGCGGAATCTTAGTTGGAACTTCTGCACCAGTTGTTTTAACTTCACGCGCTGA
CAGCCATGAAACAAAAATGAACTCTATTGCACTTGCAGCTTTAGTTGCAGGCAATAAATAA

B.

ATGATTAAGAGTTTTAATGAAATTATCATGAAGGTAAAGAGCAAAGAAATGAAAAAAGTTGCTGT
TGCTGTAGCACAAGACGAGCCAGTACTTGAAGCAGTACGCGATGCTAAGAAAAATGGTATTGCCG
ATGCTATTCTGGTTGGCGACCATGACGAAATCGTGTCTATCGCGCTGAAAATAGGCATGGATGTA
AATGATTTTGAAATTGTTAACGAGCCTAACGTTAAGAAAGCTGCGTTAAAGGCAGTAGAGCTGGT
ATCAACTGGAAAAGCTGATATGGTAATGAAGGGACTGGTAAATACCGCAACTTTCTTACGCTCTG
TATTAAACAAAGAAGTTGGTCTGCGTACAGGAAAAACCATGTCTCACGTTGCAGTATTTGAAACT
GAGAAATTTGATCGTCTGTTATTTTTAACAGATGTTGCTTTCAATACTTATCCTGAATTAAAGGA
AAAAATTGATATCGTTAACAATAGCGTTAAGGTTGCACATGCCATTGGTATTGAAAATCCAAAGG
TTGCTCCAATTTGTGCAGTTGAGGTTATTAACCCGAAAATGCCATCAACACTTGATGCAGCAATG
CTTTCAAAAATGAGTGACCGCGGACAAATTAAAGGTTGTGTAGTTGACGGACCGCTGGCACTTGA
TATCGCTTTATCAGAAGAAGCAGCACATCATAAAGGCGTAACAGGAGAAGTTGCTGGAAAAGCTG
ATATCTTCTTAATGCCAAACATTGAAACAGGAAATGTAATGTATAAGACGTTAACCTATACCACT
GATAGCAAAAATGGCGGCATCCTGGTTGGAACTTCTGCACCAGTTGTTTTAACTTCACGCGCTGA
CAGCCATGAAACAAAAATGAACTCTATTGCACTGGCAGCGCTGGTTGCAGGCAATAAATAA

ATGATTAAGAGTTTTAATGAAATTATCATGAAGGTAAAGAGCAAAGAAATGAAAAAAGTTGCTGT
TGCTGTTGCACAAGACGAGCCGGTACTGGAAGCGGTACGCGATGCTAAGAAAAATGGTATTGCCG
ATGCTATTCTGGTTGGCGACCATGACGAAATCGTCTCTATCGCGCTGAAAATTGGCATGGATGTT
AATGATTTTGAAATTGTTAACGAGCCTAACGTTAAGAAAGCTGCGCTGAAGGCGGTAGAGCTGGT
TTCCACCGGAAAAGCTGATATGGTAATGAAAGGGCTGGTGAATACCGCAACTTTCTTACGCAGCG
TACTGAACAAGAAGTTGGTCTGCGTACCGGAAAAACCATGAGTCACGTTGCGGTATTTGAAACT
GAGAAATTTGATCGTCTGCTGTTTCTGACCGATGTTGCTTTCAATACTTATCCTGAATTAAAAGA
AAAAATTGATATCGTTAACAATAGCGTTAAGGTTGCGCATGCCATTGGTATTGAAAATCCAAAGG
TTGCTCCAATTTGTGCAGTTGAGGTTATTAACCCGAAAATGCCATCAACACTTGATGCCGCAATG
CTTAGCAAAATGAGTGACCGCGGACAAATTAAAGGTTGTGTGGTTGACGGCCCGCTGGCACTGGA
TATCGCGTTAAGCGAAGAAGCGGCACATCATAAAGGCGTAACCGGCGAAGTTGCTGGAAAAGCTG
ATATCTTCCTGATGCCAAACATTGAAACAGGCAATGTAATGTATAAAACGTTAACCTATACCACT
GATAGCAAAAATGGCGGCATCCTGGTTGGAACTTCTGCACCAGTTGTTTTAACCTCACGCGCTGA
CAGCCATGAAACCAAAATGAACAGCATTGCACTGGCAGCGCTGGTTGCAGGCAATAAATAA

D.

ATGATTAAAAGTTTTAACGAAATTATCATGAAAGTGAAAAGCAAAGAGATGAAAAAAGTGGCGGT
TGCGGTTGCGCAGGATGAACCGGTGCTGGAAGCGGTGCGCGATGCCAAAAAAAACGGTATTGCCG
ATGCCATTCTGGTGGGCGATCACGATGAAATTGTCTCTATTGCGCTGAAAATTGGCATGGATGTT
AACGATTTTGAAATTGTTAATGAACCGAACGTGAAAAAAGCGGCGCTGAAAGCGGTTGAACTGGT
TTCCACCGGTAAAGCCGATATGGTGATGAAAGGGCTGGTGAATACCGCAACCTTCCTGCGCAGCG
TGCTGAATAAAGAAGTGGGTCTGCGTACCGGTAAAACCATGAGTCATGTTGCGGTGTTTGAAACC
GAAAAATTTGACCGTCTGCTGTTTCTGACCGATGTTGCGTTTAATACCTATCCGGAACTGAAAGA
GAAAATTGATATCGTTAATAACAGCGTGAAAGTGGCGCATGCCATTGGTATTGAAAACCCGAAAG
TGGCGCCGATTTGCGCGGTTGAAGTGATTAACCCGAAAATGCCGTCAACGCTGGATGCCGCGATG
CTCAGCAAAATGAGCGATCGCGGTCAAATCAAAGGCTGTGTGGTTGATGGCCCGCTGGCGCTGGA
TATCGCGCTTAGCGAAGAAGCGGCGCATCATAAAGGCGTGACCGGCGAAGTGGCCGGTAAAGCCG
ATATTTTCCTGATGCCGAATATTGAAACCGGCAACGTGATGTATAAAACGCTGACCTATACCACC
GACAGCAAAAACGGCGGCATTCTGGTGGGTACCAGCGCGCCGGTGGTGCTGACCTCGCGCGCCGA
CAGCCATGAAACCAAAATGAACAGCATTGCGCTGGCGGCGCTGGTGGCCGGTAATAAATAA

ATGTATCGTTTACTGATTATCAATCCTGGCTCGACCTCAACTAAAATTGGTATTTATGACGATGA
AAAAGAGATATTTGAGAAGACTTTACGTCATTCAGCTGAAGAGATAGAAAAATATAACACTATAT
TTGATCAATTTCAGTTCAGAAAGAATGTAATTCTCGATGCGTTAAAAGAAGCAAACATTGAAGTA
AGTTCTTTAAATGCTGTAGTTGGACGCGGCGGACTGTTAAAGCCAATAGTAAGTGGAACTTATGC
AGTAAATCAAAAAATGCTTGAAGACCTTAAAGTAGGCGTTCAAGGTCAGCATGCGTCAAATCTTG
GTGGAATTATTGCAAATGAAATAGCAAAAGAAATAAATGTTCCAGCATACATCGTTGATCCAGTT
GTTGTGGATGAGCTTGATGAAGTTTCACGTATATCAGGAATGGCTGACATTCCACGTAAAAGTAT
ATTCCATGCATTAAATCAAAAAGCAGTTGCTAGACGCTATGCAAAAGAAGTTGGAAAAAAATACG
AAGATCTTAATTTAATCGTGGTCCACATGGGTGGCGGTACTTCAGTAGGTACTCATAAAGATGGT
AGAGTAATTGAAGTTAATAATACACTTGATGGAGAAGGTCCATTCTCACCAGAAAGAAGTGGTGG
CGTTCCAATAGGCGATCTTGTACGTTTGTGCTTCAGCAACAAATATACTTATGAAGAAGTAATGA
AAAAGATAAACGGCAAAGGCGGCGTTGTTAGTTACTTAAATACTATCGATTTTAAGGCTGTAGTT
GATAAAGCTCTTGAAGGCGATAAGAAATGTGCACTTATATATGAAGCTTTCACATTCCAGGTAGC
AAAAGAGATAGGAAAATGTTCAACCGTTTTAAAAGGAAATGTAGATGCAATAATCTTAACAGGCG
GAATTGCGTACAACGAGCATGTATGTAATGCCATAGAGGATAGAGTAAAATTCATTGCACCTGTA
GTTCGTTATGGTGGAGAAGATGAACTTCTTGCACTTGCAGAAGGTGGACTGCGCGTTTTACGCGG
AGAAGAAAAAGCTAAGGAATACAAATAA

B.

ATGTATCGTTTACTGATTATCAATCCTGGCTCGACCTCAACTAAAATTGGTATTTATGACGATGA
AAAAGAGATATTTGAGAAGACGTTACGTCATTCAGCTGAAGAGATTGAAAAATATAACACTATAT
TTGATCAATTTCAGTTCCGCAAGAATGTGATTCTCGATGCGTTAAAAGAAGCAAACATTGAAGTC
AGTTCTTTAAATGCTGTAGTTGGACGCGGCGGACTGTTAAAGCCAATTGTCAGTGGAACTTATGC
AGTAAATCAAAAAATGCTTGAAGACCTTAAAGTGGGCGTTCAAGGTCAGCATGCCAGCAATCTTG
GTGGCATTATTGCCAATGAAATCGCAAAAGAAATCAATGTTCCAGCATACATCGTTGATCCGGTT
GTTGTGGATGAGCTTGATGAAGTTAGCCGTATAAGCGGAATGGCTGACATTCCACGTAAAAGTAT
ATTCCATGCATTAAATCAAAAAGCAGTTGCTCGTCGCTATGCAAAAGAAGTTGGTAAAAAATACG
AAGATCTTAATTTAATCGTGGTCCACATGGGTGGCGGTACTTCAGTAGGTACTCATAAAGATGGT
CGCGTGATTGAAGTTAATAATACACTTGATGGCGAAGGTCCATTCTCACCAGAACGTAGTGGTGG
CGTTCCAATTGGCGATCTGGTACGTTTGTGCTTCAGCAACAAATATACTTATGAAGAAGTGATGA
AAAAGATAAACGGCAAAGGCGGCGTTGTTAGTTACCTGAATACTATCGATTTTAAGGCTGTAGTT
GATAAAGCGCTTGAAGGCGATAAGAAATGTGCACTGATTTATGAAGCTTTCACCTTCCAGGTAGC
AAAAGAGATTGGTAAATGTTCAACCGTTTTAAAAGGAAATGTTGATGCCATTATCTTAACAGGCG
GCATTGCTTACAACGAGCATGTATGTAATGCCATTGAGGATCGCGTAAAATTCATTGCACCTGTA
GTTCGTTATGGTGGCGAAGATGAACTGCTGGCACTGGCAGAAGGTGGACTGCGCGTTTTACGCGG
CGAAGAAAAGCGAAGGAATACAAATAA

ATGTATCGTCTGCTGATTATCAATCCTGGCTCGACCTCAACTAAAATTGGTATTTATGACGATGA
AAAAGAGATATTTGAGAAAACGTTACGTCATAGCGCTGAAGAGATTGAAAAATATAACACTATTT
TTGATCAATTTCAGTTCCGCAAGAATGTGATTCTCGATGCGCTGAAAGAAGCAAACATTGAAGTC
AGTTCGCTGAATGCGGTAGTTGGTCGCGGCGGTCTGCTGAAGCCAATTGTCAGCGGCACTTATGC
GGTAAATCAAAAATGCTGGAAGACCTGAAAGTGGGCGTTCAGGGCAGCATGCCAGCAATCTTG
GTGGCATTATTGCCAATGAAATCGCCAAAGAAATCAATGTCCGGCATACATCGTTGATCCGGTT
GTTGTGGATGAGCTGGATGAAGTTAGCCGTATCAGCGGAATGGCTGACATTCCACGTAAAAGTAT
TTTCCATGCACTGAATCAAAAAGCGGTTGCGCGTCGCTATGCAAAAGAAGTTGGTAAAAAATACG
AAGATCTTAATCTGATCGTGGTGCATATGGGTGGCGGTACTAGCGTCGGTACTCATAAAGATGGT
CGCGTGATTGAAGTTAATAATACACTTGATGGCGAAGGTCCATTCTCACCAGAACGTAGCGGTGG
CGTTCCAATTGGCGATCTGGTACGTTTGTGCTTCAGCAACAAATATACCTATGAAGAAGTGATGA
AAAAGATAAACGGCAAAGGCGGCGTTGTTAGTTACCTGAATACTATCGATTTTAAGGCGGTAGTT
GATAAAGCGCTGGAAGGCGATAAGAAATGTGCACTGATTTATGAAGCGTTCACCTTCCAGGTGGC
AAAAGAGATTGGTAAATGTTCAACCGTTCTGAAAGGCAATGTTGATGCCATTATCCTGACCGGCG
GCATTGCTTACAACGAGCATGTTTGTAATGCCATTGAGGATCGCGTAAAATTCATTGCACCTGTG
GTTCGTTATGGTGGCGAAGATGAACTGCTGGCACTGGCAGAAGGTGGTCTGCGCGTTTTACGCGG
CGAAGAAAAAGCGAAAGAATACAAATAA

D.

ATGTATCGTCTGCTGATTATCAACCCGGGCAGCACCTCAACCAAAATTGGTATTTACGACGATGA
AAAAGAGATTTTTGAAAAAACGCTGCGTCACAGCGCAGAAGAGATTGAAAAATACAACACCATTT
TCGATCAGTTCCAGTTCCGCAAAAACGTGATTCTCGATGCGCTGAAAGAAGCCAATATTGAAGTC
TCCTCGCTGAATGCGGTGGTCGGTCGCGGCGGTCTGCTGAAACCGATTGTCAGCGGCACTTATGC
GGTTAATCAGAAAATGCTGGAAGATCTGAAAGTGGGCGTGCAGGGCAGCATGCCAGCAATCTCG
GCGGCATTATCGCCAATGAAATCGCCAAAGAGATCAACGTGCCGGCTTATATCGTCGATCCGGTG
GTGGTTGATGAACTGGATGAAGTCAGCCGTATCAGCGGCATGGCGGATATTCCGCGTAAAAGCAT
TTTCCATGCGCTGAATCAGAAAGCGGTTGCGCGTCGCTATGCCAAAGAAGTGGGTAAAAAATATG
AAGATCTCAATCTGATTGTGGTGCATATGGGCGGCGGCACCAGCGTCGGTACGCATAAAGATGGT
CGCGTGATTGAAGTGAATAACACGCTGGATGGCGAAGGCCGTTCTCGCCGGAACGTAGCGGCGG
CGTGCCGATTGGCGATCTGGTGCGTCTGTGTTTCAGCAATAAATACACCTACGAAGAAGTGATGA
AAAAAATCAACGGCAAAGGCGGCGTGGTTAGCTATCTGAATACCATCGATTTTAAAGCGGTGGTT
GATAAAGCGCTGGAAGGCGATAAAAAATGCGCGCTGATTTATGAAGCGTTTACCTTCCAGGTGGC
GAAAGAGATTGGTAAATGTTCAACCGTGCTGAAAGGCAACGTTGATGCCATTATTCTGACCGGCG
GCATTGCTTATAACGAACATGTTTGTAATGCCATTGAAGATCGCGTGAAATTTATTGCGCCGGTG
GTGCGTTACGGCGGCGAAGATGAACTGCTGGCGCTGGCGGAAGGCGGTCTGCGCGTGCTGCGCGG
CGAAGAAAAAGCGAAAGAGTACAAATAA

ATGAATAAAGACACACTAATACCTACAACTAAAGATTTAAAAGTAAAAACAAATGGTGAAAACAT
TAATTTAAAGAACTACAAGGATAATTCTTCATGTTTCGGAGTATTCGAAAATGTTGAAAATGCTA
TAAGCAGCGCTGTACACGCACAAAAGATATTATCCCTTCATTATACAAAAGAGCAAAGAGAAAAA
ATCATAACTGAGATAAGAAAGGCCGCATTACAAAATAAAGAGGTCTTGGCTACAATGATTCTAGA
AGAAACACATATGGGAAGATATGAGGATAAAATATTAAAACATGAATTGGTAGCTAAATATACTC
CTGGTACAGAAGATTTAACTACTACTGCTTGGTCAGGTGATAATGGTCTTACAGTTGTAGAAATG
TCTCCATATGGTGTTATAGGTGCAATAACTCCTTCTACGAATCCAACTGAAACTGTAATATGTAA
TAGCATAGGCATGATAGCTGCTGGAAATGCTGTAGTATTAACGGACACCCATGCGCTAAAAAAT
GTGTTGCCTTTGCTGTTGAAATGATAAATAAGGCAATTATTTCATGTGGCGGTCCTGAAAATCTA
GTAACAACTATAAAAAATCCAACTATGGAGTCTCTAGATGCAATTATTAAGCATCCTTCAATAAA
ACTTCTTTGCGGAACTGGGGGTCCAGGAATGGTAAAAACCCTCTTAAATTCTGGTAAGAAAGCTA
TAGGTGCTGGTGCTGGAAATCCACCAGTTATTGTAGATGATACTGCTGATATAGAAAAGGCTGGT
AGGAGCATCATTGAAGGCTGTTCTTTTGATAATAATTTACCTTGTATTGCAGAAAAAGAAGTATT
TGTTTTTGAGAATGTTGCAGATGATTTAATATCTAACATGCTAAAAAATAATGCTGTAATTATAA
ATGAAGATCAAGTATCAAAATTAATAGATTTAGTATTACAAAAAAATAATGAAACTCAAGAATAC
TTTATAAACAAAAAATGGGTAGGAAAAGATGCAAAATTATTCTTAGATGAAATAGATGTTGAGTC
TCCTTCAAATGTTAAATGCATAATCTGCGAAGTAAATGCAAATCATCCATTTGTTATGACAGAAC
TCATGATGCCAATATTGCCAATTGTAAGAGTTAAAGATATAGATGAAGCTATTAAATATGCAAAG
ATAGCAGAACAAAATAGAAAACATAGTGCCTATATTTATTCTAAAAATATAGACAACCTAAATAG
ATTTGAAAGAGAAATAGATACTACTATTTTTGTAAAGAATGCTAAATCTTTTGCTGGTGTTGGTT
ATGAAGCAGAAGGATTTACAACTTTCACTATTGCTGGATCTACTGGTGAGGGAATAACCTCTGCA
AGGAATTTTACAAGACAAAGAAGATGTGTACTTGCCGGCTAA

B.

MNKDTLIPTTKDLKVKTNGENINLKNYKDNSSCFGVFENVENAISSAVHAQKILSLHYTKEQREK
IITEIRKAALQNKEVLATMILEETHMGRYEDKILKHELVAKYTPGTEDLTTTAWSGDNGLTVVEM
SPYGVIGAITPSTNPTETVICNSIGMIAAGNAVVFNGHPCAKKCVAFAVEMINKAIISCGGPENL
VTTIKNPTMESLDAIIKHPSIKLLCGTGGPGMVKTLLNSGKKAIGAGAGNPPVIVDDTADIEKAG
RSIIEGCSFDNNLPCIAEKEVFVFENVADDLISNMLKNNAVIINEDQVSKLIDLVLQKMNETQEY
FINKKWVGKDAKLFLDEIDVESPSNVKCIICEVNANHPFVMTELMMPILPIVRVKDIDEAIKYAK
IAEQNRKHSAYIYSKNIDNLNRFEREIDTTIFVKNAKSFAGVGYEAEGFTTFTIAGSTGEGITSA
RNFTRQRRCVLAG

ATGAATAAAGACACACTAATACCTACAACTAAAGATTTAAAAGTAAAAACAAATGGTGAAAACAT
TAATTTAAAGAACTACAAGGATAATTCTTCATGTTTCGGCGTATTCGAAAATGTTGAAAATGCTA
TAAGCAGCGCTGTACACGCACAAAAGATATTATCCCTTCATTATACAAAAGAGCAACGTGAAAAA
ATCATAACTGAGATAAGAAAGGCCGCATTACAAAATAAAGAGGTCTTGGCTACAATGATTCTGGA
AGAAACACATATGGGACGTTATGAGGATAAAATATTAAAACATGAATTGGTAGCTAAATATACTC
CTGGTACAGAAGATTTAACTACTACTGCCTGGTCAGGTGATAATGGTCTGACAGTTGTAGAAATG
TCTCCATATGGTGTTATTGGTGCAATAACTCCTTCTACGAATCCAACTGAAACTGTAATATGTAA
TAGCATAGGCATGATTGCTGCTGGAAATGCTGTAGTATTAACGGACACCCATGCGCTAAAAAAT
GTGTTGCCTTTGCTGTTGAAATGATAAATAAGGCAATTATTTCATGTGGCGGTCCTGAAAATCTG
GTAACAACTATAAAAAATCCAACCATGGAGTCTCTGGATGCAATTATTAAGCATCCTTCAATAAA
ACTTCTTTGCGGAACTGGGGGTCCAGGAATGGTAAAAACCCTGTTAAATTCTGGTAAGAAAGCTA
TAGGTGCTGGTGCTGGAAATCCACCAGTTATTGTCGATGATACTGCTGATATAGAAAAGGCTGGT
CGTAGCATCATTGAAGGCTGTTCTTTTGATAATAATTTACCTTGTATTGCAGAAAAAGAAGTATT
TGTTTTTGAGAATGTTGCAGATGATTTAATATCTAACATGCTAAAAAATAATGCTGTAATTATAA
ATGAAGATCAAGTATCAAAATTAATCGATTTAGTATTACAAAAAAATAATGAAACTCAAGAATAC
TTTATAAACAAAAAATGGGTAGGAAAAGATGCAAAATTATTCCTCGATGAAATAGATGTTGAGTC
TCCTTCAAATGTTAAATGCATAATCTGCGAAGTAAATGCAAATCATCCATTTGTTATGACAGAAC
TGATGATGCCAATATTGCCAATTGTACGCGTTAAAGATATCGATGAAGCTATTAAATATGCAAAG
ATAGCAGAACAAAATAGAAAACATAGTGCCTATATTTATTCTAAAAATATCGACAACCTGAATCG
CTTTGAACGTGAAATAGATACTACTATTTTTGTAAAGAATGCTAAATCTTTTGCTGGTGTTGGTT
ATGAAGCAGAAGGATTTACAACTTTCACTATTGCTGGATCTACTGGTGAGGGAATAACCTCTGCA
CGTAATTTTACACGCCAACGTCGCTGTGTACTTGCCGGCTAA

B.

ATGAATAAAGACACACTGATCCCTACAACTAAAGATTTAAAAGTAAAAACAAATGGTGAAAACAT
TAATTTAAAGAACTACAAAGATAATAGCAGTTGTTTCGGCGTATTCGAAAATGTTGAAAATGCTA
TCAGCAGCGCTGTACACGCACAAAAGATATTATCGCTGCATTATACAAAAGAGCAACGTGAAAAA
ATCATCACTGAGATACGTAAGGCCGCATTACAAAATAAAGAGGTGCTGGCTACAATGATTCTGGA
AGAAACACATATGGGACGTTATGAGGATAAAATATTAAAACATGAACTGGTAGCTAAATATACTC
CTGGTACAGAAGATTTAACTACTACTGCCTGGAGCGGTGATAATGGTCTGACAGTTGTAGAAATG
TCTCCATATGGTGTTATTGGTGCAATAACTCCTTCTACCAATCCAACTGAAACTGTAATTTGTAA
TAGCATTGGCATGATTGCTGCTGGAAATGCTGTAGTATTAACGGACACCCATGCGCTAAAAAAT
GTGTTGCCTTTGCTGTTGAAATGATCAATAAGGCAATTATTAGCTGTGGCGGTCCGGAAAATCTG
GTAACAACTATAAAAAATCCAACCATGGAGTCTCTGGATGCCATTATTAAGCATCCTTCAATAAA
ACTGCTTTGCGGAACTGGCGGTCCAGGAATGGTAAAAACCCTGTTAAATTCTGGTAAGAAAGCTA
TTGGTGCTGGTGCTGGAAATCCACCAGTTATTGTCGATGATACTGCTGATATTGAAAAGGCTGGT
CGTAGCATCATTGAAGGCTGTTCTTTTGATAATAATTTACCTTGTATTGCAGAAAAAGAAGTATT
TGTTTTTGAGAATGTTGCAGATGATTTAATATCTAACATGCTGAAAAATAATGCTGTAATTATCA
ATGAAGATCAGGTATCAAAATTAATCGATTTAGTATTACAAAAAAATAATGAAACTCAAGAATAC
TTTATCAACAAAAAATGGGTAGGTAAAGATGCAAAATTATTCCTCGATGAAATCGATGTTGAGTC
TCCTTCAAATGTTAAATGCATTATCTGCGAAGTGAATGCCAATCATCC

FIG. 28

ATTTGTTATGACAGAACTGATGATGCCAATATTGCCAATTGTGCGCGTTAAAGATATCGATGAAG
CTATTAAATATGCAAAGATTGCAGAACAAAATAGAAAACATAGTGCCTATATTTATAGCAAAAAT
ATCGACAACCTGAATCGCTTTGAACGTGAAATCGATACTACTATTTTTGTAAAGAATGCTAAATC
TTTTGCTGGTGTTGGTTATGAAGCAGAAGGATTTACCACTTTCACTATTGCTGGATCTACTGGTG
AGGGCATAACCTCTGCACGTAATTTTACCCGCCAACGTCGCTGTGTACTGGCCGGCTAA

C.

ATGAATAAAGACACGCTGATCCCGACAACTAAAGATCTGAAAGTAAAAACCAATGGTGAAAACAT
TAATCTGAAGAACTACAAAGATAATAGCAGTTGTTTCGGCGTATTCGAAAATGTTGAAAATGCTA
TCAGCAGCGCGGTACACGCACAAAAGATACTCTCGCTGCATTATACCAAAGAGCAACGTGAAAAA
ATCATCACTGAGATCCGTAAGGCCGCATTACAAAATAAAGAGGTGCTGGCAACAATGATTCTGGA
AGAAACACATATGGGACGTTATGAGGATAAAATACTGAAACATGAACTGGTGGCGAAATATACGC
CTGGTACTGAAGATTTAACCACCACTGCCTGGAGCGGTGATAATGGTCTGACCGTTGTGGAAATG
TCGCCTTATGGTGTTATTGGTGCAATTACGCCTTCAACCAATCCAACTGAAACGGTAATTTGTAA
TAGCATTGGCATGATTGCTGCTGGAAATGCGGTAGTATTTAACGGTCACCCCTGCGCTAAAAAAT
GTGTTGCCTTTGCTGTTGAAATGATCAATAAAGCGATTATTAGCTGTGGCGGTCCGGAAAATCTG
GTAACCACTATAAAAAATCCAACCATGGAGTCGCTGGATGCCATTATTAAGCATCCTTCAATCAA
ACTGCTGTGCGGCACTGGCGGTCCAGGAATGGTGAAAACCCTGCTGAATAGCGGTAAGAAAGCGA
TTGGTGCTGGTGCTGGAAATCCACCAGTTATTGTCGATGATACTGCTGATATTGAAAAAGCGGGT
CGTAGCATCATTGAAGGCTGTTCTTTTGATAATAATTTACCTTGTATTGCAGAAAAAGAAGTATT
TGTTTTTGAGAATGTTGCCGATGATCTGATCTCTAACATGCTGAAAAATAATGCGGTGATTATCA
ATGAAGATCAGGTTAGCAAACTGATCGATCTGGTATTACAAAAAAATAATGAAACTCAAGAATAC
TTTATCAACAAAAAATGGGTAGGTAAAGATGCAAAACTGTTCCTCGATGAAATCGATGTTGAGTC
GCCTTCAAATGTTAAATGCATTATCTGCGAAGTGAATGCCAATCATCCATTTGTGATGACCGAAC
TGATGATGCCAATTTTGCCGATTGTGCGCGTTAAAGATATCGATGAAGCGATTAAATATGCAAAG
ATTGCAGAACAAAATCGTAAACATAGTGCCTATATTTATAGCAAAAATATCGACAACCTGAATCG
CTTTGAACGTGAAATCGATACCACTATTTTTGTGAAGAATGCTAAATCTTTTGCTGGTGTTGGTT
ATGAAGCAGAAGGTTTTACCACTTTCACTATTGCTGGAAGCACCGGTGAAGGCATTACCTCTGCA
CGTAATTTACCCGCCAACGTCGCTGTGTACTGGCCGGCTAA

D.

ATGAATAAAGATACGCTGATCCCGACCACCAAAGATCTGAAAGTGAAAACCAACGGCGAAAATAT
CAACCTGAAAAACTATAAAGATAACAGCAGTTGCTTTGGCGTGTTTGAAAACGTTGAAAACGCCA
TCTCCAGCGCGGTGCATGCGCAAAAAATTCTCTCGCTGCATTACACCAAAGAGCAGCGTGAAAAA
ATTATCACCGAAATCCGTAAAGCGGCGCTGCAAAACAAAGAAGTGCTGGCAACCATGATCCTGGA
AGAAACGCATATGGGGCGTTATGAAGATAAAATTCTGAAACATGAACTGGTGGCGAAATACACGC
CGGGCACTGAAGATCTGACCACCACCGCCTGGAGCGGCGATAACGGCCTGACCGTGGTGGAGATG
TCGCCTTATGGCGTGATTGGCGCGATTACGCCGTCAACCAACCCGACCGAAACGGTGATTTGTAA
CAGCATTGGCATGATTGCCGCGGGTAATGCGGTGGTGTTTAACGGTCATCCCTGCGCGAAAAAAT
GTGTGGCGTTTGCCGTTGAGATGATCAACAAAGCGATTATCAGCTGCGGCGGCCCGGAAAATCTG
GTGACCACCATCAAAAATCCGACCATGGAATCGCTGGATGCCATTATCAAACATCCTTCCATCAA
ACTGCTGTGCGGCACCGGCGGCCCGGGCATGGTGAAAACGCTGCTGAACAGCGGTAAAAAAGCGA
TTGGCGCGGGCGCGGGTAACCCGCCGGTGATTGTCGATGACACCGCCGATATT

FIG. 28 (cont'd)

```
GAAAAAGCGGGGCGTAGCATTATTGAAGGCTGTTCTTTTGATAACAACCTGCCCTGCATTGCCGA
AAAAGAAGTGTTTGTCTTTGAAAACGTCGCCGATGATCTGATCAGCAATATGCTGAAAAACAACG
CGGTGATTATCAATGAAGATCAGGTTAGCAAACTGATCGATCTGGTGCTGCAAAAAAACAACGAA
ACGCAGGAATATTTTATCAACAAAAAATGGGTTGGTAAAGATGCCAAACTGTTTCTCGATGAAAT
CGATGTTGAATCGCCGTCTAACGTGAAATGTATTATCTGCGAAGTGAACGCCAACCATCCGTTTG
TGATGACCGAACTGATGATGCCGATTCTGCCGATTGTGCGCGTGAAAGATATCGATGAAGCGATT
AAATATGCCAAAATTGCCGAACAAAACCGTAAACACAGCGCCTATATTTACAGCAAAAATATCGA
TAACCTGAACCGCTTTGAACGTGAAATCGATACCACCATTTTTGTGAAAAATGCCAAAAGTTTTG
CCGGCGTTGGTTATGAAGCGGAAGGTTTTACCACCTTTACCATTGCCGGTAGCACCGGCGAAGGC
ATTACCAGCGCCCGTAATTTTACCCGCCAGCGTCGCTGCGTGCTGGCGGGCTAA
```

ATGAAAGCTGCAGTAGTAGAGCAATTTAAGGAACCATTAAAAATTAAAGAAGTGGAAAAGCCATC
TATTTCATATGGCGAAGTATTAGTCCGCATTAAAGCATGCGGTGTATGCCATACGGACTTGCACG
CCGCTCATGGCGATTGGCCAGTAAAACCAAAACTTCCTTTAATCCCTGGCCATGAAGGAGTCGGA
ATTGTTGAAGAAGTCGGTCCGGGGGTAACCCATTTAAAAGTGGGAGACCGCGTTGGAATTCCTTG
GTTATATTCTGCGTGCGGCCATTGCGAATATTGTTTAAGCGGACAAGAAGCATTATGTGAACATC
AACAAAACGCCGGCTACTCAGTCGACGGGGGTTATGCAGAATATTGCAGAGCTGCGCCAGATTAT
GTGGTGAAAATTCCTGACAACTTATCGTTTGAAGAAGCTGCTCCTATTTTCTGCGCCGGAGTTAC
TACTTATAAAGCGTTAAAAGTCACAGGTACAAAACCGGGAGAATGGGTAGCGATCTATGGCATCG
GCGGCCTTGGACATGTTGCCGTCCAGTATGCGAAAGCGATGGGGCTTCATGTTGTTGCAGTGGAT
ATCGGCGATGAGAAACTGGAACTTGCAAAAGAGCTTGGCGCCGATCTTGTTGTAAATCCTGCAAA
AGAAAATGCGGCCCAATTTATGAAAGAGAAAGTCGGCGGAGTACACGCGGCTGTTGTGACAGCTG
TATCTAAACCTGCTTTTCAATCTGCGTACAATTCTATCCGCAGAGGCGGCACGTGCGTGCTTGTC
GGATTACCGCCGGAAGAAATGCCTATTCCAATCTTTGATACGGTATTAAACGGAATTAAAATTAT
CGGTTCCATTGTCGGCACGCGGAAGACTTGCAAGAAGCGCTTCAGTTCGCTGCAGAAGGTAAAG
TAAAAACCATTATTGAAGTGCAACCTCTTGAAAAAATTAACGAAGTATTTGACAGAATGCTAAAA
GGAGAAATTAACGGACGGGTTGTTTTAACGTTAGAAAATAATAATTAA

B.

MKAAVVEQFKEPLKIKEVEKPSISYGEVLVRIKACGVCHTDLHAAHGDWPVKPKLPLIPGHEGVG
IVEEVGPGVTHLKVGDRVGIPWLYSACGHCEYCLSGQEALCEHQQNAGYSVDGGYAEYCRAAPDY
VVKIPDNLSFEEAAPIFCAGVTTYKALKVTGTKPGEWVAIYGIGGLGHVAVQYAKAMGLHVVAVD
IGDEKLELAKELGADLVVNPAKENAAQFMKEKVGGVHAAVVTAVSKPAFQSAYNSIRRGGTCVLV
GLPPEEMPIPIFDTVLNGIKIIGSIVGTRKDLQEALQPAAEGKVKTIIEVQPLEKINEVFDRMLK
GEINGRVVLTLENNN

FIG. 31

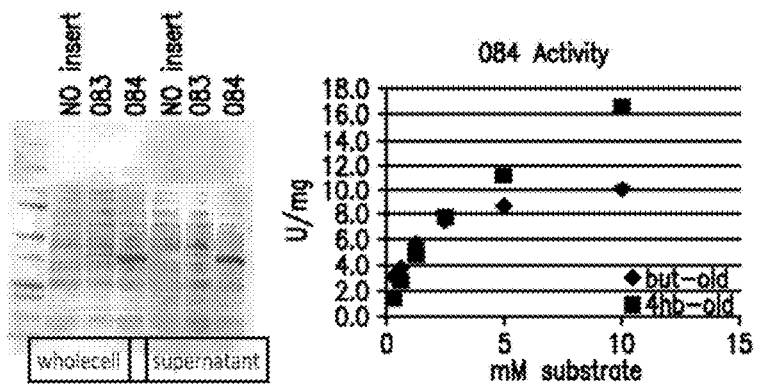
FIG. 32A  FIG. 32B
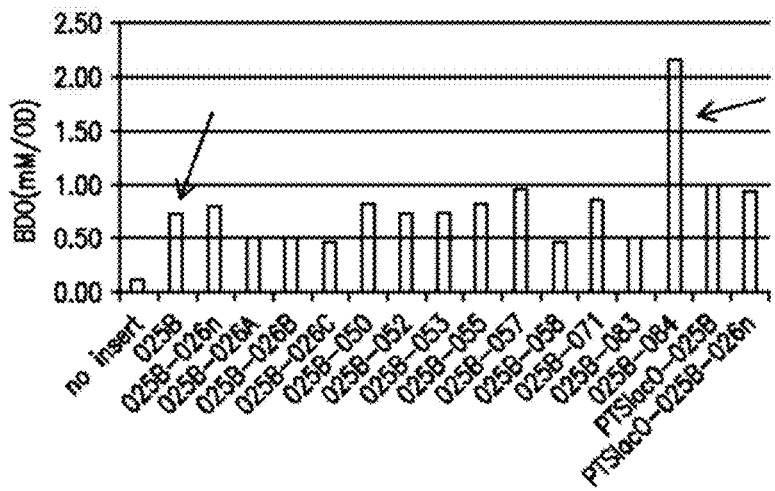
FIG. 33
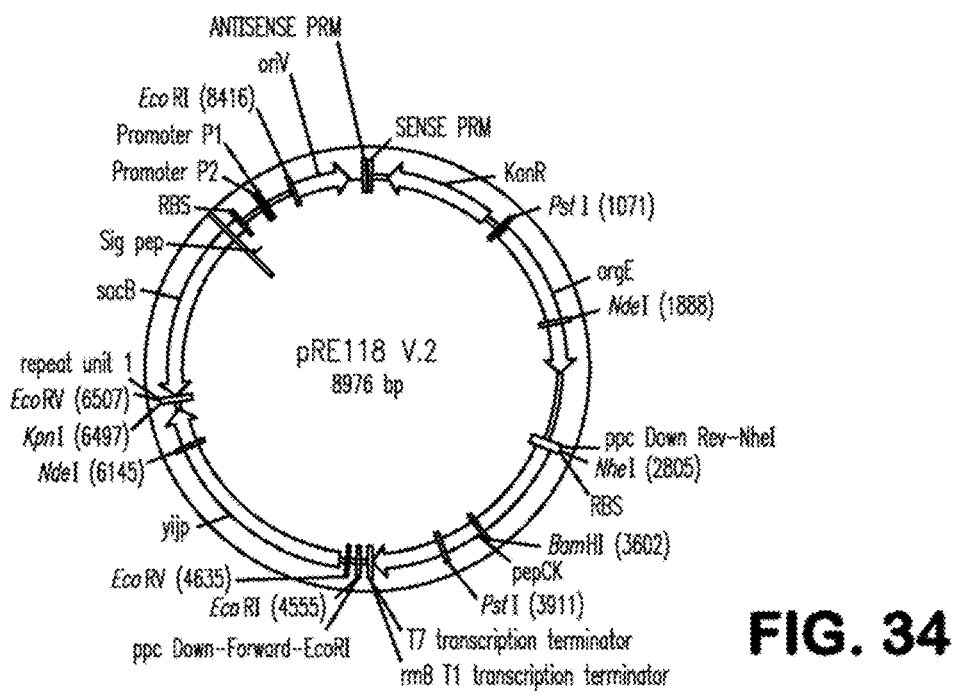
FIG. 34

A.

aTGGCTATCGAAATCAAAGTACCGGACATCGGGGCTGATGAAGTTGAAATCACCGAGATCCTGGTCAAA
GTGGGCGACAAAGTTGAAGCCGAACAGTCGCTGATCACCGTAGAAGGCGACAAAGCCTCTATGGAAGT
TCCGTCTCCGCAGGCGGGTATCGTTAAAGAGATCAAAGTCTCTGTTGGCGATAAAACCCAGACCGGCGC
ACTGATTATGATTTTCGATTCCGCCGACGGTGCAGCAGACGCTGCACCTGCTCAGGCAGAAGAGAAGAA
AGAAGCAGCTCCGGCAGCAGCACCAGCGGCTGCGGCGGCAAAAGACGTTAACGTTCCGGATATCGGCA
GCGACGAAGTTGAAGTGACCGAAATCCTGGTGAAAGTTGGCGATAAAGTTGAAGCTGAACAGTCGCTG
ATCACCGTAGAAGGCGACAAGGCTTCTATGGAAGTTCCGGCTCCGTTTGCTGGCACCGTGAAAGAGATC
AAAGTGAACGTGGGTGACAAAGTGTCTACCGGCTCGCTGATTATGGTCTTCGAAGTCGCGGGTGAAGC
AGGCGCGGCAGCTCCGGCCGCTAAACAGGAAGCAGCTCCGGCAGCGGCCCCTGCACCAGCGGCTGGC
GTGAAAGAAGTTAACGTTCCGGATATCGGCGGTGACGAAGTTGAAGTGACTGAAGTGATGGTGAAAGT
GGGCGACAAAGTTGCCGCTGAACAGTCACTGATCACCGTAGAAGGCGACAAAGCTTCTATGGAAGTTCC
GGCGCCGTTTGCAGGCGTCGTGAAGGAACTGAAAGTCAACGTTGGCGATAAAGTGAAAACTGGCTCGC
TGATTATGATCTTCGAAGTTGAAGGCGCAGCGCCTGCGGCAGCTCCTGCGAAACAGGAAGCGGCAGCG
CCGGCACCGGCAGCAAAAGCTGAAGCCCCGGCAGCAGCACCAGCTGCGAAAGCGGAAGGCAAATCTG
AATTTGCTGAAAACGACGCTTATGTTCACGCGACTCCGCTGATCCGCCGTCTGGCACGCGAGTTTGGTGT
TAACCTTGCGAAAGTGAAGGGCACTGGCCGTAAAGGTCGTATCCTGCGCGAAGACGTTCAGGCTTACGT
GAAAGAAGCTATCAAACGTGCAGAAGCAGCTCCGGCAGCGACTGGCGGTGGTATCCCTGGCATGCTGC
CGTGGCCGAAGGTGGACTTCAGCAAGTTTGGTGAAATCGAAGAAGTGGAACTGGGCCGCATCCAGAAA
ATCTCTGGTGCGAACCTGAGCCGTAACTGGGTAATGATCCCGCATGTTACTCACTTCGACAAAACCGATA
TCACCGAGTTGGAAGCGTTCCGTAAACAGCAGAACGAAGAAGCGGCGAAACGTAAGCTGGATGTGAAG
ATCACCCCGGTTGTCTTCATCATGAAAGCCGTTGCTGCAGCTCTTGAGCAGATGCCTCGCTTCAATAGTTC
GCTGTCGGAAGACGGTCAGCGTCTGACCCTGAAGAAATACATCAACATCGGTGTGGCGGTGGATACCC
CGAACGGTCTGGTTGTTCCGGTATTCAAAGACGTCAACAAGAAAGGCATCATCGAGCTGTCTCGCGAGC
TGATGACTATTTCTAAGAAAGCGCGTGACGGTAAGCTGACTGCGGGCGAAATGCAGGGCGGTTGCTTC
ACCATCTCCAGCATCGGCGGCCTGGGTACTACCCACTTCGCGCCGATTGTGAACGCGCCGGAAGTGGCT
ATCCTCGGCGTTTCCAAGTCCGCGATGGAGCCGGTGTGGAATGGTAAAGAGTTCGTGCCGCGTCTGATG
CTGCCGATTTCTCTCCTTCGACCACCGCGTGATCGACGGTGCTGATGGTGCCCGTTTCATTACCATCAT
TAACAACACGCTGTCTGACATTCGCCGTCTGGTGATGTAAGTAAAAGAGCCGGCCCAACGGCCGGCTTT
TTTCTGGTAATCTCATGAATGTATTGAGGTTATTAGCGAATAGACAAATCGGTTGCCGTTTGTTGTTTAAA
AATTGTTAACAATTTTGTAAAATACCGACGGATAGAACGACCCGGTGGTGGTTAGGGTATTACTTCACAT
ACCCTATGGATTTCTGGGTGCAGCAAGGTAGCAAGCGCCAGAATCCCCAGGAGCTTACATAAGTAAGTG
ACTGGGGTGAGGGCGTGAAGCTAACGCCGCTGCGGCCTGAAAGACGACGGGTATGACCGCCGGAGAT
AAATATATAGAGGTCATGATGAGTACTGAAATCAAAACTCAGGTCGTGGTACTTGGGGCAGGCCCCGCA
GGTTACTCCGCTGCCTTCCGTTGCGCTGATTTAGGTCTGGAAACCGTAATCGTAGAACGTTACAACACCC
TTGGCGGTGTTTGTCTGAACGTGGGTTGTATCCCTTCTAAAGCGCTGCTGCACGTGGCAAAAGTTATCGA
AGAAGCGAAAGCGCTGGCCGAACACGGCATCGTTTTCGGCGAACCGAAAACTGACATTGACAAGATCC
GCACCTGGAAAGAAAAGTCATCACTCAGCTGACCGGTGGTCTGGCTGGCATGGCCAAAGGTCGTAAA
GTGAAGGTGGTTAACGGTCTGGGTAAATTTACCGGCGCTAACACCCTGGAAGTGGAAGGCGAAAACGG
CAAAACCGTGATCAACTTCGACAACGCCATCATCGCGGCGGGTTCCCGTCCGATTCAGCTGCCGTTTATC
CCGCATGAAGATCCGCGCGTATGGGACTCCACCGACGCGCTGGAACTGAAATCTGTACCGAAACGCATG
CTGGTGATGGGCGGCGGTATCATCGGTCTGGAAATGGGTACCGTATACCATGCGCTGGGTTCAGAGATT
GACGTGGTGGAAATGTTCGACCAGGTTATCCCGGCTGCCGACAAAGACGTGGTGAAAGTCTTCACCAAA
CGCATCAGCAAGAAATTTAACCTGATGCTGGAAGCCAAAGTGACTGCCGTTGAAGCGAAAGAAGACGG

FIG. 35

TATTTACGTTTCCATGGAAGGTAAAAAAGCACCGGCGGAAGCGCAGCGTTACGACGCAGTGCTGGTCG
CTATCGGCCGCGTACCGAATGGTAAAAACCTCGATGCAGGTAAAGCTGGCGTGGAAGTTGACGATCGC
GGCTTCATCCGCGTTGACAAACAAATGCGCACCAACGTGCCGCACATCTTTGCTATCGGCGATATCGTCG
GTCAGCCGATGCTGGCGCACAAAGGTGTCCATGAAGGCCACGTTGCCGCAGAAGTTATCTCCGGTCTGA
AACACTACTTCGATCCGAAAGTGATCCCATCCATCGCCTACACTAAACCAGAAGTGGCATGGGTCGGTCT
GACCGAGAAAGAAGCGAAAGAGAAAGGCATCAGCTACGAAACCGCCACCTTCCCGTGGGCTGCTTCCG
GCCGTGCTATCGCTTCTGACTGCGCAGATGGTATGACCAAACTGATCTTCGACAAAGAGACCCACCGTG
TTATCGGCGGCGCGATTGTCGGCACCAACGGCGGCGAGCTGCTGGGTGAGATCGGCCTGGCTATCGAG
ATGGGCTGTGACGCTGAAGACATCGCCCTGACCATCCACGCTCACCCGACTCTGCACGAGTCCGTTGGC
CTGGCGGCGGAAGTGTTCGAAGGCAGCATCACCGACCTGCCAAACGCCAAAGCGAAGAAAAAGTAACT
TTTTCTTTCAGGAAAAAAGCATAAGCGGCTCCGGGAGCCGCTTTTTTTATGCCTGATGTTTAGAACTATG
TCACTGTTCATAAACCGCTACACCTCATACATACTTTAAGGGCGAATTCTGCAGATATCCATCACACTGGC
GGCCGCTCGAGCATGCATCTAGCACATCCGGCAATTAAAAAAGCGGCTAACCACGCCGCTTTTTTACGT
CTGCAATTTACCTTTCCAGTCTTCTTGCTCCACGTTCAGAGAGACGTTCGCATACTGCTGACCGTTGCTCG
TTATTCAGCCTGACAGTATGGTTACTGTCGTTTAGACGTTGTGGGCGGCTCTCCTGAACTTTCTCCCGAA
AAACCTGACGTTGTTCAGGTGATGCCGATTGAACACGCTGGCGGGCGTTATCACGTTGCTGTTGATTCA
GTGGGCGCTGCTGTACTTTTTCCTT

FIG. 35 (cont'd)

```
                                                                    Section 1
              (1)    1         10        20        30        40       52
EC-IpdA      (1)    MMSTEIKTQVVVLGAGPAGYSAAFRCADLGLETVIVERYNTLGGVCLNVGCI
KP-IpdA mutated (1) MMSTEIKTQVVVLGAGPAGYSAAFRCADLGLETVIVERYSTLGGVCLNVGCI
                                                                    Section 2
              (53)   53        60        70        80        90      104
EC-IpdA      (53)   PSKALLHVAKVIEEAKALAEHGIVFGEPKTDIDKIRTWKEKVINQLTGGLAG
KP-IpdA mutated (53) PSKALLHVAKVIEEAKALAEHGIVFGEPKTDIDKIRTWKEKVITQLTGGLAG
                                                                    Section 3
              (105)  105   110        120       130       140       156
EC-IpdA      (105)  MAKGRKVKVVNGLGKFTGANTLEVEGENGKTVINFDNAIIAAGSRPIQLPFI
KP-IpdA mutated (105) MAKGRKVKVVNGLGKFTGANTLEVEGENGKTVINFDNAIIAAGSRPIQLPFI
                                                                    Section 4
              (157)  157       170       180       190              208
EC-IpdA      (157)  PHEDPRIWDSTDALELKEVPERLLVMGGGIIGLEMGTVYHALGSQIDVVEMF
KP-IpdA mutated (157) PHEDPRVWDSTDALELKSVPKRMLVMGGGIIGLEMGTVYHALGSEIDVVEMF
                                                                    Section 5
              (209)  209       220       230       240       250    260
EC-IpdA      (209)  DQVIPAADKDIVKVFTKRISKKFNLMLETKVTAVEAKEDGIYVIMEGKKAPA
KP-IpdA mutated (209) DQVIPAADKDVVKVFTKRISKKFNLMLEAKVTAVEAKEDGIYVSMEGKKAPA
                                                                    Section 6
              (261)  261       270       280       290       300    312
EC-IpdA      (261)  EPQRYDAVLVAIGRVPNGKNLDAGKAGVEVDDRGFIRVDKQLRTNVPHIFAI
KP-IpdA mutated (261) EAQRYDAVLVAIGRVPNGKNLDAGKAGVEVDDRGFIRVDKQMRTNVPHIFAI
                                                                    Section 7
              (313)  313       320       330       340       350    364
EC-IpdA      (313)  GDIVGQPMLAHKGVHEGHVAAEVIAGKKHYFDPKVIPSIAYTEPEVAWVGLT
KP-IpdA mutated (313) GDIVGQPMLAHKGVHEGHVAAEVISGLKHYFDPKVIPSIAYTKPEVAWVGLT
                                                                    Section 8
              (365)  365   370       380       390       400        416
EC-IpdA      (365)  EKEAKEKGISYETATFPWAASGRAIASDCADGMTKLIFDKESHRVIGGAIVG
KP-IpdA mutated (365) EKEAKEKGISYETATFPWAASGRAIASDCADGMTKLIFDKETHRVIGGAIVG
                                                                    Section 9
              (417)  417       430       440       450              468
EC-IpdA      (417)  TNGGELLGEIGLAIEMGCDAEDIALTIHAHPTLHESVGLAAEVFEGSITDLP
KP-IpdA mutated (417) TNGGELLGEIGLAIEMGCDAEDIALTIHAHPTLHESVGLAAEVFEGSITDLP (469)  469   476
EC-IpdA      (469)  NPKAKKK-
KP-IpdA mutated (469) NAKAKKK-
```

FIG. 36

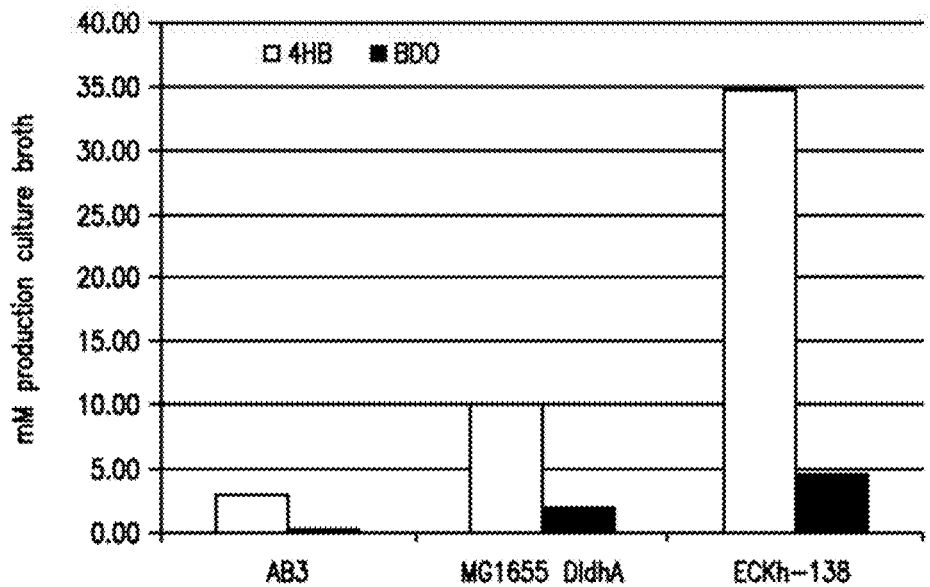

FIG. 37

*ataataatacalatgaaccat*gcgagttacgggcctataaagccaggcgagata<u>atgatctatatcaa</u>tttctcatctataatgctttgtta gtatctcgtcgccgacttaataaagagagagttagtgtgaaagctgacaaccctttgatcttttacttcctgctgcaatggccaaagtgg ccgaagaggcgggtgtctataaagcaacgaaacatccgcttaagactttctatctggcgattaccgccggtgttttcatctcaatcgcattc accactggcacaggcacaGAAGGTAGGTGTTACatgtcagaacgtttacaca*atgacgtggatcctattattat*

FIG. 38

```
AAGAGGTAAAAGAATAATGGCTATCGAAATCAAAGTACCGGACATCGGGGCTGATGAAGTTGAAATCA
CCGAGATCCTGGTCAAAGTGGGCGACAAAGTTGAAGCCGAACAGTCGCTGATCACCGTAGAAGGCGAC
AAAGCCTCTATGGAAGTTCCGTCTCCGCAGGCGGGTATCGTTAAAGAGATCAAAGTCTCTGTTGGCGAT
AAAACCCAGACCGGCGCACTGATTATGATTTTCGATTCCGCCGACGGTGCAGCAGACGCTGCACCTGCT
CAGGCAGAAGAGAAGAAAGAAGCAGCTCCGGCAGCAGCACCAGCGGCTGCGGCGGCAAAAGACGTTA
ACGTTCCGGATATCGGCAGCGACGAAGTTGAAGTGACCGAAATCCTGGTGAAAGTTGGCGATAAAGTT
GAAGCTGAACAGTCGCTGATCACCGTAGAAGGCGACAAGGCTTCTATGGAAGTTCCGGCTCCGTTTGCT
GGCACCGTGAAAGAGATCAAAGTGAACGTGGGTGACAAAGTGTCTACCGGCTCGCTGATTATGGTCTTC
GAAGTCGCGGGTGAAGCAGGCGCGGCAGCTCCGGCCGCTAAACAGGAAGCAGCTCCGGCAGCGGCCC
CTGCACCAGCGGCTGGCGTGAAAGAAGTTAACGTTCCGGATATCGGCGGTGACGAAGTTGAAGTGACT
GAAGTGATGGTGAAAGTGGGCGACAAAGTTGCCGCTGAACAGTCACTGATCACCGTAGAAGGCGACAA
AGCTTCTATGGAAGTTCCGGCGCCGTTTGCAGGCGTCGTGAAGGAACTGAAAGTCAACGTTGGCGATAA
AGTGAAAACTGGCTCGCTGATTATGATCTTCGAAGTTGAAGGCGCAGCGCCTGCGGCAGCTCCTGCGAA
ACAGGAAGCGGCAGCGCCGGCACCGGCAGCAAAAGCTGAAGCCCCGGCAGCAGCACCAGCTGCGAAA
GCGGAAGGCAAATCTGAATTTGCTGAAAACGACGCTTATGTTCACGCGACTCCGCTGATCCGCCGTCTG
GCACGCGAGTTTGGTGTTAACCTTGCGAAAGTGAAGGGCACTGGCCGTAAAGGTCGTATCCTGCGCGA
AGACGTTCAGGCTTACGTGAAAGAAGCTATCAAACGTGCAGAAGCAGCTCCGGCAGCGACTGGCGGTG
GTATCCCTGGCATGCTGCCGTGGCCGAAGGTGGACTTCAGCAAGTTTGGTGAAATCGAAGAAGTGGAA
CTGGGCCGCATCCAGAAAATCTCTGGTGCGAACCTGAGCCGTAACTGGGTAATGATCCCGCATGTTACT
CACTTCGACAAAACCGATATCACCGAGTTGGAAGCGTTCCGTAAACAGCAGAACGAAGAAGCGGCGAA
ACGTAAGCTGGATGTGAAGATCACCCCGGTTGTCTTCATCATGAAAGCCGTTGCTGCAGCTCTTGAGCA
GATGCCTCGCTTCAATAGTTCGCTGTCGGAAGACGGTCAGCGTCTGACCCTGAAGAAATACATCAACAT
CGGTGTGGCGGTGGATACCCCGAACGGTCTGGTTGTTCCGGTATTCAAAGACGTCAACAAGAAAGGCA
TCATCGAGCTGTCTCGCGAGCTGATGACTATTTCTAAGAAAGCGCGTGACGGTAAGCTGACTGCGGGCG
AAATGCAGGGCGGTTGCTTCACCATCTCCAGCATCGGCGGCCTGGGTACTACCCACTTCGCGCCGATTGT
GAACGCGCCGGAAGTGGCTATCCTCGGCGTTTCCAAGTCCGCGATGGAGCCGGTGTGGAATGGTAAAG
AGTTCGTGCCGCGTCTGATGCTGCCGATTTCTCTCCTTCGACCACCGCGTGATCGACGGTGCTGATGG
TGCCCGTTTCATTACCATCATTAACAACACGCTGTCTGACATTCGCCGTCTGGTGATGTAAGTAAAAGAG
CCGGCCCAACGGCCGGCTTTTTCTGGTAATCTCATGAATGTATTGAGGTTATTAGCGAATAGACAAATC
GGTTGCCGTTTGTTAAGCCAGGCGAGATATGATCTATATCAATTTCTCATCTATAATGCTTTGTTAGTATC
TCGTCGCCGACTTAATAAAGAGAGAGTTAGTCTTCTATATCACAGCAAGAAGGTAGGTGTTACATGATG
AGTACTGAAATCAAAACTCAGGTCGTGGTACTTGGGGCAGGCCCCGCAGGTTACTCTGCAGCCTTCCGT
TGCGCTGATTTAGGTCTGGAAACCGTCATCGTAGAACGTTACAGCACCCTCGGTGGTGTTTGTCTGAACG
TGGGTTGTATCCCTTCTAAAGCGCTGCTGCACGTGGCAAAAGTTATCGAAGAAGCGAAAGCGCTGGCCG
AACACGGCATCGTTTTCGGCGAACCGAAAACTGACATTGACAAGATCCGCACCTGGAAAGAAAAAGTCA
TCACTCAGCTGACCGGTGGTCTGGCTGGCATGGCCAAAGGTCGTAAAGTGAAGGTGGTTAACGGTCTG
GGTAAATTTACCGGCGCTAACACCCTGGAAGTGGAAGGCGAAAACGGCAAAACCGTGATCAACTTCGA
CAACGCCATCATCGCGGCGGGTTCCCGTCCGATTCAGCTGCCGTTTATCCCGCATGAAGATCCGCGCGTA
TGGGACTCCACCGACGCGCTGGAACTGAAATCTGTACCGAAACGCATGCTGGTGATGGGCGGCGGTAT
CATCGGTCTGGAAATGGGTACCGTATACCATGCGCTGGGTTCAGAGATTGACGTGGTGGAAATGTTCGA
CCAGGTTATCCCGGCTGCCGACAAAGACGTGGTGAAAGTCTTCACCAAACGCATCAGCAAGAAATTTAA
CCTGATGCTGGAAGCCAAAGTGACTGCCGTTGAAGCGAAAGAAGACGGTATTTACGTTTCCATGGAAG
GTAAAAAGCACCGGCGGAAGCGCAGCGTTACGACGCAGTGCTGGTCGCTATCGGCCGCGTACCGAAT
GGTAAAAACCTCGATGCAGGTAAAGCTGGCGTGGAAGTTGACGATCGCGGCTTCATCCGCGTTGACAA
```

FIG. 39

```
ACAAATGCGCACCAACGTGCCGCACATCTTTGCTATCGGCGATATCGTCGGTCAGCCGATGCTGGCGCA
CAAAGGTGTCCATGAAGGCCACGTTGCCGCAGAAGTTATCTCCGGTCTGAAACACTACTTCGATCCGAA
AGTGATCCCATCCATCGCCTACACTAAACCAGAAGTGGCATGGGTCGGTCTGACCGAGAAAGAAGCGA
AAGAGAAAGGCATCAGCTACGAAACCGCCACCTTCCCGTGGGCTGCTTCCGGCCGTGCTATCGCTTCTG
ACTGCGCAGATGGTATGACCAAACTGATCTTCGACAAAGAGACCCACCGTGTTATCGGCGGCGCGATTG
TCGGCACCAACGGCGGCGAGCTGCTGGGTGAGATCGGCCTGGCTATCGAGATGGGCTGTGACGCTGAA
GACATCGCCCTGACCATCCACGCTCACCCGACTCTGCACGAGTCCGTTGGCCTGGCGGCGGAAGTGTTC
GAAGGCAGCATCACCGACCTGCCAAACGCCAAAGCGAAGAAAAAGTAACTTTTTCTTTCAGGAAAAAAG
CATAAGCGGCTCCGGGAGCCGCTTTTTTTATGCCTGATGTTTAGAACTATGTCACTGTTCATAAACCGCTA
CACCTCATACATACTTTAAGGGCGAATTCTGCAGATATCCATCACACTGGCGGCCGCTCGAGCATGCATC
TAGCACATCCGGCAATTAAAAAAGCGGCTAACCACGCCGCTTTTTTACGTCTGCAATTTACCTTTCCAGT
CTTCTTGCTCCACGTTCAGAGAGACGTTCGCATACTGCTGACCGTTGCTCGTTATTCAGCCTGACAGTAT
GGTTACTGTCGTTTAGACGTTGTGGGCGGCTCTCCTGAACTTTCTCCCGAAAAACCTGACGTTGTTCAGG
TGATGCCGATTGAACACGCTGGCGGGCGTTATCACGTTGCTGTTGATTCAGTGGGCGCTGCTGTACTTTT
TCCTTAAACACCTGGCGCTGCTCTGGTGATGCGGACTGAATACGCTCACGCGCTGCGTCTCTTCGCTGCT
GGTTCTGCGGGTTAGTCTGCATTTTCTCGCGAACCGCCTGGCGCTGCTCAGGCGAGGCGGACTGAATGC
GCTCACGCGCTGCCTCTCTTCGCTGCTGGATCTTCGGGTTAGTCTGCATTCTCTCGCGAACTGCCTGGCG
CTGCTCAGGCGAGGCGGACTGATAACGCTGACGAGCGGCGTCCTTTTGTTGCTGGGTCAGTGGTTGGC
GACGGCTGAAGTCGTGGAAGTCGTCATAGCTCCCATAGTGTTCAGCTTCATTAAACCGCTGTGCCGCTGC
CTGACGTTGGGTACCTCGTGTAATGACTGGTGCGGCGTGTTCGTTGCTGAAACTGATTTGCTGCCGCC
TGACGCTGGCTGTCGCGCGTTGGGCAGGTAATTGCGTGGCGCTCATTCCGCCGTTGACATCGGTTTGA
TGAAACCGCTTTGCCATATCCTGATCATGATAGGGCACACCATTACGGTAGTTTGGATTGTGCCGCCATG
CCATATTCTTATCAGTAAGATGCTCACCGGTGATACGGTTGAAATTGTTGACGTCGATATTGATGTTGTC
GCCGTTGTGTTGCCAGCCATTACCGTCACGATGACCGCCATCGTGGTGATGATAATCAT
```

```
TTATTTGGTGATATTGGTACCAATATCATGCAGCAAACGGTGCAACATTGCCGTGTCTCGTTGCTCTAAA
AGCCCCAGGCGTTGTTGTAACCAGTCGACCAGTTTTATGTCATCTGCCACTGCCAGAGTCGTCAGCAATG
TCATGGCTCGTTCGCGTAAAGCTTGCAGTTGATGTTGGTCTGCCGTTGCATCACTTTTCGCCGGTTGTTGT
ATTAATGTTGCTAATTGATAGCAATAGACCATCACCGCCTGCCCCAGATTGAGCGAAGGATAATCCGCCA
CCATCGGCACACCAGTAAGAACGTCAGCCAACGCTAACTCTTCGTTAGTCAACCCGGAATCTTCGCGACC
AAACACCAGCGCGGCATGGCTCATCCATGAAGATTTTTCCTCTAACAGCGGCACCAGTTCAACTGGCGT
GGCGTAGTAATGATATTTCGCCCGACTGCGCGCAGTGGTGGCGACAGTGAAATCGACATCGTGTAACG
ATTCAGCCAATGTCGGGAAAACTTTAATATTATCAATAATATCACCAGATCCATGTGCGACCCAGCGGGT
GGCTGGCTCCAGGTGTGCCTGACTATCGACAATCCGCAGATCGCTAAACCCCATCGTTTTCATTGCCCGC
GCCGCTGCCCCAATATTTTCTGCTCTGGCGGGTGCGACCAGAATAATCGTTATACGCATATTGCCACTCTT
CTTGATCAAATAACCGCGAACCGGGTGATCACTGTCAACTTATTACGCGGTGCGAATTTACAAATTCTTA
ACGTAAGTCGCAGAAAAGCCCTTTACTTAGCTTAAAAAAGGCTAAACTATTTCCTGACTGTACTAACGG
TTGAGTTGTTAAAAAATGCTACATATCCTTCTGTTTACTTAGGATAATTTTATAAAAAATAAATCTCGACA
ATTGGATTCACCACGTTTATTAGTTGTATGATGCAACTAGTTGGATTATTAAAATAATGTGACGAAAGCT
AGCATTTAGATACGATGATTTCATCAAACTGTTAACGTGCTACAATTGAACTTGATATATGTCAACGAAG
CGTAGTTTTATTGGGTGTCCGGCCCCTCTTAGCCTGTTATGTTGCTGTTAAAATGGTTAGGATGACAGCC
GTTTTTGACACTGTCGGGTCCTGAGGGAAAGTACCCACGACCAAGCTAATGATGTTGTTGACGTTGATG
GAAAGTGCATCAAGAACGCAATTACGTACTTTAGTCATGTTACGCCGATCATGTTAATTTGCAGCATGCA
TCAGGCAGGTCAGGGACTTTTGTACTTCCTGTTTCGATTTAGTTGGCAATTTAGGTAGCAAACGAATTCA
TCGGCTTTACCACCGTCAAAAAAACGGCGCTTTTTAGCGCCGTTTTTATTTTTCAACCTTATTTCCAGATA
CGTAACTCATCGTCCGTTGTAACTTCTTTACTGGCTTTCATTTTCGGCAGTGAAAACGCATACCAGTCGAT
ATTACGGGTCACAAACATCATGCCGGCCAGCGCCACCACCAGCACACTGGTTCCCAACAACAGCGCGCT
ATCGGCAGAGTTGAGCAGTCCCCACATCACACCATCCAGCAACAACAGCGCGAGGGTAAACAACATGCT
GTTGCACCAACCTTTCAATACCGCTTGCAAATAAATACCGTTCATTATCGCCCCAATCAGACTGGCGATTA
TCCATGCCACGGTAAAACCGGTATGTTCAGAAAGCGCCAGCAAGAGCAAATAAAACATCACCAATGAAA
GCCCCACCAGCAAATATTGCATTGGGTGTAAACGTTGCGCGGTGAGCGTTTCAAAAACAAAGAACGCCA
TAAAAGTCAGTGCAATCAGCAGAATGGCGTACTTAGTCGCCCGGTCAGTTAATTGGTATTGATCGGCTG
GCGTCGTTACTGCGACGCTAAACGCCGGGAAGTTTTCCCAGCCGGTATCATTGCCTGAAGCAAAACGCT
CACCGAGATTATTAGCAAACCAGCTGCTTTGCCAGTGCGCCTGAAAACCTGACTCGCTAACTTCCCGTTT
GGCTGGTAGAAAATCACCTAAAAAACTGGGATGCGGCCAGTTGCTGGTTAAGGTCATTTCGCTATTACG
CCCGCCAGGCACCACAGAAAGATCGCCGGTACCGCTTAAATTCAGGGCCATATTCAGCTTCAGGTTCTG
CTTCCGCCAGTCCCCTTCAGGTAAAGGGATATGCACGCCCTGCCCGCCTTGCTCTAACCCGGTGCCGGGT
TCAATGGTCAGCGCCGTTCCGTTAACTTCAGGCGCTTTCACCACACCAATACCACGCGCATCCCCGACGC
TAATCACAATAAATGGCTTGCCTAAGGTGATATTTGGCGCGTTGAGTTCGCTAAGACGCGAAACATCGA
AATCGGCTTTTAACGTTAAATCACTGTGCCAGACCTGACCGGTATAAATCCCTATCTTGCGTTCTTCCACG
TTCTGATTGCCATCAACCATCAATGACTCAGGTAACCAAAAATGGATAAAACTTCGTTTCCGCTGCAGGG
TTTTAT
```

FIG. 42

AAGCCACAGCAGGATGCCCACTGCAACAAAGGTGATCACACCGGAAACGCGATGGAGAATGGACGCTA
TCGCCGTGATGGGGAACCGGATGGTCTGTAGGTCCAGATTAACAGGTCTTTGTTTTTTCACATTTCTTAT
CATGAATAACGCCCACATGCTGTTCTTATTATTCCCTGGGGACTACGGGCACAGAGGTTAACTTTCTGTT
ACCTGGAGACGTCGGGATTTCCTTCCTCCGGTCTGCTTGCGGGTCAGACAGCGTCCTTTCTATAACTGCG
CGTCATGCAAAACACTGCTTCCAGATGCGAAAACGACACGTTACAACGCTGGGTGGCTCGGGATTGCAG
GGTGTTCCGGAGACCTGGCGGCAGTATAGGCTGTTCACAAAATCATTACAATTAACCTACATATAGTTTG
TCGGGTTTTATCCTGAACAGTGATCCAGGTCACGATAACAACATTTATTTAATTTTTAATCATCTAATTTG
ACAATCATTCAACAAAGTTGTTACAAACATTACCAGGAAAAGCATATAATGCGTAAAAGTTATGAAGTC
GGTATTTCACCTAAGATTAACTTATGTAACAGTGTGGAAGTATTGACCAATTCATTCGGGACAGTTATTA
GTGGTAGACAAGTTTAATAATTCGGATTGCTAAGTACTTGATTCGCCATTTATTCGTCATCAATGGATCCT
TTACCTGCAAGCGCCCAGAGCTCTGTACCCAGGTTTTCCCCTCTTTCACAGAGCGGCGAGCCAAATAAAA
AACGGGTAAAGCCAGGTTGATGTGCGAAGGCAAATTTAAGTTCCGGCAGTCTTACGCAATAAGGCGCT
AAGGAGACCTTAAATGGCTGATACAAAAGCAAAACTCACCCTCAACGGGGATACAGCTGTTGAACTGGA
TGTGCTGAAAGGCACGCTGGGTCAAGATGTTATTGATATCCGTACTCTCGGTTCAAAAGGTGTGTTCACC
TTTGACCCAGGCTTCACTTCAACCGCATCCTGCGAATCTAAAATTACTTTTATTGATGGTGATGAAGGTAT
TTTGCTGCACCGCGGTTTCCCGATCGATCAGCTGGCGACCGATTCTAACTACCTGGAAGTTTGTTACATC
CTGCTGAATGGTGAAAAACCGACTCAGGAACAGTATGACGAATTTAAAACTACGGTGACCCGTCATACC
ATGATCCACGAGCAGATTACCCGTCTGTTCCATGCTTTCCGTCGCGACTCGCATCCAATGGCAGTCATGT
GTGGTATTACCGGCGCGCTGGCGGCGTTCTATCACGACTCGCTGGATGTTAACAATCCTCGTCACCGTGA
AATTGCCGCGTTCCTCCTGCTGTCGAAAATGCCGACCATGGCCGCGATGTGTTACAAGTATTCCATTGGT
CAGCCATTTGTTTACCCGCGCAACGATCTCTCCTACGCCGGTAACTTCCTGAATATGATGTTCTCCACGCC
GTGCGAACCGTATGAAGTTAATCCGATTCTGGAACGTGCTATGGACCGTATTCTGATCCTGCACGCTGAC
CATGAACAGAACGCCTCTACCTCCACCGTGCGTACCGCTGGCTCTTCGGGTGCGAACCCGTTTGCCTGTA
TCGCAGCAGGTATTGCTTCACTGTGGGACCTGCGCACGGCGGTGCTAACGAAGCGGCGCTGAAAATG
CTGGAAGAAATCAGCTCCGTTAAACACATTCCGGAATTTGTTCGTCGTGCGAAAGACAAAAATGATTCTT
TCCGCCTGATGGGCTTCGGTCACCGCGTGTACAAAAATTACGACCCGCGCGCCACCGTAATGCGTGAAA
CCTGCCATGAAGTGCTGAAAGAGCTGGGCACGAAGGATGACCTGCTGGAAGTGGCTATGGAGCTGGAA
AACATCGCGCTGAACGACCCGTACTTTATCGAGAAGAAACTGTACCCGAACGTCGATTTCTACTCTGGTA
TCATCCTGAAAGCGATGGGTATTCCGTCTTCCATGTTCACCGTCATTTTCGCAATGGCACGTACCGTTGG
CTGGATCGCCCACTGGAGCGAAATGCACAGTGACGGTATGAAGATTGCCCGTCCGCGTCAGCTGTATAC
AGGATATGAAAAACGCGACTTTAAAAGCGATATCAAGCGTTAATGGTTGATTGCTAAGTTGTAAATATTT
TAACCCGCCGTTCATATGGCGGGTTGATTTTTATATGCCTAAACACAAAAAATTGTAAAATAAAATCCA
TTAACAGACCTATATAGATATTTAAAAGAATAGAACAGCTCAAATTATCAGCAACCCAATACTTTCAATT
AAAAACTTCATGGTAGTCGCATTTATAACCCTATGAAAATGACGTCTATCTATACCCCCTATATTTTATTC
ATCATACAACAAATTCATGATACCAATAATTTAGTTTTGCATTTAATAAAACTAACAATATTTTTAAGCAA
AACTAAAAACTAGCAATAATCAAATACGATATTCTGGCGTAGCTATACCCCTATTCTATATCCTTAAAGGA
CTCTGTTATGTTTAAAGGACAAAAACATTGGCCGCACTGGCCGTATCTCTGCTGTTCACTGCACCTGTTT
ATGCTGCTGATGAAGGTTCTGGCGAAATTCACTTTAAGGGGGAGGTTATTGAAGCACCTTGTGAAATTC
ATCCAGAAGATATTGATAAAAACATAGATCTTGGACAAGTCACGACAACCCATATAAACCGGGAGCATC
ATAGCAATAAAGTGGCCGTCGACATTCGCTTGATCAACTGTGATCTGCCTGCTTCTGACAACGGTAGCG
GAATGCCGGTATCCAAAGTTGGCGTAACCTTCGATAGCACGGCTAAGACAACTGGTGCTACGCCTTTGT
TGAGCAACACCAGTGCAGGCGAAGCAACTGGGGTCGGTGTACGACTGATGGACAAAAATGACGGTAAC
ATCGTATTAGGTTCAGCCGCGCCAGATCTTGACCTGGATGCAAGCTCATCAGAACAGACGCTGAACTTTT
TCGCCTGGAT
```

FIG. 43

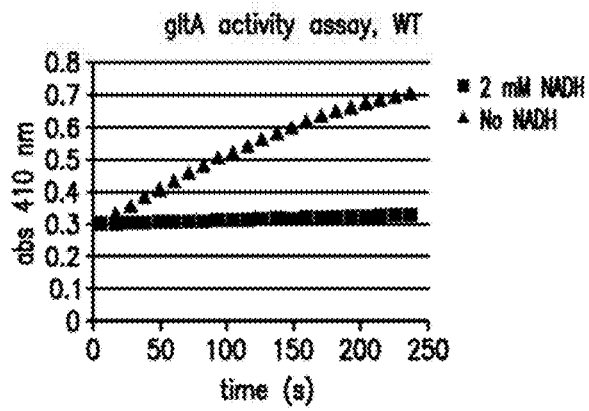 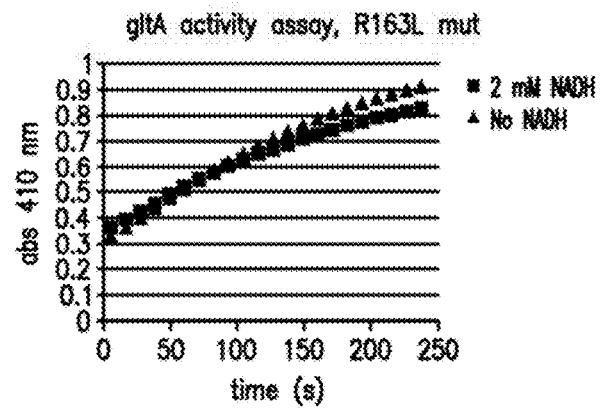
FIG. 44A  FIG. 44B
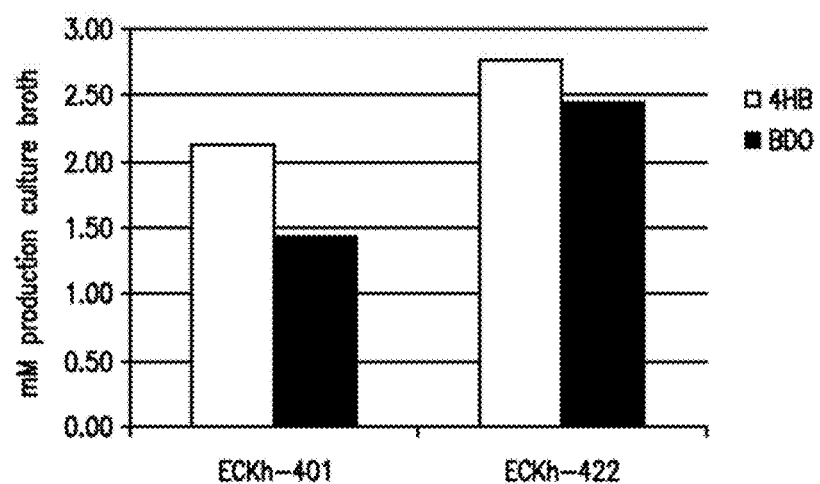
FIG. 45

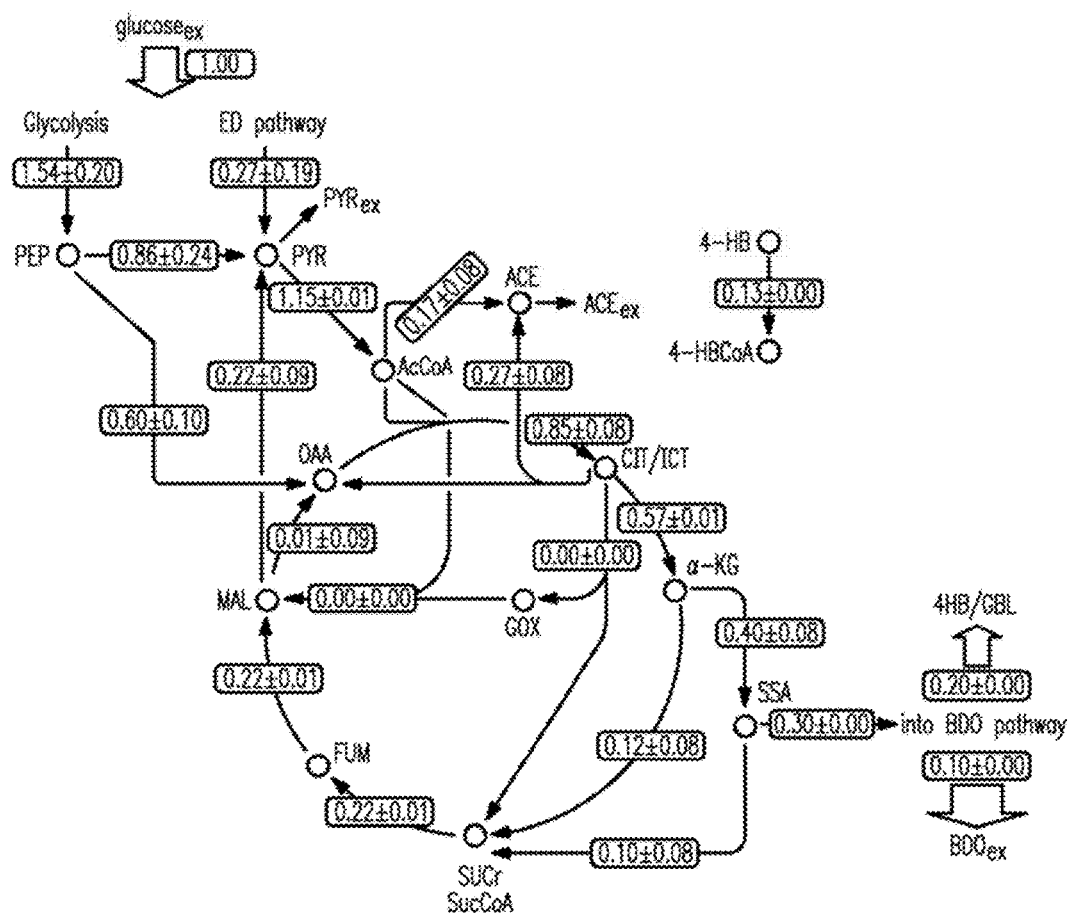
FIG. 46
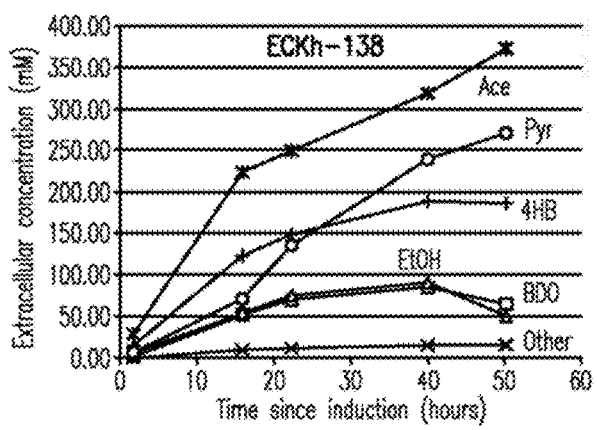 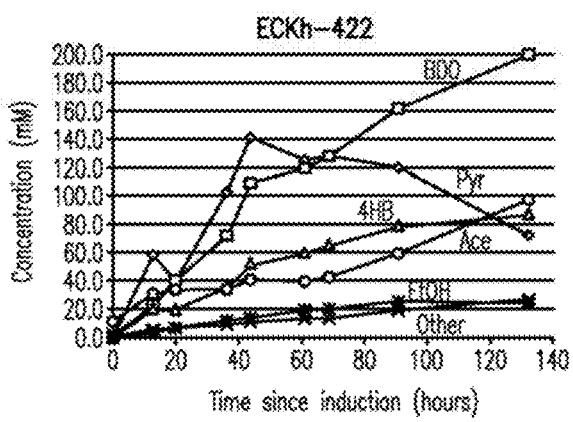
FIG. 47A  FIG. 47B

CGCGATGTCGACGTCACGAAACTGAAAAAACCGCTCTACATTCTGGCGACTGCTGATGAAGAAACCAGT
ATGGCCGGAGCGCGTTATTTTGCCGAAACTACCGCCCTGCGCCCGGATTGCGCCATCATTGGCGAACCG
ACGTCACTACAACCGGTACGCGCACATAAAGGTCATATCTCTAACGCCATCCGTATTCAGGGCCAGTCG
GGGCACTCCAGCGATCCAGCACGCGGAGTTAACGCTATCGAACTAATGCACGACGCCATCGGGCATATT
TTGCAATTGCGCGATAACCTGAAAGAACGTTATCACTACGAAGCGTTTACCGTGCCATACCCTACGCTCA
ACCTCGGGCATATTCACGGTGGCGACGCTTCTAACCGTATTTGCGCTTGCTGTGAGTTGCATATGGATAT
TCGTCCGCTGCCTGGCATGACACTCAATGAACTTAATGGTTTGCTCAACGATGCATTGGCTCCGGTGAGC
GAACGCTGGCCGGGTCGTCTGACGGTCGACGAGCTGCATCCGCCGATCCCTGGCTATGAATGCCCACCG
AATCATCAACTGGTTGAAGTGGTTGAGAAATTGCTCGGAGCAAAAACCGAAGTGGTGAACTACTGTACC
GAAGCGCCGTTTATTCAAACGTTATGCCCGACGCTGGTGTTGGGGCCTGGCTCAATTAATCAGGCTCATC
AACCTGATGAATATCTGGAAACACGGTTTATCAAGCCCACCCGCGAACTGATAACCCAGGTAATTCACCA
TTTTTGCTGGCATTAAAACGTAGGCCGGATAAGGCGCTCGCGCCGCATCCGGCGCTGTTGCCAAACTCC
AGTGCCGCAATAATGTCGGATGCGATGCTTGCGCATCTTATCCGACCTACAGTGACTCAAACGATGCCCA
ACCGTAGGCCGGATAAGGCGCTCGCGCCGCATCCGGCACTGTTGCCAAACTCCAGTGCCGCAATAATGT
CGGATGCGATACTTGCGCATCTTATCCGACCGACAGTGACTCAAACGATGCCCAACTGTAGGCCGGATA
AGGCGCTCGCGCCGCATCCGGCACTGTTGCCAAACTCCAGTGCCGCAATAATGTCGGATGCGATACTTG
CGCATCTTATCCGACCTACACCTTTGGTGTTACTTGGGGCGATTTTTTAACATTTCCATAAGTTACGCTTAT
TTAAAGCGTCGTGAATTTAATGACGTAAATTCCTGCTATTTATTCGTTTGCTGAAGCGATTTCGCAGCATT
TGACGTCACCGCTTTTACGTGGCTTTATAAAGACGACGAAAAGCAAAGCCCGAGCATATTCGCGCCAA
TGCTAGCAAGAGGAGAAGTCGAC<u>ATGACAGACTTAAATAAAGTGGTAAAAGAACTTGAAGCTCTTGGT</u>
<u>ATTTATGACGTAAAAGAAGTTGTTTACAATCCAAGCTACGAGCAATTGTTCGAAGAAGAAACTAAACCA</u>
<u>GGTTTAGAAGGCTTTGAAAAAGGTACTTTAACTACGACTGGTGCAGTGGCAGTAGATACAGGTATCTTC</u>
<u>ACAGGTCGTTCTCCAAAAGATAAATATATCGTGTTAGATGAAAAAACCAAAGATACTGTTTGGTGGACA</u>
<u>TCTGAAACAGCAAAAACGACAACAAGCCAATGAACCAAGCTACATGGCAAAGCTTAAAAGACTTGGTA</u>
<u>ACCAACCAGCTTTCTCGTAAACGCTTATTTGTAGTTGATGGTTTCTGTGGTGCGAGCGAACACGACCGTA</u>
<u>TTGCAGTACGTATTGTCACTGAAGTAGCGTGGCAAGCACATTTTGTAAAAAATATGTTTATTCGCCCAAC</u>
<u>TGAAGAACAACTCAAAAATTTTGAACCAGATTTCGTTGTAATGAATGGTTCTAAAGTAACCAATCCAAAC</u>
<u>TGGAAAGAACAAGGTTTAAATTCAGAAAACTTTGTTGCTTTCAACTTGACTGAACGCATTCAATTAATCG</u>
<u>GTGGTACTTGGTACGGCGGTGAAATGAAAAAAGGTATGTTCTCAATCATGAACTACTTCCTACCACTTAA</u>
<u>AGGTGTTGGTGCAATGCACTGCTCAGCTAACGTTGGTAAAGATGGCGATGTAGCAATCTTCTTCGGCTT</u>
<u>ATCTGGCACAGGTAAAACAACCCTTTCAACGGATCCAAAACGTGAATTAATCGGTGACGATGAACACGG</u>
<u>CTGGGATGATGTGGGTATCTTTAACTTTGAAGGTGGTTGCTATGCGAAAACCATTCACCTTTCAGAAGAA</u>
<u>AATGAACCAGATATTTACCGCGCTATCCGTCGCGACGCATTATTAGAAACGTGGTTGTTCGTGCAGATG</u>
<u>GTTCTGTTGATTTCGATGATGGTTCAAAAACAGAAAATACTCGCGTGTCTTACCCAATTTATCACATTGAT</u>
<u>AACATTGTAAAACCAGTTTCTCGTGCAGGTCACGCAACTAAAGTGATTTTCTTAACTGCAGATGCATTTG</u>
<u>GCGTATTACCACCAGTATCTAAATTGACACCAGAACAAACTAAATACTACTTCTTATCTGGTTTCACAGCA</u>
<u>AAATTAGCAGGTACTGAACGTGGTATTACTGAACCAACTCCAACTTTCTCAGCATGTTTCGGTGCTGCGT</u>
<u>TCTTAACCCTTCACCCAACTCAATATGCAGAAGTGTTAGTAAAACGTATGCAAGCAGTGGGTGCTGAAG</u>
<u>CTTACTTAGTAAATACTGGTTGGAATGGCACAGGCAAACGTATCTCAATCAAAGATACTCGCGGAATCAT</u>
<u>TGATGCAATCTTAGATGGCTCAATTGAAAAAGCTGAAATGGGCGAATTACCAATCTTTAACTTAGCCATT</u>
<u>CCTAAAGCATTACCAGGTGTAGATTCTGCAATCTTAGATCCTCGCGATACTTACGCAGATAAAGCACAAT</u>
<u>GGCAATCAAAAGCTGAAGACTTAGCAGGTCGTTTTGTGAAAAACTTTGTTAAATATGCAACTAACGAAG</u>
<u>AAGGCAAAGCTTTAATTGCAGCTGGTCCTAAAGCTTAA</u>TCTAGAAAGCTTCCTAGAGGCATCAAATAAA
ACGAAAGGCTCAGTCGAAAGACTGGGCCTTTCGTTTTATCTGTTGTTTGTCGGTGAACGCTCTCCTGAGT

FIG. 48

```
AGGACGAATTCACTTCTGTTCTAACACCCTCGTTTTCAATATATTTCTGTCTGCATTTTATTCAAATTCTGA
ATATACCTTCAGATATCCTTAAGGAATTGTCGTTACATTCGGCGATATTTTTCAAGACAGGTTCTTACTA
TGCATTCCACAGAAGTCCAGGCTAAACCTCTTTTTAGCTGGAAAGCCCTGGGTTGGGCACTGCTCTACTT
TTGGTTTTTCTCTACTCTGCTACAGGCCATTATTTACATCAGTGGTTATAGTGGCACTAACGGCATTCGCG
ACTCGCTGTTATTCAGTTCGCTGTGGTTGATCCCGGTATTCCTCTTTCCGAAGCGGATTAAAATTATTGCC
GCAGTAATCGGCGTGGTGCTATGGGCGGCCTCTCTGGCGGCGCTGTGCTACTACGTCATCTACGGTCAG
GAGTTCTCGCAGAGCGTTCTGTTTGTGATGTTCGAAACCAACACCAACGAAGCCAGCGAGTATTTAAGC
CAGTATTTCAGCCTGAAAATTGTGCTTATCGCGCTGGCCTATACGGCGGTGGCAGTTCTGCTGTGGACAC
GCCTGCGCCCGGTCTATATTCCAAAGCCGTGGCGTTATGTTGTCTCTTTTGCCCTGCTTTATGGCTTGATT
CTGCATCCGATCGCCATGAATACGTTTATCAAAAACAAGCCGTTTGAGAAAACGTTGGATAACCTGGCCT
CGCGTATGGAGCCTGCCGCACCGTGGCAATTCCTGACCGGCTATTATCAGTATCGTCAGCAACTAAACTC
GCTAACAAAGTTACTGAATGAAAATAATGCCTTGCCGCCACTGGCTAATTTCAAAGATGAATCGGGTAA
CGAACCGCGCACTTTAGTGCTGGTGATTGGCGAGTCGACCCAGCGCGGACGCATGAGTCTGTACGGTTA
TCCGCGTGAAACCACGCCGGAGCTGGATGCGCTGCATAAAACCGATCCGAATCTGACCGTGTTTAATAA
CGTAGTTACGTCTCGTCCGTACACCATTGAAATCCTGCAACAGGCGCTGACCTTTGCCAATGAAAAGAAC
CCGGATCTGTATCTGACGCAGCCGTCGCTGATGAACATGATGAAACAGGCGGGTTATAAAACCTTC
```

FIG. 48 (cont'd)

```
AATAGGCGTATCACGAGGCCCTTTCGTCTTCACCTCGAGAATTGTGAGCGGATAACAATTGACATTGTGA
GCGGATAACAAGATACTGAGCACATCAGCAGGACGCACTGACCGAATTCAATTAAGCTAGCAAGAGGA
GAAGTCGAGATGAACTTACATGAATATCAGGCAAAACAACTTTTTGCCCGCTATGGCTTACCAGCACCG
GTGGGTTATGCCTGTACTACTCCGCGCAAGCAGAAGAAGCCGCTTCAAAAATCGGTGCCGGTCCGTGG
GTAGTGAAATGTCAGGTTCACGCTGGTGGCCGCGGTAAAGCGGGCGGTGTGAAAGTTGTAAACAGCAA
AGAAGACATCCGTGCTTTTGCAGAAAACTGGCTGGGCAAGCGTCTGGTAACGTATCAAACAGATGCCAA
TGGCCAACCGGTTAACCAGATTCTGGTTGAAGCAGCGACCGATATCGCTAAAGAGCTGTATCTCGGTGC
CGTTGTTGACCGTAGTTCCCGTCGTGTGGTCTTTATGGCCTCCACCGAAGGCGGCGTGGAAATCGAAAA
AGTGGCGGAAGAAACTCCGCACCTGATCCATAAAGTTGCGCTTGATCCGCTGACTGGCCCGATGCCGTA
TCAGGGACGCGAGCTGGCGTTCAAACTGGGTCTGGAAGGTAAACTGGTTCAGCAGTTCACCAAAATCTT
CATGGGCCTGGCGACCATTTTCCTGGAGCGCGACCTGGCGTTGATCGAAATCAACCCGCTGGTCATCAC
CAAACAGGGCGATCTGATTTGCCTCGACGGCAAACTGGGCGCTGACGGCAACGCACTGTTCCGCCAGCC
TGATCTGCGCGAAATGCGTGACCAGTCGCAGGAAGATCCGCGTGAAGCACAGGCTGCACAGTGGGAAC
TGAACTACGTTGCGCTGGACGGTAACATCGGTTGTATGGTTAACGGCGCAGGTCTGGCGATGGGTACG
ATGGACATCGTTAAACTGCACGGCGGCGAACCGGCTAACTTCCTTGACGTTGGCGGCGGCGCAACCAAA
GAACGTGTAACCGAAGCGTTCAAAATCATCCTCTCTGACGACAAAGTGAAAGCCGTTCTGGTTAACATCT
TCGGCGGTATCGTTCGTTGCGACCTGATCGCTGACGGTATCATCGGCGCGGTAGCAGAAGTGGGTGTTA
ACGTACCGGTCGTGGTACGTCTGGAAGGTAACAACGCCGAACTCGGCGCGAAGAAACTGGCTGACAGC
GGCCTGAATATTATTGCAGCAAAAGGTCTGACGGATGCAGCTCAGCAGGTTGTTGCCGCAGTGGAGGG
GAAATAATGTCCATTTTAATCGATAAAAACACCAAGGTTATCTGCCAGGGCTTTACCGGTAGCCAGGGG
ACTTTCCACTCAGAACAGGCCATTGCATACGGCACTAAAATGGTTGGCGGCGTAACCCCAGGTAAAGGC
GGCACCACCCACCTCGGCCTGCCGGTGTTCAACACCGTGCGTGAAGCCGTTGCTGCCACTGGCGCTACC
GCTTCTGTTATCTACGTACCAGCACCGTTCTGCAAAGACTCCATTCTGGAAGCCATCGACGCAGGCATCA
AACTGATTATCACCATCACTGAAGGCATCCCGACGCTGGATATGCTGACCGTGAAAGTGAAGCTGGATG
AAGCAGGCGTTCGTATGATCGGCCCGAACTGCCCAGGCGTTATCACTCCGGGTGAATGCAAAATCGGTA
TCCAGCCTGGTCACATTCACAAACCGGGTAAAGTGGGTATCGTTTCCCGTTCCGGTACACTGACCTATGA
AGCGGTTAAACAGACCACGGATTACGGTTTCGGTCAGTCGACCTGTGTCGGTATCGGCGGTGACCCGAT
CCCGGGCTCTAACTTTATCGACATTCTCGAAATGTTCGAAAAAGATCCGCAGACCGAAGCGATCGTGAT
GATCGGTGAGATCGGCGGTAGCGCTGAAGAAGAAGCAGCTGCGTACATCAAAGAGCACGTTACCAAGC
CAGTTGTGGGTTACATCGCTGGTGTGACTGCGCCGAAAGGCAAACGTATGGGCCACGCGGGTGCCATC
ATTGCCGGTGGGAAAGGGACTGCGGATGAGAAATTCGCTGCTCTGGAAGCCGCAGGCGTGAAAACCGT
TCGCAGCCTGGCGGATATCGGTGAAGCACTGAAAACTGTTCTGAAATAATCTAGCAAGAGGAGAAGTC
GACATGGAAATCAAAGAAATGGTGAGCCTTGCACGCAAGGCTCAGAAGGAGTATCAAGCTACCCATAA
CCAAGAAGCAGTTGACAACATTTGCCGAGCTGCAGCAAAAGTTATTTATGAAAATGCAGCTATTCTGGC
TCGCGAAGCAGTAGACGAAACCGGCATGGGCGTTTACGAACACAAAGTGGCCAAGAATCAAGGCAAAT
CCAAAGGTGTTTGGTACAACCTCCACAATAAAAAATCGATTGGTATCCTCAATATAGACGAGCGTACCG
GTATGATCGAGATTGCAAAGCCTATCGGAGTTGTAGGAGCCGTAACGCCGACGACCAACCCGATCGTTA
CTCCGATGAGCAATATCATCTTTGCTCTTAAGACCTGCAATGCCATCATTATTGCCCCCCACCCCAGATCC
AAAAAATGCTCTGCACACGCAGTTCGTCTGATCAAAGAAGCTATCGCTCCGTTCAACGTACCGGAAGGT
ATGGTTCAGATCATCGAAGAACCCAGCATCGAGAAGACGCAGGAACTCATGGGCGCCGTAGACGTAGT
AGTTGCTACGGGTGGTATGGGCATGGTGAAGTCTGCATATTCTTCAGGAAAGCCTTCTTTCGGTGTTGG
AGCCGGTAACGTTCAGGTGATCGTGGATAGCAACATCGATTTCGAAGCTGCTGCAGAAAAAATCATCAC
```

FIG. 52

CGGTCGTGCTTTCGACAACGGTATCATCTGCTCAGGCGAACAGAGCATCATCTACAACGAGGCTGACAA
GGAAGCAGTTTTCACAGCATTCCGCAACCACGGTGCATATTTCTGTGACGAAGCCGAAGGAGATCGGGC
TCGTGCAGCTATCTTCGAAAATGGAGCCATCGCGAAAGATGTAGTAGGTCAGAGCGTTGCCTTCATTGC
CAAGAAAGCAAACATCAATATCCCCGAGGGTACCCGTATTCTCGTTGTTGAAGCTCGCGGCGTAGGAGC
AGAAGACGTTATCTGTAAGGAAAAGATGTGTCCCGTAATGTGCGCCCTCAGCTACAAGCACTTCGAAGA
AGGTGTAGAAATCGCACGTACGAACCTCGCCAACGAAGGTAACGGCCACACCTGTGCTATCCACTCCAA
CAATCAGGCACACATCATCCTCGCAGGATCAGAGCTGACGGTATCTCGTATCGTAGTGAATGCTCCGAG
TGCCACTACAGCAGGCGGTCACATCCAAAACGGTCTTGCCGTAACCAATACGCTCGGATGCGGATCATG
GGGTAATAACTCTATCTCCGAGAACTTCACTTACAAGCACCTCCTCAACATTTCACGCATCGCACCGTTGA
ATTCAAGCATTCACATCCCCGATGACAAAGAAATCTGGGAACTCTAATCTAGCAAGAGGAGAAGTCGAC
ATGCAACTTTTCAAACTCAAGAGTGTAACACATCACTTTGACACTTTTGCAGAATTTGCCAAGGAATTCTG
TCTTGGAGAACGCGACTTGGTAATTACCAACGAGTTCATCTATGAACCGTATATGAAGGCATGCCAGCTC
CCCTGCCATTTTGTTATGCAGGAGAAATATGGGCAAGGCGAGCCTTCTGACGAAATGATGAATAACATC
TTGGCAGACATCCGTAATATCCAGTTCGACCGCGTAATCGGTATCGGAGGAGGTACGGTTATTGACATC
TCTAAACTTTTCGTTCTGAAAGGATTAAATGATGTACTCGATGCATTCGACCGCAAAATACCTCTTATCAA
AGAGAAAGAACTGATCATTGTGCCCACAACATGCGGAACGGGTAGCGAGGTGACGAACATTTCTATCG
CAGAAATCAAAAGCCGTCACACCAAAATGGGATTGGCTGACGATGCCATTGTTGCAGACCATGCCATCA
TCATACCTGAACTTCTGAAGAGCTTGCCTTTCCACTTCTACGCATGCAGTGCAATCGATGCTCTTATCCAT
GCCATCGAGTCATACGTATCTCCTAAAGCCAGTCCATATTCTCGTCTGTTCAGTGAGGCGGCTTGGGACA
TTATCCTGGAAGTATTCAAGAAAATCGCCGAACACGGCCCTGAATACCGCTTCGAAAAGCTGGGAGAAA
TGATCATGGCCAGCAACTATGCCGGTATAGCCTTCGGAAATGCAGGAGTAGGAGCCGTCCACGCACTAT
CCTACCCGTTGGGAGGCAACTATACGTGCCGCATGGAGAAGCAAACTATCAGTTCTTCACAGAGGTAT
TCAAAGTATACCAAAAGAAGAATCCTTTCGGCTATATAGTCGAACTCAACTGGAAGCTCTCCAAGATACT
GAACTGCCAGCCCGAATACGTATATCCGAAGCTGGATGAACTTCTCGGATGCCTTCTTACCAAGAAACCT
TTGCACGAATACGGCATGAAGGACGAAGAGGTAAGAGGCTTTGCGGAATCAGTGCTTAAGACACAGCA
AAGATTGCTCGCCAACAACTACGTAGAGCTTACTGTAGATGAGATCGAAGGTATCTACAGAAGACTCTA
CTAATCTAGAAAGCTTCCTAGAGGCATCAAATAAAACGAAAGGCTCAGTCGAAAGACTGGGCCTTTCGT
TTTATCTGTTGTTTGTCGGTGAACGCTCTCCTGAGTAGGACAAATCCGCCGCCCTAGACCTAGGCGTTCG
GCTGCGACACGTCTTGAGCGATTGTGTAGGCTGGAGCTGCTTCGAAGTTCCTATACTTTCTAGAGAATAG
GAACTTCGGAATAGGAACTAAGGAGGATATTCATATGGACCATGGCTAATTCCCAT

FIG. 52 (cont'd)

TCGAGAAATTTATCAAAAAGAGTGTTGACTTGTGAGCGGATAACAATGATACTTAGATTCAATTGTGAG
CGGATAACAATTTCACACAGAATTCAATTAAGCTAGCAAGAGGAGAAGTCGACATGGCCAACATAAGTT
CACCATTCGGGCAAAACGAATGGCTGGTTGAAGAGATGTACCGCAAGTTCCGCGACGACCCCTCCTCGG
TCGATCCCAGCTGGCACGAGTTCCTGGTTGACTACAGCCCCGAACCCACCTCCCAACCAGCTGCCGAACC
AACCCGGGTTACCTCGCCACTCGTTGCCGAGCGGGCCGCTGCGGCCGCCCCGCAGGCACCCCCAAGCC
GGCCGACACCGCGGCCGCGGGCAACGGCGTGGTCGCCGCACTGGCCGCCAAAACTGCCGTTCCCCCGC
CAGCCGAAGGTGACGAGGTAGCGGTGCTGCGCGGCGCCGCCGCGGCCGTCGTCAAGAACATGTCCGC
GTCGTTGGAGGTGCCGACGGCGACCAGCGTCCGGGCGGTCCCGGCCAAGCTACTGATCGACAACCGGA
TCGTCATCAACAACCAGTTGAAGCGGACCCGCGGCGGCAAGATCTCGTTCACGCATTTGCTGGGCTACG
CCCTGGTGCAGGCGGTGAAGAAATTCCCGAACATGAACCGGCACTACACCGAAGTCGACGGCAAGCCC
ACCGCGGTCACGCCGGCGCACACCAATCTCGGCCTGGCGATCGACCTGCAAGGCAAGGACGGGAAGCG
TTCCCTGGTGGTGGCCGGCATCAAGCGGTGCGAGACCATGCGATTCGCGCAGTTCGTCACGGCCTACGA
AGACATCGTACGCCGGGCCCGCGACGGCAAGCTGACCACTGAAGACTTTGCCGGCGTGACGATTTCGCT
GACCAATCCCGGAACCATCGGCACCGTGCATTCGGTGCCGCGGCTGATGCCCGGCCAGGGCGCCATCAT
CGGCGTGGGCGCCATGGAATACCCCGCCGAGTTTCAAGGCGCCAGCGAGGAACGCATCGCCGAGCTGG
GCATCGGCAAATTGATCACTTTGACCTCCACCTACGACCACCGCATCATCCAGGGCGCGGAATCGGGCG
ACTTCCTGCGCACCATCCACGAGTTGCTGCTCTCGGATGGCTTCTGGGACGAGGTCTTCCGCGAACTGAG
CATCCCATATCTGCCGGTGCGCTGGAGCACCGACAACCCCGACTCGATCGTCGACAAGAACGCTCGCGT
CATGAACTTGATCGCGGCCTACCGCAACCGCGGCCATCTGATGGCCGATACCGACCCGCTGCGGTTGGA
CAAAGCTCGGTTCCGCAGTCACCCCGACCTCGAAGTGCTGACCCACGGCCTGACGCTGTGGGATCTCGA
TCGGGTGTTCAAGGTCGACGGCTTTGCCGGTGCGCAGTACAAGAAACTGCGCGACGTGCTGGGCTTGCT
GCGCGATGCCTACTGCCGCCACATCGGCGTGGAGTACGCCCATATCCTCGACCCCGAACAAAAGGAGTG
GCTCGAACAACGGGTCGAGACCAAGCACGTCAAACCCACTGTGGCCCAACAGAAATACATCCTCAGCAA
GCTCAACGCCGCCGAGGCCTTTGAAACGTTCCTACAGACCAAGTACGTCGGCCAGAAGCGGTTCTCGCT
GGAAGGCGCCGAAAGCGTGATCCCGATGATGGACGCGGCGATCGACCAGTGCGCTGAGCACGGCCTC
GACGAGGTGGTCATCGGGATGCCGCACCGGGGCCGGCTCAACGTGCTGGCCAACATCGTCGGCAAGCC
GTACTCGCAGATCTTCACCGAGTTCGAGGGCAACCTGAATCCGTCGCAGGCGCACGGCTCCGGTGACGT
CAAGTACCACCTGGGCGCCACCGGGCTGTACCTGCAGATGTTCGGCGACAACGACATTCAGGTGTCGCT
GACCGCCAACCCGTCGCATCTGGAGGCCGTCGACCCGGTGCTGGAGGGATTGGTGCGGGCCAAGCAGG
ATCTGCTCGACCACGGAAGCATCGACAGCGACGGCCAACGGGCGTTCTCGGTGGTGCCGCTGATGTTGC
ATGGCGATGCCGCGTTCGCCGGTCAGGGTGTGGTCGCCGAGACGCTGAACCTGGCGAATCTGCCGGGC
TACCGCGTCGGCGGCACCATCCACATCATCGTCAACAACCAGATCGGCTTCACCACCGCGCCCGAGTATT
CCAGGTCCAGCGAGTACTGCACCGACGTCGCAAAGATGATCGGGGCACCGATCTTTCACGTCAACGGCG
ACGACCCGGAGGCGTGTGTCTGGGTGGCGCGGTTGGCGGTGGACTTCCGACAACGGTTCAAGAAGGAC
GTCGTCATCGACATGCTGTGCTACCGCCGCCGCGGGCACAACGAGGGTGACGACCCGTCGATGACCAA
CCCCTACATGTACGACGTCGTCGACACCAAGCGCGGGGCCCGCAAAAGCTACACCGAAGCCCTGATCGG
ACGTGGCGACATCTCGATGAAGGAGGCCGAGGACGCGCTGCGCGACTACCAGGGCCAGCTGGAACGG
GTGTTCAACGAAGTGCGCGAGCTGGAGAAGCACGGTGTGCAGCCGAGCGAGTCGGTCGAGTCCGACC
AGATGATTCCCGCGGGGCTGGCCACTGCGGTGGACAAGTCGCTGCTGGCCCGGATCGGCGATGCGTTC
CTCGCCTTGCCGAACGGCTTCACCGCGCACCCGCGAGTCCAACCGGTGCTGGAGAAGCGCCGGAGAT
GGCCTATGAAGGCAAGATCGACTGGGCCTTTGGCGAGCTGCTGGCGCTGGGCTCGCTGGTGGCCGAAG
GCAAGCTGGTGCGCTTGTCGGGGCAGGACAGCCGCCGCGGCACCTTCTCCCAGCGGCATTCGGTTCTCA
TCGACCGCCACACTGGCGAGGAGTTCACACCACTGCAGCTGCTGGCGACCAACTCCGACGGCAGCCCGA
CCGGCGGAAAGTTCCTGGTCTACGACTCGCCACTGTCGGAGTACGCCGCCGTCGGCTTCGAGTACGGCT
ACACTGTGGGCAATCCGGACGCCGTGGTGCTCTGGGAGGCGCAGTTCGGCGACTTCGTCAACGGCGCA

FIG. 53

```
CAGTCGATCATCGACGAGTTCATCAGCTCCGGTGAGGCCAAGTGGGGCCAATTGTCCAACGTCGTGCTG
CTGTTACCGCACGGGCACGAGGGGCAGGGACCCGACCACACTTCTGCCCGGATCGAACGCTTCTTGCAG
TTGTGGGCGGAAGGTTCGATGACCATCGCGATGCCGTCGACTCCGTCGAACTACTTCCACCTGCTACGCC
GGCATGCCCTGGACGGCATCCAACGCCCGCTGATCGTGTTCACGCCCAAGTCGATGTTGCGTCACAAGG
CCGCCGTCAGCGAAATCAAGGACTTCACCGAGATCAAGTTCCGCTCAGTGCTGGAGGAACCCACCTATG
AGGACGGCATCGGAGACCGCAACAAGGTCAGCCGGATCCTGCTGACCAGTGGCAAGCTGTATTACGAG
CTGGCCGCCCGCAAGGCCAAGGACAACCGCAATGACCTCGCGATCGTGCGGCTTGAACAGCTCGCCCC
GCTGCCCAGGCGTCGACTGCGTGAAACGCTGGACCGCTACGAGAACGTCAAGGAGTTCTTCTGGGTCCA
AGAGGAACCGGCCAACCAGGGTGCGTGGCCGCGATTCGGGCTCGAACTACCCGAGCTGCTGCCTGACA
AGTTGGCCGGGATCAAGCGAATCTCGCGCCGGGCGATGTCAGCCCCGTCGTCAGGCTCGTCGAAGGTG
CACGCCGTCGAACAGCAGGAGATCCTCGACGAGGCGTTCGGCTAATCTAGCAAGAGGAGAAGTCGACA
TGAAGTTATTAAAATTGGCACCTGATGTTTATAAATTTGATACTGCAGAGGAGTTTATGAAATACTTTAA
GGTTGGAAAAGGTGACTTTATACTTACTAATGAATTTTTATATAAACCTTTCCTTGAGAAATTCAATGATG
GTGCAGATGCTGTATTTCAGGAGAAATATGGACTCGGTGAACCTTCTGATGAAATGATAAACAATATAA
TTAAGGATATTGGAGATAAACAATATAATAGAATTATTGCTGTAGGGGAGGATCTGTAATAGATATAG
CCAAAATCCTCAGTCTTAAGTATACTGATGATTCATTGGATTTGTTTGAGGGAAAAGTACCTCTTGTAAA
AAACAAAGAATTAATTATAGTTCCAACTACATGTGGAACAGGTTCAGAAGTTACAAATGTATCAGTTGCA
GAATTAAAGAGAAGACATACTAAAAAAGGAATTGCTTCAGACGAATTATATGCAACTTATGCAGTACTT
GTACCAGAATTTATAAAAGGACTTCCATATAAGTTTTTTGTAACCAGCTCCGTAGATGCCTTAATACATGC
AACAGAAGCTTATGTATCTCCAAATGCAAATCCTTATACTGATATGTTTAGTGTAAAAGCTATGGAGTTA
ATTTTAAATGGATACATGCAAATGGTAGAGAAAGGAAATGATTACAGAGTTGAAATAATTGAGGATTTT
GTTATAGGCAGCAATTATGCAGGTATAGCTTTTGGAAATGCAGGAGTGGGAGCGGTTCACGCACTCTCA
TATCCAATAGGCGGAAATTATCATGTGCCTCATGGAGAAGCAAATTATCTGTTTTTTACAGAAATATTTA
AAACTTATTATGAGAAAAATCCAAATGGCAAGATTAAAGATGTAAATAAACTATTAGCAGGCATACTAA
AATGTGATGAAAGTGAAGCTTATGACAGTTTATCACAACTTTTAGATAAATTATTGTCAAGAAAACCATT
AAGAGAATATGGAATGAAAGAGGAAGAAATTGAAACTTTTGCTGATTCAGTAATAGAAGGACAGCAGA
GACTGTTGGTAAACAATTATGAACCTTTTTCAAGAGAAGACATAGTAAACACATATAAAAAGTTATATTA
ATCTAGAAAGCTTCCTAGAGGCATCAAATAAAACGAAAGGCTCAGTCGAAAGACTGGGCCTTTCGTTTT
ATCTGTTGTTTGTCGGTGAACGCTCTCCTGAGTAGGACAAATCCGCCGCCCTAGACCTA
```

```
ATGGCAGTGGATTCACCGGATGAGCGGCTACAGCGCCGCATTGCACAGTTGTTTGCAGAAGATG
AGCAGGTCAAGGCCGCACGTCCGCTCGAAGCGGTGAGCGCGGCGGTGAGCGCGCCCGGTATGCG
GCTGGCGCAGATCGCCGCCACTGTTATGGCGGGTTACGCCGACCGCCCGGCCGCCGGGCAGCGT
GCGTTCGAACTGAACACCGACGACGCGACGGGCCGCACCTCGCTGCGGTTACTTCCCCGATTCG
AGACCATCACCTATCGCGAACTGTGGCAGCGAGTCGGCGAGGTTGCCGCGGCCTGGCATCATGA
TCCCGAGAACCCCTTGCGCGCAGGTGATTTCGTCGCCCTGCTCGGCTTCACCAGCATCGACTAC
GCCACCCTCGACCTGGCCGATATCCACCTCGGCGCGGTTACCGTGCCGTTGCAGGCCAGCGCGG
CGGTGTCCCAGCTGATCGCTATCCTCACCGAGACTTCGCCGCGGCTGCTCGCCTCGACCCCGGA
GCACCTCGATGCGGCGGTCGAGTGCCTACTCGCGGGCACCACACCGGAACGACTGGTGGTCTTC
GACTACCACCCCGAGGACGACGACCAGCGTGCGGCCTTCGAATCCGCCCGCCGCCGCCTTGCCG
ACGCGGGCAGCTTGGTGATCGTCGAAACGCTCGATGCCGTGCGTGCCCGGGCCGCGACTTACC
GGCCGCGCCACTGTTCGTTCCCGACACCGACGACGACCCGCTGGCCCTGCTGATCTACACCTCC
GGCAGCACCGGAACGCCGAAGGGCGCGATGTACACCAATCGGTTGGCCGCCACGATGTGGCAGG
GGAACTCGATGCTGCAGGGGAACTCGCAACGGGTCGGGATCAATCTCAACTACATGCCGATGAG
CCACATCGCCGGTCGCATATCGCTGTTCGGCGTGCTCGCTCGCGGTGGCACCGCATACTTCGCG
GCCAAGAGCGACATGTCGACACTGTTCGAAGACATCGGCTTGGTACGTCCCACCGAGATCTTCT
TCGTCCCGCGCGTGTGCGACATGGTCTTCCAGCGCTATCAGAGCGAGCTGGACCGGCGCTCGGT
GGCGGGCGCCGACCTGGACACGCTCGATCGGGAAGTGAAAGCCGACCTCCGGCAGAACTACCTC
GGTGGGCGCTTCCTGGTGGCGGTCGTCGGCAGCGCGCCGCTGGCCGCGGAGATGAAGACGTTCA
TGGAGTCCGTCCTCGATCTGCCACTGCACGACGGGTACGGGTCGACCGAGGCGGGCGCAAGCGT
GCTGCTCGACAACCAGATCCAGCGGCCGCCGGTGCTCGATTACAAGCTCGTCGACGTGCCCGAA
CTGGGTTACTTCCGCACCGACCGGCCGCATCCGCGCGGTGAGCTGTTGTTGAAGGCGGAGACCA
CGATTCCGGGCTACTACAAGCGGCCCGAGGTCACCGCGGAGATCTTCGACGAGGACGGCTTCTA
CAAGACCGGCGATATCGTGGCCGAGCTCGAGCACGATCGGCTGGTCTATGTCGACCGTCGCAAC
AATGTGCTCAAACTGTCGCAGGGCGAGTTCGTGACCGTCGCCCATCTCGAGGCCGTGTTCGCCA
GCAGCCCGCTGATCCGGCAGATCTTCATCTACGGCAGCAGCGAACGTTCCTATCTGCTCGCGGT
GATCGTCCCCACCGACGACGCGCTGCGCGGCCGCGACACCGCCACCTTGAAATCGGCACTGGCC
GAATCGATTCAGCGCATCGCCAAGGACGCGAACCTGCAGCCCTACGAGATTCCGCGCGATTTCC
TGATCGAGACCGAGCCGTTCACCATCGCCAACGGACTGCTCTCCGGCATCGCGAAGCTGCTGCG
CCCCAATCTGAAGGAACGCTACGGCGCTCAGCTGGAGCAGATGTACACCGATCTCGCGACAGGC
CAGGCCGATGAGCTGCTCGCCCTGCGCCGCGAAGCCGCCGACCTGCCGGTGCTCGAAACCGTCA
GCCGGGCAGCGAAAGCGATGCTCGGCGTCGCCTCCGCCGATATGCGTCCCGACGCGCACTTCAC
CGACCTGGGCGGCGATTCCCTTTCCGCGCTGTCGTTCTCGAACCTGCTGCACGAGATCTTCGGG
GTCGAGGTGCCGGTGGGTGTCGTCGTCAGCCCGGCGAACGAGCTGCGCGATCTGGCGAATTACA
TTGAGGCGGAACGCAACTCGGGCGCGAAGCGTCCCACCTTCACCTCGGTGCACGGCGGCGGTTC
CGAGATCCGCGCCGCCGATCTGACCCTCGACAAGTTCATCGATGCCCGCACCCTGGCCGCCGCC
GACAGCATTCCGCACGCGCCGGTGCCAGCGCAGACGGTGCTGCTGACCGGCGCGAACGGCTACC
TCGGCCCGGTTCCTGTGCCTGGAATGGCTGGAGCGGCTGGACAAGACGGGTGGCACGCTGATCTG
CGTCGTGCGCGGTAGTGACGCGGCCGCGGCCCGTAAACGGCTGGACTCGGCGTTCGACAGCGGC
GATCCCGGCCTGCTCGAGCACTACCAGCAACTGGCCGCACGGACCCTGGAAGTCCTCGCCGGTG
ATATCGGCGACCCGAATCTCGGTCTGGACGACGCGACTTGGCAGCGGTTGGCCGAAACCGTCGA
CCTGATCGTCCATCCCGCCGCGTTGGTCAACCACGTCCTTCCCTACACCCAGCTGTTCGGCCCC
```

FIG. 59A

```
AATGTCGTCGGCACCGCCGAAATCGTCCGGTTGGCGATCACGGCGCGGCGCAAGCCGGTCACCT
ACCTGTCGACCGTCGGAGTGGCCGACCAGGTCGACCCGGCGGAGTATCAGGAGGACAGCGACGT
CCGCGAGATGAGCGCGGTGCGCGTCGTGCGCGAGAGTTACGCCAACGGCTACGGCAACAGCAAG
TGGGCGGGGGAGGTCCTGCTGCGCGAAGCACACGATCTGTGTGGCTTGCCGGTCGCGGTGTTCC
GTTCGGACATGATCCTGGCGCACAGCCGGTACGCGGGTCAGCTCAACGTCCAGGACGTGTTCAC
CCGGCTGATCCTCAGCCTGGTCGCCACCGGCATCGCGCCGTACTCGTTCTACCGAACCGACGCG
GACGGCAACCGGCAGCGGGCCCACTATGACGGCTTGCCGGCGGACTTCACGGCGGCGGCGATCA
CCGCGCTCGGCATCCAAGCCACCGAAGGCTTCCGGACCTACGACGTGCTCAATCCGTACGACGA
TGGCATCTCCCTCGATGAATTCGTCGACTGGCTCGTCGAATCCGGCCACCCGATCCAGCGCATC
ACCGACTACAGCGACTGGTTCCACCGTTTCGAGACGGCGATCCGCGCGCTGCCGGAAAAGCAAC
GCCAGGCCTCGGTGCTGCCGTTGCTGGACGCCTACCGCAACCCCTGCCCGGCGGTCCGCGGCGC
GATACTCCCGGCCAAGGAGTTCCAAGCGGCGGTGCAAACAGCCAAAATCGGTCCGGAACAGGAC
ATCCCGCATTTGTCCGCGCCACTGATCGATAAGTACGTCAGCGATCTGGAACTGCTTCAGCTGC
TCTAA
```

FIG. 59A (cont'd)

```
mavdspderlqrriaqlfaedeqvkaarpleavsaavsapgmrlaqiaatvmagyadrpaagqr
afelntddatgrtslrllprfetityrelwqrvgevaaawhhdpenplragdfvallgftsidy
atldladihlgavtvplqasaavsqliailtetsprllastpehldaaveclagttperlvvf
dyhpedddqraafesarrrladagslvivetldavrargrdlpaaplfvpdtdddplalliyts
gstgtpkgamytnrlaatmwqgnsmlqgnsqrvginlnympmshiagrislfgvlarggtayfa
aksdmstlfediglvrpteiffvprvcdmvfqryqseldrrsvagadldtldrevkadlrqnyl
ggrflvavvgsaplaaemktfmesvldlplhdgygsteagasvlldnqiqrppvldyklvdvpe
lgyfrtdrphprgelllkaettipgyykrpevtaeifdedgfyktgdivaelehdrlvyvdrrn
nvlklsqgefvtvahleavfassplirqifiygssersyllavivptddalrgrdtatlksala
esiqriakdanlqpyeiprdflietepftiangllsgiakllrpnlkerygaqleqmytdlatg
qadellalrreaadlpvletvsraakamlgvasadmrpdahftdlggdslsalsfsnllheifg
vevpvgvvvspanelrdlanyieaernsgakrptftsvhgggseiraadltldkfidartlaaa
dsiphapvpaqtvlltgangylgrflclewlerldktggtlicvvrgsdaaaarkrldsafdsg
dpgllehyqqlaartlevlagdigdpnlglddatwqrlaetvdlivhpaalvnhvlpytqlfgp
nvvgtaeivrlaitarrkpvtylstvgvadqvdpaeyqedsdvremsavrvvresyangygnsk
wagevllreahdlcglpvavfrsdmilahsryagqlnvqdvftrlilslvatgiapysfyrtda
dgnrqrahydglpadftaaaitalgiqategfrtydvlnpyddgisldefvdwlvesghpiqri
tdysdwfhrfetairalpekqrqasvlplldayrnpcpavrgailpakefqaavqtakigpeqd
iphlsaplidkyvsdlellqll*
```

FIG. 59B

ATGATTGAAACCATTCTGCCTGCAGGCGTTGAAAGCGCAGAACTGCTGGAATATCCGGAAGATC
TGAAAGCACATCCGGCAGAAGAACATCTGATTGCCAAAAGCGTTGAAAAACGTCGTCGTGATTT
TATTGGTGCACGTCATTGTGCACGTCTGGCACTGGCAGAACTGGGTGAACCTCCGGTTGCAATT
GGTAAAGGTGAACGTGGTGCACCGATTTGGCCTCGTGGTGTTGTTGGTAGCCTGACCCATTGTG
ATGGTTATCGTGCAGCAGCAGTTGCACATAAAATGCGCTTTCGCAGCATTGGTATTGATGCAGA
ACCGCATGCAACCCTGCCGGAAGGTGTTCTGGATAGCGTTAGCCTGCCGCCGGAACGTGAATGG
CTGAAAACCACCGATAGCGCACTGCATCTGGATCGTCTGCTGTTTTGTGCAAAAGAAGCCACCT
ATAAAGCCTGGTGGCCGCTGACAGCACGTTGGCTGGGTTTTGAAGAAGCCCATATTACCTTTGA
AATTGAAGATGGTAGCGCAGATAGCGGTAATGGCACCTTTCATAGCGAACTGCTGGTTCCGGGT
CAGACCAATGATGGTGGTACACCGCTGCTGAGCTTTGATGGTCGTTGGCTGATTGCAGATGGTT
TTATTCTGACCGCAATTGCCTATGCCTAA

FIG. 60A mietilpagvesaelleypedlkahpaeehliaksvekrrrdfigarhcarlalaelgeppvai
gkgergapiwprgvvgslthcdgyraaavahkmrfrsigidaephatlpegvldsvslpperew
lkttdsalhldrllfcakeatykawwpltarwlgfeeahitfeiedgsadsgngtfhsellvpg
qtndggtpllsfdgrwliadgfiltaiaya*

FIG. 60B

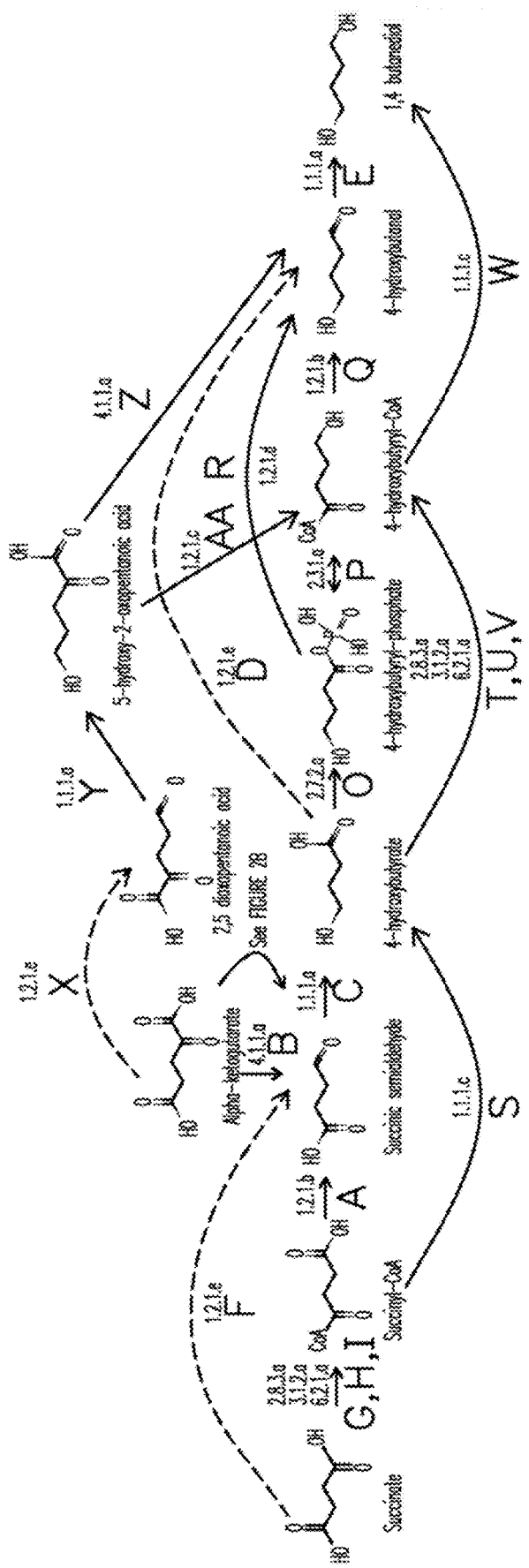
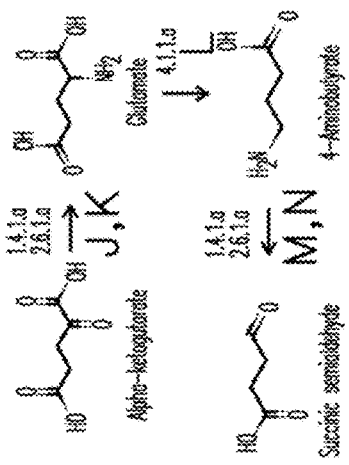
FIG. 62A
FIG. 62B

```
atgaccagcgatgttcacgacgccacagacggcgtcaccgaaaccgactcgacgacgagcagtcgaccgccgcat
cgccgagctgtacgccaccgatcccgagttcgccgccgccgcaccgttgcccgccgtggtcgacgcggcgcacaaa
ccgggctgcggctggcagagatcctgcagaccctgttcaccggctacggtgaccgcccggcgctgggataccgcgcc
cgtgaactggccaccgacgagggcgggcgcacgtgacgcgtctgctgccgcggttcgacaccctcacctacgccca
ggtgtggtcgcgcgtgcaagcggtcgccgcgggccctgcgccacaacttcgagcagccgatctacccggcgacgccg
tcgcgacgatcggtttcgcgagtcccgattacctgacgctggatctcgtatgcgcctacctgggcctcgtgagtgtt
ccgctgcagcacaacgcaccggtcagccggctcgccccgatcctggccgaggtcgaaccgcggatcctcaccgtgag
cgccgaatacctcgacctcgcagtcgaatccgtgcgggacgtcaactcggtgtcgcagctcgtggtgttcgaccatc
accccgaggtcgacgaccaccgcgacgcactggcccgcgcgcgtgaacaactcgccggcaagggcatcgccgtcacc
accctggacgcgatcgccgacgagggcgccggcgctgccggccgaaccgatctacaccgccgaccatgatcagcgcct
cgcgatgatcctgtacacctcgggttccaccggcgcacccaagggtgcgatgtacaccgaggcgatggtggcgcggc
tgtggaccatgtcgttcatcacgggtgaccccacgccggtcatcaacgtcaacttcatgccgctcaaccacctgggc
gggcgcatccccatttccaccgccgtgcagaacggtggaaccagttacttcgtaccggaatccgacatgtccacgct
gttcgaggatctcgcgctggtgcgcccgaccgaactcggctggttccgcgcgtcgccgacatgctctaccagcacc
acctcgccacgtcgaccgcctggtcacgcagggcgccgacgaactgaccgccgagaagcaggccggtgccgaactg
cgtgagcaggtgctcggcggacgcgtgatcaccggattcgtcagcaccgcaccgctggccgcggagatgagggcgtt
cctcgacatcaccctgggcgcacacatcgtcgacggctacgggctcaccgagaccggcgccgtgacacgcgacggtg
tgatcgtgcggccaccggtgatcgactacaagctgatcgacgttcccgaactcggctacttcagcacgacaagccc
taccgcgtggcgaactgctggtcaggtcgcaaacgctgactcccgggtactacaagcgccccgaggtcaccgcgag
cgtcttcgaccgggacggctactaccacaccggcgacgtcatggccgagaccgcacccgaccacctggtgtacgtgg
accgtcgcaacaacgtcctcaaactcgcgcagggcgagttcgtggcggtcgccaacctggaggcgtgttctccggc
gcggcgctggtgcgccagatcttcgtgtacggcaacagcgagcgcagtttccttctggccgtggtggtcccgacgcc
ggaggcgctcgagcagtacgatccggccgcgctcaaggccgcgctggccgactcgctgcagcgcaccgcacgcgacg
ccgaactgcaatcctacgaggtgccggccgatttcatcgtcgagaccgagccgttcagcgccgcaacgggctgctg
tcgggtgtcggaaaactgctgcggcccaacctcaaagaccgctacgggcagcgcctggagcagatgtacgccgatat
cgcggccacgcaggcaaccagttgcgcgaactgcggcgcgcggccgccacacaaccggtgatcgacaccctcaccc
aggccgctgccacgatcctcggcaccgggagcgaggtggcatccgacgccacttcaccgacctggggcggggattcc
ctgtcggcgctgacactttcgaacctgctgagcgatttcttcggtttcgaagttcccgtcggcaccatcgtgaaccc
ggccaccaacctcgccaactcgcccagcacatcgaggcgcagcgcaccgcgggtgaccgcaggccgagtttcacca
ccgtgcacggcgcggacgccaccgagatccgggcgagtgagctgaccctggacaagttcatcgacgccgaaacgctc
cgggccgcaccgggtctgcccaaggtcaccacgagccacgacggtgttgctctcgggcgccaacggctggctggg
ccggttcctcacgttgcagtggctggaacgcctggcacctgtcggcggcaccctcatcacgatcgtgcggggccgcg
acgacgccgcggcccgcgcacggctgacccaggcctacgacaccgatcccgagttgtccgccgcttcgccgagctg
gccgaccgccacctgcgggtggtcgccggtgacatcggcgacccgaatctgggcctcacacccgagatctggcaccg
gctcgccgccgaggtcgacctggtggtgcatccggcagcgctggtcaaccacgtgctccctaccggcagctgttcg
gccccaacgtcgtgggcacggccgaggtgatcaagctggccctcaccgaacggatcaagcccgtcacgtacctgtcc
accgtgtcggtggccatggggatccccgacttcgaggaggacggcgacatccggaccgtgagcccggtcgcccgct
cgacggcggatacgccaacggctacggcaacagcaagtgggccggcgaggtgctgctgcggggaggccacgatctgt
ggggctgcccgtggcgacgttccgctcggacatgatcctggcgcatccgcgctaccgcggtcaggtcaacgtgcca
gacatgttcacgcgactcctgttgagcctcttgatcacggcgtcgcgccgcggtcgttctacatcggagacggtga
gcgcccgcgggcgcactacccggcctgacggtcgatttcgtggccgaggcggtcacgacgctcggcgcgcagcagc
gcgagggatacgtgtcctacgacgtgatgaaccgcacgacgacgggatctccctggatgtgttcgtggactggctg
atccgggcggccatccgatcgaccgggtcgacgactacgacgactgggtgcgtcggttcgagaccgcgttgaccgc
gcttccgagaagcgccgcgcacagaccgtactgccgcgctgtgcacgcgttccgcgctccgcaggcaccgttgcgcg
gcgcacccgaaccacggaggtgttccacgccgcggtgcgcaccgcgaaggtgggccgggagacatcccgcacctc
gacgaggcgctgatcgacaagtacatacgcgatctgcgtgagttcggtctgatctaa
```

FIG. 64A

MTSDVHDATDGVTETALDDEQSTRRIAELYATDPEPAAAAPLPAVVDAAHKPGLRLAEILQTLFTGYGDRPALGYRA
RELATDEGGRTVTRLLPREDTLIFYAQVWSRVQAVAALRHNFAQPIYPGDAVATIGFASPDYLTLDLVCAYLGLVSV
PLQHNAPVSRLAPILAEVEPRILTVSAEYLDLAVESVRDVNSVEQLVVFDHHPEVDHRDALARAEQLAGKGIAVT
TLDAIADEGAGLPARPIYTADHIDQRLAMILYTSGSTGAPKGAMYTRAMVARLWTMSFITGDPTFVINVNPMPLNHLG
GRIPISTAVQNGGTSYPVPEGDMSTLFEDLALVRPTELGLVPRVADMLYQHHLATVDRLVTQGADELIAEKQAGAEL
REQVLQGRVITGFVSTAPLAAEMRAFLDITLGAHIVDGYGLTETQAVTRDGVIVRPPVIDYKLIDVPELGYFSTDKP
YPRGELLVRSQTLTFGYYKRPEVTASVFDRDGYYHTGDVMAETAPDHLVYDRRNNVLKLAQGEFVAVANLEAVFSG
AALVRQIFVYGNSERSFLLAVVPTPEALBQYDPAALKAALADSLQRTARDAELQSYEVPADFIVETEPPSAANGLI
SGVCKLLRPNLKDRYGQRLEQMYADIAATOANQLRELRRAAATQPVIDTLTQAATILGTGSEVASDAHPTDLGGDS
LSALTLSNLLSDFFGFEVPVGTIVNPATNLAQLAQHIEAQRTAGDRRPSFTTVHQADATEIRASELITLDKFIDAETL
RAAPGLPKVTEPRTVLLSGANGWLGRFLTLQWLERLAPVGGTLITIVRGRDAAARARLTQAYDTDPELSRRFAEL
ADRHLRVVAGDIGDPNLGLTPEIWHRLAAEWDLVHPAALVNHVLPYRQLFSPNVVGTAEVIKLALTERIKPVITYLS
TVSVAMGIPDFEEDGDIRTVSPVRFLDGGYANGVGNSKWAGEVLLREAHDLCGLPVATFRSDMILAHPRYRGQVNVP
DMFTRLLLSLLITGVAPRSFYIGDGERPRAHYPGLTVDFVAEAVTTLGAQQREGYVSYDVMNPHDDGISLDVFVDWL
IRAGHPIDRVDDYDDWVRRFETALITALPEKRRAQTVLPLLHAFRAPQAPLRGAPEPTEVFHAAVRTAKVGPGDIPHL
DEALIDKYIRDLREFGLI

FIG. 64B

```
atgtcgactgccacccatgacgaacgactcgaccgtcgcgtccacgaactcatcgccaccgaccgcaattcgccgc
cgcccaacccgacccggcgatcaccgccgcctcgaacagcccgggctgcggctgccgcagatcatccgcaccgtgc
tcgacggctacgccgaccggccggcgctgggacagcgcgtggtggagttcgtcacggacgccaagacggggcgcacg
tgggcgcagctgctccccggcttcgagaccatcacgtacagcgaagtagcgcagcgtgtttcggcgctgggccgcgc
cctgtccgacgacgcggtgcaccccggcgaccgggtgtgcgtgctgggcttcaacagcgtcgactacgccaccatcg
acatggcgctgggcgccatcggcgccgtctcggtgccgctgcagaccagcgcggcaatcagctcgctgcagccgatc
gtggccgagaccgagccaccctgatcgcgtccagcgtgaaccagctgtccgacgcggtgcagctgatcaccggcgc
cgagcaggcgcccacccggctggtggtgttcgactaccaccgcaggtcgacgaccagcgcgaggccgtccaggacg
ccgcggcgcggctgtccagcaccggcgtggccgtccagacgctggccgagctgctggagcgcggcaaggacctgccc
gccgtcgcggagccgccgccgacgaggactcgctggccctgctgatctacacctccgggtccaccggcgcccccaa
gggcgcgatgtacccacagagcaacgtcggcaagatgtggcgccgcggcagcaagaactggttcggcgagagcgccg
cgtcgatcaccctgaacttcatgccgatgagccacgtgatgggccgaagcatcctctacggcacgctgggcaacggc
ggcaccgcctactcgccgccgcagcgacctgtccaccctgcttgaggacctcgagctggtgcgccaccgagct
caacttcgtcccgcgggatctgggagacgctgtacggcgaattccagcgtcaggtcgagcggcggctctccgaggcg
gggacgccggcgaacgtgcgcgccgtcgaggccgaggtgctggccgagcagcgccagtacctgctgggcgggcggttc
accttcgcgatgacgggctcggcgcccatctcgccggagctgcgcaactgggtcgagtcgctgctcgaaatgcacct
gatggacggctacggctccaccgaggccggaatggtgttgttcgacggggagattcagcgcccgccggtgatcgact
acaagctggtcgacgtgccggacctgggctacttcagcaccgaccggccgcatccgcgcggcgagctgctgctgcgc
accgagaacatgttcccgggctactacaagcgggccgaaaccaccgcgggcgtcttcgacgaggacggctactaccg
caccggcgacgtgttcgccgagatcgccccggaccggctggtctacgtcgaccgcgccaacaacgtgctcaagctgg
cgcagggcgaattcgtcacgctggccaagctggaggcggtgttcggcaacagccgctgatccgccagatctacgtc
tacggcaacagcgcccagccctacctgctggcggtcgtggtgcccaccgaggaggcgctggcctcgggtgaccccga
gacgctcaagcccaagatcgccgactcgctgcagcaggtcgccaaggaggccggcctgcagtcctacgaggtgccgc
gcgacttcatcatcgagaccacccgttcagcctggaaaacggtctgctgaccgggatccggaagctggcgtggccg
aaactgaagcagcactacggggaacggctggagcagatgtacgccgacctggccgccggacaggccaacgagctggc
cgagctgcgccgcaacggtgcccaggcgccggtgttgcagaccgtgagccgcgccgggcgccatgctgggttcgg
ccgctccgacctgtccccgacgcccacttcaccgatctgggcggagactcgttgtcggcgttgacattcggcaac
ctgctgcgcgagatcttcgacgtcgacgtgccggtaggcgtgatcgtcagccggccaacgacctggcggccatcgc
gagctacatcgaggccgagcggcagggcagcaagcgcccgacgttcgcctcggtgcacggccgggacgcgaccgtgg
tgcgcgccgccgacctgacgctggacaagttcctcgacgccgagacgctggccgccgcgccgaacctgccaagccg
gccaccgaggtgcgcaccgtgctgctgacggcgccaccggcttcctgggccgctaccggccctggaatggctgga
gcggatggacatggtggacggcaaggtcatcgccctggtccgggccgctccgacgaggaggcacgcgccggctgg
acaagaccttcgacagcggcgacccgaaactgctcgcgcactaccagcagctggccgccgatcacctggaggtcatc
gccggcgacaagggcgaggccaatctgggcctgggcaagacgtttggcaacgactggccgacacggtcgacgtgat
cgtcgaccccgccgcgctggtcaaccacgtgttgccgtacagcgagctgttcgggcccaacgccctgggcaccgcgg
agctgatccggctggcgctgacgtccaagcagaagccgtacacctacgtgtccaccatcggcgtgggcgaccagatc
gagccgggcaagttcgtcgagaacgccgacatccggcagatgagcgccaccggcgatcaacgacagctacgccaa
cggctatggcaacagcaagtgggccggcgaggtgctgctgcgcgaggcgcacgacctgtgcggctgccgtcgcgg
tgttccgctgcgacatgatcctggccgacaccacgtatgccggcagctcaacctgcggacatgttcacccggctg
atgctgagcctggtggccaccgggatcgcgccggctcgttctacgagctcgacgccgacggcaaccggcagcgggc
gcactacgacggcctgccggtcgagttcatcgccgcggcgatctcgacgctgggttcgcagatcaccgacagcgaca
ccggcttccagacctaccacgtgatgaaccctacgatgacggcgtcggtctggacgagtacgtcgattggctggtg
gacgccggctattcgatcgagcggatcgccgactactccgaatggctgcgcgggttcgagacctcgctgcgggcct
gccggaccggcagcgccagtactcgctgctgccgctgctgcacaactaccgcacgccggagaagccgatcaacgggt
cgatagctcccaccgacgtgttccgggcagcggtgcaggaggcgaaaatcggcccgacaaagacattccgcacgtg
tcgccgccggtcatcgtcaagtacatcaccgacctgcagctgctcgggctgctctaa
```

FIG. 65A

MSTATHDERLDRKVHHLIATDPQFAAAQPDPAITAALEQPGLRLPQIIRTVLDGYADRPALGQRVVEFVTDAKTGRT
SAQLLPRFTITYSEVAQRVSALGRALSDDAVHPGDRVCVLGPNSVDYATIDMALGAIGAVSVFLQTSAAISSLQPI
VAETEPTLIASSVNQLSDAVQLITGAEQAPTRLVFDYHPQVDQREAVQDAAARLSTGVAVQTLAELLERGKDLP
AVAEPPADEDSLALLIYTSGSTGAPKGAMYFQSNVGKMWRGSKNWFGESAASTTLNFMFMSHVMGRSILYGTLGNG
GTAYFAARSDLSTLLEEDLELVRPTELMFVFRIWETLYGEFQRQVERRLSEAGDAGERRAVRAEVLAEQRQYLLQGRP
TFAMTQSAPISPELRNMVHSLLEMHLMDGYGSTEAGMVLFFKGEIQRPVIIDYKLVIDVFDLGYFSTDKPHPRGELLIR
TENMFFQYYKRAETTAGVFDEDGYYRTGDVFAEIAPDRLVYYDRRNNVLKLAQEFVTLAKLEAVFQNSPLIRQIYV
YGNSAQPYLLAVVVPTHEALASGDPETLKPKIADSLQQVAKEAGLQSYEVPRDFIIETTPFSLENGLITGIRKLAWP
KLKQHYGERLEQMYADLAAGQANELABLIRRNGAQAPVLQTVSRAAGAMLGSAASDLSPDAHFTDLGGDSLSALTFGN
LLREIFDVDVPVGVIVSPANDLAAIASYIEAERQGSKRFTFASVHGRDATVVRAADLTLDKFLDAETLAAAPNLPKP
ATEVRTVLITGATGFLGRYLALEWLERMDMVDGKVIALVRARSDEEARARLDKTFDSGDPKLLAHYQLAADHLEVI
AGDKGEANLGLGQDVWQRLADTYDVIVDPAALVNHYLPYSELFGPNALGTAELIRLALTSKQKFYTYVSTIGVGDQI
EPGKFVENADIRQMSATRAINDSYANGYGNSKWAGEVLLREAHDLCGLPVAVFRCDMILADTTYAGQLNLPDMFTRL
MLSLVATGIAPGSFYELDADGNRQRAHYDGLPVEFIAAAISTLGSQITDSDTGFQTYHVMNPYDDGVGLDEYVDWLV
DAGYSIERIADYSEWLRRFETSLRALPDKQRQYSLLPLLHNYRTFEKPINGSIAPTDVFRAAVQEAKIGPDKDIPHV
SPPVTVRYITDLQLLGLL

FIG. 65B

```
atgtcgccaatcacgcgtgaagagcggctcgagcgccgcatccaggacctctacgccaacgacccgcagttcgccgc
cgccaaacccgccacggcgatcaccgcagcaatcgagcggccgggtctaccgctaccccagatcatcgagaccgtca
tgaccggatacgccgatcggccggctctcgctcagcgctcggtcgaattcgtgaccgacgccggcaccggccacacc
acgctgcgactgctccccacttcgaaaccatcagctacggcgagctttgggaccgcatcagcgcactggcgacgt
gctcagcaccgaacagacggtgaaaccgggcgaccgggtctgcttgttgggcttcaacagcgtcgactacgccacga
tcgacatgactttggcgcggctgggcgcggtggccgtaccactgcagaccagcgcggcgataaccagctgcagccg
atcgtcgccgagaccagcccaccatgatcgcggccagcgtcgacgcactcgctgacgccaccgaattggctctgtc
cggtcagaccgctacccgagtcctggtgttcgaccaccaccggcaggttgacgcacaccgcgcagcggtcgaatccg
ccgggagcgcctggccggctcggcggtcgtcgaaaccctggccgaggccatcgcgcgcggcgacgtgcccgcggt
gcgtccgccggctcggcgcccggcaccgatgtgtccgacgactcgctcgcgctactgatctacacctcgggcagcac
gggtgcgcccaagggcgcgatgtaccccgacgcaacgttgcgacctcctggcgcaagcgcacctggttcgaaggcg
gctacgagccgtcgatcacgctgaacttcatgccaatgagccacgtcatgggccgccaaatcctgtacggcacgctg
tgcaatggcgccaccgcctactcgtggcgaaaagcgatctctccaccttgttcgaagacctggcgctggtgcggcc
accgagctgaccttcgtgccgcgcgtgtgggacatggtgttcgacgagtttcagagtgaggtcgaccgccgctgg
tcgacggcgccgaccgggtcgcgctcgaagcccaggtcaaggccgagatacgcaacgacgtgctcggtggacggtat
accagcgcactgaccggctccgcccctatctcgacgagatgaaggcgtgggtcgaggagctgctcgacatgcatct
ggtcgagggctacggctccacgaggccgggatgatcctgatcgacggagccattcggcgcccggcggtactcgact
acaagctggtcgatgttccgacctgggttacttcctgaccgaccggccacatccgggggcgagttgctggtcaag
accgatagtttgttccgggctactaccagcgagccgaagtcaccgccgacgtgttcgatgctgacggcttctaccg
gaccggcgacatcatggccgaggtcggccccgaacagttcgtgtacctcgaccgccgcaacaacgtgttgaagctgt
cgcagggcgagttcgtcaccgtctccaaactcgaagcggtgtttggcgacagcccactggtacggcagatctacatc
tacggcaacagcgcccgtgcctacctgttggcggtgatcgtccccaccaggaggcgctggaccgcgtgcctgtcga
ggagctcaaggcgcggctgggcgactcgctgcaagaggtcgcaaaggccgccggcctgcagtcctacgagatcccgc
gcgacttcatcatcgaaacaacaccatggacgctggagaacggcctgctcaccggcatccgcaagttggccaggccg
cagctgaaaaagcattacggcgagcttctcgagcagatctacacggacctggcacacggccaggccgacgaactgcg
ctcgctgcgccaaagcggtgccgatgcgccggtgctggtgacggtgtgccgtgcggcggccgcgctgttgggcggca
gcgcctctgacgtccagcccgatgcgcacttcaccgatttgggcggcgactcgctgtcggcgctgtcgttcaccaac
ctgctgcacgagatcttcgacatcgaagtgccggtgggcgtcatcgtcagcccgccaacgacttgcaggccctggc
cgactacgtcgaggcggctcgcaaacccggctcgtcacgccgaccttcgcctcggtccacggcgctcgaatgggc
aggtcaccgaggtgcatgccggtgacctgtccctggacaaattcatcgatgccgcaacccctggccgaagctcccgg
ctgcccgccgcaaacacccaagtgcgcaccgtgctgctgaccggcgccaccggcttcctcgggcgctacctggccct
ggaatggctgctgagcggatggaccctggtcgacggcaaactgatctgcctggtccgggccaagtccgacaccgaagcac
gggcgcggctggacaagacgttcgacagcggcgaccccgaactgctggcccactaccgcgcactggccggcgaccac
ctcgaggtgctcgccggtgacaagggcgaagccgacctcggactggaccggcagacctggcaacgcctggccgacac
ggtcgacctgatcgtcgaccccgcggccctggtcaaccacgtactgcatacagccagctgttcgggccaacgcgc
tgggcaccgccgagctgctgcggctggcgctcacctccaagatcaagccctacagctacacctcgacaatcggtgtc
gccgaccagatcccgccgtcggcgttcaccgaggacgccgacatccgggtcatcagcgccaccgcgcggtcgacga
cagctacgccaatggctactcgaacagcaagtgggccggcgaggtgctgttgcgcgaggcgcatgacctgtgtggcc
tgccggttgcggtgttccgctgcgacatgatcctggccgacaccacatgggcgggacagctcaatgtgccggacatg
ttcacccggatgatcctgagcctggcggccaccggtatcgcgccgggttcgttctatgagcttgcggccgacggcgc
ccggcaacgcgccactatgacggtctgcccgtcgagttcatcgccgaggcgatttcgactttgggtgcgcagagcc
aggatggtttccacacgtatcacgtgatgaaccctacgacgacggcatcggactcgacgagttcgtcgactggctc
aacgagtccggttgcccatccagcgcatcgctgactatggcgactggctgcagcgcttcgaaaccgcactgcgcgc
actgcccgatcggcagcggcacagctcactgctgccgctgttgcacaactatcggcagccggagcggcccgtccgcg
ggtcgatcgccctaccgatcgcttccgggcagcggtgcaagaggccaagatcggccccgacaaagacattccgcac
gtcggcgcgccgatcatcgtgaagtacgtcagcgacctgcgcctactcggcctgctctaa
```

FIG. 66A

MSPITRERLERRIQDLYANDPQPAAAKPATAITAAIERPGLPLRQIIETYMTGYADRPALAQRSVEFVTDAGTGHT
TLRLLPHFETISYGELWDRISALADVLSTEQTVKPGDRVCLLGFNSVDYATIDMTLARLGAVAVPLQTSAAITQLQP
TVAETQPTMIAASVDALADATELALSGQTATRVLVFDHHRQVDAHRAAVESARERLAGSAVVETLAEAIARGDVPRG
ASAGSAPGTDVSDDSLALLIYTSGSTGAPKJAMYPRRNVATFWRKRTWFEGKYEPSITLNPMPMSHVMGRQILLYGTL
CNGGTAYFVAKSDLSTLFEDLALYRPTELTFVPRVWDMVFDEFQSEVDRRLVDGADRVALRAQVKAEIRNDVLGGRY
TSALTGSAPISDEMKAWVEELLDMHLVRGYGSTEAGMILIDGAIRRPAVLDYKLVDVPDLGYFLTDRPHPRGELLVK
TDSLFPGYYQRAEVTADVFDADGFYRTQDIMAEVGPBQPVYLDRRNNVLKLSQGEPVTVSKLEAVFGDSPLVRQIYI
YGNSARAYLLAVIVPTQEALDAVPVEELKARLGDSLQEVAKAAGLQSYEIPRDFIIETTPWTLENGLLTGIRKLARP
QLKKHYGELLEQIYTDLAHGQADELRSLRQSGADAPVLVTVCRAAAALLGGSASDVQPDAHFTDLGADSLSALSPTN
LLHEIFDIEVPVGVTVSPANDLQALADYVBAARKPGSSRPTFASVHGASNGQVTBVHAGDLSLDKFIDAATLABAPR
LPAANTQVRTVLLTGATGFLGRYLAEWLBRMDLVDGELLICLVRAKSDTEARARLDKTFDSEDPELLAHYRALAGDH
LEVLAGDKGEADLGLDRQTWQRLADTVDLIVDPAALVNHVLPYSQLFGPNALGTAELLRLALTSKIKPYSYTSTIGV
ADQIPPSAFTEDADIRVISATRAVDDSYANGYSNSKWAGEVLLREAHDLCGLPVAVFRCDMILADTTWAGQLNVPDM
FTRMILSLAATGIAPGSFYELAADGARQRAHYDGLPVBFIAEAISTLGAQSQDGFHKTYHVMNPYDEGIGLDEFVDWL
NESGCPIQRIADYGDWLQRFETALRALPDRQRHSSILPLIHNYRQPERPVRGSIAPTDRPRAAVQBAKIGPDKDIPH
VGAPIIVKYVSDLRLLGLL
```

FIG. 66B

ATGACCGATATTCGCTTGTATATGTTTCAAACTGGCTCGCTGAAGTGCAAAGTCCACAATATCAAAATGA
ATCAAGGAGGTGGAGCGGATTATGAAATCCCTGTCCCGTTCTTCCTGCTGACCCATCCTGATGGTCACAC
GCTGATTGATGGCGGGAATGCTGTCGAAACCGCCACTGATCCCAAAGGGTATTGGGGCGGGATTACCGAG
GTTTATTGGCCGGTAATGCGTGAAGATGAGGGCTGTGTAGCGCAGCTTAAAAAAATGGGGATCAATCCCG
AAGATATCCGGTATGTCTTGCAGTCGCACTTGCATCTTGATCATACCGGTGCGATTGGCCGATTCCCCAA
TGCGACACACATCGTTCAGCGCCGTGAGTACGAGTATGCCTTTACTCCTGACTGGTTTGCTGCGGGAGGC
TATATCAGAAACGACTTTGACCGGCCGGGTCTGAAATGGGCGTTTCTGGAAGGCGAAAACAATGATTTTT
ATGATATCTATGGCGACGGTACGCTGAAAACAGTATTTACACCCGGCCATTCGCCTGGGCATCAGTCAAT
ACTGGTCACCTTGCCCAACTCAGGTCCGATGCTACTGACTATTGATGCAGCATACACCACGGATCACTGG
GAAGAAAAAGCTCTGCCAGGATTTATGTCCTCAGCCGTTGAGACGGTGCGTTCGGTGCAGAAGATGCGCA
TGTTGGCTAGCCGCACAAGTGCGCAAGTGGTGACAGGCCATGACCCGGATGCCTGGCAAACGTTCAGGCA
CGCGCCTGAATACTACGATTGA

FIGURE 89

ATGCTTCAGTCGGGTACGCTGAAATGCAAGGTACACAACATTAAGATGAACCAGGGGAACGGTGCAGACT
ATGAGATCCCCGTTCCGTTTTTCCTGATTACCCATCCGGCCGGGCACACCGTGATCGACGGCGGCAACGC
GATTGAAGTTGCAACAGATCCGCGTGGCCATTGGGGCGGCATCTGCGATGTCTATTGGCCAGTACTGGAC
AAGGACCAGGGCTGCGTTGACCAGATCAAGGCGCTTGGTTTCGATCCGGCCGATGTCAAATATGTTGTGC
AGTCGCACCTGCATCTCGATCATACCGGCGCCATCGGTCGCTTCCCCAACGCAACCCACATCGTGCAGCG
CTCTGAATATGAATATGCCTTTACGCCCGACTGGTTTGCTGGCGGCGGCTATATCCGCAAGGACTTCGAC
AAGCCGGGTCTGAAGTGGCAGTTCCTCAACGGTGCGCAGGACGATTATTACGATGTTTACGGCGACGGCA
CGCTCACCACGATCTTCACGCCCGGTCATGCGCCCGGCCACCAGTCCTTCCTGGTGCGCCTGCCAAACAG
CAAACCGCTTCTCCTGACGATCGATGCTGCCTACACACTGGACCACTGGGAAGAGAAGGCTTTGCCTGGC
TTCCTTGCCTCGACCGTTGACACGGTCCGTTCTGTTCAGAAGCTCCGCACCTATGCCGAAAGCATGATG
CGACAGTCGTCACCGGCCATGACCCTGACGCCTGGGCGAACTTCAAGAAGGCTCCCGAATTTTACGCGTA
A

FIGURE 90

SEQUENCE LISTING

```
<160> NUMBER OF SEQ ID NOS: 178

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacgaattcg ctagcaagag gagaagtcga catgtccaat tcactggccg tcgttttac       59

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaccctagga agctttctag agtcgaccta tgcggcatca gagcaga                    47

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```
atgtaccgca agttccgc                                            18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caatttgccg atgcccag                                            18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgaccact gaagactttg                                          20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatcagggct tcggtgtag                                           19

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttggtgcggg ccaagcagga tctgctc                                  27

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcagccgaac gcctcgtcga ggatctcctg                               30

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
tggccaacat aagttcacca ttcgggcaaa ac                                       32

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctcttcaac cagccattcg ttttgcccg                                           29

<210> SEQ ID NO 11
<211> LENGTH: 27
<212> TYPE: DNA
<213> ORGANISM: Clostridium acetobutylicum

<400> SEQUENCE: 11
attaaagtta agtggaggaa tgttaac                                             27

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acacgcggat ccaacgtccc gg                                                  22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcggctccg ctagccgctt atg                                                 23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagccgttgc tgcagctctt gagc                                                24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atctccggcg gtcggatccg tcg                                                 23

<210> SEQ ID NO 16
```

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagcggcta gccacgccgc                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
attacacgag gtacccaacg                                              20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgctggcgt acaaaggtgt cc                                           22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggacaccttt gtacgccagc at                                           22

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atcgcctaca ctaaaccaga agtgg                                        25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccacttctgg tttagtgtag gcgat                                        25

<210> SEQ ID NO 22
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aggcagttcc ataggatggc                                              20

<210> SEQ ID NO 23
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgacatgtaa cacctacctt ctgtgcctgt gccagtggtt gctgtgatat agaag       55

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ataataatac atatgaacca tgcgagttac gggcctataa gccaggcg               48

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtttttcga tatctgcatc agacaccggc acattgaaac gg                     42

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctggcacagg cacagaaggt aggtgttaca tgtcagaacg tttacacaat gacgtggatc  60

<210> SEQ ID NO 27
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agacaaatcg gttgccgttt gttaagccag gcgagatatg atctatatc              49

<210> SEQ ID NO 28
<211> LENGTH: 54
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 28
gagttttgat tcagtactc atcatgtaac acctaccttc ttgctgtgat atag          54

<210> SEQ ID NO 29
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctatatcaca gcaagaaggt aggtgttaca tgatgagtac tgaaatcaaa actc          54

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatatagatc atatctcgcc tggcttaaca aacggcaacc gatttgtct               49

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tattgtgcat acagatgaat ttttatgcaa acagtcagcc ctgaagaagg gtgtaggctg    60
gagctgcttc                                                           70

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 caaaaaccg gagtctgtgc tccggttttt tattatccgc taatcaatta catatgaata    60
tcctccttag                                                           70

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ataataatag aattcgtttg ctacctaaat tgccaactaa atcgaaacag g             51
```

```
<210> SEQ ID NO 34
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tattattatg gtaccaatat catgcagcaa acggtgcaac attgccg                   47

<210> SEQ ID NO 35
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgatctggaa gaattcatcg gctttaccac cgtcaaaaaa aacggcg                   47

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36 ataaaacccct gcagcggaaa cgaagttttta tccattttttg gttacctg              48

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaagagagg ctggtaccca gaagccacag cagga                                35

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtaatcactg cgtaagcgcc atgccccggc gttaattc                             38

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
attgccgcgt tcctcctgct gtcga                                           25

<210> SEQ ID NO 40
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgacagcagg aggaacgcgg caat                                            24

<210> SEQ ID NO 41
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtttgcacgc tatagctgag gttgttgtct tccagcaacg taccgtatac aataggcgta    60
tcacgaggcc ctttc                                                     75

<210> SEQ ID NO 42
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gctacagcat gtcacacgat ctcaacggtc ggatgaccaa tctggctggt atgggaatta    60
gccatggtcc                                                           70

<210> SEQ ID NO 43
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tgtgagtgaa agtcacctgc cttaatatct caaaactcat cttcgggtga cgaaatatgg    60
cgtgactcga tac                                                       73

<210> SEQ ID NO 44
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tctgtatcag gctgaaaatc ttctctcatc cgccaaaaca gcttcggcgt taagatgcgc    60
gctcaaggac                                                           70

<210> SEQ ID NO 45
<211> LENGTH: 20
<212> TYPE: PRT
<213> ORGANISM: Euglena gracilis

<400> SEQUENCE: 45
```

```
Met Thr Tyr Lys Ala Pro Val Lys Asp Val Lys Phe Leu Leu Asp Lys
1               5                   10                  15

Val Phe Lys Val
            20
```

<210> SEQ ID NO 46
<211> LENGTH: 2036
<212> TYPE: DNA
<213> ORGANISM: Escherichia coli

<400> SEQUENCE: 46

| | | | |
|---|---|---|---|
| atgaacttac atgaatatca ggcaaaacaa cttttttgccc gctatggctt accagcaccg | 60 |
| gtgggttatg cctgtactac tccgcgcgaa gcagaagaag ccgcttcaaa aatcggtgcc | 120 |
| ggtccgtggg tagtgaaatg tcaggttcac gctggtggcc gcggtaaagc gggcggtgtg | 180 |
| aaagttgtaa acagcaaaga agacatccgt gcttttgcag aaaactggct gggcaagcgt | 240 |
| ctggtaacgt atcaaacaga tgccaatggc caaccggtta accagattct ggttgaagca | 300 |
| gcgaccgata tcgctaaaga gctgtatctc ggtgccgttt tgaccgtag ttcccgtcgt | 360 |
| gtggtcttta tggcctccac cgaaggcggc gtggaaatcg aaaaagtggc ggaagaaact | 420 |
| ccgcacctga tccataaagt tgcgcttgat ccgctgactg gcccgatgcc gtatcaggga | 480 |
| cgcgagctgg cgttcaaact gggtctggaa ggtaaactgg ttcagcagtt caccaaaatc | 540 |
| ttcatgggcc tggcgaccat tttcctggag cgcgacctgg cgttgatcga atcaacccg | 600 |
| ctggtcatca ccaaacaggg cgatctgatt tgcctcgacg gcaaactggg cgctgacggc | 660 |
| aacgcactgt tccgccagcc tgatctgcgc gaaatgcgtg accagtcgca ggaagatccg | 720 |
| cgtgaagcac aggctgcaca gtgggaactg aactacgttg cgctggacgg taacatcggt | 780 |
| tgtatggtta acgcgcaggg tctggcgatg gtacgatgg acatcgttaa actgcacggc | 840 |
| ggcgaaccgg ctaacttcct tgacgttggc ggcggcgcaa ccaaagaacg tgtaaccgaa | 900 |
| gcgttcaaaa tcatcctctc tgacgacaaa gtgaaagccg ttctggttaa catcttcggc | 960 |
| ggtatcgttc gttgcgacct gatcgctgac ggtatcatcg gcgcggtagc agaagtgggt | 1020 |
| gttaacgtac cggtcgtggt acgtctggaa ggtaacaacg ccgaactcgg cgcgaagaaa | 1080 |
| ctggctgaca gcggcctgaa tattattgca gcaaaaggtc tgacggatgc agctcagcag | 1140 |
| gttgttgccg cagtggaggg gaaataatgt ccattttaat cgataaaaac accaaggtta | 1200 |
| tctgccaggg ctttaccggt agccagggga cttttccactc agaacaggcc attgcatacg | 1260 |
| gcactaaaat ggttggcggc gtaaccccag gtaaaggcgg caccaccac ctcggcctgc | 1320 |
| cggtgttcaa caccgtgcgt gaagccgttg ctgccactgg cgctaccgct tctgttatct | 1380 |
| acgtaccagc accgttctgc aaagactcca ttctggaagc catcgacgca ggcatcaaac | 1440 |
| tgattatcac catcactgaa ggcatcccga cgctggatat gctgaccgtg aaagtgaagc | 1500 |
| tggatgaagc aggcgttcgt atgatcggcc cgaactgccc aggcgttatc actccgggtg | 1560 |
| aatgcaaaat cggtatccag cctggtcaca ttcacaaacc gggtaaagtg gtatcgtttt | 1620 |
| cccgttccgg tacactgacc tatgaagcgg ttaaacagac cacggattac ggtttcggtc | 1680 |
| agtcgacctg tgtcggtatc ggcggtgacc cgatcccggg ctctaacttt atcgacattc | 1740 |
| tcgaaatgtt cgaaaaagat ccgcagaccg aagcgatcgt gatgatcggt gagatcggcg | 1800 |
| gtagcgctga agaagaagca gctgcgtaca tcaaagagca cgttaccaag ccagttgtgg | 1860 |
| gttacatcgc tggtgtgact gcgccgaaag gcaaacgtat gggccacgcg ggtgccatca | 1920 |
| ttgccggtgg gaaagggact gcggatgaga aattcgctgc tctggaagcc gcaggcgtga | 1980 |

```
aaaccgttcg cagcctggcg gatatcggtg aagcactgaa aactgttctg aaataa        2036
```

<210> SEQ ID NO 47
<211> LENGTH: 388
<212> TYPE: PRT
<213> ORGANISM: Escherichia coli

<400> SEQUENCE: 47

| | | | | | | | | | | | | | | |
|---|---|---|---|---|---|---|---|---|---|---|---|---|---|---|
| Met | Asn | Leu | His | Glu | Tyr | Gln | Ala | Lys | Gln | Leu | Phe | Ala | Arg | Tyr | Gly |
| 1 | | | | 5 | | | | | 10 | | | | | 15 | |
| Leu | Pro | Ala | Pro | Val | Gly | Tyr | Ala | Cys | Thr | Thr | Pro | Arg | Glu | Ala | Glu |
| | | | 20 | | | | | 25 | | | | | 30 | | |
| Glu | Ala | Ala | Ser | Lys | Ile | Gly | Ala | Gly | Pro | Trp | Val | Val | Lys | Cys | Gln |
| | | | | 35 | | | | | 40 | | | | | 45 | |
| Val | His | Ala | Gly | Gly | Arg | Gly | Lys | Ala | Gly | Gly | Val | Lys | Val | Val | Asn |
| | | 50 | | | | | 55 | | | | | 60 | | | |
| Ser | Lys | Glu | Asp | Ile | Arg | Ala | Phe | Ala | Glu | Asn | Trp | Leu | Gly | Lys | Arg |
| 65 | | | | | 70 | | | | | 75 | | | | | 80 |
| Leu | Val | Thr | Tyr | Gln | Thr | Asp | Ala | Asn | Gly | Gln | Pro | Val | Asn | Gln | Ile |
| | | | | 85 | | | | | 90 | | | | | 95 | |
| Leu | Val | Glu | Ala | Ala | Thr | Asp | Ile | Ala | Lys | Glu | Leu | Tyr | Leu | Gly | Ala |
| | | | | 100 | | | | | 105 | | | | | 110 | |
| Val | Val | Asp | Arg | Ser | Ser | Arg | Arg | Val | Val | Phe | Met | Ala | Ser | Thr | Glu |
| | | | 115 | | | | | 120 | | | | | 125 | | |
| Gly | Gly | Val | Glu | Ile | Glu | Lys | Val | Ala | Glu | Glu | Thr | Pro | His | Leu | Ile |
| | | 130 | | | | | 135 | | | | | 140 | | | |
| His | Lys | Val | Ala | Leu | Asp | Pro | Leu | Thr | Gly | Pro | Met | Pro | Tyr | Gln | Gly |
| 145 | | | | | 150 | | | | | 155 | | | | | 160 |
| Arg | Glu | Leu | Ala | Phe | Lys | Leu | Gly | Leu | Glu | Gly | Lys | Leu | Val | Gln | Gln |
| | | | | 165 | | | | | 170 | | | | | 175 | |
| Phe | Thr | Lys | Ile | Phe | Met | Gly | Leu | Ala | Thr | Ile | Phe | Leu | Glu | Arg | Asp |
| | | | 180 | | | | | 185 | | | | | 190 | | |
| Leu | Ala | Leu | Ile | Glu | Ile | Asn | Pro | Leu | Val | Ile | Thr | Lys | Gln | Gly | Asp |
| | | | | 195 | | | | | 200 | | | | | 205 | |
| Leu | Ile | Cys | Leu | Asp | Gly | Lys | Leu | Gly | Ala | Asp | Gly | Asn | Ala | Leu | Phe |
| | | 210 | | | | | 215 | | | | | 220 | | | |
| Arg | Gln | Pro | Asp | Leu | Arg | Glu | Met | Arg | Asp | Gln | Ser | Gln | Glu | Asp | Pro |
| 225 | | | | | 230 | | | | | 235 | | | | | 240 |
| Arg | Glu | Ala | Gln | Ala | Ala | Gln | Trp | Glu | Leu | Asn | Tyr | Val | Ala | Leu | Asp |
| | | | | 245 | | | | | 250 | | | | | 255 | |
| Gly | Asn | Ile | Gly | Cys | Met | Val | Asn | Gly | Ala | Gly | Leu | Ala | Met | Gly | Thr |
| | | | 260 | | | | | 265 | | | | | 270 | | |
| Met | Asp | Ile | Val | Lys | Leu | His | Gly | Gly | Glu | Pro | Ala | Asn | Phe | Leu | Asp |
| | | | | 275 | | | | | 280 | | | | | 285 | |
| Val | Gly | Gly | Gly | Ala | Thr | Lys | Glu | Arg | Val | Thr | Glu | Ala | Phe | Lys | Ile |
| | | 290 | | | | | 295 | | | | | 300 | | | |
| Ile | Leu | Ser | Asp | Asp | Lys | Val | Lys | Ala | Val | Leu | Val | Asn | Ile | Phe | Gly |
| 305 | | | | | 310 | | | | | 315 | | | | | 320 |
| Gly | Ile | Val | Arg | Cys | Asp | Leu | Ile | Ala | Asp | Gly | Ile | Ile | Gly | Ala | Val |
| | | | | 325 | | | | | 330 | | | | | 335 | |
| Ala | Glu | Val | Gly | Val | Asn | Val | Pro | Val | Val | Val | Arg | Leu | Glu | Gly | Asn |
| | | | 340 | | | | | 345 | | | | | 350 | | |
| Asn | Ala | Glu | Leu | Gly | Ala | Lys | Lys | Leu | Ala | Asp | Ser | Gly | Leu | Asn | Ile |
| | | | | 355 | | | | | 360 | | | | | 365 | |

Ile Ala Ala Lys Gly Leu Thr Asp Ala Ala Gln Gln Val Val Ala Ala
     370                 375                 380

Val Glu Gly Lys
385

<210> SEQ ID NO 48
<211> LENGTH: 289
<212> TYPE: PRT
<213> ORGANISM: Escherichia coli

<400> SEQUENCE: 48

Met Ser Ile Leu Ile Asp Lys Asn Thr Lys Val Ile Cys Gln Gly Phe
1               5                   10                  15

Thr Gly Ser Gln Gly Thr Phe His Ser Glu Gln Ala Ile Ala Tyr Gly
            20                  25                  30

Thr Lys Met Val Gly Gly Val Thr Pro Gly Lys Gly Gly Thr Thr His
        35                  40                  45

Leu Gly Leu Pro Val Phe Asn Thr Val Arg Glu Ala Val Ala Ala Thr
    50                  55                  60

Gly Ala Thr Ala Ser Val Ile Tyr Val Pro Ala Pro Phe Cys Lys Asp
65                  70                  75                  80

Ser Ile Leu Glu Ala Ile Asp Ala Gly Ile Lys Leu Ile Ile Thr Ile
                85                  90                  95

Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
        115                 120                 125

Thr Pro Gly Glu Cys Lys Ile Gly Ile Gln Pro Gly His Ile His Lys
    130                 135                 140

Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
        195                 200                 205

Glu Ile Gly Gly Ser Ala Glu Glu Ala Ala Ala Tyr Ile Lys Glu
    210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
        275                 280                 285

Lys

<210> SEQ ID NO 49
<211> LENGTH: 3696
<212> TYPE: DNA
<213> ORGANISM: Mycobacterium bovis

<400> SEQUENCE: 49

-continued

| | | | | | |
|---|---|---|---|---|---|
| atggccaaca | taagttcacc | attcgggcaa | aacgaatggc | tggttgaaga | gatgtaccgc | 60 |
| aagttccgcg | acgacccctc | ctcggtcgat | cccagctggc | acgagttcct | ggttgactac | 120 |
| agccccgaac | ccacctccca | accagctgcc | gaaccaaccc | gggttacctc | gccactcgtt | 180 |
| gccgagcggg | ccgctgcggc | cgccccgcag | gcaccccca | agccggccga | caccgcggcc | 240 |
| gcggcaacg | gcgtggtcgc | cgcactggcc | gccaaaactg | ccgttccccc | gccagccgaa | 300 |
| ggtgacgagg | tagcggtgct | gcgcggcgcc | gccgcggccg | tcgtcaagaa | catgtccgcg | 360 |
| tcgttggagg | tgccgacggc | gaccagcgtc | cgggcggtcc | cggccaagct | actgatcgac | 420 |
| aaccggatcg | tcatcaacaa | ccagttgaag | cggacccgcg | gcggcaagat | ctcgttcacg | 480 |
| catttgctgg | gctacgccct | ggtgcaggcg | gtgaagaaat | cccgaacat | gaaccggcac | 540 |
| tacaccgaag | tcgacggcaa | gcccaccgcg | gtcacgccgg | cgcacaccaa | tctcggcctg | 600 |
| gcgatcgacc | tgcaaggcaa | ggacgggaag | cgttccctgg | tggtggccgg | catcaagcgg | 660 |
| tgcgagacca | tgcgattcgc | gcagttcgtc | acggcctacg | aagacatcgt | acgccgggcc | 720 |
| cgcgacggca | agctgaccac | tgaagacttt | gccggcgtga | cgatttcgct | gaccaatccc | 780 |
| ggaaccatcg | gcaccgtgca | ttcggtgccg | cggctgatgc | ccggccaggg | cgccatcatc | 840 |
| ggcgtgggcg | ccatggaata | ccccgccgag | tttcaaggcg | ccagcgagga | acgcatcgcc | 900 |
| gagctgggca | tcggcaaatt | gatcactttg | acctccacct | acgaccaccg | catcatccag | 960 |
| ggcgcggaat | cgggcgactt | cctgcgcacc | atccacgagt | gctgctctc | ggatggcttc | 1020 |
| tgggacgagg | tcttccgcga | actgagcatc | ccatatctgc | cggtgcgctg | gagcaccgac | 1080 |
| aaccccgact | cgatcgtcga | caagaacgct | cgcgtcatga | acttgatcgc | ggcctaccgc | 1140 |
| aaccgcggcc | atctgatggc | cgataccgac | ccgctgcggt | tggacaaagc | tcggttccgc | 1200 |
| agtcaccccg | acctcgaagt | gctgacccac | ggcctgacgc | tgtgggatct | cgatcgggtg | 1260 |
| ttcaaggtcg | acggctttgc | cggtgcgcag | tacaagaaac | tgcgcgacgt | gctgggcttg | 1320 |
| ctgcgcgatg | cctactgccg | ccacatcggc | gtggagtacg | cccatatcct | cgaccccgaa | 1380 |
| caaaaggagt | ggctcgaaca | acgggtcgag | accaagcacg | tcaaacccac | tgtggcccaa | 1440 |
| cagaaataca | tcctcagcaa | gctcaacgcc | gccgaggcct | ttgaaacgtt | cctacagacc | 1500 |
| aagtacgtcg | gccagaagcg | gttctcgctg | gaaggcgccg | aaagcgtgat | cccgatgatg | 1560 |
| gacgcggcga | tcgaccagtg | cgctgagcac | ggcctgacg | aggtggtcat | cgggatgccg | 1620 |
| caccggggcc | ggctcaacgt | gctggccaac | atcgtcggca | agccgtactc | gcagatcttc | 1680 |
| accgagttcg | agggcaacct | gaatccgtcg | caggcgcacg | gctccggtga | cgtcaagtac | 1740 |
| cacctgggcg | ccaccgggct | gtacctgcag | atgttcggcg | acaacgacat | tcaggtgtcg | 1800 |
| ctgaccgcca | acccgtcgca | tctggaggcc | gtcgacccgg | tgctggaggg | attggtgcgg | 1860 |
| gccaagcagg | atctgctcga | ccacggaagc | atcgacagcg | acggccaacg | ggcgttctcg | 1920 |
| gtggtgccgc | tgatgttgca | tggcgatgcc | gcgttcgccg | tcagggtgt | ggtcgccgag | 1980 |
| acgctgaacc | tggcgaatct | gccgggctac | cgcgtcggcg | gcaccatcca | catcatcgtc | 2040 |
| aacaaccaga | tcggcttcac | caccgcgccc | gagtattcca | ggtccagcga | gtactgcacc | 2100 |
| gacgtcgcaa | agatgatcgg | ggcaccgatc | tttcacgtca | acggcgacga | cccggaggcg | 2160 |
| tgtgtctggg | tggcgcggtt | ggcggtggac | ttccgacaac | ggttcaagaa | ggacgtcgtc | 2220 |
| atcgacatgc | tgtgctaccg | ccgccgcggg | cacaacgagg | gtgacgaccc | gtcgatgacc | 2280 |
| aaccccctaca | tgtacgacgt | cgtcgacacc | aagcgcgggg | cccgcaaaag | ctacaccgaa | 2340 |
| gccctgatcg | gacgtggcga | catctcgatg | aaggaggccg | aggacgcgct | gcgcgactac | 2400 |

-continued cagggccagc tggaacgggt gttcaacgaa gtgcgcgagc tggagaagca cggtgtgcag 2460
ccgagcgagt cggtcgagtc cgaccagatg attcccgcgg ggctggccac tgcggtggac 2520
aagtcgctgc tggcccggat cggcgatgcg ttcctcgcct tgccgaacgg cttcaccgcg 2580
cacccgcgag tccaaccggt gctggagaag cgccgggaga tggcctatga aggcaagatc 2640
gactgggcct ttggcgagct gctggcgctg ggctcgctgg tggccgaagg caagctggtg 2700
cgcttgtcgg ggcaggacag ccgccgcggc accttctccc agcggcattc ggttctcatc 2760
gaccgccaca ctggcgagga gttcacacca ctgcagctgc tggcgaccaa ctccgacggc 2820
agcccgaccg gcggaaagtt cctggtctac gactcgccac tgtcggagta cgccgccgtc 2880
ggcttcgagt acggctacac tgtgggcaat ccggacgccg tggtgctctg ggaggcgcag 2940
ttcggcgact tcgtcaacgg cgcacagtcg atcatcgacg agttcatcag ctccggtgag 3000
gccaagtggg gccaattgtc caacgtcgtg ctgctgttac cgcacgggca cgaggggcag 3060
ggacccgacc acacttctgc ccggatcgaa cgcttcttgc agttgtgggc ggaaggttcg 3120
atgaccatcg cgatgccgtc gactccgtcg aactacttcc acctgctacg ccggcatgcc 3180
ctggacggca tccaacgccc gctgatcgtg ttcacgccca agtcgatgtt gcgtcacaag 3240
gccgccgtca gcgaaatcaa ggacttcacc gagatcaagt tccgctcagt gctggaggaa 3300
cccacctatg aggacggcat cggagaccgc aacaaggtca gccggatcct gctgaccagt 3360
ggcaagctgt attacgagct ggccgcccgc aaggccaagg acaaccgcaa tgacctcgcg 3420
atcgtgcggc ttgaacagct cgccccgctg cccaggcgtc gactgcgtga aacgctggac 3480
cgctacgaga acgtcaagga gttcttctgg gtccaagagg aaccggccaa ccagggtgcg 3540
tggccgcgat tcgggctcga actacccgag ctgctgcctg acaagttggc cgggatcaag 3600
cgaatctcgc gccgggcgat gtcagccccg tcgtcaggct cgtcgaaggt gcacgccgtc 3660
gaacagcagg agatcctcga cgaggcgttc ggctaa 3696

<210> SEQ ID NO 50
<211> LENGTH: 1231
<212> TYPE: PRT
<213> ORGANISM: Mycobacterium bovis

<400> SEQUENCE: 50

Met Ala Asn Ile Ser Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
            20                  25                  30

Trp His Glu Phe Leu Val Asp Tyr Ser Pro Glu Pro Thr Ser Gln Pro
        35                  40                  45

Ala Ala Glu Pro Thr Arg Val Thr Ser Pro Leu Val Ala Glu Arg Ala
    50                  55                  60

Ala Ala Ala Ala Pro Gln Ala Pro Pro Lys Pro Ala Asp Thr Ala Ala
65                  70                  75                  80

Ala Gly Asn Gly Val Val Ala Ala Leu Ala Ala Lys Thr Ala Val Pro
                85                  90                  95

Pro Pro Ala Glu Gly Asp Glu Val Ala Val Leu Arg Gly Ala Ala Ala
            100                 105                 110

Ala Val Val Lys Asn Met Ser Ala Ser Leu Glu Val Pro Thr Ala Thr
        115                 120                 125

Ser Val Arg Ala Val Pro Ala Lys Leu Leu Ile Asp Asn Arg Ile Val
    130                 135                 140

```
Ile Asn Asn Gln Leu Lys Arg Thr Arg Gly Gly Lys Ile Ser Phe Thr
145                 150                 155                 160

His Leu Leu Gly Tyr Ala Leu Val Gln Ala Val Lys Lys Phe Pro Asn
            165                 170                 175

Met Asn Arg His Tyr Thr Glu Val Asp Gly Lys Pro Thr Ala Val Thr
        180                 185                 190

Pro Ala His Thr Asn Leu Gly Leu Ala Ile Asp Leu Gln Gly Lys Asp
    195                 200                 205

Gly Lys Arg Ser Leu Val Val Ala Gly Ile Lys Arg Cys Glu Thr Met
210                 215                 220

Arg Phe Ala Gln Phe Val Thr Ala Tyr Glu Asp Ile Val Arg Arg Ala
225                 230                 235                 240

Arg Asp Gly Lys Leu Thr Thr Glu Asp Phe Ala Gly Val Thr Ile Ser
            245                 250                 255

Leu Thr Asn Pro Gly Thr Ile Gly Thr Val His Ser Val Pro Arg Leu
        260                 265                 270

Met Pro Gly Gln Gly Ala Ile Ile Gly Val Gly Ala Met Glu Tyr Pro
    275                 280                 285

Ala Glu Phe Gln Gly Ala Ser Glu Glu Arg Ile Ala Glu Leu Gly Ile
290                 295                 300

Gly Lys Leu Ile Thr Leu Thr Ser Thr Tyr Asp His Arg Ile Ile Gln
305                 310                 315                 320

Gly Ala Glu Ser Gly Asp Phe Leu Arg Thr Ile His Glu Leu Leu Leu
            325                 330                 335

Ser Asp Gly Phe Trp Asp Glu Val Phe Arg Glu Leu Ser Ile Pro Tyr
        340                 345                 350

Leu Pro Val Arg Trp Ser Thr Asp Asn Pro Asp Ser Ile Val Asp Lys
    355                 360                 365

Asn Ala Arg Val Met Asn Leu Ile Ala Ala Tyr Arg Asn Arg Gly His
370                 375                 380

Leu Met Ala Asp Thr Asp Pro Leu Arg Leu Asp Lys Ala Arg Phe Arg
385                 390                 395                 400

Ser His Pro Asp Leu Glu Val Leu Thr His Gly Leu Thr Leu Trp Asp
            405                 410                 415

Leu Asp Arg Val Phe Lys Val Asp Gly Phe Ala Gly Ala Gln Tyr Lys
        420                 425                 430

Lys Leu Arg Asp Val Leu Gly Leu Leu Arg Asp Ala Tyr Cys Arg His
    435                 440                 445

Ile Gly Val Glu Tyr Ala His Ile Leu Asp Pro Glu Gln Lys Glu Trp
450                 455                 460

Leu Glu Gln Arg Val Glu Thr Lys His Val Lys Pro Thr Val Ala Gln
465                 470                 475                 480

Gln Lys Tyr Ile Leu Ser Lys Leu Asn Ala Ala Glu Ala Phe Glu Thr
            485                 490                 495

Phe Leu Gln Thr Lys Tyr Val Gly Gln Lys Arg Phe Ser Leu Glu Gly
        500                 505                 510

Ala Glu Ser Val Ile Pro Met Met Asp Ala Ala Ile Asp Gln Cys Ala
    515                 520                 525

Glu His Gly Leu Asp Glu Val Val Ile Gly Met Pro His Arg Gly Arg
530                 535                 540

Leu Asn Val Leu Ala Asn Ile Val Gly Lys Pro Tyr Ser Gln Ile Phe
545                 550                 555                 560
```

Thr Glu Phe Glu Gly Asn Leu Asn Pro Ser Gln Ala His Gly Ser Gly
                565                 570                 575

Asp Val Lys Tyr His Leu Gly Ala Thr Gly Leu Tyr Leu Gln Met Phe
        580                 585                 590

Gly Asp Asn Asp Ile Gln Val Ser Leu Thr Ala Asn Pro Ser His Leu
            595                 600                 605

Glu Ala Val Asp Pro Val Leu Glu Gly Leu Val Arg Ala Lys Gln Asp
610                 615                 620

Leu Leu Asp His Gly Ser Ile Asp Ser Asp Gly Gln Arg Ala Phe Ser
625                 630                 635                 640

Val Val Pro Leu Met Leu His Gly Asp Ala Ala Phe Ala Gly Gln Gly
                645                 650                 655

Val Val Ala Glu Thr Leu Asn Leu Ala Asn Leu Pro Gly Tyr Arg Val
            660                 665                 670

Gly Gly Thr Ile His Ile Ile Val Asn Asn Gln Ile Gly Phe Thr Thr
        675                 680                 685

Ala Pro Glu Tyr Ser Arg Ser Glu Tyr Cys Thr Asp Val Ala Lys
    690                 695                 700

Met Ile Gly Ala Pro Ile Phe His Val Asn Gly Asp Asp Pro Glu Ala
705                 710                 715                 720

Cys Val Trp Val Ala Arg Leu Ala Val Asp Phe Arg Gln Arg Phe Lys
                725                 730                 735

Lys Asp Val Val Ile Asp Met Leu Cys Tyr Arg Arg Arg Gly His Asn
            740                 745                 750

Glu Gly Asp Asp Pro Ser Met Thr Asn Pro Tyr Met Tyr Asp Val Val
        755                 760                 765

Asp Thr Lys Arg Gly Ala Arg Lys Ser Tyr Thr Glu Ala Leu Ile Gly
770                 775                 780

Arg Gly Asp Ile Ser Met Lys Glu Ala Glu Asp Ala Leu Arg Asp Tyr
785                 790                 795                 800

Gln Gly Gln Leu Glu Arg Val Phe Asn Glu Val Arg Glu Leu Glu Lys
                805                 810                 815

His Gly Val Gln Pro Ser Glu Ser Val Glu Ser Asp Gln Met Ile Pro
            820                 825                 830

Ala Gly Leu Ala Thr Ala Val Asp Lys Ser Leu Leu Ala Arg Ile Gly
        835                 840                 845

Asp Ala Phe Leu Ala Leu Pro Asn Gly Phe Thr Ala His Pro Arg Val
850                 855                 860

Gln Pro Val Leu Glu Lys Arg Arg Glu Met Ala Tyr Glu Gly Lys Ile
865                 870                 875                 880

Asp Trp Ala Phe Gly Glu Leu Leu Ala Leu Gly Ser Leu Val Ala Glu
                885                 890                 895

Gly Lys Leu Val Arg Leu Ser Gly Gln Asp Ser Arg Arg Gly Thr Phe
            900                 905                 910

Ser Gln Arg His Ser Val Leu Ile Asp Arg His Thr Gly Glu Glu Phe
        915                 920                 925

Thr Pro Leu Gln Leu Leu Ala Thr Asn Ser Asp Gly Ser Pro Thr Gly
930                 935                 940

Gly Lys Phe Leu Val Tyr Asp Ser Pro Leu Ser Glu Tyr Ala Ala Val
945                 950                 955                 960

Gly Phe Glu Tyr Gly Tyr Thr Val Gly Asn Pro Asp Ala Val Val Leu
                965                 970                 975

Trp Glu Ala Gln Phe Gly Asp Phe Val Asn Gly Ala Gln Ser Ile Ile

```
                980            985              990
Asp Glu Phe Ile Ser Ser Gly Glu  Ala Lys Trp Gly Gln  Leu Ser Asn
                     995              1000              1005
Val Val Leu Leu Leu Pro His  Gly His Glu Gly Gln  Gly Pro Asp
    1010             1015              1020

His Thr Ser Ala Arg Ile Glu  Arg Phe Leu Gln Leu  Trp Ala Glu
    1025             1030              1035

Gly Ser Met Thr Ile Ala Met  Pro Ser Thr Pro Ser  Asn Tyr Phe
    1040             1045              1050

His Leu Leu Arg Arg His Ala  Leu Asp Gly Ile Gln  Arg Pro Leu
    1055             1060              1065

Ile Val Phe Thr Pro Lys Ser  Met Leu Arg His Lys  Ala Ala Val
    1070             1075              1080

Ser Glu Ile Lys Asp Phe Thr  Glu Ile Lys Phe Arg  Ser Val Leu
    1085             1090              1095

Glu Glu Pro Thr Tyr Glu Asp  Gly Ile Gly Asp Arg  Asn Lys Val
    1100             1105              1110

Ser Arg Ile Leu Leu Thr Ser  Gly Lys Leu Tyr Tyr  Glu Leu Ala
    1115             1120              1125

Ala Arg Lys Ala Lys Asp Asn  Arg Asn Asp Leu Ala  Ile Val Arg
    1130             1135              1140

Leu Glu Gln Leu Ala Pro Leu  Pro Arg Arg Arg Leu  Arg Glu Thr
    1145             1150              1155

Leu Asp Arg Tyr Glu Asn Val  Lys Glu Phe Phe Trp  Val Gln Glu
    1160             1165              1170

Glu Pro Ala Asn Gln Gly Ala  Trp Pro Arg Phe Gly  Leu Glu Leu
    1175             1180              1185

Pro Glu Leu Leu Pro Asp Lys  Leu Ala Gly Ile Lys  Arg Ile Ser
    1190             1195              1200

Arg Arg Ala Met Ser Ala Pro  Ser Ser Gly Ser Ser  Lys Val His
    1205             1210              1215

Ala Val Glu Gln Gln Glu Ile  Leu Asp Glu Ala Phe  Gly
    1220             1225              1230

<210> SEQ ID NO 51
<211> LENGTH: 1356
<212> TYPE: DNA
<213> ORGANISM: Porphyromonas gingivalis

<400> SEQUENCE: 51
atggaaatca aagaaatggt gagccttgca cgcaaggctc agaaggagta tcaagctacc      60
cataaccaag aagcagttga caacatttgc cgagctgcag caaagttat ttatgaaaat      120 gcagctattc tggctcgcga agcagtagac gaaaccggca tgggcgttta cgaacacaaa      180
gtggccaaga tcaaggcaa atccaaaggt gtttggtaca acctccacaa taaaaaatcg      240
attggtatcc tcaatataga cgagcgtacc ggtatgatcg agattgcaaa gcctatcgga      300
gttgtaggag ccgtaacgcc gacgaccaac ccgatcgtta ctccgatgag caatatcatc      360
tttgctctta agacctgcaa tgccatcatt attgcccccc accccagatc caaaaaatgc      420
tctgcacacg cagttcgtct gatcaaagaa gctatcgctc cgttcaacgt accggaaggt      480
atggttcaga tcatcgaaga acccagcatc gagaagacgc aggaactcat gggcgccgta      540
gacgtagtag ttgctacggg tggtatgggc atggtgaagt ctgcatattc ttcaggaaag      600
ccttctttcg gtgttggagc cggtaacgtt caggtgatcg tggatagcaa catcgatttc      660
```

```
gaagctgctg cagaaaaaat catcaccggt cgtgctttcg acaacggtat catctgctca    720
ggcgaacaga gcatcatcta caacgaggct gacaaggaag cagttttcac agcattccgc    780
aaccacggtg catatttctg tgacgaagcc gaaggagatc gggctcgtgc agctatcttc    840
gaaaatggag ccatcgcgaa agatgtagta ggtcagagcg ttgccttcat tgccaagaaa    900
gcaaacatca atatccccga gggtacccgt attctcgttg ttgaagctcg cggcgtagga    960
gcagaagacg ttatctgtaa ggaaaagatg tgtcccgtaa tgtgcgccct cagctacaag   1020
cacttcgaag aaggtgtaga atcgcacgt acgaacctcg ccaacgaagg taacggccac    1080
acctgtgcta tccactccaa caatcaggca cacatcatcc tcgcaggatc agagctgacg   1140
gtatctcgta tcgtagtgaa tgctccgagt gccactacag caggcggtca catccaaaac   1200
ggtcttgccg taaccaatac gctcggatgc ggatcatggg gtaataactc tatctccgag   1260
aacttcactt acaagcacct cctcaacatt tcacgcatcg caccgttgaa ttcaagcatt   1320
cacatccccg atgacaaaga aatctgggaa ctctaa                             1356
```

<210> SEQ ID NO 52
<211> LENGTH: 451
<212> TYPE: PRT
<213> ORGANISM: Porphyromonas gingivalis

<400> SEQUENCE: 52

```
Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
        35                  40                  45

Val Asp Glu Thr Gly Met Gly Val Tyr Glu His Lys Val Ala Lys Asn
    50                  55                  60

Gln Gly Lys Ser Lys Gly Val Trp Tyr Asn Leu His Asn Lys Lys Ser
65                  70                  75                  80

Ile Gly Ile Leu Asn Ile Asp Glu Arg Thr Gly Met Ile Glu Ile Ala
                85                  90                  95

Lys Pro Ile Gly Val Val Gly Ala Val Thr Pro Thr Asn Pro Ile
            100                 105                 110

Val Thr Pro Met Ser Asn Ile Ile Phe Ala Leu Lys Thr Cys Asn Ala
        115                 120                 125

Ile Ile Ile Ala Pro His Pro Arg Ser Lys Lys Cys Ser Ala His Ala
    130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
                165                 170                 175

Met Gly Ala Val Asp Val Val Ala Thr Gly Gly Met Gly Met Val
            180                 185                 190

Lys Ser Ala Tyr Ser Ser Gly Lys Pro Ser Phe Gly Val Gly Ala Gly
        195                 200                 205

Asn Val Gln Val Ile Val Asp Ser Asn Ile Asp Phe Glu Ala Ala Ala
    210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
```

```
                245                 250                 255
Thr Ala Phe Arg Asn His Gly Ala Tyr Phe Cys Asp Glu Ala Glu Gly
            260                 265                 270

Asp Arg Ala Arg Ala Ala Ile Phe Glu Asn Gly Ala Ile Ala Lys Asp
        275                 280                 285

Val Val Gly Gln Ser Val Ala Phe Ile Ala Lys Lys Ala Asn Ile Asn
    290                 295                 300

Ile Pro Glu Gly Thr Arg Ile Leu Val Val Glu Ala Arg Gly Val Gly
305                 310                 315                 320

Ala Glu Asp Val Ile Cys Lys Glu Lys Met Cys Pro Val Met Cys Ala
                325                 330                 335

Leu Ser Tyr Lys His Phe Glu Glu Gly Val Glu Ile Ala Arg Thr Asn
            340                 345                 350

Leu Ala Asn Glu Gly Asn Gly His Thr Cys Ala Ile His Ser Asn Asn
        355                 360                 365

Gln Ala His Ile Ile Leu Ala Gly Ser Glu Leu Thr Val Ser Arg Ile
    370                 375                 380

Val Val Asn Ala Pro Ser Ala Thr Thr Ala Gly Gly His Ile Gln Asn
385                 390                 395                 400

Gly Leu Ala Val Thr Asn Thr Leu Gly Cys Gly Ser Trp Gly Asn Asn
                405                 410                 415

Ser Ile Ser Glu Asn Phe Thr Tyr Lys His Leu Leu Asn Ile Ser Arg
            420                 425                 430

Ile Ala Pro Leu Asn Ser Ser Ile His Ile Pro Asp Asp Lys Glu Ile
        435                 440                 445

Trp Glu Leu
    450

<210> SEQ ID NO 53
<211> LENGTH: 1116
<212> TYPE: DNA
<213> ORGANISM: Porphyromonas gingivalis

<400> SEQUENCE: 53
atgcaacttt tcaaactcaa gagtgtaaca catcactttg cacttttgc agaatttgcc      60 aaggaattct gtcttggaga acgcgacttg gtaattacca acgagttcat ctatgaaccg     120
tatatgaagg catgccagct ccctgccat tttgttatgc aggagaaata tgggcaaggc     180
gagccttctg acgaaatgat gaataacatc ttggcagaca tccgtaatat ccagttcgac     240
cgcgtaatcg gtatcggagg aggtacggtt attgacatct ctaaactttt cgttctgaaa     300
ggattaaatg atgtactcga tgcattcgac cgcaaaatac ctcttatcaa agagaaagaa     360
ctgatcattg tgcccacaac atgcggaacg ggtagcgagg tgacgaacat ttctatcgca     420
gaaatcaaaa gccgtcacac caaaatggga ttggctgacg atgccattgt tgcagaccat     480
gccatcatca tacctgaact tctgaagagc ttgcctttcc acttctacgc atgcagtgca     540
atcgatgctc ttatccatgc catcgagtca tacgtatctc taaagccag tccatattct     600 cgtctgttca gtgaggcggc ttgggacatt atcctggaag tattcaagaa aatcgccgaa     660
cacggccctg aataccgctt cgaaaagctg gagaaatga tcatggccag caactatgcc     720
ggtatagcct tcggaaatgc aggagtagga gccgtccacg cactatccta cccgttggga     780
ggcaactatc acgtgccgca tggagaagca aactatcagt tcttcacaga ggtattcaaa     840
gtataccaaa agaagaatcc tttcggctat atagtcgaac tcaactggaa gctctccaag     900
```

```
atactgaact gccagcccga atacgtatat ccgaagctgg atgaacttct cggatgcctt      960
cttaccaaga aacctttgca cgaatacggc atgaaggacg aagaggtaag aggctttgcg     1020
gaatcagtgc ttaagacaca gcaaagattg ctcgccaaca actacgtaga gcttactgta    1080
gatgagatcg aaggtatcta cagaagactc tactaa                              1116
```

<210> SEQ ID NO 54
<211> LENGTH: 371
<212> TYPE: PRT
<213> ORGANISM: Porphyromonas gingivalis

<400> SEQUENCE: 54

```
Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
            20                  25                  30

Thr Asn Glu Phe Ile Tyr Glu Pro Tyr Met Lys Ala Cys Gln Leu Pro
        35                  40                  45

Cys His Phe Val Met Gln Glu Lys Tyr Gly Gln Gly Glu Pro Ser Asp
    50                  55                  60

Glu Met Met Asn Asn Ile Leu Ala Asp Ile Arg Asn Ile Gln Phe Asp
65                  70                  75                  80

Arg Val Ile Gly Ile Gly Gly Thr Val Ile Asp Ile Ser Lys Leu
                85                  90                  95

Phe Val Leu Lys Gly Leu Asn Asp Val Leu Asp Ala Phe Asp Arg Lys
            100                 105                 110

Ile Pro Leu Ile Lys Glu Lys Glu Leu Ile Ile Val Pro Thr Thr Cys
        115                 120                 125

Gly Thr Gly Ser Glu Val Thr Asn Ile Ser Ile Ala Glu Ile Lys Ser
    130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
            180                 185                 190

Ser Pro Lys Ala Ser Pro Tyr Ser Arg Leu Phe Ser Glu Ala Ala Trp
        195                 200                 205

Asp Ile Ile Leu Glu Val Phe Lys Lys Ile Ala Glu His Gly Pro Glu
    210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
            260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
    290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335
```

```
Arg Gly Phe Ala Glu Ser Val Leu Lys Thr Gln Gln Arg Leu Leu Ala
                340                 345                 350

Asn Asn Tyr Val Glu Leu Thr Val Asp Glu Ile Glu Gly Ile Tyr Arg
            355                 360                 365

Arg Leu Tyr
        370

<210> SEQ ID NO 55
<211> LENGTH: 1296
<212> TYPE: DNA
<213> ORGANISM: Porphyromonas gingivalis

<400> SEQUENCE: 55
```

| | | | | | |
|---|---|---|---|---|---|
| atgaaagacg | tattagcgga | atatgcctcc | cgaattgttt | cggccgaaga | agccgtaaaa    60 |
| catatcaaaa | atggagaacg | ggtagctttg | tcacatgctg | ccggagttcc | tcagagttgt   120 |
| gttgatgcac | tggtacaaca | ggccgacctt | ttccagaatg | tcgaaattta | tcacatgctt   180 |
| tgtctcggcg | aaggaaaata | tatggcacct | gaaatggccc | ctcacttccg | acacataacc   240 |
| aattttgtag | gtggtaattc | tcgtaaagca | gttgaggaaa | atagagccga | cttcattccg   300 |
| gtattctttt | atgaagtgcc | atcaatgatt | cgcaaagaca | tccttcacat | agatgtcgcc   360 |
| atcgttcagc | tttcaatgcc | tgatgagaat | ggttactgta | gttttggagt | atcttgcgat   420 |
| tatagcaaac | cggcagcaga | aagcgctcat | ttagttatag | ggaaatcaa  | ccgtcaaatg   480 |
| ccatatgtac | atggcgacaa | cttgattcac | atatcgaagt | tggattacat | cgtgatggca   540 |
| gactacccta | tctattctct | tgcaaagccc | aaaatcggag | aagtagaaga | agctatcggg   600 |
| cgtaattgtg | ccgagcttat | tgaagatggt | gccacactcc | aactcggtat | cggcgcgatt   660 |
| cctgatgcag | ccctgttatt | cctcaaggac | aaaaaagatc | tggggatcca | taccgagatg   720 |
| ttctccgatg | gtgttgtcga | attagttcgc | agtggagtaa | ttacaggaaa | gaaaaagaca   780 |
| cttcaccccg | gaaagatggt | cgcaaccttc | ttaatgggaa | gcgaagacgt | atatcatttc   840 |
| atcgacaaaa | atcccgatgt | agaactttat | ccggtagatt | acgtcaatga | tccgcgagta   900 |
| atcgctcaaa | atgataatat | ggtcagcatc | aatagctgta | tcgaaatcga | tcttatggga   960 |
| caagtcgtgt | ccgaatgtat | aggaagcaag | caattcagcg | gaaccggcgg | tcaagtagat  1020 |
| tatgttcgtg | gagcagcatg | gtctaaaaac | ggcaaaagca | tcatggcaat | tccctcaaca  1080 |
| gccaaaaacg | gtactgcatc | tcgaattgta | cctataattg | cagagggagc | tgctgtaaca  1140 |
| accctccgca | acgaagtcga | ttacgttgta | accgaatacg | gtatagcaca | actcaaagga  1200 |
| aagagtttgc | gccagcgagc | agaagctctt | attgccatag | cccacccgga | tttcagagag  1260 |
| gaactaacga | aacatctccg | caaacgtttc | ggataa     |            |         1296 |

```
<210> SEQ ID NO 56
<211> LENGTH: 431
<212> TYPE: PRT
<213> ORGANISM: Porphyromonas gingivalis

<400> SEQUENCE: 56

Met Lys Asp Val Leu Ala Glu Tyr Ala Ser Arg Ile Val Ser Ala Glu
1               5                   10                  15

Glu Ala Val Lys His Ile Lys Asn Gly Glu Arg Val Ala Leu Ser His
                20                  25                  30

Ala Ala Gly Val Pro Gln Ser Cys Val Asp Ala Leu Val Gln Gln Ala
            35                  40                  45

Asp Leu Phe Gln Asn Val Glu Ile Tyr His Met Leu Cys Leu Gly Glu
```

Gly Lys Tyr Met Ala Pro Glu Met Ala Pro His Phe Arg His Ile Thr
 50                  55                  60
 65                                                              80

Asn Phe Val Gly Gly Asn Ser Arg Lys Ala Val Glu Asn Arg Ala
                 85                  90                  95

Asp Phe Ile Pro Val Phe Phe Tyr Glu Val Pro Ser Met Ile Arg Lys
                100                 105                 110

Asp Ile Leu His Ile Asp Val Ala Ile Val Gln Leu Ser Met Pro Asp
                115                 120                 125

Glu Asn Gly Tyr Cys Ser Phe Gly Val Ser Cys Asp Tyr Ser Lys Pro
            130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
                180                 185                 190

Gly Glu Val Glu Glu Ala Ile Gly Arg Asn Cys Ala Glu Leu Ile Glu
            195                 200                 205

Asp Gly Ala Thr Leu Gln Leu Gly Ile Gly Ala Ile Pro Asp Ala Ala
210                 215                 220

Leu Leu Phe Leu Lys Asp Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
            260                 265                 270

Gly Ser Glu Asp Val Tyr His Phe Ile Asp Lys Asn Pro Asp Val Glu
            275                 280                 285

Leu Tyr Pro Val Asp Tyr Val Asn Asp Pro Arg Val Ile Ala Gln Asn
            290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
                325                 330                 335

Gly Gln Val Asp Tyr Val Arg Gly Ala Ala Trp Ser Lys Asn Gly Lys
            340                 345                 350

Ser Ile Met Ala Ile Pro Ser Thr Ala Lys Asn Gly Thr Ala Ser Arg
            355                 360                 365

Ile Val Pro Ile Ile Ala Glu Gly Ala Ala Val Thr Thr Leu Arg Asn
            370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
                405                 410                 415

Asp Phe Arg Glu Glu Leu Thr Lys His Leu Arg Lys Arg Phe Gly
                420                 425                 430

<210> SEQ ID NO 57
<211> LENGTH: 906
<212> TYPE: DNA
<213> ORGANISM: Clostridium acetobutylicum

<400> SEQUENCE: 57

```
atgattaaga gttttaatga aattatcatg aaggtaaaga gcaaagaaat gaaaaaagtt      60
gctgttgctg tagcacaaga cgagccagta cttgaagcag taagagatgc taagaaaaat     120
ggtattgcag atgctattct tgttggagac catgacgaaa tcgtgtcaat cgcgcttaaa     180
ataggaatgg atgtaaatga ttttgaaata gtaaacgagc ctaacgttaa gaaagctgct     240
ttaaaggcag tagagcttgt atcaactgga aaagctgata tggtaatgaa gggacttgta     300
aatacagcaa ctttcttaag atctgtatta aacaaagaag ttggacttag aacaggaaaa     360
actatgtctc acgttgcagt atttgaaact gagaaatttg atagactatt atttttaaca     420
gatgttgctt tcaatactta tcctgaatta aggaaaaaa ttgatatagt aaacaattca     480
gttaaggttg cacatgcaat aggaattgaa atccaaagg ttgctccaat tgtgcagtt      540
gaggttataa accctaaaat gccatcaaca cttgatgcag caatgctttc aaaaatgagt     600
gacagaggac aaattaaagg ttgtgtagtt gacggacctt tagcacttga tatagcttta     660
tcagaagaag cagcacatca taagggagta acaggagaag ttgctggaaa agctgatatc     720
ttcttaatgc caaacataga aacaggaaat gtaatgtata agactttaac atatacaact     780
gattcaaaaa atggaggaat cttagttgga acttctgcac cagttgtttt aacttcaaga     840
gctgacagcc atgaaacaaa aatgaactct atagcacttg cagctttagt tgcaggcaat     900
aaataa                                                                 906
```

<210> SEQ ID NO 58
<211> LENGTH: 301
<212> TYPE: PRT
<213> ORGANISM: Clostridium acetobutylicum

<400> SEQUENCE: 58

```
Met Ile Lys Ser Phe Asn Glu Ile Ile Met Lys Val Lys Ser Lys Glu
1               5                   10                  15

Met Lys Lys Val Ala Val Ala Val Ala Gln Asp Glu Pro Val Leu Glu
            20                  25                  30

Ala Val Arg Asp Ala Lys Lys Asn Gly Ile Ala Asp Ala Ile Leu Val
        35                  40                  45

Gly Asp His Asp Glu Ile Val Ser Ile Ala Leu Lys Ile Gly Met Asp
    50                  55                  60

Val Asn Asp Phe Glu Ile Val Asn Glu Pro Asn Val Lys Lys Ala Ala
65                  70                  75                  80

Leu Lys Ala Val Glu Leu Val Ser Thr Gly Lys Ala Asp Met Val Met
                85                  90                  95

Lys Gly Leu Val Asn Thr Ala Thr Phe Leu Arg Ser Val Leu Asn Lys
            100                 105                 110

Glu Val Gly Leu Arg Thr Gly Lys Thr Met Ser His Val Ala Val Phe
        115                 120                 125

Glu Thr Glu Lys Phe Asp Arg Leu Leu Phe Leu Thr Asp Val Ala Phe
    130                 135                 140

Asn Thr Tyr Pro Glu Leu Lys Glu Lys Ile Asp Ile Val Asn Asn Ser
145                 150                 155                 160

Val Lys Val Ala His Ala Ile Gly Ile Glu Asn Pro Lys Val Ala Pro
                165                 170                 175

Ile Cys Ala Val Glu Val Ile Asn Pro Lys Met Pro Ser Thr Leu Asp
            180                 185                 190

Ala Ala Met Leu Ser Lys Met Ser Asp Arg Gly Gln Ile Lys Gly Cys
        195                 200                 205
```

```
Val Val Asp Gly Pro Leu Ala Leu Asp Ile Ala Leu Ser Glu Glu Ala
    210                 215                 220

Ala His His Lys Gly Val Thr Gly Glu Val Ala Gly Lys Ala Asp Ile
225                 230                 235                 240

Phe Leu Met Pro Asn Ile Glu Thr Gly Asn Val Met Tyr Lys Thr Leu
                245                 250                 255

Thr Tyr Thr Thr Asp Ser Lys Asn Gly Gly Ile Leu Val Gly Thr Ser
            260                 265                 270

Ala Pro Val Val Leu Thr Ser Arg Ala Asp Ser His Glu Thr Lys Met
        275                 280                 285

Asn Ser Ile Ala Leu Ala Ala Leu Val Ala Gly Asn Lys
    290                 295                 300
```

```
<210> SEQ ID NO 59
<211> LENGTH: 1068
<212> TYPE: DNA
<213> ORGANISM: Clostridium acetobutylicum

<400> SEQUENCE: 59
```

| | | | | | |
|---|---|---|---|---|---|
| atgtatagat | tactaataat | caatcctggc | tcgacctcaa | ctaaaattgg | tatttatgac | 60 |
| gatgaaaaag | agatatttga | aagactttta | agacattcag | ctgaagagat | agaaaaatat | 120 |
| aacactatat | ttgatcaatt | tcaattcaga | agaatgtaa | ttttagatgc | gttaaaagaa | 180 |
| gcaaacatag | aagtaagttc | tttaaatgct | gtagttggaa | gaggcggact | cttaaagcca | 240 |
| atagtaagtg | aacttatgc | agtaaatcaa | aaatgcttg | aagaccttaa | agtaggagtt | 300 |
| caaggtcagc | atgcgtcaaa | tcttggtgga | attattgcaa | atgaaatagc | aaagaaata | 360 |
| aatgttccag | catacatagt | tgatccagtt | gttgtggatg | agcttgatga | agtttcaaga | 420 |
| atatcaggaa | tggctgacat | tccaagaaaa | agtatattcc | atgcattaaa | tcaaaaagca | 480 |
| gttgctagaa | gatatgcaaa | agaagttgga | aaaaaatacg | aagatcttaa | tttaatcgta | 540 |
| gtccacatgg | gtgaggtac | ttcagtaggt | actcataaag | atggtagagt | aatagaagtt | 600 |
| aataatacac | ttgatggaga | aggtccattc | tcaccagaaa | gaagtggtgg | agttccaata | 660 |
| ggagatcttg | taagattgtg | cttcagcaac | aaatatactt | atgaagaagt | aatgaaaaag | 720 |
| ataaacggca | aggcggagt | tgttagttac | ttaaatacta | tcgattttaa | ggctgtagtt | 780 |
| gataaagctc | ttgaaggaga | taagaaatgt | gcacttatat | atgaagcttt | cacattccag | 840 |
| gtagcaaaag | agataggaaa | atgttcaacc | gtttttaaaag | gaaatgtaga | tgcaataatc | 900 |
| ttaacaggcg | gaattgcgta | caacgagcat | gtatgtaatg | ccatagagga | tagagtaaaa | 960 |
| ttcatagcac | ctgtagttag | atatggtgga | gaagatgaac | ttcttgcact | tgcagaaggt | 1020 |
| ggacttagag | ttttaagagg | agaagaaaaa | gctaaggaat | acaaataa | | 1068 |

```
<210> SEQ ID NO 60
<211> LENGTH: 355
<212> TYPE: PRT
<213> ORGANISM: Clostridium acetobutylicum

<400> SEQUENCE: 60

Met Tyr Arg Leu Leu Ile Ile Asn Pro Gly Ser Thr Ser Thr Lys Ile
1               5                   10                  15

Gly Ile Tyr Asp Asp Glu Lys Glu Ile Phe Glu Lys Thr Leu Arg His
                20                  25                  30

Ser Ala Glu Glu Ile Glu Lys Tyr Asn Thr Ile Phe Asp Gln Phe Gln
            35                  40                  45
```

Phe Arg Lys Asn Val Ile Leu Asp Ala Leu Lys Glu Ala Asn Ile Glu
 50                  55                  60

Val Ser Ser Leu Asn Ala Val Val Gly Arg Gly Gly Leu Leu Lys Pro
 65                  70                  75                  80

Ile Val Ser Gly Thr Tyr Ala Val Asn Gln Lys Met Leu Glu Asp Leu
                 85                  90                  95

Lys Val Gly Val Gln Gly Gln His Ala Ser Asn Leu Gly Gly Ile Ile
            100                 105                 110

Ala Asn Glu Ile Ala Lys Glu Ile Asn Val Pro Ala Tyr Ile Val Asp
        115                 120                 125

Pro Val Val Asp Glu Leu Asp Glu Val Ser Arg Ile Ser Gly Met
130                 135                 140

Ala Asp Ile Pro Arg Lys Ser Ile Phe His Ala Leu Asn Gln Lys Ala
145                 150                 155                 160

Val Ala Arg Arg Tyr Ala Lys Glu Val Gly Lys Lys Tyr Glu Asp Leu
                165                 170                 175

Asn Leu Ile Val Val His Met Gly Gly Thr Ser Val Gly Thr His
            180                 185                 190

Lys Asp Gly Arg Val Ile Glu Val Asn Asn Thr Leu Asp Gly Glu Gly
        195                 200                 205

Pro Phe Ser Pro Glu Arg Ser Gly Gly Val Pro Ile Gly Asp Leu Val
210                 215                 220

Arg Leu Cys Phe Ser Asn Lys Tyr Thr Tyr Glu Val Met Lys Lys
225                 230                 235                 240

Ile Asn Gly Lys Gly Gly Val Val Ser Tyr Leu Asn Thr Ile Asp Phe
                245                 250                 255

Lys Ala Val Val Asp Lys Ala Leu Glu Gly Asp Lys Lys Cys Ala Leu
            260                 265                 270

Ile Tyr Glu Ala Phe Thr Phe Gln Val Ala Lys Glu Ile Gly Lys Cys
        275                 280                 285

Ser Thr Val Leu Lys Gly Asn Val Asp Ala Ile Ile Leu Thr Gly Gly
290                 295                 300

Ile Ala Tyr Asn Glu His Val Cys Asn Ala Ile Glu Asp Arg Val Lys
305                 310                 315                 320

Phe Ile Ala Pro Val Val Arg Tyr Gly Gly Glu Asp Glu Leu Leu Ala
                325                 330                 335

Leu Ala Glu Gly Gly Leu Arg Val Leu Arg Gly Glu Lys Ala Lys
            340                 345                 350

Glu Tyr Lys
        355

<210> SEQ ID NO 61
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgattaaga gttttaatga aattatcatg aaggtaaaga gcaaagaaat gaaaaagtt      60 gctgttgctg tagcacaaga cgagccagta cttgaagcag tacgcgatgc taagaaaaat    120
ggtattgcag atgctattct tgttggcgac catgacgaaa tcgtgtcaat cgcgcttaaa    180
ataggcatgg atgtaaatga ttttgaaata gtaaacgagc taacgttaa gaaagctgct     240

| | |
|---|---|
| ttaaaggcag tagagctggt atcaactgga aaagctgata tggtaatgaa gggacttgta | 300 |
| aatacagcaa ctttcttacg ctctgtatta acaaagaag ttggactgag acaggaaaa | 360 |
| actatgtctc acgttgcagt atttgaaact gagaaatttg atcgtctgtt attttaaca | 420 |
| gatgttgctt tcaatactta tcctgaatta aggaaaaaa ttgatatcgt aaacaattca | 480 |
| gttaaggttg cacatgcaat aggtattgaa atccaaagg ttgctccaat ttgtgcagtt | 540 |
| gaggttataa accctaaaat gccatcaaca cttgatgcag caatgctttc aaaaatgagt | 600 |
| gacagaggac aaattaaagg ttgtgtagtt gacggaccgt tagcacttga tatcgcttta | 660 |
| tcagaagaag cagcacatca taagggcgta acaggagaag ttgctggaaa agctgatatc | 720 |
| ttcttaatgc caaacattga aacaggaaat gtaatgtata agactttaac atatacaact | 780 |
| gatagcaaaa atggcggaat cttagttgga acttctgcac cagttgtttt aacttcacgc | 840 |
| gctgacagcc atgaaacaaa aatgaactct attgcacttg cagctttagt tgcaggcaat | 900 |
| aaataa | 906 |

<210> SEQ ID NO 62
<211> LENGTH: 906
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

| | |
|---|---|
| atgattaaga gttttaatga aattatcatg aaggtaaaga gcaaagaaat gaaaaaagtt | 60 |
| gctgttgctg tagcacaaga cgagccagta cttgaagcag tacgcgatgc taagaaaaat | 120 |
| ggtattgccg atgctattct ggttggcgac catgacgaaa tcgtgtctat cgcgctgaaa | 180 |
| ataggcatgg atgtaaatga ttttgaaatt gttaacgagc taacgttaa gaaagctgcg | 240 |
| ttaaaggcag tagagctggt atcaactgga aaagctgata tggtaatgaa gggactggta | 300 |
| aataccgcaa ctttcttacg ctctgtatta acaaagaag ttggtctgcg tacaggaaaa | 360 |
| accatgtctc acgttgcagt atttgaaact gagaaatttg atcgtctgtt attttaaca | 420 |
| gatgttgctt tcaatactta tcctgaatta aggaaaaaa ttgatatcgt taacaatagc | 480 |
| gttaaggttg cacatgccat tggtattgaa atccaaagg ttgctccaat ttgtgcagtt | 540 |
| gaggttatta acccgaaaat gccatcaaca cttgatgcag caatgctttc aaaaatgagt | 600 |
| gaccgcggac aaattaaagg ttgtgtagtt gacggaccgc tggcacttga tatcgcttta | 660 |
| tcagaagaag cagcacatca taaggcgta acaggagaag ttgctggaaa agctgatatc | 720 |
| ttcttaatgc caaacattga aacaggaaat gtaatgtata agacgttaac ctataccact | 780 |
| gatagcaaaa atggcggcat cctggttgga acttctgcac cagttgtttt aacttcacgc | 840 |
| gctgacagcc atgaaacaaa aatgaactct attgcactgg cagcgctggt tgcaggcaat | 900 |
| aaataa | 906 |

<210> SEQ ID NO 63
<211> LENGTH: 906
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

| | |
|---|---|
| atgattaaga gttttaatga aattatcatg aaggtaaaga gcaaagaaat gaaaaaagtt | 60 |

```
gctgttgctg ttgcacaaga cgagccggta ctggaagcgg tacgcgatgc taagaaaaat    120
ggtattgccg atgctattct ggttggcgac catgacgaaa tcgtctctat cgcgctgaaa    180
attggcatgg atgttaatga ttttgaaatt gttaacgagc ctaacgttaa gaaagctgcg    240
ctgaaggcgg tagagctggt ttccaccgga aaagctgata tggtaatgaa agggctggtg    300
aataccgcaa ctttcttacg cagcgtactg aacaaagaag ttggtctgcg taccggaaaa    360
accatgagtc acgttgcggt atttgaaact gagaaatttg atcgtctgct gtttctgacc    420
gatgttgctt tcaatactta tcctgaatta aagaaaaaa ttgatatcgt taacaatagc    480
gttaaggttg cgcatgccat tggtattgaa atccaaagg ttgctccaat ttgtgcagtt    540
gaggttatta acccgaaaat gccatcaaca cttgatgccg caatgcttag caaaatgagt    600
gaccgcggac aaattaaagg ttgtgtggtt gacggcccgc tggcactgga tatcgcgtta    660
agcgaagaag cggcacatca taaggcgta accggcgaag ttgctggaaa agctgatatc    720
ttcctgatgc aaacattga acaggcaat gtaatgtata aaacgttaac ctataccact    780
gatagcaaaa atggcggcat cctggttgga acttctgcac cagttgtttt aacctcacgc    840
gctgacagcc atgaaaccaa aatgaacagc attgcactgg cagcgctggt tgcaggcaat    900
aaataa                                                              906

<210> SEQ ID NO 64
<211> LENGTH: 906
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atgattaaaa gttttaacga aattatcatg aaagtgaaaa gcaaagagat gaaaaaagtg    60
gcggttgcgg ttgcgcagga tgaaccggtg ctggaagcgg tgcgcgatgc caaaaaaaac    120
ggtattgccg atgccattct ggtgggcgat cacgatgaaa ttgtctctat tgcgctgaaa    180
attggcatgg atgttaacga ttttgaaatt gttaatgaac cgaacgtgaa aaaagcggcg    240
ctgaaagcgg ttgaactggt ttccaccggt aaagccgata tggtgatgaa agggctggtg    300
aataccgcaa ccttcctgcg cagcgtgctg aataaagaag tgggtctgcg taccggtaaa    360
accatgagtc atgttgcggt gtttgaaacc gaaaaatttg accgtctgct gtttctgacc    420
gatgttgcgt ttaataccta tccggaactg aaagagaaaa ttgatatcgt taataacagc    480
gtgaaagtgg cgcatgccat tggtattgaa acccgaaag tggcgccgat ttgcgcggtt    540
gaagtgatta acccgaaaat gccgtcaacg ctggatgccg cgatgctcag caaaatgagc    600
gatcgcggtc aaatcaaagg ctgtgtggtt gatggcccgc tggcgctgga tatcgcgctt    660
agcgaagaag cggcgcatca taaggcgtg accggcgaag tggccggtaa agccgatatt    720
ttcctgatgc cgaatattga aaccggcaac gtgatgtata aaacgctgac ctataccacc    780
gacagcaaaa acggcggcat tctggtgggt accagcgcgc cggtggtgct gacctcgcgc    840
gccgacagcc atgaaaccaa aatgaacagc attgcgctgg cggcgctggt ggccggtaat    900
aaataa                                                              906

<210> SEQ ID NO 65
<211> LENGTH: 1068
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 65

| | | | | | |
|---|---|---|---|---|---|
| atgtatcgtt | tactgattat | caatcctggc | tcgacctcaa | ctaaaattgg | tatttatgac | 60 |
| gatgaaaaag | agatatttga | aagacttta | cgtcattcag | ctgaagagat | agaaaaatat | 120 |
| aacactatat | ttgatcaatt | tcagttcaga | aagaatgtaa | ttctcgatgc | gttaaaagaa | 180 |
| gcaaacattg | aagtaagttc | tttaaatgct | gtagttggac | gcggcggact | gttaaagcca | 240 |
| atagtaagtg | gaacttatgc | agtaaatcaa | aaaatgcttg | aagaccttaa | agtaggcgtt | 300 |
| caaggtcagc | atgcgtcaaa | tcttggtgga | attattgcaa | atgaaatagc | aaaagaaata | 360 |
| aatgttccag | catacatcgt | tgatccagtt | gttgtggatg | agcttgatga | agtttcacgt | 420 |
| atatcaggaa | tggctgacat | tccacgtaaa | agtatattcc | atgcattaaa | tcaaaaagca | 480 |
| gttgctagac | gctatgcaaa | agaagttgga | aaaaaatacg | aagatcttaa | tttaatcgtg | 540 |
| gtccacatgg | gtggcggtac | ttcagtaggt | actcataaag | atggtagagt | aattgaagtt | 600 |
| aataatacac | ttgatggaga | aggtccattc | tcaccagaaa | gaagtggtgg | cgttccaata | 660 |
| ggcgatcttg | tacgtttgtg | cttcagcaac | aaatatactt | atgaagaagt | aatgaaaaag | 720 |
| ataaacggca | aaggcggcgt | tgttagttac | ttaaatacta | tcgattttaa | ggctgtagtt | 780 |
| gataaagctc | ttgaaggcga | taagaaatgt | gcacttatat | atgaagcttt | cacattccag | 840 |
| gtagcaaaag | agataggaaa | atgttcaacc | gttttaaaag | gaaatgtaga | tgcaataatc | 900 |
| ttaacaggcg | gaattgcgta | caacgagcat | gtatgtaatg | ccatagagga | tagagtaaaa | 960 |
| ttcattgcac | ctgtagttcg | ttatggtgga | gaagatgaac | ttcttgcact | tgcagaaggt | 1020 |
| ggactgcgcg | ttttacgcgg | agaagaaaaa | gctaaggaat | acaaataa | | 1068 |

<210> SEQ ID NO 66
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

| | | | | | |
|---|---|---|---|---|---|
| atgtatcgtt | tactgattat | caatcctggc | tcgacctcaa | ctaaaattgg | tatttatgac | 60 |
| gatgaaaaag | agatatttga | aagacgtta | cgtcattcag | ctgaagagat | tgaaaaatat | 120 |
| aacactatat | ttgatcaatt | tcagttccgc | aagaatgtga | ttctcgatgc | gttaaaagaa | 180 |
| gcaaacattg | aagtcagttc | tttaaatgct | gtagttggac | gcggcggact | gttaaagcca | 240 |
| attgtcagtg | gaacttatgc | agtaaatcaa | aaaatgcttg | aagaccttaa | agtgggcgtt | 300 |
| caaggtcagc | atgccagcaa | tcttggtggc | attattgcca | atgaaatcgc | aaaagaaatc | 360 |
| aatgttccag | catacatcgt | tgatccggtt | gttgtggatg | agcttgatga | agttagccgt | 420 |
| ataagcggaa | tggctgacat | tccacgtaaa | agtatattcc | atgcattaaa | tcaaaaagca | 480 |
| gttgctcgtc | gctatgcaaa | agaagttggt | aaaaaatacg | aagatcttaa | tttaatcgtg | 540 |
| gtccacatgg | gtggcggtac | ttcagtaggt | actcataaag | atggtcgcgt | gattgaagtt | 600 |
| aataatacac | ttgatggcga | aggtccattc | tcaccagaac | gtagtggtgg | cgttccaatt | 660 |
| ggcgatctgg | tacgtttgtg | cttcagcaac | aaatatactt | atgaagaagt | gatgaaaaag | 720 |
| ataaacggca | aaggcggcgt | tgttagttac | ctgaatacta | tcgattttaa | ggctgtagtt | 780 |

```
gataaagcgc ttgaaggcga taagaaatgt gcactgattt atgaagcttt caccttccag    840
gtagcaaaag agattggtaa atgttcaacc gttttaaaag gaaatgttga tgccattatc    900
ttaacaggcg gcattgctta caacgagcat gtatgtaatg ccattgagga tcgcgtaaaa    960
ttcattgcac ctgtagttcg ttatggtggc gaagatgaac tgctggcact ggcagaaggt   1020
ggactgcgcg ttttacgcgg cgaagaaaaa gcgaaggaat acaaataa                1068
```

<210> SEQ ID NO 67
<211> LENGTH: 1068
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 67

```
atgtatcgtc tgctgattat caatcctggc tcgacctcaa ctaaaattgg tatttatgac     60
gatgaaaaag agatatttga gaaaacgtta cgtcatagcg ctgaagagat tgaaaaatat    120
aacactattt ttgatcaatt tcagttccgc aagaatgtga ttctcgatgc gctgaaagaa    180
gcaaacattg aagtcagttc gctgaatgcg gtagttggtc gcggcggtct gctgaagcca    240
attgtcagcg gcacttatgc ggtaaatcaa aaaatgctgg aagacctgaa agtgggcgtt    300
caggggcagc atgccagcaa tcttggtggc attattgcca atgaaatcgc caaagaaatc    360
aatgttccgg catacatcgt tgatccggtt gttgtggatg agctggatga agttagccgt    420
atcagcggaa tggctgacat tccacgtaaa agtatttttcc atgcactgaa tcaaaaagcg    480
gttgcgcgtc gctatgcaaa agaagttggt aaaaaatacg aagatcttaa tctgatcgtg    540
gtgcatatgg gtggcggtac tagcgtcggt actcataaag atggtcgcgt gattgaagtt    600
aataatacac ttgatggcga aggtccattc tcaccagaac gtagcggtgg cgttccaatt    660
ggcgatctgg tacgtttgtg cttcagcaac aaatatacct atgaagaagt gatgaaaaag    720
ataaacggca aaggcggcgt tgttagttac ctgaatacta tcgattttaa ggcggtagtt    780
gataaagcgc tggaaggcga taagaaatgt gcactgattt atgaagcgtt caccttccag    840
gtggcaaaag agattggtaa atgttcaacc gttctgaaag gcaatgttga tgccattatc    900
ctgaccggcg gcattgctta caacgagcat gttttgtaatg ccattgagga tcgcgtaaaa    960
ttcattgcac ctgtggttcg ttatggtggc gaagatgaac tgctggcact ggcagaaggt   1020
ggtctgcgcg ttttacgcgg cgaagaaaaa gcgaaagaat acaaataa                1068
```

<210> SEQ ID NO 68
<211> LENGTH: 1068
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 68

```
atgtatcgtc tgctgattat caacccgggc agcacctcaa ccaaaattgg tatttacgac     60
gatgaaaaag agattttga aaaaacgctg cgtcacagcg cagaagagat tgaaaaatac    120
aacaccattt tcgatcagtt ccagttccgc aaaaacgtga ttctcgatgc gctgaaagaa    180
gccaatattg aagtctcctc gctgaatgcg gtggtcggtc gcggcggtct gctgaaaccg    240
attgtcagcg gcacttatgc ggttaatcag aaaatgctgg aagatctgaa agtgggcgtg    300
caggggcagc atgccagcaa tctcggcggc attatcgcca atgaaatcgc caaagagatc    360
```

```
aacgtgccgg cttatatcgt cgatccggtg gtggttgatg aactggatga agtcagccgt    420
atcagcggca tggcggatat tccgcgtaaa agcatttttcc atgcgctgaa tcagaaagcg    480
gttgcgcgtc gctatgccaa agaagtgggt aaaaaatatg aagatctcaa tctgattgtg    540
gtgcatatgg gcgcggcac cagcgtcggt acgcataaag atggtcgcgt gattgaagtg    600
aataacacgc tggatggcga agggccgttc tcgccggaac gtagcggcgg cgtgccgatt    660
ggcgatctgg tgcgtctgtg tttcagcaat aaatacacct acgaagaagt gatgaaaaaa    720
atcaacggca aggcggcgt ggttagctat ctgaatacca tcgattttaa agcggtggtt    780
gataaagcgc tggaaggcga taaaaaatgc gcgctgattt atgaagcgtt taccttccag    840
gtggcgaaag agattggtaa atgttcaacc gtgctgaaag caacgttga tgccattatt    900 ctgaccggcg gcattgctta taacgaacat gttttgtaatg ccattgaaga tcgcgtgaaa    960
tttattgcgc cggtggtgcg ttacggcggc gaagatgaac tgctggcgct ggcggaaggc   1020
ggtctgcgcg tgctgcgcgg cgaagaaaaa gcgaaagagt acaaataa               1068

<210> SEQ ID NO 69
<211> LENGTH: 1407
<212> TYPE: DNA
<213> ORGANISM: Clostridium biejerinckii

<400> SEQUENCE: 69
atgaataaag acacactaat acctacaact aaagatttaa agtaaaaac aaatggtgaa     60 aacattaatt taaagaacta caaggataat tcttcatgtt tcggagtatt cgaaaatgtt    120
gaaaatgcta agcagcgcgc tgtacacgca caaaagatat tatcccttca ttatacaaaa    180
gagcaaagag aaaaaatcat aactgagata agaaaggccg cattacaaaa taagagggtc    240
ttggctacaa tgattctaga agaaacacat atgggaagat atgaggataa atattaaaa     300 catgaattgg tagctaaata tactcctggt acagaagatt taactactac tgcttggtca    360
ggtgataatg gtcttacagt tgtagaaatg tctccatatg gtgttatagg tgcaataact    420
ccttctacga atccaactga aactgtaata tgtaatagca taggcatgat agctgctgga    480
aatgctgtag tatttaacgg acacccatgc gctaaaaaat gtgttgcctt tgctgttgaa    540
atgataaata aggcaattat ttcatgtggc ggtcctgaaa atctagtaac aactataaaa    600
aatccaacta tggagtctct agatgcaatt attaagcatc cttcaataaa acttctttgc    660
ggaactgggg gtccaggaat ggtaaaaacc ctcttaaatt ctggtaagaa agctataggt    720
gctggtgctg gaaatccacc agttattgta gatgatactg ctgatataga aaaggctggt    780
aggagcatca ttgaaggctg ttctttgat aataattac cttgtattgc agaaaaagaa    840
gtatttgttt ttgagaatgt tgcagatgat ttaatatcta acatgctaaa aaataatgct    900
gtaattataa atgaagatca agtatcaaaa ttaatagatt tagtattaca aaaaaataat    960
gaaactcaag aatactttat aaacaaaaaa tgggtaggaa aagatgcaaa attattctta   1020
gatgaaatag atgttgagtc tccttcaaat gttaaatgca taatctgcga agtaaatgca   1080
aatcatccat tgttatgac agaactcatg atgccaatat tgccaattgt aagagttaaa   1140
gatatagatg aagctattaa atatgcaaag atagcagaac aaaatagaaa acatagtgcc   1200
tatatttatt ctaaaaatat agacaaccta atagatttg aaagagaaat agatactact   1260
atttttgtaa agaatgctaa atcttttgct ggtgttggtt atgaagcaga aggatttaca   1320
actttcacta ttgctggatc tactggtgag ggaataacct ctgcaaggaa tttttacaaga   1380
```
caaagaagat gtgtacttgc cggctaa                                          1407

<210> SEQ ID NO 70
<211> LENGTH: 468
<212> TYPE: PRT
<213> ORGANISM: Clostridium biejerinckii

<400> SEQUENCE: 70

```
Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365
```

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Phe Thr Ile Ala Gly Ser Thr
                435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 71
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atgaataaag acacactaat acctacaact aaagatttaa agtaaaaac aaatggtgaa        60 aacattaatt taagaacta caaggataat tcttcatgtt tcggcgtatt cgaaaatgtt       120
gaaaatgcta taagcagcgc tgtacacgca caaaagatat tatcccttca ttatacaaaa       180
gagcaacgtg aaaaaatcat aactgagata gaaaggccg cattacaaaa taagaggtc        240 ttggctacaa tgattctgga agaaacacat atgggacgtt atgaggataa aatattaaaa       300
catgaattgg tagctaaata tactcctggt acagaagatt taactactac tgcctggtca       360
ggtgataatg tcctgacagt tgtagaaatg tctccatatg gtgttattgg tgcaataact       420
ccttctacga atccaactga aactgtaata tgtaatagca taggcatgat gctgctggaa       480
aatgctgtag tatttaacgg acacccatgc gctaaaaaat gtgttgcctt tgctgttgaa       540 atgataaaata aggcaattat ttcatgtggc ggtcctgaaa atctggtaac aactataaaa       600
aatccaacca tggagtctct ggatgcaatt attaagcatc cttcaataaa acttcttgc       660 ggaactgggg gtccaggaat ggtaaaaacc ctgttaaatt ctggtaagaa agctataggt       720
gctggtgctg gaaatccacc agttattgtc gatgatactg ctgatataga aaaggctggt       780
cgtagcatca ttgaaggctg ttcttttgat aataatttac cttgtattgc agaaaaagaa       840
gtatttgttt ttgagaatgt tgcagatgat ttaatatcta acatgctaaa aataatgct        900 gtaattataa atgaagatca agtatcaaaa ttaatcgatt tagtattaca aaaaataat       960 gaaactcaag aatactttat aaacaaaaaa tgggtaggaa agatgcaaa attattcctc      1020 gatgaaatag atgttgagtc tccttcaaat gttaaatgca taatctgcga agtaaatgca      1080
aatcatccat ttgttatgac agaactgatg atgccaatat tgccaattgt acgcgttaaa      1140
gatatcgatg aagctattaa atatgcaaag atagcagaac aaaatagaaa acatagtgcc      1200
tatatttatt ctaaaaatat cgacaacctg aatcgctttg aacgtgaaat agatactact      1260 attttttgtaa agaatgctaa atcttttgct ggtgttggtt atgaagcaga aggatttaca      1320
actttcacta ttgctggatc tactggtgag ggaataacct ctgcacgtaa ttttacacgc      1380
caacgtcgct gtgtacttgc cggctaa                                          1407

<210> SEQ ID NO 72
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

| | |
|---|---|
| atgaataaag acacactgat ccctacaact aaagatttaa agtaaaaac aaatggtgaa | 60 |
| aacattaatt taaagaacta caaagataat agcagttgtt tcggcgtatt cgaaaatgtt | 120 |
| gaaaatgcta tcagcagcgc tgtacacgca caaaagatat tatcgctgca ttatacaaaa | 180 |
| gagcaacgtg aaaaaatcat cactgagata cgtaaggccg cattacaaaa taagagggtg | 240 |
| ctggctacaa tgattctgga agaaacacat atgggacgtt atgaggataa atattaaaa | 300 |
| catgaactgg tagctaaata tactcctggt acagaagatt taactactac tgcctggagc | 360 |
| ggtgataatg gtctgacagt tgtagaaatg tctccatatg gtgttattgg tgcaataact | 420 |
| ccttctacca atccaactga aactgtaatt tgtaatagca ttggcatgat tgctgctgga | 480 |
| aatgctgtag tatttaacgg acacccatgc gctaaaaaat gtgttgcctt tgctgttgaa | 540 |
| atgatcaata aggcaattat tagctgtggc ggtccggaaa atctggtaac aactataaaa | 600 |
| aatccaacca tggagtctct ggatgccatt attaagcatc cttcaataaa actgctttgc | 660 |
| ggaactggcg gtccaggaat ggtaaaaacc ctgttaaatt ctggtaagaa agctattggt | 720 |
| gctggtgctg gaaatccacc agttattgtc gatgatactg ctgatattga aaaggctggt | 780 |
| cgtagcatca ttgaaggctg ttcttttgat aataatttac cttgtattgc agaaaaagaa | 840 |
| gtatttgttt tgagaatgt tgcagatgat ttaatatcta acatgctgaa aaataatgct | 900 |
| gtaattatca atgaagatca ggtatcaaaa ttaatcgatt tagtattaca aaaaaataat | 960 |
| gaaactcaag aatactttat caacaaaaaa tgggtaggta agatgcaaa attattcctc | 1020 |
| gatgaaatcg atgttgagtc tccttcaaat gttaaatgca ttatctgcga agtgaatgcc | 1080 |
| aatcatccat tgttatgac agaactgatg atgccaatat tgccaattgt gcgcgttaaa | 1140 |
| gatatcgatg aagctattaa atatgcaaag attgcagaac aaaatagaaa acatagtgcc | 1200 |
| tatatttata gcaaaaatat cgacaacctg aatcgctttg aacgtgaaat cgatactact | 1260 |
| atttttgtaa agaatgctaa atcttttgct ggtgttggtt atgaagcaga aggatttacc | 1320 |
| actttcacta ttgctggatc tactggtgag gcataaacct ctgcacgtaa ttttacccgc | 1380 |
| caacgtcgct gtgtactggc cggctaa | 1407 |

<210> SEQ ID NO 73
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | |
|---|---|
| atgaataaag acacgctgat cccgacaact aaagatctga agtaaaaac caatggtgaa | 60 |
| aacattaatc tgaagaacta caaagataat agcagttgtt tcggcgtatt cgaaaatgtt | 120 |
| gaaaatgcta tcagcagcgc ggtacacgca caaaagatac tctcgctgca ttataccaaa | 180 |
| gagcaacgtg aaaaaatcat cactgagatc cgtaaggccg cattacaaaa taagagggtg | 240 |

| | |
|---|---|
| ctggcaacaa tgattctgga agaaacacat atgggacgtt atgaggataa aatactgaaa | 300 |
| catgaactgg tggcgaaata tacgcctggt actgaagatt taaccaccac tgcctggagc | 360 |
| ggtgataatg gtctgaccgt tgtggaaatg tcgccttatg gtgttattgg tgcaattacg | 420 |
| ccttcaacca atccaactga aacggtaatt tgtaatagca ttggcatgat tgctgctgga | 480 |
| aatgcggtag tatttaacgg tcacccctgc gctaaaaaat gtgttgcctt tgctgttgaa | 540 |
| atgatcaata aagcgattat tagctgtggc ggtccggaaa atctggtaac cactataaaa | 600 |
| aatccaacca tggagtcgct ggatgccatt attaagcatc cttcaatcaa actgctgtgc | 660 |
| ggcactggcg gtccaggaat ggtgaaaacc ctgctgaata gcggtaagaa agcgattggt | 720 |
| gctggtgctg gaaatccacc agttattgtc gatgatactg ctgatattga aaaagcgggt | 780 |
| cgtagcatca ttgaaggctg ttcttttgat aataatttac cttgtattgc agaaaaagaa | 840 |
| gtatttgttt ttgagaatgt tgccgatgat ctgatctcta acatgctgaa aaataatgcg | 900 |
| gtgattatca atgaagatca ggttagcaaa ctgatcgatc tggtattaca aaaaaataat | 960 |
| gaaactcaag aatactttat caacaaaaaa tgggtaggta agatgcaaa actgttcctc | 1020 |
| gatgaaatcg atgttgagtc gccttcaaat gttaaatgca ttatctgcga agtgaatgcc | 1080 |
| aatcatccat ttgtgatgac cgaactgatg atgccaattt tgccgattgt gcgcgttaaa | 1140 |
| gatatcgatg aagcgattaa atatgcaaag attgcagaac aaaatcgtaa acatagtgcc | 1200 |
| tatatttata gcaaaaatat cgacaacctg aatcgctttg aacgtgaaat cgataccact | 1260 |
| attttgtga agaatgctaa atcttttgct ggtgttggtt atgaagcaga aggttttacc | 1320 |
| actttcacta ttgctggaag caccggtgaa ggcattacct ctgcacgtaa ttttacccgc | 1380 |
| caacgtcgct gtgtactggc cggctaa | 1407 |

<210> SEQ ID NO 74
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

| | |
|---|---|
| atgaataaag atacgctgat cccgaccacc aaagatctga agtgaaaac caacggcgaa | 60 |
| aatatcaacc tgaaaaacta aaagataac agcagttgct ttggcgtgtt tgaaaacgtt | 120 |
| gaaaacgcca ctctccagcgc ggtgcatgcg caaaaaattc tctcgctgca ttacaccaaa | 180 |
| gagcagcgtg aaaaaattat caccgaaatc cgtaaagcgg cgctgcaaaa caagaagtg | 240 |
| ctggcaacca tgatcctgga agaaacgcat atggggcgtt atgaagataa aattctgaaa | 300 |
| catgaactgg tggcgaaata cacgccgggc actgaagatc tgaccaccac cgcctggagc | 360 |
| ggcgataacg gcctgaccgt ggtggagatg tcgccttatg gcgtgattgg cgcgattacg | 420 |
| ccgtcaacca cccgaccga aacggtgatt tgtaacagca ttggcatgat tgccgcgggt | 480 |
| aatgcggtgg tgtttaacgg tcatccctgc gcgaaaaaat gtgtggcgtt tgccgttgag | 540 |
| atgatcaaca aagcgattat cagctgcggc ggcccggaaa atctggtgac caccatcaaa | 600 |
| aatccgacca tggaatcgct ggatgccatt atcaaacatc cttccatcaa actgctgtgc | 660 |
| ggcaccggcg gcccgggcat ggtgaaaacg ctgctgaaca gcggtaaaaa agcgattggc | 720 |
| gcgggcgcgg gtaacccgcc ggtgattgtc gatgacaccg ccgatattga aaaagcgggg | 780 |
| cgtagcatta ttgaaggctg ttcttttgat aacaacctgc cctgcattgc cgaaaaagaa | 840 |

```
gtgtttgtct ttgaaaacgt cgccgatgat ctgatcagca atatgctgaa aaacaacgcg      900
gtgattatca atgaagatca ggttagcaaa ctgatcgatc tggtgctgca aaaaaacaac      960
gaaacgcagg aatattttat caacaaaaaa tgggttggta agatgccaaa ctgtttctc      1020
gatgaaatcg atgttgaatc gccgtctaac gtgaaatgta ttatctgcga agtgaacgcc     1080
aaccatccgt ttgtgatgac cgaactgatg atgccgattc tgccgattgt gcgcgtgaaa     1140
gatatcgatg aagcgattaa atatgccaaa attgccgaac aaaaccgtaa acacagcgcc     1200
tatatttaca gcaaaaatat cgataacctg aaccgctttg aacgtgaaat cgataccacc     1260
attttttgtga aaaatgccaa aagttttgcc ggcgttggtt atgaagcgga aggttttacc     1320
acctttacca ttgccggtag caccggcgaa ggcattacca gcgcccgtaa ttttacccgc     1380
cagcgtcgct gcgtgctggc gggctaa                                          1407
```

<210> SEQ ID NO 75
<211> LENGTH: 1023
<212> TYPE: DNA
<213> ORGANISM: Geobacillus thermoglucosidasius

<400> SEQUENCE: 75

```
atgaaagctg cagtagtaga gcaatttaag gaaccattaa aaattaaaga agtggaaaag       60
ccatctattt catatggcga agtattagtc cgcattaaag catgcggtgt atgccatacg      120
gacttgcacg ccgctcatgg cgattggcca gtaaaaccaa acttcctttt aatccctggc      180
catgaaggag tcggaattgt tgaagaagtc ggtccggggg taacccattt aaaagtggga      240
gaccgcgttg gaattccttg gttatattct gcgtgcggcc attgcgaata ttgtttaagc      300
ggacaagaag cattatgtga acatcaacaa aacgccggct actcagtcga cgggggttat      360
gcagaatatt gcagagctgc gccagattat gtggtgaaaa ttcctgacaa cttatcgttt      420
gaagaagctg ctcctatttt ctgcgccgga gttactactt ataaagcgtt aaaagtcaca      480
ggtacaaaac cggagaatgg gtagcgatc tatggcatcg gcggccttgg acatgttgcc      540
gtccagtatg cgaaagcgat ggggcttcat gttgttgcag tggatatcgg cgatgagaaa      600
ctggaacttg caaagagct tggcgccgat cttgttgtaa atcctgcaaa agaaaatgcg      660
gcccaattta tgaaagagaa agtcggcgga gtacacgcgg ctgttgtgac agctgtatct      720
aaacctgctt tcaatctgc gtacaattct atccgcagag gcggcacgtg cgtgcttgtc      780
ggattaccgc cggaagaaat gcctattcca atctttgata cggtattaaa cggaattaaa      840
attatcggtt ccattgtcgg cacgcggaaa gacttgcaag aagcgcttca gttcgctgca      900
gaaggtaaag taaaaccat tattgaagtg caacctcttg aaaaaattaa cgaagtattt      960
gacagaatgc taaaggaga attaacggga cgggttgtt taacgttaga aaataaataat    1020
taa                                                                   1023
```

<210> SEQ ID NO 76
<211> LENGTH: 340
<212> TYPE: PRT
<213> ORGANISM: Geobacillus thermoglucosidasius

<400> SEQUENCE: 76

Met Lys Ala Ala Val Val Glu Gln Phe Lys Glu Pro Leu Lys Ile Lys
1               5                   10                  15

Glu Val Glu Lys Pro Ser Ile Ser Tyr Gly Glu Val Leu Val Arg Ile
            20                  25                  30

Lys Ala Cys Gly Val Cys His Thr Asp Leu His Ala Ala His Gly Asp

```
                35                  40                  45
Trp Pro Val Lys Pro Lys Leu Pro Leu Ile Pro Gly His Glu Gly Val
 50                  55                  60
Gly Ile Val Glu Glu Val Gly Pro Gly Val Thr His Leu Lys Val Gly
 65                  70                  75                  80
Asp Arg Val Gly Ile Pro Trp Leu Tyr Ser Ala Cys Gly His Cys Glu
                 85                  90                  95
Tyr Cys Leu Ser Gly Gln Glu Ala Leu Cys Glu His Gln Gln Asn Ala
            100                 105                 110
Gly Tyr Ser Val Asp Gly Gly Tyr Ala Glu Tyr Cys Arg Ala Ala Pro
        115                 120                 125
Asp Tyr Val Val Lys Ile Pro Asp Asn Leu Ser Phe Glu Glu Ala Ala
130                 135                 140
Pro Ile Phe Cys Ala Gly Val Thr Thr Tyr Lys Ala Leu Lys Val Thr
145                 150                 155                 160
Gly Thr Lys Pro Gly Glu Trp Val Ala Ile Tyr Gly Ile Gly Leu
                165                 170                 175
Gly His Val Ala Val Gln Tyr Ala Lys Ala Met Gly Leu His Val Val
            180                 185                 190
Ala Val Asp Ile Gly Asp Glu Lys Leu Glu Leu Ala Lys Glu Leu Gly
        195                 200                 205
Ala Asp Leu Val Val Asn Pro Ala Lys Glu Asn Ala Ala Gln Phe Met
210                 215                 220
Lys Glu Lys Val Gly Gly Val His Ala Ala Val Val Thr Ala Val Ser
225                 230                 235                 240
Lys Pro Ala Phe Gln Ser Ala Tyr Asn Ser Ile Arg Arg Gly Thr
                245                 250                 255
Cys Val Leu Val Gly Leu Pro Pro Glu Glu Met Pro Ile Pro Ile Phe
            260                 265                 270
Asp Thr Val Leu Asn Gly Ile Lys Ile Ile Gly Ser Ile Val Gly Thr
        275                 280                 285
Arg Lys Asp Leu Gln Glu Ala Leu Gln Phe Ala Ala Glu Gly Lys Val
290                 295                 300
Lys Thr Ile Ile Glu Val Gln Pro Leu Glu Lys Ile Asn Glu Val Phe
305                 310                 315                 320
Asp Arg Met Leu Lys Gly Glu Ile Asn Gly Arg Val Val Leu Thr Leu
                325                 330                 335
Glu Asn Asn Asn
            340

<210> SEQ ID NO 77
<211> LENGTH: 4090
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atggctatcg aaatcaaagt accggacatc ggggctgatg aagttgaaat caccgagatc      60
ctggtcaaag tgggcgacaa agttgaagcc gaacagtcgc tgatcaccgt agaaggcgac     120
aaagcctcta tggaagttcc gtctccgcag gcgggtatcg ttaaagagat caaagtctct     180
gttggcgata aaccagac cggcgcactg attatgattt cgattccgc cgacggtgca         240 gcagacgctg cacctgctca ggcagaagag aagaaagaag cagctccggc agcagcacca     300
```

```
gcggctgcgg cggcaaaaga cgttaacgtt ccggatatcg gcagcgacga agttgaagtg    360
accgaaatcc tggtgaaagt tggcgataaa gttgaagctg aacagtcgct gatcaccgta    420
gaaggcgaca aggcttctat ggaagttccg gctccgtttg ctggcaccgt gaaagagatc    480
aaagtgaacg tgggtgacaa agtgtctacc ggctcgctga ttatggtctt cgaagtcgcg    540
ggtgaagcag gcgcggcagc tccggccgct aaacaggaag cagctccggc agcggcccct    600
gcaccagcgg ctggcgtgaa agaagttaac gttccggata tcggcggtga cgaagttgaa    660
gtgactgaag tgatggtgaa agtgggcgac aaagttgccg ctgaacagtc actgatcacc    720
gtagaaggcg acaaagcttc tatggaagtt ccggcgccgt ttgcaggcgt cgtgaaggaa    780
ctgaaagtca cgttggcga taaagtgaaa actggctcgc tgattatgat cttcgaagtt    840
gaaggcgcag cgcctgcggc agctcctgcg aaacaggaag cggcagcgcc ggcaccggca    900
gcaaaagctg aagcccggc agcagcacca gctgcgaaag cggaaggcaa atctgaattt    960
gctgaaaacg acgcttatgt tcacgcgact ccgctgatcc gccgtctggc acgcgagttt   1020
ggtgttaacc ttgcgaaagt gaagggcact ggccgtaaag gtcgtatcct gcgcgaagac   1080
gttcaggctt acgtgaaaga agctatcaaa cgtgcagaag cagctccggc agcgactggc   1140
ggtggtatcc ctggcatgct gccgtggccg aaggtggact cagcaagtt tggtgaaatc   1200 gaagaagtgg aactgggccg catccagaaa atctctggtg cgaacctgag ccgtaactgg   1260
gtaatgatcc cgcatgttac tcacttcgac aaaaccgata tcaccgagtt ggaagcgttc   1320
cgtaaacagc agaacgaaga agcggcgaaa cgtaagctgg atgtgaagat cacccccggtt   1380 gtcttcatca tgaaagccgt tgctgcagct cttgagcaga tgcctcgctt caatagttcg   1440
ctgtcggaag acggtcagcg tctgaccctg aagaaataca tcaacatcgg tgtggcggtg   1500
gataccccga acggtctggt tgttccggta ttcaaagacg tcaacaagaa aggcatcatc   1560
gagctgtctc gcgagctgat gactatttct aagaaagcgc gtgacggtaa gctgactgcg   1620
ggcgaaatgc agggcggttg cttcaccatc tccagcatcg gcggcctggg tactacccac   1680
ttcgcgccga ttgtgaacgc gccggaagtg gctatcctcg gcgttccaa gtccgcgatg   1740 gagccggtgt ggaatggtaa agagttcgtg ccgcgtctga tgctgccgat ttctctctcc   1800
ttcgaccacc gcgtgatcga cggtgctgat ggtgcccgtt tcattaccat cattaacaac   1860
acgctgtctg acattcgccg tctggtgatg taagtaaaag agccggccca acggccggct   1920
tttttctggt aatctcatga atgtattgag gttattagcg aatagacaaa tcggttgccg   1980
tttgttgttt aaaaattgtt aacaattttg taaaataccg acggatagaa cgacccggtg   2040
gtggttaggg tattacttca catccctat ggatttctgg gtgcagcaag gtagcaagcg   2100
ccagaatccc caggagctta cataagtaag tgactgggt gagggcgtga agctaacgcc   2160
gctgcggcct gaaagacgac gggtatgacc gccggagata aatatataga ggtcatgatg   2220
agtactgaaa tcaaaactca ggtcgtggta cttgggcag gccccgcagg ttactccgct   2280
gccttccgtt gcgctgattt aggtctggaa accgtaatcg tagaacgtta caacacccct   2340
ggcggtgttt gtctgaacgt gggttgtatc ccttctaaag cgctgctgca cgtggcaaaa   2400
gttatcgaag aagcgaaagc gctggccgaa cacggcatcg tttcggcga accgaaaact   2460 gacattgaca agatccgcac ctggaaagaa aaagtcatca ctcagctgac cggtggtctg   2520
gctggcatgg ccaaaggtcg taaagtgaag gtggttaacg gtctgggtaa atttaccggc   2580
gctaacaccc tggaagtgga aggcgaaaac ggcaaaaccg tgatcaactt cgacaacgcc   2640
```

```
atcatcgcgg cgggttcccg tccgattcag ctgccgttta tcccgcatga agatccgcgc    2700
gtatgggact ccaccgacgc gctggaactg aaatctgtac cgaaacgcat gctggtgatg    2760
ggcggcggta tcatcggtct ggaaatgggt accgtatacc atgcgctggg ttcagagatt    2820
gacgtggtgg aaatgttcga ccaggttatc ccggctgccg acaaagacgt ggtgaaagtc    2880
ttcaccaaac gcatcagcaa gaaatttaac ctgatgctgg aagccaaagt gactgccgtt    2940
gaagcgaaag aagacggtat ttacgttccc atggaaggta aaaagcaccg gcggaagcg     3000 cagcgttacg acgcagtgct ggtcgctatc ggccgcgtac cgaatggtaa aaacctcgat    3060
gcaggtaaag ctggcgtgga agttgacgat cgcggcttca tccgcgttga caaacaaatg    3120
cgcaccaacg tgccgcacat ctttgctatc ggcgatatcg tcggtcagcc gatgctggcg    3180
cacaaaggtg tccatgaagg ccacgttgcc gcagaagtta tctccggtct gaaacactac    3240
ttcgatccga aagtgatccc atccatcgcc tacactaaac agaagtggc atgggtcggt     3300 ctgaccgaga agaagcgaa agagaaaggc atcagctacg aaaccgccac cttcccgtgg     3360
gctgcttccg gccgtgctat cgcttctgac tgcgcagatg gtatgaccaa actgatcttc    3420
gacaaagaga cccaccgtgt tatcggcggc gcgattgtcg gcaccaacgg cggcgagctg    3480
ctgggtgaga tcggcctggc tatcgagatg ggctgtgacg ctgaagacat cgccctgacc    3540
atccacgctc acccgactct gcacgagtcc gttggcctgg cggcggaagt gttcgaaggc    3600
agcatcaccg acctgccaaa cgccaaagcg aagaaaaagt aacttttct ttcaggaaaa     3660 aagcataagc ggctccggga ccgcttttt ttatgcctga tgtttagaac tatgtcactg     3720
ttcataaacc gctacacctc atacatactt taagggcgaa ttctgcagat atccatcaca    3780
ctggcggccg ctcgagcatg catctagcac atccggcaat taaaaaagcg gctaaccacg    3840
ccgctttttt tacgtctgca atttaccttt ccagtcttct tgctccacgt tcagagagac    3900
gttcgcatac tgctgaccgt tgctcgttat tcagcctgac agtatggtta ctgtcgttta    3960
gacgttgtgg gcggctctcc tgaactttct cccgaaaaac ctgacgttgt tcaggtgatg    4020
ccgattgaac acgctggcgg gcgttatcac gttgctgttg attcagtggg cgctgctgta    4080 cttttttcctt                                                         4090
```

<210> SEQ ID NO 78
<211> LENGTH: 475
<212> TYPE: PRT
<213> ORGANISM: Escherichia coli

<400> SEQUENCE: 78

```
Met Met Ser Thr Glu Ile Lys Thr Gln Val Val Leu Gly Ala Gly
1               5                   10                  15

Pro Ala Gly Tyr Ser Ala Ala Phe Arg Cys Ala Asp Leu Gly Leu Glu
            20                  25                  30

Thr Val Ile Val Glu Arg Tyr Asn Thr Leu Gly Gly Val Cys Leu Asn
        35                  40                  45

Val Gly Cys Ile Pro Ser Lys Ala Leu Leu His Val Ala Lys Val Ile
    50                  55                  60

Glu Glu Ala Lys Ala Leu Ala Glu His Gly Ile Val Phe Gly Glu Pro
65                  70                  75                  80

Lys Thr Asp Ile Asp Lys Ile Arg Thr Trp Lys Glu Lys Val Ile Asn
                85                  90                  95

Gln Leu Thr Gly Gly Leu Ala Gly Met Ala Lys Gly Arg Lys Val Lys
            100                 105                 110
```

-continued

```
Val Val Asn Gly Leu Gly Lys Phe Thr Gly Ala Asn Thr Leu Glu Val
            115                 120                 125

Glu Gly Glu Asn Gly Lys Thr Val Ile Asn Phe Asp Asn Ala Ile Ile
        130                 135                 140

Ala Ala Gly Ser Arg Pro Ile Gln Leu Pro Phe Ile Pro His Glu Asp
145                 150                 155                 160

Pro Arg Ile Trp Asp Ser Thr Asp Ala Leu Glu Leu Lys Glu Val Pro
                165                 170                 175

Glu Arg Leu Leu Val Met Gly Gly Ile Ile Gly Leu Glu Met Gly
                180                 185                 190

Thr Val Tyr His Ala Leu Gly Ser Gln Ile Asp Val Val Glu Met Phe
                195                 200                 205

Asp Gln Val Ile Pro Ala Ala Asp Lys Asp Ile Val Lys Val Phe Thr
    210                 215                 220

Lys Arg Ile Ser Lys Lys Phe Asn Leu Met Leu Glu Thr Lys Val Thr
225                 230                 235                 240

Ala Val Glu Ala Lys Glu Asp Gly Ile Tyr Val Thr Met Glu Gly Lys
                245                 250                 255

Lys Ala Pro Ala Glu Pro Gln Arg Tyr Asp Ala Val Leu Val Ala Ile
                260                 265                 270

Gly Arg Val Pro Asn Gly Lys Asn Leu Asp Ala Gly Lys Ala Gly Val
            275                 280                 285

Glu Val Asp Asp Arg Gly Phe Ile Arg Val Asp Lys Gln Leu Arg Thr
        290                 295                 300

Asn Val Pro His Ile Phe Ala Ile Gly Asp Ile Val Gly Gln Pro Met
305                 310                 315                 320

Leu Ala His Lys Gly Val His Glu Gly His Val Ala Ala Glu Val Ile
                325                 330                 335

Ala Gly Lys Lys His Tyr Phe Asp Pro Lys Val Ile Pro Ser Ile Ala
                340                 345                 350

Tyr Thr Glu Pro Glu Val Ala Trp Val Gly Leu Thr Glu Lys Glu Ala
            355                 360                 365

Lys Glu Lys Gly Ile Ser Tyr Glu Thr Ala Thr Phe Pro Trp Ala Ala
        370                 375                 380

Ser Gly Arg Ala Ile Ala Ser Asp Cys Ala Asp Gly Met Thr Lys Leu
385                 390                 395                 400

Ile Phe Asp Lys Glu Ser His Arg Val Ile Gly Gly Ala Ile Val Gly
                405                 410                 415

Thr Asn Gly Gly Glu Leu Leu Gly Glu Ile Gly Leu Ala Ile Glu Met
            420                 425                 430

Gly Cys Asp Ala Glu Asp Ile Ala Leu Thr Ile His Ala His Pro Thr
        435                 440                 445

Leu His Glu Ser Val Gly Leu Ala Ala Glu Val Phe Glu Gly Ser Ile
    450                 455                 460

Thr Asp Leu Pro Asn Pro Lys Ala Lys Lys Lys
465                 470                 475

<210> SEQ ID NO 79
<211> LENGTH: 475
<212> TYPE: PRT
<213> ORGANISM: Klebsiella pneumoniae

<400> SEQUENCE: 79

Met Met Ser Thr Glu Ile Lys Thr Gln Val Val Val Leu Gly Ala Gly
1               5                   10                  15
```

```
Pro Ala Gly Tyr Ser Ala Ala Phe Arg Cys Ala Asp Leu Gly Leu Glu
            20                  25                  30

Thr Val Ile Val Glu Arg Tyr Ser Thr Leu Gly Gly Val Cys Leu Asn
        35                  40                  45

Val Gly Cys Ile Pro Ser Lys Ala Leu Leu His Val Ala Lys Val Ile
 50                  55                  60

Glu Glu Ala Lys Ala Leu Ala Glu His Gly Ile Val Phe Gly Glu Pro
65                  70                  75                  80

Lys Thr Asp Ile Asp Lys Ile Arg Thr Trp Lys Glu Lys Val Ile Thr
                85                  90                  95

Gln Leu Thr Gly Gly Leu Ala Gly Met Ala Lys Gly Arg Lys Val Lys
            100                 105                 110

Val Val Asn Gly Leu Gly Lys Phe Thr Gly Ala Asn Thr Leu Glu Val
        115                 120                 125

Glu Gly Glu Asn Gly Lys Thr Val Ile Asn Phe Asp Asn Ala Ile Ile
130                 135                 140

Ala Ala Gly Ser Arg Pro Ile Gln Leu Pro Phe Ile Pro His Glu Asp
145                 150                 155                 160

Pro Arg Val Trp Asp Ser Thr Asp Ala Leu Glu Leu Lys Ser Val Pro
                165                 170                 175

Lys Arg Met Leu Val Met Gly Gly Ile Ile Gly Leu Glu Met Gly
            180                 185                 190

Thr Val Tyr His Ala Leu Gly Ser Glu Ile Asp Val Val Glu Met Phe
        195                 200                 205

Asp Gln Val Ile Pro Ala Ala Asp Lys Asp Val Val Lys Val Phe Thr
210                 215                 220

Lys Arg Ile Ser Lys Lys Phe Asn Leu Met Leu Glu Ala Lys Val Thr
225                 230                 235                 240

Ala Val Glu Ala Lys Glu Asp Gly Ile Tyr Val Ser Met Glu Gly Lys
                245                 250                 255

Lys Ala Pro Ala Glu Ala Gln Arg Tyr Asp Ala Val Leu Val Ala Ile
            260                 265                 270

Gly Arg Val Pro Asn Gly Lys Asn Leu Asp Ala Gly Lys Ala Gly Val
        275                 280                 285

Glu Val Asp Asp Arg Gly Phe Ile Arg Val Asp Lys Gln Met Arg Thr
290                 295                 300

Asn Val Pro His Ile Phe Ala Ile Gly Asp Ile Val Gly Gln Pro Met
305                 310                 315                 320

Leu Ala His Lys Gly Val His Glu Gly His Val Ala Ala Glu Val Ile
                325                 330                 335

Ser Gly Leu Lys His Tyr Phe Asp Pro Lys Val Ile Pro Ser Ile Ala
            340                 345                 350

Tyr Thr Lys Pro Glu Val Ala Trp Val Gly Leu Thr Glu Lys Glu Ala
        355                 360                 365

Lys Glu Lys Gly Ile Ser Tyr Glu Thr Ala Thr Phe Pro Trp Ala Ala
370                 375                 380

Ser Gly Arg Ala Ile Ala Ser Asp Cys Ala Asp Gly Met Thr Lys Leu
385                 390                 395                 400

Ile Phe Asp Lys Glu Thr His Arg Val Ile Gly Gly Ala Ile Val Gly
                405                 410                 415

Thr Asn Gly Gly Glu Leu Leu Gly Glu Ile Gly Leu Ala Ile Glu Met
            420                 425                 430
```

```
Gly Cys Asp Ala Glu Asp Ile Ala Leu Thr Ile His Ala His Pro Thr
        435                 440                 445
Leu His Glu Ser Val Gly Leu Ala Ala Glu Val Phe Glu Gly Ser Ile
    450                 455                 460
Thr Asp Leu Pro Asn Ala Lys Ala Lys Lys Lys
465                 470                 475

<210> SEQ ID NO 80
<211> LENGTH: 347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
ataataatac atatgaacca tgcgagttac gggcctataa gccaggcgag atatgatcta      60
tatcaatttc tcatctataa tgctttgtta gtatctcgtc gccgacttaa taaagagaga     120
gttagtgtga aagctgacaa cccttttgat cttttacttc ctgctgcaat ggccaaagtg    180
gccgaagagg cgggtgtcta taaagcaacg aaacatccgc ttaagacttt ctatctggcg    240
attaccgccg gtgttttcat ctcaatcgca ttcaccactg gcacaggcac agaaggtagg    300
tgttacatgt cagaacgttt acacaatgac gtggatccta ttattat                  347

<210> SEQ ID NO 81
<211> LENGTH: 4678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
aagaggtaaa agaataatgg ctatcgaaat caaagtaccg gacatcgggg ctgatgaagt      60
tgaaatcacc gagatcctgg tcaaagtggg cgacaaagtt gaagccgaac agtcgctgat    120
caccgtagaa ggcgacaaag cctctatgga agttccgtct ccgcaggcgg gtatcgttaa    180
agagatcaaa gtctctgttg gcgataaaac ccagaccggc gcactgatta tgattttcga    240
ttccgccgac ggtgcagcag acgctgcacc tgctcaggca gaagagaaga agaagcagc    300 tccggcagca gcaccagcgg ctgcggcggc aaaagacgtt aacgttccgg atatcggcag    360
cgacgaagtt gaagtgaccg aaatcctggt gaaagttggc gataaagttg aagctgaaca    420
gtcgctgatc accgtagaag cgacaaggc ttcatggaa gttccggctc cgtttgctgg     480
caccgtgaaa gagatcaaag tgaacgtggg tgacaaagtg tctaccggct cgctgattat    540
ggtcttcgaa gtcgcgggtg aagcaggcgc ggcagctccg gccgctaaac aggaagcagc    600
tccggcagcg gcccctgcac cagcggctgg cgtgaaagaa gttaacgttc cggatatcgg    660
cggtgacgaa gttgaagtga ctgaagtgat ggtgaaagtg ggcgacaaag ttgccgctga    720
acagtcactg atcaccgtag aaggcgacaa agcttctatg gaagttccgg cgccgtttgc    780
aggcgtcgtg aaggaactga agtcaacgt tggcgataaa gtgaaaactg gctcgctgat    840
tatgatcttc gaagttgaag cgcagcgcc tgcggcagct cctgcgaaac aggaagcggc    900
agcgccggca ccggcagcaa agctgaagc cccggcagca gcaccagctg cgaaagcgga    960
aggcaaatct gaatttgctg aaaacgacgc ttatgttcac gcgactccgc tgatccgccg   1020
tctggcacgc gagtttggtg ttaaccttgc gaaagtgaag ggcactggcc gtaaaggtcg   1080
```

```
tatcctgcgc gaagacgttc aggcttacgt gaaagaagct atcaaacgtg cagaagcagc    1140
tccggcagcg actggcggtg gtatccctgg catgctgccg tggccgaagg tggacttcag    1200
caagtttggt gaaatcgaag aagtggaact gggccgcatc cagaaaatct ctggtgcgaa    1260
cctgagccgt aactgggtaa tgatcccgca tgttactcac ttcgacaaaa ccgatatcac    1320
cgagttggaa gcgttccgta acagcagaa cgaagaagcg gcgaaacgta agctggatgt    1380
gaagatcacc ccggttgtct tcatcatgaa agccgttgct gcagctcttg agcagatgcc    1440
tcgcttcaat agttcgctgt cggaagacgg tcagcgtctg accctgaaga aatacatcaa    1500
catcggtgtg gcggtggata ccccgaacgg tctggttgtt ccggtattca agacgtcaa    1560
caagaaaggc atcatcgagc tgtctcgcga gctgatgact atttctaaga aagcgcgtga    1620
cggtaagctg actgcgggcg aaatgcaggg cggttgcttc accatctcca gcatcggcgg    1680
cctgggtact acccacttcg cgccgattgt gaacgcgccg gaagtggcta tcctcggcgt    1740
ttccaagtcc gcgatggagc cggtgtggaa tggtaaagag ttcgtgccgc gtctgatgct    1800
gccgatttct ctctccttcg accaccgcgt gatcgacggt gctgatggtg cccgtttcat    1860
taccatcatt aacaacacgc tgtctgacat tcgccgtctg gtgatgtaag taaaagagcc    1920
ggcccaacgg ccggcttttt tctggtaatc tcatgaatgt attgaggtta ttagcgaata    1980
gacaaatcgg ttgccgtttg ttaagccagg cgagatatga tctatatcaa tttctcatct    2040
ataatgcttt gttagtatct cgtcgccgac ttaataaaga gagagttagt cttctatatc    2100
acagcaagaa ggtaggtgtt acatgatgag tactgaaatc aaaactcagg tcgtggtact    2160
tggggcaggc cccgcaggtt actctgcagc cttccgttgc gctgatttag gtctggaaac    2220
cgtcatcgta gaacgttaca gcaccctcgg tggtgtttgt ctgaacgtgg gttgtatccc    2280
ttctaaagcg ctgctgcacg tggcaaaagt tatcgaagaa gcgaaagcgc tggccgaaca    2340
cggcatcgtt ttcggcgaac cgaaaactga cattgacaag atccgcacct ggaaagaaaa    2400
agtcatcact cagctgaccg gtggtctggc tggcatggcc aaaggtcgta agtgaaggt    2460
ggttaacggt ctgggtaaat ttaccggcgc taacaccctg gaagtggaag cgaaaacgg    2520
caaaaccgtg atcaacttcg acaacgccat catcgcggcg gttcccgtc cgattcagct    2580
gccgtttatc ccgcatgaag atccgcgcgt atgggactcc accgacgcgc tggaactgaa    2640
atctgtaccg aaacgcatgc tggtgatggg cggcggtatc atcggtctgg aaatgggtac    2700
cgtataccat gcgctgggtt cagagattga cgtggtggaa atgttcgacc aggttatccc    2760
ggctgccgac aaagacgtgg tgaaagtctt caccaaacgc atcagcaaga aatttaacct    2820
gatgctggaa gccaaagtga ctgccgttga agcgaaagaa gacggtattt acgtttccat    2880
ggaaggtaaa aaagcaccgg cggaagcgca gcgttacgac gcagtgctgg tcgctatcgg    2940
ccgcgtaccg aatggtaaaa acctcgatgc aggtaaagct ggcgtggaag ttgacgatcg    3000
cggcttcatc cgcgttgaca acaaatgcg caccaacgtg ccgcacatct ttgctatcgg    3060
cgatatcgtc ggtcagccga tgctggcgca caaaggtgtc catgaaggcc acgttgccgc    3120
agaagttatc tccggtctga acactactt cgatccgaaa gtgatcccat ccatcgccta    3180
cactaaacca gaagtggcat gggtcggtct gaccgagaaa gaagcgaaag agaaaggcat    3240
cagctacgaa accgccacct tcccgtgggc tgcttccggc cgtgctatcg cttctgactg    3300
cgcagatggt atgaccaaac tgatcttcga caaagagacc accgtgtta tcggcggcgc    3360
gattgtcggc accaacggcg cgagctgct gggtgagatc ggcctggcta tcgagatggg    3420
ctgtgacgct gaagacatcg ccctgaccat ccacgctcac ccgactctgc acgagtccgt    3480
```

-continued

| | |
|---|---|
| tggcctggcg gcggaagtgt tcgaaggcag catcaccgac ctgccaaacg ccaaagcgaa | 3540 |
| gaaaaagtaa cttttctttt caggaaaaaa gcataagcgg ctccgggagc cgcttttttt | 3600 |
| atgcctgatg tttagaacta tgtcactgtt cataaaccgc tacacctcat acatacttta | 3660 |
| agggcgaatt ctgcagatat ccatcacact ggcggccgct cgagcatgca tctagcacat | 3720 |
| ccggcaatta aaaaagcggc taaccacgcc gctttttta cgtctgcaat ttacctttcc | 3780 |
| agtcttcttg ctccacgttc agagagacgt tcgcatactg ctgaccgttg ctcgttattc | 3840 |
| agcctgacag tatggttact gtcgtttaga cgttgtgggc ggctctcctg aactttctcc | 3900 |
| cgaaaaacct gacgttgttc aggtgatgcc gattgaacac gctggcgggc gttatcacgt | 3960 |
| tgctgttgat tcagtgggcg ctgctgtact ttttccttaa acacctggcg ctgctctggt | 4020 |
| gatgcggact gaatacgctc acgcgctgcg tctcttcgct gctggttctg cgggttagtc | 4080 |
| tgcattttct cgcgaaccgc ctggcgctgc tcaggcgagg cggactgaat gcgctcacgc | 4140 |
| gctgcctctc ttcgctgctg gatcttcggg ttagtctgca ttctctcgcg aactgcctgg | 4200 |
| cgctgctcag gcgaggcgga ctgataacgc tgacgagcgg cgtccttttg ttgctgggtc | 4260 |
| agtggttggc gacggctgaa gtcgtggaag tcgtcatagc tcccatagtg ttcagcttca | 4320 |
| ttaaaccgct gtgccgctgc ctgacgttgg gtacctcgtg taatgactgg tgcggcgtgt | 4380 |
| gttcgttgct gaaactgatt tgctgccgcc tgacgctggc tgtcgcgcgt tggggcaggt | 4440 |
| aattgcgtgg cgctcattcc gccgttgaca tcggtttgat gaaaccgctt tgccatatcc | 4500 |
| tgatcatgat agggcacacc attacggtag tttggattgt gccgccatgc catattctta | 4560 |
| tcagtaagat gctcaccggt gatacggttg aaattgttga cgtcgatatt gatgttgtcg | 4620 |
| ccgttgtgtt gccagccatt accgtcacga tgaccgccat cgtggtgatg ataatcat | 4678 |

<210> SEQ ID NO 82
<211> LENGTH: 1114
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (323)..(958)

<400> SEQUENCE: 82

| | |
|---|---|
| caaaaaaccg gagtctgtgc tccggttttt tattatccgc taatcaatta catatgaata | 60 |
| tcctccttag ttcctattcc gaagttccta ttctctagaa agtataggaa cttcggcgcg | 120 |
| cctacctgtg acggaagatc acttcgcaga ataaataaat cctggtgtcc ctgttgatac | 180 |
| cgggaagccc tgggccaact tttggcgaaa atgagacgtt gatcggcacg taagaggttc | 240 |
| caactttcac cataatgaaa taagatcact accgggcgta ttttttgagt tgtcgagatt | 300 |
| ttcaggagct aaggaagcta aa atg gag aaa aaa atc act gga tat acc acc | 352 |
|                                      Met Glu Lys Lys Ile Thr Gly Tyr Thr Thr<br>                                     1             5                  10 | |
| gtt gat ata tcc caa tgg cat cgt aaa gaa cat ttt gag gca ttt cag<br>Val Asp Ile Ser Gln Trp His Arg Lys Glu His Phe Glu Ala Phe Gln<br>             15                  20                  25 | 400 |
| tca gtt gct caa tgt acc tat aac cag acc gtt cag ctg gat att acg<br>Ser Val Ala Gln Cys Thr Tyr Asn Gln Thr Val Gln Leu Asp Ile Thr<br>     30                  35                  40 | 448 |
| gcc ttt tta aag acc gta aag aaa aat aag cac aag ttt tat ccg gcc<br>Ala Phe Leu Lys Thr Val Lys Lys Asn Lys His Lys Phe Tyr Pro Ala | 496 |

```
                    45                  50                  55
ttt att cac att ctt gcc cgc ctg atg aat gct cat ccg gaa tta cgt      544
Phe Ile His Ile Leu Ala Arg Leu Met Asn Ala His Pro Glu Leu Arg
         60                  65                  70 atg gca atg aaa gac ggt gag ctg gta ata tgg gat agt gtt cac cct      592
Met Ala Met Lys Asp Gly Glu Leu Val Ile Trp Asp Ser Val His Pro
 75                  80                  85                  90 tgt tac acc gtt ttc cat gag caa act gaa acg ttt tca tcg ctc tgg      640
Cys Tyr Thr Val Phe His Glu Gln Thr Glu Thr Phe Ser Ser Leu Trp
                     95                 100                 105 agt gaa tac cac gac gat ttc cgg cag ttt cta cac ata tat tcg caa      688
Ser Glu Tyr His Asp Asp Phe Arg Gln Phe Leu His Ile Tyr Ser Gln
                110                 115                 120 gat gtg gcg tgt tac ggt gaa aac ctg gcc tat ttc cct aaa ggg ttt      736
Asp Val Ala Cys Tyr Gly Glu Asn Leu Ala Tyr Phe Pro Lys Gly Phe
            125                 130                 135 att gag aat atg ttt ttc gtc tca gcc aat ccc tgg gtg agt ttc acc      784
Ile Glu Asn Met Phe Phe Val Ser Ala Asn Pro Trp Val Ser Phe Thr
        140                 145                 150 agt ttt gat tta aac gtg gcc aat atg gac aac ttc ttc gcc ccc gtt      832
Ser Phe Asp Leu Asn Val Ala Asn Met Asp Asn Phe Phe Ala Pro Val
155                 160                 165                 170 ttc acc atg ggc aaa tat tat acg caa ggc gac aag gtg ctg atg ccg      880
Phe Thr Met Gly Lys Tyr Tyr Thr Gln Gly Asp Lys Val Leu Met Pro
                175                 180                 185 ctg gcg att cag gtt cat cat gcc gtt tgt gat ggc ttc cat gtc ggc      928
Leu Ala Ile Gln Val His His Ala Val Cys Asp Gly Phe His Val Gly
                190                 195                 200 aga tgc tta atg aat aca aca gta ctg cga tgagtggcag ggcggggcgt        978
Arg Cys Leu Met Asn Thr Thr Val Leu Arg
            205                 210 aaggcgcgcc atttaaatga agttcctatt ccgaagttcc tattctctag aaagtatagg   1038
aacttcgaag cagctccagc ctacacccct cttcagggct gactgtttgc ataaaaattc   1098
atctgtatgc acaata                                                  1114

<210> SEQ ID NO 83
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Leu Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110
```

Phe Arg Gln Phe Leu His Ile Tyr Ser Gln Asp Val Ala Cys Tyr Gly
            115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Cys Leu Met Asn Thr
        195                 200                 205

Thr Val Leu Arg
    210

<210> SEQ ID NO 84
<211> LENGTH: 2521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
ttatttggtg atattggtac caatatcatg cagcaaacgg tgcaacattg ccgtgtctcg      60
ttgctctaaa agccccaggc gttgttgtaa ccagtcgacc agtttatgt catctgccac      120 tgccagagtc gtcagcaatg tcatggctcg ttcgcgtaaa gcttgcagtt gatgttggtc     180
tgccgttgca tcacttttcg ccggttgttg tattaatgtt gctaattgat agcaatagac     240
catcaccgcc tgcccagat tgagcgaagg ataatccgcc accatcggca caccagtaag     300
aacgtcagcc aacgctaact cttcgttagt caacccggaa tcttcgcgac caaacaccag    360
cgcggcatgg ctcatccatg aagattttc ctctaacagc ggcaccagtt caactggcgt     420
ggcgtagtaa tgatatttcg cccgactgcg cgcagtggtg gcgacagtga atcgacatc     480 gtgtaacgat tcagccaatg tcgggaaaac tttaatatta tcaataatat caccagatcc    540
atgtgcgacc cagcgggtgg ctggctccag gtgtgcctga ctatcgacaa tccgcagatc    600
gctaaacccc atcgttttca ttgcccgcgc cgctgcccca atattttctg ctctggcggg    660
tgcgaccaga ataatcgtta tacgcatatt gccactcttc ttgatcaaat aaccgcgaac    720
cgggtgatca ctgtcaactt attacgcggt gcgaatttac aaattcttaa cgtaagtcgc    780
agaaaaagcc ctttacttag cttaaaaaag gctaaactat ttcctgactg tactaacggt    840
tgagttgtta aaaaatgcta catatccttc tgtttactta ggataatttt ataaaaaata    900
aatctcgaca attggattca ccacgtttat tagttgtatg atgcaactag ttggattatt    960
aaaataatgt gacgaaagct agcatttaga tacgatgatt tcatcaaact gttaacgtgc   1020
tacaattgaa cttgatatat gtcaacgaag cgtagtttta ttgggtgtcc ggcccctctt   1080
agcctgttat gttgctgtta aaatggttag gatgacagcc gttttgaca ctgtcgggtc    1140 ctgagggaaa gtaccacga ccaagctaat gatgttgttg acgttgatgg aaagtgcatc    1200
aagaacgcaa ttacgtactt tagtcatgtt acgccgatca tgttaatttg cagcatgcat   1260
caggcaggtc agggactttt gtacttcctg tttcgattta gttggcaatt taggtagcaa   1320
acgaattcat cggctttacc accgtcaaaa aaaacggcgc ttttagcgc cgttttttatt    1380

| | |
|---|---|
| tttcaacctt atttccagat acgtaactca tcgtccgttg taacttcttt actggctttc | 1440 |
| attttcggca gtgaaaacgc ataccagtcg atattacggg tcacaaacat catgccggcc | 1500 |
| agcgccacca ccagcacact ggttcccaac aacagcgcgc tatcggcaga gttgagcagt | 1560 |
| ccccacatca caccatccag caacaacagc gcgagggtaa acaacatgct gttgcaccaa | 1620 |
| cctttcaata ccgcttgcaa ataaataccg ttcattatcg ccccaatcag actggcgatt | 1680 |
| atccatgcca cggtaaaacc ggtatgttca gaaagcgcca gcaagagcaa ataaaacatc | 1740 |
| accaatgaaa gccccaccag caaatattgc attgggtgta aacgttgcgc ggtgagcgtt | 1800 |
| tcaaaaacaa agaacgccat aaaagtcagt gcaatcagca gaatggcgta cttagtcgcc | 1860 |
| cggtcagtta attggtattg atcggctggc gtcgttactg cgacgctaaa cgccgggaag | 1920 |
| ttttcccagc cggtatcatt gcctgaagca aaacgctcac cgagattatt agcaaaccag | 1980 |
| ctgctttgcc agtgcgcctg aaaacctgac tcgctaactt cccgtttggc tggtagaaaa | 2040 |
| tcacctaaaa aactgggatg cggccagttg ctggttaagg tcatttcgct attacgcccg | 2100 |
| ccaggcacca cagaaagatc gccggtaccg cttaaattca gggccatatt cagcttcagg | 2160 |
| ttctgcttcc gccagtcccc ttcaggtaaa gggatatgca cgccctgccc gccttgctct | 2220 |
| aacccggtgc cgggttcaat ggtcagcgcc gttccgttaa cttcaggcgc tttcaccaca | 2280 |
| ccaataccac gcgcatcccc gacgctaatc acaataaatg cttgcctaa ggtgatattt | 2340 |
| ggcgcgttga gttcgctaag acgcgaaaca tcgaatcgg cttttaacgt taaatcactg | 2400 |
| tgccagacct gaccggtata atccctatc ttgcgttctt ccacgttctg attgccatca | 2460 |
| accatcaatg actcaggtaa ccaaaaatgg ataaaacttc gtttccgctg cagggtttta | 2520 |
| t | 2521 |

<210> SEQ ID NO 85
<211> LENGTH: 3010
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

| | |
|---|---|
| aagccacagc aggatgccca ctgcaacaaa ggtgatcaca ccggaaacgc gatggagaat | 60 |
| ggacgctatc gccgtgatgg ggaaccggat ggtctgtagg tccagattaa caggtctttg | 120 |
| ttttttcaca tttcttatca tgaataacgc ccacatgctg ttcttattat ccctgggga | 180 |
| ctacgggcac agaggttaac tttctgttac ctggagacgt cgggatttcc ttcctccggt | 240 |
| ctgcttgcgg gtcagacagc gtcctttcta taactgcgcg tcatgcaaaa cactgcttcc | 300 |
| agatgcgaaa acgacacgtt acaacgctgg gtggctcggg attgcagggt gttccggaga | 360 |
| cctggcggca gtataggctg ttcacaaaat cattacaatt aacctacata tagtttgtcg | 420 |
| ggttttatcc tgaacagtga tccaggtcac gataacaaca tttatttaat ttttaatcat | 480 |
| ctaatttgac aatcattcaa caaagttgtt acaaacatta ccaggaaaag catataatgc | 540 |
| gtaaaagtta tgaagtcggt atttcaccta agattaactt atgtaacagt gtggaagtat | 600 |
| tgaccaattc attcgggaca gttattagtg gtagacaagt ttaataattc ggattgctaa | 660 |
| gtacttgatt cgccatttat tcgtcatcaa tggatccttt acctgcaagc gcccagagct | 720 |
| ctgtacccag gttttcccct cttttcacaga cggcgagcc aaataaaaaa cgggtaaagc | 780 |
| caggttgatg tgcgaaggca aatttaagtt ccggcagtct tacgcaataa ggcgctaagg | 840 |

-continued

| | |
|---|---|
| agaccttaaa tggctgatac aaaagcaaaa ctcaccctca acggggatac agctgttgaa | 900 |
| ctggatgtgc tgaaaggcac gctgggtcaa gatgttattg atatccgtac tctcggttca | 960 |
| aaaggtgtgt tcacctttga cccaggcttc acttcaaccg catcctgcga atctaaaatt | 1020 |
| acttttattg atggtgatga aggtattttg ctgcaccgcg gtttcccgat cgatcagctg | 1080 |
| gcgaccgatt ctaactacct ggaagtttgt tacatcctgc tgaatggtga aaaaccgact | 1140 |
| caggaacagt atgacgaatt taaaactacg gtgacccgtc ataccatgat ccacgagcag | 1200 |
| attacccgtc tgttccatgc tttccgtcgc gactcgcatc caatggcagt catgtgtggt | 1260 |
| attaccggcg cgctggcggc gttctatcac gactcgctgg atgttaacaa tcctcgtcac | 1320 |
| cgtgaaattg ccgcgttcct cctgctgtcg aaaatgccga ccatggccgc gatgtgttac | 1380 |
| aagtattcca ttggtcagcc atttgtttac ccgcgcaacg atctctccta cgccggtaac | 1440 |
| ttcctgaata tgatgttctc cacgccgtgc gaaccgtatg aagttaatcc gattctggaa | 1500 |
| cgtgctatgg accgtattct gatcctgcac gctgaccatg aacagaacgc ctctacctcc | 1560 |
| accgtgcgta ccgctggctc ttcgggtgcg aacccgtttg cctgtatcgc agcaggtatt | 1620 |
| gcttcactgt ggggacctgc gcacggcggt gctaacgaag cggcgctgaa atgctggaa | 1680 |
| gaaatcagct ccgttaaaca cattccggaa tttgttcgtc gtgcgaaaga caaaaatgat | 1740 |
| tctttccgcc tgatgggctt cggtcaccgc gtgtacaaaa attacgaccc gcgcgccacc | 1800 |
| gtaatgcgtg aaacctgcca tgaagtgctg aaagagctgg gcacgaagga tgacctgctg | 1860 |
| gaagtggcta tggagctgga aaacatcgcg ctgaacgacc cgtactttat cgagaagaaa | 1920 |
| ctgtacccga acgtcgattt ctactctggt atcatcctga aagcgatggg tattccgtct | 1980 |
| tccatgttca ccgtcatttt cgcaatggca cgtaccgttg gctggatcgc ccactggagc | 2040 |
| gaaatgcaca gtgacggtat gaagattgcc cgtccgcgtc agctgtatac aggatatgaa | 2100 |
| aaacgcgact ttaaaagcga tatcaagcgt taatggttga ttgctaagtt gtaaatattt | 2160 |
| taacccgccg ttcatatggc gggttgattt ttatatgcct aaacacaaaa aattgtaaaa | 2220 |
| ataaaatcca ttaacagacc tatatagata tttaaaaaga atagaacagc tcaaattatc | 2280 |
| agcaacccaa tactttcaat taaaaaacttc atggtagtcg catttataac cctatgaaaa | 2340 |
| tgacgtctat ctatacccccc ctatatttta ttcatcatac aacaaattca tgataccaat | 2400 |
| aatttagttt tgcatttaat aaaactaaca atattttttaa gcaaaactaa aaactagcaa | 2460 |
| taatcaaata cgatattctg gcgtagctat accctattc tatatcctta aaggactctg | 2520 |
| ttatgtttaa aggacaaaaa acattggccg cactggccgt atctctgctg ttcactgcac | 2580 |
| ctgtttatgc tgctgatgaa ggttctggcg aaattcactt taaggggag gttattgaag | 2640 |
| caccttgtga aattcatcca gaagatattg ataaaaacat agatcttgga caagtcacga | 2700 |
| caacccatat aaaccgggag catcatagca ataaagtggc cgtcgacatt cgcttgatca | 2760 |
| actgtgatct gcctgcttct gacaacggta gcggaatgcc ggtatccaaa gttggcgtaa | 2820 |
| ccttcgatag cacggctaag acaactggtg ctacgccttt gttgagcaac accagtgcag | 2880 |
| gcgaagcaac tggggtcggt gtacgactga tggacaaaaa tgacggtaac atcgtattag | 2940 |
| gttcagccgc gccagatctt gacctggatg caagctcatc agaacagacg ctgaactttt | 3000 |
| tcgcctggat | 3010 |

<210> SEQ ID NO 86
<211> LENGTH: 4180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

| | | | | | |
|---|---|---|---|---|---|
| cgcgatgtcg | acgtcacgaa | actgaaaaaa | ccgctctaca | ttctggcgac | tgctgatgaa | 60 |
| gaaaccagta | tggccggagc | gcgttatttt | gccgaaacta | ccgccctgcg | cccggattgc | 120 |
| gccatcattg | gcgaaccgac | gtcactacaa | ccggtacgcg | cacataaagg | tcatatctct | 180 |
| aacgccatcc | gtattcaggg | ccagtcgggg | cactccagcg | atccagcacg | cggagttaac | 240 |
| gctatcgaac | taatgcacga | cgccatcggg | catattttgc | aattgcgcga | taacctgaaa | 300 |
| gaacgttatc | actacgaagc | gtttaccgtg | ccataccctca | cgctcaacct | cgggcatatt | 360 |
| cacggtggcg | acgcttctaa | ccgtatttgc | gcttgctgtg | agttgcatat | ggatattcgt | 420 |
| ccgctgcctg | gcatgacact | caatgaactt | aatggtttgc | tcaacgatgc | attggctccg | 480 |
| gtgagcgaac | gctggccggg | tcgtctgacg | gtcgacgagc | tgcatccgcc | gatccctggc | 540 |
| tatgaatgcc | caccgaatca | tcaactggtt | gaagtggttg | agaaattgct | cggagcaaaa | 600 |
| accgaagtgg | tgaactactg | taccgaagcg | ccgtttattc | aaacgttatg | cccgacgctg | 660 |
| gtgttggggc | ctggctcaat | taatcaggct | catcaacctg | atgaatatct | ggaaacacgg | 720 |
| tttatcaagc | ccacccgcga | actgataacc | caggtaattc | accatttttg | ctggcattaa | 780 |
| aacgtaggcc | ggataaggcg | ctcgcgccgc | atccggcgct | gttgccaaac | tccagtgccg | 840 |
| caataatgtc | ggatgcgatg | cttgcgcatc | ttatccgacc | tacagtgact | caaacgatgc | 900 |
| ccaaccgtag | gccggataag | gcgctcgcgc | gcatccggc | actgttgcca | aactccagtg | 960 |
| ccgcaataat | gtcggatgcg | atacttgcgc | atcttatccg | accgacagtg | actcaaacga | 1020 |
| tgcccaactg | taggccggat | aaggcgctcg | cgccgcatcc | ggcactgttg | ccaaactcca | 1080 |
| gtgccgcaat | aatgtcggat | gcgatacttg | cgcatcttat | ccgacctaca | cctttggtgt | 1140 |
| tacttggggc | gatttttaa | catttccata | agttacgctt | attttaaagcg | tcgtgaattt | 1200 |
| aatgacgtaa | attcctgcta | tttattcgtt | tgctgaagcg | atttcgcagc | atttgacgtc | 1260 |
| accgcttta | cgtggcttta | taaaagacga | cgaaaagcaa | agcccgagca | tattcgcgcc | 1320 |
| aatgctagca | agaggagaag | tcgacatgac | agacttaaat | aaagtggtaa | agaacttga | 1380 |
| agctcttggt | atttatgacg | taaaagaagt | tgtttacaat | ccaagctacg | agcaattgtt | 1440 |
| cgaagaagaa | actaaaccag | gtttagaagg | ctttgaaaaa | ggtactttaa | ctacgactgg | 1500 |
| tgcagtggca | gtagatacag | gtatcttcac | aggtcgttct | ccaaaagata | atatatcgt | 1560 |
| gttagatgaa | aaaccaaag | atactgtttg | gtggacatct | gaaacagcaa | aaaacgacaa | 1620 |
| caagccaatg | aaccaagcta | catggcaaag | cttaaaagac | ttggtaacca | accagctttc | 1680 |
| tcgtaaacgc | ttatttgtag | ttgatggttt | ctgtggtgcg | agcgaacacg | accgtattgc | 1740 |
| agtacgtatt | gtcactgaag | tagcgtggca | agcacatttt | gtaaaaaata | tgtttattcg | 1800 |
| cccaactgaa | gaacaactca | aaaatttga | accagatttc | gttgtaatga | atggttctaa | 1860 |
| agtaaccaat | ccaaactgga | agaacaagg | tttaaattca | gaaaactttg | ttgctttcaa | 1920 |
| cttgactgaa | cgcattcaat | taatcggtgg | tacttggtac | ggcggtgaaa | tgaaaaaagg | 1980 |
| tatgttctca | atcatgaact | acttcctacc | acttaaaggt | gttggtgcaa | tgcactgctc | 2040 |
| agctaacgtt | ggtaaagatg | gcgatgtagc | aatcttcttc | ggcttatctg | gcacaggtaa | 2100 |
| aacaacccctt | tcaacggatc | caaaacgtga | attaatcggt | gacgatgaac | acggctggga | 2160 |
| tgatgtgggt | atctttaact | ttgaaggtgg | ttgctatgcg | aaaaccattc | acctttcaga | 2220 |

| | | | | |
|---|---|---|---|---|
| agaaaatgaa | ccagatattt | accgcgctat | ccgtcgcgac | gcattattag aaaacgtggt | 2280 |
| tgttcgtgca | gatggttctg | ttgatttcga | tgatggttca | aaaacagaaa atactcgcgt | 2340 |
| gtcttaccca | atttatcaca | ttgataacat | tgtaaaacca | gtttctcgtg caggtcacgc | 2400 |
| aactaaagtg | attttcttaa | ctgcagatgc | atttggcgta | ttaccaccag tatctaaatt | 2460 |
| gacaccagaa | caaactaaat | actacttctt | atctggtttc | acagcaaaat tagcaggtac | 2520 |
| tgaacgtggt | attactgaac | caactccaac | tttctcagca | tgtttcggtg ctgcgttctt | 2580 |
| aacccttcac | ccaactcaat | atgcagaagt | gttagtaaaa | cgtatgcaag cagtgggtgc | 2640 |
| tgaagcttac | ttagtaaata | ctggttggaa | tggcacaggc | aaacgtatct caatcaaaga | 2700 |
| tactcgcgga | atcattgatg | caatcttaga | tggctcaatt | gaaaaagctg aatgggcga | 2760 |
| attaccaatc | tttaacttag | ccattcctaa | agcattacca | ggtgtagatt ctgcaatctt | 2820 |
| agatcctcgc | gatacttacg | cagataaagc | acaatggcaa | tcaaaagctg aagacttagc | 2880 |
| aggtcgtttt | gtgaaaaact | tgttaaata | tgcaactaac | gaagaaggca aagctttaat | 2940 |
| tgcagctggt | cctaaagctt | aatctagaaa | gcttcctaga | ggcatcaaat aaaacgaaag | 3000 |
| gctcagtcga | aagactgggc | ctttcgtttt | atctgttgtt | tgtcggtgaa cgctctcctg | 3060 |
| agtaggacga | attcacttct | gttctaacac | cctcgttttc | aatatatttc tgtctgcatt | 3120 |
| ttattcaaat | tctgaatata | ccttcagata | tccttaagga | attgtcgtta cattcggcga | 3180 |
| tatttttca | agacaggttc | ttactatgca | ttccacagaa | gtccaggcta aacctctttt | 3240 |
| tagctggaaa | gccctgggtt | gggcactgct | ctactttgg | tttttctcta ctctgctaca | 3300 |
| ggccattatt | tacatcagtg | gttatagtgg | cactaacggc | attcgcgact cgctgttatt | 3360 |
| cagttcgctg | tggttgatcc | cggtattcct | ctttccgaag | cggattaaaa ttattgccgc | 3420 |
| agtaatcggc | gtggtgctat | gggcggcctc | tctggcggcg | ctgtgctact acgtcatcta | 3480 |
| cggtcaggag | ttctcgcaga | gcgttctgtt | tgtgatgttc | gaaaccaaca ccaacgaagc | 3540 |
| cagcgagtat | ttaagccagt | atttcagcct | gaaaattgtg | cttatcgcgc tggcctatac | 3600 |
| ggcggtggca | gttctgctgt | ggacacgcct | gcgcccggtc | tatattccaa agccgtggcg | 3660 |
| ttatgttgtc | tcttttgccc | tgctttatgg | cttgattctg | catccgatcg ccatgaatac | 3720 |
| gtttatcaaa | aacaagccgt | ttgagaaaac | gttggataac | ctggcctcgc gtatggagcc | 3780 |
| tgccgcaccg | tggcaattcc | tgaccggcta | ttatcagtat | cgtcagcaac taaactcgct | 3840 |
| aacaaagtta | ctgaatgaaa | ataatgcctt | gccgccactg | gctaatttca agatgaatc | 3900 |
| gggtaacgaa | ccgcgcactt | tagtgctggt | gattggcgag | tcgacccagc gcggacgcat | 3960 |
| gagtctgtac | ggttatccgc | gtgaaaccac | gccggagctg | gatgcgctgc ataaaaccga | 4020 |
| tccgaatctg | accgtgttta | ataacgtagt | tacgtctcgt | ccgtacacca ttgaaatcct | 4080 |
| gcaacaggcg | ctgacctttg | ccaatgaaaa | gaacccggat | ctgtatctga cgcagccgtc | 4140 |
| gctgatgaac | atgatgaaac | aggcgggtta | taaaaccttc | | 4180 |

<210> SEQ ID NO 87
<211> LENGTH: 4960
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

| | | | | |
|---|---|---|---|---|
| aataggcgta | tcacgaggcc | ctttcgtctt | cacctcgaga | attgtgagcg gataacaatt | 60 |

-continued

```
gacattgtga gcggataaca agatactgag cacatcagca ggacgcactg accgaattca      120
attaagctag caagaggaga agtcgagatg aacttacatg aatatcaggc aaaacaactt      180
tttgcccgct atggcttacc agcaccggtg ggttatgcct gtactactcc gcgcgaagca      240
gaagaagccg cttcaaaaat cggtgccggt ccgtgggtag tgaaatgtca ggttcacgct      300
ggtggccgcg gtaaagcggg cggtgtgaaa gttgtaaaca gcaaagaaga catccgtgct      360
tttgcagaaa actggctggg caagcgtctg gtaacgtatc aaacagatgc caatggccaa      420
ccggttaacc agattctggt tgaagcagcg accgatatcg ctaaagagct gtatctcggt      480
gccgttgttg accgtagttc ccgtcgtgtg gtctttatgg cctccaccga aggcggcgtg      540
gaaatcgaaa agtggcgga agaaactccg cacctgatcc ataaagttgc gcttgatccg       600
ctgactggcc cgatgccgta tcagggacgc gagctggcgt tcaaactggg tctggaaggt      660
aaactggttc agcagttcac caaaatcttc atgggcctgg cgaccatttt cctggagcgc      720
gacctggcgt tgatcgaaat caacccgctg gtcatcacca acagggcga tctgatttgc       780 ctcgacggca aactgggcgc tgacggcaac gcactgttcc gccagcctga tctgcgcgaa      840
atgcgtgacc agtcgcagga agatccgcgt gaagcacagg ctgcacagtg gaactgaac       900 tacgttgcgc tggacggtaa catcggttgt atggttaacg gcgcaggtct ggcgatgggt      960
acgatggaca tcgttaaact gcacggcggc gaaccggcta acttccttga cgttggcggc     1020
ggcgcaacca agaacgtgt aaccgaagcg ttcaaaatca tcctctctga cgacaaagtg      1080
aaagccgttc tggttaacat cttcggcggt atcgttcgtt gcgacctgat cgctgacggt      1140
atcatcggcg cggtagcaga agtgggtgtt aacgtaccgg tcgtggtacg tctggaaggt     1200
aacaacgccg aactcggcgc gaagaaactg gctgacagcg gcctgaatat tattgcagca     1260
aaaggtctga cggatgcagc tcagcaggtt gttgccgcag tggagggaa ataatgtcca      1320 ttttaatcga taaaaacacc aaggttatct gccagggctt taccggtagc cagggatt       1380 tccactcaga acaggccatt gcatacggca ctaaaatggt tggcggcgta accccaggta     1440
aaggcggcac cacccacctc ggcctgccgg tgttcaacac cgtgcgtgaa gccgttgctg     1500
ccactggcgc taccgcttct gttatctacg taccagcacc gttctgcaaa gactccattc     1560
tggaagccat cgacgcaggc atcaaactga ttatcaccat cactgaaggc atcccgacgc     1620
tggatatgct gaccgtgaaa gtgaagctgg atgaagcagg cgttcgtatg atcggcccga     1680
actgcccagg cgttatcact ccgggtgaat gcaaatcgg tatccagcct ggtcacattc      1740
acaaaccggg taaagtgggt atcgtttccc gttccggtac actgaccatat gaagcggtta    1800 aacagaccac ggattacggt ttcggtcagt cgacctgtgt cggtatcggc ggtgacccga     1860
tcccgggctc taactttatc gacattctcg aaatgttcga aaaagatccg cagaccgaag     1920
cgatcgtgat gatcggtgag atcggcggta gcgctgaaga agaagcagct gcgtacatca     1980 agagcacgt taccaagcca gttgtgggtt acatcgctgg tgtgactgcg ccgaaaggca     2040
aacgtatggg ccacgcgggt gccatcattg ccggtgggaa agggactgcg gatgagaaat     2100
tcgctgctct ggaagccgca ggcgtgaaaa ccgttcgcag cctggcggat atcggtgaag     2160
cactgaaaac tgttctgaaa taatctagca agaggagaag tcgacatgga aatcaaagaa     2220
atggtgagcc ttgcacgcaa ggctcagaag gagtatcaag ctacccataa ccaagaagca     2280
gttgacaaca tttgccgagc tgcagcaaaa gttatttatg aaaatgcagc tattctggct     2340
cgcgaagcag tagacgaaac cggcatgggc gtttacgaac acaaagtggc caagaatcaa     2400
```

```
ggcaaatcca aaggtgtttg gtacaacctc cacaataaaa aatcgattgg tatcctcaat    2460
atagacgagc gtaccggtat gatcgagatt gcaaagccta tcggagttgt aggagccgta    2520
acgccgacga ccaacccgat cgttactccg atgagcaata tcatctttgc tcttaagacc    2580
tgcaatgcca tcattattgc cccccacccc agatccaaaa aatgctctgc acacgcagtt    2640
cgtctgatca agaagctat cgctccgttc aacgtaccgg aaggtatggt tcagatcatc    2700
gaagaaccca gcatcgagaa gacgcaggaa ctcatgggcg ccgtagacgt agtagttgct    2760
acgggtggta tgggcatggt gaagtctgca tattcttcag gaaagccttc tttcggtgtt    2820
ggagccgta acgttcaggt gatcgtggat agcaacatcg atttcgaagc tgctgcagaa    2880
aaaatcatca ccggtcgtgc tttcgacaac ggtatcatct gctcaggcga acagagcatc    2940
atctacaacg aggctgacaa ggaagcagtt ttcacagcat ccgcaaccga cggtgcatat    3000
ttctgtgacg aagccgaagg agatcgggct cgtgcagcta tcttcgaaaa tggagccatc    3060
gcgaaagatg tagtaggtca gagcgttgcc ttcattgcca agaaagcaaa catcaatatc    3120
cccgagggta cccgtattct cgttgttgaa gctcgcggcg taggagcaga agacgttatc    3180
tgtaaggaaa agatgtgtcc cgtaatgtgc gccctcagct acaagcactt cgaagaaggt    3240
gtagaaatcg cacgtacgaa cctcgccaac gaaggtaacg gccacacctg tgctatccac    3300
tccaacaatc aggcacacat catcctcgca ggatcagagc tgacggtatc tcgtatcgta    3360
gtgaatgctc cgagtgccac tacagcaggc ggtcacatcc aaaacggtct tgccgtaacc    3420
aatacgctcg gatgcggatc atggggtaat aactctatct ccgagaactt cacttacaag    3480
cacctcctca acatttcacg catcgcaccg ttgaattcaa gcattcacat ccccgatgac    3540
aaagaaatct gggaactcta atctagcaag aggagaagtc gacatgcaac ttttcaaact    3600
caagagtgta acacatcact ttgacacttt tgcagaattt gccaaggaat tctgtcttgg    3660
agaacgcgac ttggtaatta ccaacgagtt catctatgaa ccgtatatga aggcatgcca    3720
gctcccctgc catttgtta tgcaggagaa atatgggcaa ggcgagcctt ctgacgaaat    3780
gatgaataac atcttggcag acatccgtaa tatccagttc gaccgcgtaa tcggtatcgg    3840
aggaggtacg gttattgaca tctctaaact ttttcgttct gaaaggattaa atgatgtact    3900
cgatgcattc gaccgcaaaa tacctcttat caaagagaaa gaactgatca ttgtgcccac    3960
aacatgcgga acgggtagcg aggtgacgaa catttctatc gcagaaatca aaagccgtca    4020
caccaaaatg ggattggctg acgatgccat tgttgcagac catgccatca tcatacctga    4080
acttctgaag agcttgcctt ccacttcta cgcatgcagt gcaatcgatg ctcttatcca    4140
tgccatcgag tcatacgtat ctcctaaagc cagtccatat tctcgtctgt tcagtgaggc    4200
ggcttgggac attatcctgg aagtattcaa gaaaatcgcc gaacacggcc tgaataccg    4260
cttcgaaaag ctgggagaaa tgatcatggc cagcaactat gccggtatag ccttcggaaa    4320
tgcaggagta ggagccgtcc acgcactatc ctacccgttg ggaggcaact atcacgtgcc    4380
gcatggagaa gcaaactatc agttcttcac agaggtattc aaagtatacc aaaagaagaa    4440
tcctttcggc tatatagtcg aactcaactg gaagctctcc aagatactga actgccagcc    4500
cgaatacgta tatccgaagc tggatgaact tctcggatgc cttcttacca agaaacctttt    4560
gcacgaatac ggcatgaagg acgaagaggt aagaggcttt gcggaatcag tgcttaagac    4620
acagcaaaga ttgctcgcca caactacgt agagcttact gtagatgaga tcgaaggtat    4680
ctacagaaga ctctactaat ctagaaagct tcctagaggg atcaaataaa acgaaaggct    4740
cagtcgaaag actgggcctt tcgttttatc tgttgtttgt cggtgaacgc tctcctgagt    4800
```

```
aggacaaatc cgccgcccta gacctaggcg ttcggctgcg acacgtcttg agcgattgtg    4860
taggctggag ctgcttcgaa gttcctatac tttctagaga ataggaactt cggaatagga    4920
actaaggagg atattcatat ggaccatggc taattcccat                          4960
```

<210> SEQ ID NO 88
<211> LENGTH: 5083
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 88

```
tcgagaaatt tatcaaaaag agtgttgact tgtgagcgga taacaatgat acttagattc      60
aattgtgagc ggataacaat ttcacacaga attcaattaa gctagcaaga ggagaagtcg     120
acatggccaa cataagttca ccattcgggc aaaacgaatg gctggttgaa gagatgtacc     180
gcaagttccg cgacgacccc tcctcggtcg atcccagctg gcacgagttc ctggttgact     240
acagccccga acccacctcc caaccagctg ccgaaccaac ccgggttacc tcgccactcg     300
ttgccgagcg ggccgctgcg gccgcccgc aggcaccccc caagccggcc gacaccgcgg     360
ccgcgggcaa cggcgtggtc gccgcactgg ccgcaaaac tgccgttccc ccgccagccg     420
aaggtgacga ggtagcggtg ctgcgcggcg ccgccgcggc cgtcgtcaag aacatgtccg     480
cgtcgttgga ggtgccgacg gcgaccagcg tccgggcggt cccggccaag ctactgatcg     540
acaaccggat cgtcatcaac aaccagttga agcggacccg cggcggcaag atctcgttca     600
cgcatttgct gggctacgcc ctggtgcagg cggtgaagaa attcccgaac atgaaccggc     660
actacaccga agtcgacggc aagcccaccg cggtcacgcc ggcgcacacc aatctcggcc     720
tggcgatcga cctgcaaggc aaggacggga agcgttccct ggtggtggcc ggcatcaagc     780
ggtgcgagac catgcgattc gcgcagttcg tcacggccta cgaagacatc gtacgccggg     840
cccgcgacgg caagctgacc actgaagact tgccggcgt gacgatttcg ctgaccaatc     900
ccggaaccat cggcaccgtg cattcggtgc cgcggctgat gccggccag ggcgccatca     960 tcggcgtggg cgccatggaa taccccgccg agtttcaagg cgccagcgag gaacgcatcg    1020
ccgagctggg catcggcaaa ttgatcactt tgacctccac ctacgaccac cgcatcatcc    1080
agggcgcgga atcgggcgac ttcctgcgca ccatccacga gttgctgctc tcggatggct    1140
tctgggacga ggtcttccgc gaactgagca tcccatatct gccggtgcgc tggagcaccg    1200
acaaccccga ctcgatcgtc gacaagaacg ctcgcgtcat gaacttgatc gcggcctacc    1260
gcaaccgcgg ccatctgatg gccgataccg accgctgcg gttggacaaa gctcggttcc    1320
gcagtcaccc cgacctcgaa gtgctgaccc acggcctgac gctgtgggat ctcgatcggg    1380
tgttcaaggt cgacggcttt gccggtgcgc agtacaagaa actgcgcgac gtgctgggct    1440
tgctgcgcga tgcctactgc cgccacatcg gcgtggagta cgcccatatc ctcgaccccg    1500
aacaaaagga gtggctcgaa caacgggtcg agaccaagca cgtcaaaccc actgtggccc    1560
aacagaaata catcctcagc aagctcaacg ccgccgagcc cttttgaaacg ttcctacaga    1620 ccaagtacgt cggccagaag cggttctcgc tggaaggcgc cgaaagcgtg atcccgatga    1680
tggacgcggc gatcgaccag tgcgctgagc acggcctcga cgaggtggtc atcgggatgc    1740
cgcaccgggg ccggctcaac gtgctggcca acatcgtcgg caagccgtac tcgcagatct    1800
tcaccgagtt cgagggcaac ctgaatccgt cgcaggcgca cggctccggt gacgtcaagt    1860
```

```
accacctggg cgccaccggg ctgtacctgc agatgttcgg cgacaacgac attcaggtgt   1920
cgctgaccgc caacccgtcg catctggagg ccgtcgaccc ggtgctggag ggattggtgc   1980
gggccaagca ggatctgctc gaccacggaa gcatcgacag cgacggccaa cgggcgttct   2040
cggtggtgcc gctgatgttg catggcgatg ccgcgttcgc cggtcagggt gtggtcgccg   2100
agacgctgaa cctggcgaat ctgccgggct accgcgtcgg cggcaccatc cacatcatcg   2160
tcaacaacca gatcggcttc accaccgcgc ccgagtattc caggtccagc gagtactgca   2220
ccgacgtcgc aaagatgatc ggggcaccga tctttcacgt caacggcgac gacccggagg   2280
cgtgtgtctg ggtggcgcgg ttggcggtgg acttccgaca acggttcaag aaggacgtcg   2340
tcatcgacat gctgtgctac cgccgccgcg gcacaacga gggtgacgac ccgtcgatga   2400
ccaaccccta catgtacgac gtcgtcgaca ccaagcgcgg ggcccgcaaa agctacaccg   2460
aagccctgat cggacgtggc gacatctcga tgaaggaggc cgaggacgcg ctgcgcgact   2520
accagggcca gctggaacgg tgttcaacg aagtgcgcga gctggagaag cacggtgtgc   2580
agccgagcga gtcggtcgag tccgaccaga tgattcccgc ggggctggcc actgcggtgg   2640
acaagtcgct gctggcccgg atcggcgatg cgttcctcgc cttgccgaac ggcttcaccg   2700
cgcacccgcg agtccaaccg gtgctggaga agcgccggga gatggcctat gaaggcaaga   2760
tcgactgggc ctttggcgag ctgctggcgc tgggctcgct ggtggccgaa ggcaagctgg   2820
tgcgcttgtc ggggcaggac agccgccgcg gcaccttctc ccagcggcat tcggttctca   2880
tcgaccgcca cactggcgag gagttcacac cactgcagct gctggcgacc aactccgacg   2940
gcagcccgac cggcggaaag ttcctggtct acgactcgcc actgtcggag tacgccgccg   3000
tcggcttcga gtacggctac actgtgggca atcggacgc cgtggtgctc tgggaggcgc   3060
agttcggcga cttcgtcaac ggcgcacagt cgatcatcga cgagttcatc agctccggtg   3120
aggccaagtg gggccaattg tccaacgtcg tgctgctgtt accgcacggg cacgaggggc   3180
agggacccga ccacacttct gcccggatcg aacgcttctt gcagttgtgg gcggaaggtt   3240
cgatgaccat cgcgatgccg tcgactccgt cgaactactt ccacctgcta cgccggcatg   3300
ccctggacgg catccaacgc ccgctgatcg tgttcacgcc caagtcgatg ttgcgtcaca   3360
aggccgccgt cagcgaaatc aaggacttca ccgagatcaa gttccgctca gtgctggagg   3420
aacccaccta tgaggacggc atcggagacc gcaacaaggt cagccggatc ctgctgacca   3480
gtggcaagct gtattacgag ctggccgccc gcaaggccaa ggacaaccgc aatgacctcg   3540
cgatcgtgcg gcttgaacag ctcgccccgc tgcccaggcg tcgactgcgt gaaacgctgg   3600
accgctacga gaacgtcaag gagttcttct gggtccaaga ggaaccggcc aaccagggtg   3660
cgtggccgcg attcgggctc gaactacccg agctgctgcc tgacaagttg gccgggatca   3720
agcgaatctc gcgccgggcg atgtcagccc cgtcgtcagg ctcgtcgaag gtgcacgccg   3780
tcaacagcga ggagatcctc gacgaggcgt tcggctaatc tagcaagagg agaagtcgac   3840
atgaagttat taaaattggc acctgatgtt tataaatttg atactgcaga ggagtttatg   3900
aaatacttta aggttggaaa aggtgacttt atacttacta atgaattttt atataaacct   3960
ttccttgaga aattcaatga tggtgcagat gctgtatttc aggagaaata tggactcggt   4020
gaaccttctg atgaaatgat aaacaatata attaaggata ttggagataa acaatataat   4080
agaattattg ctgtaggggg aggatctgta atagatatag ccaaaatcct cagtcttaag   4140
tatactgatg attcattgga tttgtttgag ggaaaagtac ctcttgtaaa aaacaaagaa   4200
```

| | |
|---|---|
| ttaattatag ttccaactac atgtggaaca ggttcagaag ttacaaatgt atcagttgca | 4260 |
| gaattaaaga gaagacatac taaaaaagga attgcttcag acgaattata tgcaacttat | 4320 |
| gcagtacttg taccagaatt tataaaagga cttccatata agttttttgt aaccagctcc | 4380 |
| gtagatgcct taatacatgc aacagaagct tatgtatctc caaatgcaaa tccttatact | 4440 |
| gatatgttta gtgtaaaagc tatggagtta attttaaatg gatacatgca aatggtagag | 4500 |
| aaaggaaatg attacagagt tgaaataatt gaggattttg ttataggcag caattatgca | 4560 |
| ggtatagctt ttggaaatgc aggagtggga gcggttcacg cactctcata tccaataggc | 4620 |
| ggaaattatc atgtgcctca tggagaagca aattatctgt tttttacaga aatatttaaa | 4680 |
| acttattatg agaaaaatcc aaatggcaag attaaagatg taaataaact attagcaggc | 4740 |
| atactaaaat gtgatgaaag tgaagcttat gacagtttat cacaacttttt agataaaatta | 4800 |
| ttgtcaagaa aaccattaag agaatatgga atgaaagagg aagaaattga aacttttgct | 4860 |
| gattcagtaa tagaaggaca gcagagactg ttggtaaaca attatgaacc ttttcaaga | 4920 |
| gaagacatag taaacacata taaaaagtta tattaatcta gaaagcttcc tagaggcatc | 4980 |
| aaataaaacg aaaggctcag tcgaaagact gggcctttcg ttttatctgt tgtttgtcgg | 5040 |
| tgaacgctct cctgagtagg acaaatccgc cgccctagac cta | 5083 |

<210> SEQ ID NO 89
<211> LENGTH: 5097
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

| | |
|---|---|
| tctgtatcag gctgaaaatc ttctctcatc cgccaaaaca gcttcggcgt taagatgcgc | 60 |
| gctcaaggac gtaagccgtc gactctcgcc gtgctggcgc aggacacggc taccactcct | 120 |
| ttctctgttg atattctgct tgccattgag caaaccgcca gcgagttcgg ctggaatagt | 180 |
| ttttaatca atatttttttc tgaagatgac gctgcccgcg cggcacgtca gctgcttgcc | 240 |
| caccgtccgg atggcattat ctatactaca atggggctgc gacatatcac gctgcctgag | 300 |
| tctctgtatg gtgaaaatat tgtattggcg aactgtgtgg cggatgaccc agcgttaccc | 360 |
| agttatatcc ctgatgatta cactgcacaa tatgaatcaa cacagcattt gctcgcggcg | 420 |
| ggctatcgtc aaccgttatg cttctggcta ccggaaagtg cgttggcaac agggtatcgt | 480 |
| cggcagggat ttgagcaggc ctggcgtgat gctggacgaa tctggctgaa ggtgaaacaa | 540 |
| tttcacatgg caacaggtga tgatcactac accgatctcg caagtttact caatgcccac | 600 |
| ttcaaaccgg gcaaaccaga ttttgatgtt ctgatatgtg gtaacgatcg cgcagccttt | 660 |
| gtggcttatc aggttcttct ggcgaagggg gtacgaatcc cgcaggatgt cgccgtaatg | 720 |
| ggctttgata atctggttgg cgtcgggcat ctgtttttac cgccgctgac cacaattcag | 780 |
| cttccacatg acattatcgg gcgggaagct gcattgcata ttattgaagg tcgtgaaggg | 840 |
| ggaagagtga cgcggatccc ttgcccgctg ttgatccgtt gttccacctg atattatgtt | 900 |
| aacccagtag ccagagtgct ccatgttgca gcacagccac tccgtgggag gcataaagcg | 960 |
| acagttcccg ttcttctggc tgcggataga ttcgactact catcaccgct tccccgtcgt | 1020 |
| taataaatac ttccacggat gatgtatcga taaatatcct tagggcgagc gtgtcacgct | 1080 |
| gcgggagggg aatactacgg tagccgtcta aattctcgtg tgggtaatac cgccacaaaa | 1140 |

-continued

```
caagtcgctc agattggtta tcaatataca gccgcattcc agtgccgagc tgtaatccgt    1200
aatgttcggc atcactgttc ttcagcgccc actgcaactg aatctcaact gcttgcgcgt    1260
tttcctgcaa aacatattta ttgctgattg tgcggggaga gacagattga tgctgctggc    1320
gtaacgactc agcttcgtgt accgggcgtt gtagaagttt gccattgctc tctgatagct    1380
cgcgcgccag cgtcatgcag cctgcccatc cttcacgttt tgagggcatt ggcgattccc    1440
acatatccat ccagccgata acaatacgcc gaccatcctt cgctaaaaag ctttgtggtg    1500
cataaaagtc atgcccgtta tcaagttcag taaaatgccc ggattgtgca aaaagtcgtc    1560
ctggcgacca cattccgggt attacgccac tttgaaagcg atttcggtaa ctgtatccct    1620
cggcattcat tccctgcggg gaaaacatca gataatgctg atcgccaagg ctgaaaaagt    1680
ccggacattc ccacatatag ctttcacccg catcagcgtg ggccagtacg cgatcgaagg    1740
tccattcacg caacgaactg ccgcgataaa gcaggatctg ccccgtgttg cctggatctt    1800
tcgccccgac taccatccac catgtgtcgg cttcacgcca cactttagga tcgcggaagt    1860
gcatgattcc ttctggtgga gtgaggatca caccctgttt ctcgaaatga ataccatccc    1920
gactggtagc cagacattgt acttcgcgaa ttgcatcgtc attacctgca ccatcgagcc    1980
agacgtgtcc ggtgtagata agtgagagga caccattgtc atcgacagca ctacctgaaa    2040
aacacccgtc tttgtcatta tcgtctcctg gcgctagcgc aataggctca tgctgccagt    2100
ggatcatatc gtcgctggtg gcatgtcccc agtgcattgg cccccagtgt tcgctcatcg    2160
gatgatgttg ataaaacgcg tgataacgat cgttaaacca gatcaggccg tttggatcgt    2220
tcatccaccc ggcaggaggc gcgaggtgaa aatggggata gaaagtgtta ccccggtgct    2280
catgaagttt tgctagggcg ttttgcgccg catgcaatcg agattgcgtc atttttaatca   2340 tcctggttaa gcaaatttgg tgaattgtta acgttaactt ttataaaaat aaagtccctt    2400
actttcataa atgcgatgaa tatcacaaat gttaacgtta actatgacgt tttgtgatcg    2460
aatatgcatg ttttagtaaa tccatgacga ttttgcgaaa aagaggttta tcactatgcg    2520
taactcagat gaatttaagg gaaaaaaatg tcagccaaag tatgggtttt aggggatgcg    2580
gtcgtagatc tcttgccaga atcagacggg cgcctactgc cttgtcctgg cggcgcgcca    2640
gctaacgttg cggtgggaat cgccagatta ggcggaacaa gtgggtttat aggtcgggtg    2700
ggggatgatc cttttggtgc gttaatgcaa agaacgctgc taactgaggg agtcgatatc    2760
acgtatctga agcaagatga atggcaccgg acatccacgg tgcttgtcga tctgaacgat    2820
caaggggaac gttcatttac gtttatggtc cgccccagtg ccgatctttt tttagagacg    2880
acagacttgc cctgctggcg acatggcgaa tggttacatc tctgttcaat tgcgttgtct    2940
gccgagcctt cgcgtaccag cgcatttact gcgatgacgg cgatccggca tgccggaggt    3000
tttgtcagct tcgatcctaa tattcgtgaa gatctatggc aagacgagca tttgctccgc    3060
ttgtgtttgc ggcaggcgct acaactggcg gatgtcgtca agctctcgga agaagaatgg    3120
cgacttatca gtggaaaaac acagaacgat caggatatat gcgccctggc aaaagagtat    3180
gagatcgcca tgctgttggt gactaaaggt gcagaagggg tggtggtctg ttatcgagga    3240
caagttcacc atttttgctgg aatgtctgtg aattgtgtcg atagcacggg ggcgggagat   3300
gcgttcgttg ccgggttact cacaggtctg tcctctacgg gattatctac agatgagaga    3360
gaaatgcgac gaattatcga tctcgctcaa cgttgcggag cgcttgcagt aacggcgaaa    3420 gggggcaatga cagcgctgcc atgtcgacaa gaactggaat agtgagaagt aaacggcgaa    3480
gtcgctctta tctctaaata ggacgtgaat tttttaacga caggcaggta attatggcac    3540
```

-continued

```
tgaatattcc attcagaaat gcgtactatc gttttgcatc cagttactca tttctctttt    3600
ttatttcctg gtcgctgtgg tggtcgttat acgctatttg gctgaaagga catctagggt    3660
tgacagggac ggaattaggt acactttatt cggtcaacca gtttaccagc attctattta    3720
tgatgttcta cggcatcgtt caggataaac tcggtctgaa gaaaccgctc atctggtgta    3780
tgagtttcat cctggtcttg accggaccgt ttatgattta cgtttatgaa ccgttactgc    3840
aaagcaattt ttctgtaggt ctaattctgg gggcgctatt ttttggcttg gggtatctgg    3900
cgggatgcgg tttgcttgat agcttcaccg aaaaaatggc gcgaaatttt catttcgaat    3960
atggaacagc gcgcgcctgg ggatcttttg gctatgctat tggcgcgttc tttgccggca    4020
tatttttttag tatcagtccc catatcaact tctggttggt ctcgctattt ggcgctgtat    4080
ttatgatgat caacatgcgt tttaaagata aggatcacca gtgcgtagcg gcagatgcgg    4140
gaggggtaaa aaagaggat tttatcgcag ttttcaagga tcgaaacttc tgggttttcg    4200
tcatatttat tgtggggacg tggtctttct ataacatttt tgatcaacaa cttttttcctg    4260
tcttttattc aggtttattc gaatcacacg atgtaggaac gcgcctgtat ggttatctca    4320
actcattcca ggtggtactc gaagcgctgt gcatggcgat tattcctttc tttgtgaatc    4380
gggtagggcc aaaaaatgca ttacttatcg gagttgtgat tatggcgttg cgtatccttt    4440
cctgcgcgct gttcgttaac ccctggatta tttcattagt gaagttgtta catgccattg    4500
aggttccact ttgtgtcata tccgtcttca aatacagcgt ggcaaacttt gataagcgcc    4560
tgtcgtcgac gatctttctg attggttttc aaattgccag ttcgcttggg attgtgctgc    4620
tttcaacgcc gactgggata ctctttgacc acgcaggcta ccagacagtt tcttcgcaa    4680
tttcgggtat tgtctgcctg atgttgctat ttggcatttt cttcttgagt aaaaaacgcg    4740
agcaaatagt tatggaaacg cctgtacctt cagcaatata gacgtaaact ttttccggtt    4800
gttgtcgata gctctatatc cctcaaccgg aaaataataa tagtaaaatg cttagccctg    4860
ctaataatcg cctaatccaa acgcctcatt catgttctgg tacagtcgct caaatgtact    4920
tcagatgcgc ggttcgctga tttccaggac attgtcgtca ttcagtgacc tgtcccgtgt    4980
atcacggtcc tgcgaattca tcaaggaatg cattgcggag tgaagtatcg agtcacgcca    5040
tatttcgtca cccgaagatg agttttgaga tattaaggca ggtgactttc actcaca       5097
```

<210> SEQ ID NO 90
<211> LENGTH: 3525
<212> TYPE: DNA
<213> ORGANISM: Nocardia iowensis

<400> SEQUENCE: 90

```
atggcagtgg attcaccgga tgagcggcta cagcgccgca ttgcacagtt gtttgcagaa      60
gatgagcagg tcaaggccgc acgtccgctc gaagcggtga gcgcggcggt gagcgcgccc     120
ggtatgcggg tggcgcagat cgccgccact gttatggcgg ttacgccga ccgcccggcc     180
gccgggcagc gtgcgttcga actgaacacc gacgacgcga cgggccgcac ctcgctgcgg     240
ttacttcccc gattcgagac catcacctat cgcgaactgt ggcagcgagt cggcgaggtt     300
gccgcggcct ggcatcatga tcccgagaac cccttgcgcg caggtgattt cgtcgccctg     360
ctcggcttca ccagcatcga ctacgccacc ctcgacctgg ccgatatcca cctcggcgcg     420
gttaccgtgc cgttgcaggc cagcgcggcg gtgtcccagc tgatcgctat cctcaccgag     480
acttcgccgc ggctgctcgc ctcgaccccg gagcacctcg atgcggcggt cgagtgccta     540
```

```
ctcgcgggca ccacaccgga acgactggtg gtcttcgact accaccccga ggacgacgac    600
cagcgtgcgg ccttcgaatc cgcccgccgc cgccttgccg acgcgggcag cttggtgatc    660
gtcgaaacgc tcgatgccgt gcgtgcccgg ggccgcgact taccggccgc gccactgttc    720
gttcccgaca ccgacgacga cccgctggcc ctgctgatct acacctccgg cagcaccgga    780
acgccgaagg gcgcgatgta caccaatcgg ttggccgcca cgatgtggca ggggaactcg    840
atgctgcagg ggaactcgca acgggtcggg atcaatctca actacatgcc gatgagccac    900
atcgccggtc gcatatcgct gttcggcgtg ctcgctcgcg gtggcaccgc atacttcgcg    960
gccaagagcg acatgtcgac actgttcgaa gacatcggct tggtacgtcc caccgagatc   1020
ttcttcgtcc cgcgcgtgtg cgacatggtc ttccagcgct atcagagcga gctggaccgg   1080
cgctcggtgg cgggcgccga cctggacacg ctcgatcggg aagtgaaagc cgacctccgg   1140
cagaactacc tcggtgggcg cttcctggtg gcggtcgtcg gcagcgcgcc gctggccgcg   1200
gagatgaaga cgttcatgga gtccgtcctc gatctgccac tgcacgacgg gtacgggtcg   1260
accgaggcgg gcgcaagcgt gctgctcgac aaccagatcc agcggccgcc ggtgctcgat   1320
tacaagctcg tcgacgtgcc cgaactgggt tacttccgca ccgaccggcc gcatccgcgc   1380
ggtgagctgt tgttgaaggc ggagaccacg attccgggct actacaagcg cccgaggtc    1440 accgcggaga tcttcgacga ggacggcttc tacaagaccg gcgatatcgt ggccgagctc   1500
gagcacgatc ggctggtcta tgtcgaccgt cgcaacaatg tgctcaaact gtcgcagggc   1560
gagttcgtga ccgtcgccca tctcgaggcc gtgttcgcca gcagcccgct gatccggcag   1620
atcttcatct acggcagcag cgaacgttcc tatctgctcg cggtgatcgt ccccaccgac   1680
gacgcgctgc gcggccgcga caccgccacc ttgaaatcgg cactggccga atcgattcag   1740
cgcatcgcca aggacgcgaa cctgcagccc tacgagattc cgcgcgattt cctgatcgag   1800
accgagccgt tcaccatcgc caacggactg ctctccggca tcgcgaagct gctgcgcccc   1860
aatctgaagg aacgctacgg cgctcagctg gagcagatgt acaccgatct cgcgacaggc   1920
caggccgatg agctgctcgc cctgcgccgc gaagccgccg acctgccggt gctcgaaacc   1980
gtcagccggg cagcgaaagc gatgctcggc gtcgcctccg ccgatatgcg tcccgacgcg   2040
cacttcaccg acctgggcgg cgattccctt tccgcgctgt cgttctcgaa cctgctgcac   2100
gagatcttcg gggtcgaggt gccggtgggt gtcgtcgtca gcccggcgaa cgagctgcgc   2160
gatctggcga attacattga ggcggaacgc aactcgggcg cgaagcgtcc caccttcacc   2220
tcggtgcacg gcggcggttc cgagatccgc gccgccgatc tgaccctcga caagttcatc   2280
gatgcccgca ccctggccgc cgccgacagc attccgcacg cgccggtgcc agcgcagacg   2340
gtgctgctga ccgcgcgcaa cggctacctc ggccggttcc tgtgcctgga atggctggag   2400
cggctggaca agacgggtgg cacgctgatc tgcgtcgtgc gcggtagtga cgcggccgcg   2460
gcccgtaaac ggctggactc ggcgttcgac agcggcgatc ccggcctgct cgagcactac   2520
cagcaactgg ccgcacggac cctggaagtc ctcgccggtg atatcggcga cccgaatctc   2580
ggtctggacg acgcgacttg gcagcggttg gccgaaaccg tcgacctgat cgtccatccc   2640
gccgcgttgg tcaaccacgt ccttccctac acccagctgt tcggcccaa tgtcgtcggc    2700 accgccgaaa tcgtccggtt ggcgatcacg gcgcggcgca agccggtcac ctacctgtcg   2760
accgtcggag tggccgacca ggtcgacccg gcggagtatc aggaggacag cgacgtccgc   2820
gagatgagcg cggtgcgcgt cgtgcgcgag agttacgcca acggctacgg caacagcaag   2880
tgggcggggg aggtcctgct gcgcgaagca cacgatctgt gtggcttgcc ggtcgcggtg   2940
```

```
ttccgttcgg acatgatcct ggcgcacagc cggtacgcgg gtcagctcaa cgtccaggac   3000
gtgttcaccc ggctgatcct cagcctggtc gccaccggca tcgcgccgta ctcgttctac   3060
cgaaccgacg cggacggcaa ccggcagcgg gcccactatg acggcttgcc ggcggacttc   3120
acggcggcgg cgatcaccgc gctcggcatc caagccaccg aaggcttccg gacctacgac   3180
gtgctcaatc cgtacgacga tggcatctcc ctcgatgaat tcgtcgactg gctcgtcgaa   3240
tccggccacc cgatccagcg catcaccgac tacagcgact ggttccaccg tttcgagacg   3300
gcgatccgcg cgctgccgga aaagcaacgc caggcctcgg tgctgccgtt gctggacgcc   3360
taccgcaacc cctgcccggc ggtccgcggc gcgatactcc cggccaagga gttccaagcg   3420
gcggtgcaaa cagccaaaat cggtccggaa caggacatcc cgcatttgtc cgcgccactg   3480
atcgataagt acgtcagcga tctggaactg cttcagctgc tctaa              3525
```

<210> SEQ ID NO 91
<211> LENGTH: 1174
<212> TYPE: PRT
<213> ORGANISM: Nocardia iowensis

<400> SEQUENCE: 91

```
Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270
```

```
Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
                340                 345                 350

Arg Tyr Gln Ser Glu Leu Asp Arg Arg Ser Val Ala Gly Ala Asp Leu
            355                 360                 365

Asp Thr Leu Asp Arg Glu Val Lys Ala Asp Leu Arg Gln Asn Tyr Leu
370                 375                 380

Gly Gly Arg Phe Leu Val Ala Val Gly Ser Ala Pro Leu Ala Ala
385                 390                 395                 400

Glu Met Lys Thr Phe Met Glu Ser Val Leu Asp Pro Leu His Asp
                405                 410                 415

Gly Tyr Gly Ser Thr Glu Ala Gly Ala Ser Val Leu Leu Asp Asn Gln
                420                 425                 430

Ile Gln Arg Pro Pro Val Leu Asp Tyr Lys Leu Val Asp Val Pro Glu
            435                 440                 445

Leu Gly Tyr Phe Arg Thr Asp Arg Pro His Pro Arg Gly Glu Leu Leu
            450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
            515                 520                 525

Glu Ala Val Phe Ala Ser Ser Pro Leu Ile Arg Gln Ile Phe Ile Tyr
        530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
            675                 680                 685
```

```
Ser Leu Ser Ala Leu Ser Phe Ser Asn Leu Leu His Glu Ile Phe Gly
    690             695                 700

Val Glu Val Pro Val Gly Val Val Ser Pro Ala Asn Glu Leu Arg
705             710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
                755                 760                 765

Asp Ser Ile Pro His Ala Pro Val Pro Ala Gln Thr Val Leu Leu Thr
    770                 775                 780

Gly Ala Asn Gly Tyr Leu Gly Arg Phe Leu Cys Leu Glu Trp Leu Glu
785             790                 795                 800

Arg Leu Asp Lys Thr Gly Gly Thr Leu Ile Cys Val Val Arg Gly Ser
                805                 810                 815

Asp Ala Ala Ala Arg Lys Arg Leu Asp Ser Ala Phe Asp Ser Gly
                820                 825                 830

Asp Pro Gly Leu Leu Glu His Tyr Gln Gln Leu Ala Ala Arg Thr Leu
                835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
                900                 905                 910

Arg Lys Pro Val Thr Tyr Leu Ser Thr Val Gly Val Ala Asp Gln Val
            915                 920                 925

Asp Pro Ala Glu Tyr Gln Glu Asp Ser Asp Val Arg Glu Met Ser Ala
    930                 935                 940

Val Arg Val Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
                980                 985                 990

Ala Gly Gln Leu Asn Val Gln Asp Val Phe Thr Arg Leu Ile Leu Ser
            995                 1000                1005

Leu Val Ala Thr Gly Ile Ala Pro Tyr Ser Phe Tyr Arg Thr Asp
    1010                1015                1020

Ala Asp Gly Asn Arg Gln Arg Ala His Tyr Asp Gly Leu Pro Ala
    1025                1030                1035

Asp Phe Thr Ala Ala Ala Ile Thr Ala Leu Gly Ile Gln Ala Thr
    1040                1045                1050

Glu Gly Phe Arg Thr Tyr Asp Val Leu Asn Pro Tyr Asp Asp Gly
    1055                1060                1065

Ile Ser Leu Asp Glu Phe Val Asp Trp Leu Val Glu Ser Gly His
    1070                1075                1080

Pro Ile Gln Arg Ile Thr Asp Tyr Ser Asp Trp Phe His Arg Phe
    1085                1090                1095

Glu Thr Ala Ile Arg Ala Leu Pro Glu Lys Gln Arg Gln Ala Ser
```

Val Leu Pro Leu Leu Asp Ala Tyr Arg Asn Pro Cys Pro Ala Val
    1115                1120                1125

Arg Gly Ala Ile Leu Pro Lys Glu Phe Gln Ala Ala Val Gln
    1130                1135                1140

Thr Ala Lys Ile Gly Pro Glu Gln Asp Ile Pro His Leu Ser Ala
    1145                1150                1155

Pro Leu Ile Asp Lys Tyr Val Ser Asp Leu Glu Leu Leu Gln Leu
    1160                1165                1170

Leu

<210> SEQ ID NO 92
<211> LENGTH: 669
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atgattgaaa ccattctgcc tgcaggcgtt gaaagcgcag aactgctgga atatccggaa      60
gatctgaaag cacatccggc agaagaacat ctgattgcca aaagcgttga aaacgtcgt     120 cgtgatttta ttggtgcacg tcattgtgca cgtctggcac tggcagaact gggtgaacct     180
ccggttgcaa ttggtaaagg tgaacgtggt gcaccgattt ggcctcgtgg tgttgttggt     240
agcctgaccc attgtgatgg ttatcgtgca gcagcagttg cacataaaat gcgctttcgc     300
agcattggta ttgatgcaga accgcatgca accctgccgg aaggtgttct ggatagcgtt     360
agcctgccgc cggaacgtga atggctgaaa accaccgata cgcactgca tctggatcgt     420 ctgctgtttt gtgcaaaaga agccacctat aaagcctggt ggccgctgac agcacgttgg     480
ctgggttttg aagaagccca tattacctt gaaattgaag atggtagcgc agatagcggt     540
aatggcacct ttcatagcga actgctggtt ccgggtcaga ccaatgatgg tggtacaccg     600
ctgctgagct tgatggtcg ttggctgatt gcagatggtt ttattctgac cgcaattgcc     660
tatgcctaa                                                             669

<210> SEQ ID NO 93
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Arg Asp Phe Ile Gly Ala Arg His
        35                  40                  45

Cys Ala Arg Leu Ala Leu Ala Glu Leu Gly Glu Pro Pro Val Ala Ile
    50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Ala Val Ala His Lys
                85                  90                  95

```
Met Arg Phe Arg Ser Ile Gly Ile Asp Ala Glu Pro His Ala Thr Leu
                100                 105                 110

Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
        130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
    210                 215                 220

<210> SEQ ID NO 94
<211> LENGTH: 3522
<212> TYPE: DNA
<213> ORGANISM: Mycobacterium smegmatis

<400> SEQUENCE: 94
atgaccagcg atgttcacga cgccacagac ggcgtcaccg aaaccgcact cgacgacgag      60
cagtcgaccc gccgcatcgc cgagctgtac gccaccgatc ccgagttcgc cgccgccgca     120
ccgttgcccg ccgtggtcga cgcggcgcac aaacccgggc tgcggctggc agagatcctg     180
cagaccctgt tcaccggcta cggtgaccgc cggcgctgg ataccgcgc ccgtgaactg       240 gccaccgacg agggcgggcg caccgtgacg cgtctgctgc gcggttcga cccctcacc      300 tacgcccagg tgtggtcgcg cgtgcaagcg gtcgccgcgg ccctgcgcca caacttcgcg     360
cagccgatct accccggcga cgccgtcgcg acgatcggtt cgcgagtcc cgattacctg     420 acgctggatc tcgtatgcgc ctacctgggc ctcgtgagtg ttccgctgca gcacaacgca     480
ccggtcagcc ggctcgcccc gatcctggcc gaggtcgaac gcggatcct caccgtgagc     540 gccgaatacc tcgacctcgc agtcgaatcc gtgcgggacg tcaactcggt gtcgcagctc     600
gtggtgttcg accatcaccc cgaggtcgac gaccaccgcg acgcactggc ccgcgcgcgt     660
gaacaactcg ccggcaaggg catcgccgtc accaccctgg acgcgatcgc cgacgagggc     720
gccgggctgc cggccgaacc gatctacacc gccgaccatg atcagcgcct cgcgatgatc     780
ctgtacacct cgggttccac cggcgcaccc aagggtgcga tgtacaccga ggcgatggtg     840
gcgcggctgt ggaccatgtc gttcatcacg ggtgacccca cgccggtcat caacgtcaac     900
ttcatgccgc tcaaccacct gggcgggcgc atccccattt ccaccgccgt gcagaacggt     960
ggaaccagtt acttcgtacc ggaatccgac atgtccacgc tgttcgagga tctcgcgctg    1020
gtgcgcccga ccgaactcgg cctggttccg cgcgtcgccg acatgctcta ccagcaccac    1080
ctcgccaccg tcgaccgcct ggtcacgcag ggcgccgacg aactgaccgc cgagaagcag    1140
gccggtgccg aactgcgtga gcaggtgctc ggcggacgcg tgatcaccgg attcgtcagc    1200
accgcaccgc tggccgcgga gatgagggcg ttcctcgaca tcaccctggg cgcacacatc    1260
gtcgacggct acgggctcac cgagaccggc gccgtgacac gcgacggtgt gatcgtgcgg    1320
ccaccggtga tcgactacaa gctgatcgac gttcccgaac tcggctactt cagcaccgac    1380
```

```
aagccctacc cgcgtggcga actgctggtc aggtcgcaaa cgctgactcc cgggtactac    1440
aagcgccccg aggtcaccgc gagcgtcttc gaccgggacg gctactacca caccggcgac    1500
gtcatggccg agaccgcacc cgaccacctg gtgtacgtgg accgtcgcaa caacgtcctc    1560
aaactcgcgc agggcgagtt cgtggcggtc gccaacctgg aggcggtgtt ctccggcgcg    1620
gcgctggtgc gccagatctt cgtgtacggc aacagcgagc gcagtttcct tctggccgtg    1680
gtggtcccga cgccggaggc gctcgagcag tacgatccgg ccgcgctcaa ggccgcgctg    1740
gccgactcgc tgcagcgcac cgcacgcgac gccgaactgc aatcctacga ggtgccggcc    1800
gatttcatcg tcgagaccga gccgttcagc ccgccaacg ggctgctgtc gggtgtcgga    1860
aaactgctgc ggcccaacct caaagaccgc tacgggcagc gcctggagca gatgtacgcc    1920
gatatcgcgg ccacgcaggc caaccagttg cgcgaactgc ggcgcgcggc cgccacacaa    1980
ccggtgatcg acaccctcac ccaggccgct gccacgatcc tcggcaccgg gagcgaggtg    2040
gcatccgacg cccacttcac cgacctgggc ggggattccc tgtcggcgct gacactttcg    2100
aacctgctga gcgatttctt cggttttcgaa gttcccgtcg gcaccatcgt gaacccggcc    2160
accaacctcg cccaactcgc ccagcacatc gaggcgcagc gcaccgcggg tgaccgcagg    2220
ccgagtttca ccaccgtgca cggcgcggac gccaccgaga tccgggcgag tgagctgacc    2280
ctggacaagt tcatcgacgc cgaaacgctc cgggccgcac cgggtctgcc caaggtcacc    2340
accgagccac ggacggtgtt gctctcgggc gccaacggct ggctgggccg gttcctcacg    2400
ttgcagtggc tggaacgcct ggcacctgtc ggcggcaccc tcatcacgat cgtgcggggc    2460
cgcgacgacg ccgcggcccg cgcacggctg acccaggcct acgacaccga tcccgagttg    2520
tcccgccgct tcgccgagct ggccgaccgc cacctgcggg tggtcgccgg tgacatcggc    2580
gacccgaatc tgggcctcac acccgagatc tggcaccggc tcgccgccga ggtcgacctg    2640
gtggtgcatc cggcagcgct ggtcaaccac gtgctcccct accggcagct gttcggcccc    2700
aacgtcgtgg gcacggccga ggtgatcaag ctggccctca ccgaacggat caagcccgtc    2760
acgtacctgt ccaccgtgtc ggtggccatg gggatccccg acttcgagga ggacggcgac    2820
atccggaccg tgagcccggt gcgcccgctc gacggcggat acgccaacgg ctacggcaac    2880
agcaagtggg ccggcgaggt gctgctgcgg gaggcccacg atctgtgcgg gctgcccgtg    2940
gcgacgttcc gctcggacat gatcctggcg catccgcgct accgcggtca ggtcaacgtg    3000
ccagacatgt tcacgcgact cctgttgagc ctcttgatca ccggcgtcgc gccgcggtcg    3060
ttctacatcg gagacggtga gcgcccgcgg gcgcactacc ccggcctgac ggtcgatttc    3120
gtggccgagg cggtcacgac gctcggcgcg cagcagcgcg agggatacgt gtcctacgac    3180
gtgatgaacc gcacgacga cgggatctcc ctggatgtgt tcgtggactg gctgatccgg    3240
gcgggccatc cgatcgaccg gtcgacgac tacgacgact gggtgcgtcg gttcgagacc    3300
gcgttgaccg cgcttcccga gaagcgccgc gcacagaccg tactgccgct gctgcacgcg    3360
ttccgcgctc cgcaggcacc gttgcgcggc gcacccgaac ccacggaggt gttccacgcc    3420
gcggtgcgca ccgcgaaggt gggcccggga gacatcccgc acctcgacga ggcgctgatc    3480
gacaagtaca tacgcgatct gcgtgagttc ggtctgatct aa                      3522
```

<210> SEQ ID NO 95
<211> LENGTH: 1173
<212> TYPE: PRT
<213> ORGANISM: Mycobacterium smegmatis

<400> SEQUENCE: 95

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65              70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145             150                 155                 160

Pro Val Ser Arg Leu Ala Pro Ile Leu Ala Glu Val Glu Pro Arg Ile
            165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
    275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
    355                 360                 365

Thr Gln Gly Ala Asp Glu Leu Thr Ala Glu Lys Gln Ala Gly Ala Glu
    370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415
```

```
Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
            485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
            515                 520                 525

Ala Val Ala Asn Leu Glu Ala Val Phe Ser Gly Ala Ala Leu Val Arg
            530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
            565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
            595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
            645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
            675                 680                 685

Leu Gly Gly Asp Ser Leu Ser Ala Leu Thr Leu Ser Asn Leu Leu Ser
            690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
            725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
            755                 760                 765

Thr Leu Arg Ala Ala Pro Gly Leu Pro Lys Val Thr Thr Glu Pro Arg
            770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
            805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
```

Asp Arg His Leu Arg Val Val Ala Gly Asp Ile Gly Asp Pro Asn Leu
835                 840                 845

Gly Leu Thr Pro Glu Ile Trp His Arg Leu Ala Ala Glu Val Asp Leu
850                 855                 860

Val Val His Pro Ala Ala Leu Val Asn His Val Leu Pro Tyr Arg Gln
865                 870                 875                 880

Leu Phe Gly Pro Asn Val Val Gly Thr Ala Glu Val Ile Lys Leu Ala
            885                 890                 895

Leu Thr Glu Arg Ile Lys Pro Val Thr Tyr Leu Ser Thr Val Ser Val
900                 905                 910

Ala Met Gly Ile Pro Asp Phe Glu Glu Asp Gly Asp Ile Arg Thr Val
915                 920                 925

Ser Pro Val Arg Pro Leu Asp Gly Gly Tyr Ala Asn Gly Tyr Gly Asn
930                 935                 940

Ser Lys Trp Ala Gly Glu Val Leu Leu Arg Glu Ala His Asp Leu Cys
945                 950                 955                 960

Gly Leu Pro Val Ala Thr Phe Arg Ser Asp Met Ile Leu Ala His Pro
            965                 970                 975

Arg Tyr Arg Gly Gln Val Asn Val Pro Asp Met Phe Thr Arg Leu Leu
980                 985                 990

Leu Ser Leu Leu Ile Thr Gly Val Ala Pro Arg Ser Phe Tyr Ile
995                 1000                1005

Gly Asp Gly Glu Arg Pro Arg Ala His Tyr Pro Gly Leu Thr Val
1010                1015                1020

Asp Phe Val Ala Glu Ala Val Thr Thr Leu Gly Ala Gln Gln Arg
1025                1030                1035

Glu Gly Tyr Val Ser Tyr Asp Val Met Asn Pro His Asp Asp Gly
1040                1045                1050

Ile Ser Leu Asp Val Phe Val Asp Trp Leu Ile Arg Ala Gly His
1055                1060                1065

Pro Ile Asp Arg Val Asp Tyr Asp Asp Trp Val Arg Arg Phe
1070                1075                1080

Glu Thr Ala Leu Thr Ala Leu Pro Glu Lys Arg Arg Ala Gln Thr
1085                1090                1095

Val Leu Pro Leu Leu His Ala Phe Arg Ala Pro Gln Ala Pro Leu
1100                1105                1110

Arg Gly Ala Pro Glu Pro Thr Glu Val Phe His Ala Ala Val Arg
1115                1120                1125

Thr Ala Lys Val Gly Pro Gly Asp Ile Pro His Leu Asp Glu Ala
1130                1135                1140

Leu Ile Asp Lys Tyr Ile Arg Asp Leu Arg Glu Phe Gly Leu Ile
1145                1150                1155
                    1160                1165                1170

<210> SEQ ID NO 96
<211> LENGTH: 3522
<212> TYPE: DNA
<213> ORGANISM: Mycobacterium avium

<400> SEQUENCE: 96
atgtcgactg ccacccatga cgaacgactc gaccgtcgcg tccacgaact catcgccacc    60
gacccgcaat tcgccgccgc ccaacccgac ccggcgatca ccgccgccct cgaacagccc   120
gggctgcggc tgccgcagat catccgcacc gtgctcgacg gctacgccga ccggccggcg   180

```
ctgggacagc gcgtggtgga gttcgtcacg gacgccaaga ccgggcgcac gtcggcgcag      240
ctgctccccc gcttcgagac catcacgtac agcgaagtag cgcagcgtgt ttcggcgctg      300
ggccgcgccc tgtccgacga cgcggtgcac cccggcgacc gggtgtgcgt gctgggcttc      360
aacagcgtcg actacgccac catcgacatg gcgctgggcg ccatcggcgc cgtctcggtg      420
ccgctgcaga ccagcgcggc aatcagctcg ctgcagccga tcgtggccga gaccgagccc      480
accctgatcg cgtccagcgt gaaccagctg tccgacgcgg tgcagctgat caccggcgcc      540
gagcaggcgc ccacccggct ggtggtgttc gactaccacc gcaggtcga cgaccagcgc       600 gaggccgtcc aggacgccgc ggcgcggctg tccagcaccg gcgtggccgt ccagacgctg      660
gccgagctgc tggagcgcgg caaggacctg cccgccgtcg cggagccgcc cgccgacgag      720
gactcgctgg ccctgctgat ctacacctcc gggtccaccg gcgcccccaa gggcgcgatg      780
tacccacaga gcaacgtcgg caagatgtgg cgccgcggca gcaagaactg gttcggcgag      840
agcgccgcgt cgatcaccct gaacttcatg ccgatgagcc acgtgatggg ccgaagcatc      900
ctctacggca cgctgggcaa cggcggcacc gcctacttcg ccgcccgcag cgacctgtcc      960
accctgcttg aggacctcga gctggtgcgg cccaccgagc tcaacttcgt cccgcggatc      1020
tgggagacgc tgtacggcga attccagcgt caggtcgagc ggcggctctc cgaggccggg      1080
gacgccggcg aacgtcgcgc cgtcgaggcc gaggtgctgg ccgagcagcg ccagtacctg      1140
ctgggcgggc ggttcacctt cgcgatgacg ggctcggcgc ccatctcgcc ggagctgcgc      1200
aactgggtcg agtcgctgct cgaaatgcac ctgatggacg gctacggctc caccgaggcc      1260
ggaatggtgt tgttcgacgg ggagattcag cgcccgccgg tgatcgacta caagctggtc      1320
gacgtgccgg acctgggcta cttcagcacc gaccggccgc atccgcgcgg cgagctgctg      1380
ctgcgcaccg agaacatgtt cccgggctac tacaagcggg ccgaaaccac cgcgggcgtc      1440
ttcgacgagg acggctacta ccgcaccggc gacgtgttcg ccgagatcgc cccggaccgg      1500
ctggtctacg tcgaccgccg caacaacgtg ctcaagctgg cgcagggcga attcgtcacg      1560
ctggccaagc tggaggcggt gttcggcaac agcccgctga tccgccagat ctacgtctac      1620
ggcaacagcg cccagcccta cctgctggcg gtcgtggtgc ccaccgagga ggcgctggcc      1680
tcgggtgacc ccgagacgct caagcccaag atcgccgact cgctgcagca ggtcgccaag      1740
gaggccggcc tgcagtccta cgaggtgccg cgcgacttca tcatcgagac cacccccgttc    1800 agcctggaaa acggtctgct gaccgggatc cggaagctgg cgtggccgaa actgaagcag      1860
cactacgggg aacggctgga gcagatgtac gccgacctgg ccgccggaca ggccaacgag      1920
ctggccgagc tgcgccgcaa cggtgcccag gcgccggtgt tgcagaccgt gagccgcgcc      1980
gcgggcgcca tgctgggttc ggccgcctcc gacctgtccc ccgacgccca cttcaccgat      2040
ctgggcggag actcgttgtc ggcgttgaca ttcggcaacc tgctgcgcga gatcttcgac      2100
gtcgacgtgc cggtaggcgt gatcgtcagc ccggccaacg acctggcggc catcgcgagc      2160
tacatcgagg ccgagcggca gggcagcaag cgcccgacgt tcgcctcggt gcacggccgg      2220
gacgcgaccg tggtgcgcgc cgccgacctg acgctggaca agttcctcga cgccgagacg      2280
ctggccgccg cgccgaacct gcccaagccg gccaccgagg tgcgcaccgt gctgctgacc      2340
ggcgccaccg gcttcctggg ccgctacctg gccctggaat ggctggagcg gatggacatg      2400
gtggacggca aggtcatcgc cctggtccgg gcccgctccg acgaggaggc acgcgcccgg      2460
ctggacaaga ccttcgacag cggcgacccg aaactgctcg cgcactacca gcagctggcc      2520
gccgatcacc tggaggtcat cgccggcgac aagggcgagg ccaatctggg cctgggccaa      2580
```

```
gacgtttggc aacgactggc cgacacggtc gacgtgatcg tcgaccccgc cgcgctggtc   2640
aaccacgtgt tgccgtacag cgagctgttc gggcccaacg ccctgggcac cgcggagctg   2700
atccggctgg cgctgacgtc caagcagaag ccgtacacct acgtgtccac catcggcgtg   2760
ggcgaccaga tcgagccggg caagttcgtc gagaacgccg acatccggca gatgagcgcc   2820
acccgggcga tcaacgacag ctacgccaac ggctatggca acagcaagtg ggccggcgag   2880
gtgctgctgc gcgaggcgca cgacctgtgc gggctgcccg tcgcggtgtt ccgctgcgac   2940
atgatcctgg ccgacaccac gtatgccggg cagctcaacc tgccggacat gttcacccgg   3000
ctgatgctga gcctggtggc caccgggatc gcgcccggct cgttctacga gctcgacgcc   3060
gacggcaacc ggcagcgggc gcactacgac ggcctgccgg tcgagttcat cgccgcggcg   3120
atctcgacgc tgggttcgca gatcaccgac agcgacaccg gcttccagac ctaccacgtg   3180
atgaacccct acgatgacgg cgtcggtctg gacgagtacg tcgattggct ggtggacgcc   3240
ggctattcga tcgagcggat cgccgactac tccgaatggc tgcggcggtt cgagacctcg   3300
ctgcgggccc tgccggaccg gcagcgccag tactcgctgc tgccgctgct gcacaactac   3360
cgcacgccgg agaagccgat caacgggtcg atagctccca ccgacgtgtt ccgggcagcg   3420
gtgcaggagg cgaaaatcgg ccccgacaaa gacattccgc acgtgtcgcc gccggtcatc   3480
gtcaagtaca tcaccgacct gcagctgctc gggctgctct aa                      3522
```

<210> SEQ ID NO 97
<211> LENGTH: 1173
<212> TYPE: PRT
<213> ORGANISM: Mycobacterium avium

<400> SEQUENCE: 97

```
Met Ser Thr Ala Thr His Asp Glu Arg Leu Asp Arg Arg Val His Glu
1               5                   10                  15

Leu Ile Ala Thr Asp Pro Gln Phe Ala Ala Ala Gln Pro Asp Pro Ala
            20                  25                  30

Ile Thr Ala Ala Leu Glu Gln Pro Gly Leu Arg Leu Pro Gln Ile Ile
        35                  40                  45

Arg Thr Val Leu Asp Gly Tyr Ala Asp Arg Pro Ala Leu Gly Gln Arg
    50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
        115                 120                 125

Asp Met Ala Leu Gly Ala Ile Gly Ala Val Ser Val Pro Leu Gln Thr
    130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
        195                 200                 205
```

```
Arg Leu Ser Ser Thr Gly Val Ala Val Gln Thr Leu Ala Glu Leu Leu
    210                 215                 220

Glu Arg Gly Lys Asp Leu Pro Ala Val Ala Glu Pro Pro Ala Asp Glu
225                 230                 235                 240

Asp Ser Leu Ala Leu Leu Ile Tyr Thr Ser Gly Ser Thr Gly Ala Pro
                    245                 250                 255

Lys Gly Ala Met Tyr Pro Gln Ser Asn Val Gly Lys Met Trp Arg Arg
                260                 265                 270

Gly Ser Lys Asn Trp Phe Gly Glu Ser Ala Ala Ser Ile Thr Leu Asn
            275                 280                 285

Phe Met Pro Met Ser His Val Met Gly Arg Ser Ile Leu Tyr Gly Thr
290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                325                 330                 335

Val Pro Arg Ile Trp Glu Thr Leu Tyr Gly Glu Phe Gln Arg Gln Val
                340                 345                 350

Glu Arg Arg Leu Ser Glu Ala Gly Asp Ala Gly Glu Arg Arg Ala Val
            355                 360                 365

Glu Ala Glu Val Leu Ala Glu Gln Arg Gln Tyr Leu Leu Gly Gly Arg
370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
                405                 410                 415

Ser Thr Glu Ala Gly Met Val Leu Phe Asp Gly Glu Ile Gln Arg Pro
                420                 425                 430

Pro Val Ile Asp Tyr Lys Leu Val Asp Val Pro Asp Leu Gly Tyr Phe
            435                 440                 445

Ser Thr Asp Arg Pro His Pro Arg Gly Glu Leu Leu Leu Arg Thr Glu
450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
                500                 505                 510

Leu Ala Gln Gly Glu Phe Val Thr Leu Ala Lys Leu Glu Ala Val Phe
            515                 520                 525

Gly Asn Ser Pro Leu Ile Arg Gln Ile Tyr Val Tyr Gly Asn Ser Ala
530                 535                 540

Gln Pro Tyr Leu Leu Ala Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
                595                 600                 605

Gly Ile Arg Lys Leu Ala Trp Pro Lys Leu Lys Gln His Tyr Gly Glu
610                 615                 620
```

```
Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
            645                 650                 655

Val Ser Arg Ala Ala Gly Ala Met Leu Gly Ser Ala Ala Ser Asp Leu
        660                 665                 670

Ser Pro Asp Ala His Phe Thr Asp Leu Gly Gly Asp Ser Leu Ser Ala
    675                 680                 685

Leu Thr Phe Gly Asn Leu Leu Arg Glu Ile Phe Asp Val Asp Val Pro
690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
                725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Pro Asn Leu Pro
        755                 760                 765

Lys Pro Ala Thr Glu Val Arg Thr Val Leu Leu Thr Gly Ala Thr Gly
770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
                805                 810                 815

Ala Arg Ala Arg Leu Asp Lys Thr Phe Asp Ser Gly Asp Pro Lys Leu
            820                 825                 830

Leu Ala His Tyr Gln Gln Leu Ala Ala Asp His Leu Glu Val Ile Ala
            835                 840                 845

Gly Asp Lys Gly Glu Ala Asn Leu Gly Leu Gly Gln Asp Val Trp Gln
            850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
            885                 890                 895

Thr Ala Glu Leu Ile Arg Leu Ala Leu Thr Ser Lys Gln Lys Pro Tyr
            900                 905                 910

Thr Tyr Val Ser Thr Ile Gly Val Gly Asp Gln Ile Glu Pro Gly Lys
            915                 920                 925

Phe Val Glu Asn Ala Asp Ile Arg Gln Met Ser Ala Thr Arg Ala Ile
930                 935                 940

Asn Asp Ser Tyr Ala Asn Gly Tyr Gly Asn Ser Lys Trp Ala Gly Glu
945                 950                 955                 960

Val Leu Leu Arg Glu Ala His Asp Leu Cys Gly Leu Pro Val Ala Val
            965                 970                 975

Phe Arg Cys Asp Met Ile Leu Ala Asp Thr Thr Tyr Ala Gly Gln Leu
            980                 985                 990

Asn Leu Pro Asp Met Phe Thr Arg Leu Met Leu Ser Leu Val Ala Thr
            995                 1000                1005

Gly Ile Ala Pro Gly Ser Phe Tyr Glu Leu Asp Ala Asp Gly Asn
        1010                1015                1020

Arg Gln Arg Ala His Tyr Asp Gly Leu Pro Val Glu Phe Ile Ala
        1025                1030                1035

Ala Ala Ile Ser Thr Leu Gly Ser Gln Ile Thr Asp Ser Asp Thr
```

```
    1040                1045                1050

Gly Phe  Gln Thr Tyr His Val  Met Asn Pro Tyr Asp  Asp Gly Val
    1055                1060                1065

Gly Leu  Asp Glu Tyr Val Asp  Trp Leu Val Asp Ala  Gly Tyr Ser
    1070                1075                1080

Ile Glu  Arg Ile Ala Asp Tyr  Ser Glu Trp Leu Arg  Arg Phe Glu
    1085                1090                1095

Thr Ser  Leu Arg Ala Leu Pro  Asp Arg Gln Arg Gln  Tyr Ser Leu
    1100                1105                1110

Leu Pro  Leu Leu His Asn Tyr  Arg Thr Pro Glu Lys  Pro Ile Asn
    1115                1120                1125

Gly Ser  Ile Ala Pro Thr Asp  Val Phe Arg Ala Ala  Val Gln Glu
    1130                1135                1140

Ala Lys  Ile Gly Pro Asp Lys  Asp Ile Pro His Val  Ser Pro Pro
    1145                1150                1155

Val Ile  Val Lys Tyr Ile Thr  Asp Leu Gln Leu Leu  Gly Leu Leu
    1160                1165                1170
```

```
<210> SEQ ID NO 98
<211> LENGTH: 3525
<212> TYPE: DNA
<213> ORGANISM: Mycobacterium marinum

<400> SEQUENCE: 98
atgtcgccaa tcacgcgtga agagcggctc gagcgccgca tccaggacct ctacgccaac     60
gacccgcagt tcgccgccgc caaacccgcc acggcgatca ccgcagcaat cgagcggccg    120
ggtctaccgc taccccagat catcgagacc gtcatgaccg gatacgccga tcggccggct    180
ctcgctcagc gctcggtcga attcgtgacc gacgccggca ccggccacac cacgctgcga    240
ctgctccccc acttcgaaac catcagctac ggcgagcttt gggaccgcat cagcgcactg    300
gccgacgtgc tcagcaccga acagacggtg aaaccgggcg accgggtctg cttgttgggc    360
ttcaacagcg tcgactacgc cacgatcgac atgactttgg cgcggctggg cgcggtggcc    420
gtaccactgc agaccagcgc ggcgataacc cagctgcagc cgatcgtcgc cgagacccag    480
cccaccatga tcgcggccag cgtcgacgca ctcgctgacg ccaccgaatt ggctctgtcc    540
ggtcagaccg ctacccgagt cctggtgttc gaccaccacc ggcaggttga cgcacaccgc    600
gcagcggtcg aatccgcccg ggagcgcctg gccggctcgg cggtcgtcga aaccctggcc    660
gaggccatcg cgcgcggcga cgtgccccgc ggtgcgtccg ccggctcggc gcccggcacc    720
gatgtgtccg acgactcgct cgcgctactg atctacacct cgggcagcac gggtgcgccc    780
aagggcgcga tgtacccccg acgcaacgtt gcgaccttct ggcgcaagcg cacctggttc    840
gaaggcggct acgagccgtc gatcacgctg aacttcatgc caatgagcca cgtcatgggc    900
cgccaaatcc tgtacggcac gctgtgcaat ggcggcaccg cctacttcgt ggcgaaaagc    960
gatctctcca ccttgttcga agacctggcg ctggtgcggc ccaccgagct gaccttcgtg   1020
ccgcgcgtgt gggacatggt gttcgacgag tttcagagtg aggtcgaccg ccgcctggtc   1080
gacggcgccg accgggtcgc gctcgaagcc caggtcaagg ccgagatacg caacgacgtg   1140
ctcggtggac ggtataccag cgcactgacc ggctccgccc ctatctccga cgagatgaag   1200
gcgtgggtcg aggagctgct cgacatgcat ctggtcgagg gctacggctc caccgaggcc   1260
gggatgatcc tgatcgacgg agccattcgg cgcccggcgg tactcgacta caagctggtc   1320
gatgttcccg acctgggtta cttcctgacc gaccggccac atccgcgggg cgagttgctg   1380
```

```
gtcaagaccg atagtttgtt cccgggctac taccagcgag ccgaagtcac cgccgacgtg    1440
ttcgatgctg acggcttcta ccggaccggc gacatcatgg ccgaggtcgg ccccgaacag    1500
ttcgtgtacc tcgaccgccg caacaacgtg ttgaagctgt cgcagggcga gttcgtcacc    1560
gtctccaaac tcgaagcggt gtttggcgac agcccactgg tacggcagat ctacatctac    1620
ggcaacagcg cccgtgccta cctgttggcg gtgatcgtcc ccacccagga ggcgctggac    1680
gccgtgcctg tcgaggagct caaggcgcgg ctgggcgact cgctgcaaga ggtcgcaaag    1740
gccgccggcc tgcagtccta cgagatcccg cgcgacttca tcatcgaaac aacaccatgg    1800
acgctggaga acgcctgct caccggcatc cgcaagttgg ccaggccgca gctgaaaaag    1860
cattacggcg agcttctcga gcagatctac acggacctgg cacacggcca ggccgacgaa    1920
ctgcgctcgc tgccaaaag cggtgccgat gcgccggtgc tggtgacggt gtgccgtgcg    1980
gcggccgcgc tgttgggcgg cagcgcctct gacgtccagc ccgatgcgca cttcaccgat    2040
ttgggcggcg actcgctgtc ggcgctgtcg ttcaccaacc tgctgcacga gatcttcgac    2100
atcgaagtgc cggtgggcgt catcgtcagc cccgccaacg acttgcaggc cctggccgac    2160
tacgtcgagg cggctcgcaa acccggctcg tcacggccga ccttcgcctc ggtccacggc    2220
gcctcgaatg ggcaggtcac cgaggtgcat gccggtgacc tgtccctgga caaattcatc    2280
gatgccgcaa ccctggccga agctccccgg ctgcccgccg caaacaccca agtgcgcacc    2340
gtgctgctga ccggcgccac cggcttcctc gggcgctacc tggccctgga atggctggag    2400
cggatggacc tggtcgacgg caaactgatc tgcctggtcc gggccaagtc cgacaccgaa    2460
gcacgggcgc ggctggacaa gacgttcgac agcggcgacc ccgaactgct ggcccactac    2520
cgcgcactgg ccggcgacca cctcgaggtg ctcgccggtg acaagggcga agccgacctc    2580
ggactggacc ggcagacctg gcaacgcctg gccgacacgg tcgacctgat cgtcgacccc    2640
gcggccctgg tcaaccacgt actgccatac agccagctgt tcgggcccaa cgcgctgggc    2700
accgccgagc tgctgcggct ggcgctcacc tccaagatca agccctacag ctacacctcg    2760
acaatcggtg tcgccgacca gatcccgccg tcggcgttca ccgaggacgc cgacatccgg    2820
gtcatcagcg ccacccgcgc ggtcgacgac agctacgcca atggctactc gaacagcaag    2880
tgggccggcg aggtgctgtt gcgcgaggcg catgacctgt gtggcctgcc ggttgcggtg    2940
ttccgctgcg acatgatcct ggccgacacc acatgggcgg gacagctcaa tgtgccggac    3000
atgttcaccc ggatgatcct gagcctggcg gccaccggta tcgcgccggg ttcgttctat    3060
gagcttgcgc ccgacggcgc ccggcaacgc gcccactatg acggtctgcc cgtcgagttc    3120
atcgccgagg cgatttcgac tttgggtgcg cagagccagg atggtttcca cacgtatcac    3180
gtgatgaacc cctacgacga cggcatcgga ctcgacgagt cgtcgactg gctcaacgag    3240 tccggttgcc ccatccagcg catcgctgac tatggcgact ggctgcagcg cttcgaaacc    3300
gcactgcgcg cactgcccga tcggcagcgg cacagctcac tgctgccgct gttgcacaac    3360
tatcggcagc cggagcggcc cgtccgcggg tcgatcgccc ctaccgatcg cttccgggca    3420
gcggtgcaag aggccaagat cggccccgac aaagacattc cgcacgtcgg cgcgccgatc    3480
atcgtgaagt acgtcagcga cctgcgccta ctcggcctgc tctaa    3525
```

<210> SEQ ID NO 99
<211> LENGTH: 1174
<212> TYPE: PRT
<213> ORGANISM: Mycobacterium marinum

```
<400> SEQUENCE: 99

Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Lys Pro Ala Thr Ala
            20                  25                  30

Ile Thr Ala Ala Ile Glu Arg Pro Gly Leu Pro Leu Pro Gln Ile Ile
            35                  40                  45

Glu Thr Val Met Thr Gly Tyr Ala Asp Arg Pro Ala Leu Ala Gln Arg
        50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
        130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
        275                 280                 285

Thr Leu Asn Phe Met Pro Met Ser His Val Met Gly Arg Gln Ile Leu
        290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
        355                 360                 365

Glu Ala Gln Val Lys Ala Glu Ile Arg Asn Asp Val Leu Gly Gly Arg
370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415
```

-continued

Ser Thr Glu Ala Gly Met Ile Leu Ile Asp Gly Ala Ile Arg Arg Pro
                420                 425                 430

Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
            755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

-continued

Asp Pro Glu Leu Leu Ala His Tyr Arg Ala Leu Ala Gly Asp His Leu
        835                 840                 845

Glu Val Leu Ala Gly Asp Lys Gly Ala Asp Leu Gly Leu Asp Arg
850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
    930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
        995                 1000                1005

Leu Ala Ala Thr Gly Ile Ala Pro Gly Ser Phe Tyr Glu Leu Ala
    1010                1015                1020

Ala Asp Gly Ala Arg Gln Ala His Tyr Asp Gly Leu Pro Val
    1025                1030                1035

Glu Phe Ile Ala Glu Ala Ile Ser Thr Leu Gly Ala Gln Ser Gln
    1040                1045                1050

Asp Gly Phe His Thr Tyr His Val Met Asn Pro Tyr Asp Asp Gly
    1055                1060                1065

Ile Gly Leu Asp Glu Phe Val Asp Trp Leu Asn Glu Ser Gly Cys
    1070                1075                1080

Pro Ile Gln Arg Ile Ala Asp Tyr Gly Asp Trp Leu Gln Arg Phe
    1085                1090                1095

Glu Thr Ala Leu Arg Ala Leu Pro Asp Arg Gln Arg His Ser Ser
    1100                1105                1110

Leu Leu Pro Leu Leu His Asn Tyr Arg Gln Pro Glu Arg Pro Val
    1115                1120                1125

Arg Gly Ser Ile Ala Pro Thr Asp Arg Phe Arg Ala Ala Val Gln
    1130                1135                1140

Glu Ala Lys Ile Gly Pro Asp Lys Asp Ile Pro His Val Gly Ala
    1145                1150                1155

Pro Ile Ile Val Lys Tyr Val Ser Asp Leu Arg Leu Leu Gly Leu
    1160                1165                1170

Leu

<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

```
gaggagaagt cgacatgaac gaacaatatt ccgcattgcg                           40

<210> SEQ ID NO 101
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ggaagctttc tagattagcc ggtattacgc atacctgcc                            39

<210> SEQ ID NO 102
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
taagctagca agaggagaag tcgacatgca gaacagcgct ttgaaag                   47

<210> SEQ ID NO 103
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcctctagga agctttctag attacttttt cttcgctttg gcg                       43

<210> SEQ ID NO 104
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ctagcaagag gagaagtcga catgcctgac gctaaaaaac aggggcggt                 49

<210> SEQ ID NO 105
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ctaggaagct ttctagagtc gttaatcgtg agcgcctatt tcgcgcag                  48

<210> SEQ ID NO 106
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ctagcaagag gagaagtcga catgacaaag tatgcattag tcggtgatgt g              51
```

<210> SEQ ID NO 107
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ctaggaagct ttctagagtc gttacagaat gtgacctaag gtctggcgta aatg          54

<210> SEQ ID NO 108
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ctagcaagag gagaagtcga catgagttct gaaagtagtc agggtctagt c             51

<210> SEQ ID NO 109
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ctaggaagct ttctagagtc gttacttctg ggagcgccac atctc                    45

<210> SEQ ID NO 110
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tagcaagagg agaagtcgac atggactgga agaagatcta tgaag                    45

<210> SEQ ID NO 111
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cctctaggaa gctttctaga ttagaatgcc gcgttgaag                           39

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tagcaagagg agaagtcgac atgagctggc aagaactgta tc                       42

<210> SEQ ID NO 113
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
cctctaggaa gctttctaga ttaatatttc tctttaaagc gcttttc 47

<210> SEQ ID NO 114
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
tagcaagagg agaagtcgac atggcacgtt ttactttacc aag 43

<210> SEQ ID NO 115
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
cctctaggaa gctttctaga ttacaaatta actttagttc catagtatgt gc 52

<210> SEQ ID NO 116
<211> LENGTH: 100
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
accggtaaac gactcagcag cctgacgcac tggcgatatt attttgcctt ctcctcacca 60
cagaatgttc tgccacctga cgatatcaaa ttacgccccg 100

<210> SEQ ID NO 117
<211> LENGTH: 104
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
tgcttatcca caacattttg cgcacggtta tgtggacaaa atacctggtt acccaggccg 60
tgccggcacg ttaaccgggc cctaggtcta gggcggcgga tttg 104

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
aggcagttcc ataggatggc                                               20

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
ataataatag gtaccggcgg cgctggcgca gcttgctgcg                          40

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
tattattatg gatccaaccc gataatggta gatctccctc t                        41

<210> SEQ ID NO 121
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ataataatag gatccggagc agaaacaatg tggtatttac t                        41

<210> SEQ ID NO 122
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tattattatc tgcagatgct cttttttatg cattacaaac tgc                      43

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
taataataag gtaccaactg ggcttgcttc actgg                               35

<210> SEQ ID NO 124
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
taataataaa gatctgcctc gaccgttcag gaagg                                    35

<210> SEQ ID NO 125
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
taataataaa gatcttaact ctccagtaac aaagctgc                                 38

<210> SEQ ID NO 126
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
taataataac tgcaggctat gtcaccactt acgg                                     34

<210> SEQ ID NO 127
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tattattatt cctgcaggcg tctttgttct tccgtcc                                  37

<210> SEQ ID NO 128
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tattattatc ttcggtacct ttagcatctg cttcggcc                                 38

<210> SEQ ID NO 129
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tattattatg gatcccggta atgcaacaaa agttagagc                                39

<210> SEQ ID NO 130
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tattattatg gatccaaagt gactgacatg aatatccttg atttgttc                      48

<210> SEQ ID NO 131
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 131
taataataag gatcctacac tggcggatgt ggcataaac                    39

<210> SEQ ID NO 132
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 132
taataatttg gtacccattc acagtcacca ggtacaacg                    39

<210> SEQ ID NO 133
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 133
taataataag gatccgagaa taacatgaat ggtgcattg                    39

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 134
taataatatc tgcagatcca caaaaagccc tggcaattg                    39

<210> SEQ ID NO 135
<211> LENGTH: 31
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 135
gataatcccc cctgcaggga gcggtaaata g                           31

<210> SEQ ID NO 136
<211> LENGTH: 34
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 136
tattattttg gatccttctc tggtgttgtt tggg                        34

<210> SEQ ID NO 137
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tattattatg gatccgcgtg gtgttgaaag ccg                                    33

<210> SEQ ID NO 138
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tattataaag gtaccgcctc ttccaggtca gtgaaggg                               38

<210> SEQ ID NO 139
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
taataataag gtacccagtt ttggctatgc cttaag                                 36

<210> SEQ ID NO 140
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
taataatcat taagcttgct ccctttgctg ggcc                                   34

<210> SEQ ID NO 141
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
taataataat aagcttttta cgcctcaaac tttcg                                  35

<210> SEQ ID NO 142
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
taataataaa ttgccctgca gcgtaagatt gtcgttcagg g                           41

<210> SEQ ID NO 143
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
tattattatt gtttggtacc tctgtgccgc t                                31

<210> SEQ ID NO 144
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
aatgttccac tctgcaggga tgataataag ggg                              33

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
atcggatcca atcgcacact aacagactg                                   29

<210> SEQ ID NO 146
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
acagctttgg atcctcattg tgtttactcc tgattagc                         38

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
ataataatat ctagagcagc aagccgcgcg gcaggtggtc ag                    42

<210> SEQ ID NO 148
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
tattattatc tgcagacgcc atcctgatcc atatgtatat gg                    42

<210> SEQ ID NO 149

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tattattatg gatccagttc ctccttttcg gatgatgttc tg                          42

<210> SEQ ID NO 150
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ataataatag gatccgaggc ctttgctgcg actgccatgt tc                          42

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cgccacaacc agtgacaccc                                                   20

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ggggttttag tcgcccttto tggc                                              24

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
cgggatctgg tggcgtttaa agtg                                              24

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
tgacggcgtt tgtcttcacc g                                                 21

<210> SEQ ID NO 155
<211> LENGTH: 53
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
acgctatgga actgcaggat gagagcatga aatggaacgg atgcgcgcct tat         53

<210> SEQ ID NO 156
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acgctatgga actgcaggat gagagcatct gccccagatc gttggctttt tgc         53

<210> SEQ ID NO 157
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tttgaaaaca ggatgtagcg atgaccgata ttcgcttgta                         40

<210> SEQ ID NO 158
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
tacaagcgaa tatcggtcat cgctacatcc tgttttcaaa                         40

<210> SEQ ID NO 159
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
cgcctgaata ctacgattga ctggagaatg cgaatgaaca                         40

<210> SEQ ID NO 160
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
tgttcattcg cattctccag tcaatcgtag tattcaggcg                         40

<210> SEQ ID NO 161
<211> LENGTH: 39
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 161
tttgaaaaca ggatgtagcg gcccgtagtc tgcaaatcc        39

<210> SEQ ID NO 162
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
ggatttgcag actacgggcc gctacatcct gttttcaaa        39

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
gcattacgct gacttgacgg ctggagaatg cgaatgaaca       40

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
tgttcattcg cattctccag ccgtcaagtc agcgtaatgc       40

<210> SEQ ID NO 165
<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165
actggagaat gcgaatgaac agcaataaag agttaatgca gcgccgcagt caggcgattc        60
cccgtggcgt tgggcaaatt cacccgattt tcgctgaccg cgcggaaaac tgccgggtgt       120
gggacgttga aggccgtgag tatcttgatt tcgcgggcgg gattgcggtg ctcaataccg       180
ggcacctgca tccgaaggtg                                                    200

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
ggcgaaagag tctgctccgg c        21

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cattcagaca caacgcatcg cgg                                            23

<210> SEQ ID NO 168
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ggcttaccag caccggtggg ttatgcccgt agtctgcaaa tcc                      43

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gcattacgct gacttgacgg gtgaaaaccg ttcgcagcct gg                       42

<210> SEQ ID NO 170
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggcttaccag caccggtggg ttatgcccgt agtctgcaaa tcc                      43

<210> SEQ ID NO 171
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ccaggctgcg aacggttttc acccgtcaag tcagcgtaat gc                       42

<210> SEQ ID NO 172
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggcttaccag caccggtggg ttatgtgaaa accgttcgca gcctgg                   46

<210> SEQ ID NO 173
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
ccaggctgcg aacggttttc acataaccca ccggtgctgg taagcc        46

<210> SEQ ID NO 174
<211> LENGTH: 1317
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 174
atggactgga agaagatcta tgaagacaga acctgcactg cagatgaagc agtaaagagc      60
attaagtcag gtgaccgcgt gctgtttgcg cactgtgttg ctgaaccgcc agttctggta     120
gaagcaatgg ttgcgaatgc agctgcatac aagaatgtca cggtttcaca catggttacc     180
cttggtaagg gtgaatactc aaaaccagaa tataaagaaa actttacttt gaaggttgg     240 tttaccagcc cttcaacacg tggatccatt gcagaaggac acgacagtt tgtccctgta     300 ttcttccacg aggtaccatc tttaatccgt aaagacattt tccatgttga tgtattcatg     360
gtaatggtat ccccgccaga tcataacggt ttctgctgtg tgggtgtatc ttctgactat     420
accatgcagg ctatcaaatc agcaaaaatt gtactggctg aagtgaatga tcaggtacct     480
gtagtttatg gcgataccctt tgttcacgtt agtgaaatcg acaagttcgt tgaaacttca     540
catccactgc cagaaatcgg tctgccgaag atcggtgaag tagaagctgc tattggtaag     600
cactgcgctt cgctgatcga agatggttcc acattacagc ttggtatcgg cgctattccg     660
gatgctgtac tttcacagct taaggacaag aaacaccttg gtatccactc tgaaatgatt     720
tccgacggtg ttgttgatct ttacgaagca ggcgttattg actgcagcca aaagtctatc     780
gacaaaggca aaatggcaat aacattctta atgggaacga agcgtcttta tgatttcgct     840
gcaaacaatc caaggttga attaaagccg gttgactaca tcaatcatcc atctgtagtt     900
gcacagtgca gcaaaatggt ttgcatcaat gcttgcttgc aagttgattt tatgggtcag     960
attgtctccg atagtattgg cacaaagcag ttctccggcg taggcggtca ggttgacttc    1020
gtacgcggtg catccatgtc tattgacggc aaaggtaaag cgatcatcgc gatgccttcc    1080
gttgcaaaga gaaagatgg cagtatgatt tcgaagatcg ttccattcat cgatcacggt    1140
gcagctgtaa ctacatcccg taacgatgcg gactatgtcg taacggaata tggtattgct    1200
gaaatgaagg gtaagtcgtt acaggaccgc gcacgcgcgt taatcaatat tgcccaccct    1260
gatttcaaag atgaattaaa ggctgaattt gaaaagcgct tcaacgcggc attctaa      1317

<210> SEQ ID NO 175
<211> LENGTH: 1308
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175

| | | | | | |
|---|---|---|---|---|---|
| atgagctggc | aagaactgta | tcaaagtaaa | ttatgttcag | ccacagaagc | ggtaaaacag | 60 |
| attaaaaacg | gtgataccgt | ggtatttgcc | cattgtgtag | gtgaaccgcc | tgcactggtg | 120 |
| gaggcgatga | ttgaaaatgc | tgaacaatat | aaagatgttg | agattaaaca | tatggttagc | 180 |
| ctgggtagtg | gtggttatac | tgcgaaaggg | atggaagcgc | attttcgcgt | aaatccaatg | 240 |
| tttgtcagcg | gcaatgtacg | taaggcgatt | gaaaatggcg | atggtgattt | tacacctgca | 300 |
| ttcttccatg | aagtaccaaa | gttgctgcgt | gaaaaacgtc | tgaaatgtga | tgttgttctg | 360 |
| gcacaggtaa | cgccaccaga | tgaacatggt | tattgttcgc | tgggaacaag | cgttgattat | 420 |
| acctatgaag | ccattaaaac | cgcgcgcacc | gtaattgttc | aggtgaatga | ccagtttcct | 480 |
| cgcacctatg | gtgaggtggt | gcatgtcagc | gagtttgact | atatcgttga | aaaatcacaa | 540 |
| ccgctgtttg | aactgcaacc | tgcaaagatt | ggcgaagttg | aagaagcgat | tggtaaaaat | 600 |
| tgtgcctcgc | tgattgaaga | tggtagcacg | ttacagctgg | ggattggtgg | gattccggat | 660 |
| gcggtgatgt | tatttctgac | tgataaaaaa | gatttaggga | ttcatagcga | aatgattagc | 720 |
| gatggcacgc | tggcgcttta | tgaaaaaggt | gttattaatg | gtaaatataa | aaattttgat | 780 |
| aaagaaaaaa | tgacggttac | cttcctgatg | ggtactaaaa | aactgtatga | ctttgccaat | 840 |
| aataacccgg | cagtagaggt | aaaaccggta | gactatgtga | atcatccggc | aattatcatg | 900 |
| aaacaacata | agatggtttc | tattaatagc | gccattcagg | ttgatttaat | ggggcaggtg | 960 |
| gttgcagagg | cgatgggact | gcgccaattt | tccggtgttg | gcggtcaggt | tgactttatt | 1020 |
| cgtggcgtgt | cgatgggtga | agatggcaag | gcgattatcg | cgatgccttc | aatcactaca | 1080 |
| aaaaaagatg | gtacggtaat | tagcaaaatc | gtctctattg | tcgatgaagg | tgcaccgatt | 1140 |
| accacctcac | gtaatgatgt | tgattatatt | gtcacagaat | acggtattgc | agaattaaaa | 1200 |
| ggcaaatcgc | tgcgtgaacg | cgcacgtaat | ctgattaata | ttgctcatcc | atcggtacgt | 1260 |
| gaatcgctgg | cagtagaatt | tgaaaagcgc | tttaaagaga | aatattaa | | 1308 |

<210> SEQ ID NO 176
<211> LENGTH: 1539
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176

| | | | | | |
|---|---|---|---|---|---|
| atggatttga | agctgaccga | tgcggacgtt | gaggcaatcg | tagcgcaagt | catggctaac | 60 |
| attgagcgcc | gtctgggtag | cgcggaagcg | ggcagcgcag | catccgctgc | gtcgccggca | 120 |
| ccggctgcgc | cggttcgtac | cgctccgggt | ggcagcccgg | cagccagccc | gcgtccggag | 180 |
| tacggtgttt | ttgatcgtgc | ggaggatgca | gtcgccgctg | ccgccgaagc | tcaggaagcc | 240 |
| ttcctgcgcc | agtgtcgtct | gcaagaccgt | gagcgcattc | tgcgtgccat | ccgtgaagag | 300 |
| actctggcac | gcaaggaaga | attggcacgc | tgatttggg | aggaaacgaa | gctgggtcgc | 360 |
| ttggaacaca | aaattgcaaa | gctggaattg | acggcgctga | aaaccccggg | tacggaggat | 420 |
| ctgcgcaccg | aggcatttag | cggcgacaac | ggcctgacca | tcgtcgaaca | tgcgccgtac | 480 |
| ggtgtgattg | gcgcggttac | cccggttacg | aaccctgcgg | agactattat | caacaacgcg | 540 |
| atcggcatgc | tggcaagcgg | taatgcagtg | gtgttcaacg | tgcaccctag | cgctaaacgt | 600 |
| tgctccgcgt | ataccgtcca | gatgatcaat | aaagcagtga | tggcagcggg | tggtccgccg | 660 |
| aatctggtta | cgatggttcg | cgagccgacc | atggaaaccc | tgaatgcgat | catccgcagc | 720 |

```
ccgagcgtga agctgctggt gggcaccggc ggtccgggtc tggttagcac cctgctgcgc    780
tctggtaaga aagcgattgg tgcgggtgcg ggcaatccgc cggtcgttgt ggatgatacc    840
gccgacctgg agcatgcggc aaaggaaatc atcaaaggcg cgtcctttga caacaatatt    900
ctgtgtattg cggagaaaga ggttttgtg gttgataaag cggccgacgg tctgatctat     960
cacatgctgg ataacggcgc atacatgctg ggtcgtgacg agctggagaa ggtgatgcaa   1020
ttcgcgctga ccgcggacga aagccagggc ggtgcgggtt gctctattga tccgcgtcgt   1080
gcgtggcatg tgactaagga gtgggtgggc aaagatgcgc gcttgttcct ggagaagatt   1140
ggtgtcaaga ctgaccgtcc ggttgacttg ctgttgtgcg aggttgactt tgaccacccg   1200
ttcgtgcagc tggaacaaat gatgccagta ctgccgattg ttcgtgtccg tgacctggat   1260
gaagccatcg gtatggccgt ccgtgcggag cacggcaatc gtcacaccgc aattatgcat   1320
agccgtaacg tggacaatct gacccgtttt gcccgtgcca ttgccacgac catcttcgtc   1380
aaaaacgcaa gcagcttggc gggtgttggt tatggcggtg aaggttttac caccatgacg   1440
atcgccggtc aacgggcga gggtctgacg tcggctcgta cgttcacgcg caaagtccgc   1500
tgtgtcctgg cggacggcgg tttccgtatc gttggttaa                          1539
```

<210> SEQ ID NO 177
<211> LENGTH: 792
<212> TYPE: DNA
<213> ORGANISM: Yersinia intermedia

<400> SEQUENCE: 177

```
atgaccgata ttcgcttgta tatgtttcaa actggctcgc tgaagtgcaa agtccacaat     60
atcaaaatga atcaaggagg tggagcggat tatgaaatcc ctgtcccgtt cttcctgctg    120
acccatcctg atggtcacac gctgattgat ggcgggaatg ctgtcgaaac cgccactgat    180
cccaaagggt attggggcgg gattaccgag gtttattggc cggtaatgcg tgaagatgag    240
ggctgtgtag cgcagcttaa aaaaatgggg atcaatcccg aagatatccg gtatgtcttg    300
cagtcgcact gcatcttga tcataccggt gcgattggcc gattccccaa tgcgacacac     360
atcgttcagc gccgtgagta cgagtatgcc tttactcctg actggtttgc tgcgggaggc    420
tatatcagaa acgactttga ccggccgggt ctgaaatggg cgtttctgga aggcgaaaac    480
aatgattttt atgatatcta tggcgacggt acgctgaaaa cagtatttac acccggccat    540
tcgcctgggc atcagtcaat actggtcacc ttgcccaact caggtccgat gctactgact    600
attgatgcag catacaccac ggatcactgg gaagaaaaag ctctgccagg atttatgtcc    660
tcagccgttg agacggtgcg ttcggtgcag aagatgcgca tgttggctag ccgcacaagt    720
gcgcaagtgg tgacaggcca tgacccggat gcctggcaaa cgttcaggca cgcgcctgaa    780
tactacgatt ga                                                        792
```

<210> SEQ ID NO 178
<211> LENGTH: 771
<212> TYPE: DNA
<213> ORGANISM: Agrobacterium tumefaciens

<400> SEQUENCE: 178

```
atgcttcagt cgggtacgct gaaatgcaag gtacacaaca ttaagatgaa ccaggggaac     60
ggtgcagact atgagatccc cgttccgttt ttcctgatta cccatccggc cgggcacacc    120
gtgatcgacg gcgcaacgc gattgaagtt gcaacagatc cgcgtggcca ttggggcggc    180
atctgcgatg tctattggcc agtactggac aaggaccagg gctgcgttga ccagatcaag    240
```

-continued

```
gcgcttggtt tcgatccggc cgatgtcaaa tatgttgtgc agtcgcacct gcatctcgat    300
cataccggcg ccatcggtcg cttccccaac gcaacccaca tcgtgcagcg ctctgaatat    360
gaatatgcct ttacgcccga ctggtttgct ggcggcggct atatccgcaa ggacttcgac    420
aagccgggtc tgaagtggca gttcctcaac ggtgcgcagg acgattatta cgatgtttac    480
ggcgacggca cgctcaccac gatcttcacg cccggtcatg cgcccggcca ccagtccttc    540
ctggtgcgcc tgccaaacag caaaccgctt ctcctgacga tcgatgctgc ctacacactg    600
gaccactggg aagagaaggc tttgcctggc ttccttgcct cgaccgttga cacggtccgt    660
tctgttcaga agctccgcac ctatgccgaa aagcatgatg cgacagtcgt caccggccat    720
gaccctgacg cctgggcgaa cttcaagaag gctcccgaat tttacgcgta a             771
```

MICROORGANISMS AND METHODS FOR PRODUCTION OF 4-HYDROXYBUTYRATE, 1,4-BUTANEDIOL AND RELATED COMPOUNDS

This application is a continuation of application Ser. No. 13/908,907, filed Jun. 3, 2013, which claims the benefit of U.S. Provisional application No. 61/655,429, filed Jun. 4, 2012, the entire contents of each of which are incorporated herein by reference.

This application incorporates by reference a Sequence Listing submitted as an ASCII text file entitled "12956-415-999_SeqList.TXT" created on May 2, 2017, and having a size of 238,465 bytes.

This invention relates generally to in silico design of organisms and engineering of organisms, more particularly to organisms having 1,4-butanediol, 4-hydroxybutyryl-CoA, 4-hydroxybutanal or putrescine biosynthesis capability.

BACKGROUND OF THE INVENTION

The compound 4-hydroxybutanoic acid (4-hydroxybutanoate, 4-hydroxybutyrate, 4-HB) is a 4-carbon carboxylic acid that has industrial potential as a building block for various commodity and specialty chemicals. In particular, 4-HB has the potential to serve as a new entry point into the 1,4-butanediol family of chemicals, which includes solvents, resins, polymer precursors, and specialty chemicals. 1,4-Butanediol (BDO) is a polymer intermediate and industrial solvent with a global market of about 3 billion lb/year. BDO is currently produced from petrochemical precursors, primarily acetylene, maleic anhydride, and propylene oxide.

For example, acetylene is reacted with 2 molecules of formaldehyde in the Reppe synthesis reaction (Kroschwitz and Grant, *Encyclopedia of Chem. Tech.*, John Wiley and Sons, Inc., New York (1999)), followed by catalytic hydrogenation to form 1,4-butanediol. It has been estimated that 90% of the acetylene produced in the U.S. is consumed for butanediol production. Alternatively, it can be formed by esterification and catalytic hydrogenation of maleic anhydride, which is derived from butane. Downstream, butanediol can be further transformed; for example, by oxidation to γ-butyrolactone, which can be further converted to pyrrolidone and N-methyl-pyrrolidone, or hydrogenolysis to tetrahydrofuran. These compounds have varied uses as polymer intermediates, solvents, and additives, and have a combined market of nearly 2 billion lb/year. It is desirable to develop a method for production of these chemicals by alternative means that not only substitute renewable for petroleum-based feedstocks, and also use less energy- and capital-intensive processes.

Thus, there exists a need for alternative means for effectively producing commercial quantities of 1,4-butanediol and its chemical precursors. The present invention satisfies this need and provides related advantages as well.

SUMMARY OF INVENTION

The invention provides non-naturally occurring microbial organisms having a 4-hydroxybutyrate pathway and being capable of producing 4-hydroxybutyrate, wherein the microbial organism comprises one or more genetic modifications. The invention additionally provides methods of producing 4-hydroxybutyrate or related products using the microbial organisms.

BRIEF DESCRIPTION OF THE DRAWINGS

(FIG. 3a) 4-HB concentration in culture broth; (FIG. 3b) succinate concentration in culture broth; (FIG. 3c) culture OD, measured at 600 nm. Clusters of bars represent the 24 hour, 48 hour, and 72 hour (if measured) timepoints. The codes along the x-axis indicate the strain/plasmid combination used. The first index refers to the host strain: 1, MG1655 lacI$^Q$; 2, MG1655 ΔgabD lacI$^Q$; 3, MG1655 ΔgabD ΔaldA lacI$^Q$. The second index refers to the plasmid combination used: 1, pZE13-0004-0035 and pZA33-0036; 2, pZE13-0004-0035 and pZA33-0010n; 3, pZE13-0004-0008 and pZA33-0036; 4, pZE13-0004-0008 and pZA33-0010n; 5, Control vectors pZE13 and pZA33.

FIG. 8A shows BDO pathways from succinyl-CoA. FIG. 8B shows BDO pathways from alpha-ketoglutarate.

FIGS. 9A-9C show exemplary BDO pathways. FIGS. 9A and 9B show pathways from 4-aminobutyrate. FIG. 9C shows a pathway from acetoactyl-CoA to 4-aminobutyrate.

FIG. 11 shows exemplary BDO pathways from glutamate.

FIG. 12 shows exemplary BDO pathways from acetoacetyl-CoA.

FIGS. 14A-14C show the nucleotide and amino acid sequences of E. coli succinyl-CoA synthetase. FIG. 14A shows the nucleotide sequence (SEQ ID NO:46) of the E. coli sucCD operon. FIGS. 14B (SEQ ID NO:47) and 14C (SEQ ID NO:48) show the amino acid sequences of the succinyl-CoA synthetase subunits encoded by the sucCD operon.

FIGS. 15A and 15B show the nucleotide and amino acid sequences of Mycobacterium bovis alpha-ketoglutarate decarboxylase. FIG. 15A shows the nucleotide sequence (SEQ ID NO:49) of Mycobacterium bovis sucA gene. FIG. 15B shows the amino acid sequence (SEQ ID NO:50) of M. bovis alpha-ketoglutarate decarboxylase.

FIG. 18 A shows the nucleotide sequence (SEQ ID NO:51) of CoA-dependent succinate semialdehyde dehydrogenase (sucD) from Porphyromonas gingivalis, and FIG. 18B shows the encoded amino acid sequence (SEQ ID NO:52).

FIG. 19A shows the nucleotide sequence (SEQ ID NO:53) of 4-hydroxybutyrate dehydrogenase (4hbd) from Porphymonas gingivalis, and FIG. 19B shows the encoded amino acid seqence (SEQ ID NO:54).

FIG. 20A shows the nucleotide sequence (SEQ ID NO:55) of 4-hydroxybutyrate CoA transferase (cat2) from Porphyromonas gingivalis, and FIG. 20B shows the encoded amino acid sequence (SEQ ID NO:56).

FIG. 21A shows the nucleotide sequence (SEQ ID NO:57) of phosphotransbutyrylase (ptb) from Clostridium acetobutylicum, and FIG. 21B shows the encoded amino acid sequence (SEQ ID NO:58).

FIG. 22A shows the nucleotide sequence (SEQ ID NO:59) of butyrate kinase (bukl) from Clostridium acetobutylicum, and FIG. 22B shows the encoded amino acid sequence (SEQ ID NO:60).

FIGS. 23A-23D show alternative nucleotide sequences for C. acetobutylicum 020 (phosphtransbutyrylase) with altered codons for more prevalent E. coli codons relative to the C. acetobutylicum native sequence. FIGS. 23A-23D (020A-020D, SEQ ID NOS:61-64, respectively) contain sequences with increasing numbers of rare E. coli codons replaced by more prevalent codons (A<B<C<D).

FIGS. 24A-24D show alternative nucleotide sequences for C. acetobuytlicum 021 (butyrate kinase) with altered codons for more prevalent E. coli codons relative to the C. acetobutylicum native sequence. FIGS. 24A-24D (021A-021B, SEQ ID NOS:65-68, respectively) contain sequences with increasing numbers of rare E. coli codons replaced by more prevalent codons (A<B<C<D).

FIG. 25A shows sodium dodecyl sulfate polyacrylamide gel electrophoresis (SDS-PAGE) stained for proteins with Coomassie blue; lane 1, control vector with no insert; lane 2, expression of C. acetobutylicum native sequences in E. coli; lane 3, expression of 020B-021B codon optimized PTB-BK; lane 4, expression of 020C-021C codon optimized PTB-BK. The positions of BK and PTB are shown. FIG. 25B shows the BK and PTB activities of native C. acetobutylicum sequence (2021n) compared to codon optimized 020B-021B (2021B) and 020C-021C (2021C).

FIG. 27A shows the nucleotide sequence (SEQ ID NO:69) of the native Clostridium biejerinckii ald gene (025n), and FIG. 27B shows the encoded amino acid sequence (SEQ ID NO:70).

FIGS. 28A-28D show alternative gene sequences for the Clostridium beijerinckii ald gene (025A-025D, SEQ ID NOS:71-74, respectively), in which increasing numbers of rare codons are replaced by more prevalent codons (A<B<C<D).

FIG. 30A shows BDO production in strains containing the native C. beijerinckii ald gene (025n) or variants with optimized codons for expression in E. coli (025A-025D). FIG. 30B shows production of ethanol and BDO in strains expressing the C. acetobutylicum AdhE2 enzyme (002C) compared to the codon optimized variant 025B. The third set shows expression of P. gingivalis sucD (035). In all cases, P. gingivalis Cat2 (034) is also expressed.

FIG. 31A shows the nucleotide sequence (SEQ ID NO:75) of the adh1 gene from Geobacillus thermoglucosidasius, and FIG. 31B shows the encoded amino acid sequence (SEQ ID NO:76).

FIG. 32A shows the expression of the Geobacillus thermoglucosidasius adh1 gene in E. coli. Either whole cell lysates or supernatants were analyzed by SDS-PAGE and stained with Coomassie blue for plasmid with no insert, plasmid with 083 (Geotrichum capitatum N-benzyl-3-pyrrolidinol dehydrogenase) and plasmid with 084 (Geobacillus thermoglucosidasius adh1) inserts. FIG. 32B shows the activity of 084 with butyraldehyde (diamonds) or 4-hydroxybutyraldehyde (squares) as substrates.

FIG. 33 shows the production of BDO in various strains: plasmid with no insert; 025B, 025B-026n; 025B-026A; 025B-026B; 025B-026C; 025B-050; 025B-052; 025B-053; 025B-055; 025B-057; 025B-058; 025B-071; 025B-083; 025B-084; PTSlacO-025B; PTSlacO-025B-026n.

FIG. 34 shows a plasmid map for the vector pRE118-V2.

FIG. 35 shows the sequence (SEQ ID NO:77) of the ECKh-138 region encompassing the aceF and lpdA genes. The *K. pneumonia* lpdA gene is underlined, and the codon changed in the Glu354Lys mutant shaded.

FIG. 36 shows the protein sequence comparison of the native *E. coli* lpdA (SEQ ID NO:78) and the mutant *K. pneumonia* lpdA (SEQ ID NO:79).

FIG. 37 shows 4-hydroxybutyrate (left bars) and BDO (right bars) production in the strains AB3, MG1655 ΔldhA and ECKh-138. All strains expressed *E. coli* sucCD, *P. gingivalis* sucD, *P. gingivalis* 4hbd on the medium copy plasmid pZA33, and *P. gingivalis* Cat2, *C. acetobutylicum* AdhE2 on the high copy plasmid pZE13.

FIG. 38 shows the nucleotide sequence (SEQ ID NO:80) of the 5' end of the aceE gene fused to the pflB-p6 promoter and ribosome binding site (RBS). The 5' italicized sequence shows the start of the aroP gene, which is transcribed in the opposite direction from the pdh operon. The 3' italicized sequence shows the start of the aceE gene. In upper case: pflB RBS. Underlined: FNR binding site. In bold: pflB-p6 promoter sequence.

FIG. 39 shows the nucleotide sequence (SEQ ID NO:81) in the aceF-lpdA region in the strain ECKh-456.

FIG. 41B shows the sequence (nucleotide sequence SEQ ID NO:82; amino acid sequence SEQ ID NO:83) of the PCR product of the amplification of chloramphenicol resistance gene (CAT) flanked by FRT sites and homology regions from the mdh gene from the plasmid pKD3.

FIG. 42 shows the sequence (SEQ ID NO:84) of the arcA deleted region in strain ECKh-401.

FIG. 43 shows the sequence (SEQ ID NO:85) of the region encompassing a mutated gltA gene of strain ECKh-422.

FIGS. 44A and 44B show the citrate synthase activity of wild type gltA gene product and the R163L mutant. The assay was performed in the absence (diamonds) or presence of 0.4 mM NADH (squares).

FIG. 45 shows the 4-hydroxybutyrate (left bars) and BDO (right bars) production in strains ECKh-401 and ECKh-422, both expressing genes for the complete BDO pathway on plasmids.

FIG. 46 shows central metabolic fluxes and associated 95% confidence intervals from metabolic labeling experiments. Values are molar fluxes normalized to a glucose uptake rate of 1 mmol/hr. The result indicates that carbon flux is routed through citrate synthase in the oxidative direction and that most of the carbon enters the BDO pathway rather than completing the TCA cycle.

FIGS. 47A and 47B show extracellular product formation for strains ECKh-138 and ECKh-422, both expressing the entire BDO pathway on plasmids. The products measured were acetate (Ace), pyruvate (Pyr), 4-hydroxybutyrate (4HB), 1,4-butanediol (BDO), ethanol (EtOH), and other products, which include gamma-butyrolactone (GBL), succinate, and lactate.

FIG. 48 shows the sequence (SEQ ID NO:86) of the region following replacement of PEP carboxylase (ppc) by *H. influenzae* phosphoenolpyruvate carboxykinase (pepck). The pepck coding region is underlined.

FIG. 52 shows the nucleotide sequence (SEQ ID NO:87) of the genomic DNA of strain ECKh-426 in the region of insertion of a polycistronic DNA fragment containing a promoter, sucCD gene, sucD gene, 4hbd gene and a terminator sequence.

FIG. 53 shows the nucleotide sequence (SEQ ID NO:88) of the chromosomal region of strain ECKh-432 in the region of insertion of a polycistronic sequence containing a promoter, sucA gene, *C. kluyveri* 4hbd gene and a terminator sequence.

FIG. 55 shows a PCR product (SEQ ID NO:89) containing the non-phosphotransferase (non-PTS) sucrose utilization genes flanked by regions of homology to the rrnC region.

FIG. 59A shows the nucleotide sequence (SEQ ID NO:90) of carboxylic acid reductase from *Nocardia iowensis* (GNM_720), and FIG. 59B shows the encoded amino acid sequence (SEQ ID NO:91).

FIG. 60A shows the nucleotide sequence (SEQ ID NO:92) of phosphpantetheine transferase, which was codon optimized, and FIG. 60B shows the encoded amino acid sequence (SEQ ID NO:93).

FIGS. 62A and 62B show pathways to 1,4-butanediol from succinate, succcinyl-CoA, and alpha-ketoglutarate. Abbreviations: A) Succinyl-CoA reductase (aldehyde forming), B) Alpha-ketoglutarate decarboxylase, C) 4-Hydroxybutyrate dehydrogenase, D) 4-Hydroxybutyrate reductase, E) 1,4-Butanediol dehydrogenase, F) Succinate reductase, G) Succinyl-CoA transferase, H) Succinyl-CoA hydrolase, I) Succinyl-CoA synthetase (or Succinyl-CoA ligase), J) Glutamate dehydrogenase, K) Glutamate transaminase, L) Glutamate decarboxylase, M) 4-aminobutyrate dehydrogenase, N) 4-aminobutyrate transaminase, O) 4-Hydroxybutyrate kinase, P) Phosphotrans-4-hydroxybutyrylase, Q) 4-Hydroxybutyryl-CoA reductase (aldehyde forming), R) 4-hydroxybutyryl-phosphate reductase, S) Succinyl-CoA reductase (alcohol forming), T) 4-Hydroxybutyryl-CoA transferase, U) 4-Hydroxybutyryl-CoA hydrolase, V) 4-Hydroxybutyryl-CoA synthetase (or 4-Hydroxybutyryl-CoA ligase), W) 4-Hydroxybutyryl-CoA reductase (alcohol forming), X) Alpha-ketoglutarate reductase, Y) 5-Hydroxy-2-oxopentanoate dehydrogenase, Z) 5-Hydroxy-2-oxopentanoate decarboxylase, AA) 5-hydroxy-2-oxopentanoate dehydrogenase (decarboxylation).

FIG. 64A shows the nucleotide sequence (SEQ ID NO:94) of carboxylic acid reductase from *Mycobacterium smegmatis* mc(2)155 (designated 890), and FIG. 64B shows the encoded amino acid sequence (SEQ ID NO:95).

FIG. 65A shows the nucleotide sequence (SEQ ID NO:96) of carboxylic acid reductase from *Mycobacterium avium* subspecies paratuberculosis K-10 (designated 891), and FIG. 65B shows the encoded amino acid sequence (SEQ ID NO:97).

FIG. 66A shows the nucleotide sequence (SEQ ID NO:98) of carboxylic acid reductase from *Mycobacterium marinum* M (designated 892), and FIG. 66B shows the encoded amino acid sequence (SEQ ID NO:99).

FIG. 89 shows the nucleotide sequence of the *Yersinia* gene (locus yinte0001_13710) (SEQ ID NO:177).

FIG. 90 shows the nucleotide sequence of the gene from *Agrobacterium tumefaciens* (SEQ ID NO:178).

DETAILED DESCRIPTION OF THE INVENTION

Figure 1:
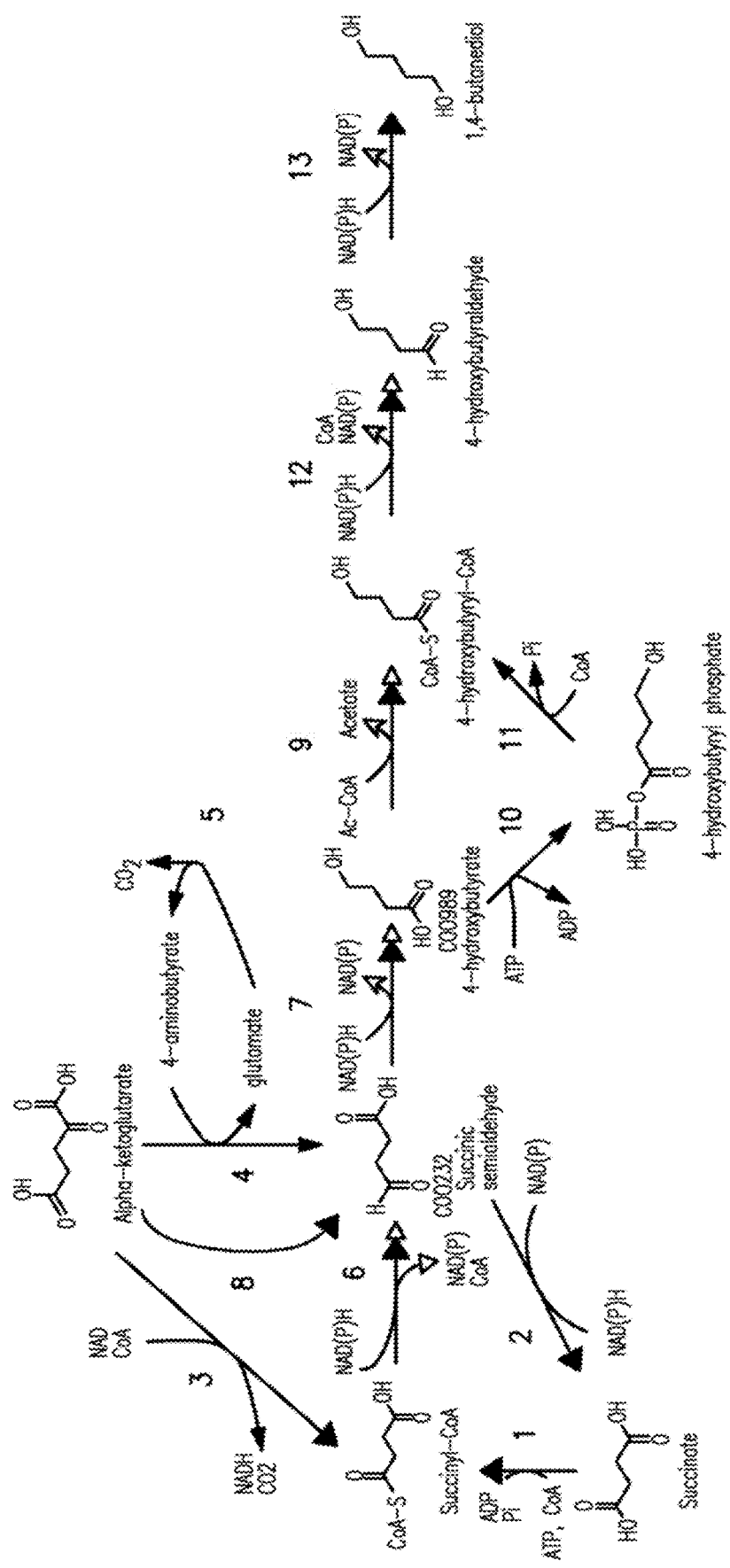
FIG. 1 is a schematic diagram showing biochemical pathways to 4-hydroxybutyurate (4-HB) and to 1,4-butanediol production. The first 5 steps are endogenous to *E. coli*, while the remainder can be expressed heterologously. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:acetyl-CoA transferase; (10) butyrate kinase; (11) phosphotransbutyrylase; (12) aldehyde dehydrogenase; (13) alcohol dehydrogenase.

The present invention is directed to the design and production of cells and organisms having biosynthetic production capabilities for 4-hydroxybutanoic acid (4-HB), γ-butyrolactone, 1,4-butanediol (BDO), 4-hydroxybutanal (4-HBal), 4-hydroxybutyryl-CoA (4-HBCoA) and/or putrescine. The invention, in particular, relates to the design of microbial organisms capable of producing BDO, 4-HBal, 4-HBCoA and/or putrescine by introducing one or more nucleic acids encoding a BDO, 4-HBal, 4-HBCoA and/or putrescine pathway enzyme.

In one embodiment, the invention utilizes in silico stoichiometric models of Escherichia coli metabolism that identify metabolic designs for biosynthetic production of 4-hydroxybutanoic acid (4-HB), 1,4-butanediol (BDO), 4-HBal, 4-HBCoA and/or putrescine. The results described herein indicate that metabolic pathways can be designed and recombinantly engineered to achieve the biosynthesis of 4-HBal, 4-HBCoA or 4-HB and downstream products such as 1,4-butanediol or putrescine in Escherichia coli and other cells or organisms. Biosynthetic production of 4-HB, 4-HBal, 4-HBCoA, BDO and/or putrescine, for example, for the in silico designs can be confirmed by construction of strains having the designed metabolic genotype. These metabolically engineered cells or organisms also can be subjected to adaptive evolution to further augment 4-HB, 4-HBal, 4-HBCoA, BDO and/or putrescine biosynthesis, including under conditions approaching theoretical maximum growth.

In certain embodiments, the 4-HB, 4-HBal, 4-HBCoA, BDO and/or putrescine biosynthesis characteristics of the designed strains make them genetically stable and particularly useful in continuous bioprocesses. Separate strain design strategies were identified with incorporation of different non-native or heterologous reaction capabilities into E. coli or other host organisms leading to 4-HB and 1,4-butanediol producing metabolic pathways from either CoA-independent succinic semialdehyde dehydrogenase, succinyl-CoA synthetase and CoA-dependent succinic semialdehyde dehydrogenase, or glutamate: succinic semialdehyde transaminase. In silico metabolic designs were identified that resulted in the biosynthesis of 4-HB in both E. coli and yeast species from each of these metabolic pathways. The 1,4-butanediol intermediate y-butyrolactone can be generated in culture by spontaneous cyclization under conditions at pH<7.5, particularly under acidic conditions, such as below pH 5.5, for example, pH<7, pH<6.5, pH<6, and particularly at pH<5.5 or lower.

Strains identified via the computational component of the platform can be put into actual production by genetically engineering any of the predicted metabolic alterations which lead to the biosynthetic production of 4-HB, 1,4-butanediol or other intermediate and/or downstream products. In yet a further embodiment, strains exhibiting biosynthetic production of these compounds can be further subjected to adaptive evolution to further augment product biosynthesis. The levels of product biosynthesis yield following adaptive evolution also can be predicted by the computational component of the system.

In other specific embodiments, microbial organisms were constructed to express a 4-HB biosynthetic pathway encoding the enzymatic steps from succinate to 4-HB and to 4-HB-CoA. Co-expression of succinate coenzyme A transferase, CoA-dependent succinic semialdehyde dehydrogenase, NAD-dependent 4-hydroxybutyrate dehydrogenase and 4-hydroxybutyrate coenzyme A transferase in a host microbial organism resulted in significant production of 4-HB compared to host microbial organisms lacking a 4-HB biosynthetic pathway. In a further specific embodiment, 4-HB-producing microbial organisms were generated that utilized α-ketoglutarate as a substrate by introducing nucleic acids encoding α-ketoglutarate decarboxylase and NAD-dependent 4-hydroxybutyrate dehydrogenase.

In another specific embodiment, microbial organisms containing a 1,4-butanediol (BDO) biosynthetic pathway were constructed that biosynthesized BDO when cultured in the presence of 4-HB. The BDO biosynthetic pathway consisted of a nucleic acid encoding either a multifunctional aldehyde/alcohol dehydrogenase or nucleic acids encoding an aldehyde dehydrogenawse and an alcohol dehydrogenase. To support growth on 4-HB substrates, these BDO-producing microbial organisms also expressed 4-hydroxybutyrate CoA transferase or 4-butyrate kinase in conjunction with phosphotranshydroxybutyrlase. In yet a further specific embodiment, microbial organisms were generated that synthesized BDO through exogenous expression of nucleic acids encoding a functional 4-HB biosynthetic pathway and a functional BDO biosynthetic pathway. The 4-HB biosynthetic pathway consisted of succinate coenzyme A transferase, CoA-dependent succinic semialdehyde dehydrogenase, NAD-dependent 4-hydroxybutyrate dehydrogenase and 4-hydroxybutyrate coenzyme A transferase. The BDO pathway consisted of a multifunctional aldehyde/alcohol dehydrogenase. Further described herein are additional pathways for production of BDO (see FIGS. 8-13).

In a further embodiment, described herein is the cloning and expression of a carboxylic acid reductase enzyme that functions in a 4-hydroxybutanal, 4-hydroxybutyryl-CoA or 1,4-butanediol metabolic pathway. Advantages of employing a carboxylic acid reductase as opposed to an acyl-CoA reductase to form 4-hydroxybutyraldehyde (4-hydroxybutanal) include lower ethanol and GBL byproduct formation accompanying the production of BDO. Also disclosed herein is the application of carboxylic acid reductase as part of additional numerous pathways to produce 1,4-butanediol and putrescine from the tricarboxylic acid (TCA) cycle metabolites, for example, succinate, succinyl-CoA, and/or alpha-ketoglutarate.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a biosynthetic pathway for a 4-HB, 4-HBal, 4-HBCoA, BDO or putrescine family of compounds.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "4-hydroxybutanoic acid" is intended to mean a 4-hydroxy derivative of butyric acid having the chemical formula $C_4H_8O_3$ and a molecular mass of 104.11 g/mol (126.09 g/mol for its sodium salt). The chemical compound 4-hydroxybutanoic acid also is known in the art as 4-HB, 4-hydroxybutyrate, gamma-hydroxybutyric acid or GHB. The term as it is used herein is intended to include any of the compound's various salt forms and include, for example, 4-hydroxybutanoate and 4-hydroxybutyrate. Specific examples of salt forms for 4-HB include sodium 4-HB and potassium 4-HB. Therefore, the terms 4-hydroxybutanoic acid, 4-HB, 4-hydroxybutyrate, 4-hydroxybutanoate, gamma-hydroxybutyric acid and GHB as well as other art recognized names are used synonymously herein.

As used herein, the term "monomeric" when used in reference to 4-HB is intended to mean 4-HB in a non-polymeric or underivatized form. Specific examples of polymeric 4-HB include poly-4-hydroxybutanoic acid and copolymers of, for example, 4-HB and 3-HB. A specific example of a derivatized form of 4-HB is 4-HB-CoA. Other polymeric 4-HB forms and other derivatized forms of 4-HB also are known in the art.

As used herein, the term "γ-butyrolactone" is intended to mean a lactone having the chemical formula $C_4H_6O_2$ and a molecular mass of 86.089 g/mol. The chemical compound γ-butyrolactone also is know in the art as GBL, butyrolactone, 1,4-lactone, 4-butyrolactone, 4-hydroxybutyric acid lactone, and gamma-hydroxybutyric acid lactone. The term as it is used herein is intended to include any of the compound's various salt forms.

As used herein, the term "1,4-butanediol" is intended to mean an alcohol derivative of the alkane butane, carrying two hydroxyl groups which has the chemical formula $C_4H_{10}O_2$ and a molecular mass of 90.12 g/mol. The chemical compound 1,4-butanediol also is known in the art as BDO and is a chemical intermediate or precursor for a family of compounds referred to herein as BDO family of compounds.

As used herein, the term "4-hydroxybutanal" is intended to mean an aledehyde having the chemical formula $C_4H_8O_2$ and a molecular mass of 88.10512 g/mol. The chemical compound 4-hydroxybutanal (4-HBal) is also known in the art as 4-hydroxybutyraldehyde.

As used herein, the term "putrescine" is intended to mean a diamine having the chemical formula $C_4H_{12}N_2$ and a molecular mass of 88.15148 g/mol. The chemical compound putrescine is also known in the art as 1,4-butanediamine, 1,4-diaminobutane, butylenediamine, tetramethylenediamine, tetramethyldiamine, and 1,4-butylenediamine.

As used herein, the term "tetrahydrofuran" is intended to mean a heterocyclic organic compound corresponding to the fully hydrogenated analog of the aromatic compound furan which has the chemical formula $C_4H_8O$ and a molecular mass of 72.11 g/mol. The chemical compound tetrahydrofuran also is known in the art as THF, tetrahydrofuran, 1,4-epoxybutane, butylene oxide, cyclotetramethylene oxide, oxacyclopentane, diethylene oxide, oxolane, furanidine, hydrofuran, tetra-methylene oxide. The term as it is used herein is intended to include any of the compound's various salt forms.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, if desired, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein are described with reference to a suitable source or host organism such as *E. coli*, yeast, or other organisms disclosed herein and their corresponding metabolic reactions or a suitable source organism for desired genetic material such as genes encoding enzymes for their corresponding metabolic reactions for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production, including growth-coupled production, of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 4-HB, GBL, 4-HBal, 4-HBCoA, BDO and/or putrescine biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. Similarly for a gene disruption, evolutionarily related genes can also be disrupted or deleted in a host microbial organism to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Disclosed herein are non-naturally occurring microbial biocatalyst or microbial organisms including a microbial organism having a 4-hydroxybutanoic acid (4-HB) biosynthetic pathway that includes at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate: succinic semialdehyde transaminase, alpha-ketoglutarate decarboxylase, or glutamate decarboxylase, wherein the exogenous nucleic acid is expressed in sufficient amounts to produce monomeric 4-hydroxybutanoic acid (4-HB). 4-hydroxybutanoate dehydrogenase is also referred to as 4-hydroxybutyrate dehydrogenase or 4-HB dehydrogenase. Succinyl-CoA synthetase is also referred to as succinyl-CoA synthase or succinyl-CoA ligase.

Also disclosed herein is a non-naturally occurring microbial biocatalyst or microbial organism including a microbial organism having a 4-hydroxybutanoic acid (4-HB) biosynthetic pathway having at least one exogenous nucleic acid encoding 4-hydroxybutanoate dehydrogenase, succinyl-CoA synthetase, CoA-dependent succinic semialdehyde dehydrogenase, or α-ketoglutarate decarboxylase, wherein the exogenous nucleic acid is expressed in sufficient amounts to produce monomeric 4-hydroxybutanoic acid (4-HB).

The non-naturally occurring microbial biocatalysts or microbial organisms can include microbial organisms that employ combinations of metabolic reactions for biosynthetically producing the compounds of the invention. The biosynthesized compounds can be produced intracellularly and/or secreted into the culture medium. Exemplary compounds produced by the non-naturally occurring microorganisms include, for example, 4-hydroxybutanoic acid, 1,4-butanediol and γ-butyrolactone.

In one embodiment, a non-naturally occurring microbial organism is engineered to produce 4-HB. This compound is one useful entry point into the 1,4-butanediol family of compounds. The biochemical reactions for formation of 4-HB from succinate, from succinate through succinyl-CoA or from γ-ketoglutarate are shown in steps 1-8 of FIG. 1.

It is understood that any combination of appropriate enzymes of a BDO, 4-HBal, 4-HBCoA and/or putrescine pathway can be used so long as conversion from a starting component to the BDO, 4-HBal, 4-HBCoA and/or putrescine product is achieved. Thus, it is understood that any of the metabolic pathways disclosed herein can be utilized and that it is well understood to those skilled in the art how to select appropriate enzymes to achieve a desired pathway, as disclosed herein.

In another embodiment, disclosed herein is a non-naturally occurring microbial organism, comprising a microbial organism having a 1,4-butanediol (BDO) pathway comprising at least one exogenous nucleic acid encoding a BDO pathway enzyme expressed in a sufficient amount to produce BDO, the BDO pathway comprising 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase (see Example VII Table 17). The BDO pathway further can comprise 4-hydroxybutyryl-CoA reductase (alcohol forming), 4-hydroxybutyryl-CoA reductase, or 1,4-butanediol dehydrogenase.

It is understood by those skilled in the art that various combinations of the pathways can be utilized, as disclosed herein. For example, in a non-naturally occurring microbial organism, the nucleic acids can encode 4-aminobutyrate CoA transferase, 4-aminobutyryl-CoA hydrolase, or 4-aminobutyrate-CoA ligase; 4-aminobutyryl-CoA oxidoreductase (deaminating) or 4-aminobutyryl-CoA transaminase; and 4-hydroxybutyryl-CoA dehydrogenase. Other exemplary combinations are specifically describe below and further can be found in FIGS. 8-13. For example, the BDO pathway can further comprise 4-hydroxybutyryl-CoA reductase (alcohol forming), 4-hydroxybutyryl-CoA reductase, or 1,4-butanediol dehydrogenase.

Additionally disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase (see Example VII and Table 18), and can further comprise 1,4-butanediol dehydrogenase. For example, the exogenous nucleic acids can encode 4-aminobutyrate CoA transferase, 4-aminobutyryl-CoA hydrolase, or 4-aminobutyrate-CoA ligase; 4-aminobutyryl-CoA reductase (alcohol forming); and 4-aminobutan-1-ol oxidoreductase (deaminating) or 4-aminobutan-1-ol transaminase. In addition, the nucleic acids can encode. 4-aminobutyrate CoA transferase, 4-aminobutyryl-CoA hydrolase, or 4-aminobutyrate-CoA ligase; 4-aminobutyryl-CoA reductase; 4-aminobutan-1-ol dehydrogenase; and 4-aminobutan-1-ol oxidoreductase (deaminating) or 4-aminobutan-1-ol transaminase.

Also disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy]phosphonic acid transaminase, 4-hydroxybutyryl-phosphate dehydrogenase, or 4-hydroxybutyraldehyde dehydrogenase (phosphorylating) (see Example VII and Table 19). For example, the exogenous nucleic acids can encode 4-aminobutyrate kinase; 4-aminobutyraldehyde dehydrogenase (phosphorylating); 4-aminobutan-1-ol dehydrogenase; and 4-aminobutan-1-ol oxidoreductase (deaminating) or 4-aminobutan-1-ol transaminase. Alternatively, the exogenous nucleic acids can encode 4-aminobutyrate kinase; [(4-aminobutanolyl)oxy]phosphonic acid oxidoreductase (deaminating) or [(4-aminobutanolyl)oxy]phosphonic acid transaminase; 4-hydroxybutyryl-phosphate dehydrogenase; and 4-hydroxybutyraldehyde dehydrogenase (phosphorylating).

Additionally disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation) (see Example VIII and Table 20). The BDO pathway can further comprise 4-hydroxybutyryl-CoA reductase (alcohol forming), 4-hydroxybutyryl-CoA reductase, or 1,4-butanediol dehydrogenase. For example, the exogenous nucleic acids can encode alpha-ketoglutarate 5-kinase; 2,5-dioxopentanoic semialdehyde dehydrogenase (phosphorylating); 2,5-dioxopentanoic acid reductase; and 5-hydroxy-2-oxopentanoic acid decarboxylase. Alternatively, the exogenous nucleic acids can encode alpha-ketoglutarate 5-kinase; 2,5-dioxopentanoic semialdehyde dehydrogenase (phosphorylating); 2,5-dioxopentanoic acid reductase; and 5-hydroxy-2-oxopentanoic acid dehydrogenase (decarboxylation). Alternatively, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase, 5-hydroxy-2-oxopentanoic acid dehydrogenase; and 5-hydroxy-2-oxopentanoic acid decarboxylase. In another embodiment, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase, 5-hydroxy-2-oxopentanoic acid dehydrogenase, and 5-hydroxy-2-oxopentanoic acid dehydrogenase (decarboxylation). Alternatively, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase (alcohol forming); and 5-hydroxy-2-oxopentanoic acid decarboxylase. In yet another embodiment, the exogenous nucleic acids can encode alpha-ketoglutarate CoA transferase, alpha-ketoglutaryl-CoA hydrolase, or alpha-ketoglutaryl-CoA ligase; alpha-ketoglutaryl-CoA reductase (alcohol forming); and 5-hydroxy-2-oxopentanoic acid dehydrogenase (decarboxylation).

Further disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5-hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation) (see Example IX and Table 21). For example, the exogenous nucleic acids can encode glutamate CoA transferase, glutamyl-CoA hydrolase, or glutamyl-CoA ligase; glutamyl-CoA reductase; glutamate-5-semialdehyde reductase; 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation). Alternatively, the exogenous nucleic acids can encode glutamate 5-kinase; glutamate-5-semialdehyde dehydrogenase (phosphorylating); glutamate-5-semialdehyde reductase; 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation). In still another embodiment, the exogenous nucleic acids can encode glutamate CoA transferase, glutamyl-CoA hydrolase, or glutamyl-CoA ligase; glutamyl-CoA reductase (alcohol forming); 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation). In yet another embodiment, the exogenous nucleic acids can encode glutamate 5-kinase; glutamate-5-semialdehyde dehydrogenase (phosphorylating); 2-amino-5-hydroxypentanoic acid oxidoreductase (deaminating) or 2-amino-5-hydroxypentanoic acid transaminase; and 5-hydroxy-2-oxopentanoic acid decarboxylase or 5-hydroxy-2-oxopentanoic acid dehydrogenase (decarboxylation).

Also disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising 3-hydroxybutyryl-CoA dehydrogenase, 3-hydroxybutyryl-CoA dehydratase, vinylacetyl-CoA Δ-isomerase, or 4-hydroxybutyryl-CoA dehydratase (see Example X and Table 22). For example, the exogenous nucleic acids can encode 3-hydroxybutyryl-CoA dehydrogenase; 3-hydroxybutyryl-CoA dehydratase; vinylacetyl-CoA Δ-isomerase; and 4-hydroxybutyryl-CoA dehydratase.

Further disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase (see Example XI and Table 23). For example, the exogenous nucleic acids can encode homoserine deaminase; 4-hydroxybut-2-enoyl-CoA transferase, 4-hydroxybut-2-enoyl-CoA hydrolase, 4-hydroxybut-2-enoyl-CoA ligase; 4-hydroxybut-2-enoyl-CoA reductase. Alternatively, the exogenous nucleic acids can encode homoserine CoA transferase, homoserine-CoA hydrolase, or homoserine-CoA ligase; homoserine-CoA deaminase; and 4-hydroxybut-2-enoyl-CoA reductase. In a further embodiment, the exogenous nucleic acids can encode homoserine deaminase; 4-hydroxybut-2-enoate reductase; and 4-hydroxybutyryl-CoA transferase, 4-hydroxybutyryl-CoA hydrolase, or 4-hydroxybutyryl-CoA ligase. Alternatively, the exogenous nucleic acids can encode homoserine CoA transferase, homoserine-CoA hydrolase, or homoserine-CoA ligase; homoserine-CoA deaminase; and 4-hydroxybut-2-enoyl-CoA reductase.

Further disclosed herein is a non-naturally occurring microbial organism, comprising a microbial organism having a BDO pathway comprising at least one exogenous nucleic acid encoding a BDO pathway enzyme expressed in a sufficient amount to produce BOD, the BDO pathway comprising succinyl-CoA reductase (alcohol forming), 4-hydroxybutyryl-CoA hydrolase, 4-hydroxybutyryl-CoA ligase, 4-hydroxybutanal dehydrogenase (phosphorylating) (see Table 15). Such a BDO pathway can further comprise succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

Additionally disclosed herein is a non-naturally occurring microbial organism, comprising a microbial organism having a BDO pathway comprising at least one exogenous nucleic acid encoding a BDO pathway enzyme expressed in a sufficient amount to produce BDO, the BDO pathway comprising glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, 4-hydroxybutanal dehydrogenase (phosphorylating)(see Table 16). Such a BDO pathway can further comprise alpha-ketoglutarate decarboxylase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

The pathways described above are merely exemplary. One skilled in the art can readily select appropriate pathways from those disclosed herein to obtain a suitable BDO pathway or other metabolic pathway, as desired.

The invention provides genetically modified organisms that allow improved production of a desired product such as BDO by increasing the product or decreasing undesirable byproducts. As disclosed herein, the invention provides a non-naturally occurring microbial organism, comprising a microbial organism having a 1,4-butanediol (BDO) pathway comprising at least one exogenous nucleic acid encoding a BDO pathway enzyme expressed in a sufficient amount to produce BDO. In one embodiment, the microbial organism is genetically modified to express exogenous succinyl-CoA synthetase (see Example XII). For example, the succinyl-CoA synthetase can be encoded by an *Escherichia coli* sucCD genes.

In another embodiment, the microbial organism is genetically modified to express exogenous alpha-ketoglutarate decarboxylase (see Example XIII). For example, the alpha-ketoglutarate decarboxylase can be encoded by the *Mycobacterium bovis* sucA gene. In still another embodiment, the microbial organism is genetically modified to express exogenous succinate semialdehyde dehydrogenase and 4-hydroxybutyrate dehydrogenase and optionally 4-hydroxybutyryl-CoA/acetyl-CoA transferase (see Example XIII). For example, the succinate semialdehyde dehydrogenase (CoA-dependent), 4-hydroxybutyrate dehydrogenase and 4-hydroxybutyryl-CoA/acetyl-CoA transferase can be encoded by *Porphyromonas gingivalis* W83 genes. In an additional embodiment, the microbial organism is genetically modified to express exogenous butyrate kinase and phosphotransbutyrylase (see Example XIII). For example, the butyrate kinase and phosphotransbutyrylase can be encoded by *Clostridium acetobutilicum* bukl and ptb genes.

In yet another embodiment, the microbial organism is genetically modified to express exogenous 4-hydroxybutyryl-CoA reductase (see Example XIII). For example, the 4-hydroxybutyryl-CoA reductase can be encoded by *Clostridium beijerinckii* ald gene. Additionally, in an embodiment of the invention, the microbial organism is genetically modified to express exogenous 4-hydroxybutanal reductase (see Example XIII). For example, the 4-hydroxybutanal reductase can be encoded by *Geobacillus thermoglucosidasius* adh1 gene. In another embodiment, the microbial organism is genetically modified to express exogenous pyruvate dehydrogenase subunits (see Example XIV). For example, the exogenous pyruvate dehydrogenase can be NADH insensitive. The pyruvate dehydrogenase subunit can be encoded by the *Klebsiella pneumonia* lpdA gene. In a particular embodiment, the pyruvate dehydrogenase subunit genes of the microbial organism can be under the control of a pyruvate formate lyase promoter.

In still another embodiment, the microbial organism is genetically modified to disrupt a gene encoding an aerobic respiratory control regulatory system (see Example XV). For example, the disruption can be of the arcA gene. Such an organism can further comprise disruption of a gene encoding malate dehydrogenase. In a further embodiment, the microbial organism is genetically modified to express an exogenous NADH insensitive citrate synthase (see Example XV). For example, the NADH insensitive citrate synthase can be encoded by gltA, such as an R163L mutant of gltA. In still another embodiment, the microbial organism is genetically modified to express exogenous phosphoenolpyruvate carboxykinase (see Example XVI). For example, the phosphoenolpyruvate carboxykinase can be encoded by an *Haemophilus influenza* phosphoenolpyruvate carboxykinase gene.

In an additional embodiment, the invention provides a non-naturally occurring microbial organism having a 4-hydroxybutyrate pathway and being capable of producing 4-hydroxybutyrate, wherein the microbial organism comprises a genetic modification that increases expression of phosphoenolpyruvate carboxylase (see Example XXXI). In such an embodiment in which phosphoenolpyruvate expression is increased, the microbial organism can exhibit decreased production of ethanol, acetate, pyruvate or alanine, or a combination thereof, relative to a parent microbial organism in the absence of the genetic modification. As disclosed herein, the overexpression of posphoenolpyruvate (PEP) carboxylase leads to conversion of more phosphoenolpyruvate into oxaloacetate, thereby reducing flux from PEP into pyruvate and subsequently into acetyl-CoA (Example XXXI). Reducing flux from PEP to pyruvate and acetyl-CoA increases flux into the TCA cycle and consequently a 4HB or BDO pathway.

In yet another embodiment, the invention provides a non-naturally occurring microbial organism having a 4-hydroxybutyrate pathway and being capable of producing 4-hydroxybutyrate, wherein the microbial organism comprises a genetic modification that increases expression of alpha-ketoglutarate dehydrogenase (see Example XXXII). The increased expression of alpha-ketoglutarate dehydrogenase can result in decreased production of glutamate relative to a parent microbial organism in the absence of the genetic modification. Such a microbial organism can also exhibit decreased production of ethanol, acetate, pyruvate or alanine, or a combination thereof, relative to a parent microbial organism in the absence of the genetic modification. As disclosed herein, the formation of glutamate can lead to a carbon loss and reduction in yield. Therefore, increased expression of alpha-ketoglutarate dehydrogenase can reduce glutamate as well as other by-products such as ethanol, acetate, alanine and/or pyruvate.

In a further embodiment, the invention provides a non-naturally occurring microbial organism having a 4-hydroxybutyrate pathway and being capable of producing 4-hydroxybutyrate, wherein the microbial organism comprises a genetic modification that increases expression of a non-phosphotransferase (PTS) glucose uptake system (see Example XXXIII). In such an embodiment, the genetic modification can comprise increased expression of a permease, glucokinase, or a glucose facilitator, or a combination thereof. In addition, such a microbial organism can exhibit decreased production of ethanol, acetate, pyruvate, or alanine, or a combination thereof, relative to a parent microbial organism in the absence of the genetic modification. The introduction of a non-PTS sucrose uptake system has been previously described in U.S. publication 2011/0045575 as a way to reduce pyruvate formation in a microbial organism utilizing sucrose as a carbon source. In contrast, the utilization of a non-PTS glucose uptake system, as described herein, is to provide a better balance between the available oxaloacetate in comparison to acetyl-CoA (see Example XXXIII).

In another embodiment, the invention provides a non-naturally occurring microbial organism having a 4-hydroxybutyrate pathway and being capable of producing 4-hydroxybutyrate, wherein the microbial organism comprises a genetic modification that increases expression of a gamma-butyrolactone esterase (Example XXXIV). Such a microbial organism can exhibit decreased production of gamma-butyrolactone relative to a parent microbial organism in the absence of the genetic modification. As disclosed herein, gamma-butyrolactone is a byproduct formed during the fermentation of sugars to 1,4-butanediol. Gamma-butyrolactone can form from the unstable pathway intermediate 4-hydroxybutyryl-CoA as well as spontaneous lactonization of 4-hydroxybutyrate. As disclosed herein, the expression of a gamma-butyrolactone can accelerate the hydrolysis of gamma-butyrolactone to BDO, thereby improving BDO product yield and eliminating a byproduct (see Example XXXIV).

In additional embodiments disclosed herein, a genetic modification can include gene disruptions or deletions to decrease expression of an enzyme. For example, in a further embodiment, the invention provides a non-naturally occurring microbial organism having a 4-hydroxybutyrate pathway and being capable of producing 4-hydroxybutyrate, wherein the microbial organism comprises a genetic modification that decreases expression of succinyl-CoA synthetase (Example XXXV). In such an embodiment, the microbial organism can exhibit increased production of 4-hydroxybutyrate relative to a parent microbial organism in the absence of the genetic modification. As described herein, repeated rounds of flux through the TCA cycle results in carbon loss as $CO_2$. The deletion of succinyl-CoA synthetase blocks the TCA cycle downstream of succinyl-CoA, thereby reducing $CO_2$ loss (see Example XXXV).

In a further embodiment, the invention provides a non-naturally occurring microbial organism having a 4-hydroxybutyrate pathway and being capable of producing 4-hydroxybutyrate, wherein the microbial organism comprises a genetic modification that decreases expression of an acyl coenzyme A thioesterase (see Example XXXVI). In such an embodiment the microbial organism can exhibit decreased production of gamma-butyrolactone relative to a parent microbial organism in the absence of the genetic modification. In yet a further embodiment, such a microbial organism can comprise at least two genetic modifications that decrease expression of at least two acyl coenzyme A thioesterases. As disclosed herein, the BDO pathway intermediate 4-hydroxybutyryl-CoA spontaneously and enzymatically cyclizes to form gamma-butyrolactone (GBL). By deleting acyl coenzyme-A thioesterases, the formation of the byproduct GBL was reduced (see Example XXXVI).

In another embodiment, the invention provides a non-naturally occurring microbial organism having a 4-hydroxybutyrate pathway and being capable of producing 4-hydroxybutyrate, wherein the microbial organism comprises a genetic modification that decreases expression of an alcohol dehydrogenase (see Example XXXVII). In such an embodiment, the microbial organism can exhibit decreased backflux from a downstream product of the 4-hydroxybutyrate pathway relative to a parent microbial organism in the absence of said genetic modification. At high titers of BDO, a downstream product from 4-hydroxybutyrate, the high concentrations of product can result in backflux within the pathway or through side reactions, thereby resulting in a decreased product yield. As described herein, several endogenous alcohol dehydrogenases were found to contribute to backflux, whereas deletion of one or more of the endogenous alcohol dehydrogenases decreased backflux without reducing production of 4-hydroxybutyrate or BDO, and in fact increased BDO formation (see Example XXXVII).

In still another embodiment, the invention provides a non-naturally occurring microbial organism having a 4-hydroxybutyrate pathway and being capable of producing 4-hydroxybutyrate, wherein the microbial organism comprises a genetic modification that decreases expression of a non-energy-producing NADH dehydrogenase (see Example XXXVIII). The decreased expression of a non-energy-producing NADH dehydrogenase suppresses depletion of the NADH pool resulting from the activity of the non-energy-producing NADH dehydrogenase. Additionally, the microbial organisms exhibit increased energy efficiency in the microbial organism relative to a parent microbial organism in the absence of the genetic modification. As described herein, the electron transport chain has multiple NADH dehydrogenases and cytochrome oxidases with varying ability to translocate protons. Some NADH dehydrogenases consume NADH without linking the consumption to proton translocation and energy production, and such NADH dehydrogenases are considered to be non-energy-producing NADH dehydrogenases. One exemplary non-energy-producing NADH dehydrogenase is NADH II of *E. coli* (see Example XXXVIII). Additional genes encoding enzymes with non-energy producing NAD (P)H dehydrogenase activities include wrbA, yieF, and kefF. One skilled in the art will readily understand the meaning of a non-energy-producing NADH dehydrogenase as one that does not couple NADH oxidation to electron transport and proton translocation and the formation of ATP. By decreasing expression of a non-energy-producing NADH dehydrogenase, the depletion of the NADH pool within the cell is suppressed, thereby making the cell more energy efficient and/or allowing NADH to be utilized in desired synthetic pathways.

In a further embodiment, the invention provides a non-naturally occurring microbial organism having a 4-hydroxybutyrate pathway and being capable of producing 4-hydroxybutyrate, wherein the microbial organism comprises a genetic modification that decreases expression of a cytochrome oxidase (see Example XXXIX). In such an embodiment, the microbial organism can exhibit increased energy efficiency relative to a parent microbial organism in the absence of the genetic modification. As disclosed herein, cytochrome oxidases involved in the electron transport chain have different energy-conserving efficiencies. By decreasing expression of one or more cytochrome oxidases, the energy efficiency of the cell can be increased (see Example XXXIX). Even in a case where an increase in product yield is not observed under certain conditions (see Example XXXIX), such genetic modifications can be advantageous in providing a greater tolerance for a range of oxygen concentrations, in particular producing a product more efficiently in a large fermentor, where the available oxygen varies within the ferementor. By improving the energy efficiency of the microbial organism, the organism can tolerate lower oxygen conditions since need for energy production from the electron transport chain is reduced. Thus, in a particular embodiment of the invention, the microbial organism can exhibit an increased tolerance to a range of oxygen concentrations relative to a parent microbial organism in the absence of said genetic modification.

The invention thus provides a non-naturally occurring microbial organism having a 4-hydroxybutyrate pathway and being capable of producing 4-hydroxybutyrate, wherein the microbial organism comprises a genetic modification, the genetic modification selected from: (A) a genetic modification that increases expression of phosphoenolpyruvate carboxylase; (B) a genetic modification that increases expression of alpha-ketoglutarate dehydrogenase; (C) a genetic modification that increases expression of a non-phosphotransferase (PTS) glucose uptake system; (D) a genetic modification that increases expression of a gamma-butyrolactone esterase; (E) a genetic modification that decreases expression of succinyl-CoA synthetase; (F) a genetic modification that decreases expression of an acyl coenzyme A thioesterase; (G) a genetic modification that decreases expression of an alcohol dehydrogenase; (H) a genetic modification that decreases expression of a non-energy-producing NADH dehydrogenase; (I) a genetic modification that decreases expression of a cytochrome oxidase; and (J) a combination of two or more of the genetic modifications of parts (A)-(I). In further particular embodiments, (K) the microbial organism of part (A), (B), or (C) has decreased production of ethanol, acetate, pyruvate or alanine, or a combination thereof, relative to a parent microbial organism in the absence of said genetic modification; (L) the microbial organism of part (B) has decreased production of glutamate relative to a parent microbial organism in the absence of said genetic modification; (M) the microbial organism of part (C) has a genetic modification comprising increased expression of a permease, glucokinase, or a glucose facilitator, or a combination thereof; (N) the microbial organism of part (D) has decreased production of gamma-butyrolactone relative to a parent microbial organism in the absence of said genetic modification; (O) the microbial organism of part (E) has increased production of 4-hydroxybutyrate relative to a parent microbial organism in the absence of said genetic modification; (P) the microbial organism of part (F) has decreased production of gamma-butyrolactone relative to a parent microbial organism in the absence of said genetic modification; (Q) the microbial organism of part (F) has a genetic modification comprising at least two genetic modifications that decrease expression of at least two acyl coenzyme A thioesterases; (R) the microbial organism of part (G) has decreased backflux from a downstream product of the 4-hydroxybutyrate pathway relative to a parent microbial organism in the absence of said genetic modification; (S) the microbial organism of part (H) has suppressed depletion of the NADH pool or increased energy efficiency in the microbial organism, or a combination thereof, relative to a parent microbial organism in the absence of said genetic modification; (T) the microbial organism of part (I) has increased energy efficiency relative to a parent microbial organism in the absence of said genetic modification; or (U) the microbial organism of part (I) has increased tolerance to a range of oxygen concentrations relative to a parent microbial organism in the absence of said genetic modification. In a further embodiment, the invention provides a microbial organism, where the microbial organism of parts (D) or (F) further comprises a 4-hydroxybutyryl-CoA pathway. The invention further provides a method for producing 4-hydroxybutyrate utilizing such microbial organisms. It is understood that such genetic modifications include, but are not limited to, the specifically described gene additions and disruptions described in Examples XXIV-XXXIX. In the case of gene disruptions, it is understood that such disruptions involve disruption of an endogenous gene encoding an activity of a corresponding gene product to be decreased.

Although the pathways immediately above are directed to 4-HB pathways, it is understood, as disclosed herein, the 4-HB is a precursor to downstream products such as 1,4-butanediol (BDO). Further, as disclosed herein, a microbial organism having a 4-HB pathway can further include enzymes that convert 4-HB to a downstream product such as BDO, as desired. In addition, any of the pathways described herein that produce 4-HB are understood to provide a 4-HB pathway, even if additional steps in a pathway are also disclosed since such a pathway produces 4-HB.

As used herein, the term "parent microbial organism," when used in the context of a genetic modification, is understood to mean a parent organism or strain in which the particular genetic modification has not been made but otherwise has the same genetic makeup. For example, if a strain of microbial organism is used to make a genetic modification that increases expression of a gene product, the parent strain would be the starting strain into which the heterologous gene is introduced. Similarly, a parent microbial organism of an organism in which a genetic modification has been made to decrease expression, such as a gene disruption or gene deletion, the parent microbial organism would have the same genetic background except for the gene disruption or deletion. However, it is understood that a parent microbial organism can differ by more than one genetic modification, either gene addition and/or disruption, depending on whether a single or multiple genetic modifications are being considered. One skilled in the art will readily understand the meaning of such a parent microbial organism in that the microbial organism is considered to be an appropriate control, as understood in the art, for observing the effect of one or more genetic modifications.

In addition, it is understood by those skilled in the art that a genetic modification such as those disclosed herein can contribute to an increase in product yield, a decrease in by-product formation, and/or improved characteristics of the microbial organism. Such improved characteristics include, but are not limited to, improved cell growth, increased energy efficiency, increased tolerance of a range of oxygen concentrations, particularly when manifested in a scaled up production process such as in large fermentors. A useful genetic modification may not alone, when compared to a parent microbial organism, exhibit an effect that can readily measured under a given set of conditions. However, a useful genetic modification can be advantageous if the modification on its on under a given set of conditions and/or in combination with one or more other genetic modifications is beneficial to the growth and/or production characteristics of the microbial organism.

It is understood that a genetic modification that increases expression of a desired enzyme is generally carried out by introducing into the microbial organism a heterologous nucleic acid encoding the desired enzyme. However, it is understood, as described herein, that a metabolic modification to increase expression can include modification of a regulatory region of an endogenous gene, such as a promoter and/or enhancer. Additionally, a genetic modification that decreases expression of a desired enzyme will generally involve a gene disruption or deletion, although modification of a regulatory to decrease expression can also be utilized, as disclosed herein.

It is further understood that any of a number of genetic modifications, as disclosed herein, can be used alone or in various combinations of one or more of the genetic modifications disclosed herein to increase the production of BDO in a BDO producing microbial organism. In a particular embodiment, the microbial organism can be genetically modified to incorporate any and up to all of the genetic modifications that lead to increased production of BDO. In a particular embodiment, the microbial organism containing a BDO pathway can be genetically modified to express exogenous succinyl-CoA synthetase; to express exogenous alpha-ketoglutarate decarboxylase; to express exogenous succinate semialdehyde dehydrogenase and 4-hydroxybutyrate dehydrogenase and optionally 4-hydroxybutyryl-CoA/acetyl-CoA transferase; to express exogenous butyrate kinase and phosphotransbutyrylase; to express exogenous 4-hydroxybutyryl-CoA reductase; and to express exogenous 4-hydroxybutanal reductase; to express exogenous pyruvate dehydrogenase; to disrupt a gene encoding an aerobic respiratory control regulatory system; to express an exogenous NADH insensitive citrate synthase; and to express exogenous phosphoenolpyruvate carboxykinase. Such strains for improved production are described in Examples XII-XIX. It is thus understood that, in addition to the modifications described above, such strains can additionally include other modifications disclosed herein. Such modifications include, but are not limited to, deletion of endogenous lactate dehydrogenase (ldhA), alcohol dehydrogenase (adhE), and/or pyruvate formate lyase (pflB)(see Examples XII-XIX and Table 28). Additional genetic modifications that can be introduced into a microbial organism include those described in Examples XXIV-XXXX, alone or in combination, including in combination with other genetic modifications disclosed herein.

Additionally provided is a microbial organism in which one or more genes encoding the exogenously expressed enzymes are integrated into the fimD locus of the host organism (see Example XVII). For example, one or more genes encoding a BDO pathway enzyme can be integrated into the fimD locus for increased production of BDO. Further provided is a microbial organism expressing a non-phosphotransferase sucrose uptake system that increases production of BDO.

Although the genetically modified microbial organisms disclosed herein are exemplified with microbial organisms containing particular BDO pathway enzymes, it is understood that such modifications can be incorporated into any microbial organism having a BDO, 4-HBal, 4-HBCoA and/or putrescine pathway suitable for enhanced production in the presence of the genetic modifications of any of the pathways disclosed herein. The microbial organisms of the invention can thus have any of the BDO, 4-HBal, 4-HBCoA and/or putrescine pathways disclosed herein. For example, the BDO pathway can comprise 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, alpha-ketoglutarate decarboxylase, aldehyde dehydrogenase, alcohol dehydrogenase or an aldehyde/alcohol dehydrogenase (see FIG. 1). Alternatively, the BDO pathway can comprise 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase (see Table 17). Such a BDO pathway can further comprise 4-hydroxybutyryl-CoA reductase (alcohol forming), 4-hydroxybutyryl-CoA reductase, or 1,4-butanediol dehydrogenase.

Additionally, the BDO pathway can comprise 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase (see Table 18). Also, the BDO pathway can comprise 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy]phosphonic acid transaminase, 4-hydroxybutyryl-phosphate dehydrogenase, or 4-hydroxybutyraldehyde dehydrogenase (phosphorylating) (see Table 19). Such a pathway can further comprise 1,4-butanediol dehydrogenase.

The BDO pathway can also comprise alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation)(see Table 20). Such a BDO pathway can further comprise 4-hydroxybutyryl-CoA reductase (alcohol forming), 4-hydroxybutyryl-CoA reductase, or 1,4-butanediol dehydrogenase. Additionally, the BDO pathway can comprise glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5-hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation)(see Table 21). Such a BDO pathway can further comprise 4-hydroxybutyryl-CoA reductase (alcohol forming), 4-hydroxybutyryl-CoA reductase, or 1,4-butanediol dehydrogenase.

Additionally, the BDO pathway can comprise 3-hydroxybutyryl-CoA dehydrogenase, 3-hydroxybutyryl-CoA dehydratase, vinylacetyl-CoA Δ-isomerase, or 4-hydroxybutyryl-CoA dehydratase (see Table 22). Also, the BDO pathway can comprise homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase (see Table 23). Such a BDO pathway can further comprise 4-hydroxybutyryl-CoA reductase (alcohol forming), 4-hydroxybutyryl-CoA reductase, or 1,4-butanediol dehydrogenase.

The BDO pathway can additionally comprise succinyl-CoA reductase (alcohol forming), 4-hydroxybutyryl-CoA hydrolase, 4-hydroxybutyryl-CoA ligase, or 4-hydroxybutanal dehydrogenase (phosphorylating) (see Table 15). Such a pathway can further comprise succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase. Also, the BDO pathway can comprise glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, or 4-hydroxybutanal dehydrogenase (phosphorylating)(see Table 16). Such a BDO pathway can further comprise alpha-ketoglutarate decarboxylase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

Figure 58:
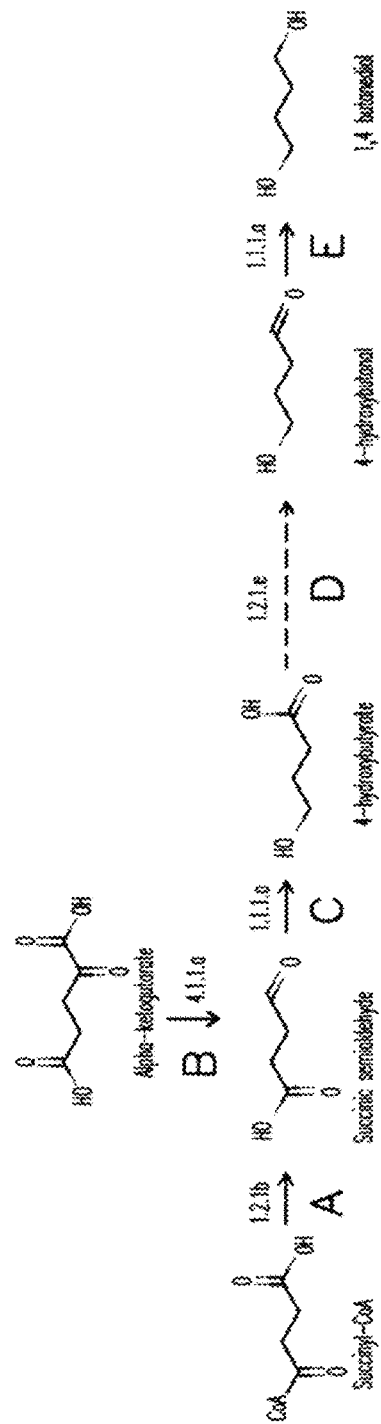
FIG. 58 shows exemplary pathways to 1,4-butanediol from succcinyl-CoA and alpha-ketoglutarate. Abbreviations: A) Succinyl-CoA reductase (aldehyde forming), B) Alpha-ketoglutarate decarboxylase, C) 4-Hydroxybutyrate dehydrogenase, D) 4-Hydroxybutyrate reductase, E) 1,4-Butanediol dehydrogenase.

The invention additionally provides a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising succinyl-CoA reductase (aldehyde forming); 4-hydroxybutyrate dehydrogenase; and 4-hydroxybutyrate reductase (see FIG. 58, steps A-C-D). The invention also provides a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising alpha-ketoglutarate decarboxylase; 4-hydroxybutyrate dehydrogenase; and 4-hydroxybutyrate reductase (FIG. 58, steps B-C-D).

The invention further provides a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising succinate reductase; 4-hydroxybutyrate dehydrogenase, and 4-hydroxybutyrate reductase (see FIG. 62, steps F-C-D). In yet another embodiment, the invention provides a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising alpha-ketoglutarate decarboxylase, or glutamate dehydrogenase or glutamate transaminase and glutamate decarboxylase and 4-aminobutyrate dehydrogenase or 4-aminobutyrate transaminase; 4-hydroxybutyrate dehydrogenase; and 4-hydroxybutyrate reductase (see FIG. 62, steps B or ((J or K)-L-(M or N))-C-D).

The invention also provides a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising alpha-ketoglutarate reductase; 5-hydroxy-2-oxopentanoate dehydrogenase; and 5-hydroxy-2-oxopentanoate decarboxylase (see FIG. 62, steps X-Y-Z). In yet another embodiment, the invention provides a non-naturally occurring microbial organism, comprising a 4-hydroxybutyryl-CoA pathway comprising at least one exogenous nucleic acid encoding a 4-hydroxybutyryl-CoA pathway enzyme expressed in a sufficient amount to produce 4-hydroxybutyryl-CoA, the 4-hydroxybutyryl-CoA pathway comprising alpha-ketoglutarate reductase; 5-hydroxy-2-oxopentanoate dehydrogenase; and 5-hydroxy-2-oxopentanoate dehydrogenase (decarboxylation) (see FIG. 62, steps X-Y-AA).

Figure 63:
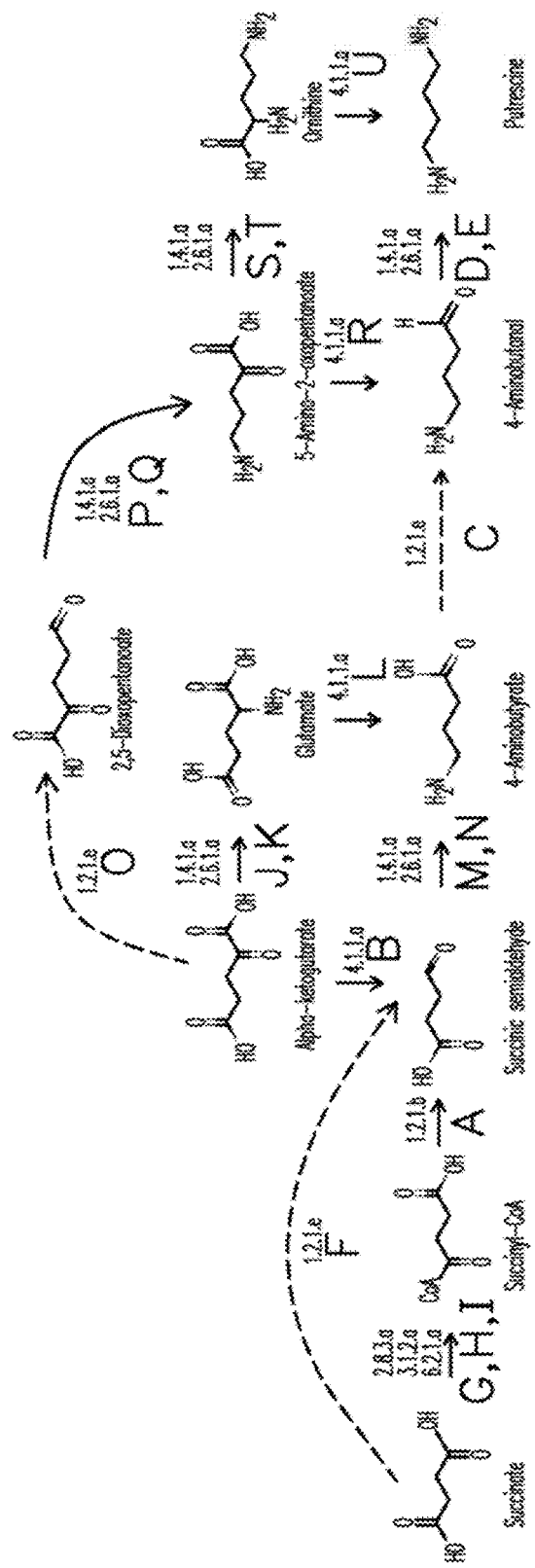
FIG. 63 shows pathways to putrescine from succinate, succcinyl-CoA, and alpha-ketoglutarate. Abbreviations: A) Succinyl-CoA reductase (aldehyde forming), B) Alpha-ketoglutarate decarboxylase, C) 4-Aminobutyrate reductase, D) Putrescine dehydrogenase, E) Putrescine transaminase, F) Succinate reductase, G) Succinyl-CoA transferase, H) Succinyl-CoA hydrolase, I) Succinyl-CoA synthetase (or Succinyl-CoA ligase), J) Glutamate dehydrogenase, K) Glutamate transaminase, L) Glutamate decarboxylase, M) 4-Aminobutyrate dehydrogenase, N) 4-Aminobutyrate transaminase, O) Alpha-ketoglutarate reductase, P) 5-Amino-2-oxopentanoate dehydrogenase, Q) 5-Amino-2-oxopentanoate transaminase, R) 5-Amino-2-oxopentanoate decarboxylase, S) Ornithine dehydrogenase, T) Ornithine transaminase, U) Ornithine decarboxylase.

The invention additionally provides a non-naturally occurring microbial organism, comprising a putrescine pathway comprising at least one exogenous nucleic acid encoding a putrescine pathway enzyme expressed in a sufficient amount to produce putrescine, the putrescine pathway comprising succinate reductase; 4-aminobutyrate dehydrogenase or 4-aminobutyrate transaminase; 4-aminobutyrate reductase; and putrescine dehydrogenase or putrescine transaminase (see FIG. 63, steps F-M/N-C-D/E). In still another embodiment, the invention provides a non-naturally occurring microbial organism, comprising a putrescine pathway comprising at least one exogenous nucleic acid encoding a putrescine pathway enzyme expressed in a sufficient amount to produce putrescine, the putrescine pathway comprising alpha-ketoglutarate decarboxylase; 4-aminobutyrate dehydrogenase or 4-aminobutyrate transaminase; 4-aminobutyrate reductase; and putrescine dehydrogenase or putrescine transaminase (see FIG. 63, steps B-M/N-C-D/E). The invention additionally provides a non-naturally occurring microbial organism, comprising a putrescine pathway comprising at least one exogenous nucleic acid encoding a putrescine pathway enzyme expressed in a sufficient amount to produce putrescine, the putrescine pathway comprising glutamate dehydrogenase or glutamate transaminase; glutamate decarboxylase; 4-aminobutyrate reductase; and putrescine dehydrogenase or putrescine transaminase (see FIG. 63, steps J/K-L-C-D/E).

The invention provides in another embodiment a non-naturally occurring microbial organism, comprising a putrescine pathway comprising at least one exogenous nucleic acid encoding a putrescine pathway enzyme expressed in a sufficient amount to produce putrescine, the putrescine pathway comprising alpha-ketoglutarate reductase; 5-amino-2-oxopentanoate dehydrogenase or 5-amino-2-oxopentanoate transaminase; 5-amino-2-oxopentanoate decarboxylase; and putrescine dehydrogenase or putrescine transaminase (see FIG. 63, steps O-P/Q-R-D/E). Also provided is a non-naturally occurring microbial organism, comprising a putrescine pathway comprising at least one exogenous nucleic acid encoding a putrescine pathway enzyme expressed in a sufficient amount to produce putrescine, the putrescine pathway comprising alpha-ketoglutarate reductase; 5-amino-2-oxopentanoate dehydrogenase or 5-amino-2-oxopentanoate transaminase; ornithine dehydrogenase or ornithine transaminase; and ornithine decarboxylase (see FIG. 63, steps O-P/Q-S/T-U).

In an additional embodiment, the invention provides a non-naturally occurring microbial organism having a 4-HB, 4-HBal, 4-HBCoA, BDO or putrescine pathway, wherein the non-naturally occurring microbial organism comprises at least one exogenous nucleic acid encoding an enzyme or protein that converts a substrate of any of the pathways disclosed herein (see, for example, the Examples and FIGS. 1, 8-13, 58, 62 and 63). In an exemplary embodiment for producing BDO, the microbial organism can convert a substrate to a product selected from the group consisting of succinate to succinyl-CoA; succinyl-CoA to succinic semialdehyde; succinic semialdehyde to 4-hydroxybutrate; 4-hydroxybutyrate to 4-hydroxybutyryl-phosphate; 4-hydroxybutyryl-phosphate to 4-hydroxtbutyryl-CoA; 4-hydroxybutyryl-CoA to 4-hydroxybutanal; and 4-hydroxybutanal to 1,4-butanediol. In a pathway for producing 4-HBal, a microbial organism can convert, for example, succinate to succinic semialdehyde; succinic semialdehyde to 4-hydroxybutyrate; and 4-hydroxybutyrate to 4-hydroxybutanal. Such an organism can additionally include activity to convert 4-hydroxybutanal to 1,4-butanediol in order to produce BDO. Yet another pathway for producing 4-HBal can be, for example, alpha-ketoglutarate to succinic semialdehyde; succinic semialdehyde to 4-hydroxybutyrate; and 4-hydroxybutyrate to 4-hydroxybutanal. An alternative pathway for producing 4-HBal can be, for example, alpha-ketoglutarate to 2,5-dioxopentanoic acid; 2,5-dioxopentanoic acid to 5-hydroxy-2-oxopentanooic acid; and 5-hydroxy-2-oxopentanoic acid to 4-hydroxybutanal. An exemplary 4-hydroxybutyryl-CoA pathway can be, for example, alpha-ketoglutarate to 2,5-dioxopentanoic acid; 2,5-dioxopentanoic acid to 5-hydroxy-2-oxopentanoic acid; and 5-hydroxy-2-oxopentanoic acid to 4-hydroxybutyryl-CoA. An exemplary putrescine pathway can be, for example, succinate to succinyl-CoA; succinyl-CoA to succinic semialdehyde; succinic semialdehyde to 4-aminobutyrate; 4-aminobutyrate to 4-aminobutanal; and 4-aminobutanal to putrescine. An alternative putrescine pathway can be, for example, succinate to succinic semialdehyde; succinic semialdehyde to 4-aminobutyrate; 4-aminobutyrate to 4-aminobutanal; and 4-aminobutanal to putrescine. One skilled in the art will understand that these are merely exemplary and that any of the substrate-product pairs disclosed herein suitable to produce a desired product and for which an appropriate activity is available for the conversion can be readily determined by one skilled in the art based on the teachings herein. Thus, the invention provides a nonnaturally occurring microbial organism containing at least one exogenous nucleic acid encoding an enzyme or protein, where the enzyme or protein converts the substrates and products of a pathway (see FIGS. 1, 8-13, 58, 62 and 63).

While generally described herein as a microbial organism that contains a 4-HB, 4-HBal, 4-HBCoA, BDO or putrescine pathway, it is understood that the invention additionally provides a non-naturally occurring microbial organism comprising at least one exogenous nucleic acid encoding a 4-HB, 4-HBal, 4-HBCoA, BDO or putrescine pathway enzyme or protein expressed in a sufficient amount to produce an intermediate of a 4-HB, 4-HBal, 4-HBCoA, BDO or putrescine pathway. For example, as disclosed herein, 4-HB, 4-HBal, 4-HBCoA, BDO and putrescine pathways are exemplified in FIGS. 1, 8-13, 58, 62 and 63. Therefore, in addition to a microbial organism containing, for example, a BDO pathway that produces BDO, the invention additionally provides a non-naturally occurring microbial organism comprising at least one exogenous nucleic acid encoding a BDO pathway enzyme, where the microbial organism produces a BDO pathway intermediate as a product rather than an intermediate of the pathway. In one exemplary embodiment as shown in FIG. 62, for example, the invention provides a microbial organism that produces succinyl-CoA, succinic semialdehyde, 4-hydroxybutyrate, 4-hydroxybutyryl-phosphate, 4-hydroxybutyryl-CoA, or 4-hydroxybutanal as a product rather than an intermediate. Another exemplary embodiment includes, for example, a microbial organism that produces alpha-ketoglutarate, 2,5-dioxopentanoic acid, 5-hydroxy-2-oxopentanoic acid, or 4-hydroxybutanal as a product rather than an intermediate. An exemplary embodiment in a putrescine pathway includes, for example, a microbial organism that produces glutamate, 4-aminobutyrate, or 4-aminobutanal as a product rather than an intermediate. An alternative embodiment in a putrescine pathway can be, for example, a microbial organism that produces 2,5-dioxopentanoate, 5-amino-2-oxopentanoate, or ornithine as a product rather than an intermediate.

It is understood that any of the pathways disclosed herein, as described in the Examples and exemplified in the Figures, including the pathways of FIGS. 1, 8-13, 58, 62 and 63, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 4-HB, 4-HBal, 4-HBCoA, BDO or putrescine pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

As disclosed herein, the product 4-hydroxybutyrate, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl 4-hydroxybutyrate, ethyl 4-hydroxybutyrate, and n-propyl 4-hydroxybutyrate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The production of 4-HB via biosynthetic modes using the microbial organisms of the invention is particularly useful because it can produce monomeric 4-HB. The non-naturally occurring microbial organisms of the invention and their biosynthesis of 4-HB and BDO family compounds also is particularly useful because the 4-HB product can be (1) secreted; (2) can be devoid of any derivatizations such as Coenzyme A; (3) avoids thermodynamic changes during biosynthesis; (4) allows direct biosynthesis of BDO, and (5) allows for the spontaneous chemical conversion of 4-HB to γ-butyrolactone (GBL) in acidic pH medium. This latter characteristic also is particularly useful for efficient chemical synthesis or biosynthesis of BDO family compounds such as 1,4-butanediol and/or tetrahydrofuran (THF), for example.

Microbial organisms generally lack the capacity to synthesize 4-HB and therefore any of the compounds disclosed herein to be within the 1,4-butanediol family of compounds or known by those in the art to be within the 1,4-butanediol family of compounds. Moreover, organisms having all of the requisite metabolic enzymatic capabilities are not known to produce 4-HB from the enzymes described and biochemical pathways exemplified herein. Rather, with the possible exception of a few anaerobic microorganisms described further below, the microorganisms having the enzymatic capability to use 4-HB as a substrate to produce, for example, succinate. In contrast, the non-naturally occurring microbial organisms of the invention can generate 4-HB, 4-HBal, 4-HBCoA, BDO and/or putrescine as a product. As described above, the biosynthesis of 4-HB in its monomeric form is not only particularly useful in chemical synthesis of BDO family of compounds, it also allows for the further biosynthesis of BDO family compounds and avoids altogether chemical synthesis procedures.

The non-naturally occurring microbial organisms of the invention that can produce 4-HB, 4-HBal, 4-HBCoA, BDO and/or putrescine are produced by ensuring that a host microbial organism includes functional capabilities for the complete biochemical synthesis of at least one 4-HB, 4-HBal, 4-HBCoA, BDO and/or putrscine biosynthetic pathway of the invention. Ensuring at least one requisite 4-HB, 4-HBal, 4-HBCoA or BDO biosynthetic pathway confers 4-HB biosynthesis capability onto the host microbial organism.

Several 4-HB biosynthetic pathways are exemplified herein and shown for purposes of illustration in FIG. 1. Additional 4-HB and BDO pathways are described in FIGS. 8-13. One 4-HB biosynthetic pathway includes the biosynthesis of 4-HB from succinate (the succinate pathway). The enzymes participating in this 4-HB pathway include CoA-independent succinic semialdehyde dehydrogenase and 4-hydroxybutanoate dehydrogenase. In this pathway, CoA-independent succinic semialdehyde dehydrogenase catalyzes the reverse reaction to the arrow shown in FIG. 1. Another 4-HB biosynthetic pathway includes the biosynthesis from succinate through succinyl-CoA (the succinyl-CoA pathway). The enzymes participating in this 4-HB pathway include succinyl-CoA synthetase, CoA-dependent succinic semialdehyde dehydrogenase and 4-hydroxybutanoate dehydrogenase. Three other 4-HB biosynthetic pathways include the biosynthesis of 4-HB from α-ketoglutarate (the α-ketoglutarate pathways). Hence, a third 4-HB biosynthetic pathway is the biosynthesis of succinic semialdehyde through glutamate: succinic semialdehyde transaminase, glutamate decarboxylase and 4-hydroxybutanoate dehydrogenase. A fourth 4-HB biosynthetic pathway also includes the biosynthesis of 4-HB from α-ketoglutarate, but utilizes α-ketoglutarate decarboxylase to catalyze succinic semialdehyde synthesis. 4-hydroxybutanoate dehydrogenase catalyzes the conversion of succinic semialdehyde to 4-HB. A fifth 4-HB biosynthetic pathway includes the biosynthesis from α-ketoglutarate through succinyl-CoA and utilizes α-ketoglutarate dehydrogenase to produce succinyl-CoA, which funnels into the succinyl-CoA pathway described above. Each of these 4-HB biosynthetic pathways, their substrates, reactants and products are described further below in the Examples. As described herein, 4-HB can further be biosynthetically converted to BDO by inclusion of appropriate enzymes to produce BDO (see Example). Thus, it is understood that a 4-HB pathway can be used with enzymes for converting 4-HB to BDO to generate a BDO pathway.

The non-naturally occurring microbial organisms of the invention can be produced by introducing expressible nucleic acids encoding one or more of the enzymes participating in one or more 4-HB, 4-HBal, 4-HBCoA, BDO or putrescine biosynthetic pathways. Depending on the host microbial organism chosen for biosynthesis, nucleic acids for some or all of a particular 4-HB, 4-HBal, 4-HBCoA, BDO or putrescine biosynthetic pathway can be expressed. For example, if a chosen host is deficient in one or more enzymes in a desired biosynthetic pathway, for example, the succinate to 4-HB pathway, then expressible nucleic acids for the deficient enzyme(s), for example, both CoA-independent succinic semialdehyde dehydrogenase and 4-hydroxybutanoate dehydrogenase in this example, are introduced into the host for subsequent exogenous expression. Alternatively, if the chosen host exhibits endogenous expression of some pathway enzymes, but is deficient in others, then an encoding nucleic acid is needed for the deficient enzyme(s) to achieve 4-HB, 4-HBal, 4-HBCoA, BDO or putrescine biosynthesis. For example, if the chosen host exhibits endogenous CoA-independent succinic semialdehyde dehydrogenase, but is deficient in 4-hydroxybutanoate dehydrogenase, then an encoding nucleic acid is needed for this enzyme to achieve 4-HB biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 4-HB, 4-HBal, 4-HBCoA, BDO and/or putrescine.

In like fashion, where 4-HB biosynthesis is selected to occur through the succinate to succinyl-CoA pathway (the succinyl-CoA pathway), encoding nucleic acids for host deficiencies in the enzymes succinyl-CoA synthetase, CoA-dependent succinic semialdehyde dehydrogenase and/or 4-hydroxybutanoate dehydrogenase are to be exogenously expressed in the recipient host. Selection of 4-HB biosynthesis through the α-ketoglutarate to succinic semialdehyde pathway (the α-ketoglutarate pathway) can utilize exogenous expression for host deficiencies in one or more of the enzymes for glutamate:succinic semialdehyde transaminase, glutamate decarboxylase and/or 4-hydroxybutanoate dehydrogenase, or α-ketoglutarate decarboxylase and 4-hydroxybutanoate dehydrogenase. One skilled in the art can readily determine pathway enzymes for production of 4-HB or BDO, as disclosed herein.

Depending on the 4-HB, 4-HBal, 4-HBCoA, BDO or putrescine biosynthetic pathway constituents of a selected host microbial organism, the non-naturally occurring microbial organisms of the invention will include at least one exogenously expressed 4-HB, 4-HB, 4-HBCoA, BDO or putrescine pathway-encoding nucleic acid and up to all encoding nucleic acids for one or more 4-HB or BDO biosynthetic pathways. For example, 4-HB, 4-HBal, 4-HBCoA, BDO or putrescine biosynthesis can be established in a host deficient in a pathway enzyme or protein through exogenous expression of the corresponding encoding nucleic acid. In a host deficient in all enzymes or proteins of a 4-HB, 4-HB, 4-HBCoA, BDO or putrescine pathway, exogenous expression of all enzyme or proteins in the pathway can be included, although it is understood that all enzymes or proteins of a pathway can be expressed even if the host contains at least one of the pathway enzymes or proteins. If desired, exogenous expression of all enzymes or proteins in a pathway for production of 4-HB, 4-HB, 4-HBCoA, BDO or putrescine can be included. For example, 4-HB biosynthesis can be established from all five pathways in a host deficient in 4-hydroxybutanoate dehydrogenase through exogenous expression of a 4-hydroxybutanoate dehydrogenase encoding nucleic acid. In contrast, 4-HB biosynthesis can be established from all five pathways in a host deficient in all eight enzymes through exogenous expression of all eight of CoA-independent succinic semialdehyde dehydrogenase, succinyl-CoA synthetase, CoA-dependent succinic semialdehyde dehydrogenase, glutamate: succinic semialdehyde transaminase, glutamate decarboxylase, α-ketoglutarate decarboxylase, α-ketoglutarate dehydrogenase and 4-hydroxybutanoate dehydrogenase.

Given the teachings and guidance provided herein, those skilled in the art will understand that the number of encoding nucleic acids to introduce in an expressible form will, at least, parallel 4-HB, 4-HBal, 4-HBCoA, BDO or putrescine pathway deficiencies of the selected host microbial organism. Therefore, a non-naturally occurring microbial organism of the invention can have one, two, three, four, five, six, seven, eight or up to all nucleic acids encoding the enzymes disclosed herein constituting one or more 4-HB, 4-HBal, 4-HBCoA, BDO or putrescine biosynthetic pathways. In some embodiments, the non-naturally occurring microbial organisms also can include other genetic modifications that facilitate or optimize 4-HB, 4-HBal, 4-HBCoA, BDO or putrescine biosynthesis or that confer other useful functions onto the host microbial organism. One such other functionality can include, for example, augmentation of the synthesis of one or more of 4-HB pathway precursors such as succinate, succinyl-CoA, α-ketoglutarate, 4-aminobutyrate, glutamate, acetoacetyl-CoA, and/or homoserine.

Generally, a host microbial organism is selected such that it produces the precursor of a 4-HB, 4-HBal, 4-HBCoA, BDO or putrescine pathway, either as a naturally produced molecule or as an engineered product that either provides de novo production of a desired precursor or increased production of a precursor naturally produced by the host microbial organism. For example, succinyl-CoA, α-ketoglutarate, 4-aminobutyrate, glutamate, acetoacetyl-CoA, and homoserine are produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a 4-HB, 4-HBal, 4-HBCoA, BDO or putrescine pathway.

In some embodiments, a non-naturally occurring microbial organism of the invention is generated from a host that contains the enzymatic capability to synthesize 4-HB, 4-HBal, 4-HBCoA, BDO or putrescine. In this specific embodiment it can be useful to increase the synthesis or accumulation of a 4-HB, 4-HBal, 4-HBCoA, BDO or putrescine pathway product to, for example, drive 4-HB, 4-HBal, 4-HBCoA, BDO or putrescine pathway reactions toward 4-HB, 4-HBal, 4-HBCoA, BDO or putrescine production. Increased synthesis or accumulation can be accomplished by, for example, overexpression of nucleic acids encoding one or more of the 4-HB, 4-HBal, 4-HBCoA, BDO or putrescine pathway enzymes disclosed herein. Over expression of the 4-HB, 4-HBal, 4-HBCoA, BDO or putrescine pathway enzyme or enzymes can occur, for example, through exogenous expression of the endogenous gene or genes, or through exogenous expression of the heterologous gene or genes. Therefore, naturally occurring organisms can be readily generated to be non-naturally 4-HB, 4-HBal, 4-HBCoA, BDO or putrescine producing microbial organisms of the invention through overexpression of one, two, three, four, five, six and so forth up to all nucleic acids encoding 4-HB, 4-HBal, 4-HBCoA, BDO or putrescine biosynthetic pathway enzymes. In addition, a non-naturally occurring organism can be generated by mutagenesis of an endogenous gene that results in an increase in activity of an enzyme in the 4-HB, 4-HBal, 4-HBCoA, BDO or putrescine biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism (see Examples).

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene which results in a truncated gene product, or by any of various mutation strategies that inactivate the encoded gene product. One particularly useful method of gene disruption is complete gene deletion because it reduces or eliminates the occurrence of genetic reversions in the non-naturally occurring microorganisms of the invention.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can optionally be obligatory, meaning that the biosynthesis of the referenced biochemical is an obligatory product produced during the growth phase of a microorganism.

Sources of encoding nucleic acids for a 4-HB, 4-HBal, 4-HBCoA, BDO or putrescine pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum*, marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K-10, *Mycobacterium marinum M, Tsukamurella paurometabola* DSM 20162, *Cyanobium* PCC7001, *Dictyostelium discoideum* AX4, and others disclosed herein (see Examples). For example, microbial organisms having 4-HB, 4-HBal, 4-HBCoA, BDO or putrescine biosynthetic production are exemplified herein with reference to *E. coli* and yeast hosts. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 4-HB, 4-HBal, 4-HBCoA, BDO or putrescine biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 4-HB, 4-HBal, 4-HBCoA, BDO or putrescine and other compounds of the invention described herein with reference to a particular organism such as *E. coli* or yeast can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 4-HB, 4-HBal, BDO or putrescine biosynthetic pathway exists in an unrelated species, 4-HB, 4-HBal, BDO or putrescine biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 4-HB, such as monomeric 4-HB, 4-HBal, BDO or putrescine.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizobus oryzae,* and the like. *E. coli* is a particularly useful host organisms since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Methods for constructing and testing the expression levels of a non-naturally occurring 4-HB-, 4-HBal-, 4-HBCoA-, BDO-, or putrescine-producing host can be performed, for example, by recombinant and detection methods well known in the art. Such methods can be found described in, for example, Sambrook et al., *Molecular Cloning: A Laboratory Manual, Third Ed.*, Cold Spring Harbor Laboratory, New York (2001); Ausubel et al., *Current Protocols in Molecular Biology*, John Wiley and Sons, Baltimore, Md. (1999). 4-HB and GBL can be separated by, for example, HPLC using a Spherisorb 5 ODS1 column and a mobile phase of 70% 10 mM phosphate buffer (pH=7) and 30% methanol, and detected using a UV detector at 215 nm (Hennessy et al. 2004, J. Forensic Sci. 46(6):1-9). BDO is detected by gas chromatography or by HPLC and refractive index detector using an Aminex HPX-87H column and a mobile phase of 0.5 mM sulfuric acid (Gonzalez-Pajuelo et al., *Met. Eng.* 7:329-336 (2005)).

Exogenous nucleic acid sequences involved in a pathway for production of 4-HB, 4-HBal, 4-HBCoA, BDO or putrescine can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to harbor one or more 4-HB, 4-HBal, 4-HBCoA, BDO or putrescine biosynthetic pathway and/or one or more biosynthetic encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The non-naturally occurring microbial organisms of the invention are constructed using methods well known in the art as exemplified herein to exogenously express at least one nucleic acid encoding a 4-HB, 4-HBal, 4-HBCoA, BDO or putrescine pathway enzyme in sufficient amounts to produce 4-HB, such as monomeric 4-HB, 4-HBal, 4-HBCoA, BDO or putrescine. It is understood that the microbial organisms of the invention are cultured under conditions sufficient to produce 4-HB, 4-HBal, 4-HBCoA, BDO or putrescine. Exemplary levels of expression for 4-HB, 4-HBal, 4-HBCoA, BDO or putrescine enzymes in each pathway are described further below in the Examples. Following the teachings and guidance provided herein, the non-naturally occurring microbial organisms of the invention can achieve biosynthesis of 4-HB, such as monomeric 4-HB, 4-HBal, 4-HBCoA, BDO or putrescine resulting in intracellular concentrations between about 0.1-200 mM or more, for example, 0.1-25 mM or more. Generally, the intracellular concentration of 4-HB, such as monomeric 4-HB, 4-HBal, 4-HBCoA, BDO or putrescine is between about 3-150 mM or more, particularly about 5-125 mM or more, and more particularly between about 8-100 mM, for example, about 3-20 mM, particularly between about 5-15 mM and more particularly between about 8-12 mM, including about 10 mM, 20 mM, 50 mM, 80 mM or more. Intracellular concentrations between and above each of these exemplary ranges also can be achieved from the non-naturally occurring microbial organisms of the invention. In particular embodiments, the microbial organisms of the invention, particularly strains such as those disclosed herein (see Examples XII-XIX and Table 28), can provide improved production of a desired product such as 4-HB, 4-HBal, 4-HBCoA, BDO or putrescine by increasing the production of 4-HB, 4-HBal, 4-HBCoA, BDO or putrescine and/or decreasing undesirable byproducts. Such production levels include, but are not limited to, those disclosed herein and including from about 1 gram to about 25 grams per liter, for example about 2, 3, 4, 5, 6, 7, 8, 9, 10, 11, 12, 13, 14, 15, 16, 17, 18, 19, 20, 21, 22, 23, 24, or even higher amounts of product per liter.

In addition to the culturing and fermentation conditions disclosed herein, growth condition for achieving biosynthesis of BDO, 4-HB, 4-HBCoA, 4-HBal and/or putrescine can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethyl slfoniopropionate, 3-dimethylsulfonio-2-methyl-propionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic conditions or substantially anaerobic, the 4-HB, 4-HBal, 4-HBCoA, BDO or putrescine producers can synthesize 4-HB, 4-HBal, 4-HBCoA, BDO or putrescine at intracellular concentrations of 5-10 mM or more as well as all other concentrations exemplified herein. It is understood that, even though the above description refers to intracellular concentrations, 4-HB, 4-HBal, 4-HBCoA, BDO or putrescine producing microbial organisms can produce 4-HB, 4-HBal, 4-HBCoA, BDO or putrescine intracellularly and/or secrete the product into the culture medium.

In some embodiments, the carbon feedstock and other cellular uptake sources such as phosphate, ammonia, sulfate, chloride and other halogens can be chosen to alter the isotopic distribution of the atoms present in 4-HB, 4-HBal, 4-HBCoA, BDO or putrescine or any 4-HB, 4-HBal, 4-HBCoA, BDO or putrescine pathway intermediate. The various carbon feedstock and other uptake sources enumerated above will be referred to herein, collectively, as "uptake sources." Uptake sources can provide isotopic enrichment for any atom present in the product 4-HB, 4-HBal, 4-HBCoA, BDO or putrescine or 4-HB, 4-HBal, 4-HBCoA, BDO or putrescine pathway intermediate including any 4-HB, 4-HBal, 4-HBCoA, BDO or putrescine impurities generated in diverging away from the pathway at any point. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S-B)/(M-B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil. Olsson, *The use of Oxalic acid as a Standard*. in, *Radiocarbon Variations and Absolute Chronology*, Nobel Symposium, 12th Proc., John Wiley & Sons, New York (1970). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×$10^{12}$ (Karlen et al., Arkiv Geoftsik, 4:465-471 (1968)). The standard calculations take into account the differential uptake of one istope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since March 2011 of the polymeric carbon derives from renewable 1,3-propanediol and August 2011 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides 4-HB, 4-HBal, 4-HBCoA, BDO or putrescine or a 4-HB, 4-HBal, 4-HBCoA, BDO or putrescine intermediate that has a carbon-12, carbon-13, and carbon-14 ratio that reflects an atmospheric carbon uptake source. For example, in some aspects the 4-HB, 4-HBal, 4-HBCoA, BDO or putrescine or a 4-HB, 4-HBal, 4-HBCoA, BDO or putrescine intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides 4-HB, 4-HBal, 4-HBCoA, BDO or putrescine or a 4-HB, 4-HBal, 4-HBCoA, BDO or putrescine intermediate that has a carbon-12, carbon-13, and carbon-14 ratio that reflects petroleum-based carbon uptake source. In this aspect, the 4-HB, 4-HBal, 4-HBCoA, BDO or putrescine or a 4-HB, 4-HBal, 4-HBCoA, BDO or putrescine intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides 4-HB, 4-HBal, 4-HBCoA, BDO or putrescine or a 4-HB, 4-HBal, 4-HBCoA, BDO or putrescine intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced 4-HB, 4-HBal, 4-HBCoA, BDO or putrescine or 4-HB, 4-HBal, 4-HBCoA, BDO or putrescine intermediate as disclosed herein, and to the products derived therefrom, wherein the 4-HB, 4-HBal, 4-HBCoA, BDO or putrescine or a 4-HB, 4-HBal, 4-HBCoA, BDO or putrescine intermediate has a carbon-12, carbon-13, and carbon-14 isotope ratio of about the same value as the $CO_2$ that occurs in the environment. For example, in some aspects the invention provides: bioderived 4-HB, 4-HBal, 4-HBCoA, BDO or putrescine or a bioderived 4-HB, 4-HBal, 4-HBCoA, BDO or putrescine intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived 4-HB, 4-HBal, 4-HBCoA, BDO or putrescine or a bio-derived 4-HB, 4-HBal, 4-HBCoA, BDO or putrescine intermediate as disclosed herein, wherein the bioderived product is chemically modified to generate a final product. Methods of chemically modifying a bioderived product of 4-HB, 4-HBal, 4-HBCoA, BDO or putrescine, or an intermediate thereof, to generate a desired product are well known to those skilled in the art, as described herein. The invention further provides plastics, elastic fibers, polyurethanes, polyesters, including polyhydroxyalkanoates such as poly-4-hydroxybutyrate (P4HB) or co-polymers thereof, poly(tetramethylene ether) glycol (PTMEG) (also referred to as PTMO, polytetramethylene oxide) and polyurethane-polyurea copolymers, referred to as spandex, elastane orLycra™, nylons, and the like, having a carbon-12 versus carbon-13 versus carbon-14 isotope ratio of about the same value as the $CO_2$ that occurs in the environment, wherein the plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, and nylons are generated directly from or in combination with bioderived 4-HB, 4-HBal, 4-HBCoA, BDO or putrescine or a bioderived 4-HB, 4-HBal, 4-HBCoA, BDO or putrescine intermediate as disclosed herein.

The products 4-HB, 4-HBal, 4-HBCoA, BDO or putrescine are chemicals commonly used in many commercial and industrial applications. Non-limiting examples of such applications include production of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane orLycra™, and nylons. Moreover, 4-HB, 4-HBal, 4-HBCoA, BDO or putrescine are also used as a raw material in the production of a wide range of products including plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane orLycra™, nylons. Accordingly, in some embodiments, the invention provides biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, nylons comprising one or more bioderived 4-HB, 4-HBal, 4-HBCoA, BDO or putrescine or bioderived 4-HB, 4-HBal, 4-HBCoA, BDO or putrescine intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, nylons comprising bioderived 4-HB, 4-HBal, 4-HBCoA, BDO or putrescine or bioderived 4-HB, 4-HBal, 4-HBCoA, BDO or putrescine intermediate, wherein the bioderived 4-HB, 4-HBal, 4-HBCoA, BDO or putrescine or bioderived 4-HB, 4-HBal, 4-HBCoA, BDO or putrescine intermediate includes all or part of the 4-HB, 4-HBal, 4-HBCoA, BDO or putrescine or 4-HB, 4-HBal, 4-HBCoA, BDO or putrescine intermediate used in the production of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, and nylons. Thus, in some aspects, the invention provides a biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, and nylons comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 4-HB, 4-HBal, 4-HBCoA, BDO or putrescine or bioderived 4-HB, 4-HBal, 4-HBCoA, BDO or putrescine intermediate as disclosed herein. Additionally, in some aspects, the invention provides a biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, and nylons wherein the 4-HB, 4-HBal, 4-HBCoA, BDO or putrescine or 4-HB, 4-HBal, 4-HBCoA, BDO or putrescine intermediate used in its production is a combination of bioderived and petroleum derived 4-HB, 4-HBal, 4-HBCoA, BDO or putrescine or 4-HB, 4-HBal, 4-HBCoA, BDO or putrescine intermediate. For example, a biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, and nylons can be produced using 50% bioderived the 4-HB, 4-HBal, 4-HBCoA, BDO or putrescine and 50% petroleum derived 4-HB, 4-HBal, 4-HBCoA, BDO or putrescine or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide) and polyurethane-polyurea copolymers, referred to as spandex, elastane or Lycra™, and nylons using the bioderived 4-HB, 4-HBal, 4-HBCoA, BDO or putrescine or bioderived 4-HB, 4-HBal, 4-HBCoA, BDO or putrescine intermediate of the invention are well known in the art.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 4-HB, 4-HBal, 4-HBCoA, BDO or putrescine includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The invention also provides a non-naturally occurring microbial biocatalyst including a microbial organism having 4-hydroxybutanoic acid (4-HB) and 1,4-butanediol (BDO) biosynthetic pathways that include at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate: succinic semialdehyde transaminase, glutamate decarboxylase, CoA-independent aldehyde dehydrogenase, CoA-dependent aldehyde dehydrogenase or alcohol dehydrogenase, wherein the exogenous nucleic acid is expressed in sufficient amounts to produce 1,4-butanediol (BDO). 4-Hydroxybutyrate:CoA transferase also is known as 4-hydroxybutyryl CoA:acetyl-CoA transferase. Additional 4-HB or BDO pathway enzymes are also disclosed herein (see Examples and FIGS. 8-13).

The invention further provides non-naturally occurring microbial biocatalyst including a microbial organism having 4-hydroxybutanoic acid (4-HB) and 1,4-butanediol (BDO) biosynthetic pathways, the pathways include at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-butyrate kinase, phosphotransbutyrylase, α-ketoglutarate decarboxylase, aldehyde dehydrogenase, alcohol dehydrogenase or an aldehyde/alcohol dehydrogenase, wherein the exogenous nucleic acid is expressed in sufficient amounts to produce 1,4-butanediol (BDO).

Non-naturally occurring microbial organisms also can be generated which biosynthesize BDO. As with the 4-HB producing microbial organisms of the invention, the BDO producing microbial organisms also can produce intracellularly or secret the BDO into the culture medium. Following the teachings and guidance provided previously for the construction of microbial organisms that synthesize 4-HB, additional BDO pathways can be incorporated into the 4-HB producing microbial organisms to generate organisms that also synthesize BDO and other BDO family compounds. The chemical synthesis of BDO and its downstream products are known. The non-naturally occurring microbial organisms of the invention capable of BDO biosynthesis circumvent these chemical synthesis using 4-HB as an entry point as illustrated in FIG. 1. As described further below, the 4-HB producers also can be used to chemically convert 4-HB to GBL and then to BDO or THF, for example. Alternatively, the 4-HB producers can be further modified to include biosynthetic capabilities for conversion of 4-HB and/or GBL to BDO.

The additional BDO pathways to introduce into 4-HB producers include, for example, the exogenous expression in a host deficient background or the overexpression of one or more of the enzymes exemplified in FIG. 1 as steps 9-13. One such pathway includes, for example, the enzyme activities necessary to carryout the reactions shown as steps 9, 12 and 13 in FIG. 1, where the aldehyde and alcohol dehydrogenases can be separate enzymes or a multifunctional enzyme having both aldehyde and alcohol dehydrogenase activity. Another such pathway includes, for example, the enzyme activities necessary to carry out the reactions shown as steps 10, 11, 12 and 13 in FIG. 1, also where the aldehyde and alcohol dehydrogenases can be separate enzymes or a multifunctional enzyme having both aldehyde and alcohol dehydrogenase activity. Accordingly, the additional BDO pathways to introduce into 4-HB producers include, for example, the exogenous expression in a host deficient background or the overexpression of one or more of a 4-hydroxybutyrate: CoA transferase, butyrate kinase, phosphotransbutyrylase, CoA-independent aldehyde dehydrogenase, CoA-dependent aldehyde dehydrogenase or an alcohol dehydrogenase. In the absence of endogenous acyl-CoA synthetase capable of modifying 4-HB, the non-naturally occurring BDO producing microbial organisms can further include an exogenous acyl-CoA synthetase selective for 4-HB, or the combination of multiple enzymes that have as a net reaction conversion of 4-HB into 4-HB-CoA. As exemplified further below in the Examples, butyrate kinase and phosphotransbutyrylase exhibit BDO pathway activity and catalyze the conversions illustrated in FIG. 1 with a 4-HB substrate. Therefore, these enzymes also can be referred to herein as 4-hydroxybutyrate kinase and phosphotranshydroxybutyrylase respectively.

Exemplary alcohol and aldehyde dehydrogenases that can be used for these in vivo conversions from 4-HB to BDO are listed below in Table 1.

TABLE 1

Alcohol and Aldehyde Dehydrogenases for Conversion of 4-HB to BDO.

ALCOHOL DEHYDROGENASES

| | |
|---|---|
| ec:1.1.1.1 | alcohol dehydrogenase |
| ec:1.1.1.2 | alcohol dehydrogenase (NADP+) |
| ec:1.1.1.4 | (R,R)-butanediol dehydrogenase |
| ec:1.1.1.5 | acetoin dehydrogenase |
| ec:1.1.1.6 | glycerol dehydrogenase |
| ec:1.1.1.7 | propanediol-phosphate dehydrogenase |
| ec:1.1.1.8 | glycerol-3-phosphate dehydrogenase (NAD+) |
| ec:1.1.1.11 | D-arabinitol 4-dehydrogenase |
| ec:1.1.1.12 | L-arabinitol 4-dehydrogenase |
| ec:1.1.1.13 | L-arabinitol 2-dehydrogenase |
| ec:1.1.1.14 | L-iditol 2-dehydrogenase |

TABLE 1-continued

Alcohol and Aldehyde Dehydrogenases for Conversion of 4-HB to BDO.

| | |
|---|---|
| ec:1.1.1.15 | D-iditol 2-dehydrogenase |
| ec:1.1.1.16 | galactitol 2-dehydrogenase |
| ec:1.1.1.17 | mannitol-1-phosphate 5-dehydrogenase |
| ec:1.1.1.18 | inositol 2-dehydrogenase |
| ec:1.1.1.21 | aldehyde reductase |
| ec:1.1.1.23 | histidinol dehydrogenase |
| ec:1.1.1.26 | glyoxylate reductase |
| ec:1.1.1.27 | L-lactate dehydrogenase |
| ec:1.1.1.28 | D-lactate dehydrogenase |
| ec:1.1.1.29 | glycerate dehydrogenase |
| ec:1.1.1.30 | 3-hydroxybutyrate dehydrogenase |
| ec:1.1.1.31 | 3-hydroxyisobutyrate dehydrogenase |
| ec:1.1.1.35 | 3-hydroxyacyl-CoA dehydrogenase |
| ec:1.1.1.36 | acetoacetyl-CoA reductase |
| ec:1.1.1.37 | malate dehydrogenase |
| ec:1.1.1.38 | malate dehydrogenase (oxaloacetate-decarboxylating) |
| ec:1.1.1.39 | malate dehydrogenase (decarboxylating) |
| ec:1.1.1.40 | malate dehydrogenase (oxaloacetate-decarboxylating) (NADP+) |
| ec:1.1.1.41 | isocitrate dehydrogenase (NAD+) |
| ec:1.1.1.42 | isocitrate dehydrogenase (NADP+) |
| ec:1.1.1.54 | allyl-alcohol dehydrogenase |
| ec:1.1.1.55 | lactaldehyde reductase (NADPH) |
| ec:1.1.1.56 | ribitol 2-dehydrogenase |
| ec:1.1.1.59 | 3-hydroxypropionate dehydrogenase |
| ec:1.1.1.60 | 2-hydroxy-3-oxopropionate reductase |
| ec:1.1.1.61 | 4-hydroxybutyrate dehydrogenase |
| ec:1.1.1.66 | omega-hydroxydecanoate dehydrogenase |
| ec:1.1.1.67 | mannitol 2-dehydrogenase |
| ec:1.1.1.71 | alcohol dehydrogenase [NAD(P)+] |
| ec:1.1.1.72 | glycerol dehydrogenase (NADP+) |
| ec:1.1.1.73 | octanol dehydrogenase |
| ec:1.1.1.75 | (R)-aminopropanol dehydrogenase |
| ec:1.1.1.76 | (S,S)-butanediol dehydrogenase |
| ec:1.1.1.77 | lactaldehyde reductase |
| ec:1.1.1.78 | methylglyoxal reductase (NADH-dependent) |
| ec:1.1.1.79 | glyoxylate reductase (NADP+) |
| ec:1.1.1.80 | isopropanol dehydrogenase (NADP+) |
| ec:1.1.1.81 | hydroxypyruvate reductase |
| ec:1.1.1.82 | malate dehydrogenase (NADP+) |
| ec:1.1.1.83 | D-malate dehydrogenase (decarboxylating) |
| ec:1.1.1.84 | dimethylmalate dehydrogenase |
| ec:1.1.1.85 | 3-isopropylmalate dehydrogenase |
| ec:1.1.1.86 | ketol-acid reductoisomerase |
| ec:1.1.1.87 | homoisocitrate dehydrogenase |
| ec:1.1.1.88 | hydroxymethylglutaryl-CoA reductase |
| ec:1.1.1.90 | aryl-alcohol dehydrogenase |
| ec:1.1.1.91 | aryl-alcohol dehydrogenase (NADP+) |
| ec:1.1.1.92 | oxaloglycolate reductase (decarboxylating) |
| ec:1.1.1.94 | glycerol-3-phosphate dehydrogenase [NAD(P)+] |
| ec:1.1.1.95 | phosphoglycerate dehydrogenase |
| ec:1.1.1.97 | 3-hydroxybenzyl-alcohol dehydrogenase |
| ec:1.1.1.101 | acylglycerone-phosphate reductase |
| ec:1.1.1.103 | L-threonine 3-dehydrogenase |
| ec:1.1.1.104 | 4-oxoproline reductase |
| ec:1.1.1.105 | retinol dehydrogenase |
| ec:1.1.1.110 | indolelactate dehydrogenase |
| ec:1.1.1.112 | indanol dehydrogenase |
| ec:1.1.1.113 | L-xylose 1-dehydrogenase |
| ec:1.1.1.129 | L-threonate 3-dehydrogenase |
| ec:1.1.1.137 | ribitol-5-phosphate 2-dehydrogenase |
| ec:1.1.1.138 | mannitol 2-dehydrogenase (NADP+) |
| ec:1.1.1.140 | sorbitol-6-phosphate 2-dehydrogenase |
| ec:1.1.1.142 | D-pinitol dehydrogenase |
| ec:1.1.1.143 | sequoyitol dehydrogenase |
| ec:1.1.1.144 | perillyl-alcohol dehydrogenase |
| ec:1.1.1.156 | glycerol 2-dehydrogenase (NADP+) |
| ec:1.1.1.157 | 3-hydroxybutyryl-CoA dehydrogenase |
| ec:1.1.1.163 | cyclopentanol dehydrogenase |
| ec:1.1.1.164 | hexadecanol dehydrogenase |
| ec:1.1.1.165 | 2-alkyn-1-ol dehydrogenase |
| ec:1.1.1.166 | hydroxycyclohexanecarboxylate dehydrogenase |
| ec:1.1.1.167 | hydroxymalonate dehydrogenase |
| ec:1.1.1.174 | cyclohexane-1,2-diol dehydrogenase |
| ec:1.1.1.177 | glycerol-3-phosphate 1-dehydrogenase (NADP+) |
| ec:1.1.1.178 | 3-hydroxy-2-methylbutyryl-CoA dehydrogenase |
| ec:1.1.1.185 | L-glycol dehydrogenase |

TABLE 1-continued

Alcohol and Aldehyde Dehydrogenases for Conversion of 4-HB to BDO.

| EC Number | Enzyme Name |
|---|---|
| ec:1.1.1.190 | indole-3-acetaldehyde reductase (NADH) |
| ec:1.1.1.191 | indole-3-acetaldehyde reductase (NADPH) |
| ec:1.1.1.192 | long-chain-alcohol dehydrogenase |
| ec:1.1.1.194 | coniferyl-alcohol dehydrogenase |
| ec:1.1.1.195 | cinnamyl-alcohol dehydrogenase |
| ec:1.1.1.198 | (+)-borneol dehydrogenase |
| ec:1.1.1.202 | 1,3-propanediol dehydrogenase |
| ec:1.1.1.207 | (−)-menthol dehydrogenase |
| ec:1.1.1.208 | (+)-neomenthol dehydrogenase |
| ec:1.1.1.216 | farnesol dehydrogenase |
| ec:1.1.1.217 | benzyl-2-methyl-hydroxybutyrate dehydrogenase |
| ec:1.1.1.222 | (R)-4-hydroxyphenyllactate dehydrogenase |
| ec:1.1.1.223 | isopiperitenol dehydrogenase |
| ec:1.1.1.226 | 4-hydroxycyclohexanecarboxylate dehydrogenase |
| ec:1.1.1.229 | diethyl 2-methyl-3-oxosuccinate reductase |
| ec:1.1.1.237 | hydroxyphenylpyruvate reductase |
| ec:1.1.1.244 | methanol dehydrogenase |
| ec:1.1.1.245 | cyclohexanol dehydrogenase |
| ec:1.1.1.250 | D-arabinitol 2-dehydrogenase |
| ec:1.1.1.251 | galactitol 1-phosphate 5-dehydrogenase |
| ec:1.1.1.255 | mannitol dehydrogenase |
| ec:1.1.1.256 | fluoren-9-ol dehydrogenase |
| ec:1.1.1.257 | 4-(hydroxymethyl)benzenesulfonate dehydrogenase |
| ec:1.1.1.258 | 6-hydroxyhexanoate dehydrogenase |
| ec:1.1.1.259 | 3-hydroxypimeloyl-CoA dehydrogenase |
| ec:1.1.1.261 | glycerol-1-phosphate dehydrogenase [NAD(P)+] |
| ec:1.1.1.265 | 3-methylbutanal reductase |
| ec:1.1.1.283 | methylglyoxal reductase (NADPH-dependent) |
| ec:1.1.1.286 | isocitrate-homoisocitrate dehydrogenase |
| ec:1.1.1.287 | D-arabinitol dehydrogenase (NADP+) butanol dehydrogenase |

ALDEHYDE DEHYDROGENASES

| EC Number | Enzyme Name |
|---|---|
| ec:1.2.1.2 | formate dehydrogenase |
| ec:1.2.1.3 | aldehyde dehydrogenase (NAD+) |
| ec:1.2.1.4 | aldehyde dehydrogenase (NADP+) |
| ec:1.2.1.5 | aldehyde dehydrogenase [NAD(P)+] |
| ec:1.2.1.7 | benzaldehyde dehydrogenase (NADP+) |
| ec:1.2.1.8 | betaine-aldehyde dehydrogenase |
| ec:1.2.1.9 | glyceraldehyde-3-phosphate dehydrogenase (NADP+) |
| ec:1.2.1.10 | acetaldehyde dehydrogenase (acetylating) |
| ec:1.2.1.11 | aspartate-semialdehyde dehydrogenase |
| ec:1.2.1.12 | glyceraldehyde-3-phosphate dehydrogenase (phosphorylating) |
| ec:1.2.1.13 | glyceraldehyde-3-phosphate dehydrogenase (NADP+) (phosphorylating) |
| ec:1.2.1.15 | malonate-semialdehyde dehydrogenase |
| ec:1.2.1.16 | succinate-semialdehyde dehydrogenase [NAD(P)+] |
| ec:1.2.1.17 | glyoxylate dehydrogenase (acylating) |
| ec:1.2.1.18 | malonate-semialdehyde dehydrogenase (acetylating) |
| ec:1.2.1.19 | aminobutyraldehyde dehydrogenase |
| ec:1.2.1.20 | glutarate-semialdehyde dehydrogenase |
| ec:1.2.1.21 | glycolaldehyde dehydrogenase |
| ec:1.2.1.22 | lactaldehyde dehydrogenase |
| ec:1.2.1.23 | 2-oxoaldehyde dehydrogenase (NAD+) |
| ec:1.2.1.24 | succinate-semialdehyde dehydrogenase |
| ec:1.2.1.25 | 2-oxoisovalerate dehydrogenase (acylating) |
| ec:1.2.1.26 | 2,5-dioxovalerate dehydrogenase |
| ec:1.2.1.27 | methylmalonate-semialdehyde dehydrogenase (acylating) |
| ec:1.2.1.28 | benzaldehyde dehydrogenase (NAD+) |
| ec:1.2.1.29 | aryl-aldehyde dehydrogenase |
| ec:1.2.1.30 | aryl-aldehyde dehydrogenase (NADP+) |
| ec:1.2.1.31 | L-aminoadipate-semialdehyde dehydrogenase |
| ec:1.2.1.32 | aminomuconate-semialdehyde dehydrogenase |
| ec:1.2.1.36 | retinal dehydrogenase |
| ec:1.2.1.39 | phenylacetaldehyde dehydrogenase |
| ec:1.2.1.41 | glutamate-5-semialdehyde dehydrogenase |
| ec:1.2.1.42 | hexadecanal dehydrogenase (acylating) |
| ec:1.2.1.43 | formate dehydrogenase (NADP+) |
| ec:1.2.1.45 | 4-carboxy-2-hydroxymuconate-6-semialdehyde dehydrogenase |
| ec:1.2.1.46 | formaldehyde dehydrogenase |
| ec:1.2.1.47 | 4-trimethylammoniobutyraldehyde dehydrogenase |
| ec:1.2.1.48 | long-chain-aldehyde dehydrogenase |
| ec:1.2.1.49 | 2-oxoaldehyde dehydrogenase (NADP+) |
| ec:1.2.1.51 | pyruvate dehydrogenase (NADP+) |
| ec:1.2.1.52 | oxoglutarate dehydrogenase (NADP+) |
| ec:1.2.1.53 | 4-hydroxyphenylacetaldehyde dehydrogenase |
| ec:1.2.1.57 | butanal dehydrogenase |
| ec:1.2.1.58 | phenylglyoxylate dehydrogenase (acylating) |
| ec:1.2.1.59 | glyceraldehyde-3-phosphate dehydrogenase (NAD(P)+) (phosphorylating) |
| ec:1.2.1.62 | 4-formylbenzenesulfonate dehydrogenase |
| ec:1.2.1.63 | 6-oxohexanoate dehydrogenase |
| ec:1.2.1.64 | 4-hydroxybenzaldehyde dehydrogenase |
| ec:1.2.1.65 | salicylaldehyde dehydrogenase |
| ec:1.2.1.66 | mycothiol-dependent formaldehyde dehydrogenase |
| ec:1.2.1.67 | vanillin dehydrogenase |
| ec:1.2.1.68 | coniferyl-aldehyde dehydrogenase |
| ec:1.2.1.69 | fluoroacetaldehyde dehydrogenase |
| ec:1.2.1.71 | succinylglutamate-semialdehyde dehydrogenas |

Other exemplary enzymes and pathways are disclosed herein (see Examples). Furthermore, it is understood that enzymes can be utilized for carry out reactions for which the substrate is not the natural substrate. While the activity for the non-natural substrate may be lower than the natural substrate, it is understood that such enzymes can be utilized, either as naturally occurring or modified using the directed evolution or adaptive evolution, as disclosed herein (see also Examples).

BDO production through any of the pathways disclosed herein are based, in part, on the identification of the appropriate enzymes for conversion of precursors to BDO. A number of specific enzymes for several of the reaction steps have been identified. For those transformations where enzymes specific to the reaction precursors have not been identified, enzyme candidates have been identified that are best suited for catalyzing the reaction steps. Enzymes have been shown to operate on a broad range of substrates, as discussed below. In addition, advances in the field of protein engineering also make it feasible to alter enzymes to act efficiently on substrates, even if not a natural substrate. Described below are several examples of broad-specificity enzymes from diverse classes suitable for a BDO pathway as well as methods that have been used for evolving enzymes to act on non-natural substrates.

A key class of enzymes in BDO pathways is the oxidoreductases that interconvert ketones or aldehydes to alcohols (1.1.1). Numerous exemplary enzymes in this class can operate on a wide range of substrates. An alcohol dehydrogenase (1.1.1.1) purified from the soil bacterium *Brevibacterium* sp KU 1309 (Hirano et al., J. Biosc. Bioeng. 100: 318-322 (2005)) was shown to operate on a plethora of aliphatic as well as aromatic alcohols with high activities. Table 2 shows the activity of the enzyme and its $K_m$ on different alcohols. The enzyme is reversible and has very high activity on several aldehydes also (Table 3).

TABLE 2

Relative activities of an alcohol dehydrogenase from *Brevibacterium* sp KU to oxidize various alcohols.

| Substrate | Relative Activity (0%) | $K_m$ (mM) |
|---|---|---|
| 2-Phenylethanol | 100* | 0.025 |
| (S)-2-Phenylpropanol | 156 | 0.157 |
| (R)-2-Phenylpropanol | 63 | 0.020 |
| Bynzyl alcohol | 199 | 0.012 |
| 3-Phenylpropanol | 135 | 0.033 |

TABLE 2-continued

Relative activities of an alcohol dehydrogenase from
Brevibacterium sp KU to oxidize various alcohols.

| Substrate | Relative Activity (0%) | $K_m$ (mM) |
|---|---|---|
| Ethanol | 76 | |
| 1-Butanol | 111 | |
| 1-Octanol | 101 | |
| 1-Dodecanol | 68 | |
| 1-Phenylethanol | 46 | |
| 2-Propanol | 54 | |

*The activity of 2-phenylethanol, corresponding to 19.2 U/mg, was taken as 100%.

TABLE 3

Relative activities of an alcohol dehydrogenase from Brevibacterium
sp KU 1309 to reduce various carbonyl compounds.

| Substrate | Relative Activity (%) | $K_m$ (mM) |
|---|---|---|
| Phenylacetaldehyde | 100 | 0.261 |
| 2-Phenylpropionaldehyde | 188 | 0.864 |
| 1-Octylaldehyde | 87 | |
| Acetophenone | 0 | |

Lactate dehydrogenase (1.1.1.27) from *Ralstonia eutropha* is another enzyme that has been demonstrated to have high activities on several 2-oxoacids such as 2-oxobutyrate, 2-oxopentanoate and 2-oxoglutarate (a C5 compound analogous to 2-oxoadipate) (Steinbuchel and Schlegel, *Eur. J. Biochem.* 130:329-334 (1983)). Column 2 in Table 4 demonstrates the activities of ldhA from *R. eutropha* (formerly *A. eutrophus*) on different substrates (Steinbuchel and Schlegel, supra, 1983).

TABLE 4

The in vitro activity of R. eutropha ldhA (Steinbuchel
and Schlegel, supra, 1983) on different substrates
and compared with that on pyruvate.

| Substrate | Activity (%) of L(+)-lactate dehydrogenase from A. eutrophus | L(+)-lactate dehydrogenase from rabbit muscle | D(−)-lactate dehydrogenase from L. leichmanii |
|---|---|---|---|
| Glyoxylate | 8.7 | 23.9 | 5.0 |
| Pyruvate | 100.0 | 100.0 | 100.0 |
| 2-Oxobutyrate | 107.0 | 18.6 | 1.1 |
| 2-Oxovalerate | 125.0 | 0.7 | 0.0 |
| 3-Methyl-2-oxobutyrate | 28.5 | 0.0 | 0.0 |
| 3-Methyl-2-oxovalerate | 5.3 | 0.0 | 0.0 |
| 4-Methyl-2-oxopentanoate | 39.0 | 1.4 | 1.1 |
| Oxaloacetate | 0.0 | 33.1 | 23.1 |
| 2-Oxoglutarate | 79.6 | 0.0 | 0.0 |
| 3-Fluoropyruvate | 33.6 | 74.3 | 40.0 |

Oxidoreductases that can convert 2-oxoacids to their acyl-CoA counterparts (1.2.1) have been shown to accept multiple substrates as well. For example, branched-chain 2-keto-acid dehydrogenase complex (BCKAD), also known as 2-oxoisovalerate dehydrogenase (1.2.1.25), participates in branched-chain amino acid degradation pathways, converting 2-keto acids derivatives of valine, leucine and isoleucine to their acyl-CoA derivatives and $CO_2$. In some organisms including *Rattus norvegicus* (Paxton et al., *Biochem. J.* 234:295-303 (1986)) and *Saccharomyces cerevisiae* (Sinclair et al., *Biochem. Mol Biol. Int.* 32:911-922 (1993), this complex has been shown to have a broad substrate range that includes linear oxo-acids such as 2-oxobutanoate and alpha-ketoglutarate, in addition to the branched-chain amino acid precursors.

Members of yet another class of enzymes, namely aminotransferases (2.6.1), have been reported to act on multiple substrates. Aspartate aminotransferase (aspA7) from *Pyrococcus fursious* has been identified, expressed in *E. coli* and the recombinant protein characterized to demonstrate that the enzyme has the highest activities towards aspartate and alpha-ketoglutarate but lower, yet significant activities towards alanine, glutamate and the aromatic amino acids (Ward et al., *Archaea* 133-141 (2002)). In another instance, an aminotransferase indentified from *Leishmania mexicana* and expressed in *E. coli* (Vernal et al., *FEMS Microbiol. Lett.* 229:217-222 (2003)) was reported to have a broad substrate specificity towards tyrosine (activity considered 100% on tyrosine), phenylalanine (90%), tryptophan (85%), aspartate (30%), leucine (25%) and methionine (25%), respectively (Vernal et al., *Mol. Biochem. Parasitol* 96:83-92 (1998)). Similar broad specificity has been reported for a tyrosine aminotransferase from *Trypanosoma cruzi*, even though both of these enzymes have a sequence homology of only 6%. The latter enzyme can accept leucine, methionine as well as tyrosine, phenylalanine, tryptophan and alanine as efficient amino donors (Nowicki et al., *Biochim. Biophys. Acta* 1546: 268-281 (2001)).

CoA transferases (2.8.3) have been demonstrated to have the ability to act on more than one substrate. Specifically, a CoA transferase was purified from *Clostridium acetobutylicum* and was reported to have the highest activities on acetate, propionate, and butyrate. It also had significant activities with valerate, isobutyrate, and crotonate (Wiesenborn et al., *Appl. Environ. Microbiol.* 55:323-329 (1989)). In another study, the *E. coli* enzyme acyl-CoA:acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink, *App. Environm. Microbiol.* 58:1435-1439 (1992)), valerate (Vanderwinkel et al., *Biochem. Biophys. Res Commun.* 33:902-908 (1968b)) and butanoate (Vanderwinkel et al., *Biochem. Biophys. Res Commun.* 33:902-908 (1968a).

Other enzyme classes additionally support broad substrate specificity for enzymes. Some isomerases (5.3.3) have also been proven to operate on multiple substrates. For example, L-rhamnose isomerase from *Pseudomonas stutzeri* catalyzes the isomerization between various aldoalses and ketoses (Yoshida et al., *J. Mol. Biol.* 365:1505-1516 (2007)). These include isomerization between L-rhamnose and L-rhamnulose, L-mannose and L-fructose, L-xylose and L-xylulose, D-ribose and D-ribulose, and D-allose and D-psicose.

In yet another class of enzymes, the phosphotransferases (2.7.1), the homoserine kinase (2.7.1.39) from *E. coli* that converts L-homoserine to L-homoserine phosphate, was found to phosphorylate numerous homoserine analogs. In these substrates, the carboxyl functional group at the R-position had been replaced by an ester or by a hydroxymethyl group (Huo and Viola, *Biochemistry* 35:16180-16185 (1996)). Table 5 demonstrates the broad substrate specificity of this kinase.

TABLE 5

The substrate specificity of homoserine kinase.

| Substrate | $k_{cat}$ | % $k_{cat}$ | $K_m$ (mM) | $k_{cat}/K_m$ |
|---|---|---|---|---|
| L-homoserine | 18.3 ± 0.1 | 100 | 0.14 ± 0.04 | 184 ± 17 |
| D-homoserine | 8.3 ± 1.1 | 32 | 31.8 ± 7.2 | 0.26 ± 0.03 |
| L-aspartate β-semialdehyde | 2.1 ± 0.1 | 8.2 | 0.28 ± 0.02 | 7.5 ± 0.3 |
| L-2-amino-1,4-butanediol | 2.0 ± 0.5 | 7.9 | 11.6 ± 6.5 | 0.17 ± 0.06 |
| L-2-amino-5-hydroxyvalerate | 2.5 ± 0.4 | 9.9 | 1.1 ± 0.5 | 2.3 ± 0.3 |
| L-homoserine methyl ester | 14.7 ± 2.6 | 80 | 4.9 ± 2.0 | 3.0 ± 0.6 |
| L-homoserine ethyl ester | 13.6 ± 0.8 | 74 | 1.9 ± 0.5 | 7.2 ± 1.7 |
| L-homoserine isopropyl ester | 13.6 ± 1.4 | 74 | 1.2 ± 0.5 | 11.3 ± 1.1 |
| L-homoserine n-propyl ester | 14.0 ± 0.4 | 76 | 3.5 ± 0.4 | 4.0 ± 1.2 |
| L-homoserine isobutyl ester | 16.4 ± 0.8 | 84 | 6.9 ± 1.1 | 2.4 ± 0.3 |
| L-homserine n-butyl ester | 29.1 ± 1.2 | 160 | 5.8 ± 0.8 | 5.0 ± 0.5 |

Another class of enzymes useful in BDO pathways is the acid-thiol ligases (6.2.1). Like enzymes in other classes, certain enzymes in this class have been determined to have broad substrate specificity. For example, acyl CoA ligase from Pseudomonas putida has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., Appl. Environ. Microbiol. 59:1149-1154 (1993)). A related enzyme, malonyl CoA synthetase (6.3.4.9) from Rhizobium trifolii could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., J. Am. Chem. Soc. 123:5822-5823 (2001)). Similarly, decarboxylases (4.1.1) have also been found with broad substrate ranges. Pyruvate decarboxylase (PDC), also termed keto-acid decarboxylase, is a key enzyme in alcoholic fermentation, catalyzing the decarboxylation of pyruvate to acetaldehyde. The enzyme isolated from Saccharomyces cerevisiae has a broad substrate range for aliphatic 2-keto acids including 2-ketobutyrate, 2-ketovalerate, and 2-phenylpyruvate (Li and Jordan, Biochemistry 38:10004-10012 (1999)). Similarly, benzoylformate decarboxylase has a broad substrate range and has been the target of enzyme engineering studies. The enzyme from Pseudomonas putida has been extensively studied and crystal structures of this enzyme are available (Polovnikova et al., Biochemistry 42:1820-1830 (2003); Hasson et al., Biochemistry 37:9918-9930 (1998)). Branched chain alpha-ketoacid decarboxylase (BCKA) has been shown to act on a variety of compounds varying in chain length from 3 to 6 carbons (Oku and Kaneda, J. Biol. Chem. 263:18386-18396 (1998); Smit et al., Appl. Environ. Microbiol. 71:303-311 (2005b)). The enzyme in Lactococcus lactis has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., Appl. Environ. Microbiol. 71:303-311 (2005a)).

Interestingly, enzymes known to have one dominant activity have also been reported to catalyze a very different function. For example, the cofactor-dependent phosphoglycerate mutase (5.4.2.1) from Bacillus stearothermophilus and Bacillus subtilis is known to function as a phosphatase as well (Rigden et al., Protein Sci. 10:1835-1846 (2001)). The enzyme from B. stearothermophilus is known to have activity on several substrates, including 3-phosphoglycerate, alpha-napthylphosphate, p-nitrophenylphosphate, AMP, fructose-6-phosphate, ribose-5-phosphate and CMP.

In contrast to these examples where the enzymes naturally have broad substrate specificities, numerous enzymes have been modified using directed evolution to broaden their specificity towards their non-natural substrates. Alternatively, the substrate preference of an enzyme has also been changed using directed evolution. Therefore, it is feasible to engineer a given enzyme for efficient function on a natural, for example, improved efficiency, or a non-natural substrate, for example, increased efficiency. For example, it has been reported that the enantioselectivity of a lipase from Pseudomonas aeruginosa was improved significantly (Reetz et al., Agnew. Chem. Int. Ed Engl. 36:2830-2832 (1997)). This enzyme hydrolyzed p-nitrophenyl 2-methyldecanoate with only 2% enantiomeric excess (ee) in favor of the (S)-acid. However, after four successive rounds of error-prone mutagenesis and screening, a variant was produced that catalyzed the requisite reaction with 81% ee (Reetz et al., Agnew. Chem. Int. Ed Engl. 36:2830-2832 (1997)).

Directed evolution methods have been used to modify an enzyme to function on an array of non-natural substrates. The substrate specificity of the lipase in P. aeruginosa was broadened by randomization of amino acid residues near the active site. This allowed for the acceptance of alpha-substituted carboxylic acid esters by this enzyme (Reetz et al., Agnew. Chem. Int. Ed Engl. 44:4192-4196 (2005)). In another successful modification of an enzyme, DNA shuffling was employed to create an Escherichia coli aminotransferase that accepted β-branched substrates, which were poorly accepted by the wild-type enzyme (Yano et al., Proc. Nat. Acad. Sci. U.S.A. 95:5511-5515 (1998)). Specifically, at the end of four rounds of shuffling, the activity of aspartate aminotransferase for valine and 2-oxovaline increased by up to five orders of magnitude, while decreasing the activity towards the natural substrate, aspartate, by up to 30-fold. Recently, an algorithm was used to design a retro-aldolase that could be used to catalyze the carbon-carbon bond cleavage in a non-natural and non-biological substrate, 4-hydroxy-4-(6-methoxy-2-naphthyl)-2-butanone (Jiang et al., Science 319:1387-1391 (2008)). These algorithms used different combinations of four different catalytic motifs to design new enzyme, and 20 of the selected designs for experimental characterization had four-fold improved rates over the uncatalyzed reaction (Jiang et al., Science 319: 1387-1391 (2008)). Thus, not only are these engineering approaches capable of expanding the array of substrates on which an enzyme can act, but they allow the design and construction of very efficient enzymes. For example, a method of DNA shuffling (random chimeragenesis on transient templates or RACHITT) was reported to lead to an engineered monooxygenase that had an improved rate of desulfurization on complex substrates as well as 20-fold faster conversion of a non-natural substrate (Coco et al., Nat. Biotechnol. 19:354-359 (2001)). Similarly, the specific activity of a sluggish mutant triosephosphate isomerase enzyme was improved up to 19-fold from 1.3 fold (Hermes et al., Proc. Nat. Acad. Sci. U.S.A. 87:696-700 1990)). This enhancement in specific activity was accomplished by using random mutagenesis over the whole length of the protein and the improvement could be traced back to mutations in six amino acid residues.

The effectiveness of protein engineering approaches to alter the substrate specificity of an enzyme for a desired substrate has also been demonstrated in several studies. Isopropylmalate dehydrogenase from *Thermus thermophilus* was modified by changing residues close to the active site so that it could now act on malate and D-lactate as substrates (Fujita et al., *Biosci. Biotechnol. Biochem.* 65:2695-2700 (2001)). In this study as well as in others, it was pointed out that one or a few residues could be modified to alter the substrate specificity. For example, the dihydroflavonol 4-reductase for which a single amino acid was changed in the presumed substrate-binding region could preferentially reduce dihydrokaempferol (Johnson et al., *Plant. J.* 25:325-333 (2001)). The substrate specificity of a very specific isocitrate dehydrogenase from *Escherichia coli* was changed form isocitrate to isopropylmalate by changing one residue in the active site (Doyle et al., *Biochemistry* 40:4234-4241 (2001)). Similarly, the cofactor specificity of a $NAD^+$-dependent 1,5-hydroxyprostaglandin dehydrogenase was altered to $NADP^+$ by changing a few residues near the N-terminal end (Cho et al., *Arch. Biochem. Biophys.* 419:139-146 (2003)). Sequence analysis and molecular modeling analysis were used to identify the key residues for modification, which were further studied by site-directed mutagenesis.

Numerous examples exist spanning diverse classes of enzymes where the function of enzyme was changed to favor one non-natural substrate over the natural substrate of the enzyme. A fucosidase was evolved from a galactosidase in *E. coli* by DNA shuffling and screening (Zhang et al., *Proc. Natl Acad. Sci. U.S.A.* 94:4504-4509 (1997)). Similarly, aspartate aminotransferase from *E. coli* was converted into a tyrosine aminotransferase using homology modeling and site-directed mutagenesis (Onuffer and Kirsch, *Protein Sci.*, 4:1750-1757 (1995)). Site-directed mutagenesis of two residues in the active site of benzoylformate decarboxylase from *P. putida* reportedly altered the affinity ($K_m$) towards natural and non-natural substrates (Siegert et al., *Protein Eng Des Sel* 18:345-357 (2005)). Cytochrome c peroxidase (CCP) from *Saccharomyces cerevisiae* was subjected to directed molecular evolution to generate mutants with increased activity against the classical peroxidase substrate guaiacol, thus changing the substrate specificity of CCP from the protein cytochrome c to a small organic molecule. After three rounds of DNA shuffling and screening, mutants were isolated which possessed a 300-fold increased activity against guaiacol and up to 1000-fold increased specificity for this substrate relative to that for the natural substrate (Iffland et al., *Biochemistry* 39:10790-10798 (2000)).

In some cases, enzymes with different substrate preferences than either of the parent enzymes have been obtained. For example, biphenyl-dioxygenase-mediated degradation of polychlorinated biphenyls was improved by shuffling genes from two bacteria, *Pseudomonas pseudoalcaligens* and *Burkholderia cepacia* (Kumamaru et al., *Nat. Biotechnol.* 16:663-666 (1998)). The resulting chimeric biphenyl oxygenases showed different substrate preferences than both the parental enzymes and enhanced the degradation activity towards related biphenyl compounds and single aromatic ring hydrocarbons such as toluene and benzene which were originally poor substrates for the enzyme.

In addition to changing enzyme specificity, it is also possible to enhance the activities on substrates for which the enzymes naturally have low activities. One study demonstrated that amino acid racemase from *P. putida* that had broad substrate specificity (on lysine, arginine, alanine, serine, methionine, cysteine, leucine and histidine among others) but low activity towards tryptophan could be improved significantly by random mutagenesis (Kino et al., *Appl. Microbiol. Biotechnol.* 73:1299-1305 (2007)). Similarly, the active site of the bovine BCKAD was engineered to favor alternate substrate acetyl-CoA (Meng and Chuang, *Biochemistry* 33:12879-12885 (1994)). An interesting aspect of these approaches is that even if random methods have been applied to generate these mutated enzymes with efficacious activities, the exact mutations or structural changes that confer the improvement in activity can be identified. For example, in the aforementioned study, the mutations that facilitated improved activity on tryptophan was traced back to two different positions.

Directed evolution has also been used to express proteins that are difficult to express. For example, by subjecting horseradish peroxidase to random mutagenesis and gene recombination, mutants were identified that had more than 14-fold higher activity than the wild type (Lin et al., *Biotechnol. Prog.* 15:467-471 (1999)).

Another example of directed evolution shows the extensive modifications to which an enzyme can be subjected to achieve a range of desired functions. The enzyme lactate dehydrogenase from *Bacillus stearothermophilus* was subjected to site-directed mutagenesis, and three amino acid substitutions were made at sites that were believed to determine the specificity towards different hydroxyacids (Clarke et al., *Biochem. Biophys. Res. Commun.* 148:15-23 (1987)). After these mutations, the specificity for oxaloacetate over pyruvate was increased to 500 in contrast to the wild type enzyme that had a catalytic specificity for pyruvate over oxaloacetate of 1000. This enzyme was further engineered using site-directed mutagenesis to have activity towards branched-chain substituted pyruvates (Wilks et al., *Biochemistry* 29:8587-8591 (1990)). Specifically, the enzyme had a 55-fold improvement in $K_{cat}$ for alpha-ketoisocaproate. Three structural modifications were made in the same enzyme to change its substrate specificity from lactate to malate. The enzyme was highly active and specific towards malate (Wilks et al., *Science* 242:1541-1544 (1988)). The same enzyme from *B. stearothermophilus* was subsequently engineered to have high catalytic activity towards alpha-keto acids with positively charged side chains, such as those containing ammonium groups (Hogan et al., *Biochemistry* 34:4225-4230 (1995)). Mutants with acidic amino acids introduced at position 102 of the enzyme favored binding of such side chain ammonium groups. The results obtained proved that the mutants showed up to 25-fold improvements in $k_{cat}/K_m$ values for omega-amino-alpha-keto acid substrates. Interestingly, this enzyme was also structurally modified to function as a phenyllactate dehydrogenase instead of a lactate dehydrogenase (Wilks et al., *Biochemistry* 31:7802-7806 1992). Restriction sites were introduced into the gene for the enzyme which allowede a region of the gene to be excised. This region coded for a mobile surface loop of the polypeptide (residues 98-110) which normally seals the active site from bulk solvent and is a major determinant of substrate specificity. The variable length and sequence loops were inserted so that hydroxyacid dehydrogenases with altered substrate specificities were generated. With one longer loop construction, activity with pyruvate was reduced one-million-fold but activity with phenylpyruvate was largely unaltered. A switch in specificity ($k_{cat}/K_m$) of 390,000-fold was achieved. The 1700:1 selectivity of this enzyme for phenylpyruvate over pyruvate is that required in a phenyllactate dehydrogenase. The studies described above indicate that various approaches of enzyme engineering can be used to obtain enzymes for the BDO pathways as disclosed herein.

As disclosed herein, biosynthetic pathways to 1,4-butanediol from a number of central metabolic intermediates are can be utilized, including acetyl-CoA, succinyl-CoA, alpha-ketoglutarate, glutamate, 4-aminobutyrate, and homoserine. Acetyl-CoA, succinyl-CoA and alpha-ketoglutarate are common intermediates of the tricarboxylic acid (TCA) cycle, a series of reactions that is present in its entirety in nearly all living cells that utilize oxygen for cellular respiration and is present in truncated forms in a number of anaerobic organisms. Glutamate is an amino acid that is derived from alpha-ketoglutarate via glutamate dehydrogenase or any of a number of transamination reactions (see FIG. 8B). 4-aminobutyrate can be formed by the decarboxylation of glutamate (see FIG. 8B) or from acetoacetyl-CoA via the pathway disclosed in FIG. 9C. Acetoacetyl-CoA is derived from the condensation of two acetyl-CoA molecules by way of the enzyme, acetyl-coenzyme A acetyltransferase, or equivalently, acetoacetyl-coenzyme A thiolase. Homoserine is an intermediate in threonine and methionine metabolism, formed from oxaloacetate via aspartate. The conversion of oxaloacetate to homoserine requires one NADH, two NADPH, and one ATP.

Pathways other than those exemplified above also can be employed to generate the biosynthesis of BDO in non-naturally occurring microbial organisms. In one embodiment, biosynthesis can be achieved using a L-homoserine to BDO pathway (see FIG. 13). This pathway has a molar yield of 0.90 mol/mol glucose, which appears restricted by the availability of reducing equivalents. A second pathway synthesizes BDO from acetoacetyl-CoA and is capable of achieving the maximum theoretical yield of 1.091 mol/mol glucose (see FIG. 9). Implementation of either pathway can be achieved by introduction of two exogenous enzymes into a host organism such as $E.$ $coli$, and both pathways can additionally complement BDO production via succinyl-CoA. Pathway enzymes, thermodynamics, theoretical yields and overall feasibility are described further below.

Figure 2:
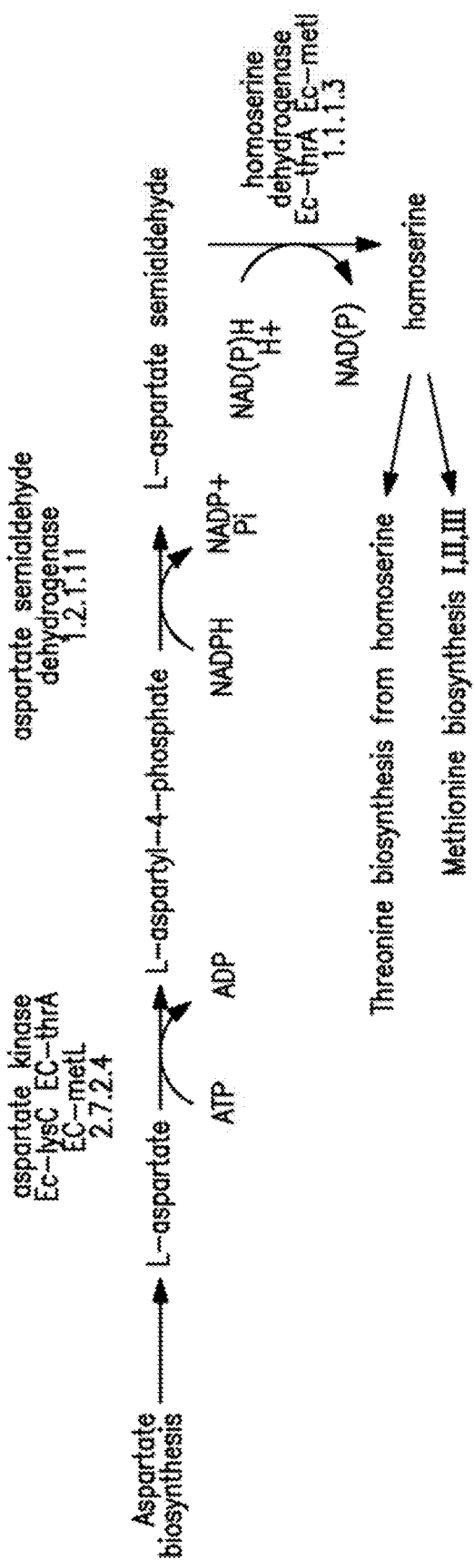
FIG. 2 is a schematic diagram showing homoserine biosynthesis in *E. coli*.

A homoserine pathway also can be engineered to generate BDO-producing microbial organisms. Homoserine is an intermediate in threonine and methionine metabolism, formed from oxaloacetate via aspartate. The conversion of oxaloacetate to homoserine requires one NADH, two NADPH, and one ATP (FIG. 2). Once formed, homoserine feeds into biosynthetic pathways for both threonine and methionine. In most organisms, high levels of threonine or methionine feedback to repress the homoserine biosynthesis pathway (Caspi et al., *Nucleic Acids Res.* 34:D511-D516 (1990)).

The transformation of homoserine to 4-hydroxybutyrate (4-HB) can be accomplished in two enzymatic steps as described herein. The first step of this pathway is deamination of homoserine by a putative ammonia lyase. In step 2, the product alkene, 4-hydroxybut-2-enoate is reduced to 4-HB by a putative reductase at the cost of one NADH. 4-HB can then be converted to BDO.

Enzymes available for catalyzing the above transformations are disclosed herein. For example, the ammonia lyase in step 1 of the pathway closely resembles the chemistry of aspartate ammonia-lyase (aspartase). Aspartase is a widespread enzyme in microorganisms, and has been characterized extensively (Viola, R. E., *Mol. Biol.* 74:295-341 (2008)). The crystal structure of the *E. coli* aspartase has been solved (Shi et al., *Biochemistry* 36:9136-9144 (1997)), so it is therefore possible to directly engineer mutations in the enzyme's active site that would alter its substrate specificity to include homoserine. The oxidoreductase in step 2 has chemistry similar to several well-characterized enzymes including fumarate reductase in the *E. coli* TCA cycle. Since the thermodynamics of this reaction are highly favorable, an endogenous reductase with broad substrate specificity will likely be able to reduce 4-hydroxybut-2-enoate. The yield of this pathway under anaerobic conditions is 0.9 mol BDO per mol glucose.

The succinyl-CoA pathway was found to have a higher yield due to the fact that it is more energetically efficient. The conversion of one oxaloacetate molecule to BDO via the homoserine pathway will require the expenditure of 2 ATP equivalents. Because the conversion of glucose to two oxaloacetate molecules can generate a maximum of 3 ATP molecules assuming PEP carboxykinase to be reversible, the overall conversion of glucose to BDO via homoserine has a negative energetic yield. As expected, if it is assumed that energy can be generated via respiration, the maximum yield of the homoserine pathway increases to 1.05 mol/mol glucose which is 96% of the succinyl-CoA pathway yield. The succinyl-CoA pathway can channel some of the carbon flux through pyruvate dehydrogenase and the oxidative branch of the TCA cycle to generate both reducing equivalents and succinyl-CoA without an energetic expenditure. Thus, it does not encounter the same energetic difficulties as the homoserine pathway because not all of the flux is channeled through oxaloacetate to succinyl-CoA to BDO. Overall, the homoserine pathway demonstrates a high-yielding route to BDO.

An acetoacetate pathway also can be engineered to generate BDO-producing microbial organisms. Acetoacetate can be formed from acetyl-CoA by enzymes involved in fatty acid metabolism, including acetyl-CoA acetyltransferase and acetoacetyl-CoA transferase. Biosynthetic routes through acetoacetate are also particularly useful in microbial organisms that can metabolize single carbon compounds such as carbon monoxide, carbon dioxide or methanol to form acetyl-CoA.

Figure 8A:
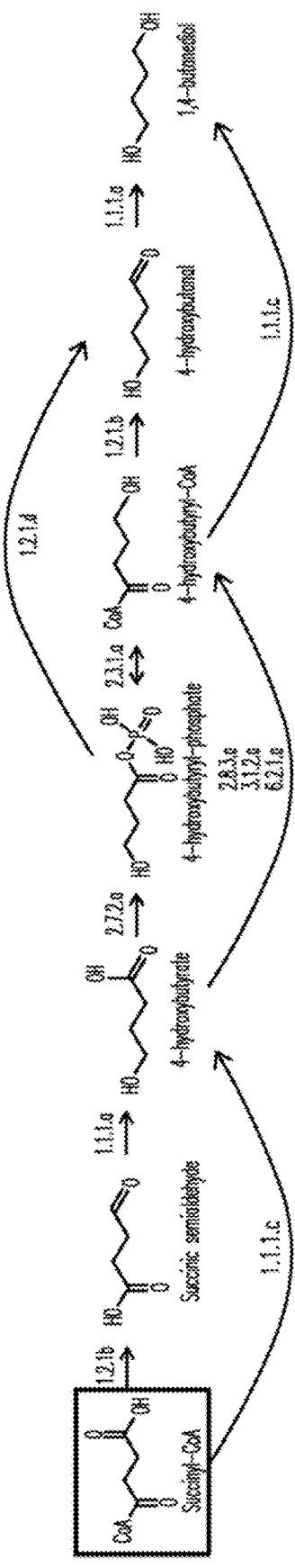
FIGS. 8A and 8B show exemplary 1,4-butanediol (BDO) pathways.
Figure 8B:
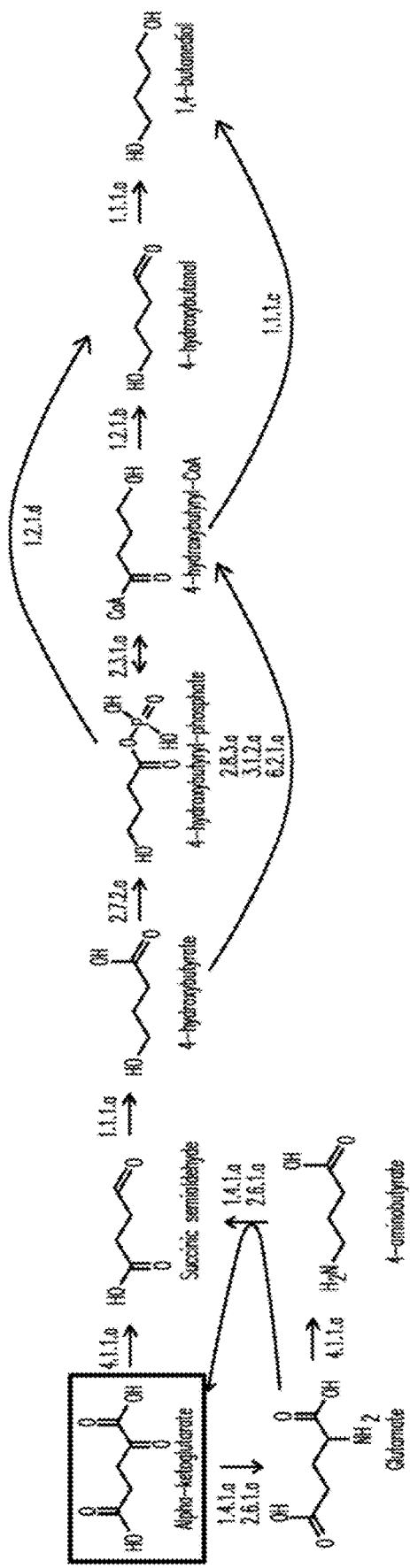

A three step route from acetoacetyl-CoA to 4-aminobutyrate (see FIG. 9C) can be used to synthesize BDO through acetoacetyl-CoA. 4-Aminobutyrate can be converted to succinic semialdehyde as shown in FIG. 8B. Succinic semialdehyde, which is one reduction step removed from succinyl-CoA or one decarboxylation step removed from α-ketoglutarate, can be converted to BDO following three reductions steps (FIG. 1). Briefly, step 1 of this pathway involves the conversion of acetoacetyl-CoA to acetoacetate by, for example, the *E. coli* acetoacetyl-CoA transferase encoded by the atoA and atoD genes (Hanai et al., *Appl. Environ. Microbiol.* 73: 7814-7818 (2007)). Step 2 of the acetoacetyl-CoA biopathway entails conversion of acetoacetate to 3-aminobutanoate by an w-aminotransferase. The w-amino acid:pyruvate aminotransferase (ω-APT) from *Alcaligens denitrificans* was overexpressed in *E. coli* and shown to have a high activity toward 3-aminobutanoate in vitro (Yun et al., *Appl. Environ. Microbiol.* 70:2529-2534 (2004)).

In step 2, a putative aminomutase shifts the amine group from the 3- to the 4-position of the carbon backbone. An aminomutase performing this function on 3-aminobutanoate has not been characterized, but an enzyme from *Clostridium sticklandii* has a very similar mechanism. The enzyme, D-lysine-5,6-aminomutase, is involved in lysine biosynthesis.

The synthetic route to BDO from acetoacetyl-CoA passes through 4-aminobutanoate, a metabolite in *E. coli* that is normally formed from decarboxylation of glutamate. Once formed, 4-aminobutanoate can be converted to succinic semialdehyde by 4-aminobutanoate transaminase (2.6.1.19), an enzyme which has been biochemically characterized.

One consideration for selecting candidate enzymes in this pathway is the stereoselectivity of the enzymes involved in steps 2 and 3. The ω-ABT in *Alcaligens denitrificans* is specific to the L-stereoisomer of 3-aminobutanoate, while D-lysine-5,6-aminomutase likely requires the D-stereoisomer. If enzymes with complementary stereoselectivity are not initially found or engineered, a third enzyme can be added to the pathway with racemase activity that can convert L-3-aminobutanoate to D-3-aminobutanoate. While amino acid racemases are widespread, whether these enzymes can function on w-amino acids is not known.

The maximum theoretical molar yield of this pathway under anaerobic conditions is 1.091 mol/mol glucose. In order to generate flux from acetoacetyl-CoA to BDO it was necessary to assume that acetyl-CoA:acetoacetyl-CoA transferase is reversible. The function of this enzyme in *E. coli* is to metabolize short-chain fatty acids by first converting them into thioesters.

While the operation of acetyl-CoA:acetoacetyl-CoA transferase in the acetate-consuming direction has not been demonstrated experimentally in *E. coli*, studies on similar enzymes in other organisms support the assumption that this reaction is reversible. The enzyme butyryl-CoA:acetate:CoA transferase in gut microbes *Roseburia* sp. and *F. prasnitzii* operates in the acetate utilizing direction to produce butyrate (Duncan et al., *Appl. Environ. Microbiol* 68:5186-5190 (2002)). Another very similar enzyme, acetyl:succinate CoA-transferase in *Trypanosoma brucei*, also operates in the acetate utilizing direction. This reaction has a $\Delta_{rxn}G$ close to equilibrium, so high concentrations of acetate can likely drive the reaction in the direction of interest. At the maximum theoretical BDO production rate of 1.09 mol/mol glucose simulations predict that *E. coli* can generate 1.098 mol ATP per mol glucose with no fermentation byproducts. This ATP yield should be sufficient for cell growth, maintenance, and production. The acetoacetatyl-CoA biopathway is a high-yielding route to BDO from acetyl-CoA.

Therefore, in addition to any of the various modifications exemplified previously for establishing 4-HB biosynthesis in a selected host, the BDO producing microbial organisms can include any of the previous combinations and permutations of 4-HB pathway metabolic modifications as well as any combination of expression for CoA-independent aldehyde dehydrogenase, CoA-dependent aldehyde dehydrogenase or an alcohol dehydrogenase or other enzymes disclosed herein to generate biosynthetic pathways for GBL and/or BDO. Therefore, the BDO producers of the invention can have exogenous expression of, for example, one, two, three, four, five, six, seven, eight, nine, or up to all enzymes corresponding to any of the 4-HB pathway and/or any of the BDO pathway enzymes disclosed herein.

Design and construction of the genetically modified microbial organisms is carried out using methods well known in the art to achieve sufficient amounts of expression to produce BDO. In particular, the non-naturally occurring microbial organisms of the invention can achieve biosynthesis of BDO resulting in intracellular concentrations between about 0.1-200 mM or more, such as about 0.1-25 mM or more, as discussed above. For example, the intracellular concentration of BDO is between about 3-20 mM, particularly between about 5-15 mM and more particularly between about 8-12 mM, including about 10 mM or more. Intracellular concentrations between and above each of these exemplary ranges also can be achieved from the non-naturally occurring microbial organisms of the invention. As with the 4-HB producers, the BDO producers also can be sustained, cultured or fermented under anaerobic conditions.

The invention further provides a method for the production of 4-HB. The method includes culturing a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate:succinic semialdehyde transaminase, α-ketoglutarate decarboxylase, or glutamate decarboxylase under substantially anaerobic conditions for a sufficient period of time to produce monomeric 4-hydroxybutanoic acid (4-HB). The method can additionally include chemical conversion of 4-HB to GBL and to BDO or THF, for example.

Additionally provided is a method for the production of 4-HB. The method includes culturing a non-naturally occurring microbial organism having a 4-hydroxybutanoic acid (4-HB) biosynthetic pathway including at least one exogenous nucleic acid encoding 4-hydroxybutanoate dehydrogenase, succinyl-CoA synthetase, CoA-dependent succinic semialdehyde dehydrogenase or α-ketoglutarate decarboxylase under substantially anaerobic conditions for a sufficient period of time to produce monomeric 4-hydroxybutanoic acid (4-HB). The 4-HB product can be secreted into the culture medium.

Further provided is a method for the production of BDO. The method includes culturing a non-naturally occurring microbial biocatalyst or microbial organism, comprising a microbial organism having 4-hydroxybutanoic acid (4-HB) and 1,4-butanediol (BDO) biosynthetic pathways, the pathways including at least one exogenous nucleic acid encoding 4-hydroxybutanoate dehydrogenase, succinyl-CoA synthetase, CoA-dependent succinic semialdehyde dehydrogenase, 4-hydroxybutyrate:CoA transferase, 4-hydroxybutyrate kinase, phosphotranshydroxybutyrylase, α-ketoglutarate decarboxylase, aldehyde dehydrogenase, alcohol dehydrogenase or an aldehyde/alcohol dehydrogenase for a sufficient period of time to produce 1,4-butanediol (BDO). The BDO product can be secreted into the culture medium.

Additionally provided are methods for producing BDO by culturing a non-naturally occurring microbial organism having a BDO pathway of the invention. The BDO pathway can comprise at least one exogenous nucleic acid encoding a BDO pathway enzyme expressed in a sufficient amount to produce BDO, under conditions and for a sufficient period of time to produce BDO, the BDO pathway comprising 4-aminobutyrate CoA transferase, 4-aminobutyryl-CoA hydrolase, 4-aminobutyrate-CoA ligase, 4-aminobutyryl-CoA oxidoreductase (deaminating), 4-aminobutyryl-CoA transaminase, or 4-hydroxybutyryl-CoA dehydrogenase (see Example VII and Table 17).

Alternatively, the BDO pathway can compare at least one exogenous nucleic acid encoding a BDO pathway enzyme expressed in a sufficient amount to produce BDO, under conditions and for a sufficient period of time to produce BDO, the BDO pathway comprising 4-aminobutyrate CoA transferase, 4-aminobutyryl-CoA hydrolase, 4-aminobutyrate-CoA ligase, 4-aminobutyryl-CoA reductase (alcohol forming), 4-aminobutyryl-CoA reductase, 4-aminobutan-1-ol dehydrogenase, 4-aminobutan-1-ol oxidoreductase (deaminating) or 4-aminobutan-1-ol transaminase (see Example VII and Table 18).

In addition, the invention provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising 4-aminobutyrate kinase, 4-aminobutyraldehyde dehydrogenase (phosphorylating), 4-aminobutan-1-ol dehydrogenase, 4-aminobutan-1-ol oxidoreductase (deaminating), 4-aminobutan-1-ol transaminase, [(4-aminobutanolyl)oxy]phosphonic acid oxidoreductase (deaminating), [(4-aminobutanolyl)oxy]phosphonic acid transaminase, 4-hydroxybutyryl-phosphate dehydrogenase, or 4-hydroxybutyraldehyde dehydrogenase (phosphorylating) (see Example VII and Table 19).

The invention further provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising alpha-ketoglutarate 5-kinase, 2,5-dioxopentanoic semialdehyde dehydrogenase (phosphorylating), 2,5-dioxopentanoic acid reductase, alpha-ketoglutarate CoA transferase, alpha-ketoglutaryl-CoA hydrolase, alpha-ketoglutaryl-CoA ligase, alpha-ketoglutaryl-CoA reductase, 5-hydroxy-2-oxopentanoic acid dehydrogenase, alpha-ketoglutaryl-CoA reductase (alcohol forming), 5-hydroxy-2-oxopentanoic acid decarboxylase, or 5-hydroxy-2-oxopentanoic acid dehydrogenase (decarboxylation)(see Example VIII and Table 20).

The invention additionally provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising glutamate CoA transferase, glutamyl-CoA hydrolase, glutamyl-CoA ligase, glutamate 5-kinase, glutamate-5-semialdehyde dehydrogenase (phosphorylating), glutamyl-CoA reductase, glutamate-5-semialdehyde reductase, glutamyl-CoA reductase (alcohol forming), 2-amino-5-hydroxypentanoic acid oxidoreductase (deaminating), 2-amino-5-hydroxypentanoic acid transaminase, 5-hydroxy-2-oxopentanoic acid decarboxylase, 5-hydroxy-2-oxopentanoic acid dehydrogenase (decarboxylation)(see Example IX and Table 21).

The invention additionally includes a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising 3-hydroxybutyryl-CoA dehydrogenase, 3-hydroxybutyryl-CoA dehydratase, vinylacetyl-CoA Δ-isomerase, or 4-hydroxybutyryl-CoA dehydratase (see Example X and Table 22).

Also provided is a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising homoserine deaminase, homoserine CoA transferase, homoserine-CoA hydrolase, homoserine-CoA ligase, homoserine-CoA deaminase, 4-hydroxybut-2-enoyl-CoA transferase, 4-hydroxybut-2-enoyl-CoA hydrolase, 4-hydroxybut-2-enoyl-CoA ligase, 4-hydroxybut-2-enoate reductase, 4-hydroxybutyryl-CoA transferase, 4-hydroxybutyryl-CoA hydrolase, 4-hydroxybutyryl-CoA ligase, or 4-hydroxybut-2-enoyl-CoA reductase (see Example XI and Table 23).

The invention additionally provides a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising succinyl-CoA reductase (alcohol forming), 4-hydroxybutyryl-CoA hydrolase, 4-hydroxybutyryl-CoA ligase, 4-hydroxybutanal dehydrogenase (phosphorylating). Such a BDO pathway can further comprise succinyl-CoA reductase, 4-hydroxybutyrate dehydrogenase, 4-hydroxybutyryl-CoA transferase, 4-hydroxybutyrate kinase, phosphotrans-4-hydroxybutyrylase, 4-hydroxybutyryl-CoA reductase, 4-hydroxybutyryl-CoA reductase (alcohol forming), or 1,4-butanediol dehydrogenase.

Also provided is a method for producing BDO, comprising culturing a non-naturally occurring microbial organism having a BDO pathway, the pathway comprising at least one exogenous nucleic acid encoding a BDO pathway enzyme expressed in a sufficient amount to produce BDO, under conditions and for a sufficient period of time to produce BDO, the BDO pathway comprising glutamate dehydrogenase, 4-aminobutyrate oxidoreductase (deaminating), 4-aminobutyrate transaminase, glutamate decarboxylase, 4-hydroxybutyryl-CoA hydrolase, 4-hydroxybutyryl-CoA ligase, 4-hydroxybutanal dehydrogenase (phosphorylating).

The invention additionally provides methods of producing a desired product using the genetically modified organisms disclosed herein that allow improved production of a desired product such as BDO by increasing the product or decreasing undesirable byproducts. Thus, the invention provides a method for producing 1,4-butanediol (BDO), comprising culturing the non-naturally occurring microbial organisms disclosed herein under conditions and for a sufficient period of time to produce BDO. In one embodiment, the invention provides a method of producing BDO using a non-naturally occurring microbial organism, comprising a microbial organism having a 1,4-butanediol (BDO) pathway comprising at least one exogenous nucleic acid encoding a BDO pathway enzyme expressed in a sufficient amount to produce BDO. In one embodiment, the microbial organism is genetically modified to express exogenous succinyl-CoA synthetase (see Example XII). For example, the succinyl-CoA synthetase can be encoded by an *Escherichia coli* sucCD genes.

In another embodiment, the microbial organism is genetically modified to express exogenous alpha-ketoglutarate decarboxylase (see Example XIII). For example, the alpha-ketoglutarate decarboxylase can be encoded by the *Mycobacterium bovis* sucA gene. In still another embodiment, the microbial organism is genetically modified to express exogenous succinate semialdehyde dehydrogenase and 4-hydroxybutyrate dehydrogenase and optionally 4-hydroxybutyryl-CoA/acetyl-CoA transferase (see Example XIII). For example, the succinate semialdehyde dehydrogenase (CoA-dependent), 4-hydroxybutyrate dehydrogenase and 4-hydroxybutyryl-CoA/acetyl-CoA transferase can be encoded by *Porphyromonas gingivalis* W83 genes. In an additional embodiment, the microbial organism is genetically modified to express exogenous butyrate kinase and phosphotransbutyrylase (see Example XIII). For example, the butyrate kinase and phosphotransbutyrylase can be encoded by *Clostridium acetobutilicum* bukl and ptb genes.

In yet another embodiment, the microbial organism is genetically modified to express exogenous 4-hydroxybutyryl-CoA reductase (see Example XIII). For example, the 4-hydroxybutyryl-CoA reductase can be encoded by *Clostridium beijerinckii* ald gene. Additionally, in an embodiment of the invention, the microbial organism is genetically modified to express exogenous 4-hydroxybutanal reductase (see Example XIII). For example, the 4-hydroxybutanal reductase can be encoded by *Geobacillus thermoglucosidasius* adh1 gene. In another embodiment, the microbial organism is genetically modified to express exogenous pyruvate dehydrogenase subunits (see Example XIV). For example, the exogenous pyruvate dehydrogenase can be NADH insensitive. The pyruvate dehydrogenase subunit can be encoded by the *Klebsiella pneumonia* lpdA gene. In a particular embodiment, the pyruvate dehydrogenase subunit genes of the microbial organism can be under the control of a pyruvate formate lyase promoter.

In still another embodiment, the microbial organism is genetically modified to disrupt a gene encoding an aerobic respiratory control regulatory system (see Example XV). For example, the disruption can be of the arcA gene. Such an organism can further comprise disruption of a gene encoding malate dehydrogenase. In a further embodiment, the microbial organism is genetically modified to express an exogenous NADH insensitive citrate synthase (see Example XV). For example, the NADH insensitive citrate synthase can be encoded by gltA, such as an R163L mutant of gltA. In still another embodiment, the microbial organism is genetically modified to express exogenous phosphoenolpyruvate carboxykinase (see Example XVI). For example, the phosphoenolpyruvate carboxykinase can be encoded by an *Haemophilus influenza* phosphoenolpyruvate carboxykinase gene. It is understood that strains exemplified herein for improved production of BDO can similarly be used, with appropriate modifications, to produce other desired products, for example, 4-hydroxybutyrate or other desired products disclosed herein.

The invention additionally provides a method for producing 4-hydroxybutanal by culturing a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising succinyl-CoA reductase (aldehyde forming); 4-hydroxybutyrate dehydrogenase; and 4-hydroxybutyrate reductase (see FIG. 58, steps A-C-D). The invention also provides a method for producing 4-hydroxybutanal by culturing a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising alpha-ketoglutarate decarboxylase; 4-hydroxybutyrate dehydrogenase; and 4-hydroxybutyrate reductase (FIG. 58, steps B-C-D).

The invention further provides a method for producing 4-hydroxybutanal by culturing a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising succinate reductase; 4-hydroxybutyrate dehydrogenase, and 4-hydroxybutyrate reductase (see FIG. 62, steps F-C-D). In yet another embodiment, the invention provides a method for producing 4-hydroxybutanal by culturing a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising alpha-ketoglutarate decarboxylase, or glutamate dehydrogenase or glutamate transaminase and glutamate decarboxylase and 4-aminobutyrate dehydrogenase or 4-aminobutyrate transaminase; 4-hydroxybutyrate dehydrogenase; and 4-hydroxybutyrate reductase (see FIG. 62, steps B or ((J or K)-L-(M or N))-C-D).

The invention also provides a method for producing 4-hydroxybutanal by culturing a non-naturally occurring microbial organism, comprising a 4-hydroxybutanal pathway comprising at least one exogenous nucleic acid encoding a 4-hydroxybutanal pathway enzyme expressed in a sufficient amount to produce 4-hydroxybutanal, the 4-hydroxybutanal pathway comprising alpha-ketoglutarate reductase; 5-hydroxy-2-oxopentanoate dehydrogenase; and 5-hydroxy-2-oxopentanoate decarboxylase (see FIG. 62, steps X-Y-Z). The invention further provides a method for producing 4-hydroxybutyryl-CoA by culturing a non-naturally occurring microbial organism, comprising a 4-hydroxybutyryl-CoA pathway comprising at least one exogenous nucleic acid encoding a 4-hydroxybutyryl-CoA pathway enzyme expressed in a sufficient amount to produce 4-hydroxybutyryl-CoA, the 4-hydroxybutyryl-CoA pathway comprising alpha-ketoglutarate reductase; 5-hydroxy-2-oxopentanoate dehydrogenase; and 5-hydroxy-2-oxopentanoate dehydrogenase (decarboxylation) (see FIG. 62, steps X-Y-AA).

The invention additionally provides a method for producing putrescine by culturing a non-naturally occurring microbial organism, comprising a putrescine pathway comprising at least one exogenous nucleic acid encoding a putrescine pathway enzyme expressed in a sufficient amount to produce putrescine, the putrescine pathway comprising succinate reductase; 4-aminobutyrate dehydrogenase or 4-aminobutyrate transaminase; 4-aminobutyrate reductase; and putrescine dehydrogenase or putrescine transaminase (see FIG. 63, steps F-M/N-C-D/E). In still another embodiment, the invention provides a method for producing putrescine by culturing a non-naturally occurring microbial organism, comprising a putrescine pathway comprising at least one exogenous nucleic acid encoding a putrescine pathway enzyme expressed in a sufficient amount to produce putrescine, the putrescine pathway comprising alpha-ketoglutarate decarboxylase; 4-aminobutyrate dehydrogenase or 4-aminobutyrate transaminase; 4-aminobutyrate reductase; and putrescine dehydrogenase or putrescine transaminase (see FIG. 63, steps B-M/N-C-D/E). The invention additionally provides a method for producing putrescine by culturing a non-naturally occurring microbial organism, comprising a putrescine pathway comprising at least one exogenous nucleic acid encoding a putrescine pathway enzyme expressed in a sufficient amount to produce putrescine, the putrescine pathway comprising glutamate dehydrogenase or glutamate transaminase; glutamate decarboxylase; 4-aminobutyrate reductase; and putrescine dehydrogenase or putrescine transaminase (see FIG. 63, steps J/K-L-C-D/E).

The invention provides in another embodiment a method for producing putrescine by culturing a non-naturally occurring microbial organism, comprising a putrescine pathway comprising at least one exogenous nucleic acid encoding a putrescine pathway enzyme expressed in a sufficient amount to produce putrescine, the putrescine pathway comprising alpha-ketoglutarate reductase; 5-amino-2-oxopentanoate dehydrogenase or 5-amino-2-oxopentanoate transaminase; 5-amino-2-oxopentanoate decarboxylase; and putrescine dehydrogenase or putrescine transaminase (see FIG. 63, steps O-P/Q-R-D/E). Also provided is a method for producing putrescine by culturing a non-naturally occurring microbial organism, comprising a putrescine pathway comprising at least one exogenous nucleic acid encoding a putrescine pathway enzyme expressed in a sufficient amount to produce putrescine, the putrescine pathway comprising alpha-ketoglutarate reductase; 5-amino-2-oxopentanoate dehydrogenase or 5-amino-2-oxopentanoate transaminase; ornithine dehydrogenase or ornithine transaminase; and ornithine decarboxylase (see FIG. 63, steps O-P/Q-S/T-U). It is understood that a microbial organism comprising any of the pathways disclosed herein can be used to produce a a desired product or intermediate, including 4-HB, 4-HBal, BDO or putrescine.

It is understood that, in methods of the invention, any of the one or more exogenous nucleic acids can be introduced into a microbial organism to produce a non-naturally occurring microbial organism of the invention. The nucleic acids can be introduced so as to confer, for example, a 4-HB, BDO, THF or GBL biosynthetic pathway onto the microbial organism. Alternatively, encoding nucleic acids can be introduced to produce an intermediate microbial organism having the biosynthetic capability to catalyze some of the required reactions to confer 4-HB, BDO, THF or GBL biosynthetic capability. For example, a non-naturally occurring microbial organism having a 4-HB biosynthetic pathway can comprise at least two exogenous nucleic acids encoding desired enzymes, such as the combination of 4-hydroxybutanoate dehydrogenase and α-ketoglutarate decarboxylase; 4-hydroxybutanoate dehydrogenase and CoA-independent succinic semialdehyde dehydrogenase; 4-hydroxybutanoate dehydrogenase and CoA-dependent succinic semialdehyde dehydrogenase; CoA-dependent succinic semialdehyde dehydrogenase and succinyl-CoA synthetase; succinyl-CoA synthetase and glutamate decarboxylase, and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, α-ketoglutarate decarboxylase and CoA-dependent succinic semialdehyde dehydrogenase; CoA-independent succinic semialdehyde dehydrogenase and succinyl-CoA synthetase; 4-hydroxybutanoate dehydrogenase, CoA-dependent succinic semialdehyde dehydrogenase and glutamate:succinic semialdehyde transaminase, and so forth, as desired, so long as the combination of enzymes of the desired biosynthetic pathway results in production of the corresponding desired product.

Similarly, for example, with respect to any one or more exogenous nucleic acids introduced to confer BDO production, a non-naturally occurring microbial organism having a BDO biosynthetic pathway can comprise at least two exogenous nucleic acids encoding desired enzymes, such as the combination of 4-hydroxybutanoate dehydrogenase and α-ketoglutarate decarboxylase; 4-hydroxybutanoate dehydrogenase and 4-hydroxybutyryl CoA:acetyl-CoA transferase; 4-hydroxybutanoate dehydrogenase and butyrate kinase; 4-hydroxybutanoate dehydrogenase and phosphotransbutyrylase; 4-hydroxybutyryl CoA:acetyl-CoA transferase and aldehyde dehydrogenase; 4-hydroxybutyryl CoA: acetyl-CoA transferase and alcohol dehydrogenase; 4-hydroxybutyryl CoA:acetyl-CoA transferase and an aldehyde/alcohol dehydrogenase, 4-aminobutyrate-CoA transferase and 4-aminobutyryl-CoA transaminase; 4-aminobutyrate kinase and 4-aminobutan-1-ol oxidoreductase (deaminating), and the like. Thus, it is understood that any combination of two or more enzymes of a biosynthetic pathway can be included in a non-naturally occurring microbial organism of the invention. Similarly, it is understood that any combination of three or more enzymes of a biosynthetic pathway can be included in a non-naturally occurring microbial organism of the invention, for example, 4-hydroxybutanoate dehydrogenase, α-ketoglutarate decarboxylase and 4-hydroxybutyryl CoA:acetyl-CoA transferase; 4-hydroxybutanoate dehydrogenase, butyrate kinase and phosphotransbutyrylase; 4-hydroxybutanoate dehydrogenase, 4-hydroxybutyryl CoA:acetyl-CoA transferase and aldehyde dehydrogenase; 4-hydroxybutyryl CoA:acetyl-CoA transferase, aldehyde dehydrogenase and alcohol dehydrogenase; butyrate kinase, phosphotransbutyrylase and an aldehyde/alcohol dehydrogenase; 4-aminobutyryl-CoA hydrolase, 4-aminobutyryl-CoA reductase and 4-amino butan-1-ol transaminase; 3-hydroxybutyryl-CoA dehydrogenase, 3-hydroxybutyryl-CoA dehydratase and 4-hydroxybutyryl-CoA dehydratase, and the like. Similarly, any combination of four, five or more enzymes of a biosynthetic pathway as disclosed herein can be included in a non-naturally occurring microbial organism of the invention, as desired, so long as the combination of enzymes of the desired biosynthetic pathway results in production of the corresponding desired product.

Any of the non-naturally occurring microbial organisms described herein can be cultured to produce and/or secrete the biosynthetic products of the invention. For example, the 4-HB producers can be cultured for the biosynthetic production of 4-HB. The 4-HB can be isolated or be treated as described below to generate GBL, THF and/or BDO. Similarly, the BDO producers can be cultured for the biosynthetic production of BDO. The BDO can be isolated or subjected to further treatments for the chemical synthesis of BDO family compounds, as disclosed herein.

The growth medium can include, for example, any carbohydrate source which can supply a source of carbon to the non-naturally occurring microorganism. Such sources include, for example, sugars such as glucose, sucrose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, sucrose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 4-HB, 4-HBal, 4-HBCoA, BDO or putrescine and other compounds of the invention.

Accordingly, given the teachings and guidance provided herein, those skilled in the art will understand that a non-naturally occurring microbial organism can be produced that secretes the biosynthesized compounds of the invention when grown on a carbon source such as a carbohydrate.

Such compounds include, for example, 4-HB, 4-HBal, 4-HBCoA, BDO or putrescine and any of the intermediates metabolites in the 4-HB, 4-HBal, 4-HBCoA, BDO or putrescine pathways and/or the combined 4-HB, 4-HBal, 4-HBCoA, BDO or putrescine pathways. All that is required is to engineer in one or more of the enzyme activities shown in Figure1 to achieve biosynthesis of the desired compound or intermediate including, for example, inclusion of some or all of the 4-HB, 4-HBal, 4-HBCoA, BDO or putrescine biosynthetic pathways. Accordingly, the invention provides a non-naturally occurring microbial organism that secretes 4-HB when grown on a carbohydrate, secretes BDO when grown on a carbohydrate and/or secretes any of the intermediate metabolites shown in FIG. 1, 8-13, 58, 62 or 63 when grown on a carbohydrate. A BDO producing microbial organisms of the invention can initiate synthesis from, for example, succinate, succinyl-CoA, α-ketogluterate, succinic semialdehyde, 4-HB, 4-hydroxybutyrylphosphate, 4-hydroxybutyryl-CoA (4-HB-CoA) and/or 4-hydroxybutyraldehyde.

In some embodiments, culture conditions include anaerobic or substantially anaerobic growth or maintenance conditions. Exemplary anaerobic conditions have been described previously and are well known in the art. Exemplary anaerobic conditions for fermentation processes are described below in the Examples. Any of these conditions can be employed with the non-naturally occurring microbial organisms as well as other anaerobic conditions well known in the art. Under such anaerobic conditions, the 4-HB, 4-HBal, 4-HBCoA, BDO or putrescine producers can synthesize monomeric 4-HB, 4-HBal, 4-HBCoA, BDO or putrescine, respectively, at intracellular concentrations of 5-10 mM or more as well as all other concentrations exemplified previously.

A number of downstream compounds also can be generated for the 4-HB, 4-HBal, 4-HBCoA, BDO or putrescine producing non-naturally occurring microbial organisms of the invention. With respect to the 4-HB producing microbial organisms of the invention, monomeric 4-HB and GBL exist in equilibrium in the culture medium. The conversion of 4-HB to GBL can be efficiently accomplished by, for example, culturing the microbial organisms in acid pH medium. A pH less than or equal to 7.5, in particular at or below pH 5.5, spontaneously converts 4-HB to GBL.

The resultant GBL can be separated from 4-HB and other components in the culture using a variety of methods well known in the art. Such separation methods include, for example, the extraction procedures exemplified in the Examples as well as methods which include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art. Separated GBL can be further purified by, for example, distillation.

Another down stream compound that can be produced from the 4-HB producing non-naturally occurring microbial organisms of the invention includes, for example, BDO. This compound can be synthesized by, for example, chemical hydrogenation of GBL. Chemical hydrogenation reactions are well known in the art. One exemplary procedure includes the chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce 1,4-butanediol.

Other procedures well known in the art are equally applicable for the above chemical reaction and include, for example, WO No. 82/03854 (Bradley, et al.), which describes the hydrogenolysis of gamma-butyrolactone in the vapor phase over a copper oxide and zinc oxide catalyst. British Pat. No. 1,230,276, which describes the hydrogenation of gamma-butyrolactone using a copper oxide-chromium oxide catalyst. The hydrogenation is carried out in the liquid phase. Batch reactions also are exemplified having high total reactor pressures. Reactant and product partial pressures in the reactors are well above the respective dew points. British Pat. No. 1,314,126, which describes the hydrogenation of gamma-butyrolactone in the liquid phase over a nickel-cobalt-thorium oxide catalyst. Batch reactions are exemplified as having high total pressures and component partial pressures well above respective component dew points. British Pat. No. 1,344,557, which describes the hydrogenation of gamma-butyrolactone in the liquid phase over a copper oxide-chromium oxide catalyst. A vapor phase or vapor-containing mixed phase is indicated as suitable in some instances. A continuous flow tubular reactor is exemplified using high total reactor pressures. British Pat. No. 1,512,751, which describes the hydrogenation of gamma-butyrolactone to 1,4-butanediol in the liquid phase over a copper oxide-chromium oxide catalyst. Batch reactions are exemplified with high total reactor pressures and, where determinable, reactant and product partial pressures well above the respective dew points. U.S. Pat. No. 4,301,077, which describes the hydrogenation to 1,4-butanediol of gamma-butyrolactone over a Ru—Ni—Co—Zn catalyst. The reaction can be conducted in the liquid or gas phase or in a mixed liquid-gas phase. Exemplified are continuous flow liquid phase reactions at high total reactor pressures and relatively low reactor productivities. U.S. Pat. No. 4,048,196, which describes the production of 1,4-butanediol by the liquid phase hydrogenation of gamma-butyrolactone over a copper oxide-zinc oxide catalyst. Further exemplified is a continuous flow tubular reactor operating at high total reactor pressures and high reactant and product partial pressures. And U.S. Pat. No. 4,652,685, which describes the hydrogenation of lactones to glycols.

A further downstream compound that can be produced form the 4-HB producing microbial organisms of the invention includes, for example, THF. This compound can be synthesized by, for example, chemical hydrogenation of GBL. One exemplary procedure well known in the art applicable for the conversion of GBL to THF includes, for example, chemical reduction of 4-HB and/or GBL or a mixture of these two components deriving from the culture using a heterogeneous or homogeneous hydrogenation catalyst together with hydrogen, or a hydride-based reducing agent used stoichiometrically or catalytically, to produce tetrahydrofuran. Other procedures well know in the art are equally applicable for the above chemical reaction and include, for example, U.S. Pat. No. 6,686,310, which describes high surface area sol-gel route prepared hydrogenation catalysts. Processes for the reduction of maleic acid to tetrahydrofuran (THF) and 1,4-butanediol (BDO) and for the reduction of gamma butyrolactone to tetrahydrofuran and 1,4-butanediol also are described.

The culture conditions can include, for example, liquid culture procedures as well as fermentation and other large scale culture procedures. As described further below in the Examples, particularly useful yields of the biosynthetic products of the invention can be obtained under anaerobic or substantially anaerobic culture conditions.

Suitable purification and/or assays to test for the production of 4-HB, 4-HBal, 4-HBCoA, BDO or putrescine can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art.

The 4-HB, 4-HBal, 4-HBCoA, BDO or putrescine product can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

The invention further provides a method of manufacturing 4-HB. The method includes fermenting a non-naturally occurring microbial organism having a 4-hydroxybutanoic acid (4-HB) biosynthetic pathway comprising at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, glutamate: succinic semialdehyde transaminase, α-ketoglutarate decarboxylase, or glutamate decarboxylase under substantially anaerobic conditions for a sufficient period of time to produce monomeric 4-hydroxybutanoic acid (4-HB), the process comprising fed-batch fermentation and batch separation; fed-batch fermentation and continuous separation, or continuous fermentation and continuous separation.

The culture and chemical hydrogenations described above also can be scaled up and grown continuously for manufacturing of 4-HB, 4-HBal, 4-HBCoA, GBL, BDO and/or THF or putrescine. Exemplary growth procedures include, for example, fed-batch fermentation and batch separation; fed-batch fermentation and continuous separation, or continuous fermentation and continuous separation. All of these processes are well known in the art. Employing the 4-HB producers allows for simultaneous 4-HB biosynthesis and chemical conversion to GBL, BDO and/or THF by employing the above hydrogenation procedures simultaneous with continuous cultures methods such as fermentation. Other hydrogenation procedures also are well known in the art and can be equally applied to the methods of the invention.

Fermentation procedures are particularly useful for the biosynthetic production of commercial quantities of 4-HB, 4-HBal, 4-HBCoA, BDO or putrescine. Generally, and as with non-continuous culture procedures, the continuous and/or near-continuous production of 4-HB, 4-HBal, 4-HBCoA, BDO or putrescine will include culturing a non-naturally occurring 4-HB, 4-HBal, 4-HBCoA, BDO or putrescine producing organism of the invention in sufficient nutrients and medium to sustain and/or nearly sustain growth in an exponential phase. Continuous culture under such conditions can be include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 4-HB, 4-HBal, 4-HBCoA, BDO or putrescine or other 4-HB, 4-HBal, 4-HBCoA, BDO or putrescine derived products, including intermediates, of the invention can be utilized in, for example, fed-batch fermentation and batch separation; fed-batch fermentation and continuous separation, or continuous fermentation and continuous separation. Examples of batch and continuous fermentation procedures well known in the art are exemplified further below in the Examples.

In addition to the above fermentation procedures using the 4-HB, 4-HBal, 4-HBCoA, BDO or putrescine producers of the invention for continuous production of substantial quantities of 4-HB, 4-HBal, 4-HBCoA, BDO or putrescine, including monomeric 4-HB, respectively, the 4-HB producers also can be, for example, simultaneously subjected to chemical synthesis procedures to convert the product to other compounds or the product as described previously for the chemical conversion of monomeric 4-HB to, for example, GBL, BDO and/or THF. The BDO producers can similarly be, for example, simultaneously subjected to chemical synthesis procedures as described previously for the chemical conversion of BDO to, for example, THF, GBL, pyrrolidones and/or other BDO family compounds. In addition, the products of the 4-HB, 4-HBal, 4-HBCoA, BDO or putrescine producers can be separated from the fermentation culture and sequentially subjected to chemical or enzymatic conversion to convert the product to other compounds, if desired, as disclosed herein.

Briefly, hydrogenation of GBL in the fermentation broth can be performed as described by Frost et al., Biotechnology Progress 18: 201-211 (2002). Another procedure for hydrogenation during fermentation include, for example, the methods described in, for example, U.S. Pat. No. 5,478,952. This method is further exemplified in the Examples below.

Therefore, the invention additionally provides a method of manufacturing γ-butyrolactone (GBL), tetrahydrofuran (THF) or 1,4-butanediol (BDO). The method includes fermenting a non-naturally occurring microbial organism having 4-hydroxybutanoic acid (4-HB) and/or 1,4-butanediol (BDO) biosynthetic pathways, the pathways comprise at least one exogenous nucleic acid encoding 4-hydroxybutanoate dehydrogenase, CoA-independent succinic semialdehyde dehydrogenase, succinyl-CoA synthetase, CoA-dependent succinic semialdehyde dehydrogenase, 4-hydroxybutyrate:CoA transferase, glutamate: succinic semialdehyde transaminase, α-ketoglutarate decarboxylase, glutamate decarboxylase, 4-hydroxybutanoate kinase, phosphotransbutyrylase, CoA-independent 1,4-butanediol semialdehyde dehydrogenase, CoA-dependent 1,4-butanediol semialdehyde dehydrogenase, CoA-independent 1,4-butanediol alcohol dehydrogenase or CoA-dependent 1,4-butanediol alcohol dehydrogenase, under substantially anaerobic conditions for a sufficient period of time to produce 1,4-butanediol (BDO), GBL or THF, the fermenting comprising fed-batch fermentation and batch separation; fed-batch fermentation and continuous separation, or continuous fermentation and continuous separation.

In addition to the biosynthesis of 4-HB, 4-HBal, 4-HBCoA, BDO or putrescine and other products of the invention as described herein, the non-naturally occurring microbial organisms and methods of the invention also can be utilized in various combinations with each other and/or with other microbial organisms and methods well known in the art to achieve product biosynthesis by other routes. For example, one alternative to produce BDO other than use of the 4-HB producers and chemical steps or other than use of the BDO producer directly is through addition of another microbial organism capable of converting 4-HB or a 4-HB product exemplified herein to BDO.

One such procedure includes, for example, the fermentation of a 4-HB producing microbial organism of the invention to produce 4-HB, as described above and below. The 4-HB can then be used as a substrate for a second microbial organism that converts 4-HB to, for example, BDO, GBL and/or THF. The 4-HB can be added directly to another culture of the second organism or the original culture of 4-HB producers can be depleted of these microbial organisms by, for example, cell separation, and then subsequent addition of the second organism to the fermentation broth can utilized to produce the final product without intermediate purification steps. One exemplary second organism having the capacity to biochemically utilize 4-HB as a substrate for conversion to BDO, for example, is *Clostridium acetobutylicum* (see, for example, Jewell et al., *Current Microbiology*, 13:215-19 (1986)).

Thus, such a procedure includes, for example, the fermentation of a microbial organism that produces a 4-HB, 4-HBal, 4-HBCoA, BDO or putrescine pathway intermediate. The 4-HB, 4-HBal, 4-HBCoA, BDO or putrescine pathway intermediate can then be used as a substrate for a second microbial organism that converts the 4-HB, 4-HBal, 4-HBCoA, BDO or putrescine pathway intermediate to 4-HB, 4-HBal, 4-HBCoA, BDO or putrescine. The 4-HB, 4-HBal, 4-HBCoA, BDO or putrescine pathway intermediate can be added directly to another culture of the second organism or the original culture of the 4-HB, 4-HBal, 4-HBCoA BDO or putrescine pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 4-HB and/or BDO as described. In these embodiments, biosynthetic pathways for a desired product of the invention can be segregated into different microbial organisms and the different microbial organisms can be co-cultured to produce the final product. In such a biosynthetic scheme, the product of one microbial organism is the substrate for a second microbial organism until the final product is synthesized. For example, the biosynthesis of BDO can be accomplished as described previously by constructing a microbial organism that contains biosynthetic pathways for conversion of one pathway intermediate to another pathway intermediate or the product, for example, a substrate such as endogenous succinate through 4-HB to the final product BDO. Alternatively, BDO also can be biosynthetically produced from microbial organisms through co-culture or co-fermentation using two organisms in the same vessel. A first microbial organism being a 4-HB producer with genes to produce 4-HB from succinic acid, and a second microbial organism being a BDO producer with genes to convert 4-HB to BDO. For example, the biosynthesis of 4-HB, 4-HBal, 4-HBCoA, BDO or putrescine can be accomplished by constructing a microbial organism that contains biosynthetic pathways for conversion of one pathway intermediate to another pathway intermediate or the product. Alternatively, 4-HB, 4-HBal, 4-HBCoA, BDO or putrescine also can be biosynthetically produced from microbial organisms through co-culture or co-fermentation using two organisms in the same vessel, where the first microbial organism produces a 4-HB, 4-HBal, 4-HBCoA, BDO or putrescine intermediate and the second microbial organism converts the intermediate to 4-HB, 4-HBal, 4-HBCoA, BDO or putrescine.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 4-HB, BDO, GBL, THF and putrescine products of the invention.

Similarly, it is understood by those skilled in the art that a host organism can be selected based on desired characteristics for introduction of one or more gene disruptions to increase production of 4-HB, 4-HBal, 4-HBCoA, BDO or putrescine. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will increase 4-HB, 4-HBal, 4-HBCoA, BDO or putrescine biosynthesis. In a particular embodiment, the increased production couples biosynthesis of 4-HB, 4-HBal, 4-HBCoA, BDO or putrescine to growth of the organism, and can obligatorily couple production of 4-HB, 4-HBal, 4-HBCoA, BDO or putrescine to growth of the organism if desired and as disclosed herein.

It is understood that, in methods of the invention, any of the one or more exogenous nucleic acids can be introduced into a microbial organism to produce a non-naturally occurring microbial organism of the invention. The nucleic acids can be introduced so as to confer, for example, a 4-HB, 4-HBal, 4-HBCoA, BDO or putrescine biosynthetic pathway onto the microbial organism. Alternatively, encoding nucleic acids can be introduced to produce an intermediate microbial organism having the biosynthetic capability to catalyze some of the required reactions to confer 4-HB, 4-HBal, 4-HBCoA, BDO or putrescine biosynthetic capability. For example, a non-naturally occurring microbial organism having a 4-HB, 4-HBal, 4-HBCoA, BDO or putrescine biosynthetic pathway can comprise at least two exogenous nucleic acids encoding desired enzymes or proteins, such as the combination of enzymes as disclosed herein (see Examples and FIGS. 1, 8-13, 58, 62 and 63), and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example,], and so forth, as desired and disclosed herein, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 4-HB, 4-HBal, 4-HBCoA, BDO or putrescine.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

The methods exemplified above and further illustrated in the Examples below allow the construction of cells and organisms that biosynthetically produce, including obligatory couple production of a target biochemical product to growth of the cell or organism engineered to harbor the identified genetic alterations. In this regard, metabolic alterations have been identified that result in the biosynthesis of 4-HB and 1,4-butanediol. Microorganism strains constructed with the identified metabolic alterations produce elevated levels of 4-HB, 4-HBal, 4-HBCoA, BDO or putrescine compared to unmodified microbial organisms. These strains can be beneficially used for the commercial production of 4-HB, BDO, THF, GBL, 4-HBal, 4-HBCoA or putrescine, for example, in continuous fermentation process without being subjected to the negative selective pressures.

Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

It is understood that modifications which do not substantially affect the activity of the various embodiments of this invention are also included within the definition of the invention provided herein. Accordingly, the following examples are intended to illustrate but not limit the present invention.

Any of the non-naturally occurring microbial organisms described herein can be cultured to produce and/or secrete the biosynthetic products of the invention. For example, the 4-HB, 4-HBal, 4-HBCoA, BDO or putrescine producers can be cultured for the biosynthetic production of 4-HB, 4-HBal, 4-HBCoA, BDO or putrescine.

For the production of 4-HB, 4-HBal, 4-HBCoA, BDO or putrescine, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. publication 2009/0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In addition to renewable feedstocks such as those exemplified above, the 4-HB, 4-HBal, 4-HBCoA, BDO or putrescine producing microbial organisms of the invention also can be modified for growth on syngas as its source of carbon. In this specific embodiment, one or more proteins or enzymes are expressed in the 4-HB, 4-HBal, 4-HBCoA, BDO or putrescine producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

$2CO_2 + 4H_2 + nPi \rightarrow CH_3COOH + 2H_2O + nATP$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a 4-HB, 4-HBal, 4-HBCoA, BDO or putrescine pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle is and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or H2 by carbon monoxide dehydrogenase and hydrogenase are utilized to fix CO2 via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the 4-HB, 4-HBal, 4-HBCoA, BDO or putrescine precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a 4-HB, 4-HBal, 4-HBCoA, BDO or putrescine pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 4-HB, 4-HBal, 4-HBCoA, BDO or putrescine and any of the intermediate metabolites in the 4-HB, 4-HBal, 4-HBCoA, BDO or putrescine pathway. All that is required is to engineer in one or more of the required enzyme or protein activities to achieve biosynthesis of the desired compound or intermediate including, for example, inclusion of some or all of the 4-HB, 4-HBal, 4-HBCoA, BDO or putrescine biosynthetic pathways. Accordingly, the invention provides a non-naturally occurring microbial organism that produces and/or secretes 4-HB, 4-HBal, 4-HBCoA, BDO or putrescine when grown on a carbohydrate or other carbon source and produces and/or secretes any of the intermediate metabolites shown in the 4-HB, 4-HBal, 4-HBCoA, BDO or putrescine pathway when grown on a carbohydrate or other carbon source. The 4-HB, 4-HBal, 4-HBCoA, BDO or putrescine producing microbial organisms of the invention can initiate synthesis from an intermediate in a 4-HB, 4-HBal, 4-HBCoA, BDO or putrescine pathway, as disclosed herein.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 4-HB, 4-HBal, 4-HBCoA, BDO or putrescine.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

Employing the methods exemplified above and herein, the methods of the invention allow the construction of cells and organisms that increase production of a desired product, for example, by coupling the production of a desired product to growth of the cell or organism engineered to harbor the identified genetic alterations. As disclosed herein, metabolic alterations have been identified that couple the production of 4-HB, 4-HBal, 4-HBCoA, BDO or putrescine to growth of the organism. Microbial organism strains constructed with the identified metabolic alterations produce elevated levels, relative to the absence of the metabolic alterations, of 4-HB, 4-HBal, 4-HBCoA, BDO or putrescine during the exponential growth phase. These strains can be beneficially used for the commercial production of 4-HB, 4-HBal, 4-HBCoA, BDO or putrescine in continuous fermentation process without being subjected to the negative selective pressures described previously. Although exemplified herein as metabolic alterations, in particular one or more gene disruptions, that confer growth coupled production of 4-HB, 4-HBal, 4-HBCoA, BDO or putrescine, it is understood that any gene disruption that increases the production of 4-HB, 4-HBal, 4-HBCoA, BDO or putrescine can be introduced into a host microbial organism, as desired.

Therefore, the methods of the invention provide a set of metabolic modifications that are identified by an in silico method such as OptKnock. The set of metabolic modifications can include functional disruption of one or more metabolic reactions including, for example, disruption by gene deletion. For 4-HB, 4-HBal, 4-HBCoA, BDO or putrescine production, metabolic modifications can be selected from the set of metabolic modifications described herein, including the Examples.

Also provided is a method of producing a non-naturally occurring microbial organisms having stable growth-coupled production of 4-HB, 4-HBal, 4-HBCoA, BDO or putrescine. The method can include identifying in silico a set of metabolic modifications that increase production of 4-HB, 4-HBal, 4-HBCoA, BDO or putrescine, for example, increase production during exponential growth; genetically modifying an organism to contain the set of metabolic modifications that increase production of 4-HB, 4-HBal, 4-HBCoA, BDO or putrescine, and culturing the genetically modified organism. If desired, culturing can include adaptively evolving the genetically modified organism under conditions requiring production of 4-HB, 4-HBal, 4-HBCoA, BDO or putrescine. The methods of the invention are applicable to bacterium, yeast and fungus as well as a variety of other cells and microorganism, as disclosed herein.

Thus, the invention provides a non-naturally occurring microbial organism comprising one or more gene disruptions that confer increased production of 4-HB, 4-HBal, 4-HBCoA, BDO or putrescine. In one embodiment, the one or more gene disruptions confer growth-coupled production of 4-HB, 4-HBal, 4-HBCoA, BDO or putrescine, and can, for example, confer stable growth-coupled production of 4-HB, 4-HBal, 4-HBCoA, BDO or putrescine. In another embodiment, the one or more gene disruptions can confer obligatory coupling of 4-HB, 4-HBal, 4-HBCoA, BDO or putrescine production to growth of the microbial organism. Such one or more gene disruptions reduce the activity of the respective one or more encoded enzymes.

The non-naturally occurring microbial organism can have one or more gene disruptions included in a metabolic modification as described herein. As disclosed herein, the one or more gene disruptions can be a deletion. Such non-naturally occurring microbial organisms of the invention include bacteria, yeast, fungus, or any of a variety of other microorganisms applicable to fermentation processes, as disclosed herein.

Thus, the invention provides a non-naturally occurring microbial organism, comprising one or more gene disruptions, where the one or more gene disruptions occur in genes encoding proteins or enzymes where the one or more gene disruptions confer increased production of 4-HB, 4-HBal, 4-HBCoA, BDO or putrescine in the organism. The production of 4-HB, 4-HBal, 4-HBCoA, BDO or putrescine can be growth-coupled or not growth-coupled. In a particular embodiment, the production of 4-HB, 4-HBal, 4-HBCoA, BDO or putrescine can be obligatorily coupled to growth of the organism, as disclosed herein.

The invention provides non naturally occurring microbial organisms having genetic alterations such as gene disruptions that increase production of 4-HB, 4-HBal, 4-HBCoA, BDO or putrescine, for example, growth-coupled production of 4-HB, 4-HBal, 4-HBCoA, BDO or putrescine. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Sets of metabolic alterations or transformations that result in increased production and elevated levels of 4-HB, 4-HBal, 4-HBCoA, BDO or putrescine biosynthesis are described herein. Each alteration within a set corresponds to the requisite metabolic reaction that should be functionally disrupted. Functional disruption of all reactions within each set can result in the increased production of 4-HB, 4-HBal, 4-HBCoA, BDO or putrescine by the engineered strain during the growth phase.

A number of metablic modifications that include gene disruptions are described herein. It is understood by those skilled in the art that one or more of the metabolic modifications, including gene disruptions, can be combined to increase 4-HB, 4-HBal, 4-HBCoA, BDO or putrescine or otherwise improve characteristics of the microorganisms of th invention. Each of these non-naturally occurring alterations can result in increased production and an enhanced level of 4-HB, 4-HBal, 4-HBCoA, BDO or putrescine production, for example, during the exponential growth phase of the microbial organism, or otherwise improve the growth or production characteristics of the microorganisms producing 4-HB, 4-HBal, 4-HBCoA, BDO or putrescine compared to a strain that does not contain such metabolic alterations, under appropriate culture conditions. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration such as disruption of an enzymatic reaction, it is necessary to disrupt the catalytic activity of the one or more enzymes involved in the reaction. Alternatively, a metabolic alteration can include disruption of expression of a regulatory protein or cofactor necessary for enzyme activity or maximal activity. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the increased production of 4-HB, 4-HBal, 4-HBCoA, BDO or putrescine or growth-coupled product production.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The 4-HB, 4-HBal, 4-HBCoA, BDO or putrescine production strategies identified by the methods disclosed herein such as the OptKnock framework are generally ranked on the basis of their (i) theoretical yields, and optionally (ii) growth-coupled 4-HB, 4-HBal, 4-HBCoA, BDO or putrescine formation characteristics.

Accordingly, the invention also provides a non-naturally occurring microbial organism having a set of metabolic modifications that increase the yield of 4-HB, 4-HBal, 4-HBCoA, BDO or putrescine, optionally coupling 4-HB, 4-HBal, 4-HBCoA, BDO or putrescine production to growth of the organism, or otherwise improve characteristics of the microorganisms producing 4-HB, 4-HBal, 4-HBCoA, BDO or putrescine, where the set of metabolic modifications includes disruption of one or more genes, as described herein.

Each of the strains can be supplemented with additional deletions if it is determined that the strain designs do not sufficiently increase the production of 4-HB, 4-HBal, 4-HBCoA, BDO or putrescine and/or couple the formation of the product with biomass formation. Alternatively, some other enzymes not known to possess significant activity under the growth conditions can become active due to adaptive evolution or random mutagenesis. Such activities can also be knocked out. However, the list of gene deletion sets disclosed herein allows the construction of strains exhibiting high-yield production of 4-HB, 4-HBal, 4-HBCoA, BDO or putrescine, including growth-coupled production of 4-HB, 4-HBal, 4-HBCoA, BDO or putrescine.

4-HB, 4-HBal, 4-HBCoA, BDO or putrescine can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of 4-HB, 4-HBal, 4-HBCoA, BDO or putrescine can be produced.

Therefore, the invention additionally provides a method for producing 4-HB, 4-HBal, 4-HBCoA, BDO or putrescine that includes culturing a non-naturally occurring microbial organism having one or more gene disruptions, as disclosed herein. The disruptions can occur in one or more genes encoding an enzyme that increases production of 4-HB, 4-HBal, 4-HBCoA, BDO or putrescine, including optionally coupling 4-HB, 4-HBal, 4-HBCoA, BDO or putrescine production to growth of the microorganism when the gene disruption reduces or eliminates an activity of the enzyme.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational or other predictions are made of one or more genes sets disruption to increase production of 4-HB, 4-HBal, 4-HBCoA, BDO or putrescine, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth rates until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36:1056-1058 (2004)). The growth improvements brought about by adaptive evolution can be accompanied by enhanced rates of 4-HB, 4-HBal, 4-HBCoA, BDO or putrescine production. The strains can optionally be adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarra et al., *Nature* 420:186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields alongside the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

Adaptive evolution is a powerful technique that can be used to increase growth rates of mutant or engineered microbial strains, or of wild-type strains growing under unnatural environmental conditions. It is especially useful for strains designed via methods such as OptKnock, which results in growth-coupled product formation. Therefore, evolution toward optimal growing strains will indirectly optimize production as well. Unique strains of E. coli K-12 MG1655 were created through gene knockouts and adaptive evolution. (Fong and Palsson, Nat. Genet. 36:1056-1058 (2004)). In this work, all adaptive evolutionary cultures were maintained in prolonged exponential growth by serial passage of batch cultures into fresh medium before the stationary phase was reached, thus rendering growth rate as the primary selection pressure. Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (within 10%) at predicting the post-evolution growth rate of the knockout strains in 38 out of the 50 cases examined. Furthermore, a combination of OptKnock design with adaptive evolution has led to improved lactic acid production strains. (Fong et al., Biotechnol. Bioeng. 91:643-648 (2005)). Similar methods can be applied to the strains disclosed herein and applied to various host strains.

There are a number of developed technologies for carrying out adaptive evolution. Exemplary methods are disclosed herein. In some embodiments, optimization of a non-naturally occurring organism of the present invention includes utilizing adaptive evolution techniques to increase 4-HB, 4-HBal, 4-HBCoA, BDO or putrescine production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, Proc. Natl. Acad. Sci. USA 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, Methods Enzymol. 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, J. Gen. Microbiol 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

Evolugator™ is a continuous culture device developed by Evoluate, LLC (Gainesville, Fla.) and exhibits significant time and effort savings over traditional evolution techniques (de Crecy et al., Appl. Microbiol. Biotechnol. 77:489-496 (2007)). The cells are maintained in prolonged exponential growth by the serial passage of batch cultures into fresh medium before the stationary phase is attained. By automating optical density measurement and liquid handling, the Evolugator™ can perform serial transfer at high rates using large culture volumes, thus approaching the efficiency of a chemostat in evolution of cell fitness. For example, a mutant of Acinetobacter sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%. A drawback to this device is that it is large and costly, thus running large numbers of evolutions in parallel is not practical. Furthermore, gas addition is not well regulated, and strict anaerobic conditions are not maintained with the current device configuration. Nevertheless, this is an alternative method to adaptively evolve a production strain.

As disclosed herein, a nucleic acid encoding a desired activity of a 4-HB, 4-HBal, 4-HBCoA, BDO or putrescine pathway can be introduced into a host organism. In some cases, it can be desirable to modify an activity of a 4-HB, 4-HBal, 4-HBCoA BDO or putrescine pathway enzyme or protein to increase production of 4-HB, 4-HBal, 4-HBCoA BDO or putrescine. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a 4-HB, 4-HBal, 4-HBCoA, BDO or putrescine pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., Nat. Biotechnol. 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego, Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

Example I

Biosynthesis of 4-Hydroxybutanoic Acid

This example describes exemplary biochemical pathways for 4-HB production.

Previous reports of 4-HB synthesis in microbes have focused on this compound as an intermediate in production of the biodegradable plastic poly-hydroxyalkanoate (PHA) (U.S. Pat. No. 6,117,658). The use of 4-HB/3-HB copolymers over poly-3-hydroxybutyrate polymer (PHB) can result in plastic that is less brittle (Saito and Doi, *Intl. J. Biol. Macromol.* 16:99-104 (1994)). The production of monomeric 4-HB described herein is a fundamentally distinct process for several reasons: (1) the product is secreted, as opposed to PHA which is produced intracellularly and remains in the cell; (2) for organisms that produce hydroxybutanoate polymers, free 4-HB is not produced, but rather the Coenzyme A derivative is used by the polyhydroxyalkanoate synthase; (3) in the case of the polymer, formation of the granular product changes thermodynamics; and (4) extracellular pH is not an issue for production of the polymer, whereas it will affect whether 4-HB is present in the free acid or conjugate base state, and also the equilibrium between 4-HB and GBL.

4-HB can be produced in two enzymatic reduction steps from succinate, a central metabolite of the TCA cycle, with succinic semialdehyde as the intermediate (FIG. 1). The first of these enzymes, succinic semialdehyde dehydrogenase, is native to many organisms including *E. coli*, in which both NADH- and NADPH-dependent enzymes have been found (Donnelly and Cooper, *Eur. J. Biochem.* 113:555-561 (1981); Donnelly and Cooper, *J. Bacteriol.* 145:1425-1427 &; (1981); Marek and Henson, *J. Bacteriol.* 170:991-994 (1988)). There is also evidence supporting succinic semialdehyde dehydrogenase activity in *S. cerevisiae* (Ramos et al., *Eur. J. Biochem.* 149:401-404 (1985)), and a putative gene has been identified by sequence homology. However, most reports indicate that this enzyme proceeds in the direction of succinate synthesis, as shown in FIG. 1 (Donnelly and Cooper, supra; Lutke-Eversloh and Steinbuchel, *FEMS Microbiol. Lett.* 181:63-71 (1999)), participating in the degradation pathway of 4-HB and gamma-aminobutyrate. Succinic semialdehyde also is natively produced by certain microbial organisms such as *E. coli* through the TCA cycle intermediate α-ketogluterate via the action of two enzymes: glutamate:succinic semialdehyde transaminase and glutamate decarboxylase. An alternative pathway, used by the obligate anaerobe *Clostridium kluyveri* to degrade succinate, activates succinate to succinyl-CoA, then converts succinyl-CoA to succinic semialdehyde using an alternative succinic semialdehyde dehydrogenase which is known to function in this direction (Sohling and Gottschalk, *Eur. J. Biochem.* 212:121-127 (1993)). However, this route has the energetic cost of ATP required to convert succinate to succinyl-CoA.

The second enzyme of the pathway, 4-hydroxybutanoate dehydrogenase, is not native to *E. coli* or yeast but is found in various bacteria such as *C. kluyveri* and *Ralstonia eutropha* (Lutke-Eversloh and Steinbuchel, supra; Sohling and Gottschalk, *J. Bacteriol.* 178:871-880 (1996); Valentin et al., *Eur. J. Biochem.* 227:43-60 (1995); Wolff and Kenealy, *Protein Expr. Purif.* 6:206-212 (1995)). These enzymes are known to be NADH-dependent, though NADPH-dependent forms also exist. An additional pathway to 4-HB from alpha-ketoglutarate was demonstrated in *E. coli* resulting in the accumulation of poly(4-hydroxybutyric acid) (Song et al., *Wei Sheng Wu Xue. Bao.* 45:382-386 (2005)). The recombinant strain required the overexpression of three heterologous genes, PHA synthase (*R. eutropha*), 4-hydroxybutyrate dehydrogenase (*R. eutropha*) and 4-hydroxybutyrate:CoA transferase (*C. kluyveri*), along with two native *E. coli* genes: glutamate:succinic semialdehyde transaminase and glutamate decarboxylase. Steps 4 and 5 in FIG. 1 can alternatively be carried out by an alpha-ketoglutarate decarboxylase such as the one identified in *Euglena gracilis* (Shigeoka et al., *Biochem. J.* 282(Pt2):319-323 (1992); Shigeoka and Nakano, *Arch. Biochem. Biophys.* 288:22-28 (1991); Shigeoka and Nakano, *Biochem J.* 292(Pt 2):463-467 (1993)). However, this enzyme has not previously been applied to impact the production of 4-HB or related polymers in any organism.

The microbial production capabilities of 4-hydroxybutyrate were explored in two microbes, *Escherichia coli* and *Saccharomyces cerevisiae*, using in silico metabolic models of each organism. Potential pathways to 4-HB proceed via a succinate, succinyl-CoA, or alpha-ketoglutarate intermediate as shown in FIG. 1.

A first step in the 4-HB production pathway from succinate involves the conversion of succinate to succinic semialdehyde via an NADH- or NADPH-dependant succinic semialdehyde dehydrogenase. In *E. coli*, gabD is an NADP-dependant succinic semialdehyde dehydrogenase and is part of a gene cluster involved in 4-aminobutyrate uptake and degradation (Niegemann et al., *Arch. Microbiol.* 160:454-460 (1993); Schneider et al., *J. Bacteriol.* 184:6976-6986 (2002)). sad is believed to encode the enzyme for NAD-dependant succinic semialdehyde dehydrogenase activity (Marek and Henson, supra). *S. cerevisiae* contains only the NADPH-dependant succinic semialdehyde dehydrogenase, putatively assigned to UGA2, which localizes to the cytosol (Huh et al., *Nature* 425:686-691 (2003)). The maximum yield calculations assuming the succinate pathway to 4-HB in both *E. coli* and *S. cerevisiae* require only the assumption that a non-native 4-HB dehydrogenase has been added to their metabolic networks.

The pathway from succinyl-CoA to 4-hydroxybutyrate was described in U.S. Pat. No. 6,117,658 as part of a process for making polyhydroxyalkanoates comprising 4-hydroxybutyrate monomer units. *Clostridium kluyveri* is one example organism known to possess CoA-dependant succinic semialdehyde dehydrogenase activity (Sohling and Gottschalk, supra; Sohling and Gottschalk, supra). In this study, it is assumed that this enzyme, from *C. kluyveri* or another organism, is expressed in *E. coli* or *S. cerevisiae* along with a non-native or heterologous 4-HB dehydrogenase to complete the pathway from succinyl-CoA to 4-HB. The pathway from alpha-ketoglutarate to 4-HB was demonstrated in *E. coli* resulting in the accumulation of poly(4-hydroxybutyric acid) to 30% of dry cell weight (Song et al., supra). As *E. coli* and *S. cerevisiae* natively or endogenously possess both glutamate:succinic semialdehyde transaminase and glutamate decarboxylase (Coleman et al., *J. Biol. Chem.* 276:244-250 (2001)), the pathway from AKG to 4-HB can be completed in both organisms by assuming only that a non-native 4-HB dehydrogenase is present.

Example II

Biosynthesis of 1,4-Butanediol from Succinate and Alpha-ketoglutarate

This example illustrates the construction and biosynthetic production of 4-HB and BDO from microbial organisms. Pathways for 4-HB and BDO are disclosed herein.

There are several alternative enzymes that can be utilized in the pathway described above. The native or endogenous enzyme for conversion of succinate to succinyl-CoA (Step 1 in FIG. 1) can be replaced by a CoA transferase such as that encoded by the cat1 gene *C. kluyveri* (Sohling and Gottschalk, *Eur. J Biochem.* 212:121-127 (1993)), which functions in a similar manner to Step 9. However, the production of acetate by this enzyme may not be optimal, as it might be secreted rather than being converted back to acetyl-CoA. In this respect, it also can be beneficial to eliminate acetate formation in Step 9. As one alternative to this CoA transferase, a mechanism can be employed in which the 4-HB is first phosphorylated by ATP and then converted to the CoA derivative, similar to the acetate kinase/phosphotransacetylase pathway in *E. coli* for the conversion of acetate to acetyl-CoA. The net cost of this route is one ATP, which is the same as is required to regenerate acetyl-CoA from acetate. The enzymes phosphotransbutyrylase (ptb) and butyrate kinase (bk) are known to carry out these steps on the non-hydroxylated molecules for butyrate production in *C. acetobutylicum* (Cary et al., *Appl Environ Microbiol* 56:1576-1583 (1990); Valentine, R. C. and R. S. Wolfe, *J Biol Chem.* 235:1948-1952 (1960)). These enzymes are reversible, allowing synthesis to proceed in the direction of 4-HB.

BDO also can be produced via α-ketoglutarate in addition to or instead of through succinate. A described previously, and exemplified further below, one pathway to accomplish product biosynthesis is with the production of succinic semialdehyde via α-ketoglutarate using the endogenous enzymes (FIG. 1, Steps 4-5). An alternative is to use an α-ketoglutarate decarboxylase that can perform this conversion in one step (FIG. 1, Step 8; Tian et al., *Proc Natl Acad Sci U.S.A* 102:10670-10675 (2005)).

For the construction of different strains of BDO-producing microbial organisms, a list of applicable genes was assembled for corroboration. Briefly, one or more genes within the 4-HB and/or BDO biosynthetic pathways were identified for each step of the complete BDO-producing pathway shown in FIG. 1, using available literature resources, the NCBI genetic database, and homology searches. The genes cloned and assessed in this study are presented below in in Table 6, along with the appropriate references and URL citations to the polypeptide sequence. As discussed further below, some genes were synthesized for codon optimization while others were cloned via PCR from the genomic DNA of the native or wild-type organism. For some genes both approaches were used, and in this case the native genes are indicated by an "n" suffix to the gene identification number when used in an experiment. Note that only the DNA sequences differ; the proteins are identical.

TABLE 6

Genes expressed in host BDO-producting microbial organisms.

| Gene ID number | Reaction number (FIG. 1) | Gene name | Source organism | Enzyme name | Link to protein sequence | Reference |
|---|---|---|---|---|---|---|
| 0001 | 9 | Cat2 | *Clostridium kluyveri* DSM 555 | 4-hydroxybutyrate coenzyme A transferase | www.ncbi.nlm.nih.gov/entrez/viewer.fcgi?db=nuccore&id=1228100 | 1 |
| 0002 | 12/13 | adhE | *Clostridium acetobutylicum* ATCC 824 | Aldehyde/alcohol dehydrogenase | www.ncbi.nlm.nih.gov/entrez/viewer.fcgi?db=protein&val=15004739 | 2 |
| 0003 | 12/13 | adhE2 | *Clostridium acetobutylicum* ATCC 824 | Aldehyde/alcohol dehydrogenase | www.ncbi.nlm.nih.gov/entrez/viewer.fcgi?val=NP_149325.1 | 2 |
| 0004 | 1 | Cat1 | *Clostridium kluyveri* DSM 555 | Succinate coenzyme A transferase | www.ncbi.nlm.nih.gov/entrez/viewer.fcgi?db=nuccore&id=1228100 | 1 |

TABLE 6-continued

Genes expressed in host BDO-producting microbial organisms.

| Gene ID number | Reaction number (FIG. 1) | Gene name | Source organism | Enzyme name | Link to protein sequence | Reference |
|---|---|---|---|---|---|---|
| 0008 | 6 | sucD | Clostridium kluyveri DSM 555 | Succinic semialdehyde dehydrogenase (CoA-dependent) | www.ncbi.nlm.nih.gov/entrez/viewer.fcgi?db=nuccore&id=1228100 | 1 |
| 0009 | 7 | 4-HBd | Ralstonia eutropha H16 | 4-hydroxybutyrate dehydrogenase (NAD-dependent) | www.ncbi.nlm.nih.gov/entrez/viewer.fcgi?val=YP_726053.1 | 2 |
| 0010 | 7 | 4-HBd | Clostridium kluyveri DSM 555 | 4-hydroxybutyrate dehydrogenase (NAD-dependent) | www.ncbi.nlm.nih.gov/entrez/viewer.fcgi?db=nuccore&id=1228100 | 1 |
| 0011 | 12/13 | adhE | E. coli | Aldehyde/alcohol dehydrogenase | www.shigen.nig.ac.jp/ecoli/pec/genes.List.DetailAction.do?fromListFlag=true&featureType=1&orfId=1219 | |
| 0012 | 12/13 | yqhD | E. coli | Aldehyde/alcohol dehydrogenase | www.shigen.nig.ac.jp/ecoli/pec/genes.List.DetailAction.do | |
| 0013 | 13 | bdhB | Clostridium acetobutylicum ATCC 824 | Butanol dehydrogenase II | www.ncbi.nlm.nih.gov/entrez/viewer.fcgi?val=NP_349891.1 | 2 |
| 0020 | 11 | ptb | Clostridium acetobutylicum ATCC 824 | Phospho-transbutyrylase | www.ncbi.nlm.nih.gov/entrez/viewer.fcgi?db=protein&id=15896327 | 2 |
| 0021 | 10 | buk1 | Clostridium acetobutylicum ATCC 824 | Butyrate kinase I | www.ncbi.nlm.nih.gov/entrez/viewer.fcgi?db=protein&id=20137334 | 2 |
| 0022 | 10 | buk2 | Clostridium acetobutylicum ATCC 824 | Butyrate kinase II | www.ncbi.nlm.nih.gov/entrez/viewer.fcgi?db=protein&id=20137415 | 2 |
| 0023 | 13 | adhEm | isolated from metalibrary of anaerobic sewage digester microbial consortia | Alcohol dehydrogenase | | (37)d} |
| 0024 | 13 | adhE | Clostridium thermocellum | Alcohol dehydrogenase | www.genome.jp/dbget-bin/www_bget?cth:Cthe_0423 | |
| 0025 | 13 | ald | Clostridium beijerinckii | Coenzyme A-acylating aldehyde dehydrogenase | www.ncbi.nlm.nih.gov/entrez/viewer.fcgi?db=protein&id=49036681 | (31)d} |
| 0026 | 13 | bdhA | Clostridium acetobutylicum ATCC 824 | Butanol dehydrogenase | www.ncbi.nlm.nih.gov/entrez/viewer.fcgi?val=NP_349892.1 | 2 |
| 0027 | 12 | bld | Clostridium saccharoperbutylacetonicum | Butyraldehyde dehydrogenase | www.ncbi.nlm.nih.gov/entrez/viewer.fcgi?db=protein&id=31075383 | 4 |
| 0028 | 13 | bdh | Clostridium saccharoperbutylacetonicum | Butanol dehydrogenase | www.ncbi.nlm.nih.gov/entrez/viewer.fcgi?db=protein&id=124221917 | 4 |
| 0029 | 12/13 | adhE | Clostridium tetani | Aldehyde/alcohol dehydrogenase | www.genome.jp/dbget-bin/www_bget?ctc:CTC01366 | |
| 0030 | 12/13 | adhE | Clostridium perfringens | Aldehyde/alcohol dehydrogenase | www.genome.jp/dbget-bin/www_bget?cpe:CPE2531 | |
| 0031 | 12/13 | adhE | Clostridium difficile | Aldehyde/alcohol dehydrogenase | www.genome.jp/dbget-bin/www_bget?cdf:CD2966 | |
| 0032 | 8 | sucA | Mycobacterium bovis BCG, Pasteur | α-ketoglutarate decarboxylase | www.ncbi.nlm.nih.gov/entrez/viewer.fcgi?val=YP_977400.1 | 5 |
| 0033 | 9 | cat2 | Clostridium aminobutyricum | 4-hydroxybutyrate coenzyme A transferase | www.ncbi.nlm.nih.gov/entrez/viewer.fcgi?db=protein&val=6249316 | |
| 0034 | 9 | cat2 | Porphyromonas gingivalis W83 | 4-hydroxybutyrate coenzyme A transferase | www.ncbi.nlm.nih.gov/entrez/viewer.fcgi?db=protein&val=34541558 | |
| 0035 | 6 | sucD | Porphyromonas gingivalis W83 | Succinic semialdehyde dehydrogenase (CoA-dependent) | www.ncbi.nlm.nih.gov/entrez/viewer.fcgi?val=NP_904963.1 | |
| 0036 | 7 | 4-HBd | Porphyromonas gingivalis W83 | NAD-dependent 4-hydroxybutyrate dehydrogenase | www.ncbi.nlm.nih.gov/entrez/viewer.fcgi?val=NP_904964.1 | |

TABLE 6-continued

Genes expressed in host BDO-producing microbial organisms.

| Gene ID number | Reaction number (FIG. 1) | Gene name | Source organism | Enzyme name | Link to protein sequence | Reference |
|---|---|---|---|---|---|---|
| 0037 | 7 | gbd | Uncultured bacterium | 4-hydroxybutyrate dehydrogenase | www.ncbi.nlm.nih.gov/entrez/viewer.fcgi?db=nuccore&id=5916168 | 6 |
| 0038 | 1 | sucCD | E. coli | Succinyl-CoA synthetase | www.shigen.nig.ac.jp/ecoli/pec/genes.List.DetailAction.do | |

1 Sohling and Gottschalk, Eur. J. Biochem. 212: 121-127 (1993); Sohling and Gottschalk, J. Bacterial. 178: 871-880 (1996)
2 Nolling et al., J., J. Bacteriol. 183: 4823-4838 (2001)
3 Pohlmann et al., Nat. Biotechnol. 24: 1257-1262 (2006)
4 Kosaka et al., Biosci. Biotechnol. Biochem. 71: 58-68 (2007)
5 Brosch et al., Proc. Natl. Acad. Sci. U.S.A. 104: 5596-5601 (2007)
6 Henne et al., Appl. Environ. Microbiol. 65: 3901-3907 (1999)

Expression Vector Construction for BDO pathway. Vector backbones and some strains were obtained from Dr. Rolf Lutz of Expressys (expressys.de/). The vectors and strains are based on the pZ Expression System developed by Dr. Rolf Lutz and Prof. Hermann Bujard (Lutz, R. and H. Bujard, Nucleic Acids Res 25:1203-1210 (1997)). Vectors obtained were pZE13luc, pZA33luc, pZS*13luc and pZE22luc and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

lacZalpha-RI
(SEQ ID NO: 1)
5'GACGAATTCGCTAGCAAGAGGAGAAGTCGACATGTCCAATTCACTGG
CCGTCGTTTTAC3' lacZalpha 3'BB
(SEQ ID NO: 2)
5'-GACCCTAGGAAGCTTTCTAGAGTCGACCTATGCGGCATCAGAGCAG
A-3'.

This generated a fragment with a 5' end of EcoRI site, NheI site, a Ribosomal Binding Site, a SalI site and the start codon. On the 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a NheI/XbaI non-site that is not digested by either enzyme), the genes cloned into the vectors could be "Biobricked" together (openwetware-.org/wiki/Synthetic_Biology:BioBricks). Briefly, this method allows joining an unlimited number of genes into the vector using the same 2 restriction sites (as long as the sites do not appear internal to the genes), because the sites between the genes are destroyed after each addition.

All vectors have the pZ designation followed by letters and numbers indication the origin of replication, antibiotic resistance marker and promoter/regulatory unit. The origin of replication is the second letter and is denoted by E for ColE1, A for p15A and S for pSC101-based origins. The first number represents the antibiotic resistance marker (1 for Ampicillin, 2 for Kanamycin, 3 for Chloramphenicol, 4 for Spectinomycin and 5 for Tetracycline). The final number defines the promoter that regulated the gene of interest (1 for $P_{LtetO-1}$, 2 for $P_{LlacO-1}$, 3 for $P_{A1lacO-1}$, and 4 for $P_{lac/ara-1}$). The MCS and the gene of interest follows immediately after.

For the work discussed here we employed two base vectors, pZA33 and pZE13, modified for the biobricks insertions as discussed above. Once the gene(s) of interest have been cloned into them, resulting plasmids are indicated using the four digit gene codes given in Table 6; e.g., pZA33-XXXX-YYYY- . . .

Host Strain Construction. The parent strain in all studies described here is E. coli K-12 strain MG1655. Markerless deletion strains in adhE, gabD, and aldA were constructed under service contract by a third party using the redET method (Datsenko, K. A. and B. L. Wanner, Proc Natl Acad Sci U.S.A 97:6640-6645 (2000)). Subsequent strains were constructed via bacteriophage P1 mediated transduction (Miller, J. Experiments in Molecular Genetics, Cold Spring Harbor Laboratories, New York (1973)). Strain C600Z1 ($lacI^q$, PN25-tetR, $Sp^R$, lacY1, leuB6, mcrB+, supE44, thi-1, thr-1, tonA21) was obtained from Expressys and was used as a source of a $lacI^q$ allele for P1 transduction. Bacteriophage P1vir was grown on the C600Z1 E. coli strain, which has the spectinomycin resistance gene linked to the $lacI^q$. The P1 lysate grown on C600Z1 was used to infect MG1655 with selection for spectinomycin resistance. The spectinomycin resistant colonies were then screened for the linked $lacI^q$ by determining the ability of the transductants to repress expression of a gene linked to a $P_{A1lacO-1}$ promoter. The resulting strain was designated MG1655 $lacI^q$. A similar procedure was used to introduce $lacI^Q$ into the deletion strains.

Production of 4-HB From Succinate. For construction of a 4-HB producer from succinate, genes encoding steps from succinate to 4-HB and 4-HB-CoA (1, 6, 7, and 9 in FIG. 1) were assembled onto the pZA33 and pZE13 vectors as described below. Various combinations of genes were assessed, as well as constructs bearing incomplete pathways as controls (Tables 7 and 8). The plasmids were then transformed into host strains containing $lacI^Q$, which allow inducible expression by addition of isopropyl β-D-1-thio-galactopyranoside (IPTG). Both wild-type and hosts with deletions in genes encoding the native succinic semialdehyde dehydrogenase (step 2 in FIG. 1) were tested.

Activity of the heterologous enzymes were first tested in in vitro assays, using strain MG1655 $lacI^Q$ as the host for the plasmid constructs containing the pathway genes. Cells were grown aerobically in LB media (Difco) containing the appropriate antibiotics for each construct, and induced by addition of IPTG at 1 mM when the optical density (OD600) reached approximately 0.5. Cells were harvested after 6 hours, and enzyme assays conducted as discussed below.

In Vitro Enzyme Assays. To obtain crude extracts for activity assays, cells were harvested by centrifugation at 4,500 rpm (Beckman-Coulter, Allegera X-15R) for 10 min. The pellets were resuspended in 0.3 mL BugBuster (Novagen) reagent with benzonase and lysozyme, and lysis proceeded for 15 minutes at room temperature with gentle shaking. Cell-free lysate was obtained by centrifugation at 14,000 rpm (Eppendorf centrifuge 5402) for 30 min at 4° C. Cell protein in the sample was determined using the method of Bradford et al., *Anal. Biochem.* 72:248-254 (1976), and specific enzyme assays conducted as described below. Activities are reported in Units/mg protein, where a unit of activity is defined as the amount of enzyme required to convert 1 μmol of substrate in 1 min. at room temperature. In general, reported values are averages of at least 3 replicate assays.

Succinyl-CoA transferase (Cat1) activity was determined by monitoring the formation of acetyl-CoA from succinyl-CoA and acetate, following a previously described procedure Sohling and Gottschalk, *J. Bacteriol.* 178:871-880 (1996). Succinyl-CoA synthetase (SucCD) activity was determined by following the formation of succinyl-CoA from succinate and CoA in the presence of ATP. The experiment followed a procedure described by Cha and Parks, J. Biol. Chem. 239:1961-1967 (1964). CoA-dependent succinate semialdehyde dehydrogenase (SucD) activity was determined by following the conversion of NAD to NADH at 340 nm in the presence of succinate semialdehyde and CoA (Sohling and Gottschalk, *Eur. J. Biochem.* 212: 121-127 (1993)). 4-HB dehydrogenase (4-HBd) enzyme activity was determined by monitoring the oxidation of NADH to NAD at 340 nm in the presence of succinate semialdehyde. The experiment followed a published procedure Gerhardt et al. *Arch. Microbiol.* 174:189-199 (2000). 4-HB CoA transferase (Cat2) activity was determined using a modified procedure from Scherf and Buckel, *Appl. Environ. Microbiol.* 57:2699-2702 (1991). The formation of 4-HB-CoA or butyryl-CoA formation from acetyl-CoA and 4-HB or butyrate was determined using HPLC.

Alcohol (ADH) and aldehyde (ALD) dehydrogenase was assayed in the reductive direction using a procedure adapted from several literature sources (Durre et al., *FEMS Microbiol. Rev.* 17:251-262 (1995); Palosaari and Rogers, *J. Bacteriol.* 170:2971-2976 (1988) and Welch et al., *Arch. Biochem. Biophys.* 273:309-318 (1989). The oxidation of NADH is followed by reading absorbance at 340 nM every four seconds for a total of 240 seconds at room temperature. The reductive assays were performed in 100 mM MOPS (adjusted to pH 7.5 with KOH), 0.4 mM NADH, and from 1 to 50 μl of cell extract. The reaction is started by adding the following reagents: 100 μl of 100 mM acetaldehyde or butyraldehyde for ADH, or 100 μl of 1 mM acetyl-CoA or butyryl-CoA for ALD. The Spectrophotometer is quickly blanked and then the kinetic read is started. The resulting slope of the reduction in absorbance at 340 nM per minute, along with the molar extinction coefficient of NAD(P)H at 340 nM (6000) and the protein concentration of the extract, can be used to determine the specific activity.

The enzyme activity of PTB is measured in the direction of butyryl-CoA to butyryl-phosphate as described in Cary et al. *J. Bacteriol.* 170:4613-4618 (1988). It provides inorganic phosphate for the conversion, and follows the increase in free CoA with the reagent 5,5'-dithiobis-(2-nitrobenzoic acid), or DTNB. DTNB rapidly reacts with thiol groups such as free CoA to release the yellow-colored 2-nitro-5-mercaptobenzoic acid (TNB), which absorbs at 412 nm with a molar extinction coefficient of 14,140 M cm$^{-1}$. The assay buffer contained 150 mM potassium phosphate at pH 7.4, 0.1 mM DTNB, and 0.2 mM butyryl-CoA, and the reaction was started by addition of 2 to 50 μL cell extract. The enzyme activity of BK is measured in the direction of butyrate to butyryl-phosphate formation at the expense of ATP. The procedure is similar to the assay for acetate kinase previously described Rose et al., *J. Biol. Chem.* 211:737-756 (1954). However it has been found that another acetate kinase enzyme assay protocol provided by Sigma to be more useful and sensitive. This assay links conversion of ATP to ADP by acetate kinase to the linked conversion of ADP and phosphoenolpyruvate (PEP) to ATP and pyruvate by pyruvate kinase, followed by the conversion of pyruvate and NADH to lactate and NAD+ by lactate dehydrogenase. Substituting butyrate for acetate is the only major modification to allow the assay to follow BK enzyme activity. The assay mixture contained 80 mM triethanolamine buffer at pH 7.6, 200 mM sodium butyrate, 10 mM MgCl2, 0.1 mM NADH, 6.6 mM ATP, 1.8 mM phosphoenolpyruvate. Pyruvate kinase, lactate dehydrogenase, and myokinase were added according to the manufacturer's instructions. The reaction was started by adding 2 to 50 μL cell extract, and the reaction was monitored based on the decrease in absorbance at 340 nm indicating NADH oxidation.

Analysis of CoA Derivatives by HPLC. An HPLC based assay was developed to monitor enzymatic reactions involving coenzyme A (CoA) transfer. The developed method allowed enzyme activity characterization by quantitative determination of CoA, acetyl CoA (AcCoA), butyryl CoA (BuCoA) and 4-hydroxybutyrate CoA (4-HBCoA) present in in-vitro reaction mixtures. Sensitivity down to low μM was achieved, as well as excellent resolution of all the CoA derivatives of interest.

Chemical and sample preparation was performed as follows. Briefly, CoA, AcCoA, BuCoA and all other chemicals, were obtained from Sigma-Aldrich. The solvents, methanol and acetonitrile, were of HPLC grade. Standard calibration curves exhibited excellent linearity in the 0.01-1 mg/mL concentration range. Enzymatic reaction mixtures contained 100 mM Tris HCl buffer (pH 7), aliquots were taken at different time points, quenched with formic acid (0.04% final concentration) and directly analyzed by HPLC.

HPLC analysis was performed using an Agilent 1100 HPLC system equipped with a binary pump, degasser, thermostated autosampler and column compartment, and diode array detector (DAD), was used for the analysis. A reversed phase column, Kromasil 100 5um C18, 4.6×150 mm (Peeke Scientific), was employed. 25 mM potassium phosphate (pH 7) and methanol or acetonitrile, were used as aqueous and organic solvents at 1 mL/min flow rate. Two methods were developed: a short one with a faster gradient for the analysis of well-resolved CoA, AcCoA and BuCoA, and a longer method for distinguishing between closely eluting AcCoA and 4-HBCoA. Short method employed acetonitrile gradient (0 min-5%, 6 min-30%, 6.5 min-5%, 10 min-5%) and resulted in the retention times 2.7, 4.1 and 5.5 min for CoA, AcCoA and BuCoA, respectively. In the long method methanol was used with the following linear gradient: 0 min-5%, 20 min-35%, 20.5 min-5%, 25 min-5%. The retention times for CoA, AcCoA, 4-HBCoA and BuCoA were 5.8, 8.4, 9.2 and 16.0 min, respectively. The injection volume was 5 μL, column temperature 30° C., and UV absorbance was monitored at 260 nm.

The results demonstrated activity of each of the four pathway steps (Table 7), though activity is clearly dependent on the gene source, position of the gene in the vector, and the context of other genes with which it is expressed. For example, gene 0035 encodes a succinic semialdehyde dehydrogenase that is more active than that encoded by 0008, and 0036 and 0010n are more active 4-HB dehydrogenase genes than 0009. There also seems to be better 4-HB dehydrogenase activity when there is another gene preceding it on the same operon.

TABLE 7

In vitro enzyme activities in cell extracts from MG1655 lacI$^Q$ containing the plasmids expressing genes in the 4-HB-CoA pathway. Activities are reported in Units/mg protein, where a unit of activity is defined as the amount of enzyme required to convert 1 μmol of substrate in 1 min. at room temperature.

| Sample # | pZE13 (a) | pZA33 (b) | OD600 | Cell Prot (c) | Cat1 | SucD | 4HBd | Cat2 |
|---|---|---|---|---|---|---|---|---|
| 1 | cat1 (0004) | | 2.71 | 6.43 | 1.232 | 0.00 | | |
| 2 | cat1 (0004)-sucD (0035) | | 2.03 | 5.00 | 0.761 | 2.57 | | |
| 3 | cat1 (0004)-sucD (0008) | | 1.04 | 3.01 | 0.783 | 0.01 | | |
| 4 | sucD (0035) | | 2.31 | 6.94 | | 2.32 | | |
| 5 | sucD (0008) | | 1.10 | 4.16 | | 0.05 | | |
| 6 | | 4hbd (0009) | 2.81 | 7.94 | 0.003 | | 0.25 | |
| 7 | | 4hbd (0036) | 2.63 | 7.84 | | | 3.31 | |
| 8 | | 4hbd (0010n) | 2.00 | 5.08 | | | 2.57 | |
| 9 | cat1 (0004)-sucD (0035) | 4hbd (0009) | 2.07 | 5.04 | 0.600 | 1.85 | 0.01 | |
| 10 | cat1 (0004)-sucD (0035) | 4hbd (0036) | 2.08 | 5.40 | 0.694 | 1.73 | 0.41 | |
| 11 | cat1 (0004)-sucD (0035) | 4hbd (0010n) | 2.44 | 4.73 | 0.679 | 2.28 | 0.37 | |
| 12 | cat1 (0004)-sucD (0008) | 4hbd (0009) | 1.08 | 3.99 | 0.572 | −0.01 | 0.02 | |
| 13 | cat1 (0004)-sucD (0008) | 4hbd (0036) | 0.77 | 2.60 | 0.898 | −0.01 | 0.04 | |
| 14 | cat1 (0004)-sucD (0008) | 4hbd (0010n) | 0.63 | 2.47 | 0.776 | 0.00 | 0.00 | |
| 15 | | cat2 (0034) | 2.56 | 7.86 | | | | 1.283 |
| 16 | | cat2(0034)-4hbd(0036) | 3.13 | 8.04 | | | 24.86 | 0.993 |
| 17 | | cat2(0034)-4hbd(0010n) | 2.38 | 7.03 | | | 7.45 | 0.675 |
| 18 | | 4hbd(0036)-cat2(0034) | 2.69 | 8.26 | | | 2.15 | 7.490 |
| 19 | | 4hbd(0010n)-cat2(0034) | 2.44 | 6.59 | | | 0.59 | 4.101 |

Genes expressed from Plac on pZE13, a high-copy plasmid with colE1 origin and ampicillin resistance. Gene identification numbers are as given in Table 6
Genes expressed from Plac on pZA33, a medium-copy plasmid with pACYC origin and chloramphenicol resistance.
(c) Cell protein given as mg protein per mL extract.

Recombinant strains containing genes in the 4-HB pathway were then evaluated for the ability to produce 4-HB in vivo from central metabolic intermediates. Cells were grown anaerobically in LB medium to OD600 of approximately 0.4, then induced with 1 mM IPTG. One hour later, sodium succinate was added to 10 mM, and samples taken for analysis following an additional 24 and 48 hours. 4-HB in the culture broth was analyzed by GC-MS as described below. The results indicate that the recombinant strain can produce over 2 mM 4-HB after 24 hours, compared to essentially zero in the control strain (Table 8).

An alternate to using a CoA transferase (cat1) to produce succinyl-CoA from succinate is to use the native E. coli sucCD genes, encoding succinyl-CoA synthetase. This gene cluster was cloned onto pZE13 along with candidate genes for the remaining steps to 4-HB to create pZE13-0038-0035-0036.

Production of 4-HB from Glucose. Although the above experiments demonstrate a functional pathway to 4-HB from a central metabolic intermediate (succinate), an industrial process would require the production of chemicals from low-cost carbohydrate feedstocks such as glucose or sucrose. Thus, the next set of experiments was aimed to

TABLE 8

Production of 4-HB from succinate in E. coli strains harboring plasmids expressing various combinations of 4-HB pathway genes.

| Sample # | Host Strain | pZE13 | pZA33 | 24 Hours | | | 48 Hours | | |
|---|---|---|---|---|---|---|---|---|---|
| | | | | OD600 | 4HB, μM | 4HB norm. (a) | OD600 | 4HB, μM | 4HB norm. (a) |
| 1 | MG1655 lacIq | cat1 (0004)-sucD (0035) | 4hbd (0009) | 0.47 | 487 | 1036 | 1.04 | 1780 | 1711 |
| 2 | MG1655 lacIq | cat1 (0004)-sucD (0035) | 4hbd (0027) | 0.41 | 111 | 270 | 0.99 | 214 | 217 |
| 3 | MG1655 lacIq | cat1 (0004)-sucD (0035) | 4hbd (0036) | 0.47 | 863 | 1835 | 0.48 | 2152 | 4484 |
| 4 | MG1655 lacIq | cat1 (0004)-sucD (0035) | 4hbd (0010n) | 0.46 | 956 | 2078 | 0.49 | 2221 | 4533 |
| 5 | MG1655 lacIq | cat1 (0004)-sucD (0008) | 4hbd (0009) | 0.38 | 493 | 1296 | 0.37 | 1338 | 3616 |
| 6 | MG1655 lacIq | cat1 (0004)-sucD (0008) | 4hbd (0027) | 0.32 | 26 | 81 | 0.27 | 87 | 323 |
| 7 | MG1655 lacIq | cat1 (0004)-sucD (0008) | 4hbd (0036) | 0.24 | 506 | 2108 | 0.31 | 1448 | 4672 |
| 8 | MG1655 lacIq | cat1 (0004)-sucD (0008) | 4hbd (0010n) | 0.24 | 78 | 324 | 0.56 | 233 | 416 |
| 9 | MG1655 lacIq gabD | cat1 (0004)-sucD (0035) | 4hbd (0009) | 0.53 | 656 | 1237 | 1.03 | 1643 | 1595 |
| 10 | MG1655 lacIq gabD | cat1 (0004)-sucD (0035) | 4hbd (0027) | 0.44 | 92 | 209 | 0.98 | 214 | 218 |
| 11 | MG1655 lacIq gabD | cat1 (0004)-sucD (0035) | 4hbd (0036) | 0.51 | 1072 | 2102 | 0.97 | 2358 | 2431 |
| 12 | MG1655 lacIq gabD | cat1 (0004)-sucD (0035) | 4hbd (0010n) | 0.51 | 981 | 1924 | 0.97 | 2121 | 2186 |
| 13 | MG1655 lacIq gabD | cat1 (0004)-sucD (0008) | 4hbd (0009) | 0.35 | 407 | 1162 | 0.77 | 1178 | 1530 |
| 14 | MG1655 lacIq gabD | cat1 (0004)-sucD (0008) | 4hbd (0027) | 0.51 | 19 | 36 | 1.07 | 50 | 47 |
| 15 | MG1655 lacIq gabD | cat1 (0004)-sucD (0008) | 4hbd (0036) | 0.35 | 584 | 1669 | 0.78 | 1350 | 1731 |
| 16 | MG1655 lacIq gabD | cat1 (0004)-sucD (0008) | 4hbd (0010n) | 0.32 | 74 | 232 | 0.82 | 232 | 283 |
| 17 | MG1655 lacIq | vector only | vector only | 0.8 | 1 | 2 | 1.44 | 3 | 2 |
| 18 | MG1655 lacIq gabD | vector only | vector only | 0.89 | 1 | 2 | 1.41 | 7 | 5 |

Figure 3A:
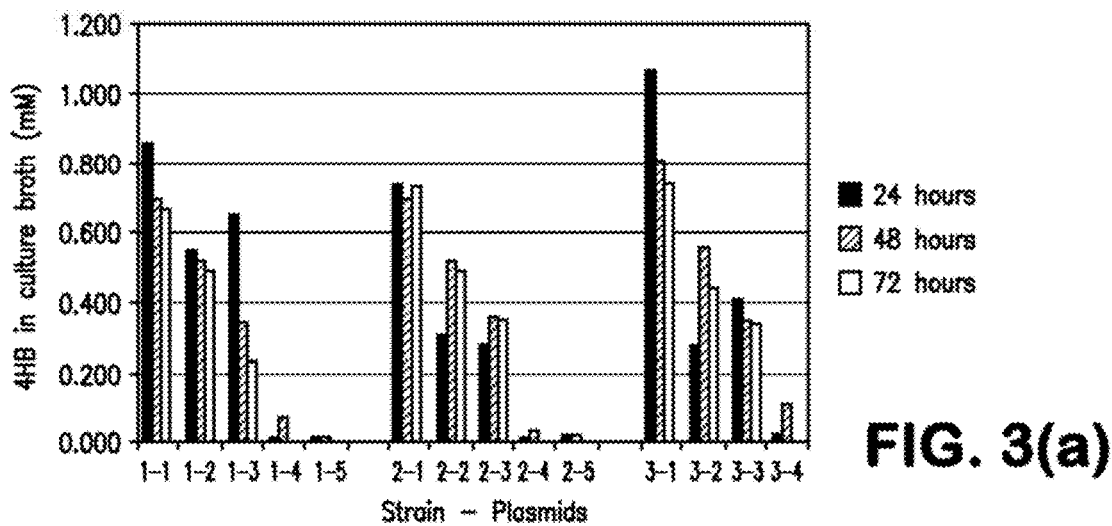
FIGS. 3(a)-3(c) show the production of 4-HB in glucose minimal medium using *E. coli* strains harboring plasmids expressing various combinations of 4-HB pathway genes.
Figure 3B:
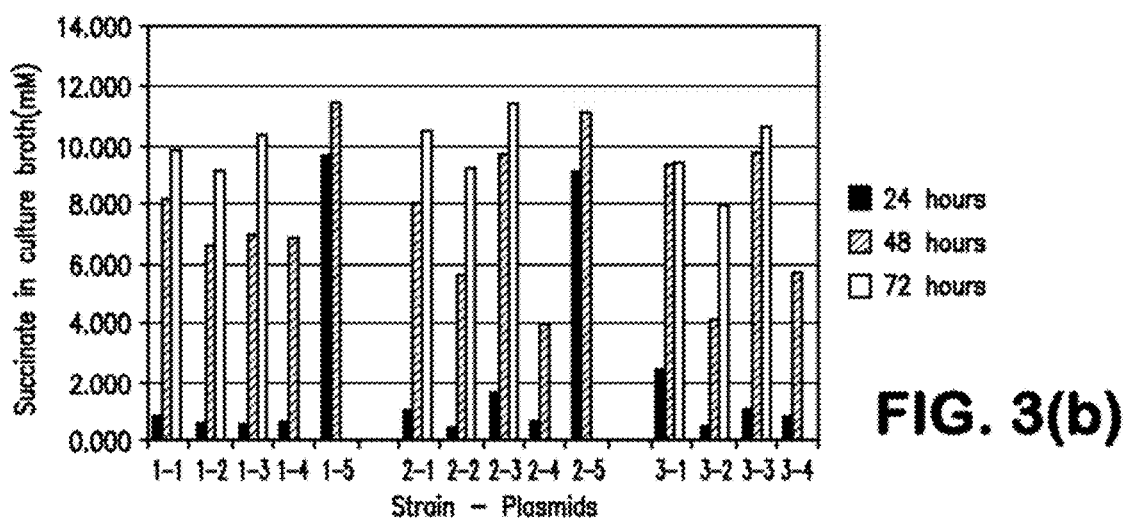
Figure 3C:
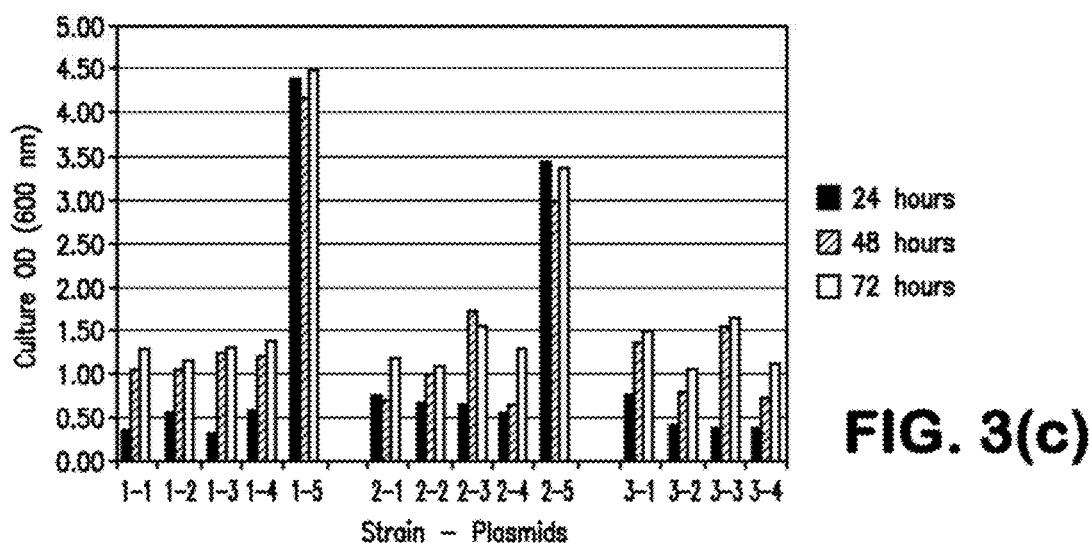

(a) Normalized 4-HB concentration, μM/OD600 units determine whether endogenous succinate produced by the cells during growth on glucose could fuel the 4-HB pathway. Cells were grown anaerobically in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 µg/mL thiamine, and the appropriate antibiotics. 0.25 mM IPTG was added when OD600 reached approximately 0.2, and samples taken for 4-HB analysis every 24 hours following induction. In all cases 4-HB plateaued after 24 hours, with a maximum of about 1 mM in the best strains (FIG. 3a), while the succinate concentration continued to rise (FIG. 3b). This indicates that the supply of succinate to the pathway is likely not limiting, and that the bottleneck may be in the activity of the enzymes themselves or in NADH availability. 0035 and 0036 are clearly the best gene candidates for CoA-dependent succinic semialdehyde dehydrogenase and 4-HB dehydrogenase, respectively. The elimination of one or both of the genes encoding known (gabD) or putative (aldA) native succinic semialdehyde dehydrogenases had little effect on performance. Finally, it should be noted that the cells grew to a much lower OD in the 4-HB-producing strains than in the controls (FIG. 3c).

Figure 4:
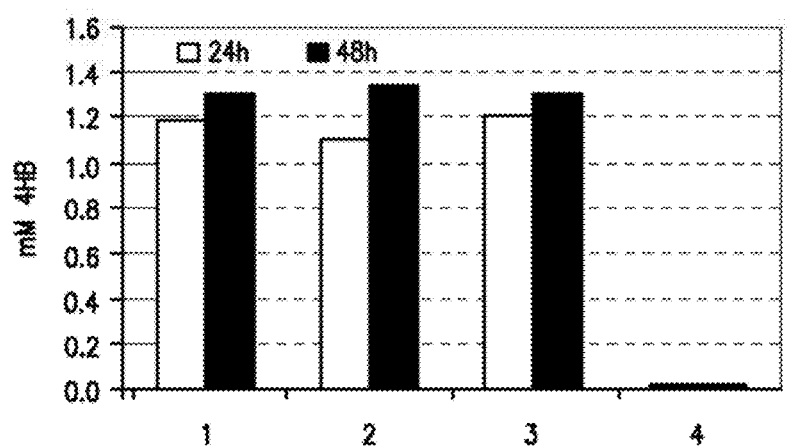
FIG. 4 shows the production of 4-HB from glucose in *E. coli* strains expressing α-ketoglutarate decarboxylase from *Mycobacterium tuberculosis*. Strains 1-3 contain pZE13-0032 and pZA33-0036. Strain 4 expresses only the empty vectors pZE13 and pZA33. Host strains are as follows: 1 and 4, MG1655 lacI$^Q$; 2, MG1655 ΔgabD lacI$^Q$; 3, MG1655 ΔgabD ΔaldA lacI$^Q$. The bars refer to concentration at 24 and 48 hours.

An alternate pathway for the production of 4-HB from glucose is via α-ketoglutarate. We explored the use of an α-ketoglutarate decarboxylase from *Mycobacterium tuberculosis* Tian et al., *Proc. Natl. Acad. Sci. USA* 102:10670-10675 (2005) to produce succinic semialdehyde directly from α-ketoglutarate (step 8 in FIG. 1). To demonstrate that this gene (0032) was functional in vivo, we expressed it on pZE13 in the same host as 4-HB dehydrogenase (gene 0036) on pZA33. This strain was capable of producing over 1.0 mM 4-HB within 24 hours following induction with 1 mM IPTG (FIG. 4). Since this strain does not express a CoA-dependent succinic semialdehyde dehydrogenase, the possibility of succinic semialdehyde production via succinyl-CoA is eliminated. It is also possible that the native genes responsible for producing succinic semialdehyde could function in this pathway (steps 4 and 5 in FIG. 1); however, the amount of 4-HB produced when the pZE13-0032 plasmid was left out of the host is the negligible.

Production of BDO from 4-HB. The production of BDO from 4-HB required two reduction steps, catalyzed by dehydrogenases. Alcohol and aldehyde dehydrogenases (ADH and ALD, respectively) are NAD+/H and/or NADP+/H-dependent enzymes that together can reduce a carboxylic acid group on a molecule to an alcohol group, or in reverse, can perform the oxidation of an alcohol to a carboxylic acid. This biotransformation has been demonstrated in wild-type *Clostridium acetobutylicum* (Jewell et al., *Current Microbiology*, 13:215-19 (1986)), but neither the enzymes responsible nor the genes responsible were identified. In addition, it is not known whether activation to 4-HB-CoA is first required (step 9 in FIG. 1), or if the aldehyde dehydrogenase (step 12) can act directly on 4-HB. We developed a list of candidate enzymes from *C. acetobutylicum* and related organisms based on known activity with the non-hydroxylated analogues to 4-HB and pathway intermediates, or by similarity to these characterized genes (Table 6). Since some of the candidates are multifunctional dehydrogenases, they could potentially catalyze both the NAD(P)H-dependent reduction of the acid (or CoA-derivative) to the aldehyde, and of the aldehyde to the alcohol. Before beginning work with these genes in *E. coli*, we first validated the result referenced above using *C. acetobutylicum* ATCC 824. Cells were grown in Schaedler broth (Accumedia, Lansing, Mich.) supplemented with 10 mM 4-HB, in an anaerobic atmosphere of 10% CO$_2$, 10% H$_2$, and 80% N$_2$ at 30° C. Periodic culture samples were taken, centrifuged, and the broth analyzed for BDO by GC-MS as described below. BDO concentrations of 0.1 mM, 0.9 mM, and 1.5 mM were detected after 1 day, 2 days, and 7 days incubation, respectively. No BDO was detected in culture grown without 4-HB addition. To demonstrate that the BDO produced was derived from glucose, we grew the best BDO producing strain MG1655 lacI$^Q$ pZE13-0004-0035-0002 pZA33-0034-0036 in M9 minimal medium supplemented with 4 g/L uniformly labeled $^{13}$C-glucose. Cells were induced at OD of 0.67 with 1 mM IPTG, and a sample taken after 24 hours. Analysis of the culture supernatant was performed by mass spectrometry.

Gene candidates for the 4-HB to BDO conversion pathway were next tested for activity when expressed in the *E. coli* host MG1655 lacI$^Q$. Recombinant strains containing each gene candidate expressed on pZA33 were grown in the presence of 0.25 mM IPTG for four hours at 37° C. to fully induce expression of the enzyme. Four hours after induction, cells were harvested and assayed for ADH and ALD activity as described above. Since 4-HB-CoA and 4-hydroxybutyraldehyde are not available commercially, assays were performed using the non-hydroxylated substrates (Table 9). The ratio in activity between 4-carbon and 2-carbon substrates for *C. acetobutylicum* adhE2 (0002) and *E. coli* adhE (0011) were similar to those previously reported in the literature a Atsumi et al., *Biochim. Biophys. Acta.* 1207:1-11 (1994).

TABLE 9

In vitro enzyme activities in cell extracts from MG1655 lacI$^Q$ containing pZA33 expressing gene candidates for aldehyde and alcohol dehydrogenases. Activities are expressed in µmol min$^{-1}$ mg cell protein$^{-1}$.

| | | Aldehyde dehydrogenase | | Alcohol dehydrogenase | |
|---|---|---|---|---|---|
| Gene | Substrate | Butyryl-CoA | Acetyl-CoA | Butyraldehyde | Acetaldehyde |
| 0002 | | 0.0076 | 0.0046 | 0.0264 | 0.0247 |
| 0003n | | 0.0060 | 0.0072 | 0.0080 | 0.0075 |
| 0011 | | 0.0069 | 0.0095 | 0.0265 | 0.0093 |
| 0013 | | N.D. | N.D. | 0.0130 | 0.0142 |
| 0023 | | 0.0089 | 0.0137 | 0.0178 | 0.0235 |
| 0025 | | 0 | 0.0001 | N.D. | N.D. |
| 0026 | | 0 | 0.0005 | 0.0024 | 0.0008 |

N.D., not determined.

Figure 5:
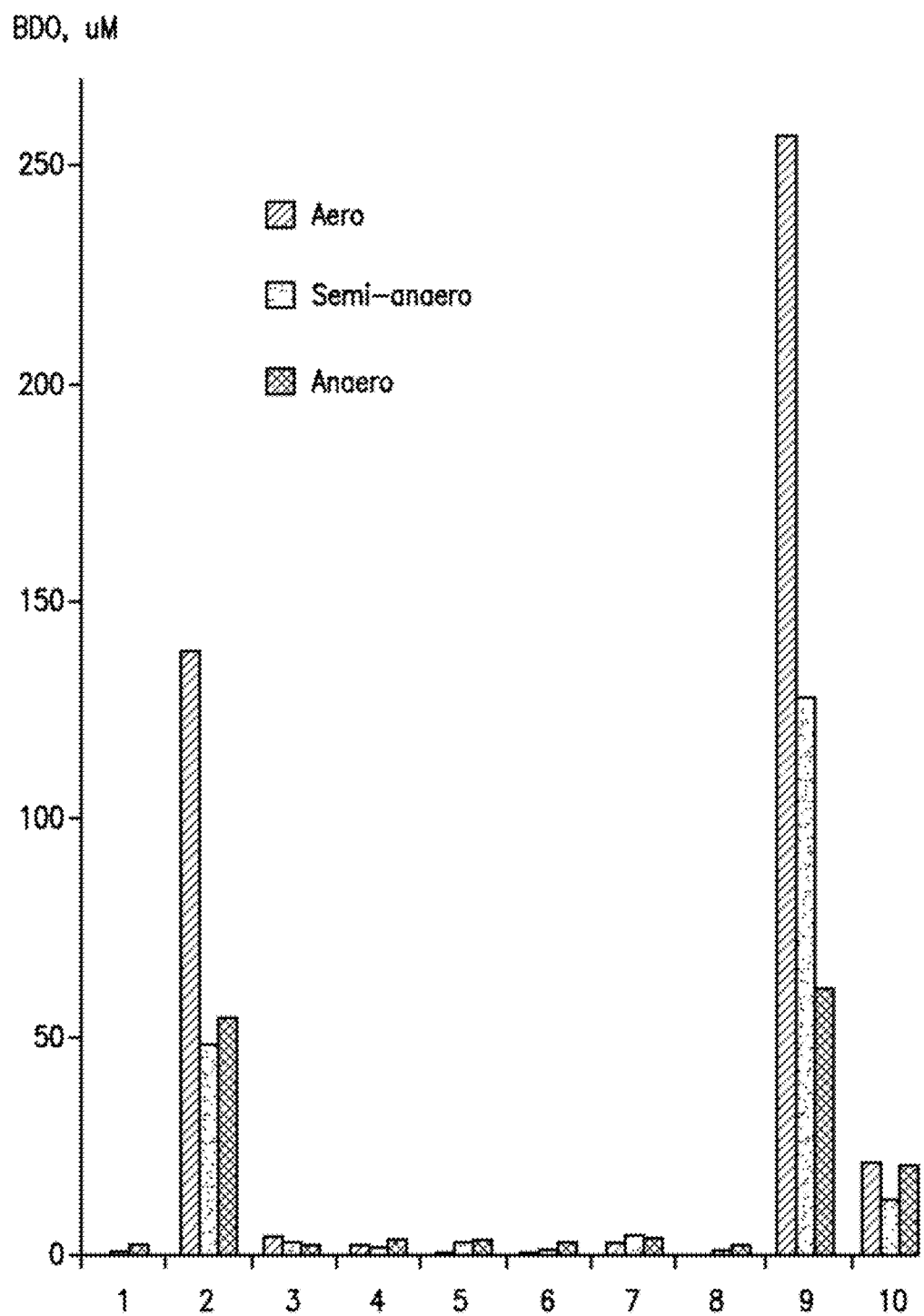
FIG. 5 shows the production of BDO from 10 mM 4-HB in recombinant *E. coli* strains. Numbered positions correspond to experiments with MG1655 lacI$^Q$ containing pZA33-0024, expressing cat2 from *P. gingivalis*, and the following genes expressed on pZE13: 1, none (control); 2, 0002; 3, 0003; 4, 0003n; 5, 0011; 6, 0013; 7, 0023; 8, 0025; 9, 0008n; 10, 0035. Gene numbers are defined in Table 6. For each position, the bars refer to aerobic, microaerobic, and anaerobic conditions, respectively. Microaerobic conditions were created by sealing the culture tubes but not evacuating them.
Figure 6A:
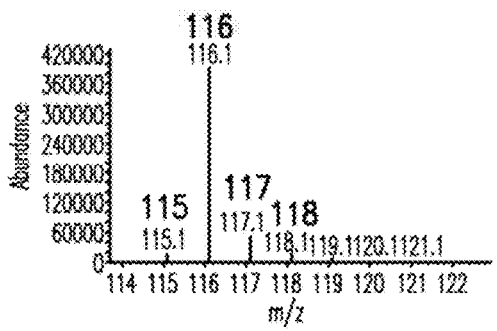
FIGS. 6(a)-6(h) show the mass spectrum of 4-HB and BDO produced by MG1655 lacI$^Q$ pZE13-0004-0035-0002 pZA33-0034-0036 grown in M9 minimal medium supplemented with 4 g/L unlabeled glucose (FIGS. 6a, 6c, 6e, and 6g) uniformly labeled $^{13}$C-glucose (FIGS. 6b, 6d, 6f, and 6h). (6a) and (6b), mass 116 characteristic fragment of derivatized BDO, containing 2 carbon atoms; (6c) and (6d), mass 177 characteristic fragment of derivatized BDO, containing 1 carbon atom; (6e) and (6f), mass 117 characteristic fragment of derivatized 4-HB, containing 2 carbon atoms; (6g) and (6h), mass 233 characteristic fragment of derivatized 4-HB, containing 4 carbon atoms.
Figure 6B:
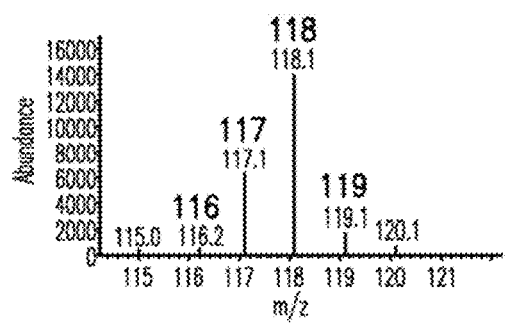
Figure 6C:
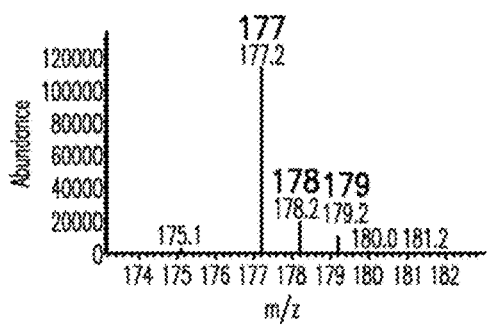
Figure 6D:
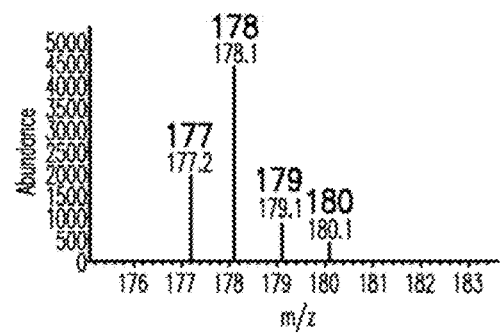
Figure 6E:
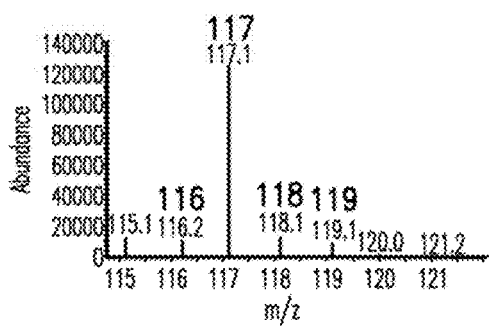
Figure 6F:
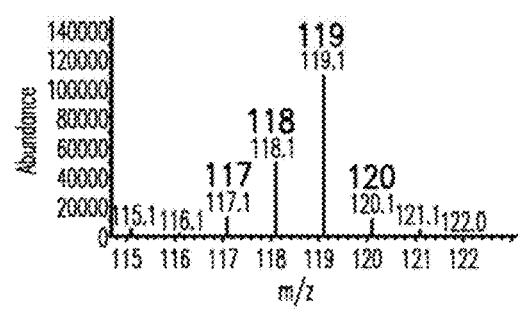
Figure 6G:
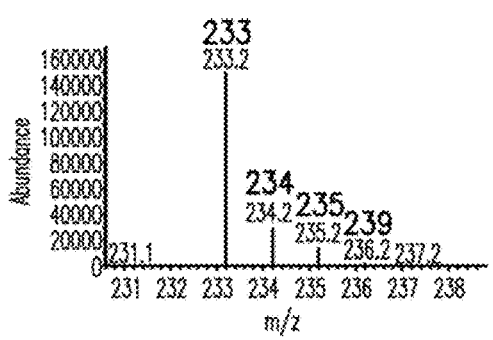
Figure 6H:
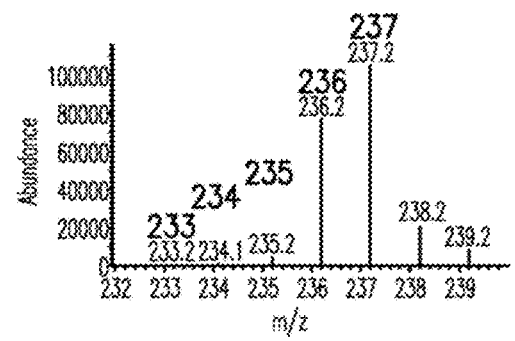

For the BDO production experiments, cat2 from *Porphyromonas gingivalis* W83 (gene 0034) was included on pZA33 for the conversion of 4-HB to 4-HB-CoA, while the candidate dehydrogenase genes were expressed on pZE13. The host strain was MG1655 lacI$^Q$. Along with the alcohol and aldehyde dehydrogenase candidates, we also tested the ability of CoA-dependent succinic semialdehyde dehydrogenases (sucD) to function in this step, due to the similarity of the substrates. Cells were grown to an OD of about 0.5 in LB medium supplemented with 10 mM 4-HB, induced with 1 mM IPTG, and culture broth samples taken after 24 hours and analyzed for BDO as described below. The best BDO production occurred using adhE2 from *C. acetobutylicum*, sucD from *C. kluyveri*, or sucD from *P. gingivalis* (FIG. 5). Interestingly, the absolute amount of BDO produced was higher under aerobic conditions; however, this is primarily due to the lower cell density achieved in anaerobic cultures.

When normalized to cell OD, the BDO production per unit biomass is higher in anaerobic conditions (Table 10).

TABLE 10

Absolute and normalized BDO concentrations from cultures of cells expressing adhE2 from C. acetobutylicum, sucD from C. kluyveri, or sucD from P. gingivalis (data from experiments 2, 9, and 10 in FIG. 3), as well as the negative control (experiment 1).

| Gene expressed | Conditions | BDO (μM) | OD (600 nm) | BDO/OD |
|---|---|---|---|---|
| none | Aerobic | 0 | 13.4 | 0 |
| none | Microaerobic | 0.5 | 6.7 | 0.09 |
| none | Anaerobic | 2.2 | 1.26 | 1.75 |
| 0002 | Aerobic | 138.3 | 9.12 | 15.2 |
| 0002 | Microaerobic | 48.2 | 5.52 | 8.73 |
| 0002 | Anaerobic | 54.7 | 1.35 | 40.5 |
| 0008n | Aerobic | 255.8 | 5.37 | 47.6 |
| 0008n | Microaerobic | 127.9 | 3.05 | 41.9 |
| 0008n | Anaerobic | 60.8 | 0.62 | 98.1 |
| 0035 | Aerobic | 21.3 | 14.0 | 1.52 |
| 0035 | Microaerobic | 13.1 | 4.14 | 3.16 |
| 0035 | Anaerobic | 21.3 | 1.06 | 20.1 |

As discussed above, it may be advantageous to use a route for converting 4-HB to 4-HB-CoA that does not generate acetate as a byproduct. To this aim, we tested the use of phosphotransbutyrylase (ptb) and butyrate kinase (bk) from C. acetobutylicum to carry out this conversion via steps 10 and 11 in FIG. 1. The native ptb/bk operon from C. acetobutylicum (genes 0020 and 0021) was cloned and expressed in pZA33. Extracts from cells containing the resulting construct were taken and assayed for the two enzyme activities as described herein. The specific activity of BK was approximately 65 U/mg, while the specific activity of PTB was approximately 5 U/mg. One unit (U) of activity is defined as conversion of 1 μM substrate in 1 minute at room temperature. Finally, the construct was tested for participation in the conversion of 4-HB to BDO. Host strains were transformed with the pZA33-0020-0021 construct described and pZE13-0002, and compared to use of cat2 in BDO production using the aerobic procedure used above in FIG. 5. The BK/PTB strain produced 1 mM BDO, compared to 2 mM when using cat2 (Table 11). Interestingly, the results were dependent on whether the host strain contained a deletion in the native adhE gene.

TABLE 11

Absolute and normalized BDO concentrations from cultures of cells expressing adhE2 from C. acetobutylicum in pZE13 along with either cat2 from P. gingivalis (0034) or the PTB/BK genes from C. acetobutylicum on pZA33. Host strains were either MG1655 lacI$^Q$ or MG1655 ΔadhE lacI$^Q$.

| Genes | Host Strain | BDO (μM) | OD (600 nm) | BDO/OD |
|---|---|---|---|---|
| 0034 | MG1655 lacI$^Q$ | 0.827 | 19.9 | 0.042 |
| 0020 + 0021 | MG1655 lacI$^Q$ | 0.007 | 9.8 | 0.0007 |
| 0034 | MG1655 ΔadhE lacI$^Q$ | 2.084 | 12.5 | 0.166 |
| 0020 + 0021 | MG1655 ΔadhE lacI$^Q$ | 0.975 | 18.8 | 0.052 |

Production of BDO from Glucose. The final step of pathway corroboration is to express both the 4-HB and BDO segments of the pathway in E. coli and demonstrate production of BDO in glucose minimal medium. New plasmids were constructed so that all the required genes fit on two plasmids. In general, cat1, adhE, and sucD genes were expressed from pZE13, and cat2 and 4-HBd were expressed from pZA33. Various combinations of gene source and gene order were tested in the MG1655 lacI$^Q$ background. Cells were grown anaerobically in M9 minimal medium (6.78 g/L Na$_2$HPO$_4$, 3.0 g/L KH$_2$PO$_4$, 0.5 g/L NaCl, 1.0 g/L NH$_4$Cl, mM MgSO$_4$, 0.1 mM CaCl$_2$) supplemented with 20 g/L glucose, 100 mM 3-(N-morpholino)propanesulfonic acid (MOPS) to improve the buffering capacity, 10 μg/mL thiamine, and the appropriate antibiotics. 0.25 mM IPTG was added approximately 15 hours following inoculation, and culture supernatant samples taken for BDO, 4-HB, and succinate analysis 24 and 48 hours following induction. The production of BDO appeared to show a dependency on gene order (Table 12). The highest BDO production, over 0.5 mM, was obtained with cat2 expressed first, followed by 4-HBd on pZA33, and cat1 followed by P. gingivalis sucD on pZE13. The addition of C. acetobutylicum adhE2 in the last position on pZE13 resulted in slight improvement. 4-HB and succinate were also produced at higher concentrations.

TABLE 12

Production of BDO, 4-HB, and succinate in recombinant E. coli strains expressing combinations of BDO pathway genes, grown in minimal medium supplemented with 20 g/L glucose. Concentrations are given in mM.

| | | | | 24 Hours | | | | 48 Hours | | | |
|---|---|---|---|---|---|---|---|---|---|---|---|
| Sample | pZE13 | pZA33 | Induction OD | OD600 nm | Su | 4HB | BDO | OD600 nm | Su | 4HB | BDO |
| 1 | cat1(0004)-sucD(0035) | 4hbd (0036)-cat2(0034) | 0.92 | 1.29 | 5.44 | 1.37 | 0.240 | 1.24 | 6.42 | 1.49 | 0.280 |
| 2 | cat1(0004)-sucD(0008N) | 4hbd (0036)-cat2(0034) | 0.36 | 1.11 | 6.90 | 1.24 | 0.011 | 1.06 | 7.63 | 1.33 | 0.011 |
| 3 | adhE(0002)-cat1(0004)-sucD(0035) | 4hbd (0036)-cat2(0034) | 0.20 | 0.44 | 0.34 | 1.84 | 0.050 | 0.60 | 1.93 | 2.67 | 0.119 |
| 4 | cat1(0004)-sucD(0035)-adhE(0002) | 4hbd (0036)-cat2(0034) | 1.31 | 1.90 | 9.02 | 0.73 | 0.073 | 1.95 | 9.73 | 0.82 | 0.077 |
| 5 | adhE(0002)-cat1(0004)-sucD(0008N) | 4hbd (0036)-cat2(0034) | 0.17 | 0.45 | 1.04 | 1.04 | 0.008 | 0.94 | 7.13 | 1.02 | 0.017 |
| 6 | cat1(0004)-sucD(0008N)-adhE(0002) | 4hbd (0036)-cat2(0034) | 1.30 | 1.77 | 10.47 | 0.25 | 0.004 | 1.80 | 11.49 | 0.28 | 0.003 |
| 7 | cat1(0004)-sucD(0035) | cat2(0034)-4hbd(0036) | 1.09 | 1.29 | 5.63 | 2.15 | 0.461 | 1.38 | 6.66 | 2.30 | 0.520 |
| 8 | cat1(0004)-sucD(0008N) | cat2(0034)-4hbd(0036) | 1.81 | 2.01 | 11.28 | 0.02 | 0.000 | 2.24 | 11.13 | 0.02 | 0.000 |
| 9 | adhE(0002)-cat1(0004)-sucD(0035) | cat2(0034)-4hbd(0036) | 0.24 | 1.99 | 2.02 | 2.32 | 0.106 | 0.89 | 4.85 | 2.41 | 0.186 |
| 10 | cat1(0004)-sucD(0035)-adhE(0002) | cat2(0034)-4hbd(0036) | 0.98 | 1.17 | 5.30 | 2.08 | 0.569 | 1.33 | 6.15 | 2.14 | 0.640 |
| 11 | adhE(0002)-cat1(0004)-sucD(0008N) | cat2(0034)-4hbd(0036) | 0.20 | 0.53 | 1.38 | 2.30 | 0.019 | 0.91 | 8.10 | 1.49 | 0.034 |
| 12 | cat1(0004)-sucD(0008N)-adhE(0002) | cat2(0034)-4hbd(0036) | 2.14 | 2.73 | 12.07 | 0.16 | 0.000 | 3.10 | 11.79 | 0.17 | 0.002 |
| 13 | vector only | vector only | 2.11 | 2.62 | 9.03 | 0.01 | 0.000 | 3.00 | 12.05 | 0.01 | 0.000 |

Analysis of BDO, 4-HB and succinate by GCMS. BDO, 4-HB and succinate in fermentation and cell culture samples were derivatized by silylation and quantitatively analyzed by GCMS using methods adapted from literature reports ((Simonov et al., *J. Anal Chem.* 59:965-971 (2004)). The developed method demonstrated good sensitivity down to 1 µM, linearity up to at least 25 mM, as well as excellent selectivity and reproducibility.

Sample preparation was performed as follows: 100 µL filtered (0.2 µm or 0.45 µm syringe filters) samples, e.g. fermentation broth, cell culture or standard solutions, were dried down in a Speed Vac Concentrator (Savant SVC-100H) for approximately 1 hour at ambient temperature, followed by the addition of 20 µL 10 mM cyclohexanol solution, as an internal standard, in dimethylformamide. The mixtures were vortexed and sonicated in a water bath (Branson 3510) for 15 min to ensure homogeneity. 100 µL silylation derivatization reagent, N,O-bis(trimethylsilyl)tri-flouro-acetimide (BSTFA) with 1% trimethylchlorosilane, was added, and the mixture was incubated at 70° C. for 30 min. The derivatized samples were centrifuged for 5 min, and the clear solutions were directly injected into GCMS. All the chemicals and reagents were from Sigma-Aldrich, with the exception of BDO which was purchased from J. T. Baker.

GCMS was performed on an Agilent gas chromatograph 6890N, interfaced to a mass-selective detector (MSD) 5973N operated in electron impact ionization (EI) mode has been used for the analysis. A DB-5MS capillary column (J&W Scientific, Agilent Technologies), 30 m×0.25 mm i.d.×0.25 µm film thickness, was used. The GC was operated in a split injection mode introducing 1 µL of sample at 20:1 split ratio. The injection port temperature was 250° C. Helium was used as a carrier gas, and the flow rate was maintained at 1.0 mL/min. A temperature gradient program was optimized to ensure good resolution of the analytes of interest and minimum matrix interference. The oven was initially held at 80° C. for 1 min, then ramped to 120° C. at 2° C./min, followed by fast ramping to 320° C. at 100° C./min and final hold for 6 min at 320° C. The MS interface transfer line was maintained at 280° C. The data were acquired using 'lowmass' MS tune settings and 30-400 m/z mass-range scan. The total analysis time was 29 min including 3 min solvent delay. The retention times corresponded to 5.2, 10.5, 14.0 and 18.2 min for BSTFA-derivatized cyclohexanol, BDO, 4-HB and succinate, respectively. For quantitative analysis, the following specific mass fragments were selected (extracted ion chromatograms): m/z 157 for internal standard cyclohexanol, 116 for BDO, and 147 for both 4-HB and succinate. Standard calibration curves were constructed using analyte solutions in the corresponding cell culture or fermentation medium to match sample matrix as close as possible. GCMS data were processed using Environmental Data Analysis ChemStation software (Agilent Technologies).

The results indicated that most of the 4-HB and BDO produced were labeled with $^{13}$C (FIG. 6, right-hand sides). Mass spectra from a parallel culture grown in unlabeled glucose are shown for comparison (FIG. 6, left-hand sides). Note that the peaks seen are for fragments of the derivatized molecule containing different numbers of carbon atoms from the metabolite. The derivatization reagent also contributes some carbon and silicon atoms that naturally-occurring label distribution, so the results are not strictly quantitative.

Production of BDO from 4-HB using alternate pathways. The various alternate pathways were also tested for BDO production. This includes use of the native *E. coli* SucCD enzyme to convert succinate to succinyl-CoA (Table 13, rows 2-3), use of α-ketoglutarate decarboxylase in the α-ketoglutarate pathway (Table 13, row 4), and use of PTB/BK as an alternate means to generate the CoA-derivative of 4HB (Table 13, row 1). Strains were constructed containing plasmids expressing the genes indicated in Table 13, which encompass these variants. The results show that in all cases, production of 4-HB and BDO occurred (Table 13).

TABLE 13

Production of BDO, 4-HB, and succinate in recombinant *E. coli* strains genes for different BDO pathway variants, grown anaerobically in minimal medium supplemented with 20 g/L glucose, and harvested 24 hours after induction with 0.1 mM IPTG. Concentrations are given in mM.

| Genes on pZE13 | Genes on pZA33 | Succinate | 4-HB | BDO |
|---|---|---|---|---|
| 0002 + 0004 + 0035 | 0020n – 0021n – 0036 | 0.336 | 2.91 | 0.230 |
| 0038 + 0035 | 0034 – 0036 | 0.814 | 2.81 | 0.126 |
| 0038 + 0035 | 0036 – 0034 | 0.741 | 2.57 | 0.114 |
| 0035 + 0032 | 0034 – 0036 | 5.01 | 0.538 | 0.154 |

Example III

Biosynthesis of 4-Hydroxybutanoic Acid, γ-Butyrolactone and 1,4-Butanediol

This Example describes the biosynthetic production of 4-hydroxybutanoic acid, γ-butyrolactone and 1,4-butanediol using fermentation and other bioprocesses.

Figure 7:
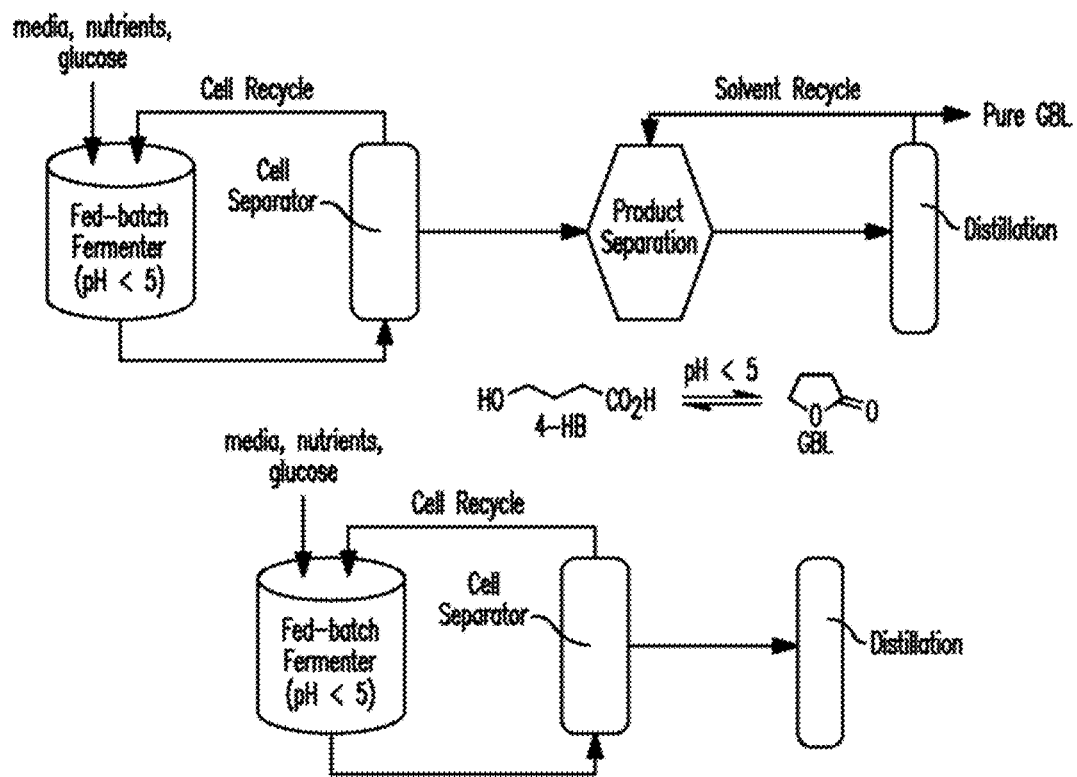
FIG. 7 is a schematic process flow diagram of bioprocesses for the production of γ-butyrolactone. Panel (a) illustrates fed-batch fermentation with batch separation and panel (b) illustrates fed-batch fermentation with continuous separation.

Methods for the integration of the 4-HB fermentation step into a complete process for the production of purified GBL, 1,4-butanediol (BDO) and tetrahydrofuran (THF) are described below. Since 4-HB and GBL are in equilibrium, the fermentation broth will contain both compounds. At low pH this equilibrium is shifted to favor GBL. Therefore, the fermentation can operate at pH 7.5 or less, generally pH 5.5 or less. After removal of biomass, the product stream enters into a separation step in which GBL is removed and the remaining stream enriched in 4-HB is recycled. Finally, GBL is distilled to remove any impurities. The process operates in one of three ways: 1) fed-batch fermentation and batch separation; 2) fed-batch fermentation and continuous separation; 3) continuous fermentation and continuous separation. The first two of these modes are shown schematically in FIG. 7. The integrated fermentation procedures described below also are used for the BDO producing cells of the invention for biosynthesis of BDO and subsequent BDO family products.

Fermentation protocol to produce 4-HB/GBL (batch): The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a product separations unit. Isolation of 4-HB and/or GBL would take place by standard separations procedures employed in the art to separate organic products from dilute aqueous solutions, such as liquid-liquid extraction using a water immiscible organic solvent (e.g., toluene) to provide an organic solution of 4-HB/GBL. The resulting solution is then subjected to standard distillation methods to remove and recycle the organic solvent and to provide GBL (boiling point 204-205° C.) which is isolated as a purified liquid.

Fermentation protocol to produce 4-HB/GBL (fully continuous): The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of 4-HB/GBL. The resulting solution is subsequently subjected to standard continuous distillation methods to remove and recycle the organic solvent and to provide GBL (boiling point 204-205° C.) which is isolated as a purified liquid.

GBL Reduction Protocol: Once GBL is isolated and purified as described above, it will then be subjected to reduction protocols such as those well known in the art (references cited) to produce 1,4-butanediol or tetrahydrofuran (THF) or a mixture thereof. Heterogeneous or homogeneous hydrogenation catalysts combined with GBL under hydrogen pressure are well known to provide the products 1,4-butanediol or tetrahydrofuran (THF) or a mixture thereof. It is important to note that the 4-HB/GBL product mixture that is separated from the fermentation broth, as described above, may be subjected directly, prior to GBL isolation and purification, to these same reduction protocols to provide the products 1,4-butanediol or tetrahydrofuran or a mixture thereof. The resulting products, 1,4-butanediol and THF are then isolated and purified by procedures well known in the art.

Fermentation and hydrogenation protocol to produce BDO or THF directly (batch):

Cells are grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until 4-HB reaches a concentration of between 20-200 g/L, with the cell density being between 5 and 10 g/L. The pH is not controlled, and will typically decrease to pH 3-6 by the end of the run. Upon completion of the cultivation period, the fermenter contents are passed through a cell separation unit (e.g., centrifuge) to remove cells and cell debris, and the fermentation broth is transferred to a reduction unit (e.g., hydrogenation vessel), where the mixture 4-HB/GBL is directly reduced to either 1,4-butanediol or THF or a mixture thereof. Following completion of the reduction procedure, the reactor contents are transferred to a product separations unit. Isolation of 1,4-butanediol and/or THF would take place by standard separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard distillation methods to remove and recycle the organic solvent and to provide 1,4-butanediol and/or THF which are isolated as a purified liquids.

Fermentation and hydrogenation protocol to produce BDO or THF directly (fully continuous): The cells are first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The 4-HB concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of 4-HB concentration. In continuous mode, fermenter contents are constantly removed as new feed medium is supplied. The exit stream, containing cells, medium, and products 4-HB and/or GBL, is then passed through a cell separation unit (e.g., centrifuge) to remove cells and cell debris, and the fermentation broth is transferred to a continuous reduction unit (e.g., hydrogenation vessel), where the mixture 4-HB/GBL is directly reduced to either 1,4-butanediol or THF or a mixture thereof. Following completion of the reduction procedure, the reactor contents are transferred to a continuous product separations unit. Isolation of 1,4-butanediol and/or THF would take place by standard continuous separations procedures employed in the art to separate organic products from dilute aqueous solutions, such as liquid-liquid extraction using a water immiscible organic solvent (e.g., toluene) to provide an organic solution of 1,4-butanediol and/or THF. The resulting solution is then subjected to standard continuous distillation methods to remove and recycle the organic solvent and to provide 1,4-butanediol and/or THF which are isolated as a purified liquids.

Fermentation protocol to produce BDO directly (batch): The production organism is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until BDO reaches a concentration of between 20-200 g/L, with the cell density generally being between 5 and 10 g/L. Upon completion of the cultivation period, the fermenter contents are passed through a cell separation unit (e.g., centrifuge) to remove cells and cell debris, and the fermentation broth is transferred to a product separations unit. Isolation of BDO would take place by standard separations procedures employed in the art to separate organic products from dilute aqueous solutions, such as liquid-liquid extraction using a water immiscible organic solvent (e.g., toluene) to provide an organic solution of BDO. The resulting solution is then subjected to standard distillation methods to remove and recycle the organic solvent and to provide BDO (boiling point 228-229° C.) which is isolated as a purified liquid.

Fermentation protocol to produce BDO directly (fully continuous): The production organism is first grown up in batch mode using the apparatus and medium composition described above, except that the initial glucose concentration is 30-50 g/L. When glucose is exhausted, feed medium of the same composition is supplied continuously at a rate between 0.5 L/hr and 1 L/hr, and liquid is withdrawn at the same rate. The BDO concentration in the bioreactor remains constant at 30-40 g/L, and the cell density remains constant between 3-5 g/L. Temperature is maintained at 30 degrees C., and the pH is maintained at 4.5 using concentrated NaOH and HCl, as required. The bioreactor is operated continuously for one month, with samples taken every day to assure consistency of BDO concentration. In continuous mode, fermenter contents are constantly removed as new feed medium is supplied. The exit stream, containing cells, medium, and the product BDO, is then subjected to a continuous product separations procedure, with or without removing cells and cell debris, and would take place by standard continuous separations methods employed in the art to separate organic products from dilute aqueous solutions, such as continuous liquid-liquid extraction using a water immiscible organic solvent (e.g., toluene) to provide an organic solution of BDO. The resulting solution is subsequently subjected to standard continuous distillation methods to remove and recycle the organic solvent and to provide BDO (boiling point 228-229° C.) which is isolated as a purified liquid (mpt 20° C.).

Example IV

Exemplary BDO Pathways

This example describes exemplary enzymes and corresponding genes for 1,4-butandiol (BDO) synthetic pathways.

Exemplary BDO synthetic pathways are shown in FIGS. 8-13. The pathways depicted in FIGS. 8-13 are from common central metabolic intermediates to 1,4-butanediol. All transformations depicted in FIGS. 8-13 fall into the 18 general categories of transformations shown in Table 14. Below is described a number of biochemically characterized candidate genes in each category. Specifically listed are genes that can be applied to catalyze the appropriate transformations in FIGS. 9-13 when cloned and expressed in a host organism. The top three exemplary genes for each of the key steps in FIGS. 9-13 are provided in Tables 15-23 (see below). Exemplary genes were provided for the pathways depicted in FIG. 8 are described herein.

TABLE 14

Enzyme types required to convert common central metabolic intermediates into 1,4-butanediol. The first three digits of each label correspond to the first three Enzyme Commission number digits which denote the general type of transformation independent of substrate specificity.

| Label | Function |
| --- | --- |
| 1.1.1.a | Oxidoreductase (ketone to hydroxyl or aldehyde to alcohol) |
| 1.1.1.c | Oxidoreductase (2 step, acyl-CoA to alcohol) |

TABLE 14-continued

Enzyme types required to convert common central metabolic intermediates into 1,4-butanediol. The first three digits of each label correspond to the first three Enzyme Commission number digits which denote the general type of transformation independent of substrate specificity.

| Label | Function |
| --- | --- |
| 1.2.1.b | Oxidoreductase (acyl-CoA to aldehyde) |
| 1.2.1.c | Oxidoreductase (2-oxo acid to acyl-CoA, decarboxylation) |
| 1.2.1.d | Oxidoreductase (phosphorylating/dephosphorylating) |
| 1.3.1.a | Oxidoreductase operating on CH—CH donors |
| 1.4.1.a | Oxidoreductase operating on amino acids |
| 2.3.1.a | Acyltransferase (transferring phosphate group) |
| 2.6.1.a | Aminotransferase |
| 2.7.2.a | Phosphotransferase, carboxyl group acceptor |
| 2.8.3.a | Coenzyme-A transferase |
| 3.1.2.a | Thiolester hydrolase (CoA specific) |
| 4.1.1.a | Carboxy-lyase |
| 4.2.1.a | Hydro-lyase |
| 4.3.1.a | Ammonia-lyase |
| 5.3.3.a | Isomerase |
| 5.4.3.a | Aminomutase |
| 6.2.1.a | Acid-thiol ligase |

1.1.1.a-Oxidoreductase (Aldehyde to alcohol or Ketone to Hydroxyl)

Aldehyde to alcohol. Exemplary genes encoding enzymes that catalyze the conversion of an aldehyde to alcohol, that is, alcohol dehydrogenase or equivalently aldehyde reductase, include alrA encoding a medium-chain alcohol dehydrogenase for C2-C14 (Tani et al. *Appl. Environ. Microbiol.* 66:5231-5235 (2000)), ADH2 from *Saccharomyces cerevisiae* (Atsumi et al. *Nature* 451:86-89 (2008)), yqhD from *E. coli* which has preference for molecules longer than C(3) (Sulzenbacher et al. *Journal of Molecular Biology* 342:489-502 (2004)), and bdh I and bdh II from *C. acetobutylicum* which converts butyryaldehyde into butanol (Walter et al. *Journal of Bacteriology* 174:7149-7158 (1992)). The protein sequences for each of these exemplary gene products, if available, can be found using the following GenBank accession numbers:

| Gene | Accession No. | GI No. | Organism |
| --- | --- | --- | --- |
| alrA | BAB12273.1 | 9967138 | *Acinetobacter* sp. Strain M-1 |
| ADH2 | NP_014032.1 | 6323961 | *Saccharymyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |

Enzymes exhibiting 4-hydroxybutyrate dehydrogenase activity (EC 1.1.1.61) also fall into this category. Such enzymes have been characterized in *Ralstonia eutropha* (Bravo et al. *J. Forensic Sci.* 49:379-387 (2004), *Clostridium kluyveri* (Wolff et al. *Protein Expr. Purif.* 6:206-212 (1995)) and *Arabidopsis thaliana* (Breitkreuz et al. *J. Biol. Chem.* 278:41552-41556 (2003)).

| Gene | Accession No. | GI No. | Organism |
| --- | --- | --- | --- |
| 4hbd | YP_726053.1 | 113867564 | *Ralstonia eutropha* H16 |
| 4hbd | L21902.1 | 146348486 | *Clostridium kluyveri* DSM 555 |
| 4hbd | Q94B07 | 75249805 | *Arabidopsis thaliana* |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al. *J Mol Blot* 352:905-17 (2005)). The reversibility of the human 3-hydroxyisobutyrate dehydrogenase was demonstrated using isotopically-labeled substrate (Manning et al. *Biochem J* 231:481-484 (1985)). Additional genes encoding this enzyme include 3hidh in *Homo sapiens* (Hawes et al. *Methods Enzymol.* 324:218-228 (2000)) and *Oryctolagus cuniculus* (Chowdhury et al. *Biosci. Biotechnol Biochem.* 60:2043-2047 (1996); Hawes et al. *Methods Enzymol.* 324:218-228 (2000)), mmsb in *Pseudomonas aeruginosa*, and dhat in *Pseudomonas putida* (Aberhart et al. *J Chem. Soc.* [Perkin 1] 6:1404-1406 (1979); Chowdhury et al. *Biosci. Biotechnol Biochem.* 67:438-441 (2003); Chowdhury et al. *Biosci. Biotechnol Biochem.* 60:2043-2047 (1996)).

| Gene | Accession No. | GI No. | Organism |
| --- | --- | --- | --- |
| P84067 | P84067 | 75345323 | *Thermus thermophilus* |
| mmsb | P28811.1 | 127211 | *Pseudomonas aeruginosa* |
| dhat | Q59477.1 | 2842618 | *Pseudomonas putida* |
| 3hidh | P31937.2 | 12643395 | *Homo sapiens* |
| 3hidh | P32185.1 | 416872 | *Oryctolagus cuniculus* |

Several 3-hydroxyisobutyrate dehydrogenase enzymes have also been shown to convert malonic semialdehyde to 3-hydroxyproprionic acid (3-HP). Three gene candidates exhibiting this activity are mmsB from *Pseudomonas aeruginosa* PAO1(62), mmsB from *Pseudomonas putida* KT2440 (Liao et al., US Publication 2005/0221466) and mmsB from *Pseudomonas putida* E23 (Chowdhury et al., *Biosci. Biotechnol. Biochem.* 60:2043-2047 (1996)). An enzyme with 3-hydroxybutyrate dehydrogenase activity in *Alcaligenes faecalis* M3A has also been identified (Gokam et al., U.S. Pat. No. 7,393,676; Liao et al., US Publication No. 2005/0221466). Additional gene candidates from other organisms including *Rhodobacter spaeroides* can be inferred by sequence similarity.

| Gene | Accession No. | GI No. | Organism |
| --- | --- | --- | --- |
| mmsB | AAA25892.1 | 151363 | *Pseudomonas aeruginosa* |
| mmsB | NP_252259.1 | 15598765 | *Pseudomonas aeruginosa* PAO1 |
| mmsB | NP_746775.1 | 26991350 | *Pseudomonas putida* KT2440 |
| mmsB | JC7926 | 60729613 | *Pseudomonas putida* E23 |
| orfB1 | AAL26884 | 16588720 | *Rhodobacter spaeroides* |

The conversion of malonic semialdehyde to 3-HP can also be accomplished by two other enzymes: NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi, B. *Journal of Plant Pathology* 159:671-674 (2002); Stadtman, E. R. *J. Am. Chem. Soc.* 77:5765-5766 (1955)). This enzyme has not been associated with a gene in any organism to date. NADPH-dependent malonate semialdehyde reductase catalyzes the reverse reaction in autotrophic $CO_2$-fixing bacteria. Although the enzyme activity has been detected in *Metallosphaera sedula*, the identity of the gene is not known (Alber et al. *J. Bacteriol.* 188:8551-8559 (2006)).

Ketone to hydroxyl. There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on substrates of various chain lengths such as lactate, 2-oxobutyrate, 2-oxopentanoate and 2-oxoglutarate (Steinbuchel and. Schlegel, *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al. Arch. Biochem. Biophys. 176:610-620 (1976); Suda et al. *Biochem. Biophys. Res. Commun.* 77:586-591 (1977)). An additional candidate for this step is the mitochondrial 3-hydroxybutyrate dehydrogenase (bdh) from the human heart which has been cloned and characterized (Marks et al. *J. Biol. Chem.* 267:15459-15463 (1992)). This enzyme is a dehydrogenase that operates on a 3-hydroxyacid. Another exemplary alcohol dehydrogenase converts acetone to isopropanol as was shown in *C. beijerinckii* (Ismaiel et al. *J. Bacteriol.* 175:5097-5105 (1993)) and *T. brockii* (Lamed et al. *Biochem. J.* 195:183-190 (1981); Peretz and Burstein *Biochemistry* 28:6549-6555 (1989)).

| Gene | Accession No. | GI No. | Organism |
| --- | --- | --- | --- |
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |

Exemplary 3-hydroxyacyl dehydrogenases which convert acetoacetyl-CoA to 3-hydroxybutyryl-CoA include hbd from *C. acetobutylicum* (Boynton et al. *Journal of Bacteriology* 178:3015-3024 (1996)), hbd from *C. beijerinckii* (Colby et al. *Appl Environ. Microbiol* 58:3297-3302 (1992)), and a number of similar enzymes from *Metallosphaera sedula* (Berg et al. Archaea. *Science* 318:1782-1786 (2007)).

| Gene | Accession No. | GI No. | Organism |
| --- | --- | --- | --- |
| hbd | NP_349314.1 | 15895965 | *Clostridium acetobutylicum* |
| hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |

1.1.1.c-Oxoredutase (2 Step, acyl-CoA to Alcohol)

Exemplary 2-step oxidoreductases that convert an acyl-CoA to alcohol include those that transform substrates such as acetyl-CoA to ethanol (for example, adhE from *E. coli* (Kessler et al. *FEBS. Lett.* 281:59-63 (1991)) and butyryl-CoA to butanol (for example, adhE2 from *C. acetobutylicum* (Fontaine et al. *J. Bacteriol.* 184:821-830 (2002)). In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al. *J. Gen. Appl. Microbiol.* 18:43-55 (1972); Koo et al. Biotechnol Lett. 27:505-510 (2005)).

| Gene | Accession No. | GI No. | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.* 184:2404-2410 (2002); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii, Erythrobacter* sp. NAP1 and marine gamma proteobacterium HTCC2080 can be inferred by sequence similarity.

| Gene | Accession No. | GI No. | Organism |
|---|---|---|---|
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al. *Plant Physiology* 122:635-644) 2000)).

| Gene | Accession No. | GI No. | Organism |
|---|---|---|---|
| FAR | AAD38039.1 | 5020215 | *Simmondsia chinensis* |

1.2.1.b-Oxidoreductase (Acyl-CoA to Aldehyde)

Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *J. Bacteriology* 179:2969-2975 (1997)), the *Acinetobacter* sp. M-1 fatty acyl-CoA reductase (Ishige et al. *Appl. Environ. Microbiol.* 68:1192-1195 (2002)), and a CoA- and NADP-dependent succinate semialdehyde dehydrogenase encoded by the sucD gene in *Clostridium kluyveri* (Sohling and Gottschalk *J Bacteriol* 178:871-80 (1996); Sohling and Gottschalk *J Bacteriol.* 178:871-880 (1996)). SucD of *P. gingivalis* is another succinate semialdehyde dehydrogenase (Takahashi et al. *J.* *Bacteriol.* 182:4704-4710 (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al. *J Bacteriol.* 175:377-385 (1993)).

| Gene | Accession No. | GI No. | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 730847 | *Clostridium kluyveri* |
| sucD | NP_904963.1 | 34540484 | *Porphyromonas gingivalis* |
| bphG | BAA03892.1 | 425213 | *Pseudomonas* sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al. *Science* 318:1782-1786 (2007); Thauer, R. K. *Science* 318:1732-1733 (2007)). The enzyme utilizes NADPH as a cofactor and has been characterized in *Metallosphaera and Sulfolobus* spp (Alber et al. *J. Bacteriol.* 188:8551-8559 (2006); Hugler et al. *J. Bacteriol.* 184:2404-2410 (2002)). The enzyme is encoded by Msed_0709 in *Metallosphaera sedula* (Alber et al. *J. Bacteriol.* 188:8551-8559 (2006); Berg et al. *Science* 318:1782-1786 (2007)). A gene encoding a malonyl-CoA reductase from *Sulfolobus tokodaii* was cloned and heterologously expressed in *E. coli* (Alber et al. *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*.

| Gene | Accession No. | GI No. | Organism |
|---|---|---|---|
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |

1.2.1.c-Oxidoreductase (2-oxo Acid to Acyl-CoA, Decarboxylation)

Enzymes in this family include 1) branched-chain 2-keto-acid dehydrogenase, 2) alpha-ketoglutarate dehydrogenase, and 3) the pyruvate dehydrogenase multienzyme complex (PDHC). These enzymes are multi-enzyme complexes that catalyze a series of partial reactions which result in acylating oxidative decarboxylation of 2-keto-acids. Each of the 2-keto-acid dehydrogenase complexes occupies key positions in intermediary metabolism, and enzyme activity is typically tightly regulated (Fries et al. *Biochemistry* 42:6996-7002 (2003)). The enzymes share a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (that is, larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al. *Appl. Environ. Microbiol.* 73:1766-1771 (2007); Kim et al. *J. Bacteriol.* 190: 3851-3858) 2008); Zhou et al. *Biotechnol. Lett.* 30:335-342 (2008)). For example, the inhibitory effect of NADH can be overcome by engineering an H322Y mutation in the E3 component (Kim et al. *J. Bacteriol.* 190:3851-3858 (2008)). Structural studies of individual components and how they work together in complex provide insight into the catalytic mechanisms and architecture of enzymes in this family (Aevarsson et al. *Nat. Struct. Biol.* 6:785-792 (1999); Zhou et al. *Proc. Natl. Acad. Sci. U.S.A.* 98:14802-14807 (2001)). The substrate specificity of the dehydrogenase complexes varies in different organisms, but generally branched-chain keto-acid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, R. G. *Curr. Top. Bioenerg.* 10:217-278 (1980)). Encoded by genes sucA, sucB and lpd in *E. coli*, AKGD gene expression is downregulated under anaerobic conditions and during growth on glucose (Park et al. *Mol. Microbiol.* 15:473-482 (1995)). Although the substrate range of AKGD is narrow, structural studies of the catalytic core of the E2 component pinpoint specific residues responsible for substrate specificity (Knapp et al. *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al. *Mol. Gen. Genet.* 234:285-296 (1992)). In yeast, the LPD1 gene encoding the E3 component is regulated at the transcriptional level by glucose (Roy and Dawes *J. Gen. Microbiol.* 133:925-933 (1987)). The E1 component, encoded by KGD1, is also regulated by glucose and activated by the products of HAP2 and HAP3 (Repetto and Tzagoloff *Mol. Cell Biol.* 9:2695-2705 (1989)). The AKGD enzyme complex, inhibited by products NADH and succinyl-CoA, is well-studied in mammalian systems, as impaired function of has been linked to several neurological diseases (Tretter and dam-Vizi *Philos. Trans. R. Soc. Lond B Biol. Sci.* 360:2335-2345 (2005)).

| Gene | Accession No. | GI No. | Organism |
|---|---|---|---|
| sucA | NP_415254.1 | 16128701 | *Escherichia coli* str. K12 substr. MG1655 |
| sucB | NP_415255.1 | 16128702 | *Escherichia coli* str. K12 substr. MG1655 |
| lpd | NP_414658.1 | 16128109 | *Escherichia coli* str. K12 substr. MG1655 |
| odhA | P23129.2 | 51704265 | *Bacillus subtilis* |
| odhB | P16263.1 | 129041 | *Bacillus subtilis* |
| pdhD | P21880.1 | 118672 | *Bacillus subtilis* |
| KGD1 | NP_012141.1 | 6322066 | *Saccharomyces cerevisiae* |
| KGD2 | NP_010432.1 | 6320352 | *Saccharomyces cerevisiae* |
| LPD1 | NP_116635.1 | 14318501 | *Saccharomyces cerevisiae* |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al. *Eur. J. Biochem.* 213:1091-1099 (1993)), *Rattus norvegicus* (Namba et al. *J. Biol. Chem.* 244:4437-4447 (1969)) and *Pseudomonas putida* (Sokatch *J. Bacteriol.* 148:647-652 (1981)). In *Bacillus subtilis* the enzyme is encoded by genes pdhD (E3 component), bfmBB (E2 component), bfmBAA and bfmBAB (E1 component) (Wang et al. *Eur. J. Biochem.* 213:1091-1099 (1993)). In mammals, the complex is regulated by phosphorylation by specific phosphatases and protein kinases. The complex has been studied in rat hepatocites (Chicco et al. *J. Biol. Chem.* 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al. *Nat. Struct. Biol.* 6:785-792 (1999); Mattevi *Science* 255:1544-1550 (1992)) and the enzyme complex has been studied (Sokatch et al. *J. Bacteriol.* 148:647-652 (1981)). Transcription of the *P. putida* BCKAD genes is activated by the gene product of bkdR (Hester et al. *Eur. J. Biochem.* 233:828-836 (1995)). In some organisms including *Rattus norvegicus* (Paxton et al. *Biochem. J.* 234:295-303 (1986)) and *Saccharomyces cerevisiae* (Sinclair et al. *Biochem. Mol. Biol. Int.* 31:911-922 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, *Biochemistry* 33:12879-12885 (1994)).

| Gene | Accession No. | GI No. | Organism |
|---|---|---|---|
| bfmBB | NP_390283.1 | 16079459 | *Bacillus subtilis* |
| bfmBAA | NP_390285.1 | 16079461 | *Bacillus subtilis* |
| bfmBAB | NP_390284.1 | 16079460 | *Bacillus subtilis* |
| pdhD | P21880.1 | 118672 | *Bacillus subtilis* |
| lpdV | P09063.1 | 118677 | *Pseudomonas putida* |
| bkdB | P09062.1 | 129044 | *Pseudomonas putida* |
| bkdA1 | NP_746515.1 | 26991090 | *Pseudomonas putida* |
| bkdA2 | NP_746516.1 | 26991091 | *Pseudomonas putida* |
| Bckdha | NP_036914.1 | 77736548 | *Rattus norvegicus* |
| Bckdhb | NP_062140.1 | 158749538 | *Rattus norvegicus* |
| Dbt | NP_445764.1 | 158749632 | *Rattus norvegicus* |
| Dld | NP_955417.1 | 40786469 | *Rattus norvegicus* |

The pyruvate dehydrogenase complex, catalyzing the conversion of pyruvate to acetyl-CoA, has also been extensively studied. In the *E. coli* enzyme, specific residues in the E1 component are responsible for substrate specificity (Bisswanger, H. *J Biol Chem.* 256:815-822 (1981); Bremer, J. *Eur. J Biochem.* 8:535-540 (1969); Gong et al. *J Biol Chem.*

275:13645-13653 (2000)). As mentioned previously, enzyme engineering efforts have improved the *E. coli* PDH enzyme activity under anaerobic conditions (Kim et al. *Appl. Environ. Microbiol.* 73:1766-1771 (2007); Kim *J. Bacteriol.* 190:3851-3858 (2008); Zhou et al. *Biotechnol. Lett.* 30:335-342 (2008)). In contrast to the *E. coli* PDH, the *B. subtilis* complex is active and required for growth under anaerobic conditions (Nakano *J. Bacteriol.* 179:6749-6755 (1997)). The *Klebsiella pneumoniae* PDH, characterized during growth on glycerol, is also active under anaerobic conditions (Menzel et al. *J. Biotechnol.* 56:135-142 (1997)). Crystal structures of the enzyme complex from bovine kidney (Zhou et al. *Proc. Natl. Acad. Sci. U.S.A.* 98:14802-14807 (2001)) and the E2 catalytic domain from *Azotobacter vinelandii* are available (Mattevi et al. *Science* 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al. *Biochem. J.* 234:295-303 (1986)).

| Gene | Accession No. | GI No. | Organism |
| --- | --- | --- | --- |
| aceE | NP_414656.1 | 16128107 | *Escherichia coli* str. K12 substr. MG1655 |
| aceF | NP_414657.1 | 16128108 | *Escherichia coli* str. K12 substr. MG1655 |
| lpd | NP_414658.1 | 16128109 | *Escherichia coli* str. K12 substr. MG1655 |
| pdhA | P21881.1 | 3123238 | *Bacillus subtilis* |
| pdhB | P21882.1 | 129068 | *Bacillus subtilis* |
| pdhC | P21883.2 | 129054 | *Bacillus subtilis* |
| pdhD | P21880.1 | 118672 | *Bacillus subtilis* |
| aceE | YP_001333808.1 | 152968699 | *Klebsiella pneumonia* MGH78578 |
| aceF | YP_001333809.1 | 152968700 | *Klebsiella pneumonia* MGH78578 |
| lpdA | YP_001333810.1 | 152968701 | *Klebsiella pneumonia* MGH78578 |
| Pdha1 | NP_001004072.2 | 124430510 | *Rattus norvegicus* |
| Pdha2 | NP_446446.1 | 16758900 | *Rattus norvegicus* |
| Dlat | NP_112287.1 | 78365255 | *Rattus norvegicus* |
| Dld | NP_955417.1 | 40786469 | *Rattus norvegicus* |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodixin as electron acceptors in lieu of NAD(P)H. While most enzymes in this family are specific to pyruvate as a substrate (POR) some 2-keto-acid:ferredoxin oxidoreductases have been shown to accept a broad range of 2-ketoacids as substrates including alpha-ketoglutarate and 2-oxobutanoate (Fukuda and Wakagi *Biochim. Biophys. Acta* 1597:74-80 (2002); Zhang et al. *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi *Biochim. Biophys. Acta* 1597:74-80 (2002); Zhang et al. *J. Biochem.* 120:587-599 (1996)). A plasmid-based expression system has been developed for efficiently expressing this protein in *E. coli* (Fukuda et al. *Eur. J. Biochem.* 268:5639-5646 (2001)) and residues involved in substrate specificity were determined (Fukuda and Wakagi *Biochim. Biophys. Acta* 1597:74-80 (2002)). Two OFORs from *Aeropyrum pernix* str. K1 have also been recently cloned into *E. coli*, characterized, and found to react with a broad range of 2-oxoacids (Nishizawa et al. *FEBS Lett.* 579:2319-2322 (2005)). The gene sequences of these OFOR candidates are available, although they do not have GenBank identifiers assigned to date. There is bioinformatic evidence that similar enzymes are present in all archaea, some anaerobic bacteria and amitochondrial eukarya (Fukuda and Wakagi *Biochim. Biophys. Acta* 1597:74-80 (2005)). This class of enzyme is also interesting from an energetic standpoint, as reduced ferredoxin could be used to generate NADH by ferredoxin-NAD reductase (Petitdemange et al. *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment.

| Gene | Accession No. | GI No. | Organism |
| --- | --- | --- | --- |
| ST2300 | NP_378302.1 | 15922633 | *Sulfolobus tokodaii* 7 |

1.2.1.d-Oxidoreductase (Phosphorylating/dephosphorylating)

Exemplary enzymes in this class include glyceraldehyde 3-phosphate dehydrogenase which converts glyceraldehyde-3-phosphate into D-glycerate 1,3-bisphosphate (for example, *E. coli* gapA (Branlant and Branlant *Eur. J. Biochem.* 150:61-66(1985)), aspartate-semialdehyde dehydrogenase which converts L-aspartate-4-semialdehyde into L-4-aspartyl-phosphate (for example, *E. coli* asd (Biellmann et al. *Eur. J. Biochem.* 104:53-58 (1980)), N-acetyl-gamma-glutamyl-phosphate reductase which converts N-acetyl-L-glutamate-5-semialdehyde into N-acetyl-L-glutamyl-5-phosphate (for example, *E. coli* argC (Parsot et al. *Gene* 68:275-283 (1988)), and glutamate-5-semialdehyde dehydrogenase which converts L-glutamate-5-semialdehyde into L-glutamyl-5-phospate (for example, *E. coli* proA (Smith et al. *J. Bacteriol.* 157:545-551 (1984)).

| Gene | Accession No. | GI No. | Organism |
| --- | --- | --- | --- |
| gapA | P0A9B2.2 | 71159358 | *Escherichia coli* |
| asd | NP_417891.1 | 16131307 | *Escherichia coli* |
| argC | NP_418393.1 | 16131796 | *Escherichia coli* |
| proA | NP_414778.1 | 16128229 | *Escherichia coli* |

1.3.1.a-Oxidoreductase Operating on CH—CH Donors

An exemplary enoyl-CoA reductase is the gene product of bcd from *C. acetobutylicum* (Atsumi et al. *Metab Eng* (2007); Boynton et al. *Journal of Bacteriology* 178:3015-3024 (1996), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al. *Journal of Biological Chemistry* 280:4329-4338 (2005)). A construct derived from this sequence following the removal of its mitochondrial targeting leader sequence was cloned in *E. coli* resulting in an active enzyme (Hoffmeister et al., supra, (2005)). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin *FEBS Letters* 581:1561-1566 (2007)).

| Gene | Accession No. | GI No. | Organism |
|---|---|---|---|
| bcd | NP_349317.1 | 15895968 | *Clostridium acetobutylicum* |
| etfA | NP_349315.1 | 15895966 | *Clostridium acetobutylicum* |
| etfB | NP_349316.1 | 15895967 | *Clostridium acetobutylicum* |
| TER | Q5EU90.1 | 62287512 | *Euglena gracilis* |
| TDE0597 | NP_971211.1 | 42526113 | *Treponema denticola* |

Exemplary 2-enoate reductase (EC 1.3.1.31) enzymes are known to catalyze the NADH-dependent reduction of a wide variety of α,β-unsaturated carboxylic acids and aldehydes (Rohdich et al. *J. Biol. Chem.* 276:5779-5787 (2001)). 2-Enoate reductase is encoded by enr in several species of *Clostridia* (Giesel and Simon *Arch Microbiol.* 135(1): p. 51-57 (2001) including *C. tyrobutyricum*, and *C. thermoaceticum* (now called *Moorella thermoaceticum*) (Rohdich et al., supra, (2001)). In the recently published genome sequence of *C. kluyveri*, 9 coding sequences for enoate reductases have been reported, out of which one has been characterized (Seedorf et al. *Proc Natl Acad Sci U.S.A.* 105(6):2128-33 (2008)). The enr genes from both *C. tyrobutyricum* and *C. thermoaceticum* have been cloned and sequenced and show 59% identity to each other. The former gene is also found to have approximately 75% similarity to the characterized gene in *C. kluyveri* (Giesel and Simon *Arch Microbiol* 135(1):51-57 (1983)). It has been reported based on these sequence results that enr is very similar to the dienoyl CoA reductase in *E. coli* (fadH) (163 Rohdich et al., supra (2001)). The *C. thermoaceticum* enr gene has also been expressed in an enzymatically active form in *E. coli* (163 Rohdich et al., supra (2001)).

| Gene | Accession No. | GI No. | Organism |
|---|---|---|---|
| fadH | NP_417552.1 | 16130976 | *Escherichia coli* |
| enr | ACA54153.1 | 169405742 | *Clostridium botulinum* A3 str |
| enr | CAA71086.1 | 2765041 | *Clostridium tyrobutyricum* |
| enr | CAA76083.1 | 3402834 | *Clostridium kluyveri* |
| enr | YP_430895.1 | 83590886 | *Moorella thermoacetica* |

1.4.1.a-Oxidoreductase Operating on Amino Acids

Most oxidoreductases operating on amino acids catalyze the oxidative deamination of alpha-amino acids with NAD+ or NADP+ as acceptor. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al. *J. Mol. Biol.* 234:1270-1273 (1993); McPherson and Wootton *Nucleic. Acids Res.* 11:5257-5266 (1983)), gdh from *Thermotoga maritima* (Kort et al. *Extremophiles* 1:52-60 (1997); Lebbink, et al. *J. Mol. Biol.* 280:287-296 (1998)); Lebbink et al. *J. Mol. Biol.* 289:357-369 (1999)), and gdhA1 from *Halobacterium salinarum* (Ingoldsby et al. Gene 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula *Biotechnol Bioeng.* 68:557-562 (2000); Stoyan et al. *J. Biotechnol* 54:77-80 (1997)). The nadX gene from *Thermotoga maritime* encoding for the aspartate dehydrogenase is involved in the biosynthesis of NAD (Yang et al. *J. Biol. Chem.* 278:8804-8808 (2003)).

| Gene | Accession No. | GI No. | Organism |
|---|---|---|---|
| gdhA | P00370 | 118547 | *Escherichia coli* |
| gdh | P96110.4 | 6226595 | *Thermotoga maritima* |
| gdhA1 | NP_279651.1 | 15789827 | *Halobacterium salinarum* |
| ldh | P0A393 | 61222614 | *Bacillus cereus* |
| nadX | NP_229443.1 | 15644391 | *Thermotoga maritima* |

The lysine 6-dehydrogenase (deaminating), encoded by lysDH gene, catalyze the oxidative deamination of the ε-amino group of L-lysine to form 2-aminoadipate-6-semialdehyde, which in turn nonenzymatically cyclizes to form Δ1-piperideine-6-carboxylate (Misono and Nagasaki *J. Bacteriol.* 150:398-401 (1982)). The lysDH gene from *Geobacillus stearothermophilus* encodes a thermophilic NAD-dependent lysine 6-dehydrogenase (Heydari et al. *Appl Environ. Microbiol* 70:937-942 (2004)). In addition, the lysDH gene from *Aeropyrum pernix* K1 is identified through homology from genome projects.

| Gene | Accession No. | GI No. | Organism |
|---|---|---|---|
| lysDH | AB052732 | 13429872 | *Geobacillus stearothermophilus* |
| lysDH | NP_147035.1 | 14602185 | *Aeropyrum pernix* K1 |
| ldh | P0A393 | 61222614 | *Bacillus cereus* |

2.3.1.a-Acyltransferase (Transferring Phosphate Group)

Exemplary phosphate transferring acyltransferases include phosphotransacetylase, encoded by pta, and phosphotransbutyrylase, encoded by ptb. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Similarly, the ptb gene from *C. acetobutylicum* encodes an enzyme that can convert butyryl-CoA into butyryl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186: 2099-2106 (2004)) and *Bacillus megaterium* (Vazquez et al. *Curr. Microbiol* 42:345-349 (2001)).

| Gene | Accession No. | GI No. | Organism |
|---|---|---|---|
| pta | NP_416800.1 | 16130232 | *Escherichia coli* |
| ptb | NP_349676 | 15896327 | *Clostridium acetobutylicum* |
| ptb | AAR19757.1 | 38425288 | butyrate-producing bacterium L2-50 |
| ptb | CAC07932.1 | 10046659 | *Bacillus megaterium* |

2.6.1.a-Aminotransferase

Aspartate aminotransferase transfers an amino group from aspartate to alpha-ketoglutarate, forming glutamate and oxaloacetate. This conversion is catalyzed by, for example, the gene products of aspC from *Escherichia coli* (Yagi et al. *FEBS Lett.* 100:81-84 (1979); Yagi et al. *Methods Enzymol.* 113:83-89 (1985)), AAT2 from *Saccharomyces cerevisiae* (Yagi et al. *J Biochem.* 92:35-43 (1982)) and ASP5 from *Arabidopsis thaliana* (48, 108, 225 48. de la et al. *Plant J* 46:414-425 (2006); Kwok and Hanson *J Exp. Bot.* 55:595-604 (2004); Wilkie and Warren *Protein Expr. Purif.* 12:381-389 (1998)). Valine aminotransferase catalyzes the conversion of valine and pyruvate to 2-ketoisovalerate and alanine. The *E. coli* gene, avtA, encodes one such enzyme (Whalen and Berg *J. Bacteriol.* 150:739-746 (1982)). This gene product also catalyzes the amination of α-ketobutyrate to generate α-aminobutyrate, although the amine donor in this reaction has not been identified (Whalen and Berg *J. Bacteriol.* 158:571-574 (1984)). The gene product of the *E. coli* serC catalyzes two reactions, phosphoserine aminotransferase and phosphohydroxythreonine aminotransferase (Lam and Winkler *J. Bacteriol.* 172:6518-6528 (1990)), and activity on non-phosphorylated substrates could not be detected (Drewke et al. *FEBS. Lett.* 390:179-182 (1996)).

| Gene | Accession No. | GI No. | Organism |
| --- | --- | --- | --- |
| aspC | NP_415448.1 | 16128895 | *Escherichia coli* |
| AAT2 | P23542.3 | 1703040 | *Saccharomyces cerevisiae* |
| ASP5 | P46248.2 | 20532373 | *Arabidopsis thaliana* |
| avtA | YP_026231.1 | 49176374 | *Escherichia coli* |
| serC | NP_415427.1 | 16128874 | *Escherichia coli* |

Cargill has developed a beta-alanine/alpha-ketoglutarate aminotransferase for producing 3-HP from beta-alanine via malonyl-semialdehyde (PCT/US2007/076252 (Jessen et al)). The gene product of SkPYD4 in *Saccharomyces kluyveri* was also shown to preferentially use beta-alanine as the amino group donor (Andersen et al. *FEBS. J.* 274:1804-1817 (2007)). SkUGA1 encodes a homologue of *Saccharomyces cerevisiae* GABA aminotransferase, UGA1 (Ramos et al. *Eur. J. Biochem.* 149:401-404 (1985)), whereas SkPYD4 encodes an enzyme involved in both β-alanine and GABA transamination (Andersen et al. *FEBS. J.* 274:1804-1817 (2007)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Kakimoto et al. *Biochim. Biophys. Acta* 156:374-380 (1968); Tamaki et al. *Methods Enzymol.* 324: 376-389 (2000)). Enzyme candidates in other organisms with high sequence homology to 3-amino-2-methylpropionate transaminase include Gta-1 in *C. elegans* and gabT in *Bacillus subtilus*. Additionally, one of the native GABA aminotransferases in *E. coli*, encoded by gene gabT, has been shown to have broad substrate specificity (Liu et al. *Biochemistry* 43:10896-10905 (2004); Schulz et al. *Appl Environ Microbiol* 56:1-6 (1990)). The gene product of puuE catalyzes the other 4-aminobutyrate transaminase in *E. coli* (Kurihara et al. *J. Biol. Chem.* 280:4602-4608 (2005)).

| Gene | Accession No. | GI No. | Organism |
| --- | --- | --- | --- |
| SkyPYD4 | ABF58893.1 | 98626772 | *Saccharomyces kluyveri* |
| SkUGA1 | ABF58894.1 | 98626792 | *Saccharomyces kluyveri* |
| UGA1 | NP_011533.1 | 6321456 | *Saccharomyces cerevisiae* |
| Abat | P50554.3 | 122065191 | *Rattus norvegicus* |
| Abat | P80147.2 | 120968 | *Sus scrofa* |
| Gta-1 | Q21217.1 | 6016091 | *Caenorhabditis elegans* |
| gabT | P94427.1 | 6016090 | *Bacillus subtilus* |
| gabT | P22256.1 | 120779 | *Escherichia coli* K12 |
| puuE | NP_415818.1 | 16129263 | *Escherichia coli* K12 |

The X-ray crystal structures of *E. coli* 4-aminobutyrate transaminase unbound and bound to the inhibitor were reported (Liu et al. *Biochemistry* 43:10896-10905 (2004)). The substrates binding and substrate specificities were studied and suggested. The roles of active site residues were studied by site-directed mutagenesis and X-ray crystallography (Liu et al. *Biochemistry* 44:2982-2992 (2005)). Based on the structural information, attempt was made to engineer *E. coli* 4-aminobutyrate transaminase with novel enzymatic activity. These studies provide a base for evolving transaminase activity for BDO pathways.

2.7.2.a-Phosphotransferase, Carboxyl Group Acceptor

Exemplary kinases include the *E. coli* acetate kinase, encoded by ackA (Skarstedt and Silverstein *J. Biol. Chem.* 251:6775-6783 (1976)), the *C. acetobutylicum* butyrate kinases, encoded by buk1 and buk2 (Walter et al. *Gene* 134(1):107-111 (1993) (Huang et al. *J Mol Microbiol Biotechnol* 2(1):33-38 (2000)], and the *E. coli* gamma-glutamyl kinase, encoded by proB (Smith et al. *J. Bacteriol.* 157:545-551 (1984)). These enzymes phosphorylate acetate, butyrate, and glutamate, respectively. The ackA gene product from *E. coli* also phosphorylates propionate (Hesslinger et al. *Mol. Microbiol* 27:477-492 (1998)).

| Gene | Accession No. | GI No. | Organism |
| --- | --- | --- | --- |
| ackA | NP_416799.1 | 16130231 | *Escherichia coli* |
| buk1 | NP_349675 | 15896326 | *Clostridium acetobutylicum* |
| buk2 | Q97II1 | 20137415 | *Clostridium acetobutylicum* |
| proB | NP_414777.1 | 16128228 | *Escherichia coli* |

2.8.3.a-Coenzyme-A Transferase

In the CoA-transferase family, *E. coli* enzyme acyl-CoA: acetate-CoA transferase, also known as acetate-CoA transferase (EC 2.8.3.8), has been shown to transfer the CoA moiety to acetate from a variety of branched and linear acyl-CoA substrates, including isobutyrate (Matthies and Schink *Appl Environ Microbiol* 58:1435-1439 (1992)), valerate (Vanderwinkel et al. *Biochem. Biophys. Res Commun.* 33:902-908 (1968)) and butanoate (Vanderwinkel, supra (1968)). This enzyme is encoded by atoA (alpha subunit) and atoD (beta subunit) in *E. coli* sp. K12 (Korolev et al. *Acta Crystallogr. D Biol Crystallogr.* 58:2116-2121 (2002); Vanderwinkel, supra (1968)) and actA and cg0592 in *Corynebacterium glutamicum* ATCC 13032 (Duncan et al. *Appl Environ Microbiol* 68:5186-5190 (2002)). Additional genes found by sequence homology include atoD and atoA in *Escherichia coli* UT 189.

| Gene | Accession No. | GI No. | Organism |
|---|---|---|---|
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* ATCC 13032 |
| cg0592 | YP_224801.1 | 62389399 | *Corynebacterium glutamicum* ATCC 13032 |
| atoA | ABE07971.1 | 91073090 | *Escherichia coli* UT189 |
| atoD | ABE07970.1 | 91073089 | *Escherichia coli* UT189 |

Similar transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Seedorf et al. *Proc Natl Acad Sci U.S.A.* 105(6):2128-2133 (2008); Sohling and Gottschalk *J Bacteriol* 178(3):871-880 (1996)].

| Gene | Accession No. | GI No. | Organism |
|---|---|---|---|
| cat1 | P38946.1 | 729048 | *Clostridium kluyveri* |
| cat2 | P38942.2 | 1705614 | *Clostridium kluyveri* |
| cat3 | EDK35586.1 | 146349050 | *Clostridium kluyveri* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack and Buckel *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al. *Eur. J. Biochem.* 118:315-321 (1981)). The enzyme has been cloned and expressed in *E. coli* (Mac et al. *Eur. J. Biochem.* 226:41-51 (1994)).

| Gene | Accession No. | GI No. | Organism |
|---|---|---|---|
| gctA | CAA57199.1 | 559392 | *Acidaminococcus fermentans* |
| gctB | CAA57200.1 | 559393 | *Acidaminococcus fermentans* |

3.1.2.a-Thiolester Hydrolase (CoA Specific)

In the CoA hydrolase family, the enzyme 3-hydroxyisobutyryl-CoA hydrolase is specific for 3-HIBCoA and has been described to efficiently catalyze the desired transformation during valine degradation (Shimomura et al. *J Biol Chem* 269:14248-14253 (1994)). Genes encoding this enzyme include hibch of *Rattus norvegicus* (Shimomura et al., supra (1994); Shimomura et al. *Methods Enzymol.* 324:229-240 (2000) and *Homo sapiens* (Shimomura et al., supra, 2000). Candidate genes by sequence homology include hibch of *Saccharomyces cerevisiae* and BC_2292 of *Bacillus cereus*.

| Gene | Accession No. | GI No. | Organism |
|---|---|---|---|
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | Q81DR3 | 81434808 | *Bacillus cereus* |

The conversion of adipyl-CoA to adipate can be carried out by an acyl-CoA hydrolase or equivalently a thioesterase. The top *E. coli* gene candidate is tesB (Naggert et al. *J Biol Chem.* 266(17):11044-11050 (1991)] which shows high similarity to the human acot8 which is a dicarboxylic acid acetyltransferase with activity on adipyl-CoA (Westin et al. *J Biol Chem* 280(46): 38125-38132 (2005). This activity has also been characterized in the rat liver (Deana, *Biochem Int.* 26(4): p. 767-773 (1992)).

| Gene | Accession No. | GI No. | Organism |
|---|---|---|---|
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |

Other potential *E. coli* thiolester hydrolases include the gene products of tesA (Bonner and Bloch, *J Biol Chem.* 247(10):3123-3133 (1972)), ybgC (Kuznetsova et al., *FEMS Microbiol Rev.* 29(2):263-279 (2005); Zhuang et al., *FEBS Lett.* 516(1-3):161-163 (2002)) paaI (Song et al., *J Biol Chem.* 281(16):11028-11038 (2006)), and ybdB (Leduc et al., *J Bacteriol.* 189(19):7112-7126 (2007)).

| Gene | Accession No. | GI No. | Organism |
|---|---|---|---|
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |

Several eukaryotic acetyl-CoA hydrolases (EC 3.1.2.1) have broad substrate specificity. The enzyme from *Rattus norvegicus* brain (Robinson et al. *Biochem. Biophys. Res. Commun.* 71:959-965 (1976)) can react with butyryl-CoA, hexanoyl-CoA and malonyl-CoA.

| Gene | Accession No. | GI No. | Organism |
|---|---|---|---|
| acot12 | NP_570103.1 | 18543355 | *Rattus norvegicus* |

4.1.1.a-Carboxy-lyase

An exemplary carboxy-lyase is acetolactate decarboxylase which participates in citrate catabolism and branched-chain amino acid biosynthesis, converting 2-acetolactate to acetoin. In *Lactococcus lactis* the enzyme is composed of six subunits, encoded by gene aldB, and is activated by valine, leucine and isoleucine (Goupil et al. *Appl. Environ. Microbiol.* 62:2636-2640 (1996); Goupil-Feuillerat et al. *J. Bacteriol.* 182:5399-5408 (2000)). This enzyme has been overexpressed and characterized in *E. coli* (Phalip et al. *FEBS Lett.* 351:95-99 (1994)). In other organisms the enzyme is a dimer, encoded by aldC in *Streptococcus thermophilus* (Monnet et al. *Lett. Appl. Microbiol.* 36:399-405 (2003)), aldB in *Bacillus brevis* (Diderichsen et al. *J. Bacteriol.* 172:4315-4321 (1990); Najmudin et al. *Acta Crystallogr. D. Biol. Crystallogr.* 59:1073-1075 (2003)) and budA from *Enterobacter aerogenes* (Diderichsen et al. *J. Bacteriol.* 172:4315-4321 (1990)). The enzyme from *Bacillus brevis* was cloned and overexpressed in *Bacillus subtilis* and characterized crystallographically (Najmudin et al. *Acta Crystallogr. D. Biol. Crystallo.* 59:1073-1075 (2003)). Additionally, the enzyme from *Leuconostoc lactis* has been purified and characterized but the gene has not been isolated (O'Sullivan et al. *FEMS Microbiol. Lett.* 194:245-249 (2001)).

| Gene | Accession No. | GI No. | Organism |
| --- | --- | --- | --- |
| aldB | NP_267384.1 | 15673210 | *Lactococcus lactis* |
| aldC | Q8L208 | 75401480 | *Streptococcus thermophilus* |
| aldB | P23616.1 | 113592 | *Bacillus brevis* |
| budA | P05361.1 | 113593 | *Enterobacter aerogenes* |

Aconitate decarboxylase catalyzes the final step in itaconate biosynthesis in a strain of *Candida* and also in the filamentous fungus *Aspergillus terreus* (Bonnarme et al. *J Bacteriol.* 177:3573-3578 (1995); Willke and Vorlop *Appl Microbiol Biotechnol* 56:289-295 (2001)). Although itaconate is a compound of biotechnological interest, the aconitate decarboxylase gene or protein sequence has not been reported to date.

4-oxalocronate decarboxylase has been isolated from numerous organisms and characterized. Genes encoding this enzyme include dmpH and dmpE in *Pseudomonas* sp. (strain 600) (Shingler et al. *J Bacteriol.* 174:711-724 (1992)), xylII and xylIII from *Pseudomonas putida* (Kato and Asano *Arch. Microbiol* 168:457-463 (1997); Lian and Whitman *J. Am. Chem. Soc.* 116:10403-10411 (1994); Stanley et al. *Biochemistry* 39:3514 (2000)) and Reut_B5691 and Reut_B5692 from *Ralstonia eutropha* JMP 134 (Hughes et al. *J Bacteriol.* 158:79-83 (1984)). The genes encoding the enzyme from *Pseudomonas* sp. (strain 600) have been cloned and expressed in *E. coli* (Shingler et al. *J Bacteriol.* 174:711-724 (1992)).

| Gene | Accession No. | GI No. | Organism |
| --- | --- | --- | --- |
| dmpH | CAA43228.1 | 45685 | *Pseudomonas* sp. CF600 |
| dmpE | CAA43225.1 | 45682 | *Pseudomonas* sp. CF600 |
| xylII | YP_709328.1 | 111116444 | *Pseudomonas putida* |
| xylIII | YP_709353.1 | 111116469 | *Pseudomonas putida* |
| Reut_B5691 | YP_299880.1 | 73539513 | *Ralstonia eutropha* JMP 134 |
| Reut_B5692 | YP_299881.1 | 73539514 | *Ralstonia eutropha* JMP 134 |

An additional class of decarboxylases has been characterized that catalyze the conversion of cinnamate (phenylacrylate) and substituted cinnamate derivatives to the corresponding styrene derivatives. These enzymes are common in a variety of organisms and specific genes encoding these enzymes that have been cloned and expressed in *E. coli* are: pad 1 from *Saccharomyces cerevisae* (Clausen et al. *Gene* 142:107-112 (1994)), pdc from *Lactobacillus plantarum* (Barthelmebs et al. *Appl Environ Microbiol* 67:1063-1069 (2001); Qi et al. *Metab Eng* 9:268-276 (2007); Rodriguez et al. *J. Agric. Food Chem.* 56:3068-3072 (2008)), pofK (pad) from *Klebsiella oxytoca* (Hashidoko et al. *Biosci. Biotech. Biochem.* 58:217-218 (1994); Uchiyama et al. *Biosci. Biotechnol. Biochem.* 72:116-123 (2008)), *Pediococcus pentosaceus* (Barthelmebs et al. *Appl Environ Microbiol* 67:1063-1069 (2001)), and padC from *Bacillus subtilis* and *Bacillus pumilus* (Lingen et al. *Protein Eng* 15:585-593 (2002)). A ferulic acid decarboxylase from *Pseudomonas fluorescens* also has been purified and characterized (Huang et al. *J. Bacteriol.* 176:5912-5918 (1994)). Importantly, this class of enzymes have been shown to be stable and do not require either exogenous or internally bound co-factors, thus making these enzymes ideally suitable for biotransformations (Sariaslani, *Annu. Rev. Microbiol.* 61:51-69 (2007)).

| Gene | Accession No. | GI No. | Organism |
| --- | --- | --- | --- |
| pad1 | AB368798 BAG32372.1 | 188496948 188496949 | *Saccharomyces cerevisae* |
| pdc | U63827 AAC45282.1 | 1762615, 1762616 | *Lactobacillus plantarum* |
| pofK (pad) | AB330293, BAF65031.1 | 149941607, 149941608 | *Klebsiella oxytoca* |
| padC | AF017117 AAC46254.1 | 2394281, 2394282 | *Bacillus subtilis* |
| pad | AJ276891 CAC16794.1 | 11322456, 11322458 | *Pediococcus pentosaceus* |
| pad | AJ278683 CAC18719.1 | 11691809, 11691810 | *Bacillus pumilus* |

Additional decarboxylase enzymes can form succinic semialdehyde from alpha-ketoglutarate. These include the alpha-ketoglutarate decarboxylase enzymes from *Euglena gracilis* (Shigeoka et al. *Biochem. J.* 282(Pt 2):319-323 (1992); Shigeoka and Nakano *Arch. Biochem. Biophys.* 288:22-28 (1991); Shigeoka and Nakano *Biochem. J.* 292 (Pt 2):463-467 (1993)), whose corresponding gene sequence has yet to be determined, and from *Mycobacterium tuberculosis* (Tian et al. *Proc Natl Acad Sci U.S.A.* 102:10670-10675 (2005)). In addition, glutamate decarboxylase enzymes can convert glutamate into 4-aminobutyrate such as the products of the *E. coli* gadA and gadB genes (De Biase et al. *Protein. Expr. Purif.* 8:430-438 (1993)).

| Gene | Accession No. | GI No. | Organism |
| --- | --- | --- | --- |
| kgd | O50463.4 | 160395583 | *Mycobacterium tuberculosis* |
| gadA | NP_417974 | 16131389 | *Escherichia coli* |
| gadB | NP_416010 | 16129452 | *Escherichia coli* |

Keto-Acid Decarboxylases

Pyruvate decarboxylase (PDC, EC 4.1.1.1), also termed keto-acid decarboxylase, is a key enzyme in alcoholic fermentation, catalyzing the decarboxylation of pyruvate to acetaldehyde. This enzyme has a broad substrate range for aliphatic 2-keto acids including 2-ketobutyrate, 2-ketovalerate, 3-hydroxypyruvate and 2-phenylpyruvate (Berg et al. *Science* 318:1782-1786 (2007)). The PDC from *Zymomonas mobilus*, encoded by pdc, has been a subject of directed engineering studies that altered the affinity for different substrates (Siegert et al. *Protein Eng Des Sel* 18:345-357 (2005)). The PDC from *Saccharomyces cerevisiae* has also been extensively studied, engineered for altered activity, and functionally expressed in *E. coli* (Killenberg-Jabs et al. *Eur. J. Biochem.* 268:1698-1704 (2001); Li and Jordan *Biochemistry* 38:10004-10012 (1999); ter Schure et al. *Appl. Environ. Microbiol.* 64:1303-1307 (1998)). The crystal structure of this enzyme is available (Killenberg-Jabs *Eur. J. Biochem.* 268:1698-1704 (2001)). Other well-characterized PDC candidates include the enzymes from *Acetobacter pasteurians* (Chandra et al. *Arch. Microbiol.* 176:443-451 (2001)) and *Kluyveromyces lactis* (Krieger et al. *Eur. J. Biochem.* 269: 3256-3263 (2002)).

| Gene | Accession No. | GI No. | Organism |
| --- | --- | --- | --- |
| pdc | P06672.1 | 118391 | *Zymomonas mobilus* |
| pdc1 | P06169 | 30923172 | *Saccharomyces cerevisiae* |
| pdc | Q8L388 | 75401616 | *Acetobacter pasteurians* |
| pdc1 | Q12629 | 52788279 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al. *Biochemistry* 37:9918-9930 (1998); Polovnikova et al. *Biochemistry* 42:1820-1830 (2003)). Site-directed mutagenesis of two residues in the active site of the *Pseudomonas putida* enzyme altered the affinity (Km) of naturally and non-naturally occuring substrates (Siegert *Protein Eng Des Sel* 18:345-357 (2005)). The properties of this enzyme have been further modified by directed engineering (Lingen et al. *Protein Eng* 15:585-593 (2002)); Lingen *Chembiochem* 4:721-726 (2003)). The enzyme from *Pseudomonas aeruginosa*, encoded by mdlC, has also been characterized experimentally (Barrowman et al. *FEMS Microbiology Letters* 34:57-60 (1986)). Additional gene candidates from *Pseudomonas stutzeri, Pseudomonas fluorescens* and other organisms can be inferred by sequence homology or identified using a growth selection system developed in *Pseudomonas putida* (Henning et al. *Appl. Environ. Microbiol.* 72:7510-7517 (2006)).

| Gene | Accession No. | GI No. | Organism |
|---|---|---|---|
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

4.2.1.a-Hydro-lyase

The 2-(hydroxymethyl)glutarate dehydratase of *Eubacterium barkeri* is an exemplary hydro-lyase. This enzyme has been studied in the context of nicotinate catabolism and is encoded by hmd (Alhapel et al. *Proc Natl Acad Sci USA* 103:12341-12346 (2006)). Similar enzymes with high sequence homology are found in *Bacteroides capillosus, Anaerotruncus colihominis*, and *Natranaerobius thermophilius*.

| Gene | Accession No. | GI No. | Organism |
|---|---|---|---|
| hmd | ABC88407.1 | 86278275 | *Eubacterium barkeri* |
| BACCAP_02294 | ZP_02036683.1 | 154498305 | *Bacteroides capillosus* ATCC 29799 |
| ANACOL_02527 | ZP_02443222.1 | 167771169 | *Anaerotruncus colihominis* DSM 17241 |
| NtherDRAFT_2368 | ZP_02852366.1 | 169192667 | *Natranaerobius thermophilus* JW/NM-WN-LF |

A second exemplary hydro-lyase is fumarate hydratase, an enzyme catalyzing the dehydration of malate to fumarate. A wealth of structural information is available for this enzyme and researchers have successfully engineered the enzyme to alter activity, inhibition and localization (Weaver, T. *Acta Crystallogr. D Biol Crystallogr.* 61:1395-1401 (2005)). Additional fumarate hydratases include those encoded by fumC from *Escherichia coli* (Estevez et al. *Protein Sci.* 11:1552-1557 (2002); Hong and Lee *Biotechnol. Bioprocess Eng.* 9:252-255 (2004); Rose and Weaver *Proc Natl Acad Sci USA* 101:3393-3397 (2004)), *Campylobacter jejuni* (Smith et al. *Int. J Biochem. Cell Biol* 31:961-975 (1999)) and *Thermus thermophilus* (Mizobata et al. *Arch. Biochem. Biophys.* 355:49-55 (1998)), and fumH from *Rattus norvegicus* (Kobayashi et al. *J Biochem.* 89:1923-1931 (1981)). Similar enzymes with high sequence homology include fumI from *Arabidopsis thaliana* and fumC from *Corynebacterium glutamicum*.

| Gene | Accession No. | GI No. | Organism |
|---|---|---|---|
| fumC | P05042.1 | 120601 | *Escherichia coli* K12 |
| fumC | O69294.1 | 9789756 | *Campylobacter jejuni* |
| fumC | P84127 | 75427690 | *Thermus thermophilus* |
| fumH | P14408.1 | 120605 | *Rattus norvegicus* |
| fum1 | P93033.2 | 39931311 | *Arabidopsis thaliana* |
| fumC | Q8NRN8.1 | 39931596 | *Corynebacterium glutamicum* |

Citramalate hydrolyase, also called 2-methylmalate dehydratase, converts 2-methylmalate to mesaconate. 2-Methylmalate dehydratase activity was detected in *Clostridium tetanomorphum, Morganella morganii, Citrobacter amalonaticus* in the context of the glutamate degradation VI pathway (Kato and Asano *Arch. Microbiol* 168:457-463 (1997)); however the genes encoding this enzyme have not been sequenced to date.

The gene product of crt from *C. acetobutylicum* catalyzes the dehydration of 3-hydroxybutyryl-CoA to crotonyl-CoA (Atsumi et al. *Metab Eng.;* 29 (2007)); Boynton et al. *Journal of Bacteriology* 178:3015-3024 (1996)). The enoyl-CoA hydratases, phaA and phaB, of *P. putida* are believed to carry out the hydroxylation of double bonds during phenylacetate catabolism; (Olivera et al. *Proc Natl Acad Sci USA* 95(11):6419-6424 (1998)). The paaA and paaB from *P. fluorescens* catalyze analogous transformations (14 Olivera et al., supra, 1998). Lastly, a number of *Escherichia coli* genes have been shown to demonstrate enoyl-CoA hydratase functionality including maoC (Park and Lee *J Bacteriol* 185(18):5391-5397 (2003)), paaF (Park and Lee *Biotechnol Bioeng.* 86(6):681-686 (2004a)); Park and Lee *Appl Biochem Biotechnol.* 113-116: 335-346 (2004b)); Ismail et al. *Eur J Biochem* 270(14):p. 3047-3054 (2003), and paaG (Park and Lee, supra, 2004; Park and Lee supra, 2004b; Ismail et al., supra, 2003).

| Gene | Accession No. | GI No. | Organism |
|---|---|---|---|
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |
| crt | NP_349318.1 | 15895969 | *Clostridium acetobutylicum* |
| paaA | NP_745427.1 | 26990002 | *Pseudomonas putida* |
| paaB | NP_745426.1 | 26990001 | *Pseudomonas putida* |
| phaA | ABF82233.1 | 106636093 | *Pseudomonas fluorescens* |
| phaB | ABF82234.1 | 106636094 | *Pseudomonas fluorescens* |

The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al. *Biochemistry* 30(27): p. 6788-6795 (1991); Yang et al. *J Biol Chem* 265(18): p. 10424-10429 (1990); Yang et al. *J Biol Chem* 266(24): p. 16255 (1991); Nakahigashi and Inokuchi *Nucleic Acids Res* 18(16): p. 4937 (1990)). The fadI and fadJ genes encode similar functions and are naturally expressed only anaerobically (Campbell et al. *Mol Microbiol* 47(3): p. 793-805 (2003). A method for producing poly[(R)-3-hydroxybutyrate] in *E. coli* that involves activating fadB (by knocking out a negative regulator, fadR) and co-expressing a non-native ketothiolase (phaA from *Ralsto-* nia eutropha) has been described previously (Sato et al. *J Biosci Bioeng* 103(1): 38-44 (2007)). This work clearly demonstrates that a β-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors.

| Gene | Accession No. | GI No. | Organism |
| --- | --- | --- | --- |
| fadA | YP_026272.1 | 49176430 | *Escherichia coli* |
| fadB | NP_418288.1 | 16131692 | *Escherichia coli* |
| fadI | NP_416844.1 | 16130275 | *Escherichia coli* |
| fadJ | NP_416843.1 | 16130274 | *Escherichia coli* |
| fadR | NP_415705.1 | 16129150 | *Escherichia coli* |

4.3.1.a-Ammonia-lyase

Aspartase (EC 4.3.1.1), catalyzing the deamination of aspartate to fumarate, is a widespread enzyme in microorganisms, and has been characterized extensively (Viola, R. E. *Adv. Enzymol. Relat Areas Mol. Biol* 74:295-341 (2000)). The crystal structure of the *E. coli* aspartase, encoded by aspA, has been solved (Shi et al. *Biochemistry* 36:9136-9144 (1997)). The *E. coli* enzyme has also been shown to react with alternate substrates aspartatephenylmethylester, asparagine, benzyl-aspartate and malate (Ma et al. *Ann N.Y. Acad Sci* 672:60-65 (1992)). In a separate study, directed evolution was been employed on this enzyme to alter substrate specificity (Asano et al. *Biomol. Eng* 22:95-101 (2005)). Enzymes with aspartase functionality have also been characterized in *Haemophilus influenzae* (Sjostrom et al. *Biochim. Biophys. Acta* 1324:182-190 (1997)), *Pseudomonas fluorescens* (Takagi et al. *J. Biochem.* 96:545-552 (1984)), *Bacillus subtilus* (Sjostrom et al. *Biochim. Biophys. Acta* 1324:182-190 (1997)) and *Serratia marcescens* (Takagi and Kisumi *J Bacteriol.* 161:1-6 (1985)).

| Gene | Accession No. | GI No. | Organism |
| --- | --- | --- | --- |
| aspA | NP_418562 | 90111690 | *Escherichia coli* K12 subsp. MG1655 |
| aspA | P44324.1 | 1168534 | *Haemophilus influenzae* |
| aspA | P07346.1 | 114273 | *Pseudomonas fluorescens* |
| ansB | P26899.1 | 114271 | *Bacillus subtilus* |
| aspA | P33109.1 | 416661 | *Serratia marcescens* |

3-methylaspartase (EC 4.3.1.2), also known as beta-methylaspartase or 3-methylaspartate ammonia-lyase, catalyzes the deamination of threo-3-methylasparatate to mesaconate. The 3-methylaspartase from *Clostridium tetanomorphum* has been cloned, functionally expressed in *E. coli*, and crystallized (Asuncion et al. *Acta Crystallogr. D Biol Crystallogr.* 57:731-733 (2001); Asuncion et al. *J Blot Chem.* 277:8306-8311 (2002); Botting et al. *Biochemistry* 27:2953-2955 (1988); Goda et al. *Biochemistry* 31:10747-10756 (1992). In *Citrobacter amalonaticus*, this enzyme is encoded by BAA28709 (Kato and Asano *Arch. Microbiol* 168:457-463 (1997)). 3-Methylaspartase has also been crystallized from *E. coli* YG 1002 (Asano and Kato *FEMS Microbiol Lett.* 118:255-258 (1994)) although the protein sequence is not listed in public databases such as GenBank. Sequence homology can be used to identify additional candidate genes, including CTC_02563 in *C. tetani* and ECs0761 in *Escherichia coli* O157:H7.

| Gene | Accession No. | GI No. | Organism |
| --- | --- | --- | --- |
| MAL | AAB24070.1 | 259429 | *Clostridium tetanomorphum* |
| BAA28709 | BAA28709.1 | 3184397 | *Citrobacter amalonaticus* |
| CTC_02563 | NP_783085.1 | 28212141 | *Clostridium tetani* |
| ECs0761 | BAB34184.1 | 13360220 | *Escherichia coli* O157:H7 str. Sakai |

Ammonia-lyase enzyme candidates that form enoyl-CoA products include beta-alanyl-CoA ammonia-lyase (EC 4.3.1.6), which deaminates beta-alanyl-CoA, and 3-aminobutyryl-CoA ammonia-lyase (EC 4.3.1.14). Two beta-alanyl-CoA ammonia lyases have been identified and characterized in *Clostridium propionicum* (Herrmann et al. *FEBS J.* 272:813-821 (2005)). No other beta-alanyl-CoA ammonia lyases have been studied to date, but gene candidates can be identified by sequence similarity. One such candidate is MXAN_4385 in *Myxococcus xanthus*.

| Gene | Accession No. | GI No. | Organism |
| --- | --- | --- | --- |
| acl2 | CAG29275.1 | 47496504 | *Clostridium propionicum* |
| acl1 | CAG29274.1 | 47496502 | *Clostridium propionicum* |
| MXAN_4385 | YP_632558.1 | 108756898 | *Myxococcus xanthus* |

5.3.3.a-Isomerase

The 4-hydroxybutyryl-CoA dehydratases from both *Clostridium aminobutyrium* and *C. kluyveri* catalyze the reversible conversion of 4-hydroxybutyryl-CoA to crotonyl-CoA and posses an intrinsic vinylacetyl-CoA Δ-isomerase activity (Scherf and Buckel *Eur. J Biochem.* 215:421-429 (1993); Scherf et al. *Arch. Microbiol* 161:239-245 (1994)). Both native enzymes were purified and characterized, including the N-terminal amino acid sequences (Scherf and Buckel, supra, 1993; Scherf et al., supra, 1994). The abfD genes from *C. aminobutyrium* and *C. kluyveri* match exactly with these N-terminal amino acid sequences, thus are encoding the 4-hydroxybutyryl-CoA dehydratases/vinylacetyl-CoA Δ-isomerase. In addition, the abfD gene from *Porphyromonas gingivalis* ATCC 33277 is identified through homology from genome projects.

| Gene | Accession No. | GI No. | Organism |
| --- | --- | --- | --- |
| abfD | YP_001396399.1 | 153955634 | *Clostridium kluyveri* DSM 555 |
| abfD | P55792 | 84028213 | *Clostridium aminobutyricum* |
| abfD | YP_001928843 | 188994591 | *Porphyromonas gingivalis* ATCC 33277 |

5.4.3.a-Aminomutase

Lysine 2,3-aminomutase (EC 5.4.3.2) is an exemplary aminomutase that converts lysine to (3S)-3,6-diaminohexanoate, shifting an amine group from the 2- to the 3-position. The enzyme is found in bacteria that ferment lysine to acetate and butyrate, including as *Fusobacterium nuleatum* (kamA) (Barker et al. *J. Bacteriol.* 152:201-207 (1982)) and *Clostridium subterminale* (kamA) (Chirpich et al. *J. Biol. Chem.* 245:1778-1789 (1970)). The enzyme from *Clostridium subterminale* has been crystallized (Lepore et al. *Proc. Natl. Acad. Sci. U.S.A* 102:13819-13824 (2005)). An enzyme encoding this function is also encoded by yodO in *Bacillus subtilus* (Chen et al. *Biochem. J.* 348 Pt 3:539-549 (2000)). The enzyme utilizes pyridoxal 5'-phosphate as a cofactor, requires activation by S-Adenosylmethoionine, and is stereoselective, reacting with the only with L-lysine. The enzyme has not been shown to react with alternate substrates.

| Gene | Accession No. | GI No. | Organism |
| --- | --- | --- | --- |
| yodO | O34676.1 | 4033499 | *Bacillus subtilus* |
| kamA | Q9XBQ8.1 | 75423266 | *Clostridium subterminale* |
| kamA | Q8RHX4 | 81485301 | *Fusobacterium nuleatum* subsp. *nuleatum* |

A second aminomutase, beta-lysine 5,6-aminomutase (EC 5.4.3.3), catalyzes the next step of lysine fermentation to acetate and butyrate, which transforms (3S)-3,6-diaminohexanoate to (3S,5S)-3,5-diaminohexanoate, shifting a terminal amine group from the 6- to the 5-position. This enzyme also catalyzes the conversion of lysine to 2,5-diaminohexanoate and is also called lysine-5,6-aminomutase (EC 5.4.3.4). The enzyme has been crystallized in *Clostridium sticklandii* (kamD, kamE) (Berkovitch et al. *Proc. Natl. Acad. Sci. U.S.A* 101:15870-15875 (2004)). The enzyme from *Porphyromonas gingivalis* has also been characterized (Tang et al. *Biochemistry* 41:8767-8776 (2002)).

| Gene | Accession No. | GI No. | Organism |
| --- | --- | --- | --- |
| kamD | AAC79717.1 | 3928904 | *Clostridium sticklandii* |
| kamE | AAC79718.1 | 3928905 | *Clostridium sticklandii* |
| kamD | NC_002950.2 | 34539880, 34540809 | *Porphyromonas gingivalis* W83 |
| kamE | NC_002950.2 | 34539880, 34540810 | *Porphyromonas gingivalis* W83 |

Ornithine 4,5-aminomutase (EC 5.4.3.5) converts D-ornithine to 2,4-diaminopentanoate, also shifting a terminal amine to the adjacent carbon. The enzyme from *Clostridium sticklandii* is encoded by two genes, oraE and oraS, and has been cloned, sequenced and expressed in *E. coli* (Chen et al. *J. Biol. Chem.* 276:44744-44750 (2001)). This enzyme has not been characterized in other organisms to date.

| Gene | Accession No. | GI No. | Organism |
| --- | --- | --- | --- |
| oraE | AAK72502 | 17223685 | *Clostridium sticklandii* |
| oraS | AAK72501 | 17223684 | *Clostridium sticklandii* |

Tyrosine 2,3-aminomutase (EC 5.4.3.6) participates in tyrosine biosynthesis, reversibly converting tyrosine to 3-amino-3-(4-hdyroxyphenyl)propanoate by shifting an amine from the 2- to the 3-position. In *Streptomyces globisporus* the enzyme has also been shown to react with tyrosine derivatives (Christenson et al. *Biochemistry* 42:12708-12718 (2003)). Sequence information is not available.

Leucine 2,3-aminomutase (EC 5.4.3.7) converts L-leucine to beta-leucine during leucine degradation and biosynthesis. An assay for leucine 2,3-aminomutase detected activity in many organisms (Poston, J. M. *Methods Enzymol.* 166:130-135 (1988)) but genes encoding the enzyme have not been identified to date.

Cargill has developed a novel 2,3-aminomutase enzyme to convert L-alanine to β-alanine, thus creating a pathway from pyruvate to 3-HP in four biochemical steps (Liao et al., U.S. Publication No. 2005-0221466).

6.2.1.a-Acid-thiol Ligase

An exemplary acid-thiol ligase is the gene products of sucCD of *E. coli* which together catalyze the formation of succinyl-CoA from succinate with the concaminant consumption of one ATP, a reaction which is reversible in vivo (Buck et al. *Biochemistry* 24(22): p. 6245-6252 (1985)). Additional exemplary CoA-ligases include the rat dicarboxylate-CoA ligase for which the sequence is yet uncharacterized (Vamecq et al. *Biochem J.* 230(3): p. 683-693 (1985)), either of the two characterized phenylacetate-CoA ligases from *P. chrysogenum* (Lamas-Maceiras et al. *Biochem J* 395(1):147-155 (2006); Wang et al. *Biochem Biophys Res Commun,* 360(2):453-458 (2007)), the phenylacetate-CoA ligase from *Pseudomonas putida* (Martinez-Blanco et al. *J Biol Chem.* 265(12):7084-7090 (1990)), and the 6-carboxyhexanoate-CoA ligase from *Bacillus subtilis* (Bower et al. *J Bacteriol* 178(14):4122-4130 (1996)).

| Gene | Accession No. | GI No. | Organism |
| --- | --- | --- | --- |
| sucC | NP_415256.1 | 16128703 | *Escherichia coli* |
| sucD | AAC73823.1 | 1786949 | *Escherichia coli* |
| phl | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |

Example V

Exemplary BDO Pathway from Succinyl-CoA

This example describes exemplary BDO pathways from succinyl-CoA.

BDO pathways from succinyl-CoA are described herein and have been described previously (see U.S. application Ser. No. 12/049,256, filed Mar. 14, 2008, and PCT application serial No. US08/57168, filed Mar. 14, 2008, each of which is incorporated herein by reference). Additional pathways are shown in FIG. 8A. Enzymes of such exemplary BDO pathways are listed in Table 15, along with exemplary genes encoding these enzymes.

Briefly, succinyl-CoA can be converted to succinic semialdehyde by succinyl-CoA reductase (or succinate semialdehyde dehydrogenase) (EC 1.2.1.b). Succinate semialdehyde can be converted to 4-hydroxybutyrate by 4-hydroxybutyrate dehydrogenase (EC 1.1.1.a), as previously described. Alternatively, succinyl-CoA can be converted to 4-hydroxybutyrate by succinyl-CoA reductase (alcohol forming) (EC 1.1.1.c). 4-Hydroxybutyrate can be converted to 4-hydroxybutyryl-CoA by 4-hydroxybutyryl-CoA transferase (EC 2.8.3.a), as previously described, or by 4-hydroxybutyryl-CoA hydrolase (EC 3.1.2.a) or 4-hydroxybutyryl-CoA ligase (or 4-hydroxybutyryl-CoA synthetase) (EC 6.2.1.a). Alternatively, 4-hydroxybutyrate can be converted to 4-hydroxybutyryl-phosphate by 4-hydroxybutyrate kinase (EC 2.7.2.a), as previously described. 4-Hydroxybutyryl-phosphate can be converted to 4-hydroxybutyryl-CoA by phosphotrans-4-hydroxybutyrylase (EC 2.3.1.a), as previously described. Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b). Alternatively, 4-hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a), as previously described.

TABLE 15

BDO pathway from succinyl-CoA.

| FIG. | EC class | Desired substrate | Desired product | Enzyme name | Gene name | GenBank ID (if available) | Organism | Known Substrates |
|---|---|---|---|---|---|---|---|---|
| 8A | 1.2.1.b | succinyl-CoA | succinic semialdehyde | succinyl-CoA reductase (or succinate semialdehyde dehydrogenase) | sucD | P38947.1 | *Clostridium kluyveri* | succinyl-CoA |
| | | | | | sucD | NP_904963.1 | *Porphyromonas gingivalis* | succinyl-CoA |
| | | | | | Msed_0709 | YP_001190808.1 | *Metallosphaera sedula* | malonyl-CoA |
| 8A | 1.1.1.a | succinate semialdehyde | 4-hydroxybutyrate | 4-hydroxybutyrate dehydrogenase | 4hbd | YP_726053.1 | *Ralstonia eutropha* H16 | 4-hydroxybutyrate |
| | | | | | 4hbd | L21902.1 | *Clostridium kluyveri* DSM 555 | 4-hydroxybutyrate |
| | | | | | 4hbd | Q94B07 | *Arabidopsis thaliana* | 4-hydroxybutyrate |
| 8A | 1.1.1.c | succinyl-CoA | 4-hydroxybutyrate | succinyl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8A | 2.8.3.a | 4-hydroxybutyrate | 4-hydroxybutyryl-CoA | 4-hydroxybutyryl-CoA transferase | cat1, cat2, cat3 | P38946.1, P38942.2, EDK35586.1 | *Clostridium kluyveri* | succinate, 4-hydroxybutyrate, butyrate |
| | | | | | gctA, gctB | CAA57199.1, CAA57200.1 | *Acidaminococcus fermentans* | glutarate |
| | | | | | atoA, atoD | P76459.1, P76458.1 | *Escherichia coli* | butanoate |
| 8A | 3.1.2.a | 4-hydroxybutyrate | 4-hydroxybutyryl-CoA | 4-hydroxybutyryl-CoA hydrolase | tesB | NP_414986 | *Escherichia coli* | adipyl-CoA |
| | | | | | acot12 | NP_570103.1 | *Rattus norvegicus* | butyryl-CoA |
| | | | | | hibch | Q6NVY1.2 | *Homo sapiens* | 3-hydroxypropanoyl-CoA |
| 8A | 6.2.1.a | 4-hydroxybutyrate | 4-hydroxybutyryl-CoA | 4-hydroxybutyryl-CoA ligase (or 4-hydroxybutyryl-CoA synthetase) | sucCD | NP_415256.1, AAC73823.1 | *Escherichia coli* | succinate |
| | | | | | phl | CAJ15517.1 | *Penicillium chrysogenum* | phenylacetate |
| | | | | | bioW | NP_390902.2 | *Bacillus subtilis* | 6-carboxy-hexanoate |
| 8A | 2.7.2.a | 4-hydroxybutyrate | 4-hydroxybutyryl-phosphate | 4-hydroxybutyrate kinase | ackA | NP_416799.1 | *Escherichia coli* | acetate, propionate |
| | | | | | buk1 | NP_349675 | *Clostridium acetobutylicum* | butyrate |
| | | | | | buk2 | Q97II1 | *Clostridium acetobutylicum* | butyrate |

TABLE 15-continued

BDO pathway from succinyl-CoA.

| FIG. | EC class | Desired substrate | Desired product | Enzyme name | Gene name | GenBank ID (if available) | Organism | Known Substrates |
|---|---|---|---|---|---|---|---|---|
| 8A | 2.3.1.a | 4-hydroxybutyryl-phosphate | 4-hydroxybutyryl-CoA | phosphotrans-4-hydroxybutyrylase | ptb | NP_349676 | *Clostridium acetobutylicum* | butyryl-phosphate |
| | | | | | ptb | AAR19757.1 | butyrate-producing bacterium L2-50 | butyryl-phosphate |
| | | | | | ptb | CAC07932.1 | *Bacillus megaterium* | butyryl-phosphate |
| 8A | 1.2.1.d | 4-hydroxybutyryl-phosphate | 4-hydroxybutanal | 4-hydroxybutanal dehydrogenase (phosphorylating) | asd | NP_417891.1 | *Escherichia coli* | L-4-aspartyl-phosphate |
| | | | | | proA | NP_414778.1 | *Escherichia coli* | L-glutamyl-5-phospate |
| | | | | | gapA | P0A9B2.2 | *Escherichia coli* | Glyceraldehyde-3-phosphate |
| 8A | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | succinyl-CoA |
| | | | | | sucD | NP_904963.1 | *Porphyromonas gingivalis* | succinyl-CoA |
| | | | | | Msed_0709 | YP_001190808.1 | *Metallosphaera sedula* | malonyl-CoA |
| 8A | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8A | 1.1.1.a | 4-hydroxybutanal | 1,4-butanediol | 1,4-butanediol dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |

Example VI

Additional Exemplary BDO Pathways from Alpha-ketoglutarate

This example describes exemplary BDO pathways from alpha-ketoglutarate.

BDO pathways from succinyl-CoA are described herein and have been described previously (see U.S. application Ser. No. 12/049,256, filed Mar. 14, 2008, and PCT application serial No. US08/57168, filed Mar. 14, 2008, each of which is incorporated herein by reference). Additional pathways are shown in FIG. 8B. Enzymes of such exemplary BDO pathways are listed in Table 16, along with exemplary genes encoding these enzymes.

Briefly, alpha-ketoglutarate can be converted to succinic semialdehyde by alpha-ketoglutarate decarboxylase (EC 4.1.1.a), as previously described. Alternatively, alpha-ketoglutarate can be converted to glutamate by glutamate dehydrogenase (EC 1.4.1.a). 4-Aminobutyrate can be converted to succinic semialdehyde by 4-aminobutyrate oxidoreductase (deaminating) (EC 1.4.1.a) or 4-aminobutyrate transaminase (EC 2.6.1.a). Glutamate can be converted to 4-aminobutyrate by glutamate decarboxylase (EC 4.1.1.a). Succinate semialdehyde can be converted to 4-hydroxybutyrate by 4-hydroxybutyrate dehydrogenase (EC 1.1.1.a), as previously described. 4-Hydroxybutyrate can be converted to 4-hydroxybutyryl-CoA by 4-hydroxybutyryl-CoA transferase (EC 2.8.3.a), as previously described, or by 4-hydroxybutyryl-CoA hydrolase (EC 3.1.2.a), or 4-hydroxybutyryl-CoA ligase (or 4-hydroxybutyryl-CoA synthetase) (EC 6.2.1.a). 4-Hydroxybutyrate can be converted to 4-hydroxybutyryl-phosphate by 4-hydroxybutyrate kinase (EC 2.7.2.a). 4-Hydroxybutyryl-phosphate can be converted to 4-hydroxybutyryl-CoA by phosphotrans-4-hydroxybutyrylase (EC 2.3.1.a), as previously described. Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b), as previously described. 4-Hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a), as previously described.

TABLE 16

BDO pathway from alpha-ketoglutarate.

| FIG. | EC class | Desired substrate | Desired product | Enzyme name | Gene name | GenBank ID (if available) | Organism | Known Substrates |
|---|---|---|---|---|---|---|---|---|
| 8B | 4.1.1.a | alpha-ketoglutarate | succinic semialdehyde | alpha-keto-glutarate decarboxylase | kgd | O50463.4 | *Mycobacterium tuberculosis* | alpha-ketoglutarate |
| | | | | | gadA | NP_417974 | *Escherichia coli* | glutamate |
| | | | | | gadB | NP_416010 | *Escherichia coli* | glutamate |
| 8B | 1.4.1.a | alpha-ketoglutarate | glutamate | glutamate dehydrogenase | gdhA | P00370 | *Escherichia coli* | glutamate |
| | | | | | gdh | P96110.4 | *Thermotoga maritima* | glutamate |
| | | | | | gdhA1 | NP_279651.1 | *Halobacterium salinarum* | glutamate |
| 8B | 1.4.1.a | 4-aminobutyrate | succinic semialdehyde | 4-aminobutyrate oxidoreductase (deaminating) | lysDH | AB052732 | *Geobacillus stearothermophilus* | lysine |
| | | | | | lysDH | NP_147035.1 | *Aeropyrum pernix* K1 | lysine |
| | | | | | ldh | P0A393 | *Bacillus cereus* | leucine, isoleucine, valine, 2-aminobutanoate |
| 8B | 2.6.1.a | 4-aminobutyrate | succinic semialdehyde | 4-aminobutyrate transaminase | gabT | P22256.1 | *Escherichia coli* | 4-aminobutyryate |
| | | | | | puuE | NP_415818.1 | *Escherichia coli* | 4-aminobutyryate |
| | | | | | UGA1 | NP_011533.1 | *Saccharomyces cerevisiae* | 4-aminobutyryate |
| 8B | 4.1.1.a | glutamate | 4-aminobutyrate | glutamate decarboxylase | gadA | NP_417974 | *Escherichia coli* | glutamate |
| | | | | | gadB | NP_416010 | *Escherichia coli* | glutamate |
| | | | | | kgd | O50463.4 | *Mycobacterium tuberculosis* | alpha-ketoglutarate |
| 8B | 1.1.1.a | succinate semialdehyde | 4-hydroxybutyrate | 4-hydroxybutyrate dehydrogenase | 4hbd | YP_726053.1 | *Ralstonia eutropha* H16 | 4-hydroxybutyrate |
| | | | | | 4hbd | L21902.1 | *Clostridium kluyveri* DSM 555 | 4-hydroxybutyrate |
| | | | | | 4hbd | Q94B07 | *Arabidopsis thaliana* | 4-hydroxybutyrate |
| 8B | 2.8.3.a | 4-hydroxybutyrate | 4-hydroxybutyryl-CoA | 4-hydroxybutyryl-CoA transferase | cat1, cat2, cat3 | P38946.1, P38942.2, EDK35586.1 | *Clostridium kluyveri* | succinate, 4-hydroxybutyrate, butyrate |
| | | | | | gctA, gctB | CAA57199.1, CAA57200.1 | *Acidaminococcus fermentans* | glutarate |
| | | | | | atoA, atoD | P76459.1, P76458.1 | *Escherichia coli* | butanoate |
| 8B | 3.1.2.a | 4-hydroxybutyrate | 4-hydroxybutyryl-CoA | 4-hydroxybutyryl-CoA hydrolase | tesB | NP_414986 | *Escherichia coli* | adipyl-CoA |
| | | | | | acot12 | NP_570103.1 | *Rattus norvegicus* | butyryl-CoA |
| | | | | | hibch | Q6NVY1.2 | *Homo sapiens* | 3-hydroxypropanoyl-CoA |
| 8B | 6.2.1.a | 4-hydroxybutyrate | 4-hydroxybutyryl-CoA | 4-hydroxybutyryl-CoA ligase (or 4-hydroxybutyryl-CoA synthetase) | sucCD | NP_415256.1, AAC73823.1 | *Escherichia coli* | succinate |
| | | | | | phl | CAJ15517.1 | *Penicillium chrysogenum* | phenylacetate |
| | | | | | bioW | NP_390902.2 | *Bacillus subtilis* | 6-carboxyhexanoate |
| 8B | 2.7.2.a | 4-hydroxybutyrate | 4-hydroxybutyryl-phosphate | 4-hydroxybutyrate kinase | ackA | NP_416799.1 | *Escherichia coli* | acetate, propionate |
| | | | | | buk1 | NP_349675 | *Clostridium acetobutylicum* | butyrate |
| | | | | | buk2 | Q97II1 | *Clostridium acetobutylicum* | butyrate |

TABLE 16-continued

BDO pathway from alpha-ketoglutarate.

| FIG. | EC class | Desired substrate | Desired product | Enzyme name | Gene name | GenBank ID (if available) | Organism | Known Substrates |
|---|---|---|---|---|---|---|---|---|
| 8B | 2.3.1.a | 4-hydroxybutyryl-phosphate | 4-hydroxybutyryl-CoA | phosphotrans-4-hydroxybutyrylase | ptb | NP_349676 | *Clostridium acetobutylicum* | butyryl-phosphate |
| | | | | | ptb | AAR19757.1 | butyrate-producing bacterium L2-50 | butyryl-phosphate |
| | | | | | ptb | CAC07932.1 | *Bacillus megaterium* | butyryl-phosphate |
| 8B | 1.2.1.d | 4-hydroxybutyryl-phosphate | 4-hydroxybutanal | 4-hydroxybutanal dehydrogenase (phosphorylating) | asd | NP_417891.1 | *Escherichia coli* | L-4-aspartyl-phosphate |
| | | | | | proA | NP_414778.1 | *Escherichia coli* | L-glutamyl-5-phospate |
| | | | | | gapA | P0A9B2.2 | *Escherichia coli* | Glyceraldehyde-3-phosphate |
| 8B | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | succinyl-CoA |
| | | | | | sucD | NP_904963.1 | *Porphyromonas gingivalis* | succinyl-CoA |
| | | | | | Msed_0709 | YP_001190808.1 | *Metallosphaera sedula* | malonyl-CoA |
| 8B | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8B | 1.1.1.a | 4-hydroxybutanal | 1,4-butanediol | 1,4-butanediol dehydrogenase | ADH2 | NP_014032.1 | *Saccharomyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |

Example VII

BDO Pathways from 4-Aminobutyrate

This example describes exemplary BDO pathwayd from 4-aminobutyrate.

Figure 9A:
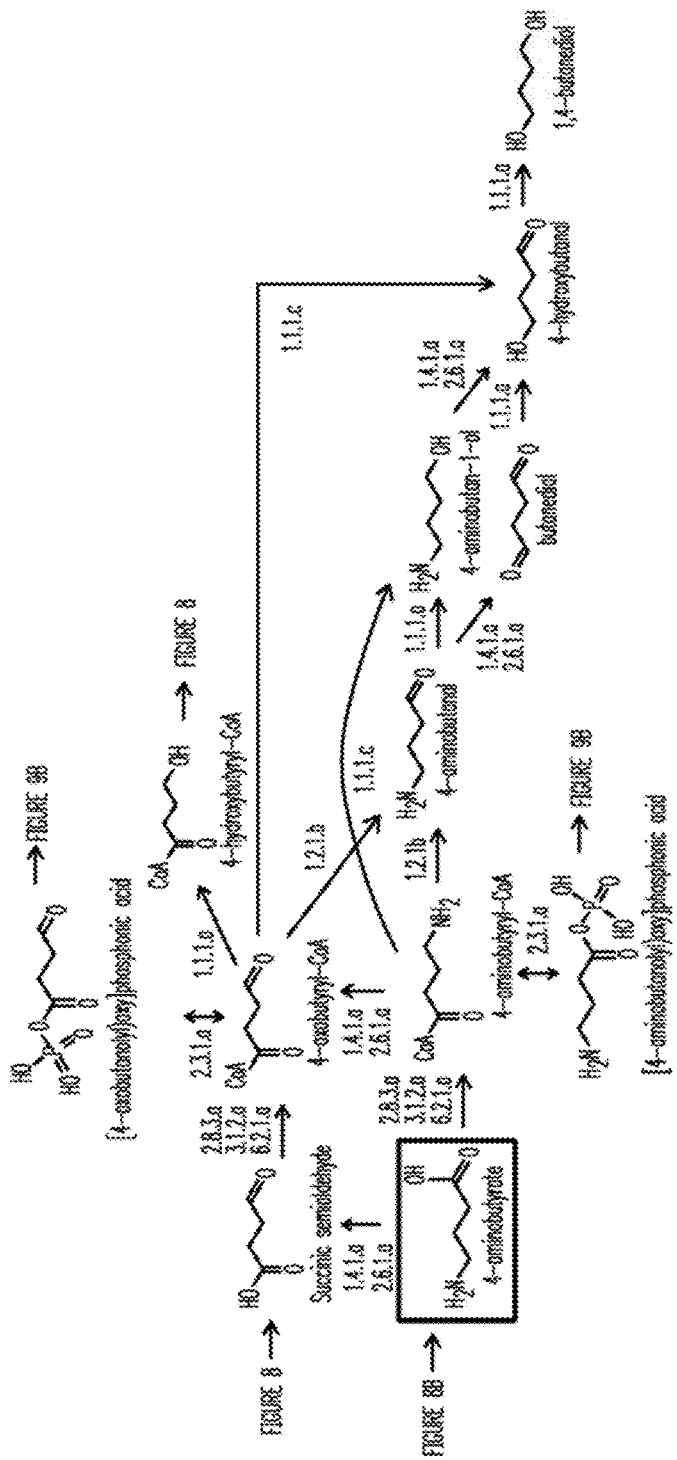

FIG. 9A depicts exemplary BDO pathways in which 4-aminobutyrate is converted to BDO. Enzymes of such an exemplary BDO pathway are listed in Table 17, along with exemplary genes encoding these enzymes.

Briefly, 4-aminobutyrate can be converted to 4-aminobutyryl-CoA by 4-aminobutyrate CoA transferase (EC 2.8.3.a), 4-aminobutyryl-CoA hydrolase (EC 3.1.2.a), or 4-aminobutyrate-CoA ligase (or 4-aminobutyryl-CoA synthetase) (EC 6.2.1.a). 4-aminobutyryl-CoA can be converted to 4-oxobutyryl-CoA by 4-aminobutyryl-CoA oxidoreductase (deaminating) (EC 1.4.1.a) or 4-aminobutyryl-CoA transaminase (EC 2.6.1.a). 4-oxobutyryl-CoA can be converted to 4-hydroxybutyryl-CoA by 4-hydroxybutyryl-CoA dehydrogenase (EC 1.1.1.a). 4-hydroxybutyryl-CoA can be converted to 1,4-butanediol by 4-hydroxybutyryl-CoA reductase (alcohol forming) (EC 1.1.1.c). Alternatively, 4-hydroxybutyryl-CoA can be converted to 4-hydroxybutanal by 4-hydroxybutyryl-CoA reductase (or 4-hydroxybutanal dehydrogenase) (EC 1.2.1.b). 4-hydroxybutanal can be converted to 1,4-butanediol by 1,4-butanediol dehydrogenase (EC 1.1.1.a).

TABLE 17

BDO pathway from 4-aminobutyrate.

| FIG. | EC class | Desired substrate | Desired product | Enzyme name | Gene name | GenBank ID (if available) | Organism | Known Substrates |
|---|---|---|---|---|---|---|---|---|
| 9A | 2.8.3.a | 4-aminobutyrate | 4-aminobutyryl-CoA | 4-aminobutyrate CoA transferase | cat1, cat2, cat3 | P38946.1, P38942.2, EDK35586.1 | *Clostridium kluyveri* | succinate, 4-hydroxybutyrate, butyrate |
| | | | | | gctA, gctB | CAA57199.1, CAA57200.1 | *Acidaminococcus fermentans* | glutarate |
| | | | | | atoA, atoD | P76459.1, P76458.1 | *Escherichia coli* | butanoate |

TABLE 17-continued

BDO pathway from 4-aminobutyrate.

| FIG. | EC class | Desired substrate | Desired product | Enzyme name | Gene name | GenBank ID (if available) | Organism | Known Substrates |
|---|---|---|---|---|---|---|---|---|
| 9A | 3.1.2.a | 4-aminobutyrate | 4-aminobutyryl-CoA | 4-aminobutyryl-CoA hydrolase | tesB | NP_414986 | *Escherichia coli* | adipyl-CoA |
| | | | | | acot12 | NP_570103.1 | *Rattus norvegicus* | butyryl-CoA |
| | | | | | hibch | Q6NVY1.2 | *Homo sapiens* | 3-hydroxypropanoyl-CoA |
| 9A | 6.2.1.a | 4-aminobutyrate | 4-aminobutyryl-CoA | 4-aminobutyrate-CoA ligase (or 4-aminobutyryl-CoA synthetase) | sucCD | NP_415256.1, AAC73823.1 | *Escherichia coli* | succinate |
| | | | | | phl | CAJ15517.1 | *Penicillium chrysogenum* | phenylacetate |
| | | | | | bioW | NP_390902.2 | *Bacillus subtilis* | 6-carboxyhexanoate |
| 9A | 1.4.1.a | 4-aminobutyryl-CoA | 4-oxobutyryl-CoA | 4-aminobutyryl-CoA oxidoreductase (deaminating) | lysDH | AB052732 | *Geobacillus stearothermophilus* | lysine |
| | | | | | lysDH | NP_147035.1 | *Aeropyrum pernix* K1 | lysine |
| | | | | | ldh | P0A393 | *Bacillus cereus* | leucine, isoleucine, valine, 2-aminobutanoate |
| 9A | 2.6.1.a | 4-aminobutyryl-CoA | 4-oxobutyryl-CoA | 4-aminobutyryl-CoA transaminase | gabT | P22256.1 | *Escherichia coli* | 4-aminobutyryate |
| | | | | | abat | P50554.3 | *Rattus norvegicus* | 3-amino-2-methylpropionate |
| | | | | | SkyPYD4 | ABF58893.1 | *Saccharomyces kluyveri* | beta-alanine |
| 9A | 1.1.1.a | 4-oxobutyryl-CoA | 4-hydroxybutyryl-CoA | 4-hydroxybutyryl-CoA dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |
| 8 | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8 | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | Succinyl-CoA |
| | | | | | sucD | NP_904963.1 | *Porphyromonas gingivalis* | Succinyl-CoA |
| | | | | | Msed_0709 | YP_001190808.1 | *Metallosphaera sedula* | Malonyl-CoA |
| 8 | 1.1.1.a | 4-hydroxybutanal | 1,4-butanediol | 1,4-butanediol dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |

Enzymes for another exemplary BDO pathway converting 4-aminobutyrate to BDO is shown in FIG. 9A. Enzymes of such an exemplary BDO pathway are listed in Table 18, along with exemplary genes encoding these enzymes.

Briefly, 4-aminobutyrate can be converted to 4-aminobutyryl-CoA by 4-aminobutyrate CoA transferase (EC 2.8.3.a), 4-aminobutyryl-CoA hydrolase (EC 3.1.2.a) or 4-aminobutyrate-CoA ligase (or 4-aminobutyryl-CoA synthetase) (EC 6.2.1.a). 4-aminobutyryl-CoA can be converted to 4-aminobutan-1-ol by 4-aminobutyryl-CoA reductase (alcohol forming) (EC 1.1.1.c). Alternatively, 4-aminobutyryl-CoA can be converted to 4-aminobutanal by 4-aminobutyryl-CoA reductase (or 4-aminobutanal dehydrogenase) (EC 1.2.1.b), and 4-aminobutanal converted to 4-aminobutan-1-ol by 4-aminobutan-1-ol dehydrogenase (EC 1.1.1.a). 4-aminobutan-1-ol can be converted to 4-hydroxybutanal by 4-aminobutan-1-ol oxidoreductase (deaminating) (EC 1.4.1.a) or 4-aminobutan-1-ol transaminase (EC 2.6.1.a). 4-hydroxybutanal can be converted to 1,4-butanediol by 1,4-butanediol dehydrogenase (EC 1.1.1.a).

TABLE 18

BDO pathway from 4-aminobutyrate.

| FIG. | EC class | Desired substrate | Desired product | Enzyme name | Gene name | GenBank ID (if available) | Organism | Known Substrate |
|---|---|---|---|---|---|---|---|---|
| 9A | 2.8.3.a | 4-aminobutyrate | 4-aminobutyryl-CoA | 4-aminobutyrate CoA transferase | cat1, cat2, cat3 | P38946.1, P38942.2, EDK35586.1 | Clostridium kluyveri | succinate, 4-hydroxybutyrate, butyrate |
| | | | | | gctA, gctB | CAA57199.1, CAA57200.1 | Acidaminococcus fermentans | glutarate |
| | | | | | atoA, atoD | P76459.1, P76458.1 | Escherichia coli | butanoate |
| 9A | 3.1.2.a | 4-aminobutyrate | 4-aminobutyryl-CoA | 4-aminobutyryl-CoA hydrolase | tesB | NP_414986 | Escherichia coli | adipyl-CoA |
| | | | | | acot12 | NP_570103.1 | Rattus norvegicus | butyryl-CoA |
| | | | | | hibch | Q6NVY1.2 | Homo sapiens | 3-hydroxypropanoyl-CoA |
| 9A | 6.2.1.a | 4-aminobutyrate | 4-aminobutyryl-CoA | 4-aminobutyrate-CoA ligase (or 4-aminobutyryl-CoA synthetase) | sucCD | NP_415256.1, AAC73823.1 | Escherichia coli | succinate |
| | | | | | phl | CAJ15517.1 | Penicillium chrysogenum | phenylacetate |
| | | | | | bioW | NP_390902.2 | Bacillus subtilis | 6-carboxyhexanoate |
| 9A | 1.1.1.c | 4-aminobutyryl-CoA | 4-aminobutan-1-ol | 4-aminobutyryl-CoA reductase (alcohol forming) | adhE2 | AAK09379.1 | Clostridium acetobutylicum | butanoyl-CoA |
| | | | | | mcr | AAS20429.1 | Chloroflexus aurantiacus | malonyl-CoA |
| | | | | | FAR | AAD38039.1 | Simmondsia chinensis | long chain acyl-CoA |
| 9A | 1.2.1.b | 4-aminobutyryl-CoA | 4-aminobutanal | 4-aminobutyryl-CoA reductase (or 4-aminobutanal dehydrogenase) | sucD | P38947.1 | Clostridium kluyveri | Succinyl-CoA |
| | | | | | sucD | NP_904963.1 | Porphyromonas gingivalis | Succinyl-CoA |
| | | | | | Msed_0709 | YP_001190808.1 | Metallosphaera sedula | Malonyl-CoA |
| 9A | 1.1.1.a | 4-aminobutanal | 4-aminobutan-1-ol | 4-aminobutan-1-ol dehydrogenase | ADH2 | NP_014032.1 | Saccharymyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |
| 9A | 1.4.1.a | 4-aminobutan-1-ol | 4-hydroxybutanal | 4-aminobutan-1-ol oxidoreductase (deaminating) | lysDH | AB052732 | Geobacillus stearothermophilus | lysine |
| | | | | | lysDH | NP_147035.1 | Aeropyrum pernix K1 | lysine |
| | | | | | ldh | P0A393 | Bacillus cereus | leucine, isoleucine, valine, 2-aminobutanoate |
| 9A | 2.6.1.a | 4-aminobutan-1-ol | 4-hydroxybutanal | 4-aminobutan-1-ol transaminase | gabT | P22256.1 | Escherichia coli | 4-aminobutyryate |
| | | | | | abat | P50554.3 | Rattus norvegicus | 3-amino-2-methylpropionate |
| | | | | | SkyPYD4 | ABF58893.1 | Saccharomyces kluyveri | beta-alanine |
| 9A | 1.1.1.a | 4-hydroxybutanal | 1,4-butanediol | 1,4-butanediol dehydrogenase | ADH2 | NP_014032.1 | Saccharymyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |

FIG. 9B depicts exemplary BDO pathway in which 4-aminobutyrate is converted to BDO. Enzymes of such an exemplary BDO pathway are listed in Table 19, along with exemplary genes encoding these enzymes.

Briefly, 4-aminobutyrate can be converted to [(4-aminobutanolyl)oxy] phosphonic acid by 4-aminobutyrate kinase (EC 2.7.2.a). [(4-aminobutanolyl)oxy] phosphonic acid can be converted to 4-aminobutanal by 4-aminobutyraldehyde dehydrogenase (phosphorylating) (EC 1.2.1.d). 4-aminobutanal can be converted to 4-aminobutan-1-ol by 4-aminobutan-1-ol dehydrogenase (EC 1.1.1.a). 4-aminobutan-1-ol can be converted to 4-hydroxybutanal by 4-aminobutan-1-ol oxidoreductase (deaminating) (EC 1.4.1.a) or 4-aminobutan-1-ol transaminase (EC 2.6.1.a). Alternatively,

[(4-aminobutanolyl)oxy] phosphonic acid can be converted to [(4-oxobutanolyl)oxy]phosphonic acid by [(4-aminobutanolyl)oxy]phosphonic acid oxidoreductase (deaminating) (EC 1.4.1.a) or [(4-aminobutanolyl)oxy]phosphonic acid transaminase (EC 2.6.1.a). [(4-oxobutanolyl)oxy] phosphonic acid can be converted to 4-hydroxybutyryl-phosphate by 4-hydroxybutyryl-phosphate dehydrogenase (EC 1.1.1.a). 4-hydroxybutyryl-phosphate can be converted to 4-hydroxybutanal by 4-hydroxybutyraldehyde dehydrogenase (phosphorylating) (EC 1.2.1.d). 4-hydroxybutanal can be converted to 1,4-butanediol by 1,4-butanediol dehydrogenase (EC 1.1.1.a).

TABLE 19

BDO pathway from 4-aminobutyrate.

| FIG. | EC class | Desired substrate | Desired product | Enzyme name | Gene name | GenBank ID (if available) | Organism | Known Substrate |
|---|---|---|---|---|---|---|---|---|
| 9B | 2.7.2.a | 4-aminobutyrate | [(4-aminobutanolyl)oxy] phosphonic acid | 4-aminobutyrate kinase | ackA | NP_416799.1 | Escherichia coli | acetate, propionate |
| | | | | | buk1 | NP_349675 | Clostridium acetobutylicum | butyrate |
| | | | | | proB | NP_414777.1 | Escherichia coli | glutamate |
| 9B | 1.2.1.d | [(4-aminobutanolyl)oxy] phosphonic acid | 4-aminobutanal | 4-aminobutyraldehyde dehydrogenase (phosphorylating) | asd | NP_417891.1 | Escherichia coli | L-4-aspartyl-phosphate |
| | | | | | proA | NP_414778.1 | Escherichia coli | L-glutamyl-5-phospate |
| | | | | | gapA | P0A9B2.2 | Escherichia coli | Glyceraldehyde-3-phosphate |
| 9B | 1.1.1.a | 4-aminobutanal | 4-aminobutan-1-ol | 4-aminobutan-1-ol dehydrogenase | ADH2 | NP_014032.1 | Saccharymyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |
| 9B | 1.4.1.a | 4-aminobutan-1-ol | 4-hydroxybutanal | 4-aminobutan-1-ol oxidoreductase (deaminating) | lysDH | AB052732 | Geobacillus stearothermophilus | lysine |
| | | | | | lysDH | NP_147035.1 | Aeropyrum pernix K1 | lysine |
| | | | | | ldh | P0A393 | Bacillus cereus | leucine, isoleucine, valine, 2-aminobutanoate |
| 9B | 2.6.1.a | 4-aminobutan-1-ol | 4-hydroxybutanal | 4-aminobutan-1-ol transaminase | gabT | P22256.1 | Escherichia coli | 4-aminobutyryate |
| | | | | | abat | P50554.3 | Rattus norvegicus | 3-amino-2-methylpropionate |
| | | | | | SkyPYD4 | ABF58893.1 | Saccharomyces kluyveri | beta-alanine |
| 9B | 1.4.1.a | [(4-aminobutanolyl)oxy] phosphonic acid | [(4-oxobutanolyl)oxy] phosphonic acid | [(4-aminobutanolyl)oxy]phosphonic acid oxidoreductase (deaminating) | lysDH | AB052732 | Geobacillus stearothermophilus | lysine |
| | | | | | lysDH | NP_147035.1 | Aeropyrum pernix K1 | lysine |
| | | | | | ldh | P0A393 | Bacillus cereus | leucine, isoleucine, valine, 2-aminobutanoate |
| 9B | 2.6.1.a | [(4-aminobutanolyl)oxy] phosphonic acid | [(4-oxobutanolyl)oxy] phosphonic acid | [(4-aminobutanolyl)oxy]phosphonic acid transaminase | gabT | P22256.1 | Escherichia coli | 4-aminobutyryate |
| | | | | | SkyPYD4 | ABF58893.1 | Saccharomyces kluyveri | beta-alanine |
| | | | | | serC | NP_415427.1 | Escherichia coli | phosphoserine, phosphohydroxythreonine |

TABLE 19-continued

BDO pathway from 4-aminobutyrate.

| FIG. | EC class | Desired substrate | Desired product | Enzyme name | Gene name | GenBank ID (if available) | Organism | Known Substrate |
|---|---|---|---|---|---|---|---|---|
| 9B | 1.1.1.a | [(4-oxobutanolyl)oxy] phosphonic acid | 4-hydroxybutyryl-phosphate | 4-hydroxybutyryl-phosphate dehydrogenase | ADH2 | NP_014032.1 | Saccharymyces cerevisiae | general |
|  |  |  |  |  | yqhD | NP_417484.1 | Escherichia coli | >C3 |
|  |  |  |  |  | 4hbd | L21902.1 | Clostridium kluyveri DSM 555 | Succinate semialdehyde |
| 9B | 1.2.1.d | 4-hydroxybutyryl-phosphate | 4-hydroxybutanal | 4-hydroxybutyraldehyde dehydrogenase (phosphorylating) | asd | NP_417891.1 | Escherichia coli | L-4-aspartyl-phosphate |
|  |  |  |  |  | proA | NP_414778.1 | Escherichia coli | L-glutamyl-5-phospate |
|  |  |  |  |  | gapA | P0A9B2.2 | Escherichia coli | Glyceraldehyde-3-phosphate |
| 9B | 1.1.1.a | 4-hydroxybutanal | 1,4-butanediol | 1,4-butanediol dehydrogenase | ADH2 | NP_014032.1 | Saccharymyces cerevisiae | general |
|  |  |  |  |  | yqhD | NP_417484.1 | Escherichia coli | >C3 |
|  |  |  |  |  | 4hbd | L21902.1 | Clostridium kluyveri DSM 555 | Succinate semialdehyde |

FIG. 9C shows an exemplary pathway through acetoacetate.

Example VIII

Exemplary BDO Pathways from Alpha-ketoglutarate

This example describes exemplary BDO pathways from alpha-ketoglutarate.

Figure 10:
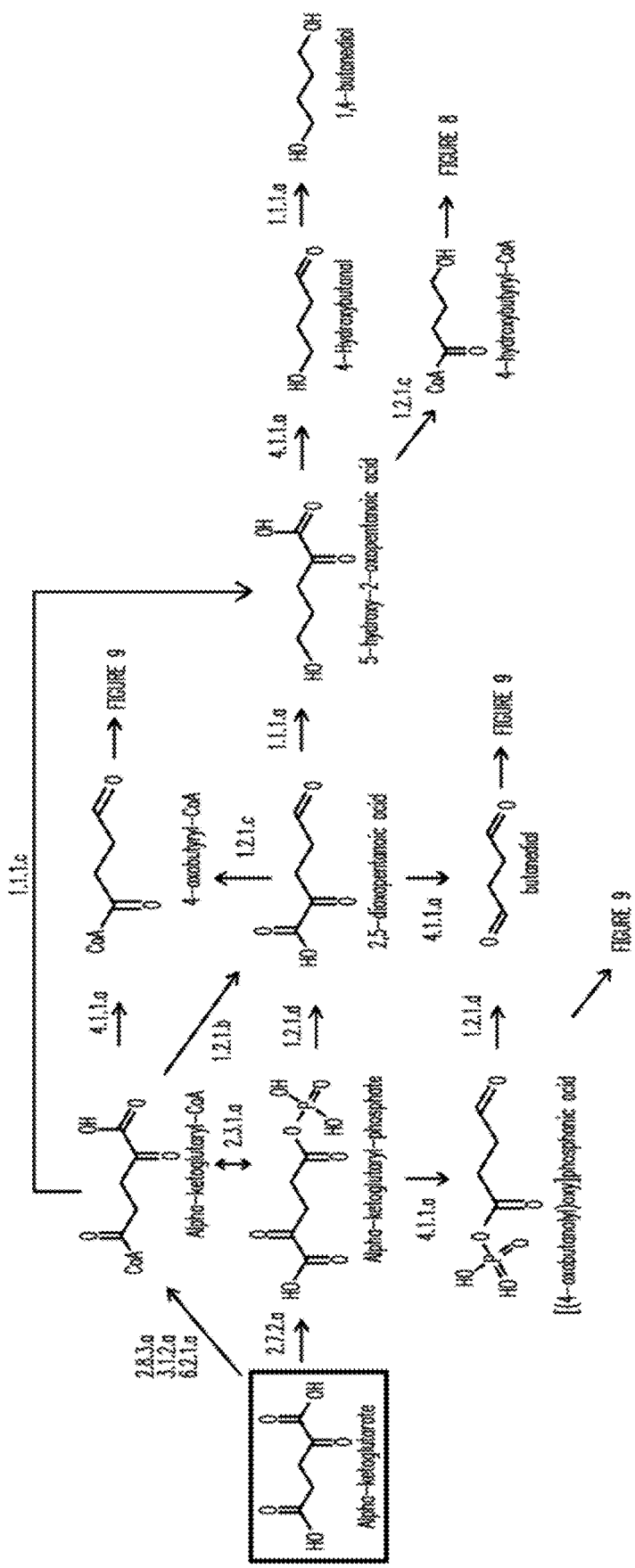
FIG. 10 shows exemplary BDO pathways from alpha-ketoglutarate.

FIG. 10 depicts exemplary BDO pathways in which alpha-ketoglutarate is converted to BDO. Enzymes of such an exemplary BDO pathway are listed in Table 20, along with exemplary genes encoding these enzymes.

Briefly, alpha-ketoglutarate can be converted to alpha-ketoglutaryl-phosphate by alpha-ketoglutarate 5-kinase (EC 2.7.2.a). Alpha-ketoglutaryl-phosphate can be converted to 2,5-dioxopentanoic acid by 2,5-dioxopentanoic semialdehyde dehydrogenase (phosphorylating) (EC 1.2.1.d). 2,5-dioxopentanoic acid can be converted to 5-hydroxy-2-oxopentanoic acid by 2,5-dioxopentanoic acid reductase (EC 1.1.1.a). Alternatively, alpha-ketoglutarate can be converted to alpha-ketoglutaryl-CoA by alpha-ketoglutarate CoA transferase (EC 2.8.3.a), alpha-ketoglutaryl-CoA hydrolase (EC 3.1.2.a) or alpha-ketoglutaryl-CoA ligase (or alpha-ketoglutaryl-CoA synthetase) (EC 6.2.1.a). Alpha-ketoglutaryl-CoA can be converted to 2,5-dioxopentanoic acid by alpha-ketoglutaryl-CoA reductase (or 2,5-dioxopentanoic acid dehydrogenase) (EC 1.2.1.b). 2,5-Dioxopentanoic acid can be converted to 5-hydroxy-2-oxopentanoic acid by 5-hydroxy-2-oxopentanoic acid dehydrogenase. Alternatively, alpha-ketoglutaryl-CoA can be converted to 5-hydroxy-2-oxopentanoic acid by alpha-ketoglutaryl-CoA reductase (alcohol forming) (EC 1.1.1.c). 5-hydroxy-2-oxopentanoic acid can be converted to 4-hydroxybutanal by 5-hydroxy-2-oxopentanoic acid decarboxylase (EC 4.1.1.a). 4-hydroxybutanal can be converted to 1,4-butanediol by 1,4-butanediol dehydrogenase (EC 1.1.1.a). 5-hydroxy-2-oxopentanoic acid can be converted to 4-hydroxybutyryl-CoA by 5-hydroxy-2-oxopentanoic acid dehydrogenase (decarboxylation) (EC 1.2.1.c).

TABLE 20

BDO pathway from alpha-ketoglutarate.

| FIG. | EC class | Desired substrate | Desired product | Enzyme name | Gene name | GenBank ID (if available) | Organism | Known Substrate |
|---|---|---|---|---|---|---|---|---|
| 10 | 2.7.2.a | alpha-ketoglutarate | alpha-ketoglutaryl-phosphate | alpha-ketoglutarate 5-kinase | ackA | NP_416799.1 | Escherichia coli | acetate, propionate |
|  |  |  |  |  | buk1 | NP_349675 | Clostridium acetobutylicum | butyrate |
|  |  |  |  |  | proB | NP_414777.1 | Escherichia coli | glutamate |
| 10 | 1.2.1.d | alpha-ketoglutaryl-phosphate | 2,5-dioxopentanoic acid | 2,5-dioxopentanoic semialdehyde dehydrogenase (phosphorylating) | proA | NP_414778.1 | Escherichia coli | L-glutamyl-5-phospate |
|  |  |  |  |  | asd | NP_417891.1 | Escherichia coli | L-4-aspartyl-phosphate |
|  |  |  |  |  | gapA | P0A9B2.2 | Escherichia coli | Glyceraldehyde-3-phosphate |

TABLE 20-continued

BDO pathway from alpha-ketoglutarate.

| FIG. | EC class | Desired substrate | Desired product | Enzyme name | Gene name | GenBank ID (if available) | Organism | Known Substrate |
|---|---|---|---|---|---|---|---|---|
| 10 | 1.1.1.a | 2,5-dioxopentanoic acid | 5-hydroxy-2-oxopentanoic acid | 2,5-dioxopentanoic acid reductase | ADH2 | NP_014032.1 | Saccharymyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |
| 10 | 2.8.3.a | alpha-ketoglutarate | alpha-ketoglutaryl-CoA | alpha-ketoglutarate CoA transferase | cat1, cat2, cat3 | P38946.1, P38942.2, EDK35586.1 | Clostridium kluyveri | succinate, 4-hydroxybutyrate, butyrate |
| | | | | | gctA, gctB | CAA57199.1, CAA57200.1 | Acidaminococcus fermentans | glutarate |
| | | | | | atoA, atoD | P76459.1, P76458.1 | Escherichia coli | butanoate |
| 10 | 3.1.2.a | alpha-ketoglutarate | alpha-ketoglutaryl-CoA | alpha-ketoglutaryl-CoA hydrolase | tesB | NP_414986 | Escherichia coli | adipyl-CoA |
| | | | | | acot12 | NP_570103.1 | Rattus norvegicus | butyryl-CoA |
| | | | | | hibch | Q6NVY1.2 | Homo sapiens | 3-hydroxypropanoyl-CoA |
| 10 | 6.2.1.a | alpha-ketoglutarate | alpha-ketoglutaryl-CoA | alpha-ketoglutaryl-CoA ligase (or alpha-ketoglutaryl-CoA synthetase) | sucCD | NP_415256.1, AAC73823.1 | Escherichia coli | succinate |
| | | | | | phl | CAJ15517.1 | Penicillium chrysogenum | phenylacetate |
| | | | | | bioW | NP_390902.2 | Bacillus subtilis | 6-carboxyhexanoate |
| 10 | 1.2.1.b | alpha-ketoglutaryl-CoA | 2,5-dioxopentanoic acid | alpha-ketoglutaryl-CoA reductase (or 2,5-dioxopentanoic acid dehydrogenase) | sucD | P38947.1 | Clostridium kluyveri | Succinyl-CoA |
| | | | | | Msed_0709 | YP_001190808.1 | Metallosphaera sedula | Malonyl-CoA |
| | | | | | bphG | BAA03892.1 | Pseudomonas sp | Acetaldehyde, Propionaldehyde, Butyraldehyde, Isobutyraldehyde and Formaldehyde |
| 10 | 1.1.1.a | 2,5-dioxopentanoic acid | 5-hydroxy-2-oxopentanoic acid | 5-hydroxy-2-oxopentanoic acid dehydrogenase | ADH2 | NP_014032.1 | Saccharymyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |
| 10 | 1.1.1.c | alpha-ketoglutaryl-CoA | 5-hydroxy-2-oxopentanoic acid | alpha-ketoglutaryl-CoA reductase (alcohol forming) | adhE2 | AAK09379.1 | Clostridium acetobutylicum | butanoyl-CoA |
| | | | | | mcr | AAS20429.1 | Chloroflexus aurantiacus | malonyl-CoA |
| | | | | | FAR | AAD38039.1 | Simmondsia chinensis | long chain acyl-CoA |
| 10 | 4.1.1.a | 5-hydroxy-2-oxopentanoic acid | 4-hydroxybutanal | 5-hydroxy-2-oxopentanoic acid decarboxylase | pdc | P06672.1 | Zymomonas mobilus | 2-oxopentanoic acid |
| | | | | | mdlC | P20906.2 | Pseudomonas putida | 2-oxopentanoic acid |
| | | | | | pdc1 | P06169 | Saccharomyces cerevisiae | pyruvate |
| 10 | 1.1.1.a | 4-hydroxybutanal | 1,4-butanediol | 1,4-butanediol dehydrogenase | ADH2 | NP_014032.1 | Saccharymyces cerevisiae | general |
| | | | | | yqhD | NP_417484.1 | Escherichia coli | >C3 |
| | | | | | 4hbd | L21902.1 | Clostridium kluyveri DSM 555 | Succinate semialdehyde |

TABLE 20-continued

BDO pathway from alpha-ketoglutarate.

| FIG. | EC class | Desired substrate | Desired product | Enzyme name | Gene name | GenBank ID (if available) | Organism | Known Substrate |
|---|---|---|---|---|---|---|---|---|
| 10 | 1.2.1.c | 5-hydroxy-2-oxopentanoic acid | 4-hydroxybutyryl-CoA | 5-hydroxy-2-oxopentanoic acid dehydrogenase (decarboxylation) | sucA, sucB, lpd | NP_415254.1, NP_415255.1, NP_414658.1 | *Escherichia coli* | Alpha-ketoglutarate |
|  |  |  |  |  | bfmBB, bfmBAA, bfmBAB, bfmBAB, pdhD | NP_390283.1, NP_390285.1, NP_390284.1, P21880.1 | *Bacillus subtilis* | 2-keto acids derivatives of valine, leucine and isoleucine |
|  |  |  |  |  | Bckdha, Bckdhb, Dbt, Dld | NP_036914.1, NP_062140.1, NP_445764.1, NP_955417.1 | *Rattus norvegicus* | 2-keto acids derivatives of valine, leucine and isoleucine |

Example IX

Exemplary BDO Pathways from Glutamate

This example describes exemplary BDO pathways from glutamate.

FIG. 11 depicts exemplary BDO pathways in which glutamate is converted to BDO. Enzymes of such an exemplary BDO pathway are listed in Table 21, along with exemplary genes encoding these enzymes.

Briefly, glutamate can be converted to glutamyl-CoA by glutamate CoA transferase (EC 2.8.3.a), glutamyl-CoA hydrolase (EC 3.1.2.a) or glutamyl-CoA ligase (or glutamyl-CoA synthetase) (EC 6.2.1.a). Alternatively, glutamate can be converted to glutamate-5-phosphate by glutamate 5-kinase (EC 2.7.2.a). Glutamate-5-phosphate can be converted to glutamate-5-semialdehyde by glutamate-5-semialdehyde dehydrogenase (phosphorylating) (EC 1.2.1.d). Glutamyl-CoA can be converted to glutamate-5-semialdehyde by glutamyl-CoA reductase (or glutamate-5-semialdehyde dehydrogenase) (EC 1.2.1.b). Glutamate-5-semialdehyde can be converted to 2-amino-5-hydroxypentanoic acid by glutamate-5-semialdehyde reductase (EC 1.1.1.a). Alternatively, glutamyl-CoA can be converted to 2-amino-5-hydroxypentanoic acid by glutamyl-CoA reductase (alcohol forming) (EC 1.1.1.c). 2-Amino-5-hydroxypentanoic acid can be converted to 5-hydroxy-2-oxopentanoic acid by 2-amino-5-hydroxypentanoic acid oxidoreductase (deaminating) (EC 1.4.1.a) or 2-amino-5-hydroxypentanoic acid transaminase (EC 2.6.1.a). 5-Hydroxy-2-oxopentanoic acid can be converted to 4-hydroxybutanal by 5-hydroxy-2-oxopentanoic acid decarboxylase (EC 4.1.1.a). 4-Hydroxybutanal can be converted to 1,4-butanediol by 1,4-butanediol dehydrogenase (EC 1.1.1.a). Alternatively, 5-hydroxy-2-oxopentanoic acid can be converted to 4-hydroxybutyryl-CoA by 5-hydroxy-2-oxopentanoic acid dehydrogenase (decarboxylation) (EC 1.2.1.c).

TABLE 21

BDO pathway from glutamate.

| FIG. | EC class | Desired substrate | Desired product | Enzyme name | Gene name | GenBank ID (if available) | Organism | Known Substrate |
|---|---|---|---|---|---|---|---|---|
| 11 | 2.8.3.a | glutamate | glutamyl-CoA | glutamate CoA transferase | cat1, cat2, cat3 | P38946.1, P38942.2, EDK35586.1 | *Clostridium kluyveri* | succinate, 4-hydroxybutyrate, butyrate |
|  |  |  |  |  | gctA, gctB | CAA57199.1, CAA57200.1 | *Acidaminococcus fermentans* | glutarate |
|  |  |  |  |  | atoA, atoD | P76459.1, P76458.1 | *Escherichia coli* | butanoate |
| 11 | 3.1.2.a | glutamate | glutamyl-CoA | glutamyl-CoA hydrolase | tesB | NP_414986 | *Escherichia coli* | adipyl-CoA |
|  |  |  |  |  | acot12 | NP_570103.1 | *Rattus norvegicus* | butyryl-CoA |
|  |  |  |  |  | hibch | Q6NVY1.2 | *Homo sapiens* | 3-hydroxypropanoyl-CoA |
| 11 | 6.2.1.a | glutamate | glutamyl-CoA | glutamyl-CoA ligase (or glutamyl-CoA synthetase) | sucCD | NP_415256.1, AAC73823.1 | *Escherichia coli* | succinate |
|  |  |  |  |  | phl | CAJ15517.1 | *Penicillium chrysogenum* | phenylacetate |
|  |  |  |  |  | bioW | NP_390902.2 | *Bacillus subtilis* | 6-carboxyhexanoate |
| 11 | 2.7.2.a | glutamate | glutamate-5-phosphate | glutamate 5-kinase | ackA | NP_416799.1 | *Escherichia coli* | acetate, propionate |
|  |  |  |  |  | buk1 | NP_349675 | *Clostridium acetobutylicum* | butyrate |
|  |  |  |  |  | proB | NP_414777.1 | *Escherichia coli* | glutamate |

TABLE 21-continued

BDO pathway from glutamate.

| FIG. | EC class | Desired substrate | Desired product | Enzyme name | Gene name | GenBank ID (if available) | Organism | Known Substrate |
|---|---|---|---|---|---|---|---|---|
| 11 | 1.2.1.d | glutamate-5-phosphate | glutamate-5-semialdehyde | glutamate-5-semialdehyde dehydrogenase (phosphorylating) | proA | NP_414778.1 | *Escherichia coli* | L-glutamyl-5-phospate |
| | | | | | asd | NP_417891.1 | *Escherichia coli* | L-4-aspartyl-phosphate |
| | | | | | gapA | P0A9B2.2 | *Escherichia coli* | Glyceraldehyde-3-phosphate |
| 11 | 1.2.1.b | glutamyl-CoA | glutamate-5-semialdehyde | glutamyl-CoA reductase (or glutamate-5-semialdehyde dehydrogenase) | sucD | P38947.1 | *Clostridium kluyveri* | Succinyl-CoA |
| | | | | | Msed_0709 | YP_001190808.1 | *Metallosphaera sedula* | Malonyl-CoA |
| | | | | | bphG | BAA03892.1 | *Pseudomonas* sp | Acetaldehyde, Propionaldehyde, Butyraldehyde, Isobutyraldehyde and Formaldehyde |
| 11 | 1.1.1.a | glutamate-5-semialdehyde | 2-amino-5-hydroxypentanoic acid | glutamate-5-semialdehyde reductase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |
| 11 | 1.1.1.c | glutamyl-CoA | 2-amino-5-hydroxypentanoic acid | glutamyl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 11 | 1.4.1.a | 2-amino-5-hydroxypentanoic acid | 5-hydroxy-2-oxopentanoic acid | 2-amino-5-hydroxypentanoic acid oxidoreductase (deaminating) | gdhA | P00370 | *Escherichia coli* | glutamate |
| | | | | | ldh | P0A393 | *Bacillus cereus* | leucine, isoleucine, valine, 2-aminobutanoate |
| | | | | | nadX | NP_229443.1 | *Thermotoga maritima* | aspartate |
| 11 | 2.6.1.a | 2-amino-5-hydroxypentanoic acid | 5-hydroxy-2-oxopentanoic acid | 2-amino-5-hydroxypentanoic acid transaminase | aspC | NP_415448.1 | *Escherichia coli* | aspartate |
| | | | | | AAT2 | P23542.3 | *Saccharomyces cerevisiae* | aspartate |
| | | | | | avtA | YP_026231.1 | *Escherichia coli* | valine, alpha-aminobutyrate |
| 11 | 4.1.1.a | 5-hydroxy-2-oxopentanoic acid | 4-hydroxybutanal | 5-hydroxy-2-oxopentanoic acid decarboxylase | pdc | P06672.1 | *Zymomonas mobilus* | 2-oxopentanoic acid |
| | | | | | mdlC | P20906.2 | *Pseudomonas putida* | 2-oxopentanoic acid |
| | | | | | pdc1 | P06169 | *Saccharomyces cerevisiae* | pyruvate |
| 11 | 1.1.1.a | 4-hydroxybutanal | 1,4-butanediol | 1,4-butanediol dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |
| 11 | 1.2.1.c | 5-hydroxy-2-oxopentanoic acid | 4-hydroxybutyryl-CoA | 5-hydroxy-2-oxopentanoic acid dehydrogenase (decarboxylation) | sucA, sucB, lpd | NP_415254.1, NP_415255.1, NP_414658.1 | *Escherichia coli* | Alpha-ketoglutarate |
| | | | | | bfmBB, bfmBAA, bfmBAB, bfmBAB, pdhD | NP_390283.1, NP_390285.1, NP_390284.1, P21880.1 | *Bacillus subtilis* | 2-keto acids derivatives of valine, leucine and isoleucine |

TABLE 21-continued

| | | | | | | | | |
|---|---|---|---|---|---|---|---|---|
| FIG. | EC class | Desired substrate | Desired product | Enzyme name | Gene name | GenBank ID (if available) | Organism | Known Substrate |
| | | | | | Bckdha, Bckdhb, Dbt, Dld | NP_036914.1, NP_062140.1, NP_445764.1, NP_955417.1 | *Rattus norvegicus* | 2-keto acids derivatives of valine, leucine and isoleucine |

Example X

Exemplary BDO from Acetoacetyl-CoA

This example describes an exemplary BDO pathway from acetoacetyl-CoA.

FIG. 12 depicts exemplary BDO pathways in which acetoacetyl-CoA is converted to BDO. Enzymes of such an exemplary BDO pathway are listed in Table 22, along with exemplary genes encoding these enzymes.

Briefly, acetoacetyl-CoA can be converted to 3-hydroxybutyryl-CoA by 3-hydroxybutyryl-CoA dehydrogenase (EC 1.1.1.a). 3-Hydroxybutyryl-CoA can be converted to crotonoyl-CoA by 3-hydroxybutyryl-CoA dehydratase (EC 4.2.1.a). Crotonoyl-CoA can be converted to vinylacetyl-CoA by vinylacetyl-CoA Δ-isomerase (EC 5.3.3.3). Vinylacetyl-CoA can be converted to 4-hydroxybutyryl-CoA by 4-hydroxybutyryl-CoA dehydratase (EC 4.2.1.a). 4-Hydroxybutyryl-CoA can be converted to 1,4-butanediol by 4-hydroxybutyryl-CoA reductase (alcohol forming) (EC 1.1.1.c). Alternatively, 4-hydroxybutyryl-CoA can be converted to 4-hydroxybutanal by 4-hydroxybutyryl-CoA reductase (or 4-hydroxybutanal dehydrogenase) (EC 1.2.1.b). 4-Hydroxybutanal can be converted to 1,4-butanediol by 1,4-butanediol dehydrogenase (EC 1.1.1.a).

TABLE 22

BDO pathway from acetoacetyl-CoA.

| FIG. | EC class | Desired substrate | Desired product | Enzyme name | Gene name | GenBank ID (if available) | Organism | Known Substrate |
|---|---|---|---|---|---|---|---|---|
| 12 | 1.1.1.a | acetoacetyl-CoA | 3-hydroxybutyryl-CoA | 3-hydroxybutyryl-CoA dehydrogenase | hbd | NP_349314.1 | *Clostridium acetobutylicum* | 3-hydroxybutyryl-CoA |
| | | | | | hbd | AAM14586.1 | *Clostridium beijerinckii* | 3-hydroxybutyryl-CoA |
| | | | | | Msed_1423 | YP_001191505 | *Metallosphaera sedula* | presumed 3-hydroxybutyryl-CoA |
| 12 | 4.2.1.a | 3-hydroxybutyryl-CoA | crotonoyl-CoA | 3-hydroxybutyryl-CoA dehydratase | crt | NP_349318.1 | *Clostridium acetobutylicum* | 3-hydroxybutyryl-CoA |
| | | | | | maoC | NP_415905.1 | *Escherichia coli* | 3-hydroxybutyryl-CoA |
| | | | | | paaF | NP_415911.1 | *Escherichia coli* | 3-hydroxyadipyl-CoA |
| 12 | 5.3.3.3 | crotonoyl-CoA | vinylacetyl-CoA | vinylacetyl-CoA Δ-isomerase | abfD | YP_001396399.1 | *Clostridium kluyveri* DSM 555 | 4-hydroxybutyryl-CoA |
| | | | | | abfD | P55792 | *Clostridium aminobutyricum* | 4-hydroxybutyryl-CoA |
| | | | | | abfD | YP_001928843 | *Porphyromonas gingivalis* ATCC 33277 | 4-hydroxybutyryl-CoA |
| 12 | 4.2.1.a | vinylacetyl-CoA | 4-hydroxybutyryl-CoA | 4-hydroxybutyryl-CoA dehydratase | abfD | YP_001396399.1 | *Clostridium kluyveri* DSM 555 | 4-hydroxybutyryl-CoA |
| | | | | | abfD | P55792 | *Clostridium aminobutyricum* | 4-hydroxybutyryl-CoA |
| | | | | | abfD | YP_001928843 | *Porphyromonas gingivalis* ATCC 33277 | 4-hydroxybutyryl-CoA |
| 12 | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |

TABLE 22-continued

BDO pathway from acetoacetyl-CoA.

| FIG. | EC class | Desired substrate | Desired product | Enzyme name | Gene name | GenBank ID (if available) | Organism | Known Substrate |
|---|---|---|---|---|---|---|---|---|
| 12 | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | Succinyl-CoA |
|  |  |  |  |  | sucD | NP_904963.1 | *Porphyromonas gingivalis* | Succinyl-CoA |
|  |  |  |  |  | Msed_0709 | YP_001190808.1 | *Metallosphaera sedula* | Malonyl-CoA |
| 12 | 1.1.1.a | 4-hydroxybutanal | 1,4-butanediol | 1,4-butanediol dehydrogenase | ADH2 | NP_014032.1 | *Saccharymyces cerevisiae* | general |
|  |  |  |  |  | yqhD | NP_417484.1 | *Escherichia coli* | >C3 |
|  |  |  |  |  | 4hbd | L21902.1 | *Clostridium kluyveri* DSM 555 | Succinate semialdehyde |

Example XI

Exemplary BDO Pathway from Homoserine

This example describes an exemplary BDO pathway from homoserine.

Figure 13:
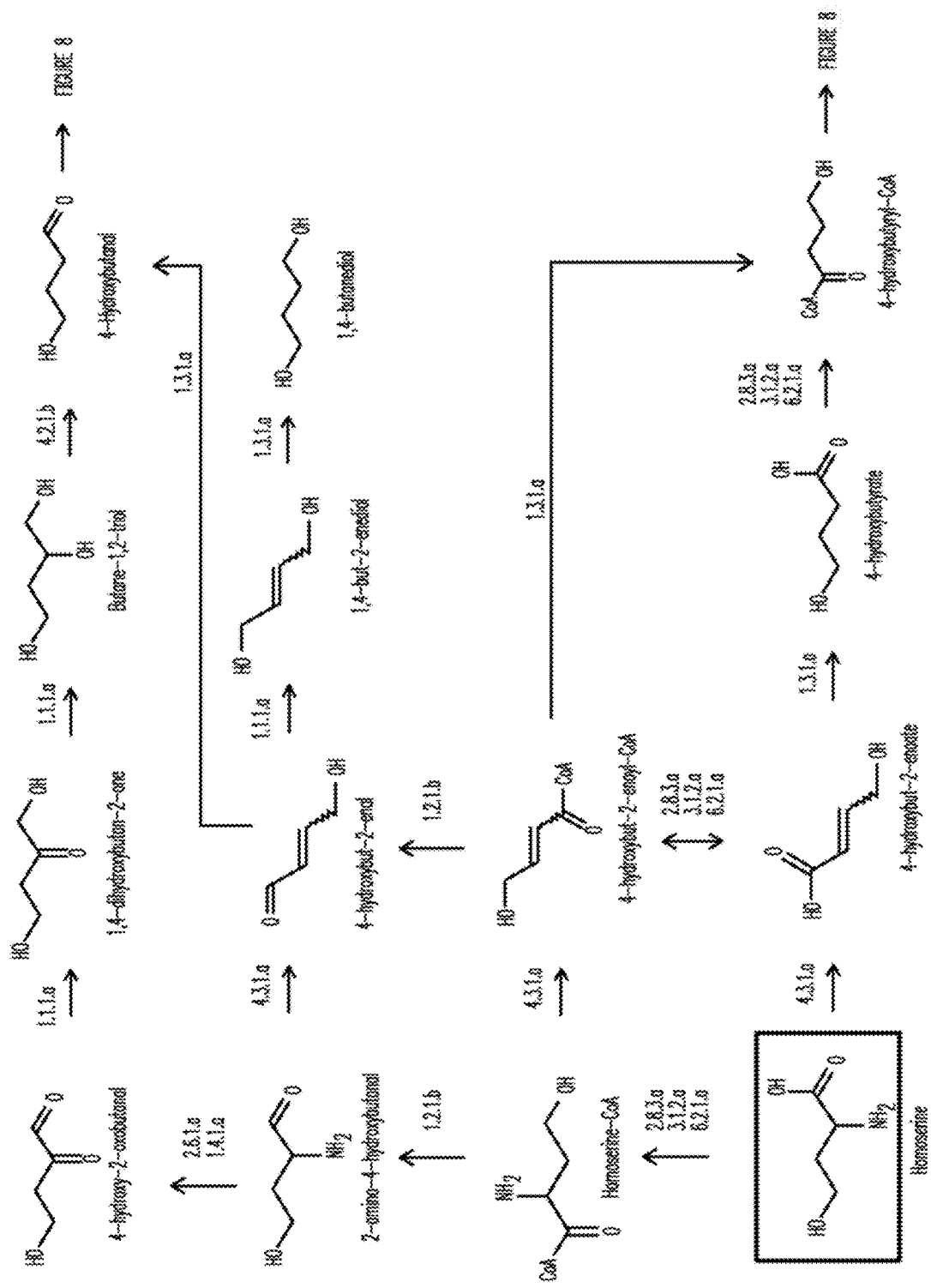
FIG. 13 shows exemplary BDO pathways from homoserine.

FIG. 13 depicts exemplary BDO pathways in which homoserine is converted to BDO. Enzymes of such an exemplary BDO pathway are listed in Table 23, along with exemplary genes encoding these enzymes.

Briefly, homoserine can be converted to 4-hydroxybut-2-enoate by homoserine deaminase (EC 4.3.1.a). Alternatively, homoserine can be converted to homoserine-CoA by homoserine CoA transferase (EC 2.8.3.a), homoserine-CoA hydrolase (EC 3.1.2.a) or homoserine-CoA ligase (or homoserine-CoA synthetase) (EC 6.2.1.a). Homoserine-CoA can be converted to 4-hydroxybut-2-enoyl-CoA by homoserine-CoA deaminase (EC 4.3.1.a). 4-Hydroxybut-2-enoate can be converted to 4-hydroxybut-2-enoyl-CoA by 4-hydroxybut-2-enoyl-CoA transferase (EC 2.8.3.a), 4-hydroxybut-2-enoyl-CoA hydrolase (EC 3.1.2.a), or 4-hydroxybut-2-enoyl-CoA ligase (or 4-hydroxybut-2-enoyl-CoA synthetase) (EC 6.2.1.a). Alternatively, 4-hydroxybut-2-enoate can be converted to 4-hydroxybutyrate by 4-hydroxybut-2-enoate reductase (EC 1.3.1.a). 4-Hydroxybutyrate can be converted to 4-hydroxybutyryl-coA by 4-hydroxybutyryl-CoA transferase (EC 2.8.3.a), 4-hydroxybutyryl-CoA hydrolase (EC 3.1.2.a), or 4-hydroxybutyryl-CoA ligase (or 4-hydroxybutyryl-CoA synthetase) (EC 6.2.1.a). 4-Hydroxybut-2-enoyl-CoA can be converted to 4-hydroxybutyryl-CoA by 4-hydroxybut-2-enoyl-CoA reductase (EC 1.3.1.a). 4-Hydroxybutyryl-CoA can be converted to 1,4-butanediol by 4-hydroxybutyryl-CoA reductase (alcohol forming) (EC 1.1.1.c). Alternatively, 4-hydroxybutyryl-CoA can be converted to 4-hydroxybutanal by 4-hydroxybutyryl-CoA reductase (or 4-hydroxybutanal dehydrogenase) (EC 1.2.1.b). 4-Hydroxybutanal can be converted to 1,4-butanediol by 1,4-butanediol dehydrogenase (EC 1.1.1.a).

TABLE 23

BDO pathway from homoserine.

| FIG. | EC class | Desired substrate | Desired product | Enzyme name | Gene name | GenBank ID (if available) | Organism | Known Substrate |
|---|---|---|---|---|---|---|---|---|
| 13 | 4.3.1.a | homoserine | 4-hydroxybut-2-enoate | homoserine deaminase | aspA | NP_418562 | *Escherichia coli* | aspartate |
|  |  |  |  |  | aspA | P44324.1 | *Haemophilus influenzae* | aspartate |
|  |  |  |  |  | aspA | P07346 | *Pseudomonas fluorescens* | aspartate |
| 13 | 2.8.3.a | homoserine | homoserine-CoA | homoserine CoA transferase | cat1, cat2, cat3 | P38946.1, P38942.2, EDK35586.1 | *Clostridium kluyveri* | succinate, 4-hydroxybutyrate, butyrate |
|  |  |  |  |  | gctA, gctB | CAA57199.1, CAA57200.1 | *Acidaminococcus fermentans* | glutarate |
|  |  |  |  |  | atoA, atoD | P76459.1, P76458.1 | *Escherichia coli* | butanoate |
| 13 | 3.1.2.a | homoserine | homoserine-CoA | homoserine-CoA hydrolase | tesB | NP_414986 | *Escherichia coli* | adipyl-CoA |
|  |  |  |  |  | acot12 | NP_570103.1 | *Rattus norvegicus* | butyryl-CoA |
|  |  |  |  |  | hibch | Q6NVY1.2 | *Homo sapiens* | 3-hydroxypropanoyl-CoA |

TABLE 23-continued

BDO pathway from homoserine.

| FIG. | EC class | Desired substrate | Desired product | Enzyme name | Gene name | GenBank ID (if available) | Organism | Known Substrate |
|---|---|---|---|---|---|---|---|---|
| 13 | 6.2.1.a | homoserine | homoserine-CoA | homoserine-CoA ligase (or homoserine-CoA synthetase) | sucCD | NP_415256.1, AAC73823.1 | Escherichia coli | succinate |
| | | | | | phl | CAJ15517.1 | Penicillium chrysogenum | phenylacetate |
| | | | | | bioW | NP_390902.2 | Bacillus subtilis | 6-carboxyhexanoate |
| 13 | 4.3.1.a | homoserine-CoA | 4-hydroxybut-2-enoyl-CoA | homoserine-CoA deaminase | acl1 | CAG29274.1 | Clostridium propionicum | beta-alanyl-CoA |
| | | | | | acl2 | CAG29275.1 | Clostridium propionicum | beta-alanyl-CoA |
| | | | | | MXAN_4385 | YP_632558.1 | Myxococcus xanthus | beta-alanyl-CoA |
| 13 | 2.8.3.a | 4-hydroxybut-2-enoate | 4-hydroxybut-2-enoyl-CoA | 4-hydroxybut-2-enoyl-CoA transferase | cat1, cat2, cat3 | P38946.1, P38942.2, EDK35586.1 | Clostridium kluyveri | succinate, 4-hydroxybutyrate, butyrate |
| | | | | | gctA, gctB | CAA57199.1, CAA57200.1 | Acidaminococcus fermentans | glutarate |
| | | | | | atoA, atoD | P76459.1, P76458.1 | Escherichia coli | butanoate |
| 13 | 3.1.2.a | 4-hydroxybut-2-enoate | 4-hydroxybut-2-enoyl-CoA | 4-hydroxybut-2-enoyl-CoA hydrolase | tesB | NP_414986 | Escherichia coli | adipyl-CoA |
| | | | | | acot12 | NP_570103.1 | Rattus norvegicus | butyryl-CoA |
| | | | | | hibch | Q6NVY1.2 | Homo sapiens | 3-hydroxypropanoyl-CoA |
| 13 | 6.2.1.a | 4-hydroxybut-2-enoate | 4-hydroxybut-2-enoyl-CoA | 4-hydroxybut-2-enoyl-CoA ligase (or 4-hydroxybut-2-enoyl-CoA synthetase) | sucCD | NP_415256.1, AAC73823.1 | Escherichia coli | succinate |
| | | | | | phl | CAJ15517.1 | Penicillium chrysogenum | phenylacetate |
| | | | | | bioW | NP_390902.2 | Bacillus subtilis | 6-carboxyhexanoate |
| 13 | 1.3.1.a | 4-hydroxybut-2-enoate | 4-hydroxybutyrate | 4-hydroxybut-2-enoate reductase | enr | CAA71086.1 | Clostridium tyrobutyricum | |
| | | | | | enr | CAA76083.1 | Clostridium kluyveri | |
| | | | | | enr | YP_430895.1 | Moorella thermoacetica | |
| 13 | 2.8.3.a | 4-hydroxybutyrate | 4-hydroxybutyryl-coA | 4-hydroxybutyryl-CoA transferase | cat1, cat2, cat3 | P38946.1, P38942.2, EDK35586.1 | Clostridium kluyveri | succinate, 4-hydroxybutyrate, butyrate |
| | | | | | gctA, gctB | CAA57199.1, CAA57200.1 | Acidaminococcus fermentans | glutarate |
| | | | | | atoA, atoD | P76459.1, P76458.1 | Escherichia coli | butanoate |
| 13 | 3.1.2.a | 4-hydroxybutyrate | 4-hydroxybutyryl-coA | 4-hydroxybutyryl-CoA hydrolase | tesB | NP_414986 | Escherichia coli | adipyl-CoA |
| | | | | | acot12 | NP_570103.1 | Rattus norvegicus | butyryl-CoA |
| | | | | | hibch | Q6NVY1.2 | Homo sapiens | 3-hydroxypropanoyl-CoA |
| 13 | 6.2.1.a | 4-hydroxybutyrate | 4-hydroxybutyryl-coA | 4-hydroxybutyryl-CoA ligase (or 4-hydroxybutyryl-CoA synthetase) | sucCD | NP_415256.1, AAC73823.1 | Escherichia coli | succinate |
| | | | | | phl | CAJ15517.1 | Penicillium chrysogenum | phenylacetate |
| | | | | | bioW | NP_390902.2 | Bacillus subtilis | 6-carboxyhexanoate |
| 13 | 1.3.1.a | 4-hydroxybut-2-enoyl-CoA | 4-hydroxybutyryl-CoA | 4-hydroxybut-2-enoyl-CoA reductase | bcd, etfA, etfB | NP_349317.1, NP_349315.1, NP_349316.1 | Clostridium acetobutylicum | |
| | | | | | TER | Q5EU90.1 | Euglena gracilis | |
| | | | | | TDE0597 | NP_971211.1 | Treponema denticola | |

TABLE 23-continued

BDO pathway from homoserine.

| FIG. | EC class | Desired substrate | Desired product | Enzyme name | Gene name | GenBank ID (if available) | Organism | Known Substrate |
|---|---|---|---|---|---|---|---|---|
| 8 | 1.1.1.c | 4-hydroxybutyryl-CoA | 1,4-butanediol | 4-hydroxybutyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |
| 8 | 1.2.1.b | 4-hydroxybutyryl-CoA | 4-hydroxybutanal | 4-hydroxybutyryl-CoA reductase (or 4-hydroxybutanal dehydrogenase) | sucD | P38947.1 | *Clostridium kluyveri* | Succinyl-CoA |
| | | | | | sucD | NP_904963.1 | *Porphyromonas gingivalis* | Succinyl-CoA |
| | | | | | Msed_0709 | YP_001190808.1 | *Metallosphaera sedula* | Malonyl-CoA |
| 8 | 1.1.1.a | 4-hydroxybutanal | 1,4-butanediol | 1,4-butanediol dehydrogenase | ADH2 | NP_014032.1 | *Saccharymyces cerevisiae* | general |
| | | | | | yqhD | NP_417484.1 | *Escherichia coli* | >C3 |
| | | | | | 4hbd | L21902.1 | *Clostridium kluyveri* DSM 555 | Succinate semialdehyde |

Example XII

BDO Producing Strains Expressing Succinyl-CoA Synthetase

This example describes increased production of BDO in BDO producing strains expressing succinyl-CoA synthetase.

As discussed above, succinate can be a precursor for production of BDO by conversion to succinyl-CoA (see also WO2008/115840, WO 2009/023493, U.S. publication 2009/0047719, U.S. publication 2009/0075351). Therefore, the host strain was genetically modified to overexpress the *E. coli* sucCD genes, which encode succinyl-CoA synthetase. The nucleotide sequence of the *E. coli* sucCD operon is shown in FIG. 14A, and the amino acid sequences for the encoded succinyl-CoA synthetase subunits are shown in FIGS. 14B and 14C. Briefly, the *E. coli* sucCD genes were cloned by PCR from *E. coli* chromosomal DNA and introduced into multicopy plasmids pZS*13, pZA13, and pZE33 behind the PA1lacO-1 promoter (Lutz and Bujard, *Nucleic Acids Res.* 25:1203-1210 (1997)) using standard molecular biology procedures.

The *E. coli* sucCD genes, which encode the succinyl-CoA synthetase, were overexpressed. The results showed that introducing into the strains sucCD to express succinyl-CoA synthetase improved BDO production in various strains compared to either native levels of expression or expression of cat1, which is a succinyl-CoA/acetyl-CoA transferase. Thus, BDO production was improved by overexpressing the native *E. coli* sucCD genes encoding succinyl-CoA synthetase.

Example XIII

Expression of Heterologous Genes Encoding BDO Pathway Enzymes

This example describes the expression of various non-native pathway enzymes to provide improved production of BDO.

Alpha-ketoglutarate decarboxylase. The *Mycobacterium bovis* sucA gene encoding alpha-ketoglutarate decarboxylase was expressed in host strains. Overexpression of *M. bovis* sucA improved BDO production (see also WO2008/115840, WO 2009/023493, U.S. publication 2009/0047719, U.S. publication 2009/0075351). The nucleotide and amino acid sequences of *M. bovis* sucA and the encoded alpha-ketoglutarate decarboxylase are shown in FIG. 15.

To construct the *M. bovis* sucA expressing strains, fragments of the sucA gene encoding the alpha-ketoglutarate decarboxylase were amplified from the genomic DNA of *Mycobacterium bovis* BCG (ATCC 19015; American Type Culture Collection, Manassas Va.) using primers shown below. The full-length gene was assembled by ligation reaction of the four amplified DNA fragments, and cloned into expression vectors pZS*13 and pZE23 behind the $P_{A1lacO-1}$ promoter (Lutz and Bujard, *Nucleic Acids Res.* 25:1203-1210 (1997)). The nucleotide sequence of the assembled gene was verified by DNA sequencing.

```
Primers for fragment 1:
                                          (SEQ ID NO: 3)
5'-ATGTACCGCAAGTTCCGC-3'

(SEQ ID NO: 4)
5'-CAATTTGCCGATGCCCAG-3'

Primers for fragment 2:
                                          (SEQ ID NO: 5)
5'-GCTGACCACTGAAGACTTTG-3'

(SEQ ID NO: 6)
5'-GATCAGGGCTTCGGTGTAG-3'

Primers for fragment 3:
                                          (SEQ ID NO: 7)
5'-TTGGTGCGGGCCAAGCAGGATCTGCTC-3'

(SEQ ID NO: 8)
5'-TCAGCCGAACGCCTCGTCGAGGATCTCCTG-3'
```

-continued

Primers for fragment 4:

(SEQ ID NO: 9)
5'-TGGCCAACATAAGTTCACCATTCGGGCAAAAC-3'

(SEQ ID NO: 10)
5'-TCTCTTCAACCAGCCATTCGTTTTGCCCG-3'

Figure 16:
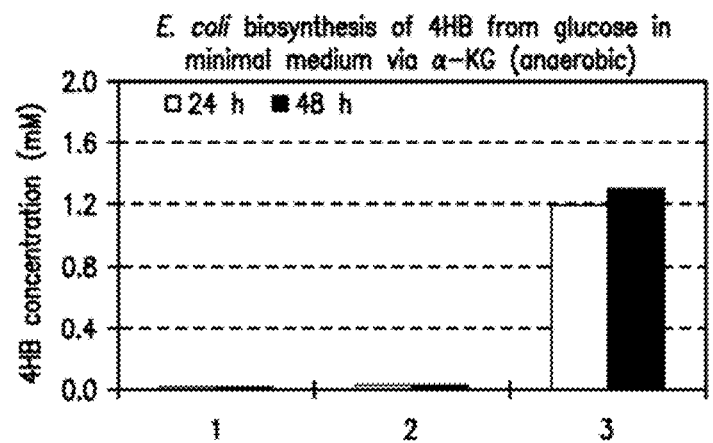
FIG. 16 shows biosynthesis in E. coli of 4-hydroxybutyrate from glucose in minimal medium via alpha-ketoglutarate under anaerobic (microaerobic) conditions. The host strain is ECKh-401. The experiments are labeled based on the upstream pathway genes present on the plasmid pZA33 as follows: 1) 4hbd-sucA; 2) sucCD-sucD-4hbd; 3) sucCD-sucD-4hbd-sucA.

Functional expression of the alpha-ketoglutarate decarboxylase was demonstrated using both in vitro and in vivo assays. The SucA enzyme activity was measured by following a previously reported method (Tian et al., *Proc. Natl. Acad. Sci. USA* 102:10670-10675 (2005)). The reaction mixture contained 50 mM potassium phosphate buffer, pH 7.0, 0.2 mM thiamine pyrophosphate, 1 mM $MgCl_2$, 0.8 mM ferricyanide, 1 mM alpha-ketoglutarate and cell crude lysate. The enzyme activity was monitored by the reduction of ferricyanide at 430 nm. The in vivo function of the SucA enzyme was verified using *E. coli* whole-cell culture. Single colonies of *E. coli* MG1655 lacI$^q$ transformed with plasmids encoding the SucA enzyme and the 4-hydroxybutyrate dehydrogenase (4Hbd) was inoculated into 5 mL of LB medium containing appropriate antibiotics. The cells were cultured at 37° C. overnight aerobically. A 200 uL of this overnight culture was introduced into 8 mL of M9 minimal medium (6.78 g/L $Na_2HPO_4$, 3.0 g/L $KH_2PO_4$, 0.5 g/L NaCl, 1.0 g/L $NH_4Cl$, 1 mM $MgSO_4$, 0.1 mM $CaCl_2$) supplemented with 20 g/L glucose, 100 mM 3-(N-morpholino)propanesulfonic acid (MOPS) to improve the buffering capacity, 10 μg/mL thiamine, and the appropriate antibiotics. Microaerobic conditions were established by initially flushing capped anaerobic bottles with nitrogen for 5 minutes, then piercing the septum with a 23G needle following inoculation. The needle was kept in the bottle during growth to allow a small amount of air to enter the bottles. The protein expression was induced with 0.2 mM isopropyl β-D-1-thiogalactopyranoside (IPTG) when the culture reached mid-log growth phase. As controls, *E. coli* MG1655 lacI$^q$ strains transformed with only the plasmid encoding the 4-hydroxybutyrate dehydrogenase and only the empty vectors were cultured under the same condition (see Table 23). The accumulation of 4-hydroxybutyrate (4HB) in the culture medium was monitored using LCMS method. Only the *E. coli* strain expressing the *Mycobacterium* alpha-ketoglutarate decarboxylase produced significant amount of 4HB (see FIG. 16).

TABLE 24

Three strains containing various plasmid controls and encoding sucA and 4-hydroxybutyrate dehydrogenase.

| | Host | pZE13 | pZA33 |
|---|---|---|---|
| 1 | MG1655 laclq | vector | vector |
| 2 | MG1655 laclq | vector | 4hbd |
| 3 | MG1655 laclq | sucA | 4hbd |

Figure 17:
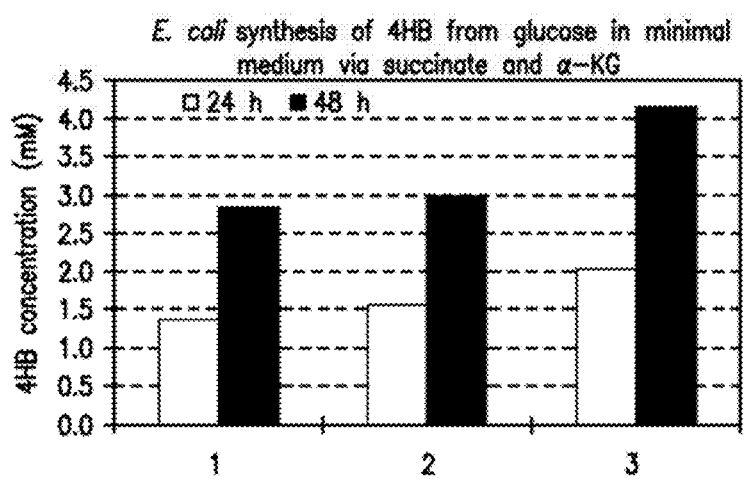
FIG. 17 shows biosynthesis in E. coli of 4-hydroxybutyrate from glucose in minimal medium via succinate and alpha-ketoglutarate. The host strain is wild-type MG1655. The experiments are labeled based on the genes present on the plasmids pZE13 and pZA33 as follows: 1) empty control vectors 2) empty pZE13, pZ A33-4hbd; 3) pZE13-sucA, pZ A33-4hbd.

A separate experiment demonstrated that the alpha-ketoglutarate decarboxylase pathway functions independently of the reductive TCA cycle. *E. coli* strain ECKh-401 (ΔadhE ΔldhA ΔpflB ΔlpdA::K.p.lpdA322 Δmdh ΔarcA) was used as the host strain (see Table 25). All the three constructs contained the gene encoding 4HB dehydrogenase (4Hbd). Construct 1 also contained the gene encoding the alpha-ketoglutarate decarboxylase (sucA). Construct 2 contained the genes encoding the succinyl-CoA synthetase (sucCD) and the CoA-dependent succinate semialdehyde dehydrogenase (sucD), which are required for the synthesis of 4HB via the reductive TCA cycle. Construct 3 contains all the genes from 1 and 2. The three *E. coli* strains were cultured under the same conditions as described above except the second culture was under the micro-aerobic condition. By expressing the SucA enzyme, construct 3 produced more 4HB than construct 2, which relies on the reductive TCA cycle for 4HB synthesis (see FIG. 17).

Further support for the contribution of alpha-ketoglutarate decarboxylase to production of 4HB and BDO was provided by flux analysis experiments. Cultures of ECKh-432, which contains both sucCD-sucD and sucA on the chromosome, were grown in M9 minimal medium containing a mixture of 1-13C-glucose (60%) and U-13C-glucose (40%). The biomass was harvested, the protein isolated and hydrolyzed to amino acids, and the label distribution of the amino acids analyzed by gas chromatography-mass spectrometry (GCMS) as described previously (Fischer and Sauer, *Eur. J. Biochem.* 270:880-891 (2003)). In addition, the label distribution of the secreted 4HB and BDO was analyzed by GCMS as described in WO2008115840 A2. This data was used to calculate the intracellular flux distribution using established methods (Suthers et al., *Metab. Eng.* 9:387-405 (2007)). The results indicated that between 56% and 84% of the alpha-ketoglutarate was channeled through alpha-ketoglutarate decarboxylase into the BDO pathway. The remainder was oxidized by alpha-ketoglutarate dehydrogenase, which then entered BDO via the succinyl-CoA route.

These results demonstrate 4-hydroxybutyrate producing strains that contain the sucA gene from *Mycobacterium bovis* BCG expressed on a plasmid. When the plasmid encoding this gene is not present, 4-hydroxybutyrate production is negligible when sucD (CoA-dependant succinate semialdehyde dehydrogenase) is not expressed. The *M. bovis* gene is a close homolog of the *Mycobacterium tuberculosis* gene whose enzyme product has been previously characterized (Tian et al., supra, 2005).

Succinate semialdehyde dehydrogenase (CoA-dependent), 4-hydroxybutyrate dehydrogenase, and 4-hydroxybutyryl-CoA/acetyl-CoA transferase. The genes from *Porphyromonas gingivalis* W83 can be effective components of the pathway for 1,4-butanediol production (see also WO2008/115840, WO 2009/023493, U.S. publication 2009/0047719, U.S. publication 2009/0075351). The nucleotide sequence of CoA-dependent succinate semialdehyde dehydrogenase (sucD) from *Porphyromonas gingivalis* is shown in FIG. 18A, and the encoded amino acid sequence is shown in FIG. 18B. The nucleotide sequence of 4-hydroxybutyrate dehydrogenase (4hbd) from *Porphymonas gingivalis* is shown in FIG. 19A, and the encoded amino acid seqence is shown in FIG. 19B. The nucleotide sequence of 4-hydroxybutyrate CoA transferase (cat2) from *Porphyromonas gingivalis* is shown in FIG. 20A, and the encoded amino acid sequence is shown in FIG. 20B.

Briefly, the genes from *Porphyromonas gingivalis* W83 encoding succinate semialdehyde dehydrogenase (CoA-dependent) and 4-hydroxybutyrate dehydrogenase, and in some cases additionally 4-hydroxybutyryl-CoA/acetyl-CoA, were cloned by PCR from *P. gingivalis* chromosomal DNA and introduced into multicopy plasmids pZS*13, pZA13, and pZE33 behind the PA1lacO-1 promoter (Lutz and Bujard, *Nucleic Acids Res.* 25:1203-1210 (1997)) using standard molecular biology procedures. These plasmids were then introduced into host strains.

The *Porphyromonas gingivalis* W83 genes were introduced into production strains as described above. Some strains included only succinate semialdehyde dehydrogenase (CoA-dependant) and 4-hydroxybutyrate dehydrogenase without 4-hydroxybutyryl-CoA/acetyl-CoA transferase.

Butyrate kinase and phosphotransbutyrylase. Butyrate kinase (BK) and phosphotransbutyrylase (PTB) enzymes can be utilized to produce 4-hydroxybutyryl-CoA (see also WO2008/115840, WO 2009/023493, U.S. publication 2009/0047719, U.S. publication 2009/0075351). In particular, the *Clostridium acetobutylicum* genes, buk1 and ptb, can be utilized as part of a functional BDO pathway.

Initial experiments involved the cloning and expression of the native *C. acetobutylicum* PTB (020) and BK (021) genes in *E. coli*. Where required, the start codon and stop codon for each gene were modified to "ATG" and "TAA," respectively, for more optimal expression in *E. coli*. The *C. acetobutylicum* gene sequences (020N and 021N) and their corresponding translated peptide sequences are shown in FIGS. 21 and 22.

The PTB and BK genes exist in *C. acetobutylicum* as an operon, with the PTB (020) gene expressed first. The two genes are connected by the sequence "atta aagttaagtg gaggaatgtt aac" (SEQ ID NO:11) that includes a re-initiation ribosomal binding site for the downstream BK (021) gene. The two genes in this context were fused to lac-controlled promoters in expression vectors for expression in *E. coli* (Lutz and Bujard, *Nucleic Acids Res.* 25:1203-1210 (1997)).

Expression of the two proteins from these vector constructs was found to be low in comparison with other exogenously expressed genes due to the high incidence of codons in the *C. acetobutylicum* genes that occur only rarely in *E. coli*. Therefore new 020 and 021 genes were predicted that changed rare codons for alternates that are more highly represented in *E. coli* gene sequences. This method of codon optimization followed algorithms described previously (Sivaraman et al., *Nucleic Acids Res.* 36:e16(2008)). This method predicts codon replacements in context with their frequency of occurrence when flanked by certain codons on either side. Alternative gene sequences for 020 (FIG. 23) and 021 (FIG. 24) were determined in which increasing numbers of rare codons were replaced by more prevalent codons (A<B<C<D) based on their incidence in the neighboring codon context. No changes in actual peptide sequence compared to the native 020 and 021 peptide sequences were introduced in these predicted sequences.

Figure 25A:
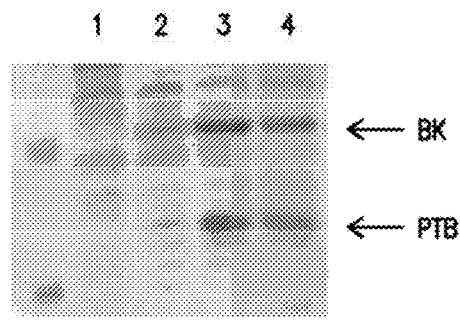
FIGS. 25A and 25B show improved expression of butyrate kinase (BK) and phosphotransbutyrylase (PTB) with optimized codons for expression in E. coli.
Figure 25B:
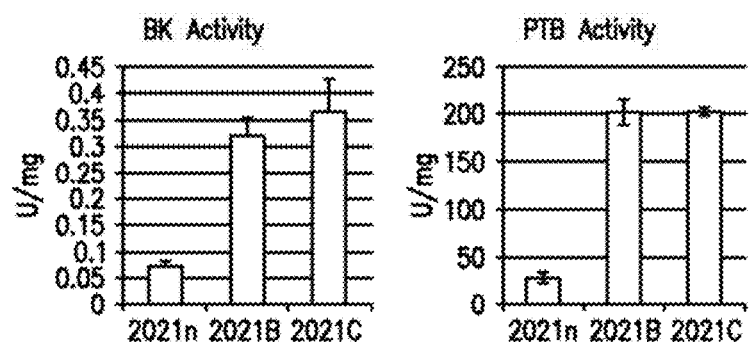

The improvement in expression of the BK and PTB proteins resulting from codon optimization is shown in FIG. 25A. Expression of the native gene sequences is shown in lane 2, while expression of the 020B-021B and 020C-021C is shown in lanes 3 and 4, respectively. Higher levels of protein expression in the codon-optimized operons 020B-021B (2021B) and 020C-021C (2021C) also resulted in increased activity compared to the native operon (2021n) in equivalently-expressed *E. coli* crude extracts (FIG. 25B).

Figure 26:
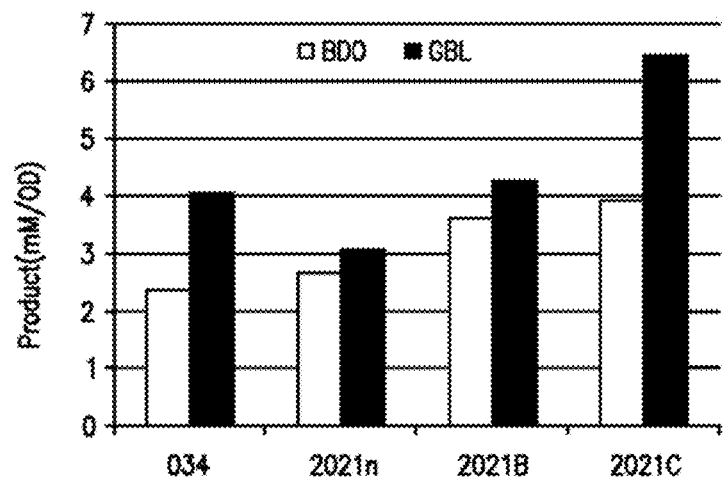
FIG. 26 shows production of BDO and gamma-butyrylactone (GBL) in various strains expressing BDO producing enzymes: Cat2 (034); 2021n; 2021B; 2021C.

The codon optimized operons were expressed on a plasmid in strain ECKh-432 (ΔadhE ΔldhA ΔpflB ΔlpdA::K.p.lpdA322 Δmdh 4arcA gltAR163L fimD::*E. coli* sucCD, *P. gingivalis* sucD, *P. gingivalis* 4hbd fimD::*M. bovis* sucA, *C. kluyveri* 4hbd) along with the *C. acetobutylicum* aldehyde dehydrogenase to provide a complete BDO pathway. Cells were cultured in M9 minimal medium containing 20 g/L glucose, using a 23G needle to maintain microaerobic conditions as described above. The resulting conversion of glucose to the final product BDO was measured. Also measured was the accumulation of gamma-butyrolactone (GBL), which is a spontaneously rearranged molecule derived from 4Hb-CoA, the immediate product of the PTB-BK enzyme pair. FIG. 26 shows that expression of the native 2021n operon resulted in comparable BDO levels to an alternative enzyme function, Cat2 (034), that is capable of converting 4HB and free CoA to 4HB-CoA. GBL levels of 034 were significantly higher than 2021n, suggesting that the former enzyme has more activity than PTB-BK expressed from the native genes. However levels of both BDO and GBL were higher than either 034 or 2021n when the codon-optimized variants 2021B and 2021C were expressed, indicating that codon optimization of the genes for PTB and BK significantly increases their contributions to BDO synthesis in *E. coli*.

These results demonstrate that butyrate kinase (BK) and phosphotransbutyrylase (PTB) enzymes can be employed to convert 4-hydroxybutyrate to 4-hydroxybutyryl-CoA. This eliminates the need for a transferase enzyme such as 4-hydroxybutyryl-CoA/Acetyl-CoA transferase, which would generate one mole of acetate per mol of 4-hydroxybutyryl-CoA produced. The enzymes from *Clostridium acetobutylicum* are present in a number of engineered strains for BDO production.

4-hydroxybutyryl-CoA reductase. The *Clostridium beijerinckii* ald gene can be utilized as part of a functional BDO pathway (see also WO2008/115840, WO 2009/023493, U.S. publication 2009/0047719, U.S. publication 2009/0075351). The *Clostridium beijerinckii* ald can also be utilized to lower ethanol production in BDO producing strains. Additionally, a specific codon-optimized ald variant (GNM0025B) was found to improve BDO production.

Figure 29:
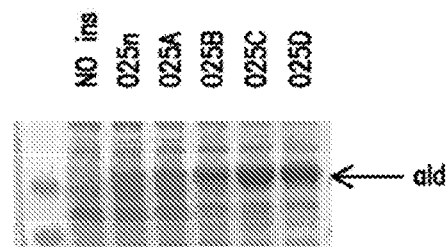
FIG. 29 shows expression of native C. beijerinckii ald gene and codon optimized variants; no ins (control with no insert), 025n, 025A, 025B, 025C, 025D.
Figure 30A:
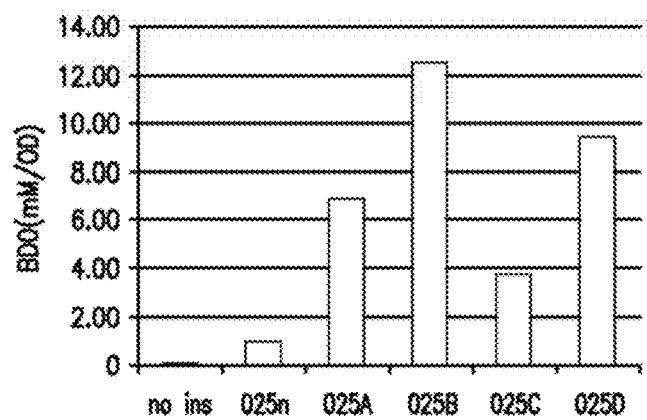
FIGS. 30A and 30B show BDO or BDO and ethanol production in various strains.

The native *C. beijerinckii* ald gene (025n) and the predicted protein sequence of the enzyme are shown in FIG. 27. As was seen for the *Clostridium acetobutylicum* PTB and BK genes, expression of the native *C. beijerinckii* ald gene was very low in *E. coli*. Therefore, four codon-optimized variants for this gene were predicted. FIGS. 28A-28D show alternative gene sequences for 025, in which increasing numbers of rare codons are replaced by more prevalent codons (A<B<C<D) based on their incidence in the neighboring codon context (25A, P=0.05; 25B, P=0.1; 25C, P=0.15; 25D, P=1). No changes in actual peptide sequence compared to the native 025 peptide sequence were introduced in these predictions. Codon optimization significantly increased expression of the *C. beijerinckii* ald (see FIG. 29), which resulted in significantly higher conversion of glucose to BDO in cells expressing the entire BDO pathway (FIG. 30A).

Figure 30B:
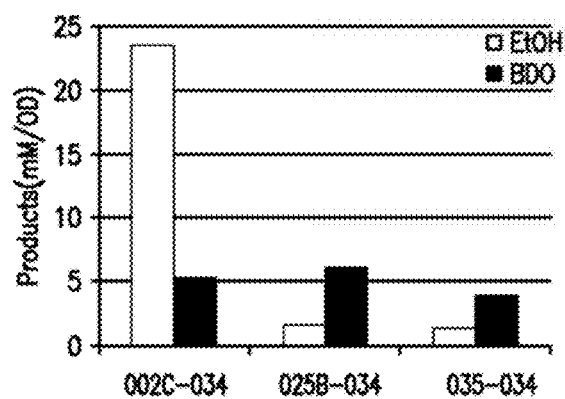

The native and codon-optimized genes were expressed on a plasmid along with *P. gingivalis* Cat2, in the host strain ECKh-432 (ΔadhE ΔldhA ΔpflB ΔlpdA::K.p.lpdA322 Δmdh ΔarcA gltAR163L ΔackA fimD::*E. coli* sucCD, *P. gingivalis* sucD, *P. gingivalis* 4hbd fimD::*M. bovis* sucA, *C. kluyveri* 4hbd), thus containing a complete BDO pathway. Cells were cultured microaerobically in M9 minimal medium containing 20 g/L glucose as described above. The relative production of BDO and ethanol by the *C. beijerinckii* Ald enzyme (expressed from codon-optimized variant gene 025B) was compared with the *C. acetobutylicum* AdhE2 enzyme (see FIG. 30B). The *C. acetobutylicum* AdhE2 enzyme (002C) produced nearly 4 times more ethanol than BDO. In comparison, the *C. beijerinckii* Ald (025B) (in conjunction with an endogenous ADH activity) produced equivalent amounts of BDO, yet the ratio of BDO to ethanol production was reversed for this enzyme compared to 002C. This suggests that the *C. beijerinckii* Ald is more specific for 4HB-CoA over acetyl-coA than the *C. acetobutylicum* AdhE2, and therefore the former is the preferred enzyme for inclusion in the BDO pathway.

The *Clostridium beijerinckii* ald gene (Toth et al., *Appl. Environ. Microbiol.* 65:4973-4980 (1999)) was tested as a candidate for catalyzing the conversion of 4-hydroxybutyryl-CoA to 4-hydroxybutanal. Over fifty aldehyde dehydrogenases were screened for their ability to catalyze the conversion of 4-hydroxybutyryl-CoA to 4-hydroxybutyraldehyde. The *C. beijerinckii* ald gene was chosen for implementation into BDO-producing strains due to the preference of this enzyme for 4-hydroxybutyryl-CoA as a substrate as opposed to acetyl-CoA. This is important because most other enzymes with aldehyde dehydrogenase functionality (for example, adhE2 from *C. acetobutylicum* (Fontaine et al., *J Bacteriol.* 184:821-830 (2002)) preferentially convert acetyl-CoA to acetaldehyde, which in turn is converted to ethanol. Utilization of the *C. beijerinckii* gene lowers the amount of ethanol produced as a byproduct in BDO-producing organisms. Also, a codon-optimized version of this gene expresses very well in *E. coli* (Sivaraman et al., *Nucleic Acids Res.* 36:e16 (2008)).

4-hydroxybutanal reductase. 4-hydroxybutanal reductase activity of adh1 from *Geobacillus thermoglucosidasius* (M10EXG) was utilized. This led to improved BDO production by increasing 4-hydroxybutanal reductase activity over endogenous levels.

Multiple alcohol dehydrogenases were screened for their ability to catalyze the reduction of 4-hydroxybutanal to BDO. Most alcohol dehydrogenases with high activity on butyraldehyde exhibited far lower activity on 4-hydroxybutyraldehyde. One notable exception is the adh1 gene from *Geobacillus thermoglucosidasius* M10EXG (Jeon et al., *J. Biotechnol.* 135:127-133 (2008)) (GNM0084), which exhibits high activity on both 4-hydroxybutanal and butanal.

The native gene sequence and encoded protein sequence if the adh1 gene from *Geobacillus thermoglucosidasius* are shown in FIG. 31. The *G. thermoglucosidasius* ald1 gene was expressed in *E. coli*.

The Adh1 enzyme (084) expressed very well from its native gene in *E. coli* (see FIG. 32A). In ADH enzyme assays, the *E. coli* expressed enzyme showed very high reductive activity when butyraldehyde or 4HB-aldehyde were used as the substrates (see FIG. 32B). The Km values determined for these substrates were 1.2 mM and 4.0 mM, respectively. These activity values showed that the Adh1 enzyme was the most active on reduction of 4HB-aldehyde of all the candidates tested.

The 084 enzyme was tested for its ability to boost BDO production when coupled with the *C. beijerinckii* ald. The 084 gene was inserted behind the *C. beijerinckii* ald variant 025B gene to create a synthetic operon that results in coupled expression of both genes. Similar constructs linked 025B with other ADH candidate genes, and the effect of including each ADH with 025B on BDO production was tested. The host strain used was ECKh-459 (ΔadhE ldhA ΔpflB 41pdA::fnr-pflB6-K.p.lpdA322 Δmdh ΔarcA gltAR163L fimD:: *E. coli* sucCD, *P. gingivalis* sucD, *P. gingivalis* 4hbd fimD:: *M. bovis* sucA, *C. kluyveri* 4hbd fimD:: *C. acetobutylicum* buk1, *C. acetobutylicum* ptb), which contains the remainder of the BDO pathway on the chromosome. The 084 ADH expressed in conjunction with 025B showed the highest amount of BDO (right arrow in FIG. 33) when compared with 025B only (left arrow in FIG. 33) and in conjunction with endogenous ADH functions. It also produced more BDO than did other ADH enzymes when paired with 025B, indicated as follows: 026A-C, codon-optimized variants of *Clostridium acetobutylicum* butanol dehydrogenase; 050, *Zymomonas mobilis* alcohol dehydrogenase I; 052, *Citrobacter freundii* 1,3-propanediol dehydrogenase; 053, *Lactobacillus brevis* 1,3-propanediol dehydrogenase; 057, *Bacteroides fragilis* lactaldehyde reductase; 058, *E. coli* 1,3-propanediol dehydrogenase; 071, *Bacillus subtilis* 168 alpha-ketoglutarate semialdehyde dehydrogenase. The constructs labeled "PT5lacO" are those in which the genes are driven by the PT5lacO promoter. In all other cases, the PA1lacO-1 promoter was used. This shows that inclusion of the 084 ADH in the BDO pathway increased BDO production.

Example XIV

BDO Producing Strains Expressing Pyruvate Dehydrogenase

This example describes the utilization of pyruvate dehydrogenase (PDH) to enhance BDO production. Heterologous expression of the *Klebsiella pneumonia* lpdA gene was used to enhance BDO production.

Computationally, the NADH-generating conversion of pyruvate to acetyl-CoA is required to reach the maximum theoretical yield of 1,4-butanediol (see also WO2008/115840, WO 2009/023493, U.S. publication 2009/0047719, U.S. publication 2009/0075351; WO 2008/018930; Kim et al., *Appl. Environ. Microbiol.* 73:1766-1771 (2007); Kim et al., *J. Bacteriol.* 190:3851-3858 (2008); Menzel et al., *J. Biotechnol.* 56:135-142 (1997)). Lack of PDH activity was shown to reduce the maximum anaerobic theoretical yield of BDO by 11% if phosphoenolpyruvate carboxykinase (PEPCK) activity cannot be attained and by 3% if PEPCK activity can be attained. More importantly, however, absence of PDH activity in the OptKnock strain #439, described in WO 2009/023493 and U.S. publication 2009/0047719, which has the knockout of ADHEr, ASPT, LDH_D, MDH and PFLi, would reduce the maximum anaerobic yield of BDO by 54% or by 43% if PEPCK activity is absent or present, respectively. In the presence of an external electron acceptor, lack of PDH activity would reduce the maximum yield of the knockout strain by 10% or by 3% assuming that PEPCK activity is absent or present, respectively.

PDH is one of the most complicated enzymes of central metabolism and is comprised of 24 copies of pyruvate decarboxylase (E1) and 12 molecules of dihydrolipoyl dehydrogenase (E3), which bind to the outside of the dihydrolipoyl transacetylase (E2) core. PDH is inhibited by high NADH/NAD, ATP/ADP, and Acetyl-CoA/CoA ratios. The enzyme naturally exhibits very low activity under oxygen-limited or anaerobic conditions in organisms such as *E. coli* due in large part to the NADH sensitivity of E3, encoded by lpdA. To this end, an NADH-insensitive version of the lpdA gene from *Klebsiella pneumonia* was cloned and expressed to increase the activity of PDH under conditions where the NADH/NAD ratio is expected to be high.

Replacement of the native lpdA. The pyruvate dehydrogenase operon of *Klebsiella pneumoniae* is between 78 and 95% identical at the nucleotide level to the equivalent operon of *E. coli*. It was shown previously that *K. pneumoniae* has the ability to grow anaerobically in presence of glycerol (Menzel et al., *J. Biotechnol.* 56:135-142 (1997); Menzel et al., *Biotechnol. Bioeng.* 60:617-626 (1998)). It has also been shown that two mutations in the lpdA gene of the operon of *E. coli* would increase its ability to grow anaerobically (Kim et al. *Appl. Environ. Microbiol.* 73:1766-1771 (2007); Kim et al., *J. Bacteriol.* 190:3851-3858 (2008)). The lpdA gene of *K. pneumonia* was amplified by PCR using genomic DNA (ATCC700721D) as template and the primers KP-lpdA-Bam (5'-acacgcggatccaacgtcccgg-3')

(SEQ ID NO:12) and KP-lpdA-Nhe (5'-agcggctccgctagccgcttatg-3')(SEQ ID NO:13). The resulting fragment was cloned into the vector pCR-BluntII-TOPO (Invitrogen; Carlsbad Calif.), leading to plasmid pCR-KP-lpdA.

The chromosomal gene replacement was performed using a non-replicative plasmid and the sacB gene from *Bacillus subtilis* as a means of counterselection (Gay et al., *J. Bacteriol.* 153:1424-1431 (1983)). The vector used is pRE118 (ATCC87693) deleted of the oriT and IS sequences, which is 3.6 kb in size and carrying the kanamycin resistance gene. The sequence was confirmed, and the vector was called pRE118-V2 (see FIG. 34).

The *E. coli* fragments flanking the lpdA gene were amplified by PCR using the combination of primers: EC-aceF-Pst (5'-aagccgttgctgcagctcttgagc-3')(SEQ ID NO:14)+EC-aceF-Bam2 (5'-atctccggcggtcggatccgtcg-3')(SEQ ID NO:15) and EC-yacH-Nhe (5'-aaagcggctagccacgccgc-3')(SEQ ID NO:16)+EC-yacH-Kpn (5'-attacacgaggtacccaacg-3')(SEQ ID NO:17). A BamHI-XbaI fragment containing the lpdA gene of *K. pneumonia* was isolated from plasmid pCR-KP-lpdA and was then ligated to the above *E. coli* fragments digested with PstI+BamHI and NheI-KpnI respectively, and the pRE118-V2 plasmid digested with KpnI and PstI. The resulting plasmid (called pRE118-M2.1 lpdA yac) was subjected to Site Directed Mutagenesis (SDM) using the combination of primers KP-lpdA-HisTyr-F (5'-atgctggcgta-caaaggtgtcc-3')(SEQ ID NO:18) and (5'-ggacacctttgtacgccagcat-3')(SEQ ID NO:19) for the mutation of the His 322 residue to a Tyr residue or primers KP-lpdA-GluLys-F (5'-atcgcctacactaaaccagaagtgg-3')(SEQ ID NO:20) and KP-lpdA-GluLys-R (5'-ccacttctggtttagtgtaggc-gat-3')(SEQ ID NO:21) for the mutation of the residue Glu 354 to Lys residue. PCR was performed with the Polymerase Pfu Turbo (Stratagene; San Diego Calif.). The sequence of the entire fragment as well as the presence of only the desired mutations was verified. The resulting plasmid was introduced into electro competent cells of *E. coli* ΔadhE:: Frt-ΔldhA::Frt by transformation. The first integration event in the chromosome was selected on LB agar plates containing Kanamycin (25 or 50 mg/L). Correct insertions were verified by PCR using 2 primers, one located outside the region of insertion and one in the kanamycin gene (5'-aggcagttccataggatggc-3')(SEQ ID NO:22). Clones with the correct insertion were selected for resolution. They were sub-cultured twice in plain liquid LB at the desired temperature and serial dilutions were plated on LB-no salt-sucrose 10% plates. Clones that grew on sucrose containing plates were screened for the loss of the kanamycin resistance gene on LB-low salt agar medium and the lpdA gene replacement was verified by PCR and sequencing of the encompassing region. Sequence of the insertion region was verified, and is as described below. One clone (named 4-4-P1) with mutation Glu354Lys was selected. This clone was then transduced with P1 lysate of *E. coli* ΔPflB::Frt leading to strain ECKh-138 (ΔadhE ΔldhA ΔpflB ΔpdA::K.p.lpdA322).

The sequence of the ECKh-138 region encompassing the aceF and lpdA genes is shown in FIG. 35. The *K. pneumonia* lpdA gene is underlined, and the codon changed in the Glu354Lys mutant shaded. The protein sequence comparison of the native *E. coli* lpdA and the mutant *K. pneumonia* lpdA is shown in FIG. 36.

To evaluate the benefit of using *K. pneumoniae* lpdA in a BDO production strain, the host strains AB3 and ECKh-138 were transformed with plasmids expressing the entire BDO pathway from strong, inducible promoters. Specifically, *E. coli* sucCD, *P. gingivalis* sucD, *P. gingivalis* 4hbd were expressed on the medium copy plasmid pZA33, and *P. gingivalis* Cat2 and *C. acetobutylicum* AdhE2 were expressed on the high copy plasmid pZE13. These plasmids have been described in the literature (Lutz and H. Bujard, Nucleic Acids Res 25:1203-1210 (1997)), and their use for BDO pathway expression is described in Example XIII and WO2008/115840.

Cells were grown anaerobically at 37° C. in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 20 g/L glucose, 100 mM 3-(N-morpholino)propanesulfonic acid (MOPS) to improve the buffering capacity, 10 μg/mL thiamine, and the appropriate antibiotics. Microaerobic conditions were established by initially flushing capped anaerobic bottles with nitrogen for 5 minutes, then piercing the septum with a 23G needle following inoculation. The needle was kept in the bottle during growth to allow a small amount of air to enter the bottles. 0.25 mM IPTG was added when OD600 reached approximately 0.2 to induce the pathway genes, and samples taken for analysis every 24 hours following induction. The culture supernatants were analyzed for BDO, 4HB, and other by-products as described in Example II and in WO2008/115840. BDO and 4HB production in ECKh-138 was significantly higher after 48 hours than in AB3 or the host used in previous work, MG1655 ΔldhA (FIG. 37).

PDH promoter replacement. It was previously shown that the replacement of the pdhR repressor by a transcriptional fusion containing the Fnr binding site, one of the pflB promoters, and its ribosome binding site (RBS), thus leading to expression of the aceEF-lpd operon by an anaerobic promoter, should increase pdh activity anaerobically (Zhou et al., *Biotechnol. Lett.* 30:335-342 (2008)). A fusion containing the Fnr binding site, the pflB-p6 promoter and an RBS binding site were constructed by overlapping PCR. Two fragments were amplified, one using the primers aceE-upstream-RC (5'-tgacatgtaacacc-taccttctgtgcctgtgccagtggttgctgtgatataagaag-3')(SEQ ID NO:23) and pflBp6-Up-Nde (5'-ataataatacatatgaac-catgcgagttacgggcctataagccaggcg-3')(SEQ ID NO:24) and the other using primers aceE-EcoRV-EC (5'-agtttttcgatatctg-catcagacaccggcacattgaaacgg-3')(SEQ ID NO:25) and aceE-upstream (5'-ctggcacaggcacagaaggtaggtgttacatgtcagaacgtt-tacacaatgacgtggatc-3')(SEQ ID NO:26). The tw fragments were assembled by overlapping PCR, and the final DNA fragment was digested with the restriction enzymes NdeI and BamHI. This fragment was subsequently introduced upstream of the aceE gene of the *E. coli* operon using pRE118-V2 as described above. The replacement was done in strains ECKh-138 and ECKh-422. The nucleotide sequence encompassing the 5' region of the aceE gene was verified and is shown in FIG. 37. FIG. 37 shows the nucleotide sequence of 5' end of the aceE gene fused to the pflB-p6 promoter and ribosome binding site (RBS). The 5' italicized sequence shows the start of the aroP gene, which is transcribed in the opposite direction from the pdh operon. The 3' italicized sequence shows the start of the aceE gene. In upper case: pflB RBS. Underlined: FNR binding site. In bold: pflB-p6 promoter sequence.

lpdA promoter replacement. The promoter region containing the fnr binding site, the pflB-p6 promoter and the RBS of the pflB gene was amplified by PCR using chromosomal DNA template and primers aceF-pflBp6-fwd (5'-agacaaatcggttgccgtttgttaagccaggcgagatatgatctatatc-3')(SEQ ID NO:27) and lpdA-RB S-B-rev (5'-gagttttgatttcagtactcat-catgtaacacctaccttcttgctgtgatatag-3')(SEQ ID NO:28). Plasmid 2-4a was amplified by PCR using primers B-RBS-lpdA fwd (5'-ctatatcacagcaagaaggtaggtgttacatgatgagtactgaaat-caaaactc-3')(SEQ ID NO:29) and pflBp6-aceF-rev (5'-gatatagatcatatctcgcctggcttaacaaacggcaaccgatttgtct-3')(SEQ ID NO:30). The two resulting fragments were assembled using the BPS cloning kit (BPS Bioscience; San Diego Calif.). The resulting construct was sequenced verified and introduced into strain ECKh-439 using the pRE118-V2 method described above. The nucleotide sequence encompassing the aceF-lpdA region in the resulting strain ECKh-456 is shown in FIG. 39.

Figure 40:
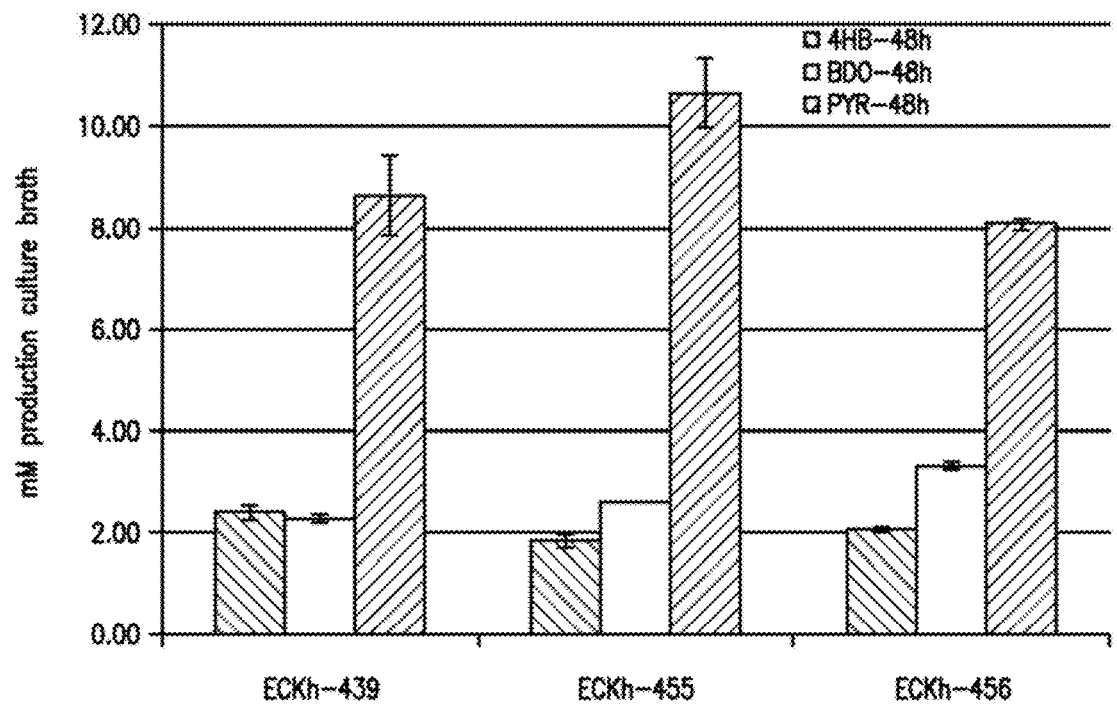
FIG. 40 shows the production of 4-hydroxybutyrate, BDO and pyruvate (left to right bars, respectively) for each of strains ECKh-439, ECKh-455 and ECKh-456.

The host strain ECKh-439 (ΔadhE ΔldhA ΔpflB ΔlpdA::K.p.lpdA322 Δmdh ΔarcA gltAR163L ackA fimD:: E. coli sucCD, P. gingivalis sucD, P. gingivalis 4hbd fimD:: M. bovis sucA, C. kluyveri 4hbd), the construction of which is described below, and the pdhR and lpdA promoter replacement derivatives ECKh-455 and ECKh-456, were tested for BDO production. The strains were transformed with pZS*13 containing P. gingivalis Cat2 and C. beijerinckii Ald to provide a complete BDO pathway. Cells were cultured in M9 minimal medium supplemented with 20 g/L glucose as described above. 48 hours after induction with 0.2 mM IPTG, the concentrations of BDO, 4HB, and pyruvate were as shown in FIG. 40. The promoter replacement strains produce slightly more BDO than the isogenic parent.

These results demonstrated that expression of pyruvate dehydrogenase increased production of BDO in BDO producing strains.

Example XV

BDO Producing Strains Expressing Citrate Synthase and Aconitase

This example describes increasing activity of citrate synthase and aconitase to increase production of BDO. An R163L mutation into gltA was found to improve BDO production. Additionally, an arcA knockout was used to improve BDO production.

Computationally, it was determined that flux through citrate synthase (CS) and aconitase (ACONT) is required to reach the maximum theoretical yield of 1,4-butanediol (see also WO2008/115840, WO 2009/023493, U.S. publication 2009/0047719, U.S. publication 2009/0075351). Lack of CS or ACONT activity would reduce the maximum theoretical yield by 14% under anaerobic conditions. In the presence of an external electron acceptor, the maximum yield is reduced by 9% or by 6% without flux through CS or ACONT assuming the absence or presence of PEPCK activity, respectively. As with pyruvate dehydrogenase (PDH), the importance of CS and ACONT is greatly amplified in the knockout strain background in which ADHEr, ASPT, LDH_D, MDH and PFLi are knocked out (design #439)(see WO 2009/023493 and U.S. publication 2009/0047719, which is incorporated herein by reference).

The minimal OptKnock strain design described in WO 2009/023493 and U.S. publication 2009/0047719 had one additional deletion beyond ECKh-138, the mdh gene, encoding malate dehydrogenase. Deletion of this gene is intended to prevent flux to succinate via the reductive TCA cycle. The mdh deletion was performed using the λ red homologous recombination method (Datsenko and Wanner, Proc. Natl. Acad. Sci. USA 97:6640-6645 (2000)). The following oligonucleotides were used to PCR amplify the chloramphenicol resistance gene (CAT) flanked by FRT sites from pKD3:

S-mdh-Kan
(SEQ ID NO: 31)
5'-TAT TGT GCA TAC AGA TGA ATT TTT ATG CAA ACA GTC
AGC CCT GAA GAA G<u>GG TGT AGG CTG GAG CTG CTT C</u>-3'

AS-mdh-Kan
(SEQ ID NO: 32)
5'-CAA AAA ACC GGA GTC TGT GCT CCG GTT TTT TAT TAT
CCG CTA ATC AAT TAC <u>ATA TGA ATA TCC TCC TTA G</u>-3'.

Figure 41A:
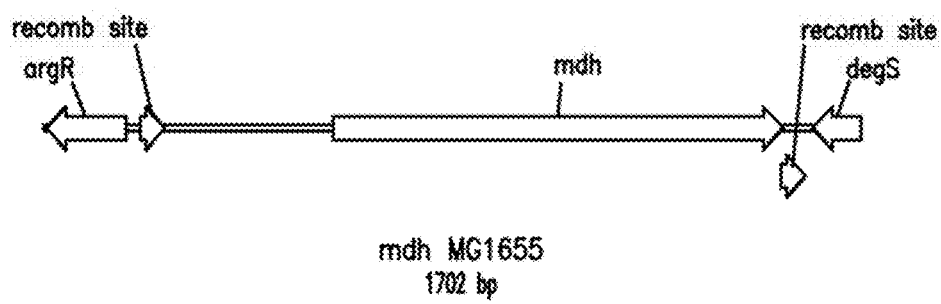
FIG. 41A shows a schematic of the recombination sites for deletion of the mdh gene.
Figure 41B:
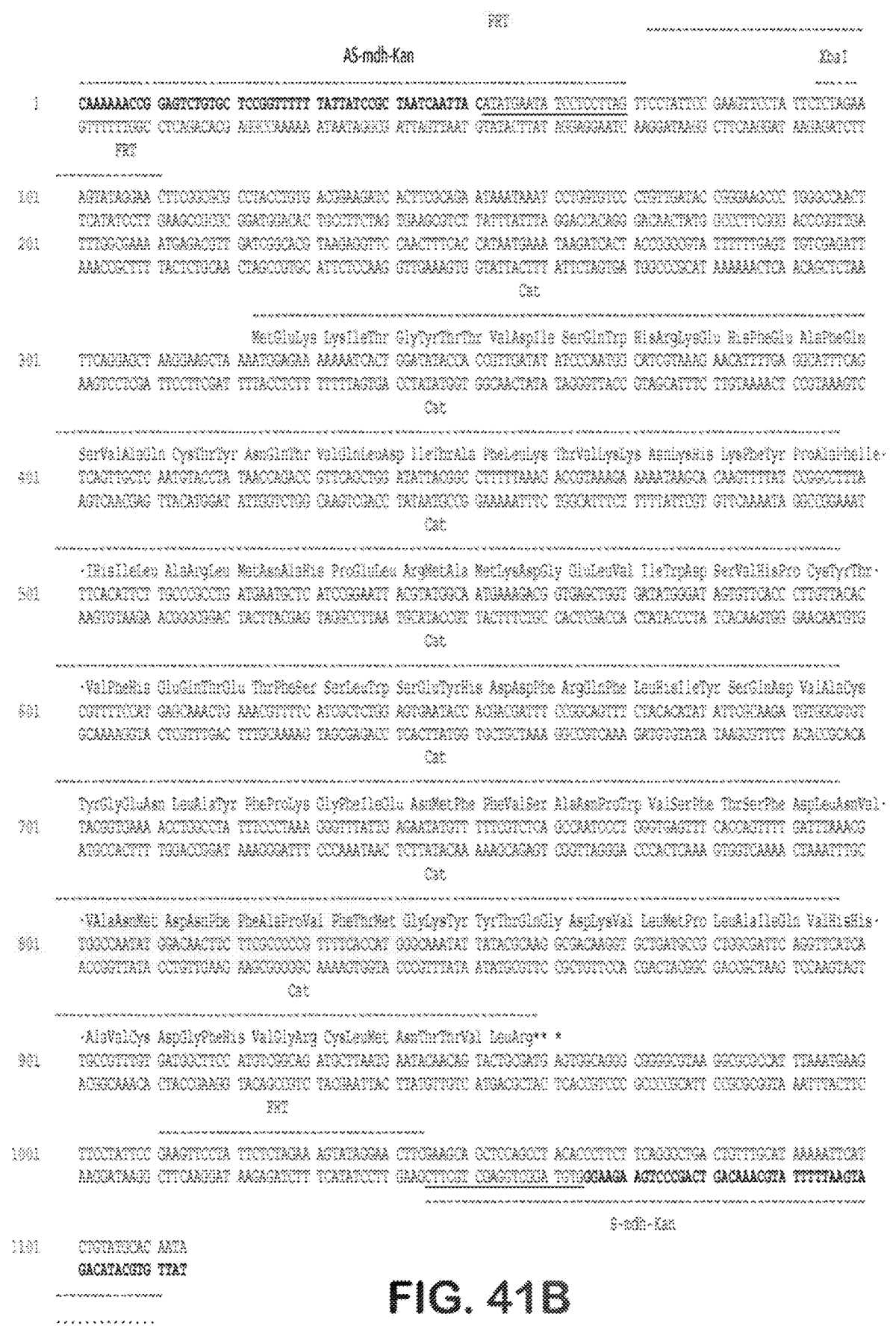

Underlined regions indicate homology to pKD3 plasmid and bold sequence refers to sequence homology upstream and downstream of the mdh ORF. After purification, the PCR product was electroporated into ECKh-138 electro-competent cells that had been transformed with pRedET (tet) and prepared according to the manufacturer's instructions (www.genebridges.com/gb/pdf/K001%20Q%20E%20BAC%20Modification%20Kit-version2.6-2007-screen.pdf). The PCR product was designed so that it integrated into the ECKh-138 genome at a region upstream of the mdh gene, as shown in FIG. 41.

Recombinants were selected for chloramphenicol resistance and streak purified. Loss of the mdh gene and insertion of CAT was verified by diagnostic PCR. To remove the CAT gene, a temperature sensitive plasmid pCP20 containing a FLP recombinase (Datsenko and Wanner, Proc. Natl. Acad. Sci. USA 97:6640-6645 (2000)) was transformed into the cell at 30° C. and selected for ampicillin resistance (AMP). Transformants were grown nonselectively at 42° C. overnight to thermally induce FLP synthesis and to cause lose of the plasmid. The culture was then streak purified, and individual colonies were tested for loss of all antibiotic resistances. The majority lost the FRT-flanked resistance gene and the FLP helper plasmid simultaneously. There was also a "FRT" scar leftover. The resulting strain was named ECKh-172.

CS and ACONT are not highly active or highly expressed under anaerobic conditions. To this end, the arcA gene, which encodes for a global regulator of the TCA cycle, was deleted. ArcA works during microaerobic conditions to induce the expression of gene products that allow the activity of central metabolism enzymes that are sensitive to low oxygen levels, aceE, pflB and adhE. It was shown that microaerobically, a deletion in arcA/arcB increases the specific activities of ldh, icd, gltA, mdh, and gdh genes (Salmon et al., J. Biol. Chem. 280:15084-15096 (2005); Shalel-Levanon et al., Biotechnol. Bioeng. 92(2):147-159 (2005). The upstream and downstream regions of the arcA gene of E. coli MG1655 were amplified by PCR using primers ArcA-up-EcoRI (5'-ataataatagaattcgtttgctacctaaattgc-caactaaatcgaaacagg-3')(SEQ ID NO:33) with ArcA-up-KpnI (5'-tattattatggtaccaatatcatgcagcaaacggtgcaacattgccg-3') (SEQ ID NO:34) and ArcA-down-EcoRI (5'-tgatctggaagaat-tcatcggctttaccaccgtcaaaaaaaacggcg-3')(SEQ ID NO:35) with ArcA-down-PstI (5'-ataaaaccctgcagcggaaacgaagttttatc-catttttggttacctg-3')(SEQ ID NO:36), respectively. These fragments were subsequently digested with the restriction enzymes EcoRI and KpnI (upstream fragment) and EcoRI and PstI (downstream). They were then ligated into the pRE118-V2 plasmid digested with PstI and KpnI, leading to plasmid pRE118-ΔarcA. The sequence of plasmid pRE118-ΔarcA was verified. pRE118-ΔarcA was introduced into electro-competent cells of E. coli strain ECKh-172 (ΔadhE ΔldhA ΔpflB ΔlpdA::K.p.lpdA322 Δmdh). After integration and resolution on LB-no salt-sucrose plates as described above, the deletion of the arcA gene in the chromosome of the resulting strain ECKh-401 was verified by sequencing and is shown in FIG. 42.

The gltA gene of *E. coli* encodes for a citrate synthase. It was previously shown that this gene is inhibited allosterically by NADH, and the amino acids involved in this inhibition have been identified (Pereira et al., *J. Biol. Chem.* 269(1):412-417 (1994); Stokell et al., *J. Biol. Chem.* 278 (37):35435-35443 (2003)). The gltA gene of *E. coli* MG1655 was amplified by PCR using primers gltA-up (5'-ggaagagaggctggtacccagaagccacagcagga-3')(SEQ ID NO:37) and gltA-PstI (5'-gtaatcactgcgtaagcgc-catgccccggcgttaattc-3')(SEQ ID NO:38). The amplified fragment was cloned into pRE118-V2 after digestion with KpnI and PstI. The resulting plasmid was called pRE118-gltA. This plasmid was then subjected to site directed mutagensis (SDM) using primers R163L-f (5'-at-tgccgcgttcctcctgctgtcga-3')(SEQ ID NO:39) and R163L-r (5'-cgacagcaggaggaacgcggcaat-3')(SEQ ID NO:40) to change the residue Arg 163 to a Lys residue. The sequence of the entire fragment was verified by sequencing. A variation of the λ red homologeous recombination method (Datsenko and Wanner, *Proc. Natl. Acad. Sci. USA* 97:6640-6645 (2000)) was used to replace the native gltA gene with the R163L mutant allele without leaving a Frt scar. The general recombination procedure is the same as used to make the mdh deletion described above. First, the strain ECKh-172 was made streptomycin resistant by introducing an rpsL null mutation using the λ red homologeous recombination method. Next, a recombination was done to replace the entire wild-type gltA coding region in this strain with a cassette comprised of a kanamycin resistance gene (kanR) and a wild-type copy of the *E. coli* rpsL gene. When introduced into an *E. coli* strain harboring an rpsL null mutation, the cassette causes the cells to change from resistance to the drug streptomycin to streptomycin sensitivity. DNA fragments were then introduced that included each of the mutant versions of the gltA gene along with appropriate homologous ends, and resulting colony growth was tested in the presence of streptomycin. This selected for strains in which the kanR/rpsL cassette had been replaced by the mutant gltA gene. Insertion of the mutant gene in the correct locus was confirmed by PCR and DNA sequencing analyses. The resulting strain was called ECKh-422, and has the genotype ΔadhE ΔldhA ΔpflB ΔlpdA::K.p.lpdA322 Δmdh ΔarcA gltAR163L. The region encompassing the mutated gltA gene of strain ECKh-422 was verified by sequencing, as shown in FIG. 43.

Crude extracts of the strains ECKh-401 and the gltAR163L mutant ECKh-422 were then evaluated for citrate synthase activity. Cells were harvested by centrifugation at 4,500 rpm (Beckman-Coulter, Allegera X-15R; Fullerton Calif.) for 10 min. The pellets were resuspended in 0.3 mL BugBuster (Novagen/EMD; San Diego Calif.) reagent with benzonase and lysozyme, and lysis proceeded for 15 minutes at room temperature with gentle shaking. Cell-free lysate was obtained by centrifugation at 14,000 rpm (Eppendorf centrifuge 5402; Hamburg Germany) for 30 min at 4° C. Cell protein in the sample was determined using the method of Bradford (Bradford, *Anal. Biochem.* 72:248-254 (1976)).

Citrate synthase activity was determined by following the formation of free coenzyme A (HS-CoA), which is released from the reaction of acetyl-CoA with oxaloacetate. The free thiol group of HS-CoA reacts with 5,5'-dithiobis-(2-nitrobenzoic acid) (DTNB) to form 5-thio-2-nitrobenzoic acid (TNB). The concentration of TNB is then monitored spectrophotometrically by measuring the absorbance at 410 nm (maximum at 412 nm). The assay mixture contained 100 mM Tris/HCl buffer (pH 7.5), 20 mM acetyl-CoA, 10 mM DTNB, and 20 mM oxaloacetate. For the evaluation of NADH inhibition, 0.4 mM NADH was also added to the reaction. The assay was started by adding 5 microliters of the cell extract, and the rate of reaction was measured by following the absorbance change over time. A unit of specific activity is defined as the μmol of product converted per minute per mg protein.

FIG. 44 shows the citrate synthase activity of wild type gltA gene product and the R163L mutant. The assay was performed in the absence or presence of 0.4 mM NADH.

Strains ECKh-401 and ECKh-422 were transformed with plasmids expressing the entire BDO pathway. *E. coli* sucCD, *P. gingivalis* sucD, *P. gingivalis* 4hbd, and *M. bovis* sucA were expressed on the low copy plasmid pZS*13, and *P. gingivalis* Cat2 and *C. acetobutylicum* AdhE2 were expressed on the medium copy plasmid pZE23. Cultures of these strains were grown microaerobically in M9 minimal medium supplemented with 20 g/L glucose and the appropriate antibiotics as described above. The 4HB and BDO concentrations at 48 hours post-induction averaged from duplicate cultures are shown in FIG. 45. Both are higher in ECKh-422 than in ECKh-401, demonstrating that the enhanced citrate synthase activity due to the gltA mutation results in increased flux to the BDO pathway.

The host strain modifications described in this section were intended to redirect carbon flux through the oxidative TCA cycle, which is consistent with the OptKnock strain design described in WO 2009/023493 and U.S. publication 2009/0047719. To demonstrate that flux was indeed routed through this pathway, $^{13}$C flux analysis was performed using the strain ECKh-432, which is a version of ECKh-422 in which the upstream pathway is integrated into the chromosome (as described in Example XVII). To complete the BDO pathway, *P. gingivalis* Cat2 and *C. beijerinckii* Ald were expressed from pZ S*13. Four parallel cultures were grown in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) containing 4 g/L total glucose of four different labeling ratios ($^{1-13}$C, only the first carbon atom in the glucose molecule is labeled with $^{13}$C; uniform-$^{13}$C, all carbon atoms are $^{13}$C):

1. 80 mol % unlabeled, 20 mol % uniform-$^{13}$C
2. 10 mol % unlabeled, 90 mol % uniform-$^{13}$C
3. 90 mol % $^{1-13}$C, 10 mol % uniform-$^{13}$C
4. 40 mol % $^{1-13}$C, 60 mol % uniform-$^{13}$C Parallel unlabeled cultures were grown in duplicate, from which frequent samples were taken to evaluate growth rate, glucose uptake rate, and product formation rates. In late exponential phase, the labeled cultures were harvested, the protein isolated and hydrolyzed to amino acids, and the label distribution of the amino acids analyzed by gas chromatography-mass spectrometry (GCMS) as described previously (Fischer and Sauer, *Eur. J. Biochem.* 270:880-891 (2003)). In addition, the label distribution of the secreted 4HB and BDO in the broth from the labeled cultures was analyzed by GCMS as described in WO2008115840. This data was collectively used to calculate the intracellular flux distribution using established methods (Suthers et al., *Metab. Eng.* 9:387-405 (2007)). The resulting central metabolic fluxes and associated 95% confidence intervals are shown in FIG. 46. Values are molar fluxes normalized to a glucose uptake rate of 1 mmol/hr. The result indicates that carbon flux is routed through citrate synthase in the oxidative direction, and that most of the carbon enters the BDO pathway rather than completing the TCA cycle. Furthermore, it confirms there is essentially no flux between malate and oxaloacetate due to the mdh deletion in this strain.

The advantage of using a knockout strain such as strains designed using OptKnock for BDO production (see WO 2009/023493 and U.S. publication 2009/0047719) can be observed by comparing typical fermentation profiles of ECKh-422 with that of the original strain ECKh-138, in which BDO is produced from succinate via the reductive TCA cycle (see FIG. 47). Fermentations were performed with 1 L initial culture volume in 2 L Biostat B+ bioreactors (Sartorius; Cedex France) using M9 minimal medium supplemented with 20 g/L glucose. The temperature was controlled at 37° C., and the pH was controlled at 7.0 using 2 M $NH_4OH$ or $Na_2CO_3$. Cells were grown aerobically to an OD600 of approximately 10, at which time the cultures were induced with 0.2 mM IPTG. One hour following induction, the air flow rate was reduced to 0.02 standard liters per minute for microaerobic conditions. The agitation rate was set at 700 rpm. Concentrated glucose was fed to maintain glucose concentration in the vessel between 0.5 and 10 g/L. Both strains were transformed with plasmids bearing the entire BDO pathway, as in the examples above. In ECKh-138, acetate, pyruvate, and 4HB dominate the fermentation, while with ECKh-422 BDO is the major product.

Example XVI

BDO Strains Expression Phosphoenolpyruvate Carboxykinase

This example describes the utilization of phosphoenolpyruvate carboxykinase (PEPCK) to enhance BDO production. The *Haemophilus influenza* PEPCK gene was used for heterologous expression.

Computationally, it was demonstrated that the ATP-generating conversion of oxaloacetate to phosphoenolpyruvate is required to reach the maximum theoretical yield of 1,4-butanediol (see also WO2008/115840, WO 2009/023493, U.S. publication 2009/0047719, U.S. publication 2009/0075351). Lack of PEPCK activity was shown to reduce the maximum theoretical yield of BDO by 12% assuming anaerobic conditions and by 3% assuming an external electron acceptor such as nitrate or oxygen is present.

In organisms such as *E. coli*, PEPCK operates in the gluconeogenic and ATP-consuming direction from oxaloacetate towards phosphoenolpyruvate. It has been hypothesized that kinetic limitations of PEPCK of *E. coli* prevent it from effectively catalyzing the formation of oxaloacetate from PEP. PEP carboxylase (PPC), which does not generate ATP but is required for efficient growth, is naturally utilized by *E. coli* to form oxaloacetate from phosphoenolpyruvate. Therefore, three non native PEPCK enzymes (Table 26) were tested for their ability to complement growth of a PPC mutant strain of *E. coli* in glucose minimal media.

TABLE 26

Sources of phosphoenolpyruvate carboxykinase sequences.

| PEPCK Source Strain | Accession Number, GenBank Reference Sequence |
|---|---|
| Haemophilus influenza | NC_000907.1 |
| Actinobacillus succinogenes | YP_001343536.1 |
| Mannheimia succiniciproducens | YP_089485.1 |

Growth complementation studies involved plasmid based expression of the candidate genes in Δppc mutant *E. coli* JW3978 obtained from the Keio collection (Baba et al., Molecular Systems Biology 2:2006.0008 (2006)). The genes were cloned behind the PA1lacO-1 promoter in the expression vectors pZA23 (medium copy) and pZE13 (high copy). These plasmids have been described previously (Lutz and Bujard, *Nucleic Acids Res.* 25:1203-1210 (1997)), and their use in expression BDO pathway genes has been described previously in WO2008115840.

Pre-cultures were grown aerobically in M9 minimal media with 4 g/L glucose. All pre-cultures were supplemented with aspartate (2 mM) to provide the Δppc mutants with a source for generating TCA cycle intermediates independent of PEPCK expression. M9 minimal media was also used in the test conditions with 4 g/L glucose, but no aspartate was added and IPTG was added to 0.5 mM. Table 27 shows the results of the growth complementation studies.

TABLE 27

Complementation of Δppc mutants with PEPCK from
*H. influenzae*, *A. succinogenes* and *M. succinoproducens*
when expressed from vectors pZA23 or pZE13.

| PEPCK Source Strain | Vector | Time (h) | $OD_{600}$ |
|---|---|---|---|
| H. influenzae | pZA23BB | 40 | 0.950 |
| Δppc Control | pZA23BB | 40 | 0.038 |
| A. succinogenes | pZA23BB | 40 | 0.055 |
| M. succinoproducens | pZA23BB | 40 | 0.214 |
| A. succinogenes | pZE13BB | 40 | 0.041 |
| M. succinoproducens | pZE13BB | 40 | 0.024 |
| Δppc Control | pZE13BB | 40 | 0.042 |

*Haemophilus influenza* PEPCK was found to complement growth in Δppc mutant *E. coli* best among the genes that were tested in the plasmid based screening. This gene was then integrated into the PPC locus of wild-type *E. coli* (MG1655) using the SacB counter selection method with pRE118-V2 discussed above (Gay et al., *J. Bacteriol.* 153: 1424-1431 (1983)). PEPCK was integrated retaining the *E. coli* native PPC promoter, but utilizing the non-native PEPCK terminator. The sequence of this region following replacement of ppc by *H. influenzae* pepck is shown in FIG. 48. The pepck coding region is underlined.

Figure 49:
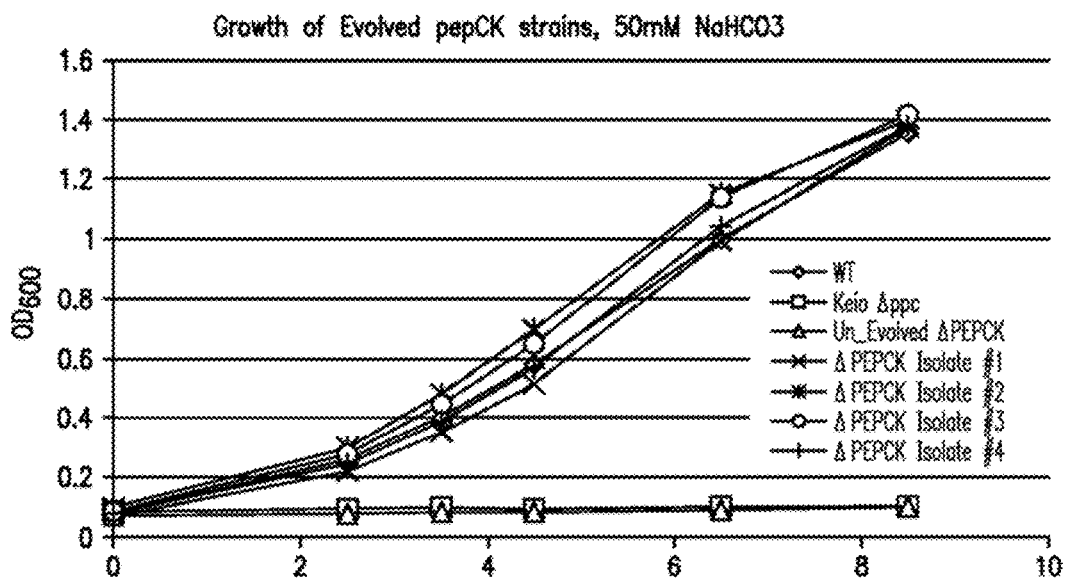
FIG. 49 shows growth of evolved pepCK strains grown in minimal medium containing 50 mM NaHCO$_3$.

Techniques for adaptive evolution were applied to improve the growth rate of the *E. coli* mutant (Δppc::H. inf pepCK). M9 minimal media with 4 g/L glucose and 50 mM sodium bicarbonate was used to culture and evolve this strain in an anaerobic environment. The high sodium bicarbonate concentration was used to drive the equilibrium of the PEPCK reaction toward oxaloacetate formation. To maintain exponential growth, the culture was diluted 2-fold whenever an OD600 of 0.5 was achieved. After about 100 generations over 3 weeks of adaptive evolution, anaerobic growth rates improved from about 8 h to that of wild type, about 2 h. Following evolution, individual colonies were isolated, and growth in anaerobic bottles was compared to that of the initial mutant and wild-type strain (see FIG. 49). M9 medium with 4 g/L glucose and 50 mM sodium bicarbonate was used.

The ppc/pepck gene replacement procedure described above was then repeated, this time using the BDO-producing strains ECKh-432 (ΔadhE ΔldhA ΔpflB ΔlpdA:: K.p.lpdA322 Δmdh ΔarcA gltAR163L ΔackA fimD:: *E. coli* sucCD, *P. gingivalis* sucD, *P. gingivalis* 4hbd fimD:: *M. bovis* sucA, *C. kluyveri* 4hbd) and ECKh-439 as the hosts. These strains contain the TCA cycle enhancements discussed above as well as the upstream pathway integrated in the chromosome. ECKh-439 is a derivative of ECKh-432 that has the ackA gene deleted, which encodes acetate kinase. This deletion was performed using the sacB counterselection method described above.

Figure 50:
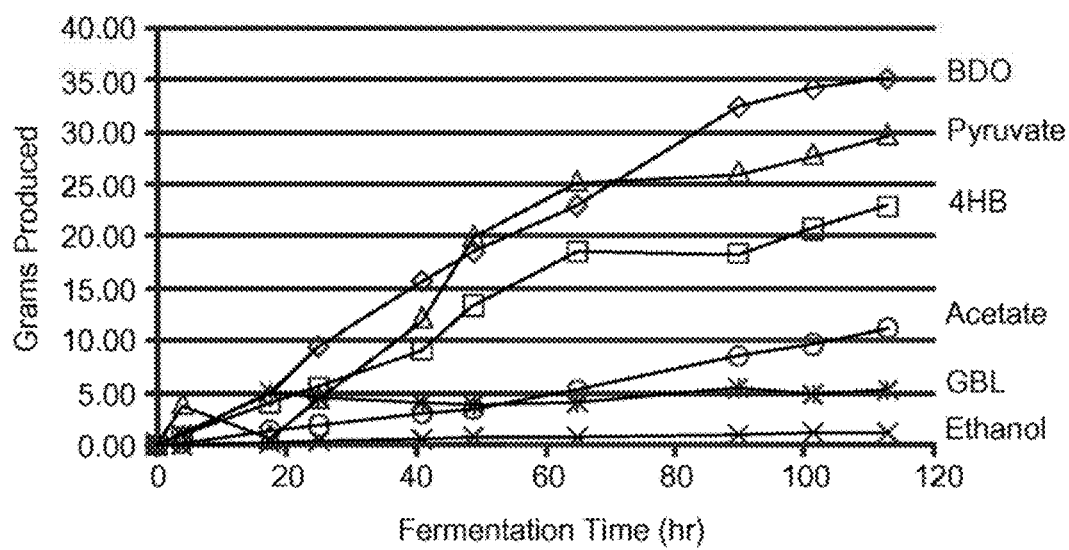
FIG. 50 shows product formation in strain ECKh-453 expressing *P. gingivalis* Cat2 and *C. beijerinckii* Ald on the plasmid pZ S*13. The products measured were 1,4-butanediol (BDO), pyruvate, 4-hydroxybutyrate (4HB), acetate, γ-butyrolactone (GBL) and ethanol.

The Δppc::H. inf pepCK derivative of ECKh-439, called ECKh-453, was run in a fermentation. The downstream BDO pathway was supplied by pZS*13 containing *P. gingivalis* Cat2 and *C. beijerinckii* Ald. This was performed with 1 L initial culture volume in 2 L Biostat B+ bioreactors (Sartorius) using M9 minimal medium supplemented with 20 g/L glucose and 50 mM NaHCO$_3$. The temperature was controlled at 37° C., and the pH was controlled at 7.0 using 2 M NH$_4$OH or Na$_2$CO$_3$. Cells were grown aerobically to an OD600 of approximately 2, at which time the cultures were induced with 0.2 mM IPTG. One hour following induction, the air flow rate was reduced to 0.01 standard liters per minute for microaerobic conditions. The agitation rate was initially set at 700 rpm. The aeration rate was gradually increased throughout the fermentation as the culture density increased. Concentrated glucose solution was fed to maintain glucose concentration in the vessel between 0.5 and 10 g/L. The product profile is shown in FIG. 50. The observed phenotype, in which BDO and acetate are produced in approximately a one-to-one molar ratio, is highly similar to that predicted in WO 2009/023493 for design #439 (ADHEr, ASPT, LDH_D, MDH, PFLi). The deletion targeting the ASPT reaction was deemed unnecessary as the natural flux through aspartate ammonia-lyase is low.

Figure 51:
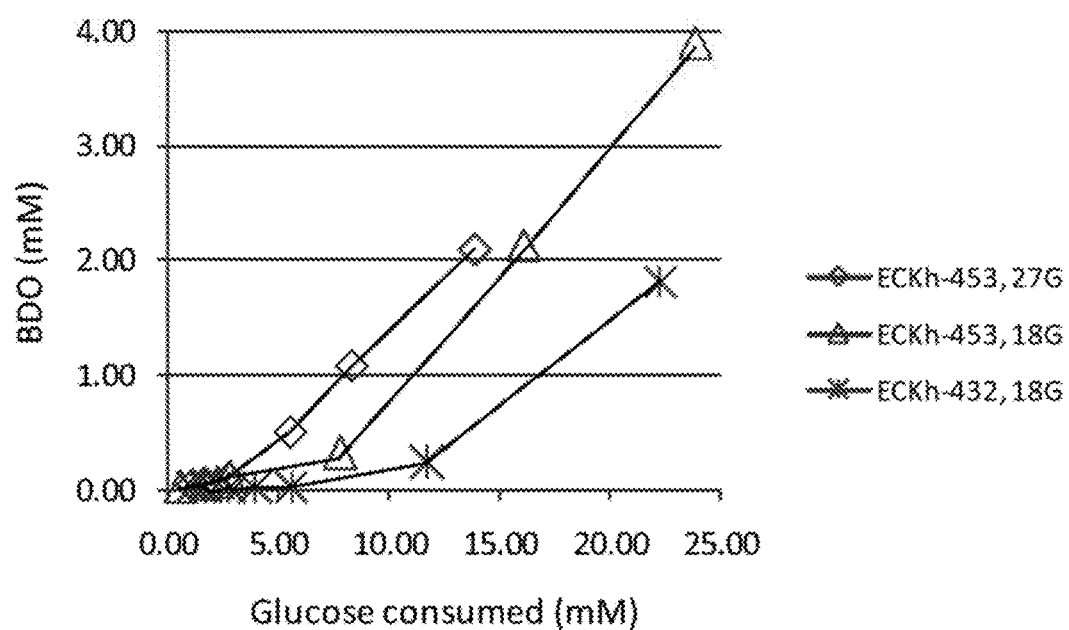
FIG. 51 shows BDO production of two strains, ECKh-453 and ECKh-432. Both contain the plasmid pZS*13 expressing *P. gingivalis* Cat2 and *C. beijerinckii* Ald. The cultures were grown under microaerobic conditions, with the vessels punctured with 27 or 18 gauge needles, as indicated.

A key feature of OptKnock strains is that production of the metabolite of interest is generally coupled to growth, and further, that, production should occur during exponential growth as well as in stationary phase. The growth coupling potential of ECKh-432 and ECKh-453 was evaluated by growth in microaerobic bottles with frequent sampling during the exponential phase. M9 medium containing 4 g/L glucose and either 10 mM NaHCO$_3$ (for ECKh-432) or 50 mM NaHCO$_3$ (for ECKh-453) was used, and 0.2 mM IPTG was included from inoculation. 18G needles were used for microaerobic growth of ECKh-432, while both 18G and 27G needles were tested for ECKh-453. The higher gauge needles result in less aeration. As shown in FIG. 51, ECKh-432 does not begin producing BDO until 5 g/L glucose has been consumed, corresponding to the onset of stationary phase. ECKh-453 produces BDO more evenly throughout the experiment. In addition, growth coupling improves as the aeration of the culture is reduced.

Example XVII

Integration of BDO Pathway Encoding Genes at Specific Integration Sites

This example describes integration of various BDO pathway genes into the fimD locus to provide more efficient expression and stability.

The entire upstream BDO pathway, leading to 4HB, has been integrated into the *E. coli* chromosome at the fimD locus. The succinate branch of the upstream pathway was integrated into the *E. coli* chromosome using the λ red homologous recombination method (Datsenko and Wanner, Proc. Natl. Acad. Sci. USA 97:6640-6645 (2000)). The recipient *E. coli* strain was ECKh-422 (ΔadhE ΔldhA ΔpflB ΔlpdA::K.p.lpdA322 Δmdh ΔarcA gltAR163L). A polycistronic DNA fragment containing a promoter, the sucCD gene, the sucD gene and the 4hbd gene and a terminator sequence was inserted into the AflIII site of the pKD3 plasmid. The following primers were used to amplify the operon together with the chloramphenicol marker from the plasmid. The underlined sequences are homologous to the target insertion site.

(SEQ ID NO: 41)
5'-<u>GTTTGCACGCTATAGCTGAGGTTGTTGTCTTCCAGCAACGTACCGTA
TA</u>CAATAGGCGTATCACGAGGCCCTTTC-3'

(SEQ ID NO: 42)
5'-<u>GCTACAGCATGTCACACGATCTCAACGGTCGGATGACCAATCTGGCT
GG</u>TATGGGAATTAGCCATGGTCC-3'

Following DpnI treatment and DNA electrophoresis, the purified PCR product was used to transform *E. coli* strain harboring plasmid pKD46. The candidate strain was selected on plates containing chloramphenicol. Genomic DNA of the candidate strain was purified. The insertion sequence was amplified and confirmed by DNA sequencing. The chloramphenicol-resistant marker was removed from chromosome by flipase. The nucleotide sequence of the region after insertion and marker removal is shown in FIG. 52.

The alpha-ketoglutarate branch of the upstream pathway was integrated into the chromosome by homologous recombination. The plasmid used in this modification was derived from vector pRE118-V2, as referenced in Example XIV, which contains a kanamycin-resistant gene, a gene encoding the levansucrase (sacB) and a R6K conditional replication ori. The integration plasmid also contained a polycistronic sequence with a promoter, the sucA gene, the *C. kluyveri* 4hbd gene, and a terminator being inserted between two 1.5-kb DNA fragments that are homologous to the flanking regions of the target insertion site. The resulting plasmid was used to transform *E. coli* strain. The integration candidate was selected on plates containing kanamycin. The correct integration site was verified by PCR. To resolve the antibiotic marker from the chromosome, the cells were selected for growth on medium containing sucrose. The final strain was verified by PCR and DNA sequencing. The nucleotide sequence of the chromosomal region after insertion and marker removal is shown in FIG. 53.

Figure 54:
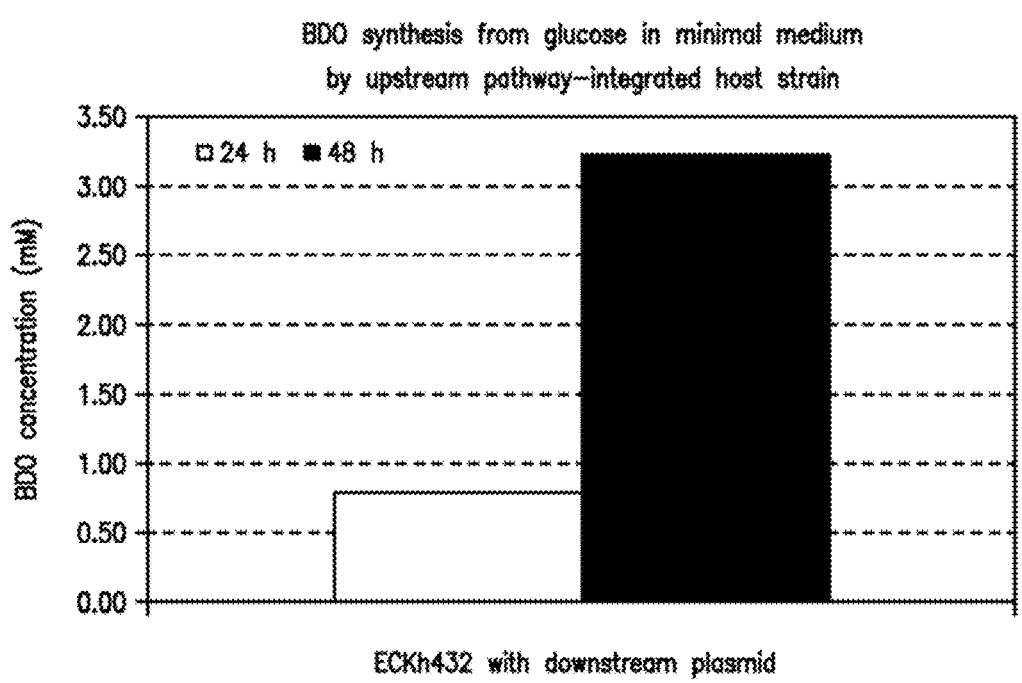
FIG. 54 shows BDO synthesis from glucose in minimal medium in the ECKh-432 strain having upstream BDO pathway encoding genes intergrated into the chromosome and containing a plasmid harboring downstream BDO pathway genes.

The resulting upstream pathway integration strain ECKh-432 was transformed with a plasmid harboring the downstream pathway genes. The construct was able to produce BDO from glucose in minimal medium (see FIG. 54).

Example XVIII

Use of a Non-Phosphotransferase Sucrose Uptake System to Reduce Pyruvate Byproduct Formation This example describes the utilization of a non-phosphotransferase (PTS) sucrose uptake system to reduce pyruvate as a byproduct in the conversion of sucrose to BDO.

Strains engineered for the utilization of sucrose via a phosphotransferase (PTS) system produce significant amounts of pyruvate as a byproduct. Therefore, the use of a non-PTS sucrose system can be used to decrease pyruvate formation because the import of sucrose would not be accompanied by the conversion of phosphoenolpyruvate (PEP) to pyruvate. This will increase the PEP pool and the flux to oxaloacetate through PPC or PEPCK.

Figure 55:
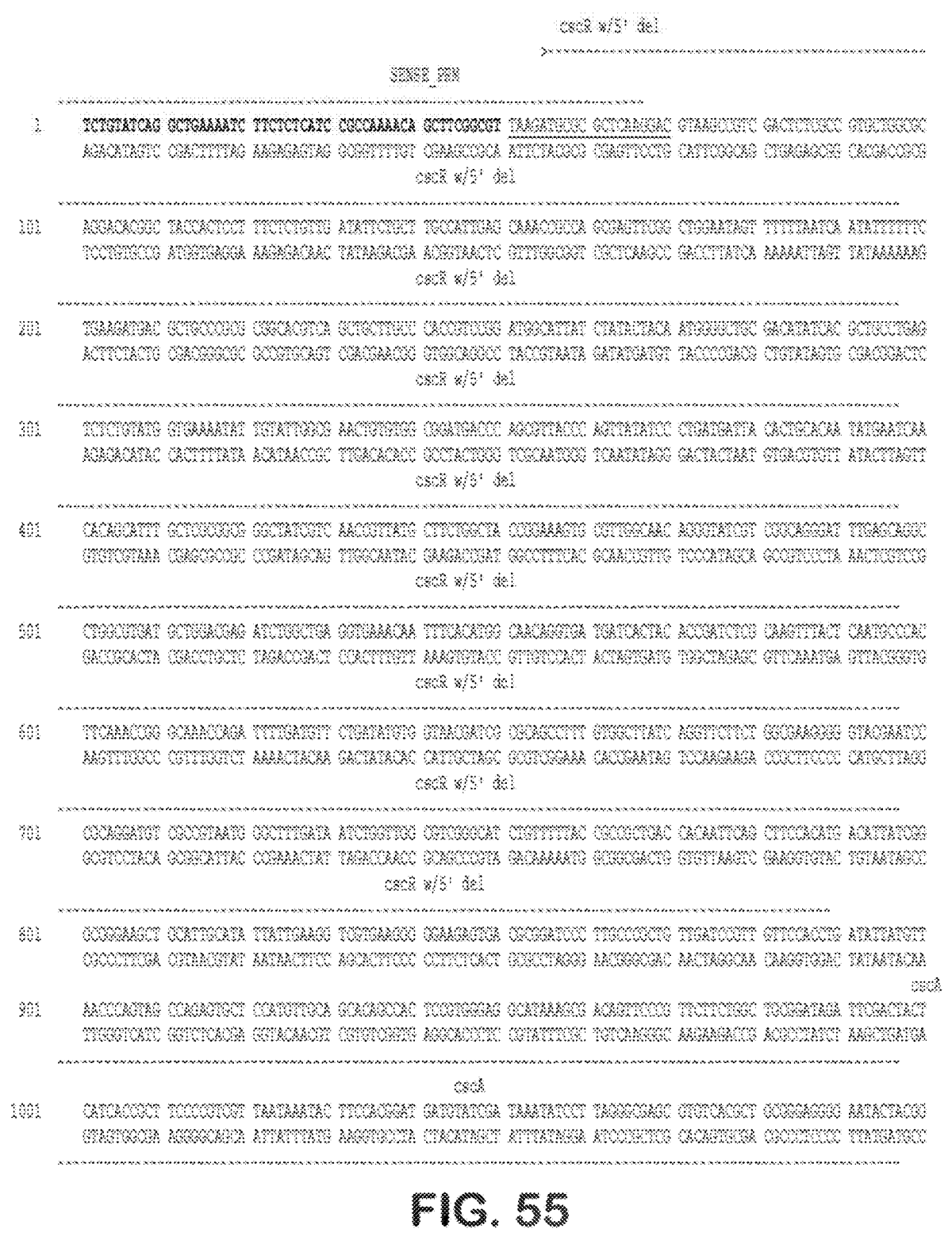
Figure 55:
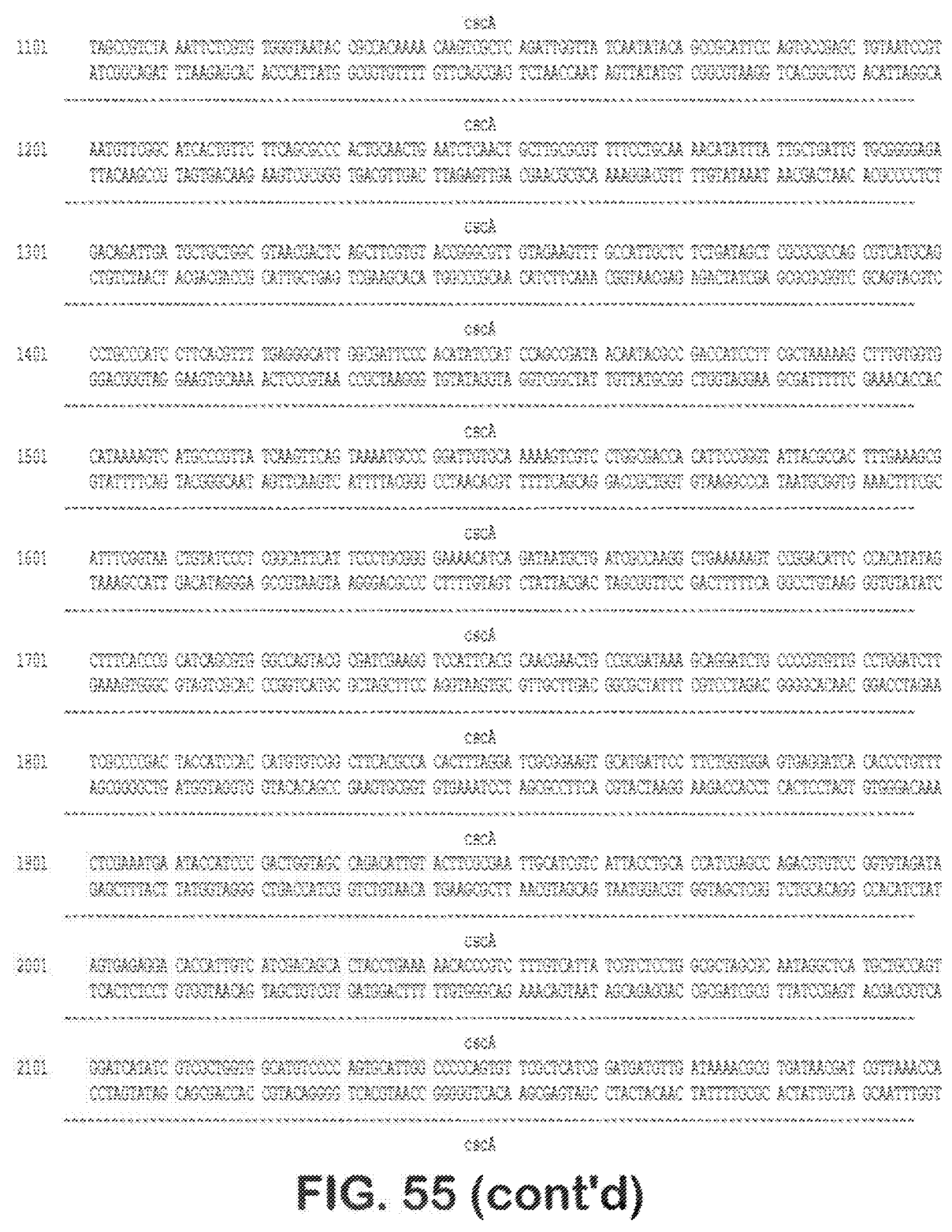
Figure 55:
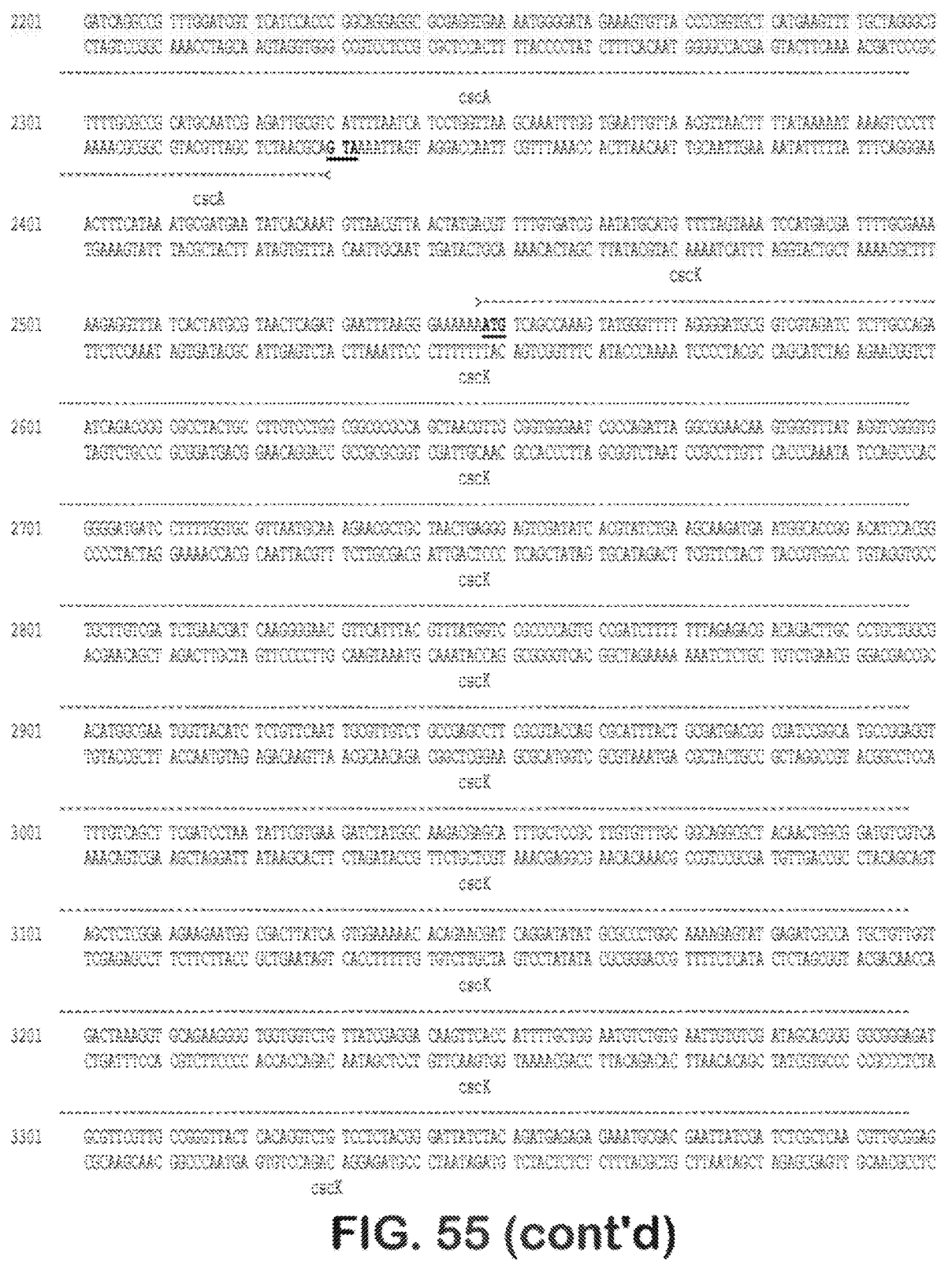
Figure 55:
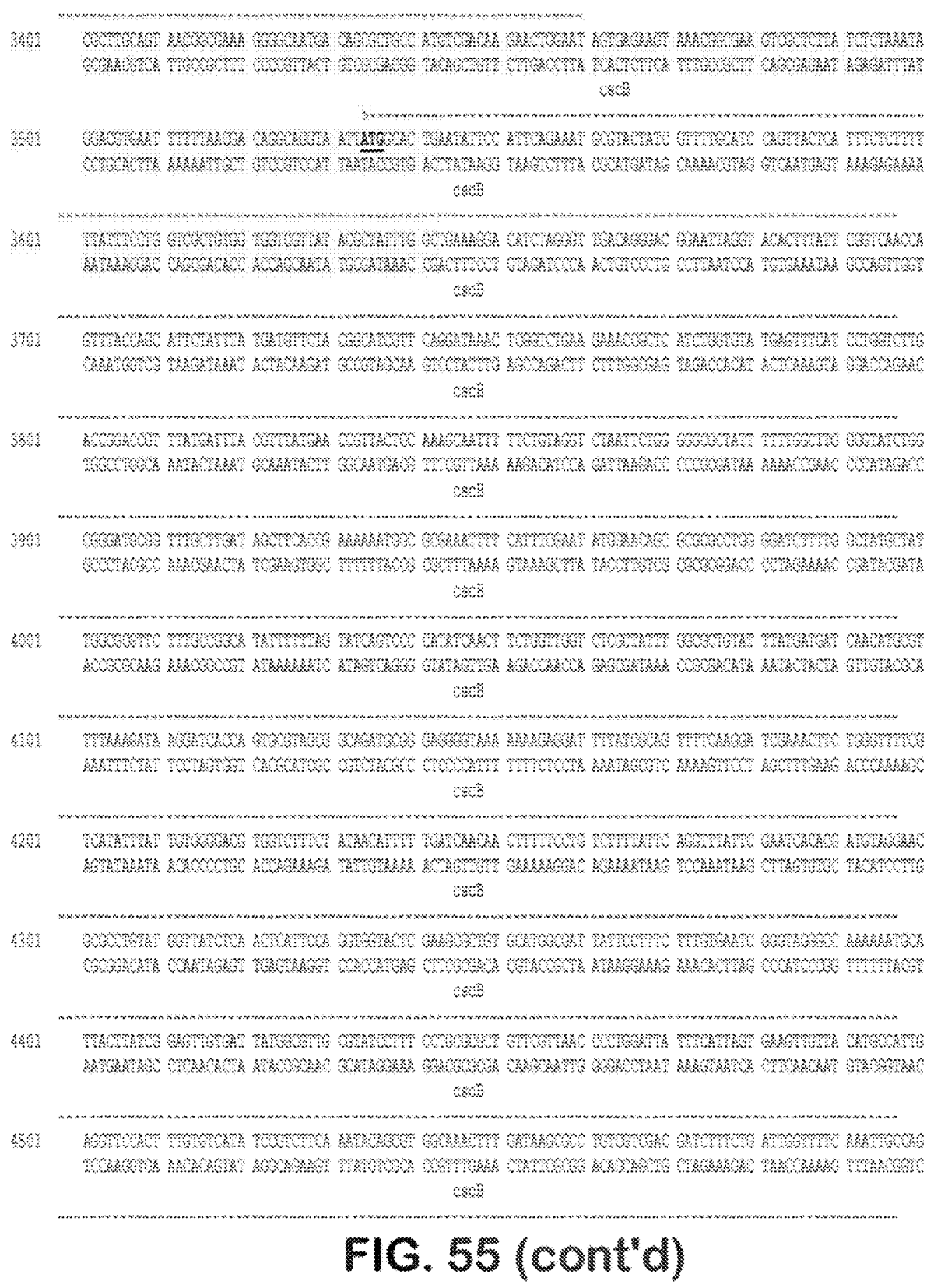
Figure 55:
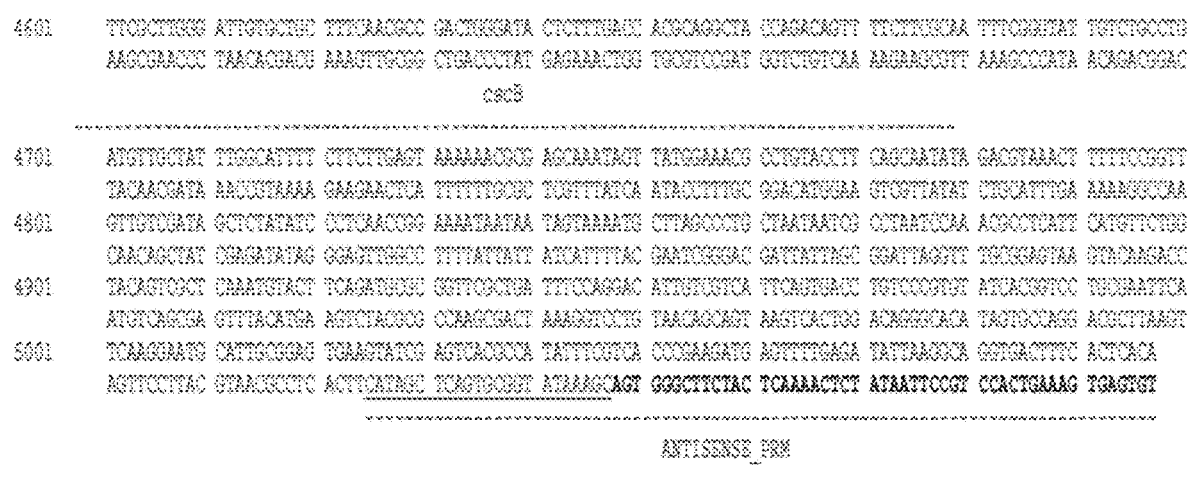

Insertion of a non-PTS sucrose operon into the rrnC region was performed. To generate a PCR product containing the non-PTS sucrose genes flanked by regions of homology to the rrnC region, two oligos were used to PCR amplify the csc genes from Mach1™ (Invitrogen, Carlsbad, Calif.). This strain is a descendent of W strain which is an *E. coli* strain known to be able to catabolize sucrose (Orencio-Trejo et al., *Biotechnology Biofuels* 1:8 (2008)). The sequence was derived from *E. coli* W strain KO11 (accession AY314757) (Shukla et al., *Biotechnol. Lett.* 26:689-693 (2004)) and includes genes encoding a sucrose permease (cscB), D-fructokinase (cscK), sucrose hydrolase (cscA), and a LacI-related sucrose-specific repressor (cscR). The first 53 amino acids of cscR was effectively removed by the placement of the AS primer. The sequences of the oligos were: rrnC 23S del S-CSC 5'-TGT GAG TGA AAG TCA CCT GCC TTA ATA TCT CAA AAC TCA TCT TCG GGT GA CGAAATATGGCGTGACTCGATAC-3' (SEQ ID NO:43) and rrnC 23S del AS-CSC 5'-TCT GTA TCA GGC TGA AAA TCT TCT CTC ATC CGC CAA AAC AGC TTC GGC GTTAAGATGCGCGCTCAAGGAC-3' (SEQ ID NO:44). Underlined regions indicate homology to the csc operon, and bold sequence refers to sequence homology upstream and downstream of the rrnC region. The sequence of the entire PCR product is shown in FIG. 55.

Figure 56:
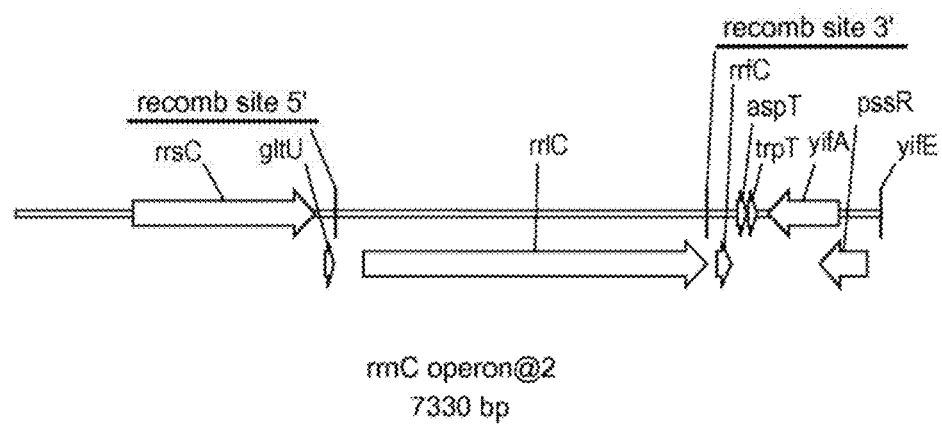
FIG. 56 shows a schematic diagram of the integrations site in the rrnC operon.

After purification, the PCR product was electroporated into MG1655 electrocompetent cells which had been transformed with pRedET (tet) and prepared according to manufacturer's instructions (www.genebridges.com/gb/pdf/K001%20Q%20E%20BAC%20Modification%20Kit-version2.6-2007-screen.pdf). The PCR product was designed so that it integrated into genome into the rrnC region of the chromosome. It effectively deleted 191 nucleotides upstream of rrlC (23S rRNA), all of the rrlC rRNA gene and 3 nucleotides downstream of rrlC and replaced it with the sucrose operon, as shown in FIG. 56.

Transformants were grown on M9 minimal salts medium with 0.4% sucrose and individual colonies tested for presence of the sucrose operon by diagnostic PCR. The entire rrnC::crcAKB region was transferred into the BDO host strain ECKh-432 by P1 transduction (Sambrook et al., *Molecular Cloning: A Laboratory Manual*, Third Ed., Cold Spring Harbor Laboratory, New York (2001), resulting in ECKh-463 (ΔadhE ΔldhA ΔpflB ΔpdA::K.p.lpdA322 Δmdh ΔarcA gltAR163L fimD::*E. coli* sucCD, *P. gingivalis* sucD, *P. gingivalis* 4hbd fimD:: *M. bovis* sucA, *C. kluyveri* 4hbd rrnC::cscAKB). Recombinants were selected by growth on sucrose and verified by diagnostic PCR.

Figure 57:
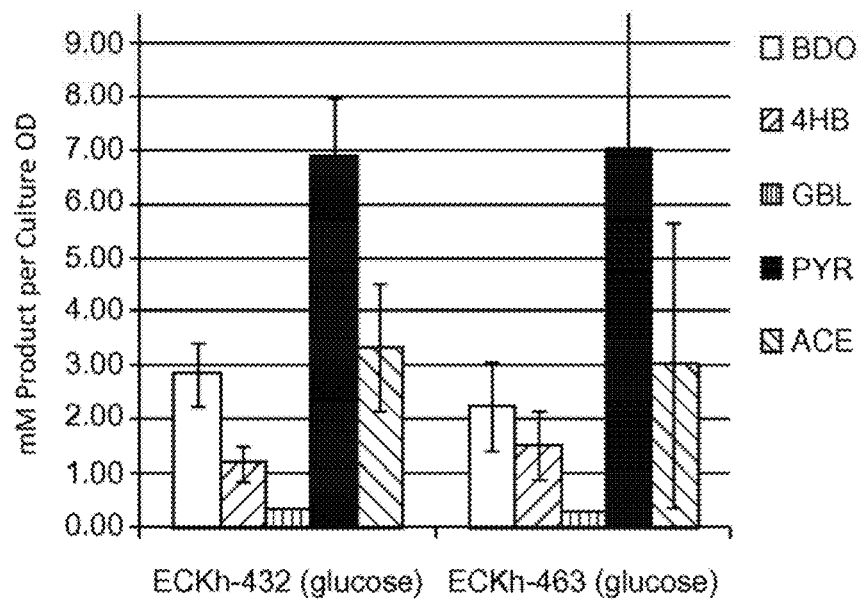
FIG. 57 shows average product concentration, normalized to culture OD600, after 48 hours of growth of strain ECKh-432 grown on glucose and strain ECKh-463 grown on sucrose. Both contain the plasmid pZ S*13 expressing *P. gingivalis* Cat2 and *C. beijerinckii* Ald. The data is for 6 replicate cultures of each strain. The products measured were 1,4-butanediol (BDO), 4-hydroxybutyrate (4HB), γ-butyrolactone (GBL), pyruvate (PYR) and acetate (ACE) (left to right bars, respectively).

ECKh-463 was transformed with pZS*13 containing *P. gingivalis* Cat2 and *C. beijerinckii* Ald to provide a complete BDO pathway. Cells were cultured in M9 minimal medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 10 g/L sucrose. 0.2 mM IPTG was present in the culture from the start. Anaerobic conditions were maintained using a bottle with 23G needle. As a control, ECKh-432 containing the same plasmid was cultured on the same medium, except with 10 g/L glucose instead of sucrose. FIG. 57 shows average product concentration, normalized to culture OD600, after 48 hours of growth. The data is for 6 replicate cultures of each strain. This demonstrates that BDO production from ECKh-463 on sucrose is similar to that of the parent strain on sucrose.

Example XIX

Summary of BDO Producing Strains

This example describes various BDO producing strains.
Table 28 summarizes various BDO producing strains disclosed above in Examples XII-XVIII.

TABLE 28

Summary of various BDO production strains.

| Strain # | Host Strain # | Host chromosome | Host Description | Plasmid-based |
|---|---|---|---|---|
| 1 | | ΔldhA | Single deletion derivative of *E. coli* MG1655 | *E. coli* sucCD, *P. gingivalis* sucD, *P. gingivalis* 4hbd, *P. gingivalis* Cat2, *C. acetobutylicum* AdhE2 |
| 2 | AB3 | ΔadhE ΔldhA ΔpflB | Succinate producing strain; derivative of *E. coli* MG1655 | *E. coli* sucCD, *P. gingivalis* sucD, *P. gingivalis* 4hbd, *P. gingivalis* Cat2, *C. acetobutylicum* AdhE2 |
| 3 | ECKh-138 | ΔadhE ΔldhA ΔpflB ΔlpdA::K.p.lpdA322 | Improvement of lpdA to increase pyruvate dehydrogenase flux | *E. coli* sucCD, *P. gingivalis* sucD, *P. gingivalis* 4hbd, *P. gingivalis* Cat2, *C. acetobutylicum* AdhE2 |
| 4 | ECKh-138 | ΔadhE ΔldhA ΔpflB ΔlpdA::K.p.lpdA322 | | *E. coli* sucCD, *P. gingivalis* sucD, *P. gingivalis* 4hbd, *C. acetobutylicum* buk1, *C. acetobutylicum* ptb, *C. acetobutylicum* AdhE2 |
| 5 | ECKh-401 | ΔadhE ΔldhA ΔpflB ΔlpdA::K.p.lpdA322 Δmdh ΔarcA | Deletions in mdh and arcA to direct flux through oxidative TCA cycle | *E. coli* sucCD, *P. gingivalis* sucD, *P. gingivalis* 4hbd, *P. gingivalis* Cat2, *C. acetobutylicum* AdhE2 |
| 6 | ECKh-401 | ΔadhE ΔldhA ΔpflB ΔlpdA::K.p.lpdA322 Δmdh ΔarcA | | *M. bovis* sucA, *E. coli* sucCD, *P. gingivalis* sucD, *P. gingivalis* 4hbd, *P. gingivalis* Cat2, *C. acetobutylicum* AdhE2 |

TABLE 28-continued

Summary of various BDO production strains.

| Strain # | Host Strain # | Host chromosome | Host Description | Plasmid-based |
|---|---|---|---|---|
| 7 | ECKh-422 | ΔadhE ΔldhA ΔpflB ΔlpdA::K.p.lpdA322 Δmdh ΔarcA gltAR163L | Mutation in citrate synthase to improve anaerobic activity | E. coli sucCD, P. gingivalis sucD, P. gingivalis 4hbd, P. gingivalis Cat2, C. acetobutylicum AdhE2 |
| 8 | ECKh-422 | ΔadhE ΔldhA ΔpflB ΔlpdA::K.p.lpdA322 Δmdh ΔarcA gltAR163L | | M. bovis sucA, E. coli sucCD, P. gingivalis sucD, P. gingivalis 4hbd, P. gingivalis Cat2, C. acetobutylicum AdhE2 |
| 9 | ECKh-422 | ΔadhE ΔldhA ΔpflB ΔlpdA::K.p.lpdA322 Δmdh ΔarcA gltAR163L | | M. bovis sucA, E. coli sucCD, P. gingivalis sucD, P. gingivalis 4hbd, P. gingivalis Cat2, C. beijerinckii Ald |
| 10 | ECKh-426 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd | Succinate branch of upstream pathway integrated into ECKh-422 | P. gingivalis Cat2, C. beijerinckii Ald |
| 11 | ECKh-432 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | Succinate and alpha-ketoglutarate upstream pathway branches integrated into ECKh-422 | P. gingivalis Cat2, C. beijerinckii Ald |
| 12 | ECKh-432 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | | C. acetobutylicum buk1, C. acetobutylicum ptb, C. beijerinckii Ald |
| 13 | ECKh-439 | ΔadhE ΔldhA ΔpflB ΔlpdA::K.p.lpdA322 Δmdh ΔarcA gltAR163L ΔackA fimD:: E. coli sucCD, P. gingivalis sucD, P. gingivalis 4hbd fimD:: M. bovis sucA, C. kluyveri 4hbd | Acetate kinase deletion of ECKh-432 | P. gingivalis Cat2, C. beijerinckii Ald |
| 14 | ECKh-453 | ΔadhE ΔldhA ΔpflB ΔlpdA::K.p.lpdA322 Δmdh ΔarcA gltAR163L ΔackA Δppc::H.i.ppck fimD:: E. coli sucCD, P. gingivalis sucD, P. gingivalis 4hbd fimD:: M. bovis sucA, C. kluyveri 4hbd | Acetate kinase deletion and PPC/PEPCK replacement of ECKh-432 | P. gingivalis Cat2, C. beijerinckii Ald |
| 15 | ECKh-456 | ΔadhE ΔldhA ΔpflB ΔlpdA::fnr-pflB6-K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd | Replacement of lpdA promoter with anaerobic promoter in ECKh-432 | P. gingivalis Cat2, C. beijerinckii Ald |
| 16 | ECKh-455 | ΔadhE ΔldhA ΔpflB ΔlpdA::K.p.lpdA322 ΔpdhR:: fnr-pflB6 Δmdh ΔarcA gltAR163L fimD:: E. coli sucCD, P. gingivalis sucD, P. gingivalis 4hbd fimD:: M. bovis sucA, C. kluyveri 4hbd | Replacement of pdhR and aceEF promoter with anaerobic promoter in ECKh-432 | P. gingivalis Cat2, C. beijerinckii Ald |
| 17 | ECKh-459 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd fimD:: C. acetobutylicum buk1, C. acetobutylicum ptb | Integration of BK/PTB into ECKh-432 | C. beijerinckii Ald |
| 18 | ECKh-459 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd fimD:: C. acetobutylicum buk1, C. acetobutylicum ptb | | C. beijerinckii Ald, G. thermoglucosidasius adh1 |

TABLE 28-continued

Summary of various BDO production strains.

| Strain # | Host Strain # | Host chromosome | Host Description | Plasmid-based |
|---|---|---|---|---|
| 19 | ECKh-463 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB | Non-PTS sucrose genes inserted into ECKh-432 | P. gingivalis Cat2, C. beijerinckii Ald |
| 20 | ECKh-463 | ΔadhE ΔldhA ΔpflB ΔlpdA::K.p.lpdA322 Δmdh ΔarcA gltAR163L fimD:: E. coli sucCD, P. gingivalis sucD, P. gingivalis 4hbd fimD:: M. bovis sucA, C. kluyveri 4hbd rrnC::cscAKB | | C. acetobutylicum buk1, C. acetobutylicum ptb, C. beijerinckii Ald |

The strains summarized in Table 28 are as follows. Strain 1: Single deletion derivative of E. coli MG1655, with deletion of endogenous ldhA; plasmid expression of E. coli sucCD, P. gingivalis sucD, P. gingivalis 4hbd, P. gingivalis Cat2, C. acetobutylicum AdhE2. Strain 2: Host strain AB3, a succinate producing strain, derivative of E. coli MG1655, with deletions of endogenous adhE ldhA pflB; plasmid expression of E. coli sucCD, P. gingivalis sucD, P. gingivalis 4hbd, P. gingivalis Cat2, C. acetobutylicum AdhE2.

Strain 3: Host strain ECKh-138, deletion of endogenous adhE, ldhA, pflB, deletion of endogenous lpdA and chromosomal insertion of Klebsiella pneumoniae pdA with a Glu354Lys mutation at the lpdA locus; plasmid expression of E. coli sucCD, P. gingivalis sucD, P. gingivalis 4hbd, P. gingivalis Cat2, C. acetobutylicum AdhE2; strain provides improvement of lpdA to increase pyruvate dehydrogenase flux. Strain 4: Host strain ECKh-138, deletion of endogenous adhE, ldhA, pflB, and lpdA, chromosomal insertion of Klebsiella pneumoniae lpdA with a Glu354Lys mutation; plasmid expression E. coli sucCD, P. gingivalis sucD, P. gingivalis 4hbd, C. acetobutylicum buk1, C. acetobutylicum ptb, C. acetobutylicum AdhE2.

Strain 5: Host strain ECKh-401, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA; plasmid expression of E. coli sucCD, P. gingivalis sucD, P. gingivalis 4hbd, P. gingivalis Cat2, C. acetobutylicum AdhE2; strain has deletions in mdh and arcA to direct flux through oxidative TCA cycle. Strain 6: host strain ECKh-401, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA; plasmid expression of M. bovis sucA, E. coli sucCD, P. gingivalis sucD, P. gingivalis 4hbd, P. gingivalis Cat2, C. acetobutylicum AdhE2.

Strain 7: Host strain ECKh-422, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of E. coli sucCD, P. gingivalis sucD, P. gingivalis 4hbd, P. gingivalis Cat2, C. acetobutylicum AdhE2; strain has mutation in citrate synthase to improve anaerobic activity. Strain 8: strain ECKh-422, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of M. bovis sucA, E. coli sucCD, P. gingivalis sucD, P. gingivalis 4hbd, P. gingivalis Cat2, C. acetobutylicum AdhE2. Strain 9: host strain ECKh-422, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant; plasmid expression of M. bovis sucA, E. coli sucCD, P. gingivalis sucD, P. gingivalis 4hbd, P. gingivalis Cat2, C. beijerinckii Ald.

Strain 10: host strain ECKh-426, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant, chromosomal insertion at the fimD locus of E. coli sucCD, P. gingivalis sucD, P. gingivalis 4hbd; plasmid expression of P. gingivalis Cat2, C. beijerinckii Ald; strain has succinate branch of upstream pathway integrated into strain ECKh-422 at the fimD locus. Strain 11: host strain ECKh-432, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant, chromosomal insertion at the fimD locus of E. coli sucCD, P. gingivalis sucD, P. gingivalis 4hbd, chromosomal insertion at thefimD locus of M. bovis sucA, C. kluyveri 4hbd; plasmid expression of P. gingivalis Cat2, C. beijerinckii Ald; strain has succinate and alpha-ketoglutarate upstream pathway branches integrated into ECKh-422. Strain 12: host strain ECKh-432, deletion of endogenous adhE, ldhA, pflB, deletion of endogenous lpdA and chromosomal insertion of Klebsiella pneumoniae lpdA with a Glu354Lys mutation at the lpdA locus, deletion of endogenous mdh and arcA, chromosomal replacement of gltA with gltA Arg163Leu mutant, chromosomal insertion at the fimD locus of E. coli sucCD, P. gingivalis sucD, P. gingivalis 4hbd, chromosomal insertion at the fimD locus of M. bovis sucA, C. kluyveri 4hbd; plasmid expression of C. acetobutylicum buk 1, C. acetobutylicum ptb, C. beijerinckii Ald.

Strain 13: host strain ECKh-439, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, deletion of endogenous ackA, chromosomal insertion at the finiD locus of *E. coli* sucCD, *P. gingivalis* sucD, *P. gingivalis* 4hbd, chromosomal insertion at the finiD locus of *M. bovis* sucA, *C. kluyveri* 4hbd; plasmid expression of *P. gingivalis* Cat2, *C. beijerinckii* Ald; strain has acetate kinase deletion in strain ECKh-432. Strain 14: host strain ECKh-453, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, deletion of endogenous ackA, deletion of endogenous ppc and insertion of *Haemophilus influenza* ppck at the ppc locus, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd; plasmid expression of *P. gingivalis* Cat2, *C. beijerinckii* Ald; strain has acetate kinase deletion and PPC/PEPCK replacement in strain ECKh-432.

Strain 15: host strain ECKh-456, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at thefimD locus of *E. coli* sucCD, *P. gingivalis* sucD, *P. gingivalis* 4hbd, chromosomal insertion at thefimD locus of *M. bovis* sucA, *C. kluyveri* 4hbd, replacement of lpdA promoter with fnr binding site, pflB-p6 promoter and RBS of pflB; plasmid expression of *P. gingivalis* Cat2, *C. beijerinckii* Ald; strain has replacement of lpdA promoter with anaerobic promoter in strain ECKh-432. Strain 16: host strain ECKh-455, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at thefimD locus of *E. coli* sucCD, *P. gingivalis* sucD, *P. gingivalis* 4hbd, chromosomal insertion at thefimD locus of *M. bovis* sucA, *C. kluyveri* 4hbdI, replacement of pdhR and aceEF promoter with fnr binding site, pflB-p6 promoter and RBS of pflB; plasmid expression of *P. gingivalis* Cat2, *C. beijerinckii* Ald; strain has replacement of pdhR and aceEF promoter with anaerobic promoter in ECKh-432.

Strain 17: host strain ECKh-459, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at thefimD locus of *E. coli* sucCD, *P. gingivalis* sucD, *P. gingivalis* 4hbd, chromosomal insertion at thefimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald; strain has integration of BK/PTB into strain ECKh-432. Strain 18: host strain ECKh-459, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, chromosomal insertion at the fimD locus of *C. acetobutylicum* buk1, *C. acetobutylicum* ptb; plasmid expression of *C. beijerinckii* Ald, *G. thermoglucosidasius* adh1.

Strain 19: host strain ECKh-463, deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon genes sucrose permease (cscB), D-fructokinase (cscK), sucrose hydrolase (cscA), and a LacI-related sucrose-specific repressor (cscR); plasmid expression of *P. gingivalis* Cat2, *C. beijerinckii* Ald; strain has non-PTS sucrose genes inserted into strain ECKh-432. Strain 20: host strain ECKh-463 deletion of endogenous adhE, ldhA, pflB, deletion of endogenous lpdA and chromosomal insertion of *Klebsiella pneumoniae* lpdA with a Glu354Lys mutation at the lpdA locus, deletion of endogenous mdh and arcA, chromosomal replacement of gltA with gltA Arg163Leu mutant, chromosomal insertion at the fimD locus of *E. coli* sucCD, *P. gingivalis* sucD, *P. gingivalis* 4hbd, chromosomal insertion at the fimD locus of *M. bovis* sucA, *C. kluyveri* 4hbd, insertion at the rrnC locus of non-PTS sucrose operon; plasmid expression of *C. acetobutylicum* buk1, *C. acetobutylicum* ptb, *C. beijerinckii* Ald.

In addition to the BDO producing strains disclosed herein, including those disclosed in Table 28, it is understood that additional modifications can be incorporated that further increase production of BDO and/or decrease undesirable byproducts. For example, a BDO producing strain, or a strain of Table 28, can incorporate additional knockouts to further increase the production of BDO or decrease an undesirable byproduct. Exemplary knockouts have been described previously (see U.S. publication 2009/0047719). Such knockout strains include, but are not limited to, one ore more genes selected from ADHEr, NADH6; ADHEr, PPCK; ADHEr, SUCD4; ADHEr, ATPS4r; ADHEr, FUM; ADHEr, MDH; ADHEr, PFLi, PPCK; ADHEr, PFLi, SUCD4; ADHEr, ACKr, NADH6; ADHEr, NADH6, PFLi; ADHEr, ASPT, MDH; ADHEr, NADH6, PPCK; ADHEr, PPCK, THD2; ADHEr, ATPS4r, PPCK; ADHEr, MDH, THD2; ADHEr, FUM, PFLi; ADHEr, PPCK, SUCD4; ADHEr, GLCpts, PPCK; ADHEr, GLUDy, MDH; ADHEr, GLUDy, PPCK; ADHEr, FUM, PPCK; ADHEr, MDH, PPCK; ADHEr, FUM, GLUDy; ADHEr, FUM, HEX1; ADHEr, HEX1, PFLi; ADHEr, HEX1, THD2; ADHEr, FRD2, LDH_D, MDH; ADHEr, FRD2, LDH_D, ME2; ADHEr, MDH, PGL, THD2; ADHEr, G6PDHy, MDH, THD2; ADHEr, PFLi, PPCK, THD2; ADHEr, ACKr, AKGD, ATPS4r; ADHEr, GLCpts, PFLi, PPCK; ADHEr, ACKr, ATPS4r, SUCOAS; ADHEr, GLUDy, PFLi, PPCK; ADHEr, ME2, PFLi, SUCD4; ADHEr, GLUDy, PFLi, SUCD4; ADHEr, ATPS4r, LDH_D, SUCD4; ADHEr, FUM, HEX1, PFLi; ADHEr, MDH, NADH6, THD2; ADHEr, ATPS4r, MDH, NADH6; ADHEr, ATPS4r, FUM, NADH6; ADHEr, ASPT, MDH, NADH6; ADHEr, ASPT, MDH, THD2; ADHEr, ATPS4r, GLCpts, SUCD4; ADHEr, ATPS4r, GLUDy, MDH; ADHEr, ATPS4r, MDH, PPCK; ADHEr, ATPS4r, FUM, PPCK; ADHEr, ASPT, GLCpts, MDH; ADHEr, ASPT, GLUDy, MDH; ADHEr, ME2, SUCD4, THD2; ADHEr, FUM, PPCK, THD2; ADHEr, MDH, PPCK, THD2; ADHEr, GLUDy, MDH, THD2; ADHEr, HEX1, PFLi, THD2; ADHEr, ATPS4r, G6PDHy, MDH; ADHEr, ATPS4r, MDH, PGL; ADHEr, ACKr, FRD2, LDH_D; ADHEr, ACKr, LDH_D, SUCD4; ADHEr, ATPS4r, FUM, GLUDy; ADHEr, ATPS4r, FUM, HEX1; ADHEr, ATPS4r, MDH, THD2; ADHEr, ATPS4r, FRD2, LDH_D; ADHEr, ATPS4r, MDH, PGDH; ADHEr, GLCpts, PPCK, THD2; ADHEr, GLUDy, PPCK, THD2; ADHEr, FUM, HEX1, THD2; ADHEr, ATPS4r, ME2, THD2; ADHEr, FUM, ME2, THD2; ADHEr, GLCpts, GLUDy, PPCK; ADHEr, ME2, PGL, THD2; ADHEr, G6PDHy, ME2, THD2; ADHEr, ATPS4r, FRD2, LDH_D, ME2; ADHEr, ATPS4r, FRD2, LDH_D, MDH; ADHEr, ASPT, LDH_D, MDH, PFLi; ADHEr, ATPS4r, GLCpts, NADH6, PFLi; ADHEr, ATPS4r, MDH, NADH6, PGL; ADHEr, ATPS4r, G6PDHy, MDH, NADH6; ADHEr, ACKr, FUM, GLUDy, LDH_D; ADHEr, ACKr, GLUDy, LDH_D, SUCD4; ADHEr, ATPS4r, G6PDHy, MDH, THD2; ADHEr, ATPS4r, MDH, PGL, THD2; ADHEr, ASPT, G6PDHy, MDH, PYK; ADHEr, ASPT, MDH, PGL, PYK; ADHEr, ASPT, LDH_D, MDH, SUCOAS; ADHEr, ASPT, FUM, LDH_D, MDH; ADHEr, ASPT, LDH_D, MALS, MDH; ADHEr, ASPT, ICL, LDH_D, MDH; ADHEr, FRD2, GLUDy, LDH_D, PPCK; ADHEr, FRD2, LDH_D, PPCK, THD2; ADHEr, ACKr, ATPS4r, LDH_D, SUCD4; ADHEr, ACKr, ACS, PPC, PPCK; ADHEr, GLUDy, LDH_D, PPC, PPCK; ADHEr, LDH_D, PPC, PPCK, THD2; ADHEr, ASPT, ATPS4r, GLCpts, MDH; ADHEr, G6PDHy, MDH, NADH6, THD2; ADHEr, MDH, NADH6, PGL, THD2; ADHEr, ATPS4r, G6PDHy, GLCpts, MDH; ADHEr, ATPS4r, GLCpts, MDH, PGL; ADHEr, ACKr, LDH_D, MDH, SUCD4.

Table 29 shows the reactions of corresponding genes to be knocked out of a host organism such as *E. coli*. The corresponding metabolite corresponding to abbreviations in Table 29 are shown in Table 30.

TABLE 29

Corresponding genes to be knocked out to prevent a particular reaction from occurring in *E. coli*.

| Reaction Abbreviation | Reaction Stoichiometry* | Genes Encoding the Enzyme(s) Catalyzing Each Reaction& |
|---|---|---|
| ACKr | [c]: ac + atp <==> actp + adp | (b3115 or b2296 or b1849) |
| ACS | [c]: ac + atp + coa --> accoa + amp + ppi | b4069 |
| ACt6 | ac[p] + h[p] <==> ac[c] + h[c] | Non-gene associated |
| ADHEr | [c]: etoh + nad <==> acald + h + nadh | (b0356 or b1478 or b1241) |
|  | [c]: acald + coa + nad <==> accoa + h + nadh | (b1241 or b0351) |
| AKGD | [c]: akg + coa + nad --> co2 + nadh + succoa | (b0116 and b0726 and b0727) |
| ASNS2 | [c]: asp-L + atp + nh4 --> amp + asn-L + h + ppi | b3744 |
| ASPT | [c]: asp-L --> fum + nh4 | b4139 |
| ATPS4r | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | [c]: atp + co2 + nh4 <==> adp + cbp + (2) h | (b0521 or b0323 or b2874) |
| EDA | [c]: 2ddg6p --> g3p + pyr | b1850 |
| ENO | [c]: 2pg <==> h2o + pep | b2779 |
| FBA | [c]: fdp <==> dhap + g3p | (b2097 or b2925 or b1773) |
| FBP | [c]: fdp + h2o --> f6p + pi | (b4232 or b3925) |
| FDH2 | for[p] + (2) h[c] + q8[c] --> co2[c] + h[p] + q8h2[c] | ((b3892 and b3893 and b3894) or (b1474 and b1475 and b1476)) |
|  | for[p] + (2) h[c] + mqn8[c] --> co2[c] + h[p] + mql8[c] |  |
| FRD2 | [c]: fum + mql8 --> mqn8 + succ | (b4151 and b4152 and b4153 and b4154) |
|  | [c]: 2dmmql8 + fum --> 2dmmq8 + succ |  |
| FTHFD | [c]: 10fthf + h2o --> for + h + thf | b1232 |
| FUM | [c]: fum + h2o <==> mal-L | (b1612 or b4122 or b1611) |
| G5SD | [c]: glu5p + h + nadph --> glu5sa + nadp + pi | b0243 |
| G6PDHy | [c]: g6p + nadp <==> 6pgl + h + nadph | b1852 |
| GLCpts | glc-D[p] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |

TABLE 29-continued

Corresponding genes to be knocked out to prevent a particular reaction from occurring in E. coli.

| Reaction Abbreviation | Reaction Stoichiometry* | Genes Encoding the Enzyme(s) Catalyzing Each Reaction& |
|---|---|---|
| GLU5K | [c]: atp + glu-L --> adp + glu5p | b0242 |
| GLUDy | [c]: glu-L + h2o + nadp <==> akg + h + nadph + nh4 | b1761 |
| GLYCL | [c]: gly + nad + thf --> co2 + mlthf + nadh + nh4 | (b2904 and b2903 and b2905 and b0116) |
| HEX1 | [c]: atp + glc-D --> adp + g6p + h | b2388 |
| ICL | [c]: icit --> glx + succ | b4015 |
| LD_D | [c]: lac-D + nad <==> h + nadh + pyr | (b2133 or b1380) |
| MALS | [c]: accoa + glx + h2o --> coa + h + mal-L | (b4014 or b2976) |
| MDH | [c]: mal-L + nad <==> h + nadh + oaa | b3236 |
| ME2 | [c]: mal-L + nadp --> co2 + nadph + pyr | b2463 |
| MTHFC | [c]: h2o + methf <==> 10fthf + h | b0529 |
| NADH12 | [c]: h + mqn8 + nadh --> mql8 + nad<br>[c]: h + nadh + q8 --> nad + q8h2<br>[c]: 2dmmq8 + h + nadh --> 2dmmql8 + nad | b1109 |
| NADH6 | (4) h[c] + nadh[c] + q8[c] --> (3) h[p] + nad[c] + q8h2[c]<br>(4) h[c] + mqn8[c] + nadh[c] --> (3) h[p] + mql8[c] + nad[c]<br>2dmmq8[c] + (4) h[c] + nadh[c] --> 2dmmql8[c] + (3) h[p] + nad[c] | (b2276 and b2277 and b2278 and b2279 and b2280 and b2281 and b2282 and b2283 and b2284 and b2285 and b2286 and b2287 and b2288) |
| PFK | [c]: atp + f6p --> adp + fdp + h | (b3916 or b1723) |
| PFLi | [c]: coa + pyr --> accoa + for | (((b0902 and b0903) and b2579) or (b0902 and b0903) or (b0902 and b3114) or (b3951 and b3952)) |
| PGDH | [c]: 6pgc + nadp --> co2 + nadph + ru5p-D | b2029 |
| PGI | [c]: g6p <==> f6p | b4025 |
| PGL | [c]: 6pgl + h2o --> 6pgc + h | b0767 |
| PGM | [c]: 2pg <==> 3pg | (b3612 or b4395 or b0755) |
| PPC | [c]: co2 + h2o + pep --> h + oaa + pi | b3956 |
| PPCK | [c]: atp + oaa --> adp + co2 + pep | b3403 |
| PRO1z | [c]: fad + pro-L --> 1pyr5c + fadh2 + h | b1014 |
| PYK | [c]: adp + h + pep --> atp + pyr | b1854 or b1676) |
| PYRt2 | h[p] + pyr[p] <==> h[c] + pyr[c] | Non-gene associated |
| RPE | [c]: ru5p-D <==> xu5p-D | (b4301 or b3386) |
| SO4t2 | so4[e] <==> so4[p] | (b0241 or b0929 or b1377 or b2215) |
| SUCD4 | [c]: q8 + succ --> fum + q8h2 | (b0721 and b0722 and b0723 and b0724) |
| SUCOAS | [c]: atp + coa + succ <==> adp + pi + succoa | (b0728 and b0729) |
| SULabc | atp[c] + h2o[c] + so4[p] --> adp[c] + h[c] + pi[c] + so4[c] | ((b2422 and b2425 and b2424 and b2423) or (b0763 and b0764 and b0765) or (b2422 and b2424 and b2423 and b3917)) |
| TAL | [c]: g3p + s7p <==> e4p + f6p | (b2464 or b0008) |
| THD2 | (2) h[p] + nadh[c] + nadp[c] --> (2) h[c] + nad[c] + nadph[c] | (b1602 and b1603) |
| THD5 | [c]: nad + nadph --> nadh + nadp | (b3962 or (b1602 and b1603)) |
| TPI | [c]: dhap <==> g3p | b3919 |

TABLE 30

Metabolite names corresponding to abbreviations used in Table 29.

| Metabolite Abbreviation | Metabolite Name |
|---|---|
| 10fthf | 10-Formyltetrahydrofolate |
| 1pyr5c | 1-Pyrroline-5-carboxylate |
| 2ddg6p | 2-Dehydro-3-deoxy-D-gluconate 6-phosphate |
| 2dmmq8 | 2-Demethylmenaquinone 8 |
| 2dmmql8 | 2-Demethylmenaquinol 8 |
| 2pg | D-Glycerate 2-phosphate |
| 3pg | 3-Phospho-D-glycerate |
| 6pgc | 6-Phospho-D-gluconate |

TABLE 30-continued

Metabolite names corresponding to abbreviations used in Table 29.

| Metabolite Abbreviation | Metabolite Name |
|---|---|
| 6pgl | 6-phospho-D-glucono-1,5-lactone |
| ac | Acetate |
| acald | Acetaldehyde |
| accoa | Acetyl-CoA |
| actp | Acetyl phosphate |
| adp | ADP |
| akg | 2-Oxoglutarate |
| amp | AMP |
| asn-L | L-Asparagine |
| asp-L | L-Aspartate |
| atp | ATP |
| cbp | Carbamoyl phosphate |
| co2 | CO2 |
| coa | Coenzyme A |
| dhap | Dihydroxyacetone phosphate |
| e4p | D-Erythrose 4-phosphate |
| etoh | Ethanol |
| f6p | D-Fructose 6-phosphate |
| fad | Flavin adenine dinucleotide oxidized |
| fadh2 | Flavin adenine dinucleotide reduced |
| fdp | D-Fructose 1,6-bisphosphate |
| for | Formate |
| fum | Fumarate |
| g3p | Glyceraldehyde 3-phosphate |
| g6p | D-Glucose 6-phosphate |
| glc-D | D-Glucose |
| glu5p | L-Glutamate 5-phosphate |
| glu5sa | L-Glutamate 5-semialdehyde |
| glu-L | L-Glutamate |
| glx | Glyoxylate |
| gly | Glycine |
| h | H+ |
| h2o | H2O |
| icit | Isocitrate |
| lac-D | D-Lactate |
| mal-L | L-Malate |
| methf | 5,10-Methenyltetrahydrofolate |
| mlthf | 5,10-Methylenetetrahydrofolate |
| mql8 | Menaquinol 8 |
| mqn8 | Menaquinone 8 |
| nad | Nicotinamide adenine dinucleotide |
| nadh | Nicotinamide adenine dinucleotide - reduced |
| nadp | Nicotinamide adenine dinucleotide phosphate |
| nadph | Nicotinamide adenine dinucleotide phosphate - reduced |
| nh4 | Ammonium |
| oaa | Oxaloacetate |
| pep | Phosphoenolpyruvate |
| pi | Phosphate |
| ppi | Diphosphate |
| pro-L | L-Proline |
| pyr | Pyruvate |
| q8 | Ubiquinone-8 |
| q8h2 | Ubiquinol-8 |
| ru5p-D | D-Ribulose 5-phosphate |
| s7p | Sedoheptulose 7-phosphate |
| so4 | Sulfate |
| succ | Succinate |
| succoa | Succinyl-CoA |
| thf | 5,6,7,8-Tetrahydrofolate |
| xu5p-D | D-Xylulose 5-phosphate |

Example XX

Exemplary Pathways for Producing BDO

This example describes exemplary pathways to produce 4-hydroxybutanal (4-HBal) and/or BDO using a carboxylic acid reductase as a BDO pathway enzyme.

An exemplary pathway for production of BDO includes use of an NAD+ or NADP+ aryl-aldehyde dehydrogenase (E.C.: 1.2.1.29 and 1.2.1.30) to convert 4-hydroxybutyrate to 4-hydroxybutanal and an alcohol dehydrogenase to convert 4-hydroxybutanal to 1,4-butanediol. 4-Hydroxybutyrate can be derived from the tricarboxylic acid cycle intermediates succinyl-CoA and/or alpha-ketoglutarate as shown in FIG. 58.

Aryl-Aldehyde Dehydrogenase (or Carboxylic Acid Reductase). An aryl-aldehyde dehydrogenase, or equivalently a carboxylic acid reductase, can be found in *Nocardia iowensis*. Carboxylic acid reductase catalyzes the magnesium, ATP and NADPH-dependent reduction of carboxylic acids to their corresponding aldehydes (Venkitasubramanian et al., *J. Biol. Chem.* 282:478-485 (2007)) and is capable of catalyzing the conversion of 4-hydroxybutyrate to 4-hydroxybutanal. This enzyme, encoded by car, was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industries*, ed. R. N. Patel, Chapter 15, pp. 425-440, CRC Press LLC, Boca Raton, Fla. (2006)).

| Gene name | GI No. | GenBank Accession No. | Organism |
|---|---|---|---|
| car | 40796035 | AAR91681.1 | *Nocardia iowensis* (sp. NRRL 5646) |
| npt | 114848891 | ABI83656.1 | *Nocardia iowensis* (sp. NRRL 5646) |

Additional car and npt genes can be identified based on sequence homology.

| Gene name | GI No. | GenBank Accession No. | Organism |
|---|---|---|---|
| fadD9 | 121638475 | YP_978699.1 | *Mycobacterium bovis* BCG |
| BCG 2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |

| Gene name | GI No. | GenBank Accession No. | Organism |
| --- | --- | --- | --- |
| SGR_665 | 182434458 | YP_001822177.1 | Streptomyces griseus subsp. griseus NBRC 13350 |
| MSMEG_2956 | YP_887275.1 | YP_887275.1 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamurella paurometabola DSM 20162 |
| TpauDRAFT_20920 | ZP_04026660.1 | ZP_04026660.1 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

| Gene name | GI No. | GenBank Accession No. | Organism |
| --- | --- | --- | --- |
| griC | 182438036 | YP_001825755.1 | Streptomyces griseus subsp. griseus NBRC 13350 |
| griD | 182438037 | YP_001825756.1 | Streptomyces griseus subsp. griseus NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene name | GI No. | GenBank Accession No. | Organism |
| --- | --- | --- | --- |
| LYS2 | 171867 | AAA34747.1 | Saccharomyces cerevisiae |
| LYS5 | 1708896 | P50113.1 | Saccharomyces cerevisiae |
| LYS2 | 2853226 | AAC02241.1 | Candida albicans |
| LYS5 | 28136195 | AAO26020.1 | Candida albicans |
| Lys1p | 13124791 | P40976.3 | Schizosaccharomyces pombe |
| Lys7p | 1723561 | Q10474.1 | Schizosaccharomyces pombe |
| Lys2 | 3282044 | CAA74300.1 | Penicillium chrysogenum |

There are several advantages of using carboxylic acid reductase for BDO p.roduction. There are at least two advantages of forming 4-hydroxybutanal from 4-hydroxybutyrate via a carboxylic acid reductase compared to forming 4-hydroxybutanal from an activated version of 4-hydroxybutyrate (for example, 4-hydroxybutyryl-CoA, 4-hydroxybutyryl-Pi) via an acyl-CoA or acyl-phosphate reductase. First, the formation of gamma-butyrolactone (GBL) as a byproduct is greatly reduced. It is believed that the activated versions of 4-hydroxybutyrate cyclize to GBL more readily than unactivated 4-hydroxybutyrate. The use of carboxylic acid reductase eliminates the need to pass through a free activated 4-hydroxybutyrate intermediate, thus reducing the formation of GBL as a byproduct accompanying BDO production. Second, the formation of ethanol as a byproduct is greatly reduced. Ethanol is often formed in varying amounts when an aldehyde- or an alcohol-forming 4-hydroxybutyryl-CoA reductase is used to convert 4-hydroxybutyryl-CoA to 4-hydroxybutanal or 1,4-butanediol, respectively. This is because most, if not all, aldehyde- or alcohol-forming 4-hydroxybutyryl-CoA reductases can accept acetyl-CoA as a substrate in addition to 4-hydroxybutyryl-CoA. Aldehyde-forming enzymes, for example, often catalyze the conversion of acetyl-CoA to acetaldehyde, which is subsequently reduced to ethanol by native or non-native alcohol dehydrogenases. Alcohol-forming 4-hydroxybutyryl-CoA reductases that accept acetyl-CoA as a substrate will convert acetyl-CoA directly to ethanol. It appears that carboxylic acid reductase enzymes have far less activity on acetyl-CoA than aldehyde- or alcohol-forming acyl-CoA reductase enzymes, and thus their application for BDO production results in minimal ethanol byproduct formation (see below).

Example XXI

Biosynthesis of 1,4-Butanediol Using A Carboxylic Acid Reductase Enzyme

This example describes the generation of a microbial organism that produces 1,4-butanediol using a carboxylic acid reductase enzyme.

*Escherichia coli* is used as a target organism to engineer the pathway for 1,4-butanediol synthesis described in FIG. 58. *E. coli* provides a good host for generating a non-naturally occurring microorganism capable of producing 1,4-butanediol. *E. coli* is amenable to genetic manipulation and is known to be capable of producing various products, like ethanol, acetic acid, formic acid, lactic acid, and succinic acid, effectively under various oxygenation conditions.

Integration of 4-Hydroxybutyrate Pathway Genes into Chromosome: Construction of ECKh-432. The carboxylic acid reductase enzyme was expressed in a strain of *E. coli* designated ECKh-432 whose construction is described in Example XVII. This strain contained the components of the BDO pathway, leading to 4HB, integrated into the chromosome of *E. coli* at the fimD locus.

As described in Example XVII, the succinate branch of the upstream pathway was integrated into the *E. coli* chromosome using the λ red homologous recombination method (Datsenko and Wanner, *Proc. Natl. Acad. Sci. USA* 97:6640-6645 (2000)). A polycistronic DNA fragment containing a promoter, the sucCD gene of *Escherichia coli* encoding succinyl-CoA ligase, the sucD gene of *Porphyromonas gingivalis* encoding succinyl-CoA reductase (aldehyde forming) (step A of FIG. 58), the 4hbd gene of *Porphyromonas gingivalis* encoding 4-hydroxybutyrate dehydrogenase (step C of FIG. 58), and a terminator sequence was inserted into the AflIII site of the pKD3 plasmid.

As described in Example XVII, the alpha-ketoglutarate branch of the upstream pathway was integrated into the chromosome by homologous recombination. The plasmid used in this modification was pRE118-V2 (pRE118 (ATCC87693) deleted of the oriT and IS sequences), which contains a kanamycin-resistant gene, a gene encoding the levansucrase (sacB) and a R6K conditional replication ori. The integration plasmid also contained a polycistronic sequence with a promoter, the sucA gene from *Mycobacterium bovis* encoding alpha-ketoglutarate decarboxylase (step B of FIG. 58), the *Clostridium kluyveri* 4hbd gene encoding 4-hydroxybutyrate dehydrogenase (step C of FIG. 58), and a terminator being inserted between two 1.5-kb DNA fragments that are homologous to the flanking regions of the target insertion site. The resulting plasmid was used to transform *E. coli* strain. The integration candidate was selected on plates containing kanamycin. The correct integration site was verified by PCR. To resolve the antibiotic marker from the chromosome, the cells were selected for growth on medium containing sucrose. The final strain was verified by PCR and DNA sequencing.

The recipient *E. coli* strain was ECKh-422 (ΔadhE ΔldhA ΔpflB ΔlpdA::K.p.lpdA322 Δmdh ΔarcA gltAR163L) whose construction is described in Example XV. ECKh-422 contains a mutation gltAR163L leading to NADH-insensitivity of citrate synthase encoded by gltA. It further contains an NADH-insensitive version of the lpdA gene from *Klebsiella pneumonia* integrated into the chromosome as described below.

Replacement of the native lpdA was replaced with a NADH-insensitive lpdA from *Klebsiella pneumonia*, as described in Example XIV. The resulting vector was designated pRE118-V2 (see FIG. 34).]

Cloning and Expression of Carboxylic Acid Reductase and PPTase. To generate an *E. coli* strain engineered to produce 1,4-butanediol, nucleic acids encoding a carboxylic acid reductase and phosphopantetheine transferase are expressed in *E. coli* using well known molecular biology techniques (see, for example, Sambrook, supra, 2001; Ausubel supra, 1999). In particular, the car (AAR91681.1) and npt (ABI83656.1) genes were cloned into the pZS*13 vector (Expressys, Ruelzheim, Germany) under the PA1/lacO promoter. The car gene (GNM_720) was cloned by PCR from Nocardia genomic DNA. Its nucleic acid and protein sequences are shown in FIGS. 59A and 59B, respectively.

Figure 61:
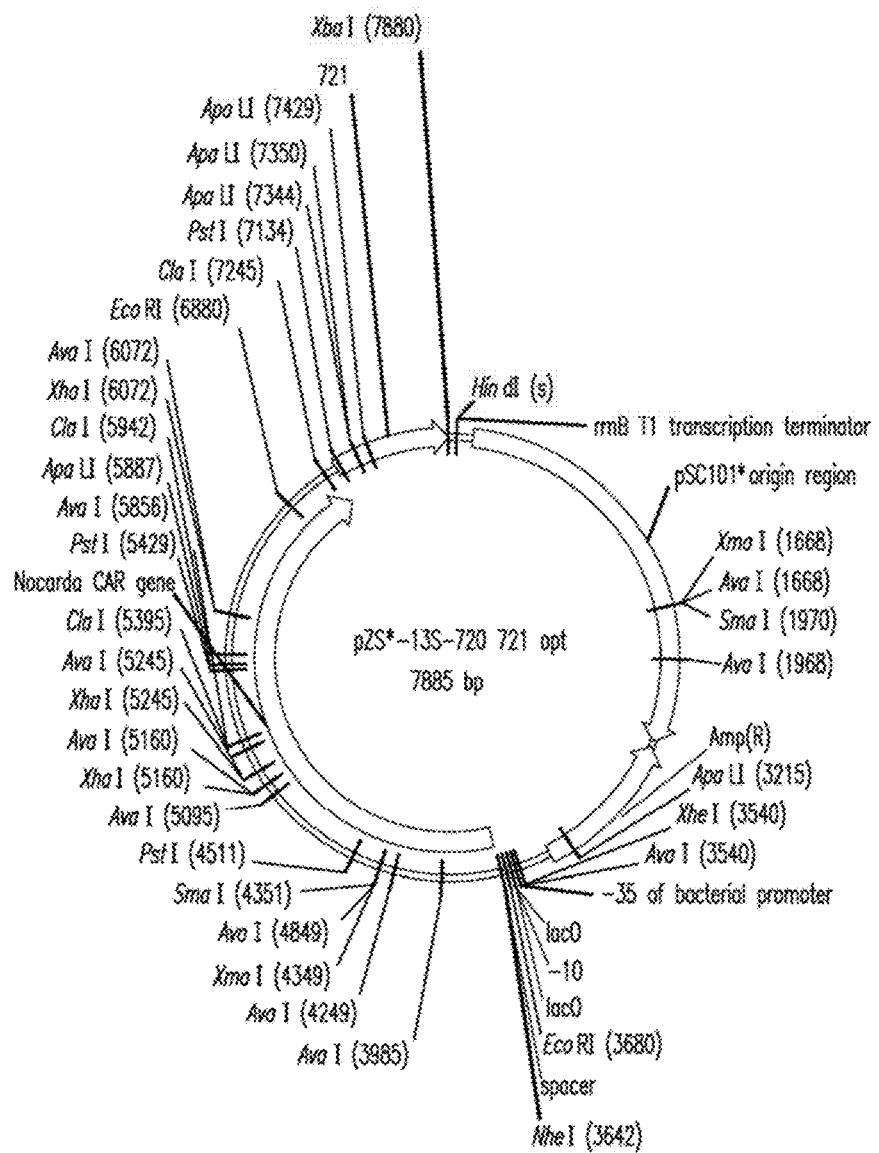
FIG. 61 shows a plasmid map of plasmid pZS*-13S-720 721opt.

A codon-optimized version of the npt gene (GNM_721) was synthesized by GeneArt (Regensburg, Germany). Its nucleic acid and protein sequences are shown in FIGS. 60A and 60B, respectively. The resulting vector from cloning GNM_720 and GNM_721 into pZS*13 is shown in FIG. 61.

The plasmid was transformed into ECKh-432 to express the proteins and enzymes required for 1,4-butanediol production. Alternate versions of the plasmid containing only GNM_720 and only GNM_721 were also constructed.

Demonstration of 1,4-BDO Production using Carboxylic Acid Reductase. Functional expression of the 1,4-butanediol pathway was demonstrated using *E. coli* whole-cell culture. A single colony of *E. coli* ECKh-432 transformed with the pZS*13 plasmid containing both GNM_720 and GNM_721 was inoculated into 5 mL of LB medium containing appropriate antibiotics. Similarly, single colonies of *E. coli* ECKh-432 transformed with the pZS*13 plasmids containing either GNM_720 or GNM_721 were inoculated into additional 5 mL aliquots of LB medium containing appropriate antibiotics. Ten mL micro-aerobic cultures were started by inoculating fresh minimal in vivo conversion medium (see below) containing the appropriate antibiotics with 1% of the first cultures.

Recipe of the minimal in vivo conversion medium (for 1000 mL) is as follows:

|  | final concentration |
|---|---|
| 1M MOPS/KOH buffer | 40 mM |
| Glucose (40%) | 1% |
| 10XM9 salts solution | 1X |
| MgSO4 (1M) | 1 mM |
| trace minerals (x1000) | 1X |
| 1M NaHCO3 | 10 mM |

Microaerobic conditions were established by initially flushing capped anaerobic bottles with nitrogen for 5 minutes, then piercing the septum with an 18G needle following inoculation. The needle was kept in the bottle during growth to allow a small amount of air to enter the bottles. Protein expression was induced with 0.2 mM IPTG when the culture reached mid-log growth phase. This is considered: time=0 hr. The culture supernatants were analyzed for BDO, 4HB, and other by-products as described above and in WO2008115840 (see Table 31).

| Strain | pZS*13S | OD600 | OD600 | PA | SA | LA | 4HB | BDO | GBL | ETOH$_{Enz}$ |
|---|---|---|---|---|---|---|---|---|---|---|
| | | | | | | mM | | | | |
| ECKh-432 | 720 | 0.420 | 2.221 | 6.36 | 0.00 | 0.10 | 7.71 | 3.03 | 0.07 | >LLOQ |
| ECKh-432 | 721 | 0.323 | 2.574 | 1.69 | 0.00 | 0.00 | 12.60 | 0.00 | 0.00 | >LLOQ |
| ECKh-432 | 720/721 | 0.378 | 2.469 | 1.70 | 0.00 | 0.01 | 4.23 | 9.16 | 0.24 | 1.52 |

PA = pyruvate,
SA = succinate,
LA = lactate,
4HB = 4-hydroxybutyrate,
BDO = 1,4-butanediol,
GBL = gamma-butyrolactone,
Etoh = ethanol,
LLOQ = lower limit of quantification These results demonstrate that the carboxylic acid reductase gene, GNM_720, is required for BDO formation in ECKh-432 and its effectiveness is increased when co-expressed with the PPTase, GNM_721. GBL and ethanol were produced in far smaller quantities than BDO in the strains expressing GNM_720 by itself or in combination with GNM_721.

Additional Pathways to BDO Employing Carboxylic Acid Reductase. It is expected that carboxylic acid reductase can function as a component of many pathways to 1,4-butanediol from the TCA cycle metabolites: succinate, succinyl-CoA, and alpha-ketoglutarate. Several of these pathways are disclosed in FIG. 62. All routes can lead to theoretical BDO yields greater than or equal to 1 mol/mol assuming glucose as the carbon source. Similar high theoretical yields can be obtained from additional substrates including sucrose, xylose, arabinose, synthesis gas, among many others. It is expected that the expression of carboxylic acid reductase alone or in combination with PPTase (that is, to catalyze steps F and D of FIG. 62) is sufficient for 1,4-butanediol production from succinate provided that sufficient endogenous alcohol dehydrogenase activity is present to catalyze steps C and E of FIG. 62. Candidate enzymes for steps A through Z of FIG. 62 are described in section XXIII.

Example XXII

Pathways to Putrescine that Employ Carboxylic Acid Reductase

This example describes exemplary putrescine pathways utilizing carboxylic acid reductase.

Putrescine, also known as 1,4-diaminobutane or butanediamine, is an organic chemical compound of the formula $NH_2(CH_2)_4NH_2$. It can be reacted with adipic acid to yield the polyamide Nylon-4,6, which is marketed by DSM (Heerlen, Netherlands) under the trade name Stanyl™ Putrescine is naturally produced, for example, by the natural breakdown of amino acids in living and dead organisms. E. coli has been engineered to produce putrescine by overexpressing the native ornithine biosynthetic machinery as well as an ornithine decarboxylase (Qian, et al., Biotechnol. Bioeng. 104(4):651-662 (2009)).

FIG. 63 describes a number of additional biosynthetic pathways leading to the production of putrescine from succinate, succinyl-CoA, or alpha-ketoglutarate and employing a carboxylic acid reductase. Note that none of these pathways require formation of an activated version of 4-aminobutyrate such as 4-aminobutyryl-CoA, which can be reduced by an acyl-CoA reductase to 4-aminobutanal but also can readily cyclize to its lactam, 2-pyrrolidinone (Ohsugi, et al., J. Biol. Chem. 256:7642-7651 (1981)). All routes can lead to theoretical putrescine yields greater than or equal to 1 mol/mol assuming glucose as the carbon source. Similar high theoretical yields can be obtained from additional substrates including sucrose, xylose, arabinose, synthesis gas, among many others. Candidate enzymes for steps A through U of FIG. 63 are described in Example XXIII.

Example XXIII

Exemplary Enzymes for Production of C4 Compounds

This example describes exemplary enzymes for production of C4 compounds such as 1,4-butanediol, 4-hydroxybutanal and putrescine.

Enzyme classes. All transformations depicted in FIGS. 58, 62 and 63 fall into the general categories of transformations shown in Table 32. This example describes a number of biochemically characterized genes in each category. Specifically listed are genes that can be applied to catalyze the appropriate transformations in FIGS. 58, 62 and 63 when cloned and expressed. The first three digits of each label correspond to the first three Enzyme Commission number digits which denote the general type of transformation independent of substrate specificity.

TABLE 32

Classes of Enzyme Transformations Depicted in FIGS. 58, 62 and 63.

| LABEL | FUNCTION |
|---|---|
| 1.1.1.a | Oxidoreductase (oxo to alcohol) |
| 1.1.1.c | Oxidoreductase (2 step, acyl-CoA to alcohol) |
| 1.2.1.b | Oxidoreductase (acyl-CoA to aldehyde) |
| 1.2.1.c | Oxidoreductase (2-oxo acid to acyl-CoA, decarboxylation) |
| 1.2.1.d | Oxidoreductase (phosphonate reductase) |
| 1.2.1.e | Acid reductase |
| 1.4.1.a | Oxidoreductase (aminating) |
| 2.3.1.a | Acyltransferase (transferring phosphate group to CoA) |
| 2.6.1.a | Aminotransferase |
| 2.7.2.a | Phosphotransferase (carboxy acceptor) |
| 2.8.3.a | CoA transferase |
| 3.1.2.a | CoA hydrolase |
| 4.1.1.a | Carboxy-lyase |
| 6.2.1.a | CoA synthetase |

1.1.1.a Oxidoreductase (Oxo to Alcohol)

Aldehyde to alcohol. Three transformations described in FIGS. 58, 62 and 63 involve the conversion of an aldehyde to alcohol. These are 4-hydroxybutyrate dehydrogenase (step C, FIGS. 58 and 62), 1,4-butanediol dehydrogenase (step E, FIGS. 58 and 62), and 5-hydroxy-2-pentanoic acid (step Y, FIG. 62). Exemplary genes encoding enzymes that catalyze the conversion of an aldehyde to alcohol, that is, alcohol dehydrogenase or equivalently aldehyde reductase, include alrA encoding a medium-chain alcohol dehydrogenase for C2-C14 (Tani et al. *Appl. Environ. Microbiol.* 66:5231-5235 (2000)), ADH2 from *Saccharomyces cerevisiae* (Atsumi et al. *Nature* 451:86-89 (2008)), yqhD from *E. coli*, which has preference for molecules longer than C(3) (Sulzenbacher et al. *J. Mol. Biol.* 342:489-502 (2004)), and bdh I and bdh II from *C. acetobutylicum*, which converts butyryaldehyde into butanol (Walter et al. *J. Bacteriol.* 174:7149-7158 (1992)). The protein sequences for each of exemplary gene products can be found using the following GenBank accession numbers:

| Gene | Accession No. | GI No. | Organism |
| --- | --- | --- | --- |
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |

Enzymes exhibiting 4-hydroxybutyrate dehydrogenase activity (EC 1.1.1.61) also fall into this category. Such enzymes have been characterized in *Ralstonia eutropha* (Bravo et al. *J. Forensic Sci.* 49:379-387 (2004)), *Clostridium kluyveri* (Wolff et al., *Protein Expr. Purif.* 6:206-212 (1995)) and *Arabidopsis thaliana* (Breitkreuz et al. *J. Biol. Chem.* 278:41552-41556 (2003)).

| Gene | Accession No. | GI No. | Organism |
| --- | --- | --- | --- |
| 4hbd | YP_726053.1 | 113867564 | *Ralstonia eutropha* H16 |
| 4hbd | EDK35022.1 | 146348486 | *Clostridium kluyveri* DSM 555 |
| 4hbd | Q94B07 | 75249805 | *Arabidopsis thaliana* |

The adh1 gene from *Geobacillus thermoglucosidasius* M10EXG (Jeon et al., *J. Biotechnol.* 135:127-133 (2008)) was shown to exhibit high activity on both 4-hydroxybutanal and butanal (see above). Thus this enzyme exhibits 1,4-butanediol dehydrogenase activity.

| Gene | Accession No. | GI No. | Organism |
| --- | --- | --- | --- |
| adh1 | AAR91477.1 | 40795502 | *Geobacillus thermoglucosidasius* M10EXG |

Another exemplary enzyme is 3-hydroxyisobutyrate dehydrogenase, which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al. *J. Mol. Biol.* 352:905-17 (2005)). The reversibility of the human 3-hydroxyisobutyrate dehydrogenase was demonstrated using isotopically-labeled substrate (Manning et al., *Biochem. J.* 231:481-484 (1985)). Additional genes encoding this enzyme include 3hidh in *Homo sapiens* (Hawes et al., *Methods Enzymol.* 324:218-228 (2000)) and *Oryctolagus cuniculus* (Chowdhury et al., *Biosci. Biotechnol. Biochem.* 60:2043-2047 (1996); Hawes et al. *Methods Enzymol.* 324:218-228 (2000)), mmsb in *Pseudomonas aeruginosa*, and dhat in *Pseudomonas putida* (Aberhart et al., *J. Chem. Soc.* [Perkin 1] 6:1404-1406 (1979); Chowdhury et al., *Biosci. Biotechnol Biochem.* 67:438-441 (2003); Chowdhury et al., *Biosci. Biotechnol. Biochem.* 60:2043-2047 (1996)).

| Gene | Accession No. | GI No. | Organism |
| --- | --- | --- | --- |
| P84067 | P84067 | 75345323 | *Thermus thermophilus* |
| mmsb | P28811.1 | 127211 | *Pseudomonas aeruginosa* |
| dhat | Q59477.1 | 2842618 | *Pseudomonas putida* |
| 3hidh | P31937.2 | 12643395 | *Homo sapiens* |
| 3hidh | P32185.1 | 416872 | *Oryctolagus cuniculus* |

Several 3-hydroxyisobutyrate dehydrogenase enzymes have also been shown to convert malonic semialdehyde to 3-hydroxyproprionic acid (3-HP). Three gene candidates exhibiting this activity are mmsB from *Pseudomonas aeruginosa* PAO1(62), mmsB from *Pseudomonas putida* KT2440 (Liao et al., US Publication 2005/0221466) and mmsB from *Pseudomonas putida* E23 (Chowdhury et al., *Biosci. Biotechnol. Biochem.* 60:2043-2047 (1996)). An enzyme with 3-hydroxybutyrate dehydrogenase activity in *Alcaligenes faecalis* M3A has also been identified (Gokarn et al., U.S. Pat. No. 7,393,676; Liao et al., US Publication No. 2005/0221466). Additional gene candidates from other organisms including *Rhodobacter spaeroides* can be inferred by sequence similarity.

| Gene | Accession No. | GI No. | Organism |
| --- | --- | --- | --- |
| mmsB | AAA25892.1 | 151363 | *Pseudomonas aeruginosa* |
| mmsB | NP_252259.1 | 15598765 | *Pseudomonas aeruginosa* PAO1 |
| mmsB | NP_746775.1 | 26991350 | *Pseudomonas putida* KT2440 |
| mmsB | JC7926 | 60729613 | *Pseudomonas putida* E23 |
| orfB1 | AAL26884 | 16588720 | *Rhodobacter spaeroides* |

The conversion of malonic semialdehyde to 3-HP can also be accomplished by two other enzymes, NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi, *J. Plant Pathol.* 159:671-674 (2002); Stadtman, *J. Am. Chem. Soc.* 77:5765-5766 (1955)). This enzyme has not been associated with a gene in any organism to date. NADPH-dependent malonate semialdehyde reductase catalyzes the reverse reaction in autotrophic $CO_2$-fixing bacteria. Although the enzyme activity has been detected in *Metallosphaera sedula*, the identity of the gene is not known (Alber et al. *J. Bacteriol.* 188:8551-8559 (2006)).

1.1.1.c Oxidoreductase (2 step, acyl-CoA to alcohol)

Steps S and W of FIG. 62 depict bifunctional reductase enzymes that can form 4-hydroxybutyrate and 1,4-butanediol, respectively. Exemplary 2-step oxidoreductases that convert an acyl-CoA to alcohol include those that transform substrates such as acetyl-CoA to ethanol (for example, adhE from *E. coli* (Kessler et al., FEBS. Lett. 281:59-63 (1991)) and butyryl-CoA to butanol (for example, adhE2 from *C. acetobutylicum* (Fontaine et al., *J. Bacteriol.* 184:821-830 (2002)). The *C. acetobutylicum* adhE2 gene was shown to convert 4-hydroxybutyryl-CoA to 1,4-butanediol (see above). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al. J., *Gen. Appl. Microbiol.* 18:43-55 (1972); Koo et al., *Biotechnol. Lett.* 27:505-510 (2005)).

| Gene | Accession No. | GI No. | Organism |
|---|---|---|---|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme can convert malonyl-CoA to 3-HP. An NADPH-dependent enzyme with this activity has characterized in *Chloroflexus aurantiacus*, where it participates in the 3-hydroxypropionate cycle (Hugler et al., *J. Bacteriol.* 184:2404-2410 (2002); Strauss and Fuchs, *Eur. J. Biochem.* 215:633-643 (1993)). This enzyme, with a mass of 300 kDa, is highly substrate-specific and shows little sequence similarity to other known oxidoreductases (Hugler et al., *J. Bacteriol.* 184:2404-2410 (2002)). No enzymes in other organisms have been shown to catalyze this specific reaction; however there is bioinformatic evidence that other organisms may have similar pathways (Klatt et al., *Environ. Microbiol.* 9:2067-2078 (2007)). Enzyme candidates in other organisms including *Roseiflexus castenholzii, Erythrobacter* sp. NAP1 and marine gamma proteobacterium HTCC2080 can be inferred by sequence similarity.

| Gene | Accession No. | GI No. | Organism |
|---|---|---|---|
| mcr | AAS20429.1 | 42561982 | *Chloroflexus aurantiacus* |
| Rcas_2929 | YP_001433009.1 | 156742880 | *Roseflexus castenholzii* |
| NAP1_02720 | ZP_01039179.1 | 85708113 | *Erythrobacter* sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR, which encodes an alcohol-forming fatty acyl-CoA reductase. Its overexpression in *E. coli* resulted in FAR activity and the accumulation of fatty alcohol (Metz et al., *Plant Physiol.* 122:635-644 2000)).

| Gene | Accession No. | GI No. | Organism |
|---|---|---|---|
| FAR | AAD38039.1 | 5020215 | *Simmondsia chinensis* |

1.2.1.b Oxidoreductase (acyl-CoA to Aldehyde)

Step A of FIGS. 58, 62 and 63 involves the conversion of succinyl-CoA to succinate semialdehyde by an aldehyde forming succinyl-CoA reductase. Step Q of FIG. 62 depicts the conversion of 4-hydroxybutyryl-CoA to 4-hydroxybutanal by an aldehyde-forming 4-hydroxybutyryl-CoA reductase. Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling and Gottschalk, *J. Bacteriol.* 178:871-80 (1996); Sohling and Gottschalk, *J. Bacteriol.* 178:871-880 (1996)). SucD of *P. gingivalis* is another aldehyde-forming succinyl-CoA reductase (Takahashi et al., *J. Bacteriol.* 182:4704-4710 (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., *Biotechnol. Lett.* 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.* 71:58-68 (2007)).

| Gene | Accession No. | GI No. | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 730847 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |

An additional enzyme type that converts an acyl-CoA to its corresponding aldehyde is malonyl-CoA reductase, which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., *Science* 318:1782-1786 (2007); Thauer, *Science* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); Hugler et al., *J. Bacteriol.* 184:2404-2410 (2002)). The enzyme is encoded by Msed_0709 in *Metallosphaera sedula* (Alber et al., *J. Bacteriol.* 188:8551-8559 (2006); Berg et al., *Science* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another candidate for CoA-acylating aldehyde dehydrogenase is the ald gene from *Clostridium beijerinckii* (Toth et al., *Appl. Environ. Microbiol.* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., *Appl. Environ. Microbiol.* 65:4973-4980 (1999)).

| Gene | Accession No. | GI No. | Organism |
| --- | --- | --- | --- |
| Msed_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |
| eutE | P77445 | 2498347 | *Escherichia coli* |

1.2.1.c Oxidoreductase (2-oxo Acid to Acyl-CoA, Decarboxylation)

Step AA in FIG. 62 depicts the conversion of 5-hydroxy-2-oxopentanoic acid to 4-hydroxybutyryl-CoA. Candidate enzymes for this transformation include 1) branched-chain 2-keto-acid dehydrogenase, 2) alpha-ketoglutarate dehydrogenase, and 3) the pyruvate dehydrogenase multienzyme complex (PDHC). These enzymes are multi-enzyme complexes that catalyze a series of partial reactions which result in acylating oxidative decarboxylation of 2-keto-acids. Each of the 2-keto-acid dehydrogenase complexes occupies key positions in intermediary metabolism, and enzyme activity is typically tightly regulated (Fries et al. *Biochemistry* 42:6996-7002 (2003)). The enzymes share a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (that is, larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al. *Appl. Environ. Microbiol.* 73:1766-1771 (2007); Kim et al. *J. Bacteriol.* 190:3851-3858) 2008); Zhou et al. *Biotechnol. Lett.* 30:335-342 (2008)). For example, the inhibitory effect of NADH can be overcome by engineering an H322Y mutation in the E3 component (Kim et al. *J. Bacteriol.* 190:3851-3858 (2008)). Structural studies of individual components and how they work together in complex provide insight into the catalytic mechanisms and architecture of enzymes in this family (Aevarsson et al. *Nat. Struct. Biol.* 6:785-792 (1999); Zhou et al. *Proc. Natl. Acad. Sci. U.S.A.* 98:14802-14807 (2001)). The substrate specificity of the dehydrogenase complexes varies in different organisms, but generally branched-chain keto-acid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, R. G. *Curr. Top. Bioenerg.* 10:217-278 (1980)). Encoded by genes sucA, sucB and lpd in *E. coli*, AKGD gene expression is downregulated under anaerobic conditions and during growth on glucose (Park et al. *Mol. Microbiol.* 15:473-482 (1995)). Although the substrate range of AKGD is narrow, structural studies of the catalytic core of the E2 component pinpoint specific residues responsible for substrate specificity (Knapp et al. *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al. *Mol. Gen. Genet.* 234:285-296 (1992)). In yeast, the LPD1 gene encoding the E3 component is regulated at the transcriptional level by glucose (Roy and Dawes *J. Gen. Microbiol.* 133:925-933 (1987)). The E1 component, encoded by KGD1, is also regulated by glucose and activated by the products of HAP2 and HAP3 (Repetto and Tzagoloff *Mol. Cell Biol.* 9:2695-2705 (1989)). The AKGD enzyme complex, inhibited by products NADH and succinyl-CoA, is well-studied in mammalian systems, as impaired function of has been linked to several neurological diseases (Tretter and dam-Vizi *Philos. Trans. R. Soc. Lond B Biol. Sci.* 360:2335-2345 (2005)).

| Gene | Accession No. | GI No. | Organism |
| --- | --- | --- | --- |
| sucA | NP_415254.1 | 16128701 | *Escherichia coli* str. K12 substr. MG1655 |
| sucB | NP_415255.1 | 16128702 | *Escherichia coli* str. K12 substr. MG1655 |
| lpd | NP_414658.1 | 16128109 | *Escherichia coli* str. K12 substr. MG1655 |
| odhA | P23129.2 | 51704265 | *Bacillus subtilis* |
| odhB | P16263.1 | 129041 | *Bacillus subtilis* |
| pdhD | P21880.1 | 118672 | *Bacillus subtilis* |
| KGD1 | NP_012141.1 | 6322066 | *Saccharomyces cerevisiae* |
| KGD2 | NP_010432.1 | 6320352 | *Saccharomyces cerevisiae* |
| LPD1 | NP_116635.1 | 14318501 | *Saccharomyces cerevisiae* |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al. *Eur. J. Biochem.* 213:1091-1099 (1993)), *Rattus norvegicus* (Namba et al. *J. Biol. Chem.* 244:4437-4447 (1969)) and *Pseudomonas putida* (Sokatch *J. Bacteriol.* 148:647-652 (1981)). In *Bacillus subtilis* the enzyme is encoded by genes pdhD (E3 component), bfmBB (E2 component), bfmBAA and bfmBAB (E1 component) (Wang et al. *Eur. J. Biochem.* 213:1091-1099 (1993)). In mammals, the complex is regulated by phosphorylation by specific phosphatases and protein kinases. The complex has been studied in rat hepatocites (Chicco et al. *J. Biol. Chem.* 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al. *Nat. Struct. Biol.* 6:785-792 (1999); Mattevi *Science* 255:1544-1550 (1992)) and the enzyme complex has been studied (Sokatch et al. *J. Bacteriol.* 148:647-652 (1981)). Transcription of the *P. putida* BCKAD genes is activated by the gene product of bkdR (Hester et al. *Eur. J. Biochem.* 233:828-836 (1995)). In some organisms including *Rattus norvegicus* (Paxton et al. *Biochem. J.* 234:295-303 (1986)) and *Saccharomyces cerevisiae* (Sinclair et al. *Biochem. Mol.*

Biol. Int. 31:911-922 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, *Biochemistry* 33:12879-12885 (1994)).

| Gene | Accession No. | GI No. | Organism |
| --- | --- | --- | --- |
| bfmBB | NP_390283.1 | 16079459 | *Bacillus subtilis* |
| bfmBAA | NP_390285.1 | 16079461 | *Bacillus subtilis* |
| bfmBAB | NP_390284.1 | 16079460 | *Bacillus subtilis* |
| pdhD | P21880.1 | 118672 | *Bacillus subtilis* |
| lpdV | P09063.1 | 118677 | *Pseudomonas putida* |
| bkdB | P09062.1 | 129044 | *Pseudomonas putida* |
| bkdA1 | NP_746515.1 | 26991090 | *Pseudomonas putida* |
| bkdA2 | NP_746516.1 | 26991091 | *Pseudomonas putida* |
| Bckdha | NP_036914.1 | 77736548 | *Rattus norvegicus* |
| Bckdhb | NP_062140.1 | 158749538 | *Rattus norvegicus* |
| Dbt | NP_445764.1 | 158749632 | *Rattus norvegicus* |
| Dld | NP_955417.1 | 40786469 | *Rattus norvegicus* |

The pyruvate dehydrogenase complex, catalyzing the conversion of pyruvate to acetyl-CoA, has also been extensively studied. In the *E. coli* enzyme, specific residues in the E1 component are responsible for substrate specificity (Bisswanger, H. *J Biol Chem.* 256:815-822 (1981); Bremer, J. *Eur. J Biochem.* 8:535-540 (1969); Gong et al. *J Blot Chem.* 275:13645-13653 (2000)). As mentioned previously, enzyme engineering efforts have improved the *E. coli* PDH enzyme activity under anaerobic conditions (Kim et al. *Appl. Environ. Microbiol.* 73:1766-1771 (2007); Kim *J. Bacteriol.* 190:3851-3858 (2008); Zhou et al. *Biotechnol. Lett.* 30:335-342 (2008)). In contrast to the *E. coli* PDH, the *B. subtilis* complex is active and required for growth under anaerobic conditions (Nakano *J. Bacteriol.* 179:6749-6755 (1997)). The *Klebsiella pneumoniae* PDH, characterized during growth on glycerol, is also active under anaerobic conditions (Menzel et al. *J. Biotechnol.* 56:135-142 (1997)). Crystal structures of the enzyme complex from bovine kidney (Zhou et al. *Proc. Natl. Acad. Sci. U.S.A.* 98:14802-14807 (2001)) and the E2 catalytic domain from *Azotobacter vinelandii* are available (Mattevi et al. *Science* 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al. *Biochem. J.* 234:295-303 (1986)).

| Gene | Accession No. | GI No. | Organism |
| --- | --- | --- | --- |
| aceE | NP_414656.1 | 16128107 | *Escherichia coli* str. K12 substr. MG1655 |
| aceF | NP_414657.1 | 16128108 | *Escherichia coli* str. K12 substr. MG1655 |
| lpd | NP_414658.1 | 16128109 | *Escherichia coli* str. K12 substr. MG1655 |
| pdhA | P21881.1 | 3123238 | *Bacillus subtilis* |
| pdhB | P21882.1 | 129068 | *Bacillus subtilis* |
| pdhC | P21883.2 | 129054 | *Bacillus subtilis* |
| pdhD | P21880.1 | 118672 | *Bacillus subtilis* |
| aceE | YP_001333808.1 | 152968699 | *Klebsiella pneumonia* MGH78578 |
| aceF | YP_001333809.1 | 152968700 | *Klebsiella pneumonia* MGH78578 |
| lpdA | YP_001333810.1 | 152968701 | *Klebsiella pneumonia* MGH78578 |
| Pdha1 | NP_001004072.2 | 124430510 | *Rattus norvegicus* |
| Pdha2 | NP_446446.1 | 16758900 | *Rattus norvegicus* |
| Dlat | NP_112287.1 | 78365255 | *Rattus norvegicus* |
| Dld | NP_955417.1 | 40786469 | *Rattus norvegicus* |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodixin as electron acceptors in lieu of NAD(P)H. While most enzymes in this family are specific to pyruvate as a substrate (POR) some 2-keto-acid:ferredoxin oxidoreductases have been shown to accept a broad range of 2-ketoacids as substrates including alpha-ketoglutarate and 2-oxobutanoate (Fukuda and Wakagi *Biochim. Biophys. Acta* 1597:74-80 (2002); Zhang et al. *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi *Biochim. Biophys. Acta* 1597:74-80 (2002); Zhang et al. *J. Biochem.* 120:587-599 (1996)). A plasmid-based expression system has been developed for efficiently expressing this protein in *E. coli* (Fukuda et al. *Eur. J. Biochem.* 268:5639-5646 (2001)) and residues involved in substrate specificity were determined (Fukuda and Wakagi *Biochim. Biophys. Acta* 1597:74-80 (2002)). Two OFORs from *Aeropyrum pernix* str. K1 have also been recently cloned into *E. coli*, characterized, and found to react with a broad range of 2-oxoacids (Nishizawa et al. *FEBS Lett.* 579:2319-2322 (2005)). The gene sequences of these OFOR candidates are available, although they do not have GenBank identifiers assigned to date. There is bioinformatic evidence that similar enzymes are present in all archaea, some anaerobic bacteria and amitochondrial eukarya (Fukuda and Wakagi *Biochim. Biophys. Acta* 1597:74-80 (2005)). This class of enzyme is also interesting from an energetic standpoint, as reduced ferredoxin could be used to generate NADH by ferredoxin-NAD reductase (Petitdemange et al. *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment.

| Gene | Accession No. | GI No. | Organism |
| --- | --- | --- | --- |
| ST2300 | NP_378302.1 | 15922633 | *Sulfolobus tokodaii* 7 |

1.2.1.d Oxidoreductase (Phosphonate Reductase)

The conversion of 4-hydroxybutyryl-phosphate to 4-hydroxybutanal can be catalyzed by an oxidoreductase in the EC class 1.2.1. Aspartate semialdehyde dehydrogenase (ASD, EC 1.2.1.11) catalyzes the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001). The *E. coli* ASD structure has been solved (Hadfield et al., *J. Mol. Biol.*

289:991-1002 (1999)) and the enzyme has been shown to accept the alternate substrate beta-3-methylaspartyl phosphate (Shames et al., *J. Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); Blanco et al., *Acta Crystallogr. D. Biol. Crystallogr.* 60:1808-1815 (2004)). Other ASD candidates are found in *Mycobacterium tuberculosis* (Shafiani et al., *J. Appl. Microbiol.* 98:832-838 (2005), *Methanococcus jannaschii* (Faehnle et al., *J. Mol. Biol.* 353:1055-1068 (2005)), and the infectious microorganisms *Vibrio cholera* and *Heliobacter pylori* (Moore et al., *Protein Expr. Purif.* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J. Biochem.* 270:1014-1024 (2003), *B. subtilis* (O'Reilly and Devine, *Microbiology* 140 (Pt 5):1023-1025 (1994)). and other organisms.

| Gene | Accession No. | GI No. | Organism |
|---|---|---|---|
| asd | NP_417891.1 | 16131307 | *Escherichia coli* |
| asd | YP_248335.1 | 68249223 | *Haemophilus influenzae* |
| asd | AAB49996 | 1899206 | *Mycobacterium tuberculosis* |
| VC2036 | NP_231670 | 15642038 | *Vibrio cholera* |
| asd | YP_002301787.1 | 210135348 | *Heliobacter pylori* |
| ARG5,6 | NP_010992.1 | 6320913 | *Saccharomyces cerevisiae* |
| argC | NP_389001.1 | 16078184 | *Bacillus subtilis* |

Other exemplary enzymes in this class include glyceraldehyde 3-phosphate dehydrogenase which converts glyceraldehyde-3-phosphate into D-glycerate 1,3-bisphosphate (for example, *E. coli* gapA (Branlant and Branlant, *Eur. J. Biochem.* 150:61-66 (1985)), N-acetyl-gamma-glutamylphosphate reductase which converts N-acetyl-L-glutamate-5-semialdehyde into N-acetyl-L-glutamyl-5-phosphate (for example, *E. coli* argC (Parsot et al., *Gene* 68:275-283 (1988)), and glutamate-5-semialdehyde dehydrogenase, which converts L-glutamate-5-semialdehyde into L-glutamyl-5-phospate (for example, *E. coli* proA (Smith et al., *J. Bacteriol.* 157:545-551 (1984)). Genes encoding glutamate-5-semialdehyde dehydrogenase enzymes from *Salmonella typhimurium* (Mahan and Csonka, *J. Bacteriol.* 156:1249-1262 (1983)) and *Campylobacter jejuni* (Louie and Chan, *Mol. Gen. Genet.* 240:29-35 (1993)) were cloned and expressed in *E. coli*.

| Gene | Accession No. | GI No. | Organism |
|---|---|---|---|
| gapA | P0A9B2.2 | 71159358 | *Escherichia coli* |
| argC | NP_418393.1 | 16131796 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

1.2.1.e Acid Reductase

Several steps in FIGS. 58, 62 and 63 depict the conversion of unactivated acids to aldehydes by an acid reductase. These include the conversion of 4-hydroxybutyrate, succinate, alpha-ketoglutarate, and 4-aminobutyrate to 4-hydroxybutanal, succinate semialdehyde, 2,5-dioxopentanoate, and 4-aminobutanal, respectively. One notable carboxylic acid reductase can be found in *Nocardia iowensis* which catalyzes the magnesium, ATP and NADPH-dependent reduction of carboxylic acids to their corresponding aldehydes (Venkitasubramanian et al., *J. Biol. Chem.* 282:478-485 (2007)). This enzyme is encoded by the car gene and was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in *Biocatalysis in the Pharmaceutical and Biotechnology Industires*, ed. R. N. Patel, Chapter 15, pp. 425-440, CRC Press LLC, Boca Raton, Fla. (2006)).

| Gene | Accession No. | GI No. | Organism |
|---|---|---|---|
| car | AAR91681.1 | 40796035 | *Nocardia iowensis* (sp. NRRL 5646) |
| npt | ABI83656.1 | 114848891 | *Nocardia iowensis* (sp. NRRL 5646) |

Additional car and npt genes can be identified based on sequence homology.

| Gene | Accession No. | GI No. | Organism |
|---|---|---|---|
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

| Gene | Accession No. | GI No. | Organism |
|---|---|---|---|
| griC | 182438036 | YP_001825755.1 | *Streptomyces griseus* subsp. *griseus* NBRC 13350 |
| griD | 182438037 | YP_001825756.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

| Gene | Accession No. | GI No. | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

1.4.1.a Oxidoreductase (Aminating)

Glutamate dehydrogenase (Step J, FIGS. 62 and 63), 4-aminobutyrate dehydrogenase (Step M, FIGS. 62 and 63), putrescine dehydrogenase (Step D, FIG. 63), 5-amino-2-oxopentanoate dehydrogenase (Step P, FIG. 63), and ornithine dehydrogenase (Step S, FIG. 63) can be catalyzed by aminating oxidoreductases. Enzymes in this EC class catalyze the oxidative deamination of alpha-amino acids with NAD+ or NADP+ as acceptor, and the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al., *J. Mol. Biol.* 234:1270-1273 (1993); McPherson and Wootton, *Nucleic Acids Res.* 11:5257-5266 (1983)), gdh from *Thermotoga maritima* (Kort et al., *Extremophiles* 1:52-60 (1997); Lebbink, et al. *J. Mol. Biol.* 280:287-296 (1998); Lebbink et al. *J. Mol. Biol.* 289:357-369 (1999)), and gdhA1 from *Halobacterium salinarum* (Ingoldsby et al., *Gene* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula, *Biotechnol. Bioeng.* 68:557-562 (2000); Stoyan et al. *J. Biotechnol.* 54:77-80 (1997)). The nadXgene from *Thermotoga maritime* encoding for the aspartate dehydrogenase is involved in the biosynthesis of NAD (Yang et al., *J. Biol. Chem.* 278:8804-8808 (2003)).

| Gene | Accession No. | GI No. | Organism |
|---|---|---|---|
| gdhA | P00370 | 118547 | *Escherichia coli* |
| gdh | P96110.4 | 6226595 | *Thermotoga maritima* |
| gdhA1 | NP_279651.1 | 15789827 | *Halobacterium salinarum* |
| ldh | P0A393 | 61222614 | *Bacillus cereus* |
| nadX | NP_229443.1 | 15644391 | *Thermotoga maritima* |

Additional glutamate dehydrogenase gene candidates are found in *Bacillus subtilis* (Khan et al., *Biosci. Biotechnol. Biochem.* 69:1861-1870 (2005)), *Nicotiana tabacum* (Purnell et al., *Planta* 222:167-180 (2005)), *Oryza sativa* (Abiko et al., *Plant Cell Physiol.* 46:1724-1734 (2005)), *Haloferax mediterranei* (Diaz et al., *Extremophiles* 10:105-115 (2006)) and *Halobactreium salinarum* (Hayden et al., *FEMS Microbiol. Lett.* 211:37-41 (2002)). The *Nicotiana tabacum* enzyme is composed of alpha and beta subunits encoded by gdh1 and gdh2 (Purnell et al., *Planta* 222:167-180 (2005)). Overexpression of the NADH-dependent glutamate dehydrogenase was found to improve ethanol production in engineered strains of S. cerevisiae (Roca et al., Appl. Environ. Microbiol. 69:4732-4736 (2003)).

| Gene | Accession No. | GI No. | Organism |
|---|---|---|---|
| rocG | NP_391659.1 | 16080831 | Bacillus subtilis |
| gdh1 | AAR11534.1 | 38146335 | Nicotiana tabacum |
| gdh2 | AAR11535.1 | 38146337 | Nicotiana tabacum |
| GDH | Q852M0 | 75243660 | Oryza sativa |
| GDH | Q977U6 | 74499858 | Haloferax mediterranei |
| GDH | P29051 | 118549 | Halobactreium salinarum |
| GDH2 | NP_010066.1 | 6319986 | Saccharomyces cerevisiae |

An exemplary enzyme for catalyzing the conversion of aldehydes to their corresponding primary amines is lysine 6-dehydrogenase (EC 1.4.1.18), encoded by the lysDH genes. The lysine 6-dehydrogenase (deaminating), encoded by lysDH gene, catalyze the oxidative deamination of the ε-amino group of L-lysine to form 2-aminoadipate-6-semialdehyde, which in turn nonenzymatically cyclizes to form Δ1-piperideine-6-carboxylate (Misono and Nagasaki, J. Bacteriol. 150:398-401 (1982)). The lysDH gene from Geobacillus stearothermophilus encodes a thermophilic NAD-dependent lysine 6-dehydrogenase (Heydari et al., Appl. Environ. Microbiol 70:937-942 (2004)). The lysDH gene from Aeropyrum pernix K1 is identified through homology from genome projects. Additional enzymes can be found in Agrobacterium tumefaciens (Hashimoto et al., J. Biochem. 106:76-80 (1989); Misono and Nagasaki, J. Bacteriol. 150: 398-401 (1982)) and Achromobacter denitrificans (Ruldeekulthamrong et al., BMB. Rep. 41:790-795 (2008)).

| Gene | Accession No. | GI No. | Organism |
|---|---|---|---|
| lysDH | BAB39707 | 13429872 | Geobacillus stearothermophilus |
| lysDH | NP_147035.1 | 14602185 | Aeropyrum pernix K1 |
| lysDH | NP_353966 | 15888285 | Agrobacterium tumefaciens |
| lysDH | AAZ94428 | 74026644 | Achromobacter denitrificans |

An enzyme that converts 3-oxoacids to 3-amino acids is 3,5-diaminohexanoate dehydrogenase (EC 1.4.1.11), an enzyme found in organisms that ferment lysine. The gene encoding this enzyme, kdd, was recently identified in Fusobacterium nucleatum (Kreimeyer et al., J. Biol. Chem. 282:7191-7197 (2007)). The enzyme has been purified and characterized in other organisms (Baker et al., J. Biol. Chem. 247:7724-7734 (1972); Baker and and van der Drift, Biochemistry 13:292-299 (1974)), but the genes associated with these enzymes are not known. Candidates in Myxococcus xanthus, Porphyromonas gingivalis W83 and other sequenced organisms can be inferred by sequence homology.

| Gene | Accession No. | GI No. | Organism |
|---|---|---|---|
| kdd | AAL93966.1 | 19713113 | Fusobacterium nucleatum |
| mxan_4391 | ABF87267.1 | 108462082 | Myxococcus xanthus |
| pg_1069 | AAQ66183.1 | 34397119 | Porphyromonas gingivalis |

2.3.1.a Acyltransferase (Transferring Phosphate Group to CoA)

Step P of FIG. 62 depicts the transformation of 4-hydroxybutyryl-CoA to 4-hydroxybutyryl-Pi. Exemplary phosphate transferring acyltransferases include phosphotransacetylase, encoded by pta, and phosphotransbutyrylase, encoded by ptb. The pta gene from E. coli encodes an enzyme that can convert acetyl-CoA into acetyl-phosphate, and vice versa (Suzuki, Biochim. Biophys. Acta 191:559-569 (1969)). This enzyme can also utilize propionyl-CoA instead of acetyl-CoA forming propionate in the process (Hesslinger et al., Mol. Microbiol. 27:477-492 (1998)). Similarly, the ptb gene from C. acetobutylicum encodes an enzyme that can convert butyryl-CoA into butyryl-phosphate (Walter et al., Gene 134:107-111 (1993)); Huang et al., J Mol. Microbiol. Biotechnol. 2:33-38 (2000). Additional ptb genes can be found in butyrate-producing bacterium L2-50 (Louis et al., J. Bacteriol. 186:2099-2106 (2004)) and Bacillus megaterium (Vazquez et al., Curr. Microbiol. 42:345-349 (2001)).

| Gene | Accession No. | GI No. | Organism |
|---|---|---|---|
| pta | NP_416800.1 | 16130232 | Escherichia coli |
| ptb | NP_349676 | 15896327 | Clostridium acetobutylicum |
| ptb | AAR19757.1 | 38425288 | butyrate-producing bacterium L2-50 |
| ptb | CAC07932.1 | 10046659 | Bacillus megaterium |

2.6.1. Aminotransferase

Aminotransferases reversibly convert an aldehyde or ketone to an amino group. Common amino donor/acceptor combinations include glutamate/alpha-ketoglutarate, alanine/pyruvate, and aspartate/oxaloacetate. Several enzymes have been shown to convert aldehydes to primary amines, and vice versa, such as 4-aminobutyrate, putrescine, and 5-amino-2-oxopentanoate. These enzymes are particularly well suited to carry out the following transformations: Step N in FIGS. 62 and 63, Steps E and Q in FIG. 63. Lysine-6-aminotransferase (EC 2.6.1.36) is one exemplary enzyme capable of forming a primary amine. This enzyme function, converting lysine to alpha-aminoadipate semialdehyde, has been demonstrated in yeast and bacteria. Candidates from Candida utilis (Hammer and Bode, J. Basic Microbiol. 32:21-27 (1992)), Flavobacterium lutescens (Fujii et al., J. Biochem. 128:391-397 (2000)) and Streptomyces clavuligenus (Romero et al., J. Ind. Microbiol. Biotechnol. 18:241-246 (1997)) have been characterized. A recombinant lysine-6-aminotransferase from S. clavuligenus was functionally expressed in E. coli (Tobin et al., J. Bacteriol. 173:6223-6229 (1991)). The F. lutescens enzyme is specific to alpha-ketoglutarate as the amino acceptor (Soda and Misono, Biochemistry 7:4110-4119 (1968)). Other enzymes which convert aldehydes to terminal amines include the dat gene product in Acinetobacter baumanii encoding 2,4-diaminobutanoate:2-ketoglutarate 4-transaminase (Ikai and Yamamoto, J. Bacteriol. 179:5118-5125 (1997)). In addition to its natural substrate, 2,4-diaminobutyrate, DAT transaminates the terminal amines of lysine, 4-aminobutyrate and ornithine.

| Gene | Accession No. | GI No. | Organism |
|---|---|---|---|
| lat | BAB13756.1 | 10336502 | Flavobacterium lutescens |
| lat | AAA26777.1 | 153343 | Streptomyces clavuligenus |
| dat | P56744.1 | 6685373 | Acinetobacter baumanii |

The conversion of an aldehyde to a terminal amine can also be catalyzed by gamma-aminobutyrate transaminase (GABA transaminase or 4-aminobutyrate transaminase). This enzyme naturally interconverts succinic semialdehyde and glutamate to 4-aminobutyrate and alpha-ketoglutarate and is known to have a broad substrate range (Liu et al., *Biochemistry* 43:10896-10905 2004); Schulz et al., *Appl. Environ. Microbiol.* 56:1-6 (1990)). The two GABA transaminases in *E. coli* are encoded by gabT (Bartsch et al., *J. Bacteriol.* 172:7035-7042 (1990)) and puuE (Kurihara et al., *J. Biol. Chem.* 280:4602-4608. (2005)). GABA transaminases in *Mus musculus, Pseudomonas fluorescens*, and *Sus scrofa* have been shown to react with a range of alternate substrates including 6-aminocaproic acid (Cooper, *Methods Enzymol.* 113:80-82 (1985); Scott and Jakoby, *J. Biol. Chem.* 234:932-936 (1959)).

| Gene | Accession No. | GI No. | Organism |
|---|---|---|---|
| gabT | NP_417148.1 | 16130576 | *Escherichia coli* |
| puuE | NP_415818.1 | 16129263 | *Escherichia coli* |
| abat | NP_766549.2 | 37202121 | *Mus musculus* |
| gabT | YP_257332.1 | 70733692 | *Pseudomonas fluorescens* |
| abat | NP_999428.1 | 47523600 | *Sus scrofa* |

Additional enzyme candidates for interconverting aldehydes and primary amines are putrescine transminases or other diamine aminotransferases. The *E. coli* putrescine aminotransferase is encoded by the ygjG gene, and the purified enzyme also was able to transaminate cadaverine and spermidine (Samsonova et al., *BMC Microbiol.* 3:2 (2003)). In addition, activity of this enzyme on 1,7-diaminoheptane and with amino acceptors other than 2-oxoglutarate (for example, pyruvate, 2-oxobutanoate) has been reported (Kim, *J. Biol. Chem.* 239:783-786 (1964); Samsonova et al., *BMC Microbiol.* 3:2 (2003)). A putrescine aminotransferase with higher activity with pyruvate as the amino acceptor than alpha-ketoglutarate is the spuC gene of *Pseudomonas aeruginosa* (Lu et al., *J. Bacteriol.* 184:3765-3773 (2002)).

| Gene | Accession No. | GI No. | Organism |
|---|---|---|---|
| ygjG | NP_417544 | 145698310 | *Escherichia coli* |
| spuC | AAG03688 | 9946143 | *Pseudomonas aeruginosa* |

Enzymes that transaminate 3-oxoacids include GABA aminotransferase (described above), beta-alanine/alpha-ketoglutarate aminotransferase and 3-amino-2-methylpropionate aminotransferase. Beta-alanine/alpha-ketoglutarate aminotransferase (WO08027742) reacts with beta-alanine to form malonic semialdehyde, a 3-oxoacid. The gene product of SkPYD4 in *Saccharomyces kluyveri* was shown to preferentially use beta-alanine as the amino group donor (Andersen and Hansen, *Gene* 124:105-109 (1993)). SkUGA1 encodes a homologue of *Saccharomyces cerevisiae* GABA aminotransferase, UGA1 (Ramos et al., *Eur. J. Biochem.* 149:401-404 (1985)), whereas SkPYD4 encodes an enzyme involved in both beta-alanine and GABA transamination (Andersen and Hansen, *Gene* 124:105-109 (1993)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Kakimoto et al., *Biochim. Biophys. Acta* 156:374-380 (1968); Tamaki et al., *Methods Enzymol.* 324:376-389 (2000)).

| Gene | Accession No. | GI No. | Organism |
|---|---|---|---|
| SkyPYD4 | ABF58893.1 | 98626772 | *Lachancea kluyveri* |
| SkUGA1 | ABF58894.1 | 98626792 | *Lachancea kluyveri* |
| UGA1 | NP_011533.1 | 6321456 | *Saccharomyces cerevisiae* |
| Abat | P50554.3 | 122065191 | *Rattus norvegicus* |
| Abat | P80147.2 | 120968 | *Sus scrofa* |

Several aminotransferases transaminate the amino groups of amino acids to form 2-oxoacids. Aspartate aminotransferase is an enzyme that naturally transfers an oxo group from oxaloacetate to glutamate, forming alpha-ketoglutarate and aspartate. Aspartate is similar in structure to OHED and 2-AHD. Aspartate aminotransferase activity is catalyzed by, for example, the gene products of aspC from *Escherichia coli* (Yagi et al., *FEBS Lett.* 100:81-84 (1979); Yagi et al., *Methods Enzymol.* 113:83-89 (1985)), AAT2 from *Saccharomyces cerevisiae* (Yagi et al., *J. Biochem.* 92:35-43 (1982)) and ASP5 from *Arabidopsis thaliana* (de la Torre et al., *Plant J.* 46:414-425 (2006); Kwok and Hanson. *J. Exp. Bot.* 55:595-604 (2004); Wilkie and Warren, *Protein Expr. Purif.* 12:381-389 (1998)). The enzyme from *Rattus norvegicus* has been shown to transaminate alternate substrates such as 2-aminohexanedioic acid and 2,4-diaminobutyric acid (Recasens et al., *Biochemistry* 19:4583-4589 (1980)). Aminotransferases that work on other amino-acid substrates can also be able to catalyze this transformation. Valine aminotransferase catalyzes the conversion of valine and pyruvate to 2-ketoisovalerate and alanine. The *E. coli* gene, avtA, encodes one such enzyme (Whalen and Berg, *J. Bacteriol.* 150:739-746 (1982)). This gene product also catalyzes the transamination of α-ketobutyrate to generate a-aminobutyrate, although the amine donor in this reaction has not been identified (Whalen and Berg, *J. Bacteriol.* 158:571-574 1984)). The gene product of the *E. coli* serC catalyzes two reactions, phosphoserine aminotransferase and phosphohydroxythreonine aminotransferase (Lam and Winkler, *J. Bacteriol.* 172:6518-6528 (1990)), and activity on non-phosphorylated substrates could not be detected (Drewke et al., *FEBS Lett.* 390:179-182 (1996)).

| Gene | Accession No. | GI No. | Organism |
|---|---|---|---|
| aspC | NP_415448.1 | 16128895 | *Escherichia coli* |
| AAT2 | P23542.3 | 1703040 | *Saccharomyces cerevisiae* |
| ASP5 | P46248.2 | 20532373 | *Arabidopsis thaliana* |
| Got2 | P00507 | 112987 | *Rattus norvegicus* |
| avtA | YP_026231.1 | 49176374 | *Escherichia coli* |
| serC | NP_415427.1 | 16128874 | *Escherichia coli* |

Another enzyme candidate is alpha-aminoadipate aminotransferase (EC 2.6.1.39), an enzyme that participates in lysine biosynthesis and degradation in some organisms. This enzyme interconverts 2-aminoadipate and 2-oxoadipate, using alpha-ketoglutarate as the amino acceptor. Gene candidates are found in *Homo sapiens* (Okuno et al., *Enzyme Protein* 47:136-148 (1993)) and *Thermus thermophilus* (Miyazaki et al., *Microbiology* 150:2327-2334 (2004)). The *Thermus thermophilus* enzyme, encoded by lysN, is active with several alternate substrates including oxaloacetate, 2-oxoisocaproate, 2-oxoisovalerate, and 2-oxo-3-methylvalerate.

| Gene | Accession No. | GI No. | Organism |
|---|---|---|---|
| lysN | BAC76939.1 | 31096548 | *Thermus thermophilus* |
| AadAT-II | Q8N5Z0.2 | 46395904 | *Homo sapiens* |

2.7.2.a Phosphotransferase (Carboxy Acceptor)

Phosphotransferase enzymes in the EC class 2.7.2 transform carboxylic acids to phosphonic acids with concurrent hydrolysis of one ATP. Step O of FIG. 62 involves the conversion of 4-hydroxybutyrate to 4-hydroxybutyryl-phosphate by such an enzyme. Butyrate kinase (EC 2.7.2.7) carries out the reversible conversion of butyryl-phosphate to butyrate during acidogenesis in *C. acetobutylicum* (Cary et al., *Appl. Environ. Microbiol.* 56:1576-1583 (1990)). This enzyme is encoded by either of the two buk gene products (Huang et al., *J. Mol. Microbiol. Biotechnol.* 2:33-38 (2000)). Other butyrate kinase enzymes are found in *C. butyricum* and *C. tetanomorphum* (Twarog and Wolfe, *J. Bacteriol.* 86:112-117 (1963)). Related enzyme isobutyrate kinase from *Thermotoga maritima* has also been expressed in *E. coli* and crystallized (Diao et al., *Acta Crystallogr. D. Biol. Crystallogr.* 59:1100-1102 (2003); Diao and Hasson, *J. Bacteriol.* 191:2521-2529 (2009)). Aspartokinase catalyzes the ATP-dependent phosphorylation of aspartate and participates in the synthesis of several amino acids. The aspartokinase III enzyme in *E. coli*, encoded by lysC, has a broad substrate range, and the catalytic residues involved in substrate specificity have been elucidated (Keng and Viola, *Arch. Biochem. Biophys.* 335:73-81 (1996)). Two additional kinases in *E. coli* are also good candidates: acetate kinase and gamma-glutamyl kinase. The *E. coli* acetate kinase, encoded by ackA (Skarstedt and Silverstein, *J. Biol. Chem.* 251:6775-6783 (1976)), phosphorylates propionate in addition to acetate (Hesslinger et al., *Mol. Microbiol.* 27:477-492 (1998)). The *E. coli* gamma-glutamyl kinase, encoded by proB (Smith et al., *J. Bacteriol.* 157:545-551 (1984)), phosphorylates the gamma carbonic acid group of glutamate.

| Gene | Accession No. | GI No. | Organism |
| --- | --- | --- | --- |
| buk1 | NP_349675 | 15896326 | *Clostridium acetobutylicum* |
| buk2 | Q97II1 | 20137415 | *Clostridium acetobutylicum* |
| buk2 | Q9X278.1 | 6685256 | *Thermotoga maritima* |
| lysC | NP_418448.1 | 16131850 | *Escherichia coli* |
| ackA | NP_416799.1 | 16130231 | *Escherichia coli* |
| proB | NP_414777.1 | 16128228 | *Escherichia coli* |

Acetylglutamate kinase phosphorylates acetylated glutamate during arginine biosynthesis. This enzyme is not known to accept alternate substrates; however, several residues of the *E. coli* enzyme involved in substrate binding and phosphorylation have been elucidated by site-directed mutagenesis (Marco-Marin et al., *J. Mol. Biol.* 334:459-476 (2003); Ramon-Maiques et al., *Structure* 10:329-342 (2002)). The enzyme is encoded by argB in *Bacillus subtilis* and *E. coli* (Parsot et al., *Gene* 68:275-283 (1988)), and ARG5,6 in *S. cerevisiae* (Pauwels et al., *Eur. J. Biochem.* 270:1014-1024 (2003)). The ARG5,6 gene of *S. cerevisiae* encodes a polyprotein precursor that is matured in the mitochondrial matrix to become acetylglutamate kinase and acetylglutamylphosphate reductase.

| Gene | Accession No. | GI No. | Organism |
| --- | --- | --- | --- |
| argB | NP_418394.3 | 145698337 | *Escherichia coli* |
| argB | NP_389003.1 | 16078186 | *Bacillus subtilis* |
| ARG5,6 | NP_010992.1 | 6320913 | *Saccharomyces cerevisiae* |

2.8.3.a CoA Transferase

The gene products of cat1, cat2, and cat3 of *Clostridium kluyveri* have been shown to exhibit succinyl-CoA (Step G, FIGS. 62 and 63), 4-hydroxybutyryl-CoA (Step T, FIG. 62), and butyryl-CoA acetyltransferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)).

| Gene | Accession No. | GI No. | Organism |
| --- | --- | --- | --- |
| cat1 | P38946.1 | 729048 | *Clostridium kluyveri* |
| cat2 | P38942.2 | 1705614 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

An additionally useful enzyme for this type of transformation is acyl-CoA:acetate-CoA transferase, also known as acetate-CoA transferase (EC 2.8.3.8), which has been shown to transfer the CoA moiety to acetate from a variety of branched and linear acyl-CoA substrates, including isobutyrate (Matthies and Schink, *Appl. Environ. Microbiol.* 58:1435-1439 (1992)), valerate (Vanderwinkel et al., *Biochem. Biophys. Res. Commun.* 33:902-908 (1968)) and butanoate (Vanderwinkel, supra (1968)). This enzyme is encoded by atoA (alpha subunit) and atoD (beta subunit) in *E. coli* sp. K12 (Korolev et al., *Acta Crystallogr. D Biol. Crystallogr.* 58:2116-2121 (2002); Vanderwinkel, supra (1968)). Similar enzymes exist in *Corynebacterium glutamicum* ATCC 13032 (Duncan et al., *Appl. Environ. Microbiol.* 68:5186-5190 (2002)), *Clostridium acetobutylicum* (Cary et al., *Appl. Environ. Microbiol.* 56:1576-1583 (1990); Wiesenborn et al., *Appl. Environ. Microbiol.* 55:323-329 (1989)), and *Clostridium saccharoperbutylacetonicum* (Kosaka et al., *Biosci. Biotechnol. Biochem.* 71:58-68 (2007)).

| Gene | Accession No. | GI No. | Organism |
| --- | --- | --- | --- |
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* |
| cg0592 | YP_224801.1 | 62389399 | *Corynebacterium glutamicum* |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack and Buckel, *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mac et al., *Eur. J. Biochem.* 226:41-51 (1994)).

| Gene | Accession No. | GI No. | Organism |
| --- | --- | --- | --- |
| gctA | CAA57199.1 | 559392 | *Acidaminococcus fermentans* |
| gctB | CAA57200.1 | 559393 | *Acidaminococcus fermentans* |

3.1.2.a CoA Hydrolase

Enzymes in the 3.1.2 family hydrolyze acyl-CoA molecules to their corresponding acids. However, such enzymes can be modified to empart CoA-ligase or synthetase functionality if coupled to an energy source such as a proton pump or direct ATP hydrolysis. Several eukaryotic acetyl-CoA hydrolases (EC 3.1.2.1) have broad substrate specificity. For example, the enzyme from *Rattus norvegicus* brain (Robinson et al., *Biochem. Biophys. Res. Commun.* 71:959-965 (1976)) can react with butyryl-CoA, hexanoyl-CoA and malonyl-CoA. Though its sequence has not been reported, the enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher and Randall, *Plant. Physiol.* 94:20-27 (1990)). The acetyl-CoA hydrolase, ACH1, from *S. cerevisiae* represents another candidate hydrolase (Buu et al., *J. Biol. Chem.* 278:17203-17209 (2003)).

| Gene | Accession No. | GI No. | Organism |
|---|---|---|---|
| acot12 | NP_570103.1 | 18543355 | *Rattus norvegicus* |
| ACH1 | NP_009538 | 6319456 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J. Biol. Chem.* 280:38125-38132 (2005)) and the closest *E. coli* homolog, tesB, which can also hydrolyze a broad range of CoA thioesters (Naggert et al., *J. Biol. Chem.* 266:11044-11050 (1991)). A similar enzyme has also been characterized in the rat liver (Deana, *Biochem. Int.* 26:767-773 (1992)). Other potential *E. coli* thioester hydrolases include the gene products of tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)).

| Gene | Accession No. | GI No. | Organism |
|---|---|---|---|
| acot8 | CAA15502 | 3191970 | *Homo sapiens* |
| tesB | NP_414986 | 16128437 | *Escherichia coli* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack and Buckel, *FEBS Lett.* 405:209-212 (1997)). This indicates that the enzymes encoding succinyl-CoA:3-ketoacid-CoA transferases and acetoacetyl-CoA:acetyl-CoA transferases can also serve as candidates for this reaction step but would likely require certain mutations to change their function.

| Gene | Accession No. | GI No. | Organism |
|---|---|---|---|
| gctA | CAA57199.1 | 559392 | *Acidaminococcus fermentans* |
| gctB | CAA57200.1 | 559393 | *Acidaminococcus fermentans* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J. Biol. Chem.* 269:14248-14253 (1994)). Genes encoding this enzyme include hibch of *Rattus norvegicus* (Shimomura et al., supra (1994); Shimomura et al., *Methods Enzymol.* 324:229-240 (2000)) and *Homo sapiens* (Shimomura et al., supra (1994). Candidate genes by sequence homology include hibch of *Saccharomyces cerevisiae* and BC_2292 of *Bacillus cereus*.

| Gene | Accession No. | GI No. | Organism |
|---|---|---|---|
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |

4.1.1.a Carboxy-lyase

Decarboxylation of Alpha-Keto Acids. Alpha-ketoglutarate decarboxylase (Step B, FIGS. 58, 62 and 63), 5-hydroxy-2-oxopentanoic acid decarboxylase (Step Z, FIG. 62), and 5-amino-2-oxopentanoate decarboxylase (Step R, FIG. 63) all involve the decarboxylation of an alpha-ketoacid. The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase.

Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (Davie et al., *J. Biol. Chem.* 267:16601-16606 (1992)). This enzyme has been extensively studied, engineered for altered activity, and functionally expressed in *E. coli* (Killenberg-Jabs et al., *Eur. J. Biochem.* 268:1698-1704 (2001); Li and Jordan, *Biochemistry* 38:10004-10012 (1999); ter Schure et al., *Appl. Environ. Microbiol.* 64:1303-1307 (1998)). The PDC from *Zymomonas mobilus*, encoded by pdc, also has a broad substrate range and has been a subject of directed engineering studies to alter the affinity for different substrates (Siegert et al., *Protein Eng. Des. Sel.* 18:345-357 (2005)). The crystal structure of this enzyme is available (Killenberg-Jabs et al., *Eur. J. Biochem.* 268:1698-1704 (2001)). Other well-characterized PDC candidates include the enzymes from *Acetobacter pasteurians* (Chandra et al., *Arch. Microbiol.* 176:443-451 (2001)) and *Kluyveromyces lactis* (Krieger et al., *Eur. J. Biochem.* 269:3256-3263 (2002)).

| Gene | Accession No. | GI No. | Organism |
|------|---------------|--------|----------|
| pdc | P06672.1 | 118391 | *Zymomonas mobilus* |
| pdc1 | P06169 | 30923172 | *Saccharomyces cerevisiae* |
| pdc | AM21208 | 20385191 | *Acetobacter pasteurians* |
| pdc1 | Q12629 | 52788279 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al., *Biochemistry* 37:9918-9930 (1998); Polovnikova et al., *Biochemistry* 42:1820-1830 (2003). Site-directed mutagenesis of two residues in the active site of the *Pseudomonas putida* enzyme altered the affinity (Km) of naturally and non-naturally occurring substrates (Siegert et al., *Protein Eng. Des. Sel.* 18:345-357 (2005)). The properties of this enzyme have been further modified by directed engineering (Lingen et al., *Protein Eng.* 15:585-593 (2002); Lingen et al., *Chembiochem.* 4:721-726 (2003)). The enzyme from *Pseudomonas aeruginosa*, encoded by mdlC, has also been characterized experimentally (Barrowman et al., *FEMS Microbiol. Lett.* 34:57-60 (1986)). Additional gene candidates from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.* 72:7510-7517 (2006)).

| Gene | Accession No. | GI No. | Organism |
|------|---------------|--------|----------|
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian et al., *Proc. Natl. Acad. Sci. USA* 102:10670-10675 (2005)) has been cloned and functionally expressed. However, it is not an ideal candidate for strain engineering because it is large (~130 kD) and GC-rich. KDC enzyme activity has been detected in several species of rhizobia including *Bradyrhizobium japonicum* and *Mesorhizobium loti* (Green et al., *J. Bacteriol.* 182:2838-2844 (2000). Although the KDC-encoding gene(s) have not been isolated in these organisms, the genome sequences are available, and several genes in each genome are annotated as putative KDCs. A KDC from *Euglena gracilis* has also been characterized, but the gene associated with this activity has not been identified to date (Shigeoka and Nakano, *Arch. Biochem. Biophys.* 288:22-28 (1991)). The first twenty amino acids starting from the N-terminus were sequenced (MTYKAPVKDVKFLL-DKVFKV; SEQ ID NO:45) (Shigeoka and Nakano, *Arch. Biochem. Biophys.* 288:22-28 (1991)). The gene can be identified by testing candidate genes containing this N-terminal sequence for KDC activity.

| Gene | Accession No. | GI No. | Organism |
|------|---------------|--------|----------|
| kgd | O50463.4 | 160395583 | *Mycobacterium tuberculosis* |
| kgd | NP_767092.1 | 27375563 | *Bradyrhizobium japonicum* |
| kgd | NP_105204.1 | 13473636 | *Mesorhizobium loti* |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku and Kaneda, *J. Biol. Chem.* 263:18386-18396 (1988); Smit et al., B. A., J. E. Hylckama Vlieg, W. J. Engels, L. Meijer, J. T. Wouters, and G. Smit. Identification, cloning, and characterization of a *Lactococcus lactis* branched-chain alpha-keto acid decarboxylase involved in flavor formation. *Appl. Environ. Microbiol.* 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., *Appl. Environ. Microbiol.* 71:303-311 (2005)). The enzyme has been structurally characterized (Berg et al., *Science* 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., *Protein Eng. Des. Sel.* 18:345-357 (2005)), so this enzyme would be a promising candidate for directed engineering. Decarboxylation of alpha-ketoglutarate by a BCKA was detected in *Bacillus subtilis*; however, this activity was low (5%) relative to activity on other branched-chain substrates (Oku and Kaneda. Biosynthesis of branched-chain fatty acids in *Bacillus subtilis*. A decarboxylase is essential for branched-chain fatty acid synthetase. *J. Biol. Chem.* 263: 18386-18396 (1988)), and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

| Gene | Accession No. | GI No. | Organism |
|------|---------------|--------|----------|
| kdcA | AAS49166.1 | 44921617 | *Lactococcus lactis* |

Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., *J. Biol. Chem.* 267:16601-16606 1992); Wynn et al., *J. Biol. Chem.* 267: 1881-1887 (1992); Wynn et al., *J. Biol. Chem.* 267:12400-12403 (1992)). In these studies, the authors found that co-expression of chaperonins GroEL and GroES enhanced the specific activity of the decarboxylase by 500-fold (Wynn et al., *J. Biol. Chem.* 267:12400-12403 (1992)). These enzymes are composed of two alpha and two beta subunits.

| Gene   | Accession No. | GI No.    | Organism     |
|--------|---------------|-----------|--------------|
| BCKDHB | NP_898871.1   | 34101272  | Homo sapiens |
| BCKDHA | NP_000700.1   | 11386135  | Homo sapiens |
| BCKDHB | P21839        | 115502434 | Bos taurus   |
| BCKDHA | P11178        | 129030    | Bos taurus   |

Decarboxylation of Alpha-Keto Acids. Several ornithine decarboxylase (Step U, FIG. 63) enzymes also exhibit activity on lysine and other similar compounds. Such enzymes are found in *Nicotiana glutinosa* (Lee and Cho, *Biochem. J.* 360:657-665 (2001)), *Lactobacillus* sp. 30a (Guirard and Snell, *J. Biol. Chem.* 255:5960-5964 (1980)) and *Vibrio vulnificus* (Lee et al., *J. Biol. Chem.* 282:27115-27125 (2007)). The enzymes from *Lactobacillus* sp. 30a (Momany et al., *J. Mol. Biol.* 252:643-655 (1995)) and *V. vulnificus* have been crystallized. The *V. vulnificus* enzyme efficiently catalyzes lysine decarboxylation, and the residues involved in substrate specificity have been elucidated (Lee et al., *J. Biol. Chem.* 282:27115-27125 (2007)). A similar enzyme has been characterized in *Trichomonas vaginalis*, but the gene encoding this enzyme is not known (Yarlett et al., *Biochem. J.* 293 (Pt 2):487-493 (1993)).

| Gene              | Accession No. | GI No.   | Organism            |
|-------------------|---------------|----------|---------------------|
| AF323910.1:1..1299| AAG45222.1    | 12007488 | Nicotiana glutinosa |
| odc1              | P43099.2      | 1169251  | Lactobacillus sp. 30a |
| VV2_1235          | NP_763142.1   | 27367615 | Vibrio vulnificus   |

Glutamate decarboxylase enzymes (Step L, FIGS. 62 and 63) are also well-characterized. Exemplary glutamate decarboxylases can be found in *E. coli* (De Biase et al., *Protein Expr. Purif.* 8:430-438 (1996)), *S. cerevisiae* (Coleman et al., *J. Biol. Chem.* 276:244-250 (2001)), and *Homo sapiens* (Bu et al., *Proc. Natl. Acad. Sci. USA* 89:2115-2119 (1992); Bu and Tobin, *Genomics* 21:222-228 (1994)).

| Gene | Accession No. | GI No.    | Organism                 |
|------|---------------|-----------|--------------------------|
| GAD1 | NP_000808     | 58331246  | Homo sapiens             |
| GAD2 | NP_001127838  | 197276620 | Homo sapiens             |
| gadA | NP_417974     | 16131389  | Escherichia coli         |
| gadB | NP_416010     | 16129452  | Escherichia coli         |
| GAD1 | NP_013976     | 6323905   | Saccharomyces cerevisiae |

Lysine decarboxylase (EC 4.1.1.18) catalyzes the decarboxylation of lysine to cadaverine. Two isozymes of this enzyme are encoded in the *E. coli* genome by genes cadA and ldcC. CadA is involved in acid resistance and is subject to positive regulation by the cadC gene product (Lemonnier and Lane, *Microbiology* 144 (Pt 3):751-760 (1998)). CadC accepts hydroxylysine and S-aminoethylcysteine as alternate substrates, and 2-Aminopimelate and 6-ACA act as competitive inhibitors to this enzyme (Sabo et al., *Biochemistry* 13:662-670 (1974)). Directed evolution or other enzyme engineering methods can be utilized to increase the activity for this enzyme to decarboxylate 2-aminopimelate. The constitutively expressed ldc gene product is less active than CadA (Lemonnier and Lane, *Microbiology* 144 (Pt 3):751-760 (1998)). A lysine decarboxylase analogous to CadA was recently identified in *Vibrio parahaemolyticus* (Tanaka et al., *J. Appl. Microbiol.* 104:1283-1293 (2008)). The lysine decarboxylase from *Selenomonas ruminantium*, encoded by ldc, bears sequence similarity to eukaryotic ornithine decarboxylases, and accepts both L-lysine and L-ornithine as substrates (Takatsuka et al., *Biosci. Biotechnol. Biochem.* 63:1843-1846 (1999)). Active site residues were identified and engineered to alter the substrate specificity of the enzyme (Takatsuka et al., *J. Bacteriol.* 182: 6732-6741 (2000)).

| Gene | Accession No. | GI No.   | Organism                |
|------|---------------|----------|-------------------------|
| cadA | AAA23536.1    | 145458   | Escherichia coli        |
| ldcC | AAC73297.1    | 1786384  | Escherichia coli        |
| ldc  | O50657.1      | 13124043 | Selenomonas ruminantium |
| cadA | AB124819.1    | 44886078 | Vibrio parahaemolyticus |

6.2.1.a CoA Synthetase

CoA synthetase or ligase reactions are required by Step I of FIGS. 62 and 63, and Step V of FIG. 62. Succinate or 4-hydroxybutyrate are the required substrates. Exemplary genes encoding enzymes likely to carry out these transformations include the sucCD genes of *E. coli*, which naturally form a succinyl-CoA synthetase complex. This enzyme complex naturally catalyzes the formation of succinyl-CoA from succinate with the concomitant consumption of one ATP, a reaction which is reversible in vivo (Buck et al., *Biochem.* 24:6245-6252 (1985)).

| Gene | Accession No. | GI No.   | Organism         |
|------|---------------|----------|------------------|
| sucC | NP_415256.1   | 16128703 | Escherichia coli |
| sucD | AAC73823.1    | 1786949  | Escherichia coli |

Additional exemplary CoA-ligases include the rat dicarboxylate-CoA ligase for which the sequence is yet uncharacterized (Vamecq et al., *Biochemical J.* 230:683-693 (1985)), either of the two characterized phenylacetate-CoA ligases from *P. chrysogenum* (Lamas-Maceiras et al., *Biochem. J* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacilis subtilis* (Bower et al., *J. Bacteriol.* 178(14):4122-4130 (1996)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)), which naturally catalyze the ATP-dependant conversion of acetoacetate into acetoacetyl-CoA. 4-Hydroxybutyryl-CoA synthetase activity has been demonstrated in *Metallosphaera sedula* (Berg et al., *Science* 318:1782-1786 (2007)). This function has been tentatively assigned to the Msed_1422 gene.

| Gene     | Accession No. | GI No.    | Organism                |
|----------|---------------|-----------|-------------------------|
| phl      | CAJ15517.1    | 77019264  | Penicillium chrysogenum |
| phlB     | ABS19624.1    | 152002983 | Penicillium chrysogenum |
| paaF     | AAC24333.2    | 22711873  | Pseudomonas putida      |
| bioW     | NP_390902.2   | 50812281  | Bacillus subtilis       |
| AACS     | NP_084486.1   | 21313520  | Mus musculus            |
| AACS     | NP_076417.2   | 31982927  | Homo sapiens            |
| Msed_1422| YP_001191504  | 146304188 | Metallosphaera sedula   |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus*, *H. marismortui* and *P. aerophilum* have all been cloned, functionally expressed, and characterized in *E. coli* (Musfeldt et al., supra; Brasen et al., supra (2004)).

| Gene | Accession No. | GI No. | Organism |
|---|---|---|---|
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

Example XXIII

Production of BDO Utilizing Carboxylic Acid Reductase

This example describes the generation of a microbial organism that produces 1,4-butanediol using carboxylic acid reductase enzymes.

*Escherichia coli* is used as a target organism to engineer the pathway for 1,4-butanediol synthesis described in FIG. 58. *E. coli* provides a good host for generating a non-naturally occurring microorganism capable of producing 1,4-butanediol. *E. coli* is amenable to genetic manipulation and is known to be capable of producing various products, like ethanol, acetic acid, formic acid, lactic acid, and succinic acid, effectively under various oxygenation conditions.

Integration of 4-Hydroxybutyrate Pathway Genes into Chromosome: Construction of ECKh-432. The carboxylic acid reductase enzymes were expressed in a strain of *E. coli* designated ECKh-761 which is a descendent of ECKh-432 with additional deletions of the sad and gabD genes encoding succinate semialdehyde dehydrogenase enzymes. This strain contained the components of the BDO pathway, leading to 4HB, integrated into the chromosome of *E. coli* at the fimD locus as described in Example XXI.

Cloning and Expression of Carboxylic Acid Reductase and PPTase. To generate an *E. coli* strain engineered to produce 1,4-butanediol, nucleic acids encoding a carboxylic acid reductase and phosphopantetheine transferase are expressed in *E. coli* using well known molecular biology techniques (see, for example, Sambrook, supra, 2001; Ausubel supra, 1999). In particular, car genes from *Nocardia iowensis* (designated 720), *Mycobacterium smegmatis* mc(2)155 (designated 890), *Mycobacterium avium* subspecies paratuberculosis K-10 (designated 891) and *Mycobacterium marinum* M (designated 892) were cloned into pZS*13 vectors (Expressys, Ruelzheim, Germany) under control of PA1/lacO promoters. The npt (ABI83656.1) gene (i.e., 721) was cloned into the pKJL33S vector, a derivative of the original mini-F plasmid vector PML31 under control of promoters and ribosomal binding sites similar to those used in pZS*13.

The car gene (GNM_720) was cloned by PCR from *Nocardia* genomic DNA. Its nucleic acid and protein sequences are shown in FIGS. 59A and 59B, respectively. A codon-optimized version of the npt gene (GNM_721) was synthesized by GeneArt (Regensburg, Germany). Its nucleic acid and protein sequences are shown in FIGS. 60A and 60B, respectively. The nucleic acid and protein sequences for the *Mycobacterium smegmatis* mc(2)155 (designated 890), *Mycobacterium avium* subspecies paratuberculosis K-10 (designated 891) and *Mycobacterium marinum* M (designated 892) genes and enzymes can be found in FIGS. 64, 65, and 66, respectively. The plasmids were transformed into ECKh-761 to express the proteins and enzymes required for 1,4-butanediol production.

Demonstration of 1,4-BDO Production using Carboxylic Acid Reductase. Functional expression of the 1,4-butanediol pathway was demonstrated using *E. coli* whole-cell culture. Single colonies of *E. coli* ECKh-761 transformed with the pZ S*13 and pKJL33S plasmids containing a car gene and GNM_721, respectively, were inoculated into 5 mL of LB medium containing appropriate antibiotics. Similarly, single colonies of *E. coli* ECKh-761 transformed with car-containing pZ S*13 plasmids and pKJL33S plasmids with no insert were inoculated into additional 5 mL aliquots of LB medium containing appropriate antibiotics. Ten mL micro-aerobic cultures were started by inoculating fresh minimal in vivo conversion medium (see below) containing the appropriate antibiotics with 1.5% of the first cultures.

Recipe of the minimal in vivo conversion medium (for 1000 mL) is as follows:

|  | Final concentration |
|---|---|
| 1M MOPS/KOH buffer | 100 mM |
| Glucose (40%) | 1% |
| 10XM9 salts solution | 1X |
| MgSO4 (1M) | 1 mM |
| trace minerals (x1000) | 1X |
| 1M NaHCO3 | 10 mM |

Microaerobic conditions were established by initially flushing capped anaerobic bottles with nitrogen for 5 minutes, then piercing the septum with an 18G needle following inoculation. The needle was kept in the bottle during growth to allow a small amount of air to enter the bottles. Protein expression was induced with 0.2 mM IPTG when the culture reached mid-log growth phase. This is considered: time=0 hr. The culture supernatants were analyzed for BDO, 4HB, and other by-products as described above and in WO2008115840 (see Table 31).

Table 33 shows the production of various products in the strains expressing various carboxylic acid reductases, including production of BDO.

TABLE 33

Production of various products in strains expressing various carboxylic acid reductases.

| Strain | Cm10 pKLJ33S | Carb100 pZS*13S | Carb100 pZShc13S | 0 h OD600 | OD600 |
|---|---|---|---|---|---|
| 1 | 761 | 034rbs55 | no insert | 0.54 | 2.13 |
| 5 | 761 | 721 | 720 | 0.48 | 1.88 |
| 7 | 761 | 721 | 890 | 0.45 | 1.63 |
| 8 | 761 | 721 | 891 | 0.48 | 1.65 |
| 9 | 761 | 721 | 892 | 0.45 | 1.31 |
| 12 | 761 | no insert | 720 | 0.50 | 1.72 |
| 14 | 761 | no insert | 890 | 0.51 | 1.96 |
| 15 | 761 | no insert | 891 | 0.19 | 2.36 |
| 16 | 761 | no insert | 892 | 0.05 | 1.40 |

48 h

| | PA | Su | La | 4HB | BDO | GBL | EtOH$_{Enz}$ |
|---|---|---|---|---|---|---|---|

48 h, mM

| | PA | Su | La | 4HB | BDO | GBL | EtOH$_{Enz}$ |
|---|---|---|---|---|---|---|---|
| 1 | 10.60 | 0.00 | 0.20 | 8.08 | 2.40 | 2.97 | 0.65 |
| 5 | 3.41 | 0.00 | 0.02 | 6.93 | 8.53 | 0.24 | 1.82 |
| 7 | 0.00 | 0.00 | 0.00 | 6.26 | 12.30 | 0.47 | 5.85 |
| 8 | 2.16 | 0.00 | 0.00 | 7.61 | 9.08 | 0.46 | 2.84 |
| 9 | 0.36 | 0.00 | 0.00 | 5.89 | 7.83 | 0.15 | 2.89 |
| 12 | 8.30 | 0.00 | 0.13 | 9.91 | 1.99 | 0.14 | 0.64 |
| 14 | 2.57 | 0.00 | 0.01 | 9.77 | 3.53 | 0.14 | 1.44 |
| 15 | 1.73 | 0.00 | 0.00 | 9.71 | 2.68 | 0.10 | 0.79 |
| 16 | 0.02 | 0.00 | 0.00 | 10.80 | 1.30 | 0.07 | 0.55 |

48 h, mM/OD

| | PA | Su | La | 4HB | BDO | GBL | EtOH$_{Enz}$ |
|---|---|---|---|---|---|---|---|
| 1 | 4.98 | 0.00 | 0.09 | 3.80 | 1.13 | 1.40 | 0.31 |
| 5 | 1.81 | 0.00 | 0.01 | 3.69 | 4.54 | 0.13 | 0.97 |
| 7 | 0.00 | 0.00 | 0.00 | 3.84 | 7.55 | 0.29 | 3.59 |
| 8 | 1.31 | 0.00 | 0.00 | 4.61 | 5.50 | 0.28 | 1.72 |
| 9 | 0.27 | 0.00 | 0.00 | 4.50 | 5.99 | 0.12 | 2.21 |
| 12 | 4.83 | 0.00 | 0.07 | 5.76 | 1.16 | 0.08 | 0.37 |
| 14 | 1.31 | 0.00 | 0.01 | 4.99 | 1.80 | 0.07 | 0.74 |
| 15 | 0.73 | 0.00 | 0.00 | 4.11 | 1.13 | 0.04 | 0.33 |
| 16 | 0.01 | 0.00 | 0.00 | 7.71 | 0.93 | 0.05 | 0.39 |

PA = pyruvate,
SA = succinate,
LA = lactate,
4HB = 4-hydroxybutyrate,
BDO = 1,4-butanediol,
GBL = gamma-butyrolactone,
Etoh = ethanol,
LLOQ = lower limit of quantification
These results show that various carboxylic acid reductases can function in a BDO pathway to produce BDO.

Example XXIV

Metabolic Modifications to Improve Engineered Microorganism Characteristics

This example describes additional metabolic modifications to improve characteristics of an engineered microorganism. Such improved characteristics include, but are not limited to, increased product yield, decreased production of by-products, improved growth characteristics of the engineered microorganisms, including improved characteristics for scale up production, and the like.

Cultivation conditions for bottles. Twenty-milliliter bottle cultivations for metabolite production or bioconversion were performed in M9 minimal salts medium (6.78 g/L Na$_2$HPO$_4$, 3.0 g/L KH$_2$PO$_4$, 0.5 g/L NaCl, 1.0 g/L NH$_4$Cl, 1 mM MgSO$_4$, 0.1 mM CaCl$_2$) supplemented with 10 mM NaHCO$_3$, 20 g/L D-glucose and 100 mM MOPS to improve the buffering capacity, 10 μg/ml thiamine and the appropriate antibiotics for plasmid maintenance. *E. coli* strain MG1655 lacIQ+ was grown anaerobically, and anaerobic conditions were obtained by flushing capped anaerobic bottles with nitrogen for at least 5 min. Microaerobic conditions were used for all other strains, which were established by initially flushing capped anaerobic bottles with nitrogen for 5 min, then piercing the septum with a 23G needle (Becton-Dickenson) after inoculation. The needle was kept in the bottle during growth to allow a small amount of air to enter. Protein expression was induced with 0.2 mM IPTG when the culture reached mid-log growth phase, unless otherwise indicated in the text.

Cultivation conditions for 96 well-plates. All the cultures in 96 well-plates were grown in 1.2 ml of M9 medium (composition provided above) with MOPS and appropriate antibiotics. Carbon source in the form of 5% glucose was also added. Microaerobic conditions were obtained by covering the plates with two gas-permeable adhesive seals. The edges of the seal were taped to minimize evaporation. All the cultures were grown at 37° C.

Bacterial strains and plasmids. Genomic DNA from bacterial strains was isolated with the PureLink Genomic DNA Mini Kit (Invitrogen) according to the manufacturer's instructions. Recombinant DNA manipulations were conducted as described (Sambrook et al., T. *Molecular Cloning: A Laboratory Manual*, Cold Spring Harbor Laboratory, Cold Spring Harbor, N.Y., (1989). Genes and open reading frames in the study were amplified from appropriate genomic DNA templates using the high-fidelity KOD DNA polymerase enzyme (EMD Chemicals; Billerica Mass.). Analytical PCR experiments for genotyping and sequencing were conducted according to standard molecular biology protocols with Taq polymerase (Promega). DNA sequencing was provided by Genewiz (South Plainfield N.J.).

Procedure for genetic manipulations. Development of expression vectors for BDO pathway. Vector backbones were obtained from Dr. Rolf Lutz of Expressys (expressys.de). The vectors and strains are based on the pZ Expression System described previously (Lutz and Bujard, *Nucleic Acids Res.* 25:1203-1210 (1997).). Vectors obtained were pZE13luc, pZA33luc, pZS*13luc and pZE22luc and contained the luciferase gene as a stuffer fragment. To replace the luciferase stuffer fragment with a lacZ-alpha fragment flanked by appropriate restriction enzyme sites, the luciferase stuffer fragment was first removed from each vector by digestion with EcoRI and XbaI. The lacZ-alpha fragment was PCR amplified from pUC19 with the following primers:

lacZalpha-RI
(SEQ ID NO: 1)
5'GACGAATTCGCTAGCAAGAGGAGAAGTCGACATGTCCAATTCACTGG

CCGTCGTTTTAC3' lacZalpha 3'BB
(SEQ ID NO: 2)
5'-GACCCTAGGAAGCTTTCTAGAGTCGACCTATGCGGCATCAGAGC

AGA-3'.

This generated a fragment with a 5' end of EcoRI site, NheI site, a Ribosomal Binding Site, a SalI site and the start codon. The 3' end of the fragment contained the stop codon, XbaI, HindIII, and AvrII sites. The PCR product was digested with EcoRI and AvrII and ligated into the base vectors digested with EcoRI and XbaI (XbaI and AvrII have compatible ends and generate a non-site). Because NheI and XbaI restriction enzyme sites generate compatible ends that can be ligated together (but generate a site after ligation that is not digested by either enzyme), the genes cloned into the vectors could be "Biobricked" together (openwetware.org/wiki/Synthetic_Biology:BioBricks). Briefly, this method allows joining an unlimited number of genes into the vector using the same 2 restriction sites, as long as the sites do not appear internal to the genes, because the sites between the genes are destroyed after each addition. Initially, expression was low from these vectors, and they were subsequently modified using the Phusion® Site-Directed Mutagenesis Kit (NEB, Ipswich, Mass.) to insert the spacer sequence AAT-TAA between the EcoRI and NheI sites. This eliminated a putative stem loop structure in the RNA that bound the RBS and start codon.

All vectors have the pZ designation followed by letters and numbers indicating the origin of replication, antibiotic resistance marker and promoter/regulatory unit. The origin of replication is the second letter and is denoted by E for ColE1, A for p15A and S for pSC101 (as well as a lower copy number version of pSC101 designated S*)-based origins. The first number represents the antibiotic resistance marker (1 for Ampicillin, 2 for Kanamycin, 3 for Chloramphenicol). The final number defines the promoter that regulated the gene of interest (1 for PLtetO-1, 2 for PLlacO-1 and 3 for PA1lacO-1) and each of these promoters became activated by its corresponding inducer molecule (pLtetO can be induced by tetracycline; pLlacO-1 and pAllacO-1 can be induced by IPTG). Three base vectors, pZS*13S, pZA33S and pZE13S, were then designed and constructed to serve as "inducible" plasmid vectors.

In addition to the "inducible" promoters mentioned above, a set of "constitutive" promoters were sampled from the Registry (partsregistry.org). Each of these "constitutive" promoters was then introduced into the pZS*13S vector backbone to replace the pAllacO-1 inducible promoter via Sequence and Ligation Independent Cloning (SLIC) method described by Li & Eledge (Nature Methods 2007, 4:251-256). Of these sampled "constitutive" promoters (p100, p104, p105, p107, p108, p111, p115 & p119), experiments were carried out to establish an order of promoter strength that was verified by protein expression levels. For these experiments, both "inducible" and "constitutive" plasmid vectors were employed, modified for the biobricks and SLIC insertions as discussed above. To further fine-tune protein expression levels of some overly expressed proteins, ribosomal binding site (RBS) S) in between promoter and gene coding sequence was modified accordingly using the RBS calculator (salis.psu.edu/software/).

The SLIC primers used for inserting a list of genes into the pZS*13S vector backbone are listed below. The lower case marks the sequences annealing to a vector backbone while the upper case marks the sequences annealing to the coding region of a gene.

1. ppc 525
Forward SLIC primer:
(SEQ ID NO: 100)
gaggagaagtcgacATGAACGAACAATATTCCGCATTGCG Reverse SLIC primer:
(SEQ ID NO: 101)
ggaagetttctagaTTAGCCGGTATTACGCATACCTGCC 2. sucAB-lpdA
Forward SLIC primer:
(SEQ ID NO: 102)
taagctagcaagaggagaagtcgacATGCAGAACAGCGCTTTGAAAG -continued
Reverse SLIC primer:
(SEQ ID NO: 103)
gcctctaggaagctttctagaTTACTTTTTCTTCGCTTTGGCG 3. galP 1120
Forward SLIC primer:
(SEQ ID NO: 104)
ctagcaagaggagaagtcgacATGCCTGACGCTAAAAAACAGGGGCGGT Reverse SLIC primer:
(SEQ ID NO: 105)
ctaggaagctttctagagtcgTTAATCGTGAGCGCCTATTTCGCGCAG 4. glk 1123
Forward SLIC primer:
(SEQ ID NO: 106)
ctagcaagaggagaagtcgacATGACAAAGTATGCATTAGTCGGTGA
TGTG Reverse SLIC primer:
(SEQ ID NO: 107)
ctaggaagctttctagagtcgTTACAGAATGTGACCTAAGGTCTGGCGT
AAATG 5. glf 1786
Forward SLIC primer:
(SEQ ID NO: 108)
ctagcaagaggagaagtcgacATGAGTTCTGAAAGTAGTCAGGGTCT
AGTC Reverse SLIC primers:
(SEQ ID NO: 109)
ctaggaagattctagagtcgTTACTTCTGGGAGCGCCACATCTC For the work discussed below, three base vectors, pZS*13S, pZA33S and pZE13S, modified for the biobricks insertions as discussed above, were employed.

The following technique describes the construction of the incW plasmids, pPSX13 and and pPSX23R. The original incW plasmid backbone (pPSX) was obtained from Dr. John M. Pemberton (Sarovich and Pemberton, *Plasmid* 57:306-313 (2007)). The pPSX plasmid was modified to insert either an ampicillin marker (bla gene), designated as pPSX13, into a BamHI restriction enzyme site or an kanamycin marker and a R6k replication origin, designated as pPSX23R, in between BamHI and SacI restriction enzyme sites. Two similar incW plasmids were also constructed to include the ald-adh gene cassette amplified from pZS*13S-ald-adh. For pPSX13-ald-adh ampicillin-resistant plasmid, the bla-ald-adh gene cassette was inserted into a BamHI restriction enzyme site of pPSX13. To construct pPSX23R-ald-adh kanamycin resistant plasmid, the ampicillin marker (bla gene) was replaced with the "kanamycine marker-R6k replication origine" cassette in between XhoI and SacI restriction enzyme sites of pPSX23R.

The genes 033B, 1210, and 956 were inserted in the mini-F-plasmid backbone pKLJ33S as follows: PCR primers were designed to amplify the genes 033B (033BFOR and 033BREV), 1210C (1210CFOR and 1210CREV), and 956 (956FOR and 956REV) from appropriate templates. These primers included the immediate 5' (FOR) and 3' (REV) ends of each gene as denoted in upper case. Each primer also included a tail that was directly homologous to the promoter region (FOR) and terminator region (REV) of plasmid pZA33S. A linear fragment of pZA33S with the promoter region and terminator regions at either extreme end was amplified using Primers pZ-5' and pZ-3' and circular pZA33S as a template. The pZA33S linear fragment was combined with each of the 033B, 1210C, and 956 gene fragments and joined using sequence- and ligation-independent cloning to form the corresponding plasmids pZA33S-033B, pZA33S-1210C, and pZA33 S-956.

| Primer Designation | Primer Sequence | SEQ ID NO |
|---|---|---|
| 033BFOR | tagcaagaggagaagtcgacATGGACTGGAAGAAGATCTATGAAG | 110 |
| 033BREV | cctctaggaagattctagaTTAGAATGCCGCGTTGAAG | 111 |
| 1210CFOR | tagcaagaggagaagtcgacATGAGCTGGCAAGAACTGTATC | 112 |
| 1210CREV | cctctaggaagctttctagaTTAATATTTCTCTTTAAAGCGCTTTTC | 113 |
| 956FOR | tagcaagaggagaagtcgacATGGCACGTTTTACTTTACCAAG | 114 |
| 956REV | cctctaggaagctttctagaTTACAAATTAACTTTAGTTCCATAGTATGTGC | 115 |
| 034Cmfor | accggtaaacgactcagcagcctgacgcactggcgatattattttgccttctcctcaccacagaatgttctgccacctgaCGATATCAAATTACGCCCCG | 116 |
| 034Cmrev | tgcttatccacaacattttgcgcacggttatgtggacaaaatacctggttacccaggccgtgccggcacgttaaccgggcCCTAGGTCTAGGGCGGCGGATTTG | 117 |

Primers 034Cmfor and 034Cmrev were used to amplify the 033B, 1210C, and 956 genes from the appropriate pZA33S plasmid background. These primers were designed to amplify the chloramphenicol resistance gene, pA1 promoter, particular gene of interest, and terminator elements from plasmid pZA33S (with the sequences denoted in upper case) while tail sequences (denoted in lower case) corresponded to regions flanking but not including the ampicillin resistance gene, arabinose responsive promoter and terminator sequences of the mini-F-plasmid pKLJ12 (Jones and Keasling, *Biotechnol. Bioengineer.* 59:659-665 (1998)).

An *E. coli* DP10B strain containing plasmid pKLJ12 and temperature-sensitive Red/ET helper plasmid pREDET (Tet) (GeneBridges GmbH, Heidelberg Germany) was inoculated into LB medium containing tetracycline at 10 µg/ml and ampicillin at 100 µg/ml final concentrations and incubated for 3 hours at 30° C. with shaking until cells were turbid. Arabinose to induce expression of the Red/ET recombination functions was added to a final concentration of 0.3%, the temperature was shifted to 37° C. and the cells were allowed to incubate for an additional hour with shaking. After being made electrocompetent by repeated centrifugation and resuspension in ice-cold sterile double-distilled water, these cells were mixed with 034Cmfor/034Cmrev PCR amplifications from the pZA33S-033B, pZA33S-1210C, or pZA33S-956 plasmids in a 1 mm cuvette and then subjected to electroporation at 1800 kV, 25 µF, 200Ω. Electroporated cells were then added to SOC growth medium, incubated at 37° C. without shaking, and then spread on LB solid medium containing chloramphenicol at 10 µg/ml final concentration and incubated at 37° C. for 18 to 24 hours. Resulting chloramphenicol-resistant single colonies were then scored for growth on solid LB media containing either tetracycline at 10 µg/ml or the ampicillin at 100 µg/ml. Colonies that were shown to be chloramphenicol resistant, tetracycline sensitive, and ampicillin sensitive were verified by PCR and DNA sequencing to contain new mini-F-plasmids that had completely exchanged the ampicillin resistance gene/arabinose responsive promoter/terminator of pKLJ12 with the chloramphenicol resistance gene/PA1 promoter/gene-of-interest/terminator of pZA33S by RED/ET-mediated homologous recombination, resulting in the new mini-F-plasmids pKLJ33S-033B, pKLJ33 S-1210C, pKLJ33 S-956.

Chromosomal replacement of genes using the sacB gene. The primary method used for the insertion or deletion of genes in the chromosome of *E. coli* was based on the utilization of the sacB gene from *Bacillus subtilis* (Gay et al., *J. Bacteriol.* 153:1424-1431 (1983)). The vector used is pRE118 (ATCC87693) deleted of the oriT and IS sequences. The resulting vector (3.6 kb in size and carrying the kanamycin resistance gene) was sequenced and called pRE118-V2. All cloning of fragments was done into the restriction sites KpnI and PstI of pRE118-V2, unless notified. All PCR amplification used genomic DNA from *E. coli* MG1655 (ATCC47076) as DNA template. The first integration event in the chromosome was selected on LB agar plates containing Kanamycin (25 or 50 mg/L). Correct insertions were verified by PCR using 2 primers: one located outside the region of insertion and one in the kanamycin gene (5'-aggcagttccataggatggc-3'; SEQ ID NO:118). Clones with the correct insertion were selected for resolution. They were sub-cultured twice in plain liquid LB at the desired temperature and serial dilutions were plated on LB-no salt-sucrose 10% plates. Clones that grew on sucrose containing plates were screened for the loss of the kanamycin resistance gene on LB-low salt agar medium and the deletion/insertion of the fragment of interest was verified by PCR and sequencing of the encompassing region.

This method was used for deleting appCB using the following primers:

| Primer Designation | Primer Sequence | SEQ ID NO |
|---|---|---|
| appCB Kpn fw | AtaataataggtaccggcggcgctggcgcagcttgctgcG | 119 |
| appCB BamHI rv | TATTATTATGGATCCAACCCGATAATGGTAGATCTCCCTCT | 120 |
| appCB BamHI fw | Ataataataggatccggagcagaaacaatgtggtatttact | 121 |
| appCB Pst rv | TATTATTATCTGCAGATGCTCTTTTTTATGCATTACAAACTGC | 122 |

As a result, the following nucleotides were deleted: 1,036,963->1,039,655 tesB and ybgC deletions were also made with aforementioned pRE-sacB-Kan vector. The primers used for making the deletion were: (5'-3')

| Primer Designation | Primer Sequence | SEQ ID NO |
|---|---|---|
| tesB-kpn-frw | taataataaggtaccaactgggcttgcttcactgg | 123 |
| tesB-bgl-rev | taataataaAGATCTGCCTCGACCGTTCAGGAAGG | 124 |
| tesB-bgl-frw | taataataaagatcttaactctccagtaacaaagctgc | 125 |
| tesB-Pst-rev | taataataaCTGCAGGCTATGTCACCACTTACGG | 126 |
| ybgC-Pst-frw | Tattattattcctgcaggcgtattgttatccgtcc | 127 |
| ybgC-Kpn-rev | tattattatCTTCGGTACCTTTAGCATCTGCTTCGGCC | 128 |
| ybgC-Bam-rev | tattattatGGATCCCGGTAATGCAACAAAAGTTAGAGC | 129 |
| ybgC-Bam-frw | tattattatggatccaaagtgactgacatgaatatccttgatttgttc | 130 |

Nucleotides deleted as a consequence were:
tesB: 473,525<-474,385
ybgC: 773,975->774,379

An ndh deletion was also made with the standard pRE-sacB-Kan vector. The primers used for making the deletion were: (5'-3')

| Primer Designation | Primer Sequence | SEQ ID NO |
|---|---|---|
| ndh-Bam-frw | taataataaggatcctacactggcggatgtggcataaac | 131 |
| ndh-Kpn-rev | taataatttggtacccATTCACAGTCACCAGGTACAACG | 132 |
| ndh-Bam-rev | taataataaGGATCCGAGAATAACATGAATGGTGCATTG | 133 |
| ndh-Pst-frw | taataatatctgcagatccacaaaaagccctggcaattg | 134 |

Nucleotides deleted as a result of the deletion were: 1,165,308->1,166,612

Deletions of yjgB, yqhD, yahK and adhP were introduced with the standard pRE-sacB-Kan vector. The primers used for making the deletion were: (5'-3')

| Primer Designation | Primer Sequence | SEQ ID NO |
|---|---|---|
| ygjB-Pst-frw | gataatcccccctgcagggagcggtaaatag | 135 |
| ygjB-Bam-rev | tattatTTTGGATCCTTCTCTGGTGTTGTTTGGG | 136 |
| yjgB-Bam-frw | tattattatggatccgcgtggtgttgaaagccg | 137 |
| yjgBKpn-rev | tattatAAAGGTACCGCCTCTTCCAGGTCAGTGAAGGG | 138 |
| yqhD-Kpn-frw | taataataaggtacccagttttggctatgccttaag | 139 |
| yqhD-Hind-rev | taataaTCATTAAGCTTGCTCCCTTTGCTGGGCC | 140 |
| yqhD-Hind-frw | taataataataagattttacgcctcaaactttcg | 141 |
| yqhD-Pst-rev | taataataaATTGCCCTGCAGCGTAAGATTGTCGTTCAGGG | 142 |
| yahK-Kpn-frw | tattattattgtttggtacctctgtgccgct | 143 |
| yahK-Pst-rev | AATGTTCCACTCTGCAGGGATGATAATAAGGGG | 144 |

| Primer Designation | Primer Sequence | SEQ ID NO |
|---|---|---|
| yahK-Bam-frw | atcggatccaatcgcacactaacagactg | 145 |
| yahK-Bam-rev | ACAGCTTTGGATCCTCATTGTGTTTACTCCTGATTAGC | 146 |
| adhP XbaI fw | ataataatatctagagcagcaagccgcgcggcaggtggtcag | 147 |
| adhP PstI rv | TATTATTATCTGCAGACGCCATCCTGATCCATATGTATATGG | 148 |
| adhP Bam up rv | TATTATTATGGATCCAGTTCCTCCTTTTCGGATGATGTTCTG | 149 |
| adhP Bam down fw | ataataataggatccgaggcctttgctgcgactgccatgttc | 150 |

Nucleotides deleted as a result of each of these deletions were: ygjB: 4,493,213<-4,494,232, yqhD: 3,153,377->3,154,540, yahK: 342,108->343,157, adhP: 1,550,852<-1,551,862.

Gene deletions using lambda-red mediated combination: Native genes cyoABCD were deleted from the chromosome by Red-mediated recombination (ncbi.nlm.nih.gov/pubmed/10829079).

For cyoABCD deletion, the following primers were used to amplify a chloramphenicol or kanamycin resistance gene from pKD3 or pKD4 (ncbi.nlm.nih.gov/pubmed/10829079), respectively, and were flanked by FRT sites and homologies to cyoABCD:

```
LK-cyo-F1
                                (SEQ ID NO: 151)
CGCCACAACCAGTGACACCC LK-cyo-R1
                                (SEQ ID NO: 152)
GGGGTTTTAGTCGCCCTTTCTGGC LK-cyo-IO-down
                                (SEQ ID NO: 153)
CGGGATCTGGTGGCGTTTAAAGTG LK-cyo-IO-up
                                (SEQ ID NO: 154)
TGACGGCGTTTGTCTTCACCG
```

E. coli K-12 MG1655 carrying the Red helper plasmid pKD46 was grown in 100 ml LB medium with ampicillin and 1 mM L-arabinose at 30° C. to an OD600 of 0.3, and electroporation-competent cells were prepared as described elsewhere (Sambrook et al., *Molecular Cloning: A Laboratory Manual*, Cold Spring Harbor Laboratory, Cold Spring Harbor, N.Y., (1989)). A measure of 50 µl of competent cells was mixed with 400 ng of the PCR fragment in an ice-cold 0.1 cm cuvette (Bio-Rad Inc., Hercules, Calif., USA). Cells were electroporated at 1.8 kV with 25 mF and 200, immediately followed by the addition of 1 ml of SOC medium (2% Bacto Tryptone (Difco), 0.5% yeast extract (Difco), 10 mM NaCl, 2.5 mM KCl, 10 mM $MgCl_2$, 10 mM $MgSO_4$, 20 mM glucose) with 1 mM L-arabinose. After incubation for 2 h at 37° C., one-tenth portion was spread onto agar plate to select chloramphenicolR or kanamycinR transformants at 37° C. The individual deletions were then transduced into new host strains using P1vir and selecting for the appropriate antibiotic (Silhavy et al., *Experiments with gene fusions*, Cold Spring Harbor Laboratory, Cold Spring Harbor, N.Y. (1984)). The chloramphenicol or kanamycin resistant colonies were then transformed with the temperature sensitive plasmid pCP20, and plated on ampicillin (100 µg/ml) plates at 30° C. pCP20 contains the yeast Flp recombinase gene, chloramphenicol and ampicillin resistant genes, and temperature sensitive replication. Colonies were grown in LB medium without antibiotics at 42° C. overnight and streak plated on prewarmed LB Agar plates and grown at 42° C. Individual clones were tested for sensitivity to ampicillin and chloramphenicol or kanamycin to isolate clones which had lost the pCP20 plasmid and had the chloramphenicol or kanamycin resistance gene lost via the Flp recombinase. Positive clones with deletions in cyoABCD contain a single FRT "scar" and were verified by PCR using primers which flanked their respective genes.

The nucleotides deleted because of the cyoABCD deletion were: 449,887->447,270

The esterase from *Yersinia intermedia* was integrated in the chromosome with the standard pRed technique described above. The primers used for making the insertion were: (5'-3')

| Primer Designation | Primer Sequence | SEQ ID NO |
|---|---|---|
| JE310 | ACGCTATGGAACTGCAGGATGAGAGCATGAAATGGAACGGGCGCGCCTTAT | 155 |
| JE311 | ACGCTATGGAACTGCAGGATGAGAGCATCTGCCCCAGATCGTTGGCTTTTTGC | 156 |
| JE312 | TTTGAAAACAGGATGTAGCGATGACCGATATTCGCTTGTA | 157 |
| JE312-rv | TACAAGCGAATATCGGTCATCGCTACATCCTGTTTTCAAA | 158 |
| JE313 | CGCCTGAATACTACGATTGACTGGAGAATGCGAATGAACA | 159 |

| Primer Designation | Primer Sequence | SEQ ID NO |
|---|---|---|
| JE313-rv | TGTTCATTCGCATTCTCCAGTCAATCGTAGTATTCAGGCG | 160 |
| JE314 | TTTGAAAACAGGATGTAGCGGCCCGTAGTCTGCAAATCC | 161 |
| JE314-rv | GGATTTGCAGACTACGGGCCGCTACATCCTGTTTTCAAA | 162 |
| JE315 | GCATTACGCTGACTTGACGGCTGGAGAATGCGAATGAACA | 163 |
| JE315-rv | TGTTCATTCGCATTCTCCAGCCGTCAAGTCAGCGTAATGC | 164 |

The sequence that was inserted at the gabD locus (ORF swap) was:

(SEQ ID NO: 165)
ACTGGAGAATGCGAATGAACAGCAATAAAGAGTTAATGCAGCGCCGCAG

TCAGGCGATTCCCCGTGGCGTTGGGCAAATTCACCCGATTTTCGCTGAC

CGCGCGGAAAACTGCCGGGTGTGGGACGTTGAAGGCCGTGAGTATCTTG

ATTTCGCGGGCGGGATTGCGGTGCTCAATACCGGGCACCTGCATCCGA

AGGTG.

Figure 67:
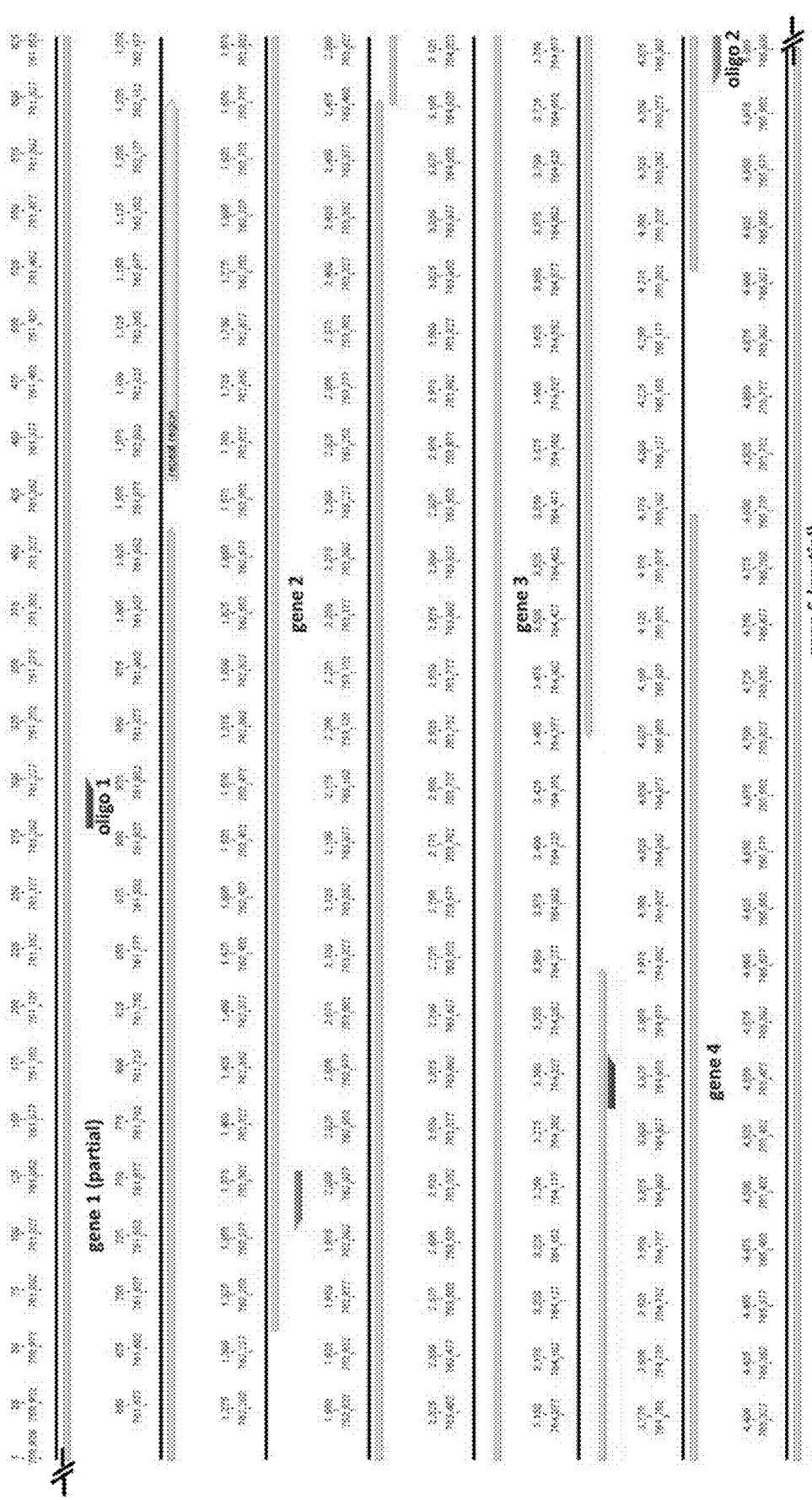
FIG. 67 shows a schematic of the *E. coli* MG1655 chromosome between nucleotides 760928 and 765930.

Markerless deletion of sucC and sucD. Deletion of the native Escherichia coli sucC (gene 2) and sucD (gene 3) from the chromosome (FIG. 67) was achieved using a two-step double-crossover homologous recombination method. Recombination was catalyzed via expression of the Lambda phage Red genes from pRED-Amp (Gene Bridges, Heidelberg, Germany). Genes encoding levansucrase (gene 6) and kanamycin resistance (gene 7) were integrated into the chromosome, replacing the majority of sucC (gene 2) and sucD (gene 3). Kanamycin was used to select for successful integrants. In a second double-crossover homologous recombination step, the integrated sequence containing the levansucrase gene (gene 6) and kanamycin resistance gene (gene 7) was replaced with an appropriate DNA sequence lacking the majority of sucC (gene 2) and sucD (gene 3), and sucrose resistant clones were selected for.

Figure 68:
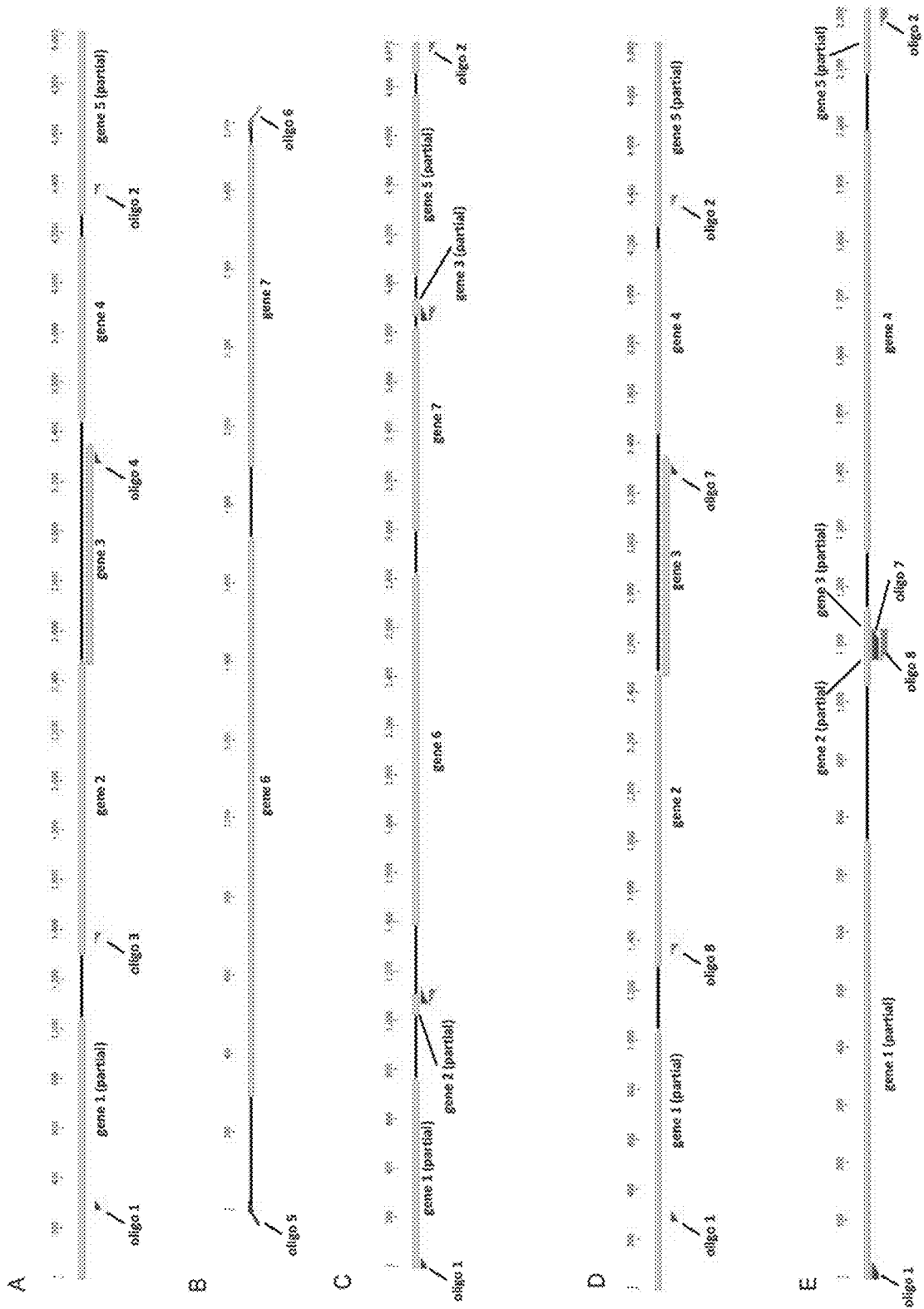
FIGS. 68A-68E shows a schematic of the sequences and oligonucleotides used in the construction of the sucCD deletion.

Linear double-stranded DNA sequences used in the two homologous recombination steps outlined above were constructed via standard molecular biological techniques. To make the sequence used in the initial integration step, a 1100 bp sequence from within sucB (gene 1) through the 69th base pair of sucC (gene 2) was amplified by PCR from Escherichia coli MG1655 genomic DNA using oligonucleotide 1 and oligonucleotide 3 (FIG. 68a). The genes encoding levansucrase (gene 6) and kanamycin resistance (gene 7) were amplified by PCR from plasmid pRE-118 DNA using oligonucleotide 5 and oligonucleotide 6 (FIG. 68b). Another 1100 bp sequence from the 811th bp of sucD (gene 3), spanning mngR (gene 4) and part of mngA (gene 5) was amplified by PCR from Escherichia coli MG1655 genomic DNA using oligonucleotide 4 and oligonucleotide 2 (FIG. 68a). 20 bp of oligonucleotide 3 overlaps with oligonucleotide 5 and 20 bp of oligonucleotide 6 overlaps with oligonucleotide 4, such that the three overlapping PCR products can be combined and amplified using standard procedures (FIG. 68c). Likewise, the linear double-stranded DNA sequences used in the second recombination for deletion of sucCD was made by combining and amplifying two overlapping PCR products. A 1100 bp sequence from within sucB (gene 1) through the 69th base pair of sucC (gene 2) was amplified by PCR from Escherichia coli MG1655 genomic DNA using oligonucleotide 1 and oligonucleotide 8 (FIG. 68d). Another 1100 bp sequence from the 811th bp of sucD (gene 3), spanning mngR (gene 4) and part of mngA (gene 5) was amplified by PCR from Escherichia coli MG1655 genomic DNA using oligonucleotide 7 and oligonucleotide 2 (FIG. 68d). Oligonucleotide 7 overlaps with oligonucleotide 8, such that the two overlapping PCR products can be combined and amplified using standard procedures (FIG. 68e). The nucleotides deleted because of the sucCD deletion are from: 762,306->764,320.

| Oligo-nucleotide | | SEQ ID NO |
|---|---|---|
| 1 | GGCGAAAGAGTCTGCTCCGGC | 166 |
| 2 | CATTCAGACACAACGCATCGCGG | 167 |
| 3 | GGCTTACCAGCACCGGTGGGTTATGCCCGTAGTCTGCAAATCC | 168 |
| 4 | GCATTACGCTGACTTGACGGGTGAAAACCGTTCGCAGCCTGG | 169 |
| 5 | GGCTTACCAGCACCGGTGGGTTATGCCCGTAGTCTGCAAATCC | 170 |
| 6 | CCAGGCTGCGAACGGTTTTCACCCGTCAAGTCAGCGTAATGC | 171 |
| 7 | GGCTTACCAGCACCGGTGGGTTATGTGAAAACCGTTCGCAGCTGG | 172 |
| 8 | CCAGGCTGCGAACGGTTTTCACATAACCCACCGGTGCTGGTAAGCC | 173 |

Analytical Procedures: HPLC, LCMS/MS and GCMS were employed for analysis of cell culture and fermentation samples. Good correlation between the two techniques (variation within 10%) provided method cross-validation and ensured data accuracy.

Organic acids, acetate, pyruvate, lactate and succinate, as well as BDO, were measured by HPLC (Agilent 1100) equipped with diode array and refractive index (RI) detectors, using an ion exclusion Carbomix H-NP5 column (Sepax) with 5 mM sulfuric acid as the mobile phase at 0.6 mL/min flow rate, and 55° C. column temperature. Organic acids were monitored in both UV absorption at 210 nm and refractive index detector, while BDO, ethanol and simple sugars were measured using RI only. All chemicals and reagents were from Sigma-Aldrich (St. Louis, Mo., USA).

LCMS/MS analysis was performed on API3200 triple quadrupole system (AB Sciex, Life Technologies, Carlsbad, Calif.), interfaced with Agilent 1200 HPLC, utilizing electrospray ionization and MRM based acquisition methods. BDO, 4HB, GBL, Glu, Ala and GABA and internal standards ($^{13}$C isotopically labeled analogs were used for each analyte, respectively, to compensate for the matrix effects and ensure linearity) were monitored in positive ionization mode. Negative ionization was used, when desired, for quantitation of acidic analytes, for example, pyruvate, lactate, succinate and 4HB. Chromatographic separation was conducted on Zorbax Eclipse XDB C18 4.6×30 mm, 1.8 μm particle size, maintaining column at 45° C., flow rate 0.7 mL/min. Injection volume was 5 uL. Eluents consisted of water with 0.1% formic acid and methanol with 0.1% formic acid, analytes of interest eluted under isocratic conditions of 5% methanol followed by the step gradient to 95% methanol, resulting in 2 min long LCMS method. Filtered samples were diluted in water, containing internal standards, dilution factor varied from 200 to 10,000 depending on concentrations of metabolites of interest. Dilution in water of 100-fold of greater resulted in no ion suppression effects observed for media composition and conditions used in 1,4-Butanediol production in *E. coli* (Yim et al., *Nature Chemical Biology* 7, 445-452, (2011)). Quantitation dynamic ranges were from 0.05-200 uM for BDO and other analytes. Quantitation was performed using Analyst software. LCMS/MS approach was a preferred method for monitoring BDO, 4HB, GBL, Glu, Ala and GABA due to its fast turnaround time allowing high throughput operation.

In GCMS approach, BDO, 4HB, lactate and succinate in culture broth samples were derivatized by trimethylsilylation and quantitatively analyzed by GCMS, using a procedure adapted from the literature with some modifications. The developed method demonstrated sensitivity down to low μM level, linearity in 0.05-15 mM range, as well as good reproducibility. 100 μL filtered samples were dried down in a speedvac concentrator for approximately 1 hour at ambient temperature, followed by the addition of 20 μL 10 mM cyclohexanol solution, as an internal standard, in dimethylformamide. 100 μL N,O-bis(trimethylsilyl)triflouro-acetimide (BSTFA) with 1% trimethylchlorosilane was added, and the mixture was incubated at 70° C. for 30 min. The derivatized samples were centrifuged for 5 min and directly injected into GCMS (Agilent 6890N/5973N). An Rtx-5SIL MS capillary column (Restek, 30 m×0.25 mm ID×0.25 μm film thickness) was used. The GC was operated in a split injection mode introducing 1 μL of sample at 20:1 split ratio. The injection port temperature was 250° C. Helium was used as a carrier gas, and the flow rate was maintained at 1.0 mL/min. A temperature gradient program was optimized to ensure good resolution of the analytes of interest and minimum matrix interference. The oven was initially held at 80° C. for 1.5 min, then ramped to 140° C. at 10° C./min and 3 min hold, followed by fast ramping to 300° C. at 100° C./min and final hold for 5 min. The MS interface transfer line was maintained at 280° C. The total analysis time was 17 min including 4 min solvent delay. Standard calibration curves were constructed using analyte solutions in the corresponding cell culture or fermentation medium to match sample matrix as close as possible. Ethanol was assayed by GCMS as well, following sample dilution in methanol, using an HP-InnoWax capillary column (30 m, 0.25 mm ID, 0.25 um film thickness). GCMS data were processed using ChemStation software (Agilent).

Residual glucose in the fermentation samples was measured using either a YSI instrument or HPLC-UV-RI. Ethanol was measured by either YSI or GCMS.

Figure 69:
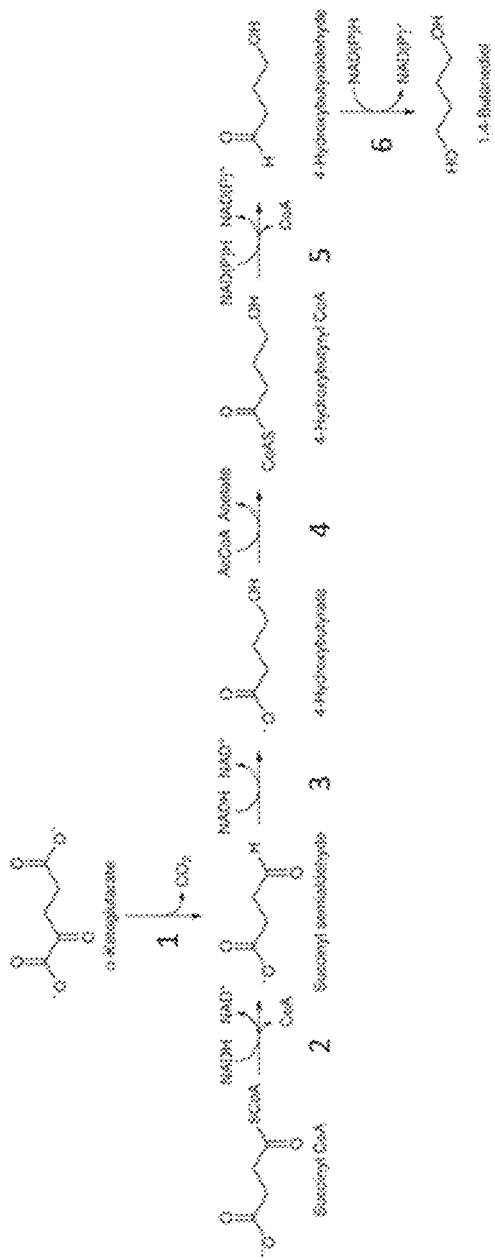
FIG. 69 shows an exemplary BDO pathway. Enzyme names for each numbered step are as follows: (1) alpha-ketoglutarate decarboxylase; (2) CoA-dependent succinate semialdehyde dehydrogenase; (3) 4-hydroxybutyrate dehydrogenase; (4) 4-hydroxybutyryl-CoA transferase; (5) 4-hydroxybutyryl-CoA reductase; (6) 4-hydroxybutyraldehyde reductase.

The metabolic engineering strategies described herein were applied to increase 1,4-butanediol production in *Escherichia coli* or otherwise improve characterisitcs of the engineered microorganisms. The employed 1,4-butanediol pathway for these studies is depicted in FIG. 69. The genes tested for each of the six steps shown in FIG. 69 are described in Tables 34, 38, 40, 42, 46 and 49.

Example XXV

Production of 4-Hydroxybutyrate and 1,4-Butanediol Upon Expression of Genes Encoding Alpha-ketoglutarate Decarboxylase Enzymes This example describes production of 4-hydroxybutyrate (4HB or 4hb) and 1,4-butanediol (BDO) in cells engineered to express genes encoding alpha-ketoglutarate decarboxylase enzymes.

Several heterologous alpha-ketoglutarate decarboxylase genes (Table 34) were expressed in *E. coli* from the pZS*-13S plasmid to allow a functional pathway from alpha-ketoglutarate to 4-hydroxybutyrate and 1,4-butanediol. Host strains include 3125, 2869, and 3812. These host strains are based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). For this study, the *M. bovis* sucA and *P. gingivalis* sucD genes were deleted in strains 3125, 2869, and 3812. Additionally, strains 3125, 2869, and 3812 each contain a chromosomally integrated copy of 4-hydroxybutyryl-CoA transferase expressed from the pA promoter at the attB locus. Strains 2869 and 3812 were tested with 4-hydroxybutyryl-CoA reductase and 4-hydroxybutyraldehyde reductase expressed from the pPSX23R plasmid. Tables 35, 36, and 37 show that expression of heterologous alpha-ketoglutarate decarboxylase genes enhances 4hb and/or BDO production in strains 3125, 2869, and 3812, respectively, over the controls denoted by "pZS*13S". Cells were cultured using the 96 well-plate protocol described previously.

TABLE 34

Genes encoding functional alpha-ketoglutarate decarboxylase enzymes.

| Gene Number | Organism | Accession | GI |
|---|---|---|---|
| 42 | Mycobacterium tuberculosis | ZP_06504371.1 | 289744993 |
| 1717 | Mycobacterium smegmatis | YP_889299.1 | 118472055 |
| 1720 | Saccharopolyspora erythraea | YP_001108480.1 | 134102819 |
| 1727 | Jonesia denitrificans | YP_003161752.1 | 256833025 |
| 1715 | Mycobacterium avium subsp. Paratuberculosis | NP_961470.1 | 41408634 |
| 1718 | Nocardia farcinica | YP_120910.2 | 161598437 |
| 1726 | Streptomyces avermitilis | NP_824148.1 | 29829514 |
| 1727 | Jonesia denitrificans | YP_003161752.1 | 256833025 |
| 1913 | Zymomonas mobilis | YP_162422.1 | 56551583 |
| 1914 | Pseudomonas putida | NP_743318.1 | 26987893 |
| 1915 | Mycobacterium avium subsp. Paratuberculosis | EGO39007.1 | 336460099 |
| 1916 | Streptomyces griseus | YP_001827718.1 | 182439999 |
| 1917 | Methanosarcina acetivorans | NP_616881.1 | 20090806 |
| 1918 | Clostridium ljungdahlii | YP_003782019.1 | 300857035 |
| 1920 | Synechocystis sp. PCC 6803 | NP_441304.1 | 16330576 |
| 1921 | Synechococcus sp. PCC 7335 | ZP_05039761.1 | 254426044 |
| 1922 | Clostridium acetobutylicum | NP_350234.1 | 15896885 |
| 1923 | Clostridium carboxidivorans P7 | ZP_05391417.1 | 255524461 |

TABLE 35

BDO and 4-hydroxybutyrate (4HB) production of E. coli host strain 3125 containing several alternative alpha-ketoglutarate decarboxylase plasmid constructs. The plasmid construct denoted by only "pZS*13S" contains no alpha-ketoglutarate decarboxylase gene. Plasmid constructs denoted by pZS*13S followed by a number express the alpha-ketoglutarate decarboxylase gene denoted by such number. BDO and 4HB concentrations are in mM.

| Host strain | Plasmid | OD 19 h | LCMS- 19 h 4HB | LCMS- 19 h BDO |
|---|---|---|---|---|
| 3125 | pZS*13S | 3.61 | 0.208 | 0.327 |
| 3125 | pZS*13S | 2.01 | 0.259 | 0.082 |
| 3125 | pZS*13S | 3.39 | 0.208 | 0.359 |
| 3125 | pZS*13S | 3.38 | 0.178 | 0.352 |
| 3125 | pZS*13S | 3.84 | 0.277 | 0.478 |
| 3125 | pZS*13S | 4.01 | 0.253 | 0.479 |
| 3125 | pZS*13S | 3.88 | 0.283 | 0.422 |
| 3125 | pZS*13S | 3.54 | 0.192 | 0.499 |
| 3125 | pZS*13S-1717 | 4.30 | 17.300 | 1.520 |
| 3125 | pZS*13S-1717 | 3.52 | 17.400 | 1.280 |
| 3125 | pZS*13S-1717 | 3.79 | 17.700 | 1.540 |
| 3125 | pZS*13S-1717 | 3.53 | 17.800 | 1.550 |
| 3125 | pZS*13S-1720 | 2.92 | 3.940 | 0.196 |
| 3125 | pZS*13S-1720 | 1.58 | 2.140 | 0.037 |
| 3125 | pZS*13S-1720 | 1.97 | 2.600 | 0.072 |
| 3125 | pZS*13S-1720 | 3.11 | 3.870 | 0.261 |
| 3125 | pZS*13S-1727 | 12.05 | 2.330 | 0.694 |
| 3125 | pZS*13S-1727 | 3.23 | 3.040 | 1.320 |
| 3125 | pZS*13S-1727 | 3.19 | 3.490 | 1.560 |
| 3125 | pZS*13S-1727 | 4.86 | 2.500 | 0.657 |
| 3125 | pZS*13S-1715 | 3.89 | 14.900 | 1.880 |
| 3125 | pZS*13S-1715 | 4.14 | 15.600 | 1.950 |
| 3125 | pZS*13S-1715 | 4.07 | 15.700 | 1.910 |
| 3125 | pZS*13S-1715 | 3.03 | 14.300 | 1.600 |
| 3125 | pZS*13S-1718 | 2.36 | 4.020 | 0.277 |
| 3125 | pZS*13S-1718 | 1.82 | 4.630 | 0.406 |
| 3125 | pZS*13S-1718 | 2.37 | 3.690 | 0.265 |
| 3125 | pZS*13S-1718 | 2.26 | 3.940 | 0.273 |
| 3125 | pZS*13S-1718 | 2.04 | 4.890 | 0.389 |
| 3125 | pZS*13S-1718 | 2.42 | 4.720 | 0.338 |
| 3125 | pZS*13S-1718 | 2.16 | 4.530 | 0.377 |
| 3125 | pZS*13S-1718 | 2.43 | 5.190 | 0.517 |

TABLE 36

BDO and 4-hydroxybutyrate (4HB) production of E. coli host strain 2869 containing several alternative alpha-ketoglutarate decarboxylase plasmid constructs. The plasmid construct denoted by only "pZS*13S" contains no alpha-ketoglutarate decarboxylase gene. Plasmid constructs denoted by pZS*13S followed by a number express the alpha-ketoglutarate decarboxylase gene denoted by such number. BDO and 4HB concentrations are in mM.

| Host strain | Plasmid | OD 16 h | LCMS- 16 h 4HB | LCMS- 16 h BDO |
|---|---|---|---|---|
| 2869 | pZS*13S | 3.39 | 0.04 | 0.42 |
| 2869 | pZS*13S | 3.41 | 0.04 | 0.42 |
| 2869 | pZS*13S | 3.43 | 0.04 | 0.35 |
| 2869 | pZS*13S | 3.51 | 0.04 | 0.39 |
| 2869 | pZS*13S | 3.51 | 0.03 | 0.39 |
| 2869 | pZS*13S | 3.50 | 0.04 | 0.40 |
| 2869 | pZS*13S | 3.55 | 0.03 | 0.36 |
| 2869 | pZS*13S | 3.50 | 0.02 | 0.35 |
| 2869 | pZS*13S-042 | 3.50 | 0.33 | 2.81 |
| 2869 | pZS*13S-042 | 3.52 | 0.32 | 2.69 |
| 2869 | pZS*13S-042 | 3.58 | 0.32 | 3.05 |
| 2869 | pZS*13S-042 | 3.49 | 0.28 | 2.61 |
| 2869 | pZS*13S-042 | 3.39 | 0.30 | 2.87 |
| 2869 | pZS*13S-042 | 3.41 | 0.28 | 3.06 |
| 2869 | pZS*13S-042 | 3.44 | 0.27 | 2.64 |
| 2869 | pZS*13S-042 | 3.28 | 0.33 | 2.90 |
| 2869 | pZS*13S-1726 | 2.74 | 0.34 | 2.27 |
| 2869 | pZS*13S-1726 | 2.78 | 0.23 | 2.75 |
| 2869 | pZS*13S-1726 | 2.96 | 0.43 | 2.80 |
| 2869 | pZS*13S-1726 | 2.84 | 0.34 | 2.33 |
| 2869 | pZS*13S-1727 | 3.43 | 0.06 | 2.39 |
| 2869 | pZS*13S-1727 | 2.79 | 0.07 | 2.18 |
| 2869 | pZS*13S-1727 | 3.09 | 0.07 | 2.12 |
| 2869 | pZS*13S-1727 | 3.03 | 0.07 | 2.38 |

TABLE 37

BDO and 4-hydroxybutyrate (4HB) production of E. coli host strain 3812 containing several alternative alpha-ketoglutarate decarboxylase plasmid constructs. The plasmid construct denoted by only "pZS*13S" contains no alpha-ketoglutarate decarboxylase gene. Plasmid constructs denoted by pZS*13S followed by a number express the alpha-ketoglutarate decarboxylase gene denoted by such number. BDO and 4HB concentrations are in mM.

| Host strain | Plasmid | OD 24 h | LCMS- 24 h 4HB | LCMS- 24 h BDO |
|---|---|---|---|---|
| 3812 | pZS*13S | 3.75 | 0.07 | 1.71 |
| 3812 | pZS*13S | 3.74 | 0.05 | 1.46 |
| 3812 | pZS*13S | 3.49 | 0.04 | 2.08 |
| 3812 | pZS*13S | 3.59 | 0.05 | 2.31 |
| 3812 | pZS*13S-1913 | 3.40 | 6.51 | 9.25 |
| 3812 | pZS*13S-1913 | 3.28 | 6.46 | 8.69 |
| 3812 | pZS*13S-1913 | 3.41 | 6.22 | 8.53 |
| 3812 | pZS*13S-1913 | 3.25 | 5.94 | 7.89 |
| 3812 | pZS*13S-1914 | 3.83 | 23.10 | 85.00 |
| 3812 | pZS*13S-1914 | 3.41 | 29.70 | 93.10 |
| 3812 | pZS*13S-1914 | 3.68 | 19.90 | 63.10 |
| 3812 | pZS*13S-1914 | 3.45 | 27.20 | 101.00 |
| 3812 | pZS*13S-1915 | 4.17 | 0.30 | 3.28 |
| 3812 | pZS*13S-1915 | 3.78 | 0.18 | 3.11 |
| 3812 | pZS*13S-1915 | 3.95 | 0.14 | 3.08 |
| 3812 | pZS*13S-1915 | 3.97 | 0.11 | 2.80 |
| 3812 | pZS*13S-1916 | 4.09 | 0.07 | 4.82 |
| 3812 | pZS*13S-1916 | 3.69 | 0.12 | 4.54 |
| 3812 | pZS*13S-1916 | 3.86 | 0.09 | 4.73 |
| 3812 | pZS*13S-1916 | 3.82 | 0.08 | 4.89 |
| 3812 | pZS*13S-1917 | 3.61 | 0.08 | 2.70 |
| 3812 | pZS*13S-1917 | 3.99 | 0.06 | 2.92 |
| 3812 | pZS*13S-1917 | 3.59 | 0.12 | 2.74 |
| 3812 | pZS*13S-1917 | 3.57 | 0.11 | 2.64 |
| 3812 | pZS*13S-1918 | 3.10 | 0.25 | 6.43 |
| 3812 | pZS*13S-1918 | 2.93 | 0.34 | 5.94 |
| 3812 | pZS*13S-1918 | 2.98 | 0.23 | 6.48 |
| 3812 | pZS*13S-1918 | 3.03 | 0.23 | 6.53 |

TABLE 37-continued

BDO and 4-hydroxybutyrate (4HB) production of E. coli host strain 3812 containing several alternative alpha-ketoglutarate decarboxylase plasmid constructs. The plasmid construct denoted by only "pZS*13S" contains no alpha-ketoglutarate decarboxylase gene. Plasmid constructs denoted by pZS*13S followed by a number express the alpha-ketoglutarate decarboxylase gene denoted by such number. BDO and 4HB concentrations are in mM.

| Host strain | Plasmid | OD 24 h | LCMS- 24 h 4HB | LCMS- 24 h BDO |
|---|---|---|---|---|
| 3812 | pZS*13S-1920 | 3.30 | 11.20 | 44.10 |
| 3812 | pZS*13S-1920 | 3.57 | 16.60 | 64.20 |
| 3812 | pZS*13S-1920 | 3.71 | 15.00 | 59.10 |
| 3812 | pZS*13S-1920 | 3.55 | 16.30 | 62.40 |
| 3812 | pZS*13S-1921 | 3.99 | 0.23 | 9.07 |
| 3812 | pZS*13S-1921 | 3.70 | 0.24 | 8.76 |
| 3812 | pZS*13S-1921 | 4.01 | 0.24 | 9.79 |
| 3812 | pZS*13S-1921 | 3.88 | 0.27 | 9.35 |
| 3812 | pZS*13S-1922 | 2.46 | 0.06 | 4.00 |
| 3812 | pZS*13S-1922 | 2.79 | 0.23 | 5.55 |
| 3812 | pZS*13S-1922 | 2.61 | 0.23 | 5.25 |
| 3812 | pZS*13S-1922 | 2.93 | 0.18 | 5.53 |
| 3812 | pZS*13S-1923 | 2.82 | 0.25 | 6.46 |
| 3812 | pZS*13S-1923 | 2.48 | 0.22 | 6.43 |
| 3812 | pZS*13S-1923 | 2.69 | 0.17 | 4.42 |
| 3812 | pZS*13S-1923 | 3.18 | 0.18 | 10.50 |

Example XXVI

Production of 4HB and BDO Upon Expression of Genes Encoding CoA-dependant Succinate Semialdehyde Dehydrogenase Enzymes This example describes production of 4HB and BDO upon expression of genes encoding CoA-dependant succinate semialdehyde dehydrogenase enzymes.

Several heterologous CoA-dependant succinate semialdehyde dehydrogenase genes (Table 38) were expressed in E. coli from the pZS*-13S plasmid to allow a functional pathway from succinyl-CoA to 4-hydroxybutyrate and 1,4-butanediol. Host strain 3744 is based on strain ECKh-432 whose construction is described above and in US20110045575. Notable modifications include deletions in adhE, ldhA, pflB, mdh, and arcA. Strain ECKh-432 also contains chromosomally integrated copies of sucD from Porphyromonas gingivalis (encoding CoA-dependant succinate semialdehyde dehydrogenase), sucA from Mycobacterium bovis (encoding alpha-ketoglutarate decarboxylase), 4hbd from P. gingivalis (encoding 4-hydroxybutyrate dehydrogenase), and 4hbd from Clostridium kluyveri (encoding 4-hydroxybutyrate dehydrogenase). For this study, the M. bovis sucA and P. gingivalis sucD genes were deleted in strain 3744. Additionally, strain 3744 contains a chromosomally integrated copy of 4-hydroxybutyryl-CoA transferase expressed from the pA promoter at the attB locus. It also contains a pPSX23R plasmid expressing 4-hydroxybutyryl-CoA reductase and 4-hydroxybutyraldehyde reductase. Table 39 shows that expression of heterologous CoA-dependant succinate semialdehyde dehydrogenase genes enhances 4hb and/or BDO production in strain 3744 over the controls denoted by "pZS*13S". Cells were cultured using the 96 well-plate protocol described previously.

TABLE 38

Genes Encoding Functional CoA-dependant Succinate Semialdehyde Dehydrogenase Enzymes

| Gene Number | Organism | Accession | GI |
|---|---|---|---|
| 35 | Porphyromonas gingivalis W83 | NP_904963.1 | 34540484 |
| 49 | Clostridium difficile 630 | YP_001088857.1 | 126699960 |
| 1870 | Metallosphaera sedula | YP_001190808.1 | 146303492 |
| 1871 | Porphyromonas endodontalis ATCC 35406 | ZP_04389701.1 | 229495977 |
| 1872 | Clostridium sporogenes | ZP_02995751.1 | 187779278 |
| 1931 | Porphyromonas asaccharolytica DSM 20707 | ZP_07821123.1 | 313887434 |
| 1932 | Odoribacter splanchnicus DSM 20712 | YP_004253242.1 | 325280700 |

TABLE 39

BDO and 4-hydroxybutyrate (4HB) production of E. coli host strain 3744 containing several alternative CoA-dependant succinate semialdehyde dehydrogenase plasmid constructs. The plasmid construct denoted by only "pZS*13S" contains no CoA-dependant succinate semialdehyde dehydrogenase gene. Plasmid constructs denoted by pZS*13S followed by a number express the CoA-dependant succinate semialdehyde dehydrogenase gene denoted by such number. BDO and 4HB concentrations are in mM.

| Host strain | Plasmid | OD - 16 h | LCMS - 16 h 4HB | LCMS - 16 h BDO |
|---|---|---|---|---|
| 3744 | pZS*13S | 3.10 | 0.47 | 3.08 |
| 3744 | pZS*13S | 2.97 | 0.54 | 2.69 |
| 3744 | pZS*13S | 3.18 | 0.89 | 4.09 |
| 3744 | pZS*13S | 1.26 | 0.44 | 2.41 |
| 3744 | pZS*13S-035 | 3.63 | 7.29 | 30.80 |
| 3744 | pZS*13S-035 | 2.89 | 6.86 | 28.30 |
| 3744 | pZS*13S-035 | 3.22 | 6.64 | 28.40 |
| 3744 | pZS*13S-035 | 3.73 | 7.55 | 28.80 |
| 3744 | pZS*13S-049 | 1.87 | 10.50 | 23.30 |
| 3744 | pZS*13S-049 | 1.65 | 10.10 | 23.70 |
| 3744 | pZS*13S-049 | 1.87 | 10.80 | 23.60 |
| 3744 | pZS*13S-049 | 1.75 | 11.40 | 23.70 |
| 3744 | pZS*13S-1870 | 3.58 | 0.43 | 7.18 |
| 3744 | pZS*13S-1870 | 3.51 | 0.57 | 7.28 |
| 3744 | pZS*13S-1870 | 3.15 | 0.50 | 5.59 |
| 3744 | pZS*13S-1870 | 2.98 | 0.44 | 6.78 |
| 3744 | pZS*13S-1871 | 3.33 | 6.73 | 37.20 |
| 3744 | pZS*13S-1871 | 3.28 | 6.42 | 31.90 |
| 3744 | pZS*13S-1871 | 3.20 | 7.18 | 32.40 |
| 3744 | pZS*13S-1871 | 3.44 | 7.03 | 33.90 |
| 3744 | pZS*13S-1872 | 3.52 | 0.44 | 4.52 |
| 3744 | pZS*13S-1872 | 3.54 | 0.49 | 4.71 |
| 3744 | pZS*13S-1872 | 3.56 | 0.38 | 4.51 |
| 3744 | pZS*13S-1872 | 3.37 | 0.37 | 4.49 |
| 3744 | pZS*13S-1872 | 3.47 | 0.50 | 4.32 |
| 3744 | pZS*13S-1872 | 3.58 | 0.56 | 4.68 |
| 3744 | pZS*13S-1872 | 3.47 | 0.49 | 4.27 |
| 3744 | pZS*13S-1872 | 3.90 | 0.43 | 4.51 |

| Host strain | Plasmid | OD - 24 hr | LCMS - 24 h | LCMS - 24 h |
|---|---|---|---|---|
| 3744 | pZS*13S | 3.89 | 0.12 | 8.85 |
| 3744 | pZS*13S | 3.79 | 0.17 | 8.57 |
| 3744 | pZS*13S | 3.85 | 0.17 | 8.87 |
| 3744 | pZS*13S | 3.84 | 0.12 | 9.05 |
| 3744 | pZS*13S-1931 | 3.78 | 3.18 | 45.10 |
| 3744 | pZS*13S-1931 | 3.64 | 3.28 | 46.50 |
| 3744 | pZS*13S-1931 | 2.91 | 4.25 | 34.00 |
| 3744 | pZS*13S-1931 | 3.73 | 3.22 | 45.40 |
| 3744 | pZS*13S-1932 | 3.71 | 3.10 | 84.20 |
| 3744 | pZS*13S-1932 | 3.63 | 3.24 | 79.50 |
| 3744 | pZS*13S-1932 | 3.61 | 3.18 | 82.60 |
| 3744 | pZS*13S-1932 | 3.61 | 3.24 | 83.90 |

Example XXVII

Production of 4HB and BDO Upon Expression of Genes Encoding 4-hydroxybutyrate Dehydrogenase Enzymes This example describes production of 4HB and BDO upon expression of genes encoding 4-hydroxybutyrate dehydrogenase enzymes.

Several heterologous 4-hydroxybutyrate dehydrogenase genes (Table 40) were expressed in *E. coli* from the pZS*-13S plasmid to allow a functional pathway from succinyl-CoA and alpha-ketoglutarate to 4-hydroxybutyrate and 1,4-butanediol. Host strain 3891 is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). For this study, the *P. gingivalis* and *C. kluyveri* 4hbd genes were deleted in strain 3891. Additionally, strain 3891 contains a chromosomally integrated copy of 4-hydroxybutyryl-CoA transferase expressed from the pA promoter at the attB locus. It also contains a pPSX23R plasmid expressing 4-hydroxybutyryl-CoA reductase and 4-hydroxybutyraldehyde reductase. Table 41 shows that expression of heterologous 4-hydroxybutyrate dehydrogenase genes enhances 4hb and/or BDO production in strain 3891 over the controls denoted by "pZS*13S". Cells were cultured using the 96 well-plate protocol described previously.

TABLE 40

Genes encoding functional 4-hydroxybutyrate dehydrogenase enzymes.

| Gene Number | Organism | Accession | GI |
|---|---|---|---|
| 36 | *Porphyromonas gingivalis* W83 | NP_904964.1 | 34540485 |
| 150 | *Clostridium acetobutylicum* ATCC 824 | NP_348201.1 | 15894852 |
| 1879 | *Porphyromonas endodontalis* ATCC 35406 | ZP_04389726.1 | 229496002 |
| 1880 | *Porphyromonas asaccharolytica* DSM 20707 | YP_004441566.1 | 332299645 |
| 1881 | *Odoribacter splanchnicus* DSM 20712 | YP_004253243.1 | 325280701 |
| 1882 | *Eubacterium saphenum* ATCC 49989 | ZP_05427218.1 | 255994083 |
| 1883 | *Clostridium ljungdahlii* DSM 13528 | YP_003782020.1 | 300857036 |
| 1884 | *Clostridium perfringens* ATCC 13124 | YP_694972.1 | 110800333 |
| 1888 | *Clostridium difficile* 630 | YP_001088853.1 | 126699956 |
| 1889 | *Geobacter sulferreducens* | NP_952425.1 | 39996474 |
| 1894 | *Metallosphaera sedula* DSM 5348 (ATCC 51363D-5) | YP_001191506.1 | 146304190 |

TABLE 41

BDO and 4-hydroxybutyrate (4HB) production of *E. coli* host strain 3891 containing several alternative 4-hydroxybutyrate dehydrogenase plasmid constructs. The plasmid construct denoted by only "pZS*13S" contains no 4-hydroxybutyrate dehydrogenase gene. Plasmid constructs denoted by pZS*13S followed by a number express the 4-hydroxybutyrate dehydrogenase gene denoted by such number. BDO and 4KB concentrations are in mM.

| Host | Plasmid | OD - 16 h | LCMS - 16 h 4HB | LCMS - 16 h BDO |
|---|---|---|---|---|
| 3891 | pZS*13S | 3.26 | 0.07 | 1.33 |
| 3891 | pZS*13S | 3.06 | 0.04 | 1.38 |
| 3891 | pZS*13S | 3.17 | 0.04 | 1.80 |
| 3891 | pZS*13S | 3.22 | 0.04 | 1.25 |
| 3891 | pZS*13S-036 | 3.11 | 7.19 | 15.90 |
| 3891 | pZS*13S-036 | 2.95 | 7.31 | 17.40 |
| 3891 | pZS*13S-036 | 3.17 | 7.00 | 16.40 |
| 3891 | pZS*13S-036 | 2.80 | 6.84 | 16.60 |
| 3891 | pZS*13S-150 | 2.99 | 2.58 | 31.20 |
| 3891 | pZS*13S-150 | 3.41 | 2.49 | 33.30 |
| 3891 | pZS*13S-150 | 3.11 | 2.88 | 32.40 |
| 3891 | pZS*13S-150 | 2.91 | 2.71 | 33.30 |
| 3891 | pZS*13S-1879 | 3.35 | 1.99 | 9.78 |
| 3891 | pZS*13S-1879 | 3.12 | 2.26 | 10.80 |
| 3891 | pZS*13S-1879 | 3.42 | 2.06 | 9.58 |
| 3891 | pZS*13S-1879 | 3.16 | 2.21 | 10.20 |
| 3891 | pZS*13S-1880 | 2.01 | 3.99 | 13.30 |
| 3891 | pZS*13S-1880 | 2.85 | 4.49 | 14.00 |
| 3891 | pZS*13S-1880 | 2.99 | 4.52 | 12.90 |
| 3891 | pZS*13S-1880 | 2.95 | 4.04 | 12.70 |
| 3891 | pZS*13S-1881 | 3.18 | 3.73 | 7.00 |
| 3891 | pZS*13S-1881 | 2.95 | 3.56 | 7.64 |
| 3891 | pZS*13S-1881 | 3.03 | 3.40 | 6.98 |
| 3891 | pZS*13S-1881 | 2.96 | 3.68 | 7.50 |
| 3891 | pZS*13S-1882 | 3.20 | 3.62 | 22.70 |
| 3891 | pZS*13S-1882 | 3.13 | 3.85 | 24.10 |
| 3891 | pZS*13S-1882 | 3.33 | 3.34 | 22.20 |
| 3891 | pZS*13S-1882 | 2.60 | 3.67 | 19.80 |
| 3891 | pZS*13S-1883 | 3.53 | 2.47 | 24.00 |
| 3891 | pZS*13S-1883 | 3.39 | 1.79 | 24.60 |
| 3891 | pZS*13S-1883 | 3.41 | 2.20 | 27.10 |
| 3891 | pZS*13S-1883 | 3.33 | 2.13 | 22.00 |
| 3891 | pZS*13S-1884 | 3.09 | 1.13 | 30.50 |
| 3891 | pZS*13S-1884 | 3.02 | 1.20 | 33.80 |
| 3891 | pZS*13S-1884 | 3.76 | 1.34 | 34.40 |
| 3891 | pZS*13S-1884 | 3.15 | 1.40 | 36.80 |
| 3891 | pZS*13S-1888 | 3.11 | 0.28 | 31.40 |
| 3891 | pZS*13S-1888 | 3.04 | 0.22 | 30.70 |
| 3891 | pZS*13S-1888 | 3.09 | 0.21 | 29.90 |
| 3891 | pZS*13S-1888 | 3.33 | 0.30 | 31.50 |
| 3891 | pZS*13S-1889 | 3.17 | 1.03 | 19.20 |
| 3891 | pZS*13S-1889 | 3.04 | 1.12 | 18.70 |
| 3891 | pZS*13S-1889 | 3.14 | 1.05 | 17.40 |
| 3891 | pZS*13S-1889 | 3.01 | 1.25 | 18.10 |
| 3891 | pZS*13S-1894 | 3.03 | 0.85 | 13.70 |
| 3891 | pZS*13S-1894 | 2.91 | 0.67 | 13.00 |
| 3891 | pZS*13S-1894 | 3.00 | 1.04 | 12.80 |
| 3891 | pZS*13S-1894 | 3.03 | 0.86 | 12.90 |

Example XXVIII

Production of 4HB and BDO Upon Expression of Genes Encoding 4-Hydroxybutyrate Transferase Enzymes This example describes production of 4hb and BDO upon expression of genes encoding 4-hydroxybutyrate transferase enzymes.

Several heterologous 4-hydroxybutyrate transferase genes (Table 42) were expressed in *E. coli* from either the pZS*-13S or F' plasmid to allow a functional pathway from alpha-ketoglutarate and succinyl-CoA to 1,4-butanediol. Host strains include 1269, 2731 Δcat2, and 1654. These host strains are based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strains 1269, 2731 Δcat2, and 1654 were all tested with 4-hydroxybutyryl-CoA reductase and 4-hydroxybutyraldehyde reductase expressed from the pZS*-13S plasmid. Tables 43, 44, and 45 show that expression of heterologous 4-hydroxybutyrate transferase genes allows BDO production in strains 1269, 2731 Δcat2, and 1654, respectively. Cells were cultured using the 96 well-plate protocol described previously.

TABLE 42

Genes encoding functional 4-hydroxybutyrate transferase enzymes.

| Gene Number | Organism | Accession | GI |
| --- | --- | --- | --- |
| 34 | *Porphyromonas gingivalis* W83 | NP_904965 | 34540486 |
| 1210 | *Clostridium difficile* 630 | YP_001088854 | 126699957 |
| 1769 | *Eubacterium saphenum* ATCC 49989 | ZP_05427217 | 255994082 |
| 1772 | *Porphyromonas endodontalis* ATCC 35406 | ZP_04389695 | 229495971 |
| 1774 | *Anaerostipes caccae* DSM 14662 | ZP_02417601 | 167745474 |
| 33B | *Clostridium aminobutyricum* | CAB60036 | 188032706 |
| 1801 | *Fusobacterium nucleatum* subsp. *vincentii* ATCC 49256 | ZP_00144049 | 34763077 |
| 1803 | *Fusobacterium ulcerans* ATCC 49185 | ZP_07928926 | 317064441 |
| 1804 | *Fusobacterium varium* ATCC 27725 | ZP_08693772 | 340757169 |
| 1805 | *Odoribacter splanchnicus* DSM 20712 | YP_004253244 | 325280702 |
| 1807 | *Porphyromonas gingivalis* | YP_001930004 | 188995752 |
| 1808 | *Fusobacterium gonidiaformans* ATCC 25563 | ZP_07914775 | 315918535 |
| 1809 | *Acetonema longum* DSM 6540 | ZP_08623452 | 338811223 |

The nucleotide sequences for 1210C and 033B are provided below as these were codon-optimized for expression in *E. coli*.

33B:

(SEQ ID NO: 174)
atggactggaagaagatctatgaagacagaacctgcactgcagatgaagc
agtaaagagcattaagtcaggtgaccgcgtgctgtttgcgcactgtgttg
ctgaaccgccagttctggtagaagcaatggttgcgaatgcagctgcatac
aagaatgtcacggtttcacacatggttaccccttggtaagggtgaatactc
aaaaccagaatataaagaaaactttacttttgaaggttggtttaccagcc
cttcaacacgtggatccattgcagaaggacacggacagtttgtccctgta
ttcttccacgaggtaccatctttaatccgtaaagacattttccatgttga
tgtattcatggtaatggtatcccgccagatcataacggtttctgctgtg
tgggtgtatcttctgactataccatgcaggctatcaaatcagcaaaaatt
gtactggctgaagtgaatgatcaggtacctgtagtttatggcgatacctt
tgttcacgttagtgaaatcgacaagttcgttgaaacttcacatccactgc
cagaaatcggtctgccgaagatcggtgaagtagaagctgctattggtaag
cactgcgcttcgctgatcgaagatggttccacattacagcttggtatcgg
cgctattccggatgctgtactttcacagataaggacaagaaacaccttgg
tatccactctgaaatgatttccgacggtgttgttgatctttacgaagcag
gcgttattgactgcagccaaaagtctatcgacaaaggcaaaatggcaata
acattcttaatgggaacgaagcgtctttatgatttcgctgcaaacaatcc
aaaggttgaattaaagccggttgactacatcaatcatccatctgtagttg
cacagtgcagcaaaatggtttgcatcaatgatgcttgcaagttgatttta
tgggtcagattgtctccgatagtattggcacaaagcagttctccggcgta
ggcggtcaggttgacttcgtacgcggtgcatccatgtctattgacggcaa
aggtaaagcgatcatcgcgatgccttccgttgcaaagaagaaagatggca
gtatgatttcgaagatcgttccattcatcgatcacggtgcagctgtaact
acatcccgtaacgatgcggactatgtcgtaacggaatatggtattgctga
aatgaagggtaagtcgttacaggaccgcgcacgcgcgttaatcaatattg
cccaccctgatttcaaagatgaattaaaggctgaatttgaaaagcgcttc
aacgcggcattctaa.

1210C:

(SEQ ID NO: 175)
atgagctggcaagaactgtatcaaagtaaattatgttcagccacagaagc
ggtaaaacagattaaaaacggtgataccgtggtatttgcccattgtgtag
gtgaaccgcctgcactggtggaggcgatgattgaaaatgctgaacaatat
aaagatgttgagattaaacatatggttagcctggggtagtggtggttatac
tgcgaaagggatggaagcgcattttcgcgtaaatccaatgtttgtcagcg
gcaatgtacgtaaggcgattgaaaatggcgatggtgattttacacctgca
ttcttccatgaagtaccaaagttgctgcgtgaaaaacgtctgaaatgtga
tgttgttctggcacaggtaacgccaccagatgaacatggttattgttcgc
tgggaacaagcgttgattatacctatgaagccattaaaaccgcgcgcacc
gtaattgttcaggtgaatgaccagtttcctcgcacctatggtgaggtggt
gcatgtcagcgagtttgactatatcgttgaaaaatcacaaccgctgtttg
aactgcaacctgcaaagattggcgaagttgaagaagcgattggtaaaaat -continued

```
tgtgcctcgctgattgaagatggtagcacgttacagctggggattggtgg gattccggatgcggtgatgttatttctgactgataaaaaagatttaggga ttcatagcgaaatgattagcgatggcacgctggcgctttatgaaaaaggt gttattaatggtaaatataaaaattttgataaagaaaaaatgacggttac cttcctgatgggtactaaaaaactgtatgactttgccaataataacccgg cagtagaggtaaaaccggtagactatgtgaatcatccggcaattatcatg aaacaacataagatggtttctattaatagcgccattcaggttgatttaat ggggcaggtggttgcagaggcgatgggactgcgccaattttccggtgttg gcggtcaggttgactttattcgtggcgtgtcgatgggtgaagatggcaag gcgattatcgcgatgccttcaatcactacaaaaaaagatggtacggtaat tagcaaaatcgtctctattgtcgatgaaggtgcaccgattaccacctcac gtaatgatgttgattatattgtcacagaatacggtattgcagaattaaaa ggcaaatcgctgcgtgaacgcgcacgtaatctgattaatattgctcatcc atcggtacgtgaatcgctggcagtagaatttgaaaagcgctttaaagaga aatattaa.
```

TABLE 43

BDO, GBL, and 4-hydroxybutyrate (4HB) production of E. coli host strain 1269 containing two alternative 4-hydroxybutyrate transferase plasmid constructs. The plasmid construct denoted by only "pZA33S (empty)" contains no 4-hydroxybutyrate transferase gene. Plasmid constructs denoted by F' followed by a number express the 4-hydroxybutyrate transferase gene denoted by such number. BDO and 4HB concentrations are in mM.

| Host Strain | Plasmid | OD 24 h | LCMS-24 h 4HB | LCMS-24 h BDO | LCMS-24 h GBL |
|---|---|---|---|---|---|
| 1269 | pZA33S (empty) | 2.92 | 27.60 | 0.00 | 0.00 |
| 1269 | pZA33S (empty) | 2.12 | 23.80 | 0.59 | 0.07 |
| 1269 | pZA33S (empty) | 2.72 | 28.80 | 2.13 | 0.03 |
| 1269 | pZA33S (empty) | 2.32 | 30.50 | 0.14 | 0.00 |
| 1269 | F'34 | 1.76 | 2.42 | 22.20 | 0.87 |
| 1269 | F'34 | 1.70 | 2.34 | 21.00 | 0.88 |
| 1269 | F'34 | 2.09 | 3.23 | 23.50 | 1.21 |
| 1269 | F'34 | 3.83 | 2.77 | 51.30 | 5.01 |
| 1269 | F'1210C | 1.99 | 2.84 | 28.20 | 1.73 |
| 1269 | F'1210C | 1.64 | 2.73 | 27.30 | 1.61 |
| 1269 | F'1210C | 1.89 | 4.28 | 32.30 | 2.59 |
| 1269 | F'1210C | 3.47 | 3.76 | 56.38 | 7.22 |

TABLE 44

BDO, GBL, and 4-hydroxybutyrate (4HB) production of E. coli host strain 2731 Δcat2 containing alternative 4-hydroxybutyrate transferase plasmid constructs. Plasmid constructs denoted by pZS*13S- followed by a number express the 4-hydroxybutyrate transferase gene denoted by such number. The pZS*13S- backbone also expresses functional 4-hydroxybutyryl-CoA reductase and 4-hydroxybutyraldehyde dehydrogenase genes. BDO and 4HB concentrations are in mM.

| Host Strain | Plasmid | OD 19 h | LCMS-19 H 4HB | LCMS-19 h BDO | LCMS-19 h GBL |
|---|---|---|---|---|---|
| 2731 Δcat2 | pZS*13S-1769 | 3.75 | 1.1 | 24.9 | 0.1 |
| 2731 Δcat2 | pZS*13S-1769 | 3.84 | 1.3 | 23.9 | 0.1 |
| 2731 Δcat2 | pZS*13S-1769 | 4.10 | 1.3 | 23.0 | 0.1 |
| 2731 Δcat2 | pZS*13S-1769 | 4.14 | 1.1 | 27.3 | 0.1 |
| 2731 Δcat2 | pZS*13S-1772 | 4.33 | 2.9 | 36.7 | 0.2 |
| 2731 Δcat2 | pZS*13S-1772 | 4.37 | 2.3 | 37.9 | 0.3 |
| 2731 Δcat2 | pZS*13S-1772 | 4.02 | 2.7 | 40.4 | 0.3 |
| 2731 Δcat2 | pZS*13S-1772 | 3.59 | 3.4 | 27.4 | 0.2 |
| 2731 Δcat2 | pZS*13S-1774 | 4.10 | 2.2 | 29.9 | 0.2 |
| 2731 Δcat2 | pZS*13S-1774 | 3.93 | 1.9 | 29.2 | 0.3 |
| 2731 Δcat2 | pZS*13S-1774 | 4.26 | 2.5 | 31.5 | 0.3 |
| 2731 Δcat2 | pZS*13S-1774 | 4.76 | 1.6 | 29.8 | 0.2 |

TABLE 45

BDO, GBL, and 4-hydroxybutyrate (4HB) production of E. coli host strain 1654 containing alternative 4-hydroxybutyrate transferase plasmid constructs. Plasmid constructs denoted by pZS*13S-followed by a number express the 4-hydroxybutyrate transferase gene denoted by such number. The pZS*13S-backbone also expresses functional 4-hydroxybutyryl-CoA reductase and 4-hydroxybutyraldehyde dehydrogenase genes. BDO and 4HB concentrations are in mM.

| Host Strain | Plasmid | OD 19 h | LCMS-19 h 4HB | LCMS-19 h BDO | LCMS-19 h GBL |
|---|---|---|---|---|---|
| 1654 | pZS*-13S-033B | 3.96 | 1.47 | 26.00 | 1.69 |
| 1654 | pZS*-13S-033B | 4.17 | 1.32 | 23.90 | 1.54 |
| 1654 | pZS*-13S-033B | 4.11 | 0.99 | 25.80 | 1.62 |
| 1654 | pZS*-13S-033B | 3.80 | 1.04 | 25.40 | 1.61 |
| 1654 | pZS*-13S-1801 | 3.68 | 1.88 | 21.80 | 1.61 |
| 1654 | pZS*-13S-1801 | 3.90 | 1.35 | 21.70 | 1.67 |
| 1654 | pZS*-13S-1801 | 3.76 | 1.76 | 20.90 | 1.55 |
| 1654 | pZS*-13S-1801 | 3.66 | 1.92 | 22.00 | 1.77 |
| 1654 | pZS*-13S-1803 | 3.69 | 1.71 | 27.60 | 1.80 |
| 1654 | pZS*-13S-1803 | 3.79 | 1.45 | 23.60 | 1.63 |
| 1654 | pZS*-13S-1803 | 3.64 | 1.09 | 24.80 | 1.72 |
| 1654 | pZS*-13S-1803 | 3.64 | 1.30 | 23.60 | 1.67 |
| 1654 | pZS*-13S-1804 | 3.74 | 1.27 | 26.00 | 1.83 |
| 1654 | pZS*-13S-1804 | 3.87 | 1.90 | 25.40 | 1.95 |
| 1654 | pZS*-13S-1804 | 4.04 | 1.48 | 22.80 | 1.65 |
| 1654 | pZS*-13S-1804 | 3.75 | 1.87 | 26.00 | 1.87 |
| 1654 | pZS*-13S-1805 | 3.84 | 1.47 | 25.20 | 1.47 |
| 1654 | pZS*-13S-1805 | 3.75 | 1.06 | 27.50 | 1.54 |
| 1654 | pZS*-13S-1805 | 3.08 | 1.67 | 22.00 | 1.26 |
| 1654 | pZS*-13S-1805 | 3.57 | 1.22 | 23.80 | 1.36 |
| 1654 | pZS*-13S-1807 | 3.24 | 0.00 | 4.80 | 0.40 |
| 1654 | pZS*-13S-1807 | 3.30 | 0.29 | 5.10 | 0.48 |
| 1654 | pZS*-13S-1807 | 3.36 | 0.17 | 4.68 | 0.39 |
| 1654 | pZS*-13S-1807 | 3.31 | 0.21 | 5.16 | 0.38 |
| 1654 | pZS*-13S-1808 | 3.38 | 2.39 | 24.50 | 1.20 |
| 1654 | pZS*-13S-1808 | 3.39 | 2.56 | 22.20 | 1.07 |
| 1654 | pZS*-13S-1808 | 3.45 | 2.16 | 22.40 | 1.10 |
| 1654 | pZS*-13S-1808 | 3.42 | 2.26 | 23.10 | 1.27 |
| 1654 | pZS*-13S-1809 | 4.26 | 1.52 | 18.10 | 0.93 |

TABLE 45-continued

BDO, GBL, and 4-hydroxybutyrate (4HB) production of
E. coli host strain 1654 containing alternative 4-hydroxybutyrate
transferase plasmid constructs. Plasmid constructs denoted by
pZS*13S-followed by a number express the 4-hydroxybutyrate
transferase gene denoted by such number. The pZS*13S-backbone
also expresses functional 4-hydroxybutyryl-CoA reductase and
4-hydroxybutyraldehyde dehydrogenase genes. BDO and 4HB
concentrations are in mM.

| Host Strain Plasmid | OD 19 h | LCMS-19 h 4HB | LCMS-19 h BDO | LCMS-19 h GBL |
|---|---|---|---|---|
| 1654 pZS*-13S-1809 | 4.37 | 1.86 | 21.50 | 1.07 |
| 1654 pZS*-13S-1809 | 3.51 | 1.67 | 16.00 | 0.81 |
| 1654 pZS*-13S-1809 | 4.49 | 0.97 | 18.60 | 0.97 |

Example XXIX

Production of 4HB and BDO Upon Expression of Genes Encoding 4-Hydroxybutyryl-CoA Reductase Enzymes This example describes production of 4hb and BDO upon expression of genes encoding 4-hydroxybutyryl-CoA reductase enzymes.

Several heterologous 4-hydroxybutyryl-CoA reductase genes (Table 46) were expressed in E. coli from the pZS*-13S plasmid to allow a functional pathway from succinyl-CoA and alpha-ketoglutarate to 1,4-butanediol. Host strain 1889 is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 1889 contains deletions in the native alcohol dehydrogenase genes adhP, yqhD, yahK, and yjgB. Additionally, strain 1889 contains a chromosomally integrated copy of 4-hydroxybutyryl-CoA transferase expressed from the pA promoter at the attB locus. Strain 1889 contains the F' plasmid expressing a functional 4-hydroxybutyraldehyde reductase gene. Strain 4269 contains a chromosomally integrated copy of a 4-hydroxybutyraldehyde reductase gene at the hemN locus under control of the p119 promoter. Tables 47 and 48 show that expression of heterologous 4-hydroxybutyryl-CoA reductase genes enhances BDO production in strains 1889 and 4269, respectively, over the controls denoted by "pZS*13S". Cells were cultured using the 96 well-plate protocol described previously.

TABLE 46

Genes encoding functional 4-hydroxybutyryl-CoA reductase enzymes.

| Gene Number | Organism | Accession | GI |
|---|---|---|---|
| 025B | *Clostridium beijerinckii* NCIMB 8052 | YP_001310903.1 | 150018649 |
| 733 | *Clostridium hylemonae* DSM 15053 | ZP_03778292.1 | 225569267 |
| 744 | *Clostridium methylpentosum* DSM 5476 | ZP_03705305.1 | 225016072 |
| 787 | *Eubacterium hallii* DSM 3353 | ZP_03715465.1 | 225026273 |
| 865 | *Ruminococcus obeum* ATCC 29174 | ZP_01962381.1 | 153809713 |
| 778 | *Bacillus selenitireducens* MLS10 | YP_003701164.1 | 297585384 |
| 714 | *Clostridium saccharoperbutylacetonicum* N1-4 | AAP42563.1 | 31075383 |
| 707 | *Lactobacillus brevis* ATCC 367 | YP_795711.1 | 116334184 |
| 141 | *Desulfatibacillum alkenivorans* AK-01 | YP_002434126.1 | 218782808 |
| 133 | *Clostridium phytofermentans* ISDg | YP_001558295.1 | 160879327 |
| 715 | *Clostridium bolteae* ATCC BAA-613 | ZP_02089671.1 | 160942363 |
| 779 | *Photobacterium profundum* 3TCK | ZP_01222600.1 | 90414628 |
| 145 | *Citrobacter koseri* ATCC BAA-895 | YP_001452373.1 | 157145054 |
| 704 | *Salmonella enterica typhimurium* | NP_460996.1 | 16765381 |
| 777 | *Sebaldella termitidis* ATCC 33386 | YP_003307836.1 | 269119659 |
| 795 | *Fusobacterium nucleatum* subsp. *polymorphum* ATCC 10953 | ZP_04969437.1 | 254302079 |
| 706 | *Tolumonas auensis* DSM 9187 | YP_002892893.1 | 237808453 |
| 137 | *Rhodospirillum rubrum* ATCC 11170 | YP_426002.1 | 83592250 |
| 1993 | Metalibrary sp | N/A | N/A |

TABLE 47

BDO and 4-hydroxybutyrate (4HB) production of E. coli host strain 1889 containing several alternative 4-hydroxybutyryl-CoA reductase plasmid constructs. The plasmid construct denoted by only "pZS*13S" contains no 4-hydroxybutyryl-CoA reductase gene. Plasmid constructs denoted by pZS*13S followed by a number express the 4-hydroxybutyryl-CoA reductase gene denoted by such number. BDO and 4HB concentrations are in mM.

| Host | Plasmid | OD 24 h | LCMS-24 hrs 4HB | LCMS-24 hrs BDO |
|---|---|---|---|---|
| 1889 | pZS*13S | 3.12 | 3.93 | 0 |
| 1889 | pZS*13S | 3.68 | 10.4 | 0.5 |
| 1889 | pZS*13S | 2.81 | 2.74 | 0 |
| 1889 | pZS*13S | 2.61 | 1.16 | 0 |
| 1889 | pZS*13S-025B | 3.25 | 0.87 | 8.42 |
| 1889 | pZS*13S-025B | 2.11 | 0.8 | 7.09 |
| 1889 | pZS*13S-025B | 3.01 | 0.65 | 7.38 |
| 1889 | pZS*13S-025B | 3.04 | 0.72 | 6.81 |
| 1889 | pZS*13S-733 | 1.67 | 1.07 | 1.64 |
| 1889 | pZS*13S-733 | 1.63 | 1.22 | 1.87 |
| 1889 | pZS*13S-733 | 2.16 | 1.16 | 1.89 |
| 1889 | pZS*13S-733 | 2.34 | 1.04 | 1.88 |
| 1889 | pZS*13S-744 | 2.75 | 0.63 | 2.17 |
| 1889 | pZS*13S-744 | 3.00 | 0.65 | 1.75 |
| 1889 | pZS*13S-744 | 2.75 | 0.5 | 1.72 |
| 1889 | pZS*13S-744 | 1.98 | 0.39 | 0.56 |
| 1889 | pZS*13S-787 | 2.63 | 0.88 | 1.82 |
| 1889 | pZS*13S-787 | 2.40 | 1 | 1.75 |
| 1889 | pZS*13S-787 | 2.88 | 1.06 | 2.41 |
| 1889 | pZS*13S-787 | 3.26 | 1.03 | 1.86 |
| 1889 | pZS*13S-865 | 2.60 | 0.95 | 1.71 |
| 1889 | pZS*13S-865 | 2.70 | 1.11 | 2.09 |
| 1889 | pZS*13S-865 | 2.69 | 0.98 | 1.4 |
| 1889 | pZS*13S-865 | 2.70 | 1.06 | 1.74 |
| 1889 | pZS*13S-778 | 2.76 | 1.15 | 5.79 |
| 1889 | pZS*13S-778 | 3.12 | 1.06 | 6.48 |
| 1889 | pZS*13S-778 | 2.83 | 1.08 | 4.98 |
| 1889 | pZS*13S-778 | 2.79 | 1.1 | 5.19 |
| 1889 | pZS*13S-714 | 2.60 | 0.63 | 6.55 |
| 1889 | pZS*13S-714 | 2.77 | 0.86 | 6.88 |
| 1889 | pZS*13S-714 | 2.67 | 0.77 | 6.51 |
| 1889 | pZS*13S-714 | 2.73 | 0.75 | 8.12 |
| 1889 | pZS*13S-707 | 1.39 | 0.3 | 1.56 |
| 1889 | pZS*13S-707 | 1.05 | 0.24 | 1.57 |
| 1889 | pZS*13S-707 | 1.99 | 0.26 | 1.62 |
| 1889 | pZS*13S-707 | 2.20 | 0.28 | 1.76 |
| 1889 | pZS*13S-141 | 2.54 | 1.08 | 2.13 |
| 1889 | pZS*13S-141 | 2.72 | 1 | 2.01 |
| 1889 | pZS*13S-141 | 2.54 | 1.04 | 1.9 |
| 1889 | pZS*13S-141 | 2.34 | 0.97 | 1.77 |
| 1889 | pZS*13S-133 | 2.63 | 0.7 | 2.69 |
| 1889 | pZS*13S-133 | 1.79 | 0.73 | 2.5 |
| 1889 | pZS*13S-133 | 3.04 | 0.69 | 2.26 |
| 1889 | pZS*13S-133 | 3.21 | 0.65 | 2.84 |
| 1889 | pZS*13S-715 | 2.79 | 1.03 | 2.31 |
| 1889 | pZS*13S-715 | 2.67 | 1.13 | 1.55 |
| 1889 | pZS*13S-715 | 2.90 | 1.02 | 1.6 |
| 1889 | pZS*13S-715 | 3.10 | 1.17 | 2.26 |
| 1889 | pZS*13S-779 | 3.21 | 8.88 | 0.46 |
| 1889 | pZS*13S-779 | 2.84 | 10.5 | 0.63 |
| 1889 | pZS*13S-779 | 3.98 | 11.9 | 0.84 |
| 1889 | pZS*13S-779 | 4.55 | 13.5 | 1.15 |
| 1889 | pZS*13S-145 | 2.08 | 0.53 | 0.76 |
| 1889 | pZS*13S-145 | 2.65 | 0.66 | 0.72 |
| 1889 | pZS*13S-145 | 2.74 | 0.55 | 0.63 |
| 1889 | pZS*13S-145 | 3.08 | 0.7 | 0.68 |
| 1889 | pZS*13S-704 | 2.49 | 0.93 | 1.65 |
| 1889 | pZS*13S-704 | 2.08 | 0.89 | 1.81 |
| 1889 | pZS*13S-704 | 2.97 | 0.76 | 1.58 |
| 1889 | pZS*13S-704 | 3.35 | 0.9 | 2.32 |
| 1889 | pZS*13S-777 | 2.65 | 1.45 | 0.94 |
| 1889 | pZS*13S-777 | 3.03 | 1.89 | 1.5 |
| 1889 | pZS*13S-777 | 3.36 | 2.16 | 1.79 |
| 1889 | pZS*13S-777 | 3.10 | 1.93 | 1.6 |
| 1889 | pZS*13S-795 | 2.60 | 3.22 | 1.55 |
| 1889 | pZS*13S-795 | 3.43 | 4.54 | 1.96 |
| 1889 | pZS*13S-795 | 3.33 | 4.24 | 1.93 |
| 1889 | pZS*13S-795 | 2.87 | 2.15 | 0.97 |
| 1889 | pZS*13S-706 | 2.67 | 0.96 | 1.36 |
| 1889 | pZS*13S-706 | 2.41 | 1.52 | 2.64 |
| 1889 | pZS*13S-706 | 2.94 | 1.4 | 2.56 |
| 1889 | pZS*13S-706 | 2.71 | 0.85 | 0.89 |
| 1889 | pZS*13S-137 | 2.85 | 1.76 | 1.4 |
| 1889 | pZS*13S-137 | 3.04 | 2.31 | 2.21 |
| 1889 | pZS*13S-137 | 3.00 | 1.89 | 1.56 |
| 1889 | pZS*13S-137 | 2.45 | 0.55 | 0.17 |

TABLE 48

BDO and 4-hydroxybutyrate (4HB) production of E. coli host strain 4269 containing either no heterologous 4-hydroxybutyryl-CoA reductase gene (i.e., pZS*13S) or expressing the 4-hydroxybutyryl-CoA reductase gene, 1993, from the pZS* plasmid under control of the p100 promoter. The gene sequence for 1993 is provided in the bottom column of the table. BDO and 4HB concentrations are in mM.

| Host | Plasmid | OD 24 h | LCMS-24 hrs 4HB | LCMS-24 hrs BDO |
|---|---|---|---|---|
| 4269 | pZS*13S | 3.12 | 49.3 | 1.9 |
| 4269 | pZS*13S | 3.08 | 50.7 | 1.7 |
| 4269 | pZS*13S | 3.31 | 48.2 | 3.0 |
| 4269 | pZS*13S | 3.18 | 55.7 | 3.2 |
| 4269 | pZS*13S-p100-1993 | 3.88 | 13.1 | 37.2 |
| 4269 | pZS*13S-p100-1993 | 3.58 | 18.3 | 44.3 |
| 4269 | pZS*13S-p100-1993 | 3.40 | 17.3 | 46.9 |
| 4269 | pZS*13S-p100-1993 | 3.40 | 16.0 | 46.5 |

Gene sequence for 1993:
atggatttgaagctgaccgatgcggacgttgaggcaatcgtagcgcaagt catggctaacattgagcgccgtctgggtagcgcggaagcgggcagcgcag catccgctgcgtcgccggcaccggctgcgccggttcgtaccgctccgggt ggcagcccggcagccagcccgcgtccggagtacggtgttttgatcgtgc ggaggatgcagtcgccgctgccgccgaagctcaggaagccttcctgcgcc agtgtcgtctgcaagaccgtgagcgcattctgcgtgccatccgtgaagag actctggcacgcaaggaagaattggcacgcctgatttgggaggaaacgaa gctgggtcgcttggaacacaaaattgcaaagctggaattgacggcgctga aaacccgggtacggaggatctgcgcaccgaggcatttagcggcgacaac ggcctgaccatcgtcgaacatgcgccgtacggtgtgattggcgcggttac cccggttacgaaccctgcggagactattatcaacaacgcgatcggcatgc tggcaagcggtaatgcagtggtgttcaacgtgcaccctagcgctaaacgt tgctccgcgtataccgtccagatgatcaataaagcagtgatggcagcggg

TABLE 48-continued

BDO and 4-hydroxybutyrate (4HB) production of E. coli host strain 4269 containing either no heterologous 4-hydroxybutyryl-CoA reductase gene (i.e., pZS*13S) or expressing the 4-hydroxybutyryl-CoA reductase gene, 1993, from the pZS* plasmid under control of the p100 promoter. The gene sequence for 1993 is provided in the bottom column of the table. BDO and 4HB concentrations are in mM.

| Host Plasmid | OD 24 h | LCMS-24 hrs 4HB | LCMS-24 hrs BDO |
|---|---|---|---| tggtccgccgaatctggttacgatggttcgcgagccgaccatggaaaccc tgaatgcgatcatccgcagcccgagcgtgaagctgctggtgggcaccggc ggtccgggtctggttagcaccctgctgcgctctggtaagaaagcgattgg tgcgggtgcgggcaatccgccggtcgttgtggatgataccgccgacctgg agcatgcggcaaaggaaatcatcaaaggcgcgtcctttgacaacaatatt ctgtgtattgcggagaaagaggttttgtggttgataaagcggccgacgg tctgatctatcacatgctggataacggcgcatacatgctgggtcgtgacg agctggagaaggtgatgcaattcgcgctgaccgcggacgaaagccagggc ggtgcgggttgctctattgatccgcgtcgtgcgtggcatgtgactaagga gtgggtgggcaaagatgcgcgcttgttcctggagaagattggtgtcaaga ctgaccgtccggttgacttgctgttgtgcgaggttgactttgaccacccg ttcgtgcagctggaacaaatgatgccagtactgccgattgttcgtgtccg tgacctggatgaagccatcggtatggccgtccgtgcggagcacggcaatc gtcacaccgcaattatgcatagccgtaacgtggacaatctgacccgtttt gcccgtgccattgccacgaccatcttcgtcaaaaacgcaagcagcttggc gggtgttggttatggcggtgaaggttttaccaccatgacgatcgccggtc

TABLE 48-continued

BDO and 4-hydroxybutyrate (4HB) production of E. coli host strain 4269 containing either no heterologous 4-hydroxybutyryl-CoA reductase gene (i.e., pZS*13S) or expressing the 4-hydroxybutyryl-CoA reductase gene, 1993, from the pZS* plasmid under control of the p100 promoter. The gene sequence for 1993 is provided in the bottom column of the table. BDO and 4HB concentrations are in mM.

| Host Plasmid | OD 24 h | LCMS-24 hrs 4HB | LCMS-24 hrs BDO |
|---|---|---|---| caacgggcgagggtctgacgtcggctcgtacgttcacgcgcaaagtccgc tgtgtcctggcggacggcggtttccgtatcgttggttaa (SEQ ID NO: 176)

Example XXX

Production of 4HB and BDO Upon Expression of Genes Encoding 4-Hydroxybutyraldehyde Reductase Enzymes This example describes production of 4hb and BDO upon expression of genes encoding 4-hydroxybutyraldehyde reductase enzymes.

Several heterologous 4-hydroxybutyraldehyde reductase genes (Table 49) were expressed in E. coli from the pZS*-13S plasmid to allow a functional pathway from succinyl-CoA and alpha-ketoglutarate to 1,4-butanediol. Host strain 1889 is based on strain ECKh-432 whose construction is described above and in US20110045575. Notable modifications include deletions in adhE, ldhA, pflB, mdh, and arcA. Strain ECKh-432 also contains chromosomally integrated copies of sucD from Porphyromonas gingivalis (encoding CoA-dependant succinate semialdehyde dehydrogenase), sucA from Mycobacterium bovis (encoding alpha-ketoglutarate decarboxylase), 4hbd from P. gingivalis (encoding 4-hydroxybutyrate dehydrogenase), and 4hbd from Clostridium kluyveri (encoding 4-hydroxybutyrate dehydrogenase). Strain 1889 contains deletions in the native alcohol dehydrogenase genes adhP, yqhD, yahK, and yjgB. Additionally, strain 1889 contains a chromosomally integrated copy of 4-hydroxybutyryl-CoA transferase expressed from the pA promoter at the attB locus. Table 50 shows that expression of heterologous 4-hydroxybutyraldehyde reductase genes enhances BDO production in strain 1889 over the controls denoted by "pZS*13S". Cells were cultured using the 96 well-plate protocol described previously.

TABLE 49

Genes encoding functional 4-hydroxybutyraldehyde reductase enzymes.

| Gene Number | Organism | Accession | GI |
|---|---|---|---|
| 12 | Escherichia coli K-12 MG1655 | AAC76047.1 | 1789386 |
| 956 | Clostridium beijerinckii NCIMB 8052 | YP_001309304.1 | 150017050 |
| 1247 | Clostridium saccharobutylicum | P13604.1 | 113352 |
| 1248 | Clostridium asparagiforme DSM 15981 | ZP_03760651.1 | 225405462 |
| 1250 | Clostridium bolteae ATCC BAA-613 | ZP_02083621.1 | 160936248 |
| 1251 | Clostridium cellulovorans 743B | YP_003845251.1 | 302876618 |
| 1256 | Clostridium hiranonis DSM 13275 | ZP_03294286.1 | 210624270 |
| 1259 | Clostridium methylpentosum DSM 5476 | ZP_03705769.1 | 225016577 |
| 1364 | Atopobium parvulum DSM 20469 | YP_003179160.1 | 257783943 |
| 1365 | Tolumonas auensis DSM 9187 | YP_002893476.1 | 237809036 |
| 1366 | Clostridium carboxidivorans P7 | ZP_05394983.1 | 255528157 |

TABLE 50

BDO and 4-hydroxybutyrate (4HB) production of E. coli host strain 1889 containing several alternative 4-hydroxybutyraldehyde reductase plasmid constructs. The plasmid construct denoted by only "pZS*13S-" contains no 4-hydroxybutyraldehyde reductase gene but does express a 4-hydroxybutyryl-CoA reductase gene. Plasmid constructs denoted by pZS*13S-followed by a number express both 4-hydroxybutyryl-CoA reductase and the 4-hydroxybutyraldehyde reductase gene denoted by such number. BDO and 4HB concentrations are in mM.

| Host | Plasmid | OD 24 h | LCMS-24 h 4HB | LCMS-24 h BDO |
|---|---|---|---|---|
| 1889 | pZS*13S | 4.68 | 21.5 | 0.4 |
| 1889 | pZS*13S | 4.33 | 15.9 | 0.1 |
| 1889 | pZS*13S | 4.83 | 18.9 | 0.3 |
| 1889 | pZS*13S | 4.25 | 19.8 | 0.6 |
| 1889 | pZS*13S-956 | 4.45 | 2.4 | 52.0 |
| 1889 | pZS*13S-956 | 4.92 | 3.5 | 52.1 |
| 1889 | pZS*13S-956 | 4.65 | 4.2 | 42.9 |
| 1889 | pZS*13S-956 | 5.37 | 4.7 | 54.2 |
| 1889 | pZS*13S-1247 | 4.99 | 2.4 | 46.6 |
| 1889 | pZS*13S-1247 | 5.38 | 2.3 | 42.5 |
| 1889 | pZS*13S-1247 | 5.68 | 2.1 | 38.6 |
| 1889 | pZS*13S-1247 | 5.18 | 2.0 | 40.4 |
| 1889 | pZS*13S-1248 | 4.25 | 2.8 | 17.6 |
| 1889 | pZS*13S-1248 | 4.4 | 1.9 | 17.8 |
| 1889 | pZS*13S-1248 | 3.06 | 2.1 | 17.3 |
| 1889 | pZS*13S-1248 | 4.22 | 2.0 | 19.5 |
| 1889 | pZS*13S-1250 | 4.76 | 0.9 | 30.4 |
| 1889 | pZS*13S-1250 | 5.05 | 1.0 | 30.9 |
| 1889 | pZS*13S-1250 | 4.67 | 1.1 | 28.5 |
| 1889 | pZS*13S-1250 | 5.57 | 1.1 | 33.5 |
| 1889 | pZS*13S-1251 | 4.68 | 2.0 | 49.9 |
| 1889 | pZS*13S-1251 | 4.65 | 2.0 | 45.3 |
| 1889 | pZS*13S-1251 | 4.86 | 1.7 | 42.6 |
| 1889 | pZS*13S-1251 | 4.76 | 1.9 | 42.7 |
| 1889 | pZS*13S-1256 | 4.63 | 15.7 | 11.9 |
| 1889 | pZS*13S-1256 | 4.48 | 16.2 | 12.6 |
| 1889 | pZS*13S-1256 | 5.1 | 15.0 | 12.8 |
| 1889 | pZS*13S-1256 | 5.51 | 15.3 | 13.4 |
| 1889 | pZS*13S-1259 | 5.01 | 1.0 | 33.7 |
| 1889 | pZS*13S-1259 | 5.29 | 1.1 | 28.9 |
| 1889 | pZS*13S-1259 | 5.49 | 1.3 | 29.5 |
| 1889 | pZS*13S-1259 | 5.25 | 1.2 | 31.5 |
| 1889 | pZS*13S-1364 | 5.52 | 5.0 | 48.8 |
| 1889 | pZS*13S-1364 | 5.12 | 8.3 | 47.7 |
| 1889 | pZS*13S-1364 | 5.47 | 7.1 | 42.2 |
| 1889 | pZS*13S-1364 | 5.48 | 7.8 | 46.0 |
| 1889 | pZS*13S-1365 | 5.49 | 1.1 | 33.1 |
| 1889 | pZS*13S-1365 | 5.65 | 0.7 | 37.7 |
| 1889 | pZS*13S-1365 | 6.08 | 1.1 | 34.8 |
| 1889 | pZS*13S-1365 | 5.5 | 0.9 | 28.6 |
| 1889 | pZS*13S-1366 | 5.13 | 2.2 | 52.6 |
| 1889 | pZS*13S-1366 | 4.76 | 2.4 | 56.1 |
| 1889 | pZS*13S-1366 | 4.93 | 2.2 | 56.9 |
| 1889 | pZS*13S-1366 | blank | 2.5 | 57.9 |

Figure 70:
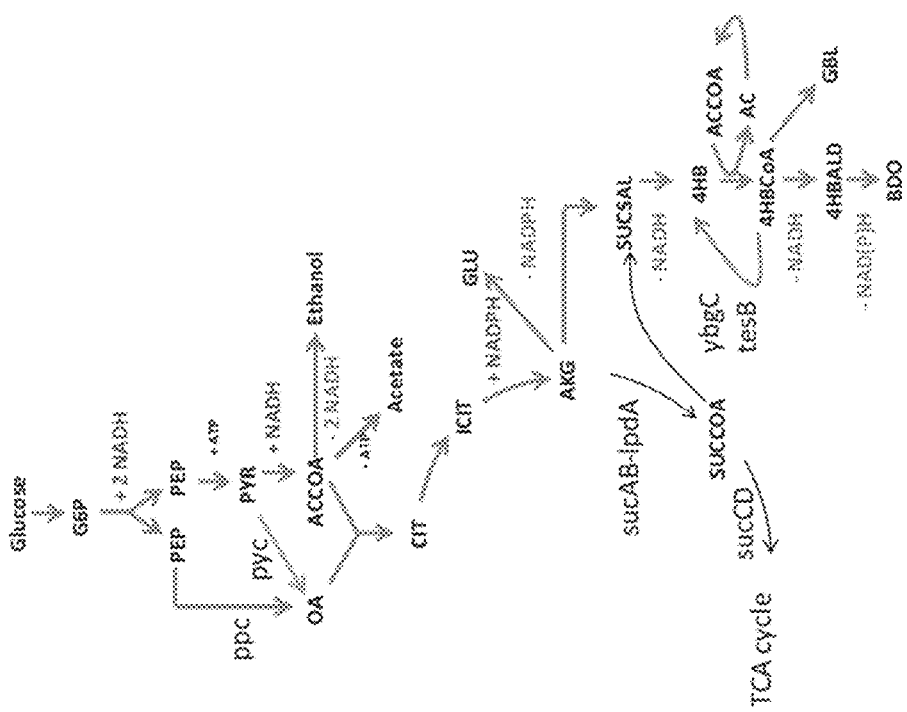
FIG. 70 shows an exemplary pathway for the formation of BDO from glucose. Abbreviations: G6P-glucsoe-6-phosphate, PEP-phosphoenolpyruvate, PYR-pyruvate, OA-oxaloacetate, ACCOA-acetyl-CoA, CIT-citrate, ICIT-isocitrate, AKG-alpha-ketoglutarate, SUCCOA-succinyl-CoA, SUC SAL-succinate semialdehyde, 4HB-4-hydroxybutyrate, 4HBCoA-4-hydroxybutyryl-CoA, 4HBALD-4hydroxybutyraldehyde, BDO-1,4-butanediol, GBL-gamma-butyrolactone. Genes of interest: ppc-PEP carboxylase, sucCD-succinyl-CoA synthetase, sucAB-lpdA—subunits of the AKG dehydrogenase complex, ybgC, tesB-acyl-CoenzymeA thioesterases

In the examples below, additional genetic manipulations are described that were made in the host strain to improve the yield of BDO on glucose. The key genes for deletion and overexpression are shown in FIG. 70.

Starting from the TCA cycle intermediate, alpha-ketoglutarate (AKG), there are two ways to channel flux into the BDO pathway. The first one comprises of an α-ketoacid decarboxylase that decarboxylates AKG into succinate semialdehyde and subsequently reduces it to 4-hydroxybutyrate (4HB). An alternative way to get to 4HB is via AKG dehydrogenase which transforms AKG into succinyl-CoA. This is then reduced to succinate semialdehye via succinate semialdehdye dehydrogenase and then to 4HB. 4HB can then be activated to 4-hydroxybutyryl-CoA (4-HBCoA) via a transferase that transfers the CoA from acetyl-CoA. 4-HB-CoA is reduced to 4-hydroxybutyraldehyde via an aldehyde dehydrogenase (ALD). The aldehyde is finally reduced to 1,4-butanediol (BDO) using an alcohol dehydrogenase (ADH).

Example XXXI

Overexpression of Phosphoenolpyruvate Carboxylase

This example describes overexpression of phosphoenolpyruvate (PEP) carboxylase.

ppc refers to a gene that encodes for phosphoenolpyruvate (PEP) carboxylase activity. The net reaction involves the conversion of PEP and bicarbonate into oxaloacetate and phosphate. The overexpression of PEP carboxylase leads to conversion of more phosphoenolpyruvate (PEP) into OAA, thus reducing the flux from PEP into pyruvate and subsequently into acetyl-CoA. This leads to increased flux into the TCA cycle and thus into the pathway. Further, this overexpression also decreases the intracellular acetyl-CoA pools available for the ethanol-forming enzymes to work with, thus reducing the formation of ethanol and acetate. The increased flux towards oxaloacetate also helps reduce pyruvate and alanine secretion. Additionally, increased availability of oxaloacetate can reduce the cellular needs for respiration and also the amount of carbon lost as $CO_2$. The gene ppc was cloned on the plasmid pZS*-13S as described above.

Figure 71:
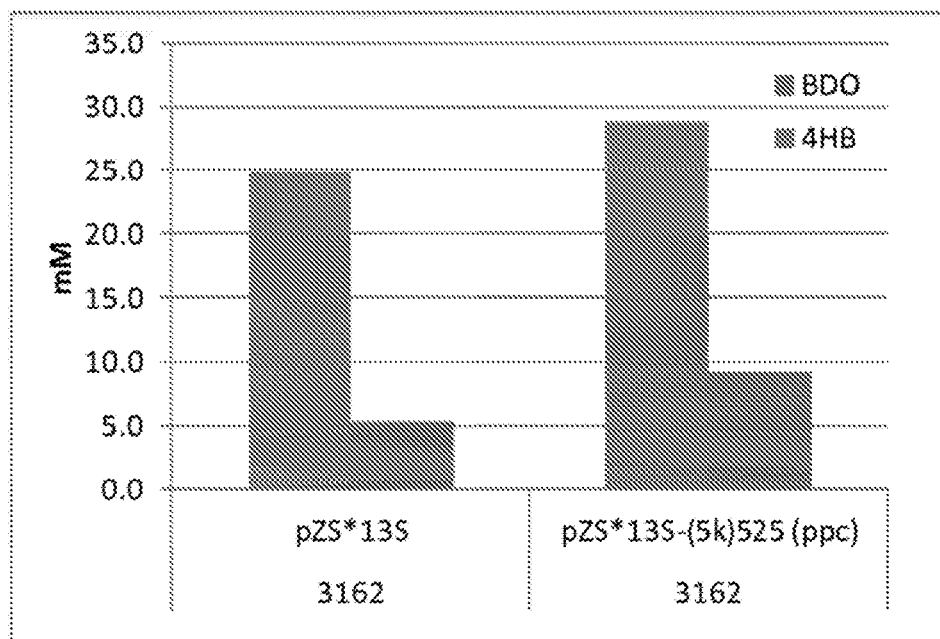
FIG. 71 shows the average BDO and 4HB numbers from four replicates of a 4HB producing host strain that had the gene ppc overexpressed compared with the corresponding averages of the control strain.
Figure 72:
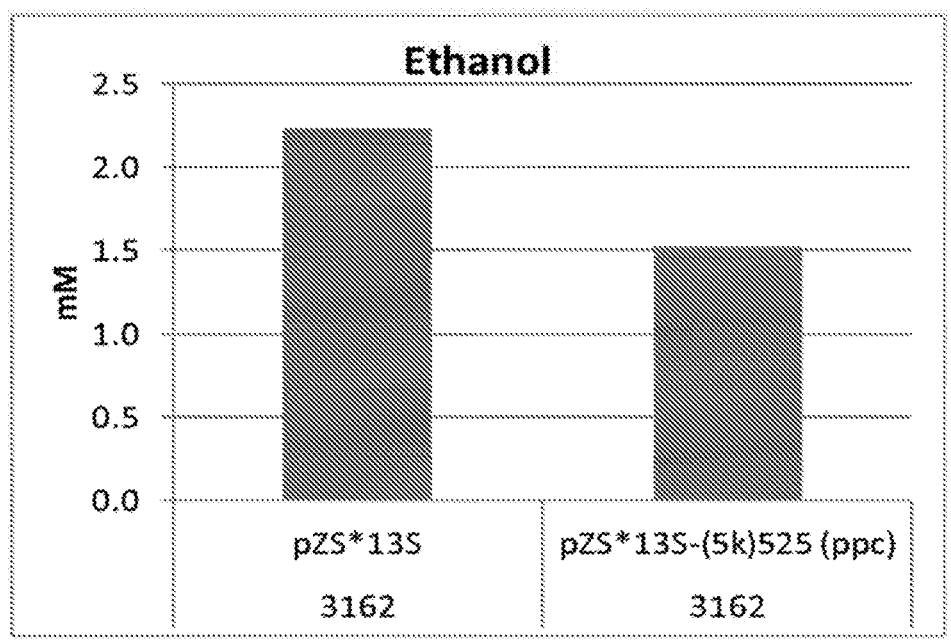
FIG. 72 shows the reduction in the average ethanol numbers from the four replicates of the strain that had ppc overexpressed and compared with those from the control.

Table 51 shows the BDO production in 96-well plates from the strain 3162 from 4 replicates. The gene ppc (#525) was overexpressed on pZS* with a pA promoter as described before and an RBK variant 5K was created. Host strain 3162 is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 3162 contains deletions in the native alcohol dehydrogenase genes adhP, yqhD, yahK, and yjgB. Additionally, strain 3162 contains a chromosomally integrated copy of 4-hydroxybutyryl-CoA transferase expressed from the pA promoter at the attB locus. It also has deletions of cytochrome oxidases, cyoABCD and appBC. The aldehyde dehydrogenase and alcohol dehydrogenase genes for converting 4-hydroxybutyryl-CoA into 4-hydoxybutyraldehyde and subsequently to 1,4-butanediol (BDO) are expressed on the pPSX23R plasmid. The gene candidates for these enzyme steps have already been described. FIG. 71 shows the average BDO and 4HB for the culture and compares it to 4 replicates from the control strain 3162. The same comparison is made in FIG. 72 for the ethanol numbers. Higher BDO and 4HB were observed in cells with ppc overexpressed. As expected, lower ethanol numbers were seen.

TABLE 51

BDO, 4-hydroxybutyrate (4HB) and ethanol data for four 4HB-producing replicates that had the gene ppc overexpressed on pZS* after 24 hours of culture time in 96-well plates. The top 4 rows show the replicate data for the control cultures. All the concentrations are in mM.

| Host | Plasmid #1 | OD | 4HB | BDO | EtOH |
|---|---|---|---|---|---|
| 3162 | pZS*13S | 3.08 | 5.16 | 23.3 | 2.11 |
| 3162 | pZS*13S | 2.96 | 5.23 | 24.5 | 2.27 |
| 3162 | pZS*13S | 2.76 | 4.98 | 25.2 | 2.23 |
| 3162 | pZS*13S | 3.05 | 6.02 | 26 | 2.3 |
| 3162 | pZS*13S-(5k)525 | 3.02 | 9.18 | 29.9 | 1.59 |
| 3162 | pZS*13S-(5k)525 | 2.50 | 9.32 | 28.8 | 1.47 |
| 3162 | pZS*13S-(5k)525 | 3.24 | 9.3 | 28 | 1.49 |
| 3162 | pZS*13S-(5k)525 | 3.38 | 24.5 | 0.72 | 0.69 |

Example XXXII

Overexpression of Alpha-ketoglutarate Dehydrogenase

This example describes overexpression of alpha-ketoglutarate dehydrogenase.

This enzyme complex is formed by sucA, sucB and lpdA in *Escherichia coli*. It converts alpha-ketoglutarate into succinyl-CoA that is subsequently channeled into the BDO pathway. A limitation in this pathway, including any limitation in the capacity of alpha-ketoglutarate dehydrogenase, can lead to the formation of glutamate via, for example, glutamate dehydrogenase (gdhA). This leads to a carbon loss and reduction in yield. Expressing an extra copy of sucAB and lpdA in the BDO-producing strain helped reduce glutamate by significant levels. It can also pull flux through the TCA cycle and help reduce other C2 (ethanol and acetate) and C3 byproducts (alanine, pyruvate). sucAB and lpdA were cloned on pZS* plasmid under the pA promoter as described above. ALD and ADH required for BDO production were expressed on pPSX23R as described earlier.

Table 52 shows the 4HB and BDO production in 96-well plates from 4 replicates of strain 3933 after 24 hours of culture time. Host strain 3933 is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). It contains deletions in the native alcohol dehydrogenase genes adhP, yqhD, yahK, and yjgB. The strain contains a chromosomally integrated copy of 4-hydroxybutyryl-CoA transferase expressed from the pA promoter at the attB locus. It also has deletions of cytochrome oxidases, cyoABCD and appBC, and adh is integrated on the chromosome under the promoter p119 at the hemN locus.

TABLE 52

BDO, 4HB and ethanol data for four 4HB producing replicates of strain 3933 that had the genes sucAB-lpdA overexpressed on a plasmid. The bottom 4 rows show the replicate data for the control cultures of the host strain 3933. All the concentrations are in mM and were measured after 24 hours of culture time in 96-well plates. 1438 refers to the native sucA gene (b0726), 1439 refers to the native wild type sucB gene (b0727), the last gene in the biobrick on pZS* is a mutant version of lpdA (b0116) described previously in Example XIV. This gene is a subunit of the pyruvate dehydrogenase complex in *Escherichia coli* and has been modified such that pyruvate dehydrogenase is not inhibited by NADH. The mutations were made as described in Yim et al., *Nature Chemical Biology* 7: 445-452 (2011)).

| Host | plasmid_1 | OD | 4HB | BDO | Glutamate |
|---|---|---|---|---|---|
| 3933 | pZS*13S_1438-1439-160D345K-lpdA-KP | 2.91 | 6.27 | 35.00 | 0.03 |
| 3933 | pZS*13S_1438-1439-160D345K-lpdA-KP | 2.89 | 6.37 | 33.50 | 0.03 |
| 3933 | pZS*13S_1438-1439-160D345K-lpdA-KP | 2.94 | 6.52 | 32.40 | 0.04 |
| 3933 | pZS*13S_1438-1439-160D345K-lpdA-KP | 2.96 | 5.76 | 31.10 | 0.04 |
| 3933 | pZS*13S | 3.06 | 6.44 | 38.30 | 2.68 |
| 3933 | pZS*13S | 3.05 | 5.42 | 36.40 | 2.20 |
| 3933 | pZS*13S | 3.22 | 5.36 | 36.40 | 2.21 |
| 3933 | pZS*13S | 3.12 | 4.95 | 35.00 | 2.08 |

Figure 73:
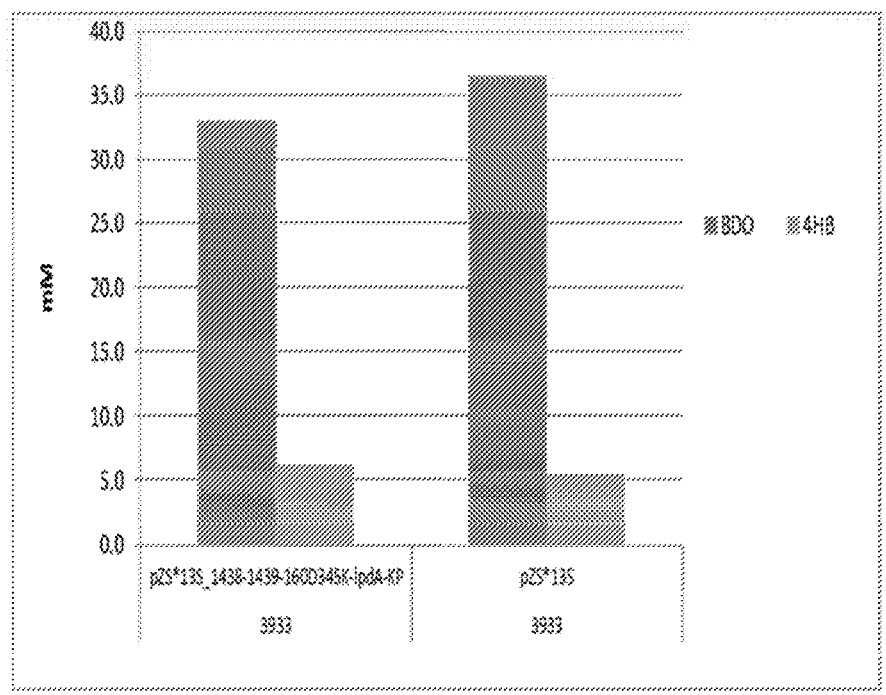
FIG. 73 shows the average BDO and 4HB numbers from four replicates of a 4HB producing host strain that had the genes sucAB and mutant lpdA overexpressed on pZS*compared with the corresponding averages from four replicates of the control strain. ALD and ADH were expressed on the plasmid pPZSX23R.
Figure 74:
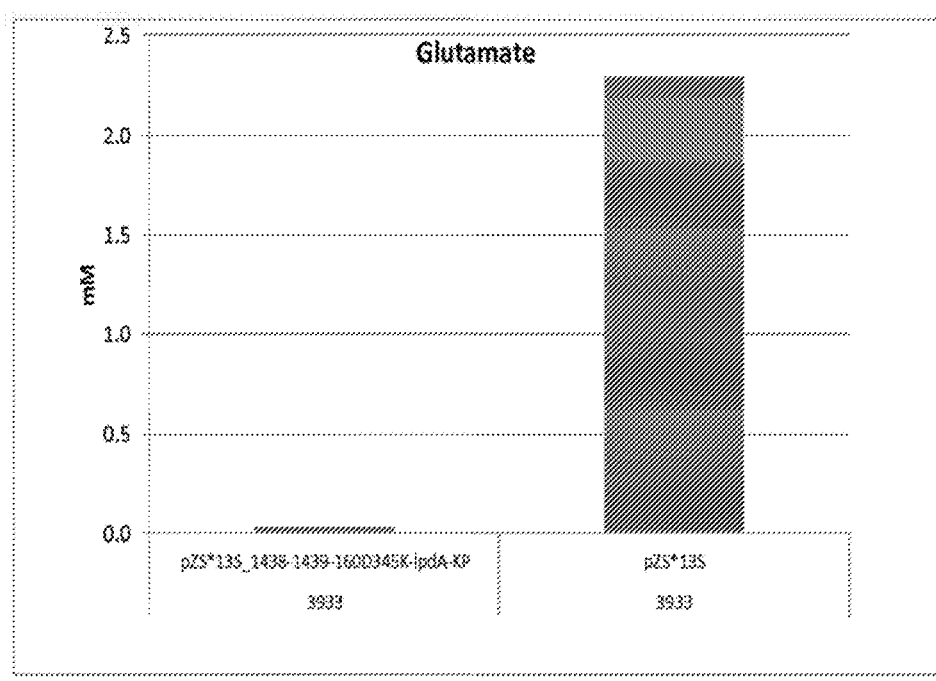
FIG. 74 shows the reduction in the average glutamate numbers from the four replicates of the strain that had the genes sucAB and mutant lpdA overexpressed on pZS* and compared with those from the control.

FIG. 73 shows the average BDO and 4HB numbers from four replicates of a 4HB producing host strain that had the genes sucAB and mutant lpdA overexpressed on pZS*compared with the corresponding averages from four replicates of the control strain. ALD and ADH were expressed on the plasmid pPZSX23R. FIG. 74 shows the reduction in the average glutamate numbers from the four replicates of the strain that had the genes sucAB and mutant lpdA overexpressed on pZS* and compared with those from the control. These results show that expression of sucAB resulted in a dramatic reduction in the amount of glutamate produced and did not adversely affect the production of BDO or 4HB.

Example XXXIII

Overexpression of a Non-Phosphotransferase Sugar Uptake System

This example describes overexpression of glucokinase, galP and or glf as representatives of a non-phosphotransferase (PTS) sugar uptake system.

The primary mode of glucose uptake in the host strains is the PTS system. Every molecule of glucose converted into glucose-6-phosphate (G6P) via this system is accompanied by the conversion of one molecule of PEP into pyruvate. Note that PEP is converted into oxaloacetate via PEP carboxylase in the strains. Additionally, PEP is also converted into pyruvate (by the PTS system as well as pyruvate kinase) and subsequently into acetyl-CoA by pyruvate dehydrogenase in the strains. The BDO pathway requires equimolar amounts of oxaloacetate and acetyl-CoA for forming each mole of BDO. The fixed stoichiometry associated with the PTS system disturbs this balance, leading to higher ratios of acetyl-CoA relative to oxaloacetate. This then leads to production of ethanol and acetate in the cells. The overexpression of non-PTS mode of sugar uptake helps alleviate this issue and balance the amount of oxaloacetate available in comparison to acetyl-CoA, thus increasing flux through the BDO pathway, reducing the C2 byproducts, acetate and ethanol, and reducing the C3 byproducts, pyruvate and alanine.

The primary mechanism of non-PTS glucose uptake is via a permease such as galP to import the sugar and then its ATP-dependent phosphorylation via the kinase encoded by glk. An alternate way to uptake glucose is via the glucose facilitator, glf. While *E. coli* does not have this facilitator, one was cloned from *Zymomonas mobilis* and introduced into *E. coli* (Parker et al. *Mol Microbiol.* 15(5):795-802 (1995)).

Example XXXIV

Expression of Gamma-butyrolactone Esterase

This example describes expression of a gamma-butyrolactone esterase.

Gamma-butyrolactone (GBL) is a byproduct formed during the fermentation of sugars to 1,4-butanediol (BDO). It is formed from the unstable pathway intermediate 4-hydroxybutyryl-CoA. To a small extent, it can also be formed by spontaneous lactonization of 4-hydroxybutyrate.

Figure 75:
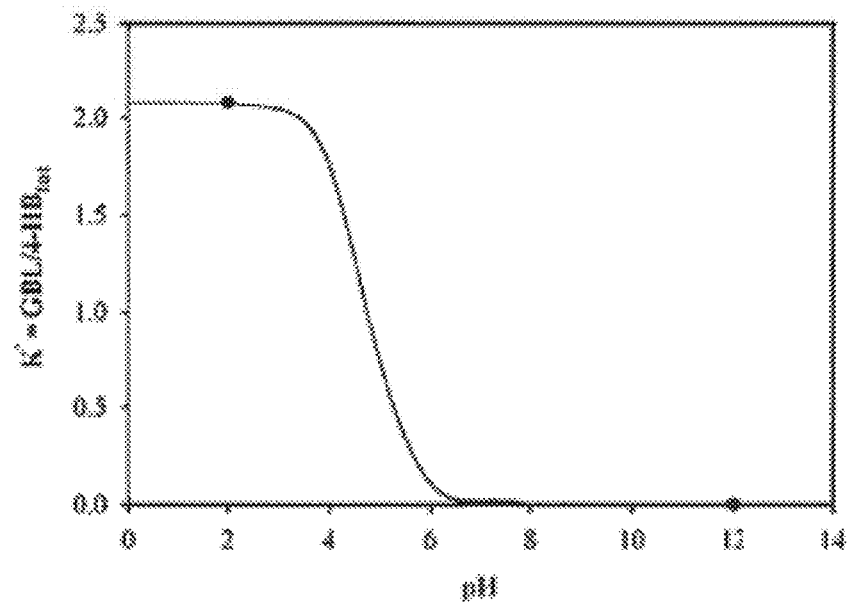
FIG. 75 shows apparent equilibrium constant for lactonization of 4-HB to GBL as a function of pH (at 22° C.) (from Efe et al., *Biotechnol. Bioeng.* 99:1392-1406 (2008)).

Hydroxyacids and their corresponding lactones exist in pH-dependent equilibrium with each other. Lactonization is acid-catalyzed and favorable at low pH. Under alkaline conditions the equilibrium is driven to the open-chain hydroxycarboxylate anion. At the cytoplasmic pH, typically 7.4, hydrolysis of the GBL lactone is favored (FIG. 75). The hydrolysis of GBL to 4-HB can be accelerated in the presence of an enzyme with GBL esterase activity, thus improving the yield and eliminating a byproduct that can complicate downstream separations of the product.

Esterases from *Yersinia intermedia* 29909 and *Agrobacterium tumefaciens* str. C58 (Carlier et al., *Mol. Plant Microbe Interact.* 17(9):951-957 (2004)) were identified and selected as exemplary esterase genes. The nucleotide sequence of the *Yersinia* gene (locus yinte0001_13710) is shown in FIG. 89. The nucleotide sequence of the gene from *Agrobacterium tumefaciens* is shown in FIG. 90.

Table 53 shows BDO, 4HB and GBL data from 96 well-plates of four replicates of a strain that had the esterase integrated (Strain 2387) and compared with the control with no esterase (strain 2237). Host strain 2237 is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 2237 contains deletions in the native alcohol dehydrogenase genes adhP, yqhD, yahK, and yjgB. It also contains a chromosomally integrated copy of 4-hydroxybutyryl-CoA transferase expressed from the pA promoter at the attB locus. An additional deletion in poxB was also introduced.

TABLE 53

BDO, 4HB and GBL data from 96 well-plates of four replicates of a strain that had the esterase integrated (Strain 2387) and compared with the control with no esterase (strain 2237). All concentrations are in mM and were measured after 19 hours of culture time.

| Host | OD | 4HB | BDO | GBL |
|------|------|------|-------|------|
| 2237 | 3.56 | 2.50 | 27.70 | 4.54 |
| 2237 | 3.42 | 2.54 | 32.20 | 5.00 |
| 2237 | 3.37 | 2.44 | 27.10 | 4.34 |
| 2237 | 3.54 | 2.19 | 22.60 | 3.26 |
| 2387 | 3.80 | 0.00 | 23.60 | 0.00 |
| 2387 | 3.87 | 2.59 | 24.70 | 0.65 |
| 2387 | 4.00 | 2.62 | 27.70 | 0.59 |
| 2387 | 4.30 | 3.20 | 29.00 | 0.68 |

Figure 76:
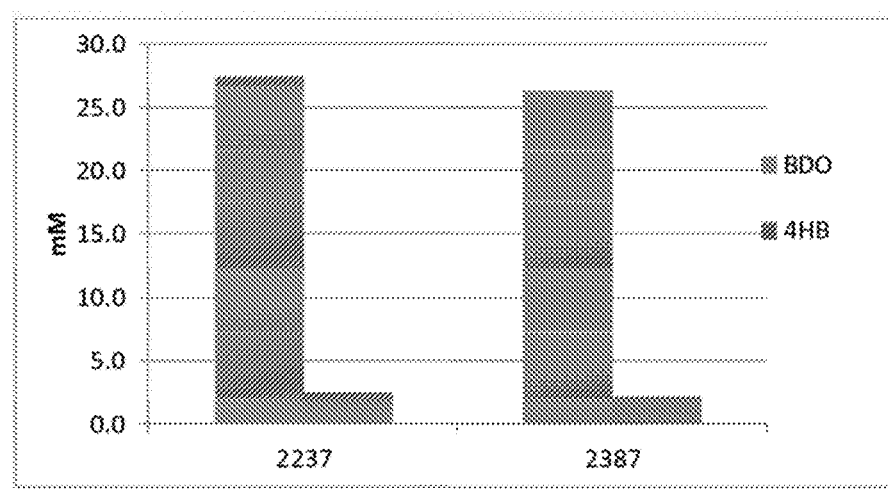
FIG. 76 shows the average BDO and 4HB numbers from four replicates of a host strain capable of producing 4-hydrobutyryl-CoA that had the esterase integrated (2387) compared with the corresponding averages from four replicates of the control strain (2237).
Figure 77:
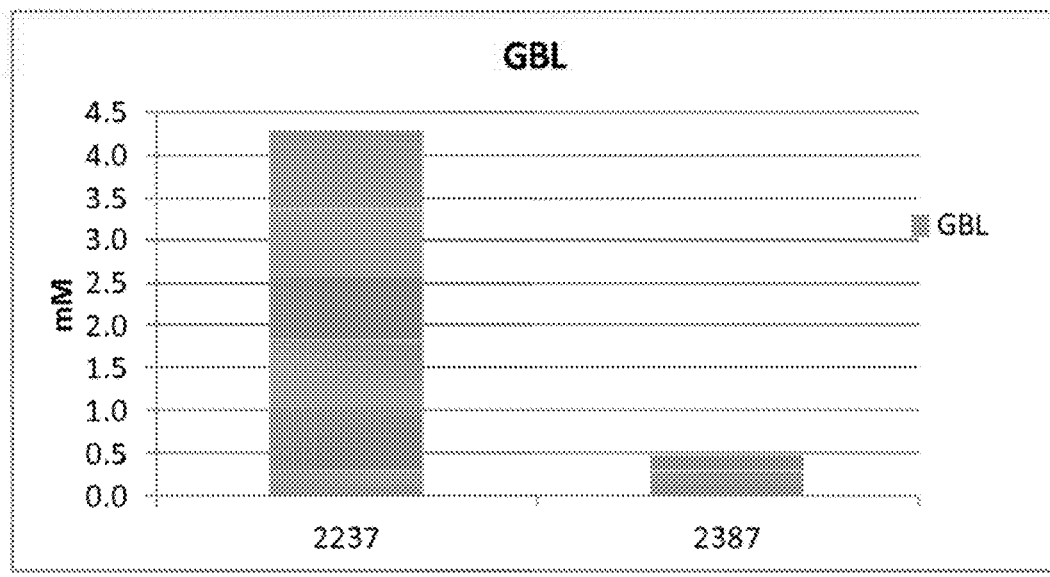
FIG. 77 shows the average GBL numbers from four replicates of a host strain that had the esterase integrated (2387) compared with the corresponding averages from four replicates of the control strain (2237). Lower GBL was ibserved with the strains that had the esterase integrated.

FIG. 76 shows the average BDO and 4HB numbers from four replicates of a host strain capable of producing 4-hydrobutyryl-CoA that had the esterase integrated (2387) compared with the corresponding averages from four replicates of the control strain (2237). FIG. 77 shows the average GBL numbers from four replicates of a host strain that had the esterase integrated (2387) compared with the corresponding averages from four replicates of the control strain (2237). Lower GBL was ibserved with the strains that had the esterase integrated. These results demonstrate expression of an enzyme having gamma-butyrolactone esterase activity without adversely affecting production of BDO or 4HB.

Example XXXV

Deletion of Succinyl-CoA Synthetase

This example describes deletion of succinyl-CoA synthetase.

Succinyl-CoA synthetase is encoded by sucCD in *Escherichia coli*. The deletion of arcA highly upregulates the expression of these genes (and the entire sdh-suc operon) in the cells. Repeated rounds of flux through the TCA cycle leads to carbon loss as $CO_2$. The deletion of sucCD blocked the TCA cycle downstream of succinyl-CoA, reducing the $CO_2$ losses by ~70% and leading to a corresponding increase in BDO titers and yields.

The deletion of sucCD was introduced in host strain 4070. This strain is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 4070 contains deletions in the native alcohol dehydrogenase genes adhP, yqhD, yahK, and yjgB. Additionally, this strain contains a chromosomally integrated copy of 4-hydroxybutyryl-CoA transferase expressed from the p119 promoter at the attB locus. It also has deletions of cytochrome oxidases, cyoABCD and appBC. The adh was integrated on the chromosome under the promoter p119 at the hemN locus.

TABLE 54

BDO and 4HB data from 96 well-plates of four replicates
of a 4-HB producing strain that had the sucCD genes
deleted (Strain 4269) compared with the no deletion
control (strain 4070). Higher 4HB was observed with strains
that had the sucCD deleted. All concentrations are in mM
and were measured after 24 hours of culture time.

| Host | OD | 4HB | BDO |
|---|---|---|---|
| 4070 | 3.62 | 0.289 | 37.2 |
| 4070 | 3.58 | 0.777 | 41.4 |
| 4070 | 3.33 | 0.377 | 28.5 |
| 4070 | 3.75 | 0.792 | 54.4 |
| 4269 | 2.95 | 8.93 | 50.5 |
| 4269 | 2.68 | 8.07 | 50.5 |
| 4269 | 3.34 | 8.65 | 50.1 |
| 4269 | 2.94 | 8.55 | 51.8 |

| Host | plasmid_1 | OD | 4HB | BDO |
|---|---|---|---|---|
| 4070 | pZS*13S-p100-ALD | 3.62 | 0.289 | 37.2 |
| 4070 | pZS*3S-p100-ALD | 3.58 | 0.777 | 41.4 |
| 4070 | pZS*13S-p100-ALD | 3.33 | 0.377 | 28.5 |
| 4070 | pZS*13S-p100-ALD | 3.75 | 0.792 | 54.4 |
| 4269 | pZS*13S-p100-ALD | 2.95 | 8.93 | 50.5 |
| 4269 | pZS*13S-p100-ALD | 2.68 | 8.07 | 50.5 |
| 4269 | pZS*13S-p100-ALD | 3.34 | 8.65 | 50.1 |
| 4269 | pZS*13S-p100-ALD | 2.94 | 8.55 | 51.8 |

Figure 78:
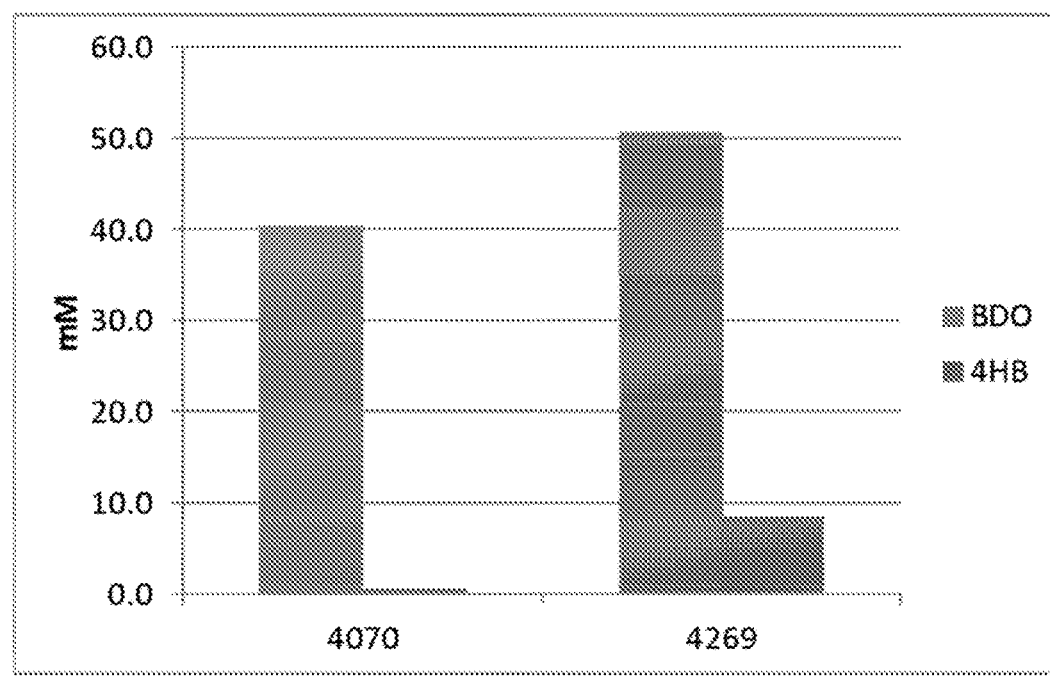
FIG. 78 shows the average BDO and 4HB numbers from four replicates of a host strain that had the genes sucCD deleted (4269) compared with the corresponding averages from four replicates of the control strain (4070).

FIG. 78 shows the average BDO and 4HB numbers from four replicates of a host strain that had the genes sucCD deleted (4269) compared with the corresponding averages from four replicates of the control strain (4070). These results demonstrate increased yield of BDO and 4HB with the deletion of sucCD.

Example XXXVI

Deletion of Acyl CoenzymeA Thioesterases

This example describes deletion of acyl coenzymeA thioesterases ybgC and tesB.

One of the intermediates in the BDO pathway is 4-hydroxybutyryl-CoA. This compound can spontaneously or enzymatically get cyclized to form GBL (gamma-butyryl-lactone). *E. coli* possesses some reversible CoA thioesterases reported to have broad substrate specificity on CoA substrates of C4 to C6 groups. The deletion of these gene candidates eliminated approximately 50% of the GBL formation via the pathway. Such activities can be found analogously in other organisms.

The deletions of tesB and ybgC were made in host strain 1136. This strain is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 1136 has additional deletions in ndh (NADH dehydrogenase II) and succinate semialdehyde dehydrogenase encoding genes, sad and gabD.

TABLE 55

OD, BDO, 4HB and GBL numbers of four replicates of
a strain capable of producing 4-hydroxybutyryl-CoA that
had both tesB and ybgC deleted (1197) and compared
with the control with neither of these deletions (Host 1136).
All concentrations are in mM and were measured after
40 hours of culture time in 20 mL bottles.

| Host | OD | BDO | 4HB | GBL |
|---|---|---|---|---|
| 1136 | 2.428 | 26.2 | 3.1 | 1.8 |
|  | 2.344 | 27.4 | 2.7 | 1.7 |
|  | 2.392 | 26.6 | 3.3 | 1.8 |
| 1197 | 3.324 | 29.9 | 2.8 | 1.0 |
|  | 2.712 | 29.1 | 2.6 | 0.9 |
|  | 2.924 | 32.0 | 2.9 | 0.9 |

Figure 79:
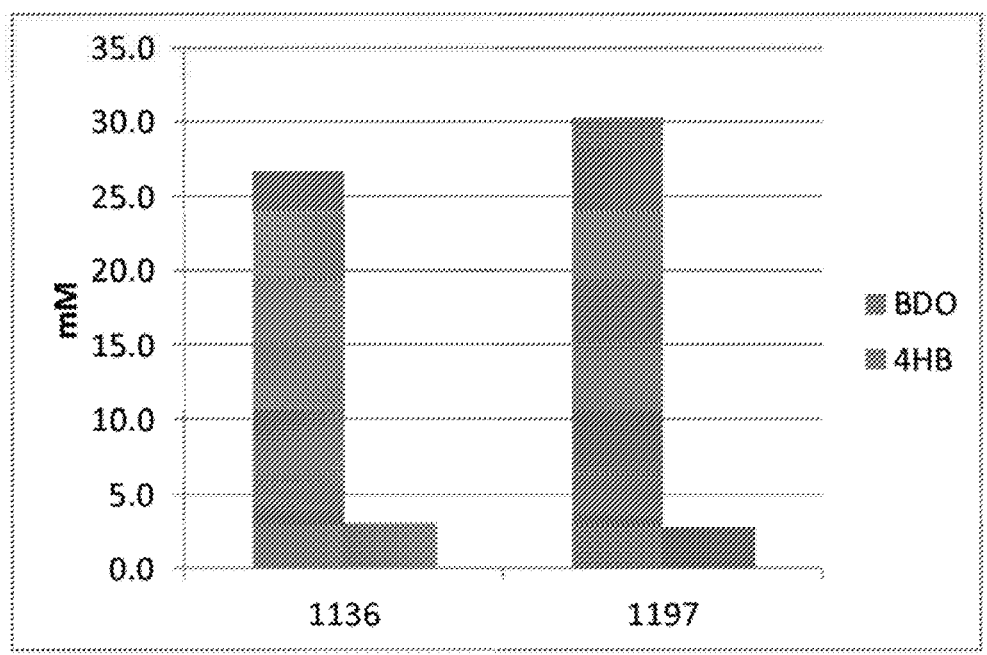
FIG. 79 shows the average BDO and 4HB numbers from three replicates of a host strain that had the genes ybgC and tesB deleted (1197) compared with the corresponding averages from three replicates of the control strain (1136).
Figure 80:
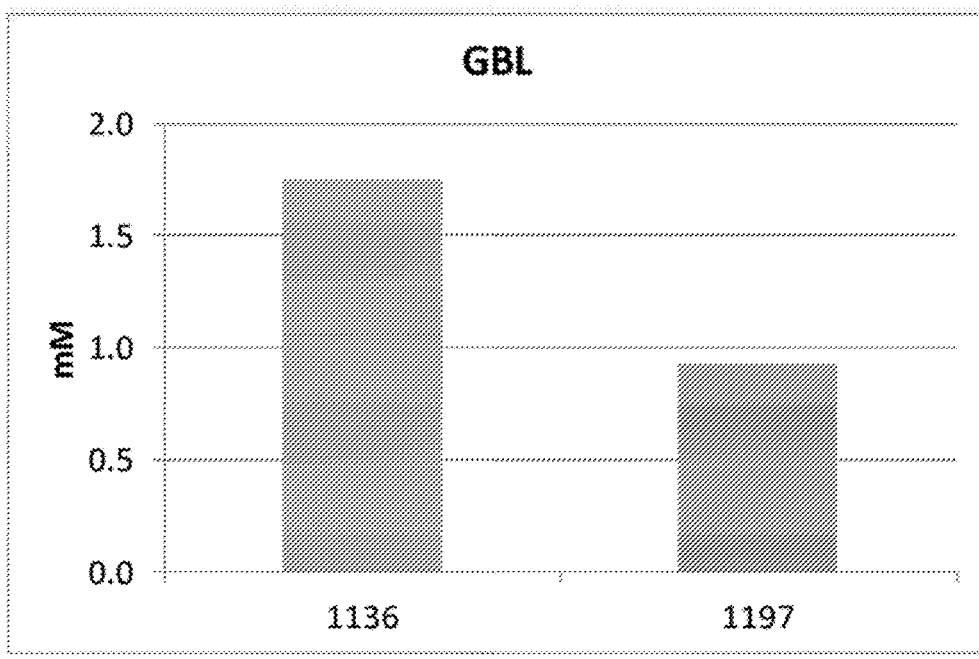
FIG. 80 shows the average GBL numbers from three replicates of a host strain that had the genes ybgC and tesB deleted (1197) compared with the corresponding averages from three replicates of the control strain (1136).

FIG. 79 shows the average BDO and 4HB numbers from three replicates of a host strain that had the genes ybgC and tesB deleted (1197) compared with the corresponding averages from three replicates of the control strain (1136). FIG. 80 shows the average GBL numbers from three replicates of a host strain that had the genes ybgC and tesB deleted (1197) compared with the corresponding averages from three replicates of the control strain (1136). These results demonstrate that deletion of one or more acyl coenzyme A thioesterases decreased production of gamma-butyrolactone, increased production of BDO and had no adverse affect on production of 4HB.

Example XXXVII

Deletions to Prevent or Reduce Backflux into the Pathway

This example describes deletions to prevent backflux into the pathway.

At high titers of 1,4-butanediol (BDO) in the culture, it starts to get reimported into the cells. Once inside the cells, it is metabolized through the TCA cycle. To prevent this backflux of BDO into the cells, alcohol dehydrogenases that were identified as candidates for the reverse flux were deleted. The candidates were identified by two approaches, first, all the alcohol dehydrogenases were listed and prioritized based on their substrate specificity. Microarrays were conducted to determine how high each one of them was expressed. Based on this, a short list of 5 candidates was generated from a list of approximately 35 adh candidates. Secondly, protein fractions with endogenous backflux activity (NADP+ dependent BDO conversion to 4-hydroxybutyraldehyde) were isolated from strain 1427 (alcohol dehydrogenase encoded by yqhD removed and no downstream pathway present, cells accumulate 4HB but do not make BDO) grown microaerobically in MM9 media. The sample was purified while following the backflux activity. The strategy employed is outlined below.

Based on early experiments, the endogenous ADH activity was found to be primarily NADPH dependent and salted out in high (>35%) ammonium sulfate. A fresh sample of 1427 cells from a 2 L LB preparation grown aerobically overnight was lysed using the microfluidizer at 15,000 psi. The sample was then fractionated via ammonium sulfate. The 35% pellet contained little ADH activity and was not processed further, while the 60% pellet contained active ADH with significant backflux activity and was moved onto further purification.

Figure 81:
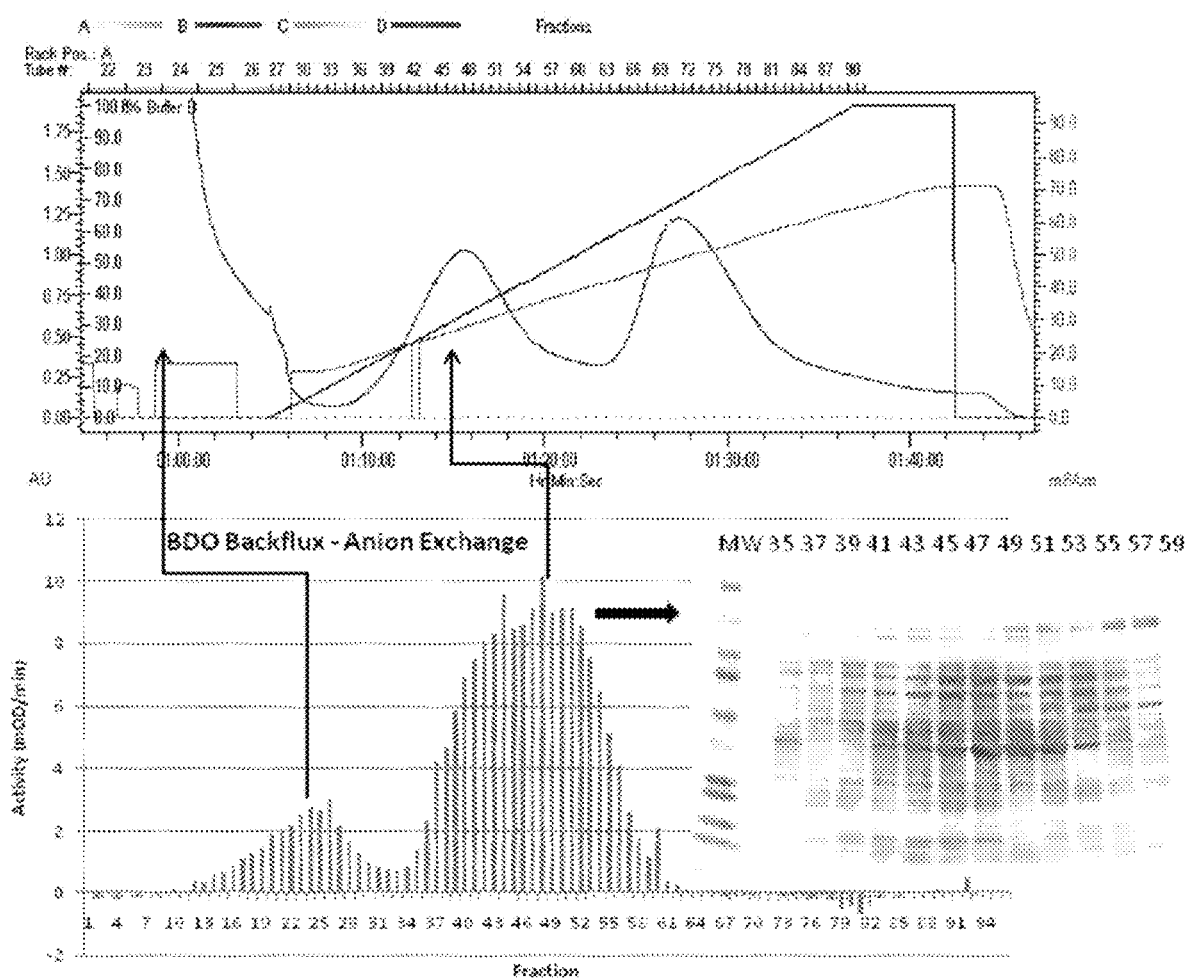
FIG. 81 shows the profile for the anion exchange elution, backflux activity, as well as the SDS page for the fractions.

Anion Exchange Purification. The 60% ammonium sulfate pellet was resuspended in a low salt buffer and dialyzed overnight to remove the residual ammonium sulfate. The sample was loaded onto a 5 ml Q-sepharose column (strong anion exchange) and eluted via a slow increasing salt gradient. The profile for the anion exchange elution, backflux activity, as well as the SDS page for the fractions is shown below in FIG. 81.

The first large peak shown on the left is off-scale and corresponds to proteins that did not bind the column. The peak had low backflux activity. The next peak shown in the middle of the chromatogram had significant backflux activity. An SDS-PAGE of this peak was run and indicates that further purification is needed in order to isolate the protein of interest.

Figure 82:
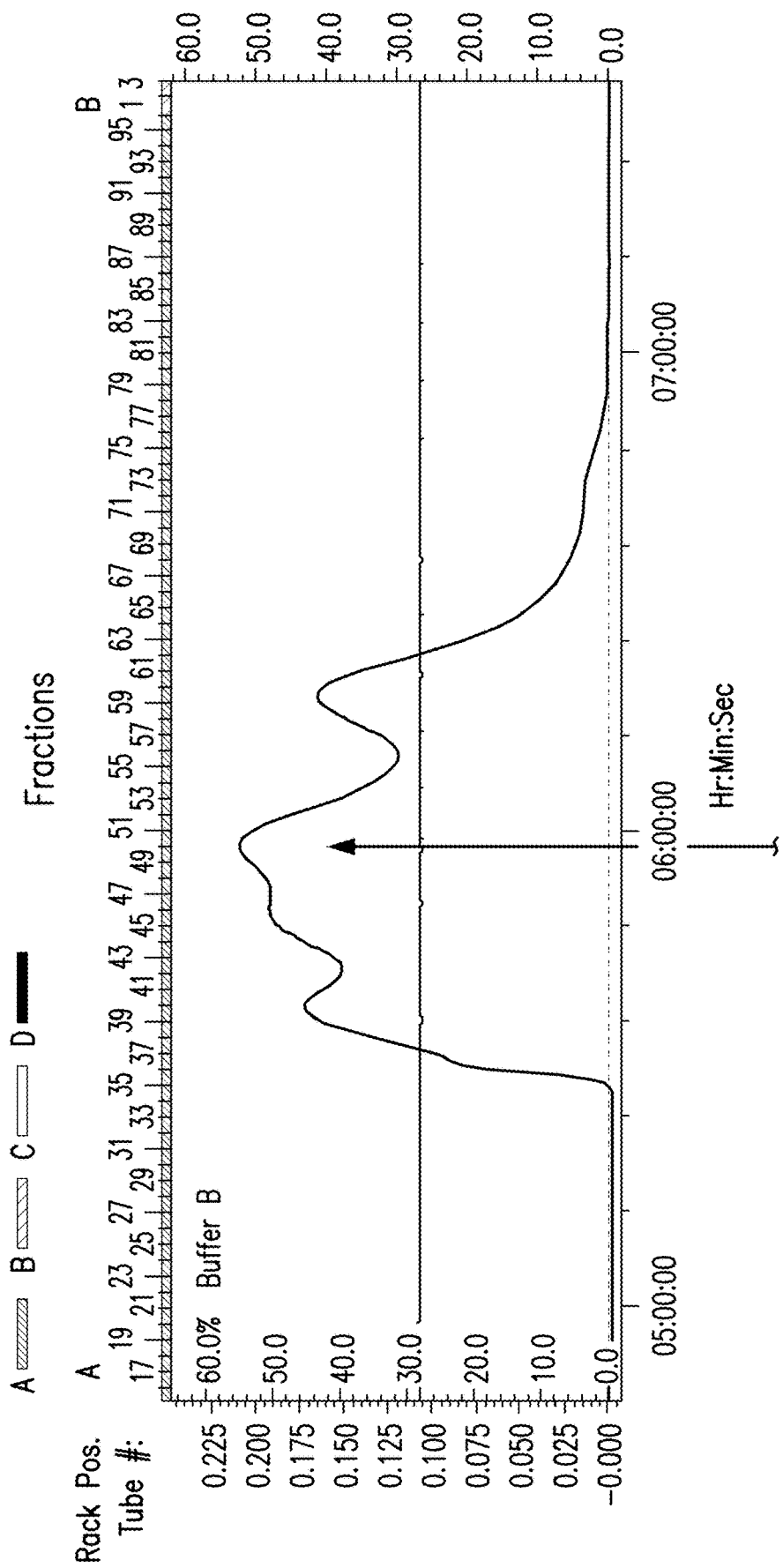
FIG. 82 shows the profile from the size exclusion chromatogrpahy, the backflux activity, as well as the SDS page for the fractions.
Figure 82:
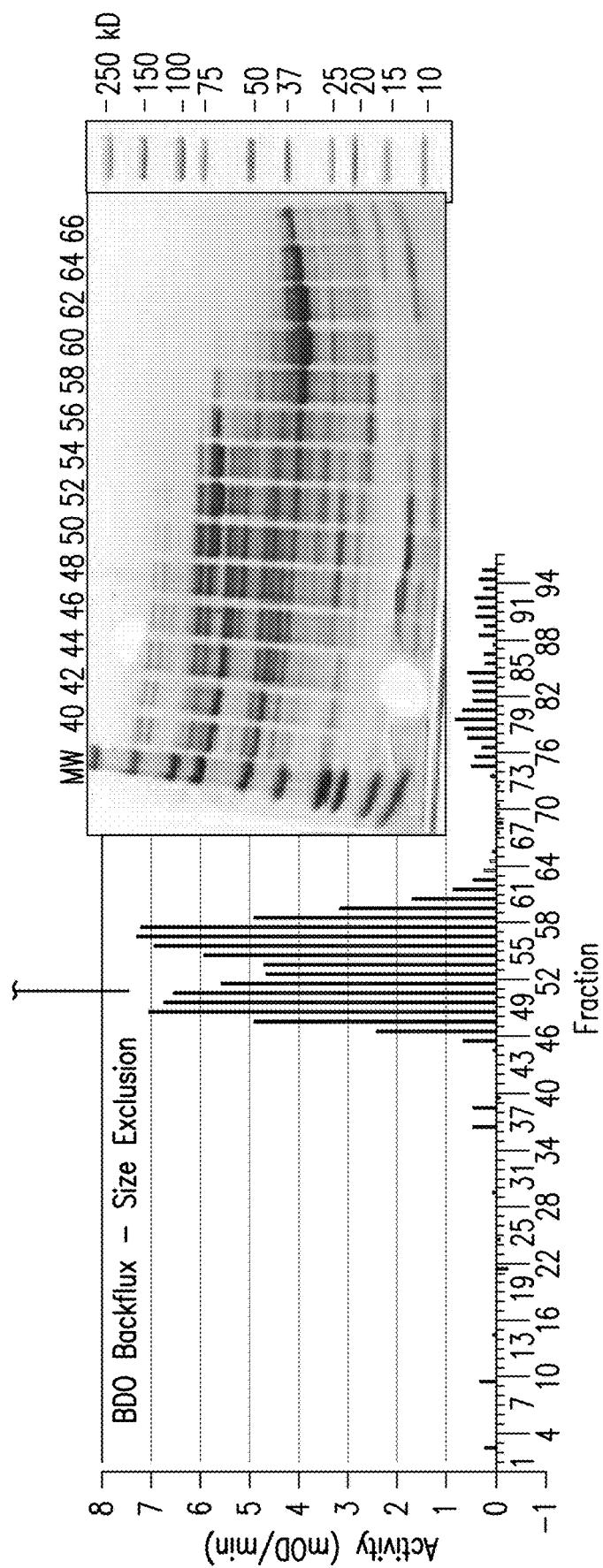

Size Exclusion Chromatography. The peak backflux activity from anion exchange was pooled and concentrated to allow for application to a S200 sephacryl size exclusion column. The column successfully removed impurities from the sample and the results are shown below (FIG. 82).

The results of the sizing column indicated that the protein of interest behaved as a mid-range MW protein, ~50 kDa. However, it was not clear what the identity of the protein was, but it narrowed down to approximately 20 bands on the gel. Additional chromatography was performed to attempt to clean up the sample prior to mass spec analysis.

Figure 83:
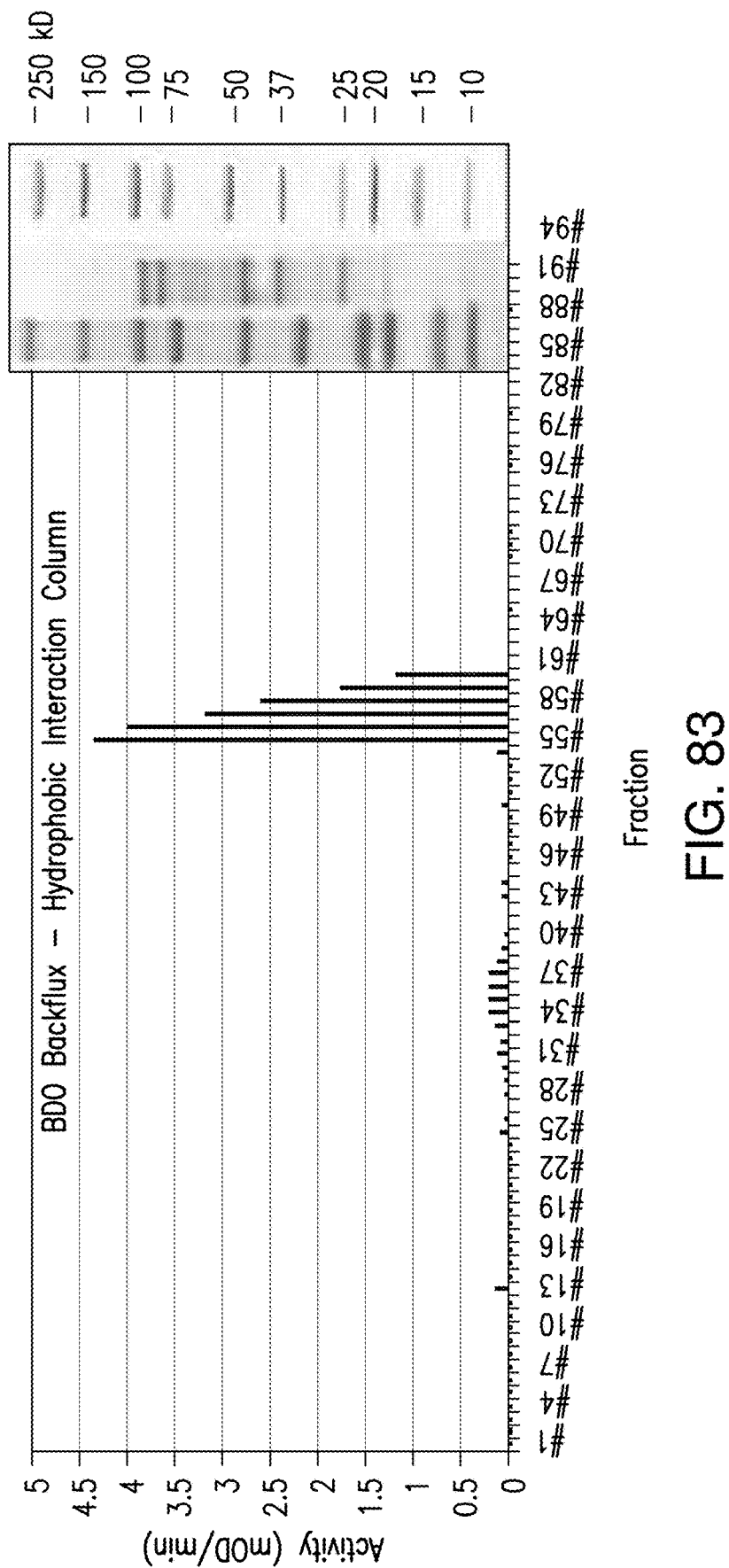
FIG. 83 shows backflux activity from the size exclusion column and the SDS page.

Hydrophobic Interaction Chromatography. The peak with the highest backflux activity from the size exclusion column was pooled and loaded on a phenyl sepharose column (hydrophobic interaction column). The ionic strength of the sample was increased to facilitate binding to the resin. The results are shown below (FIG. 83).

The sample shown on the SDS-PAGE was analyzed by mass spectrometry in order to indentify the protein(s) that is responsible for the backflux. From the gel there are 5 prominent bands alongside a small handful of background proteins (~5).

The purified sample was analyzed by mass spectrometry analysis, and a list of 30 proteins was obtained. From this list the gene selected was:

| Accession | Name | Gene |
|---|---|---|
| gi\|170083708 | Zn-dependent/NAD(P)-binding alcohol dehydrogenase | yjgB |

Figure 84:
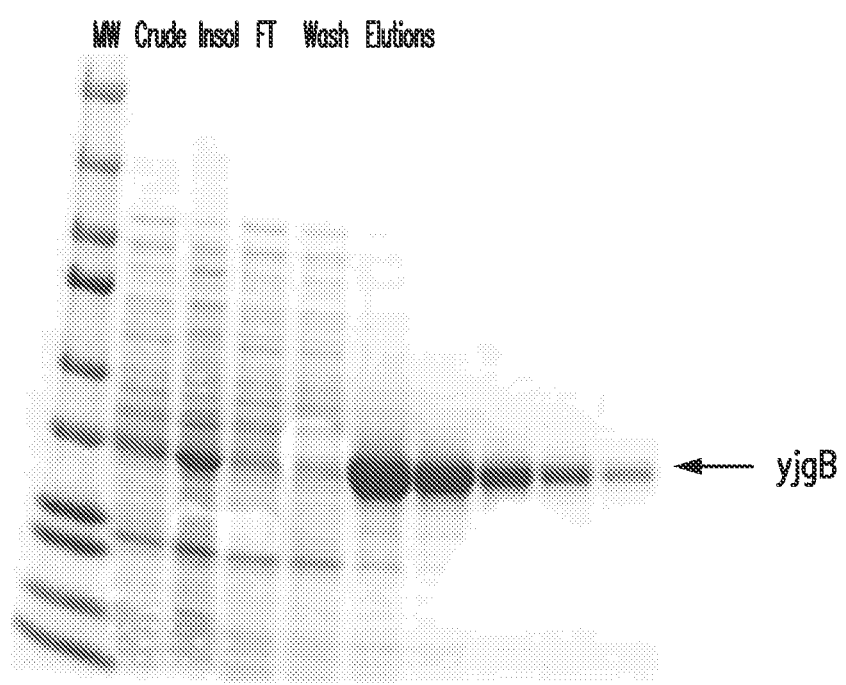
FIG. 84 shows the yjgB gene was cloned with a streptavidin tag, expressed and purified in order to characterize its properties. The results of the purification are via SDS-PAGE.
Figure 85:
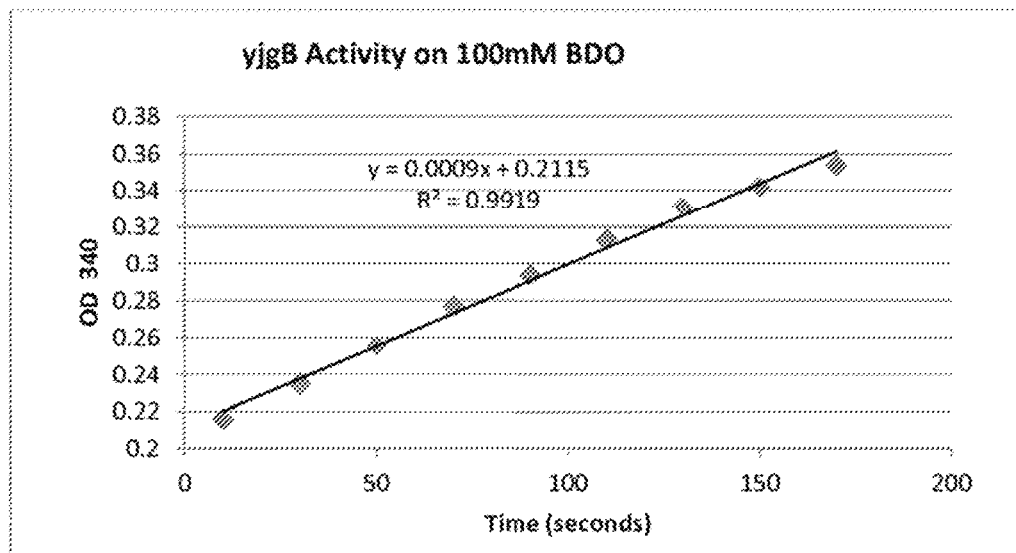
FIG. 85 shows yjgB activity in 100 mM BDO.

The yjgB gene was cloned with a streptavidin tag, expressed and purified in order to characterize its properties. The results of the purification, as analyzed by SDS-PAGE, are shown in FIG. 84. The protein expressed well, and acceptable yields of purified protein were obtained. Initial characterization with BDO as a substrate was performed in the presence of NADP+ and robust activity was confirmed (see FIG. 85).

On the basis of the protein fractionation and the microarray results, four genes were selected and deleted on top of each other to obtain strain 1889 from 1872. The genes were yqhD (b3011; GenBank NP_417484.1, GI:16130909), yjgB (b4269; GenBank NP_418690.4, GI:90111716), yahK (b0325; GenBank NP_414859.1, GI:16128310) and adhP (b1478; GenBank NP_415995.4, GI:90111280).

The deletions of these four alcohol dehydrogenases were introduced in strain 1872. This strain is based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 1872 contains a chromosomally integrated copy of 4-hydroxybutyryl-CoA transferase expressed from the pA promoter at the attB locus.

TABLE 56

OD, BDO, 4HB and GBL numbers of four replicates of a strain that had all four alcohol dehydrogenases identified for carrying backflux deleted (1889) compared with the control with neither of these deletions (Host 1872). The gene cat2 for 4HB conversion into 4-hydroxybutyryl-CoA was expressed on F' whereas ALD and ADH were expressed on pZS*-13S as described already. All concentrations are in mM and were measured after 24 hours of culture time in 96 well-plates.

| Host | OD | 4HB | BDO | GBL |
|---|---|---|---|---|
| 1872 | 4.61 | 3.3 | 60.8 | 12.5 |
| 1872 | 6.09 | 3.6 | 90.2 | 15.3 |
| 1872 | 5.88 | 3.1 | 84.4 | 17.3 |
| 1872 | 5.84 | 2.9 | 96.3 | 15.9 |
| 1889 | 5.94 | 3.6 | 92.6 | 14.0 |
| 1889 | 6.59 | 3.3 | 88.9 | 13.1 |
| 1889 | 6.59 | 3.3 | 82.4 | 13.4 |
| 1889 | 6.58 | 3.6 | 89.4 | 14.4 |

Figure 86:
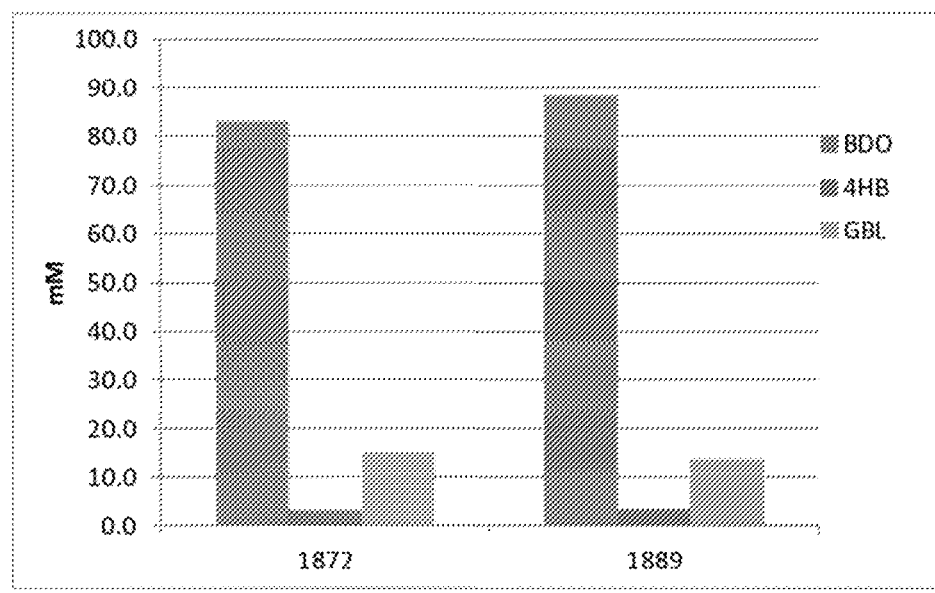
FIG. 86 shows the average BDO, 4HB and GBL numbers for the strain 1872 versus strain 1889.

FIG. 86 shows the average BDO, 4HB and GBL numbers for the strain 1872 versus strain 1889. These results demonstrate that metabolic modifications that decrease backflux result in an increased yield of BDO and no adverse affect on production of 4HB.

Example XXXVIII

Deletions to Improve the Energetic Efficiency of Oxidative Phosphorylation

This example describes deletions to improve the energetic efficiency of oxidative phosphorylation.

The electron transport chain of *Escherichia coli* has multiple NADH dehydrogenases and cytochrome oxidases, with varying ability to translocate protons. For example, NADH dehydrogenase II in *E. coli* is an NADH consuming system that is not linked with proton translocation (H+/2e−=0) whereas NADH dehydrogenase I encoded by nuo is reported to translocate 4 protons per pair of electrons. The major role of Ndh-II is to oxidize NADH and to feed electrons into the respiratory chain (Yun et al., *J. Appl. Microbiol.* 99:1404-1412 (2005)). The affinity of NdhII for NADH is relatively low (Hayashi et al., *Biochim. Biophys. Acta* 977:62-69 (1989)). It has been suggested that NdhII may operate to regulate the NADH pool independently of energy generation and is likely to be important when the capacity of bacteria to generate energy exceeds demand. The ndh gene has been shown to be repressed by the fnr gene product in such a way that the expression is optimal under conditions of high oxygen concentrations. The deletion of ndh would thus help in improving the energy efficiency of the cell. Similarly, there are several other NADH dehydrogenases that are not known to translocate any protons and thus do not help in ATP production, for example, wrbA, yieF, and kefF in *E. coli*. Homologues of these can be found in other organisms and eliminated to improve the ATP production for every unit of oxygen consumed.

Host strain 879 (the parent strain for ndh deletion) was based on strain ECKh-432 whose construction is described above and in US20110045575. Notable modifications include deletions in adhE, ldhA, pflB, mdh, and arcA. Strain ECKh-432 also contains chromosomally integrated copies of sucD from *Porphyromonas gingivalis* (encoding CoA-dependant succinate semialdehyde dehydrogenase), sucA from *Mycobacterium bovis* (encoding alpha-ketoglutarate decarboxylase), 4hbd from *P. gingivalis* (encoding 4-hydroxybutyrate dehydrogenase), and 4hbd from *Clostridium kluyveri* (encoding 4-hydroxybutyrate dehydrogenase). Strain 879 also has deletions of the succinate semialdehyde dehydrogenase genes, sad and gabD.

TABLE 57

The BDO, 4HB and GBL production in three replicates of the strain that had ndh deleted compared with the replicates of the host strain (879) with ndh intact. The experiments were conducted in 20 mL bottles as described in the protocol. The ALD and ADH were present on the plasmid pZS* to allow the conversion of 4-HB CoA to 4-HB aldehyde and subsequently to BDO. All concentrations are in mM and were measured after 24 hours of culture time.

| Host | OD | BDO | GBL | 4HB |
|---|---|---|---|---|
| 879 | 1.61 | 3.27 | 0.83 | 1.28 |
| 879 | 2.45 | 4.15 | 0.99 | 1.14 |
| 956 | 2.31 | 4.48 | 0.63 | 1.01 |
| 956 | 2.01 | 4.31 | 0.59 | 0.96 |
| 956 | 2.54 | 4.92 | 0.59 | 1.00 |

Figure 87:
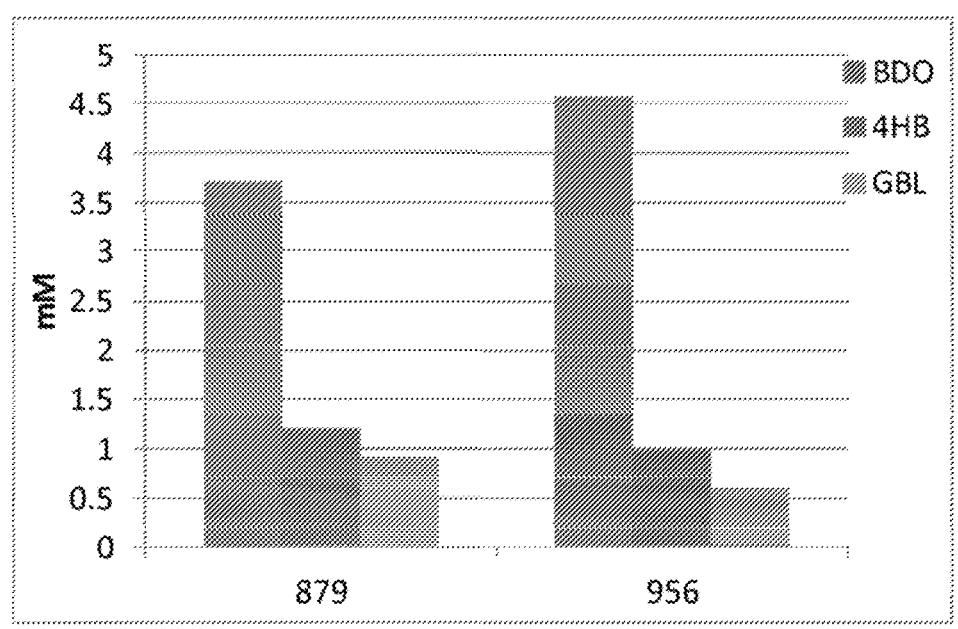
FIG. 87 shows the average BDO, 4HB and GBL numbers for the strain 956 versus strain 879.

FIG. 87 shows the average BDO, 4HB and GBL numbers for the strain 956 versus strain 879. These results demonstrate that deletions that improve the energy efficiency of oxidative phosphorylation increase the yield of BDO and have no adverse affect on 4HB production.

Example XXXIX

Deletion of Cytochrome Oxidases

This example describes deletion of cytochrome oxidases.

On the electron output side of the electron transport chain, multiple cytochrome oxidases are present that have different energy-conserving efficiencies. The cytochrome bo complex, encoded by the cyo operon, actively pumps electrons over the membrane and results in an H+/2e-stoichiometry of 4. The cytochrome bd-I complex does not actively pump protons, but due to the oxidation of the quinol on the periplasmic side of the membrane and subsequent uptake of protons from the cytoplasmic side of the membrane, which are used in the formation of water, the net electron transfer results in a H+/2e− stoichiometry of 2. This is encoded by the cyd operon. Until recently, the proton translocation stoichiometry of cytochrome bd-II oxidase, encoded by appBC, was not known, but it has now been established that this oxidase is electrogenic (Borisov et. al., *Proc. Natl. Acad. Sci. USA* 108:17320-17324 (2011)). These genes are normally induced upon entry into stationary phase or under conditions of carbon and phosphate starvation (Atlung et al., *J. Bacteriol.* 179:2141-2146 (1997)).

Properties and abundance of the cytochrome oxidases: The cyd operon is regulated in an oxygen-dependent manner by fnr and arcA and the expression is optimal under microaerophilic conditions (Calhoun et al., *J. Bacteriol.* 175:3020-3025 (1993)). The bo-type oxidase predominates when *E. coli* is grown at high oxygen tension. The cyo operon is also regulated by both arcA and fnr. A literature study indicates that in aerobically grown cells the cytochrome o oxidase is present at a level of approximately 304 molecules per cell and the cytochrome d oxidase at 204 molecules per cell (Minohara et al., *J. Biosci. Bioengineer.* 93(5):464-469 (2002)). Under anaerobic conditions, cytochrome d oxidase is predominant and is present at about 606 molecules per cell in contrast to only 2 molecules per cell of cytochrome o oxidase. The Km for $O_2$ of cytochrome bd oxidase is much lower than that of the cytochrome bo oxidase (Minohara et al, supra, 2002). The former has a Km of 10 nM, and cytochrome bo oxidase has a Km of ~1 μM.

TABLE 58

Enzymatic characteristics of the cytochrome-bd oxidases from *E. coli* (From Bekker et al., supra, 2009).

| Cytochrome | $V_{max}$ (mol O/mol cytochrome bd/s) | $K_m$ ($O_2$) at pH 7 (μM) | $K_m$ (UQ-$H_2$) at pH 7 (μM) | Cellular content (nmol/g protein) | In vivo sp act (mol $O_2$/mol cytochrome bd/s) |
|---|---|---|---|---|---|
| Cytochrome bd-I | 218 ± 20 | $0.3^b$ | 85 ± 5 | 90 ± 29 | 58 ± 11 |
| Cytochrome bd-II | 818 ± 75 | 2.0 ± 0.3 | 250 ± 45 | 91 ± 32 | 70 ± 12 |
| Cytochrome bo | $225^c$ | $6.0^d$ | $47^e$ | ND | ND |

In a study attempting to determine the P/O ratios in aerobically-grown *E. coli* (Noguchi et al., *J. Biochem.* 136:509-515 (2004)), it was determined that NDH-1 formed the predominant NADH dehydrogenase under both standard feed and limiting feed of glucose. However, cytochrome bd oxidase was found to be present in higher concentrations than cytochrome bo oxidase. The following table illustrates their findings on various NADH dehydrogenases and cytochrome oxidases.

TABLE 59

Concentrations of NADH dehydrogenases and cytochrome oxidase under aerobic growth conditions with different glucose feeding strategies (from Noguchi et al., supra, 2004)

| Conditions (Phase) | NDH-1 | NDH-2 | bo-type | bd-type | NDH-1/ | bo-type/ |
|---|---|---|---|---|---|---|
| | (μmol/s/mg of protein) | | | | Total (%) | Total (%) |
| Standard glucose | | | | | | |
| (exponential: 3 h) | 1.58 ± 0.07 | 1.11 ± 0.06 | 1.38 ± 0.12 | 1.01 ± 0.10 | 58.8 ± 2.4 | 57.9 ± 4.5 |
| (exponential: 5 h) | 1.35 ± 0.03 | 0.86 ± 0.03 | 0.70 ± 0.05 | 1.07 ± 0.04 | 61.0 ± 1.4 | 39.6 ± 2.6 |
| (early stationary: 8 h) | 1.17 ± 0.01 | 0.88 ± 0.01 | 0.46 ± 0.03 | 0.98 ± 0.02 | 57.1 ± 0.5 | 32.0 ± 1.9 |
| Limited glucose | | | | | | |
| (early stationary) | 0.97 ± 0.05 | 0.70 ± 0.03 | 0.42 ± 0.04 | 0.75 ± 0.05 | 58.1 ± 2.29 | 36.0 ± 3.7 |

Effects of deleting cytochrome oxidases: A chemostat study has been reported for understanding the ratios of specific oxygen consumption rates for strains lacking different components of the electron transport chain between dilution rates of 0.1 and 0.7/hr (Calhoun et al., supra, 1993). Strains that were constrained to use the bd-type oxidase had increased oxygen consumption rates as compared to those that used only the cytochrome bo oxidase by a factor of 1.45-1.13. The ratio of the oxygen consumption rates for a strain that had both ndh and cyo deleted as compared to the strain with only ndh deleted was between 1.46 and 1.39. The authors of Calhoun et al., supra, 1993, concluded that the bd-type oxidase is less efficient than the bo-type oxidase but is still coupled.

In yet another study, it has been reported that E. coli wild-type cells containing both cytochrome bo and bd type terminal oxidases, pumped protons with a H+/O ratio of 4.5-4.9, but mutants with cytochrome bo oxidase deleted, showed ratios of 3.5-4.1 and the mutants with cytochrome bd oxidase showed a ratio of 4.8-5.6 (Minohara et al., supra, 2002). Mutants which lacked both cyo and cyd operon could not grow under aerobic conditions, but those that overexpressed cytochrome bo oxidase and those that overexpressed cytochrome bd oxidase grew as well as the parental W3110 strains. The cell yield of each of these strains was in proportion to their H+/O ratios. Interestingly, the strain which had cydAB deleted showed very poor cell yield initially. The cell yields were, however, improved dramatically once the cytochrome bo oxidase was overexpressed. The authors Minohara et al., supra, 2002) had hypothesized that the lower cell yields in the cyd mutant strain may be caused by the high H+ permeability of the membrane in the cyd mutant. They believed that the amounts of cytochrome bo in the mutant cells lacking the high-affinity oxygen-reducing cytochrome bd may not be sufficient to reduce the oxygen molecules at a low concentration, and thus the cell membranes were injured by reactive oxygen species and were made partially permeable. This cell stress could be relieved by overexpressing cytochrome bo oxidase (Minohara et al., supra, 2002).

TABLE 60

Properties of various E. coli mutants grown in a glucose-limited chemostat culture at a dilution rate of 0.15/hr. The cytochrome shown in parentheses is the active cytochrome oxidase. Each of these strains also had nuo deleted (from Minohara et al., supra, 2002).

| Mutant | $q_{O2}$ {mmol (g [dry wt])$^{-1}$ h$^{-1}$} | $q_{glucose}$ {mmol (g [dry wt])$^{-1}$ h$^{-1}$} | $Y_{glucose}$ (g [dry wt]) (g Glc)$^{-1}$ | $q_{acetate}$ {mmol (g [dry wt])$^{-1}$ h$^{-1}$} | $q_{ATP}$ {mmol (g [dry wt])$^{-1}$ h$^{-1}$} | H$^+$/2e$^-$ |
|---|---|---|---|---|---|---|
| MB 30 (cytochrome bd-I) | 8.8 ± 1.3 | 3.2 | 0.26 | 1.5 ± 0.5 | 16.3 ± 2.2 | 2 |
| MB 37 (cytochrome bd-II) | 11.1 ± 0.6 | 6.0 | 0.14 | 5.7 ± 0.7 | 16.6 | 0.2 ± 0.1 |
| MB 34 (cytochrome bo) | 6.4 ± 0.4 | 2.3 | 0.36 | 0.4 ± 0.4 | 17.0 ± 0.4 | 4 |

A recent paper (Bekker et al., J. Bacteriol. 191:5510-5517 (2009)) investigated the effects of deleting cytochrome bd-II oxidase. The phenotype of the mutant strain lacking the cytochrome bd-II oxidase included a smaller ubiquinone pool when grown under glucose-excess conditions. This strain also had a decreased oxygen flux in glucose-limited chemostat conditions. These results suggested that cytochrome bd-II oxidase contributed significantly to the overall respiratory electron flux. Wild type E. coli MG1655 cells had a specific respiration rate that was approximately 46% higher than that of the mutant strain that lacked appBC (8.7 vs. 5.9 mmol/gDCW.hr). These were measured in glucose-limited chemostats at a dilution rate of 0.2/hr. In order to improve the energetic efficiency of the cells, the appBC was knocked out in the strains (Host strain 2424), and additionally cyoABCD was knocked out (Strain 2471). The table below shows the data for production of the C4 metabolites in 96 well plates with each of these strains. An additional advantage of deleting the two cytochrome oxidases (encoded by appBC and cyoABCD) and ndh is that it makes the cells relatively robust to a range of oxygen transfer rates in bigger fermenters. Since cydAB has a fixed stoichiometry for proton translacoation and so does nuo (NADH dehydrogenase I), the P/O ratio is rather constant and so is the biomass rate in different parts of a fermenter.

TABLE 61

The BDO, 4HB and GBL production in three replicates of the strains 1889 and 2471. The ALD and ADH were present on the plasmid pZS* to allow the conversion of 4-HB CoA to 4-HB aldehyde and subsequently to BDO. All concentrations are in mM and were measured after 24 hours of culture time in 96-well plates.

| Host | OD | 4HB | BDO | GBL |
|---|---|---|---|---|
| 1889 | 3.63 | 5.71 | 57.20 | 4.48 |
| 1889 | 3.05 | 5.65 | 50.60 | 3.49 |
| 1889 | 3.40 | 4.14 | 51.90 | 3.90 |
| 1889 | 3.19 | 4.23 | 53.10 | 3.69 |
| 2471 | 3.56 | 5.62 | 64.20 | 4.80 |
| 2471 | 2.96 | 5.73 | 53.30 | 2.75 |
| 2471 | 3.07 | 5.39 | 42.80 | 2.67 |
| 2471 | 3.11 | 4.01 | 45.90 | 2.66 |

Figure 88:
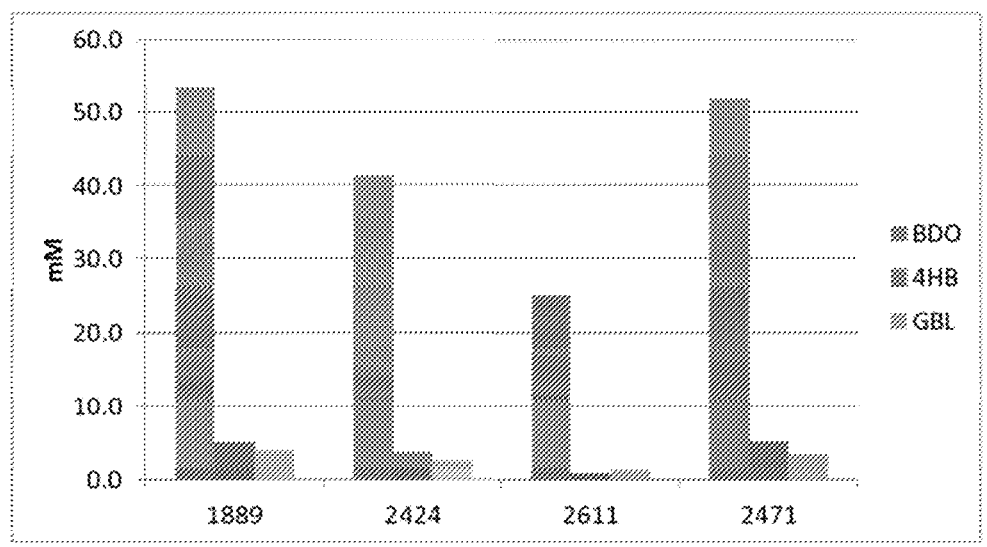
FIG. 88 shows the average BDO, 4HB and GBL numbers of the strains, 1889, 2424, 2611 and 2471.

FIG. 88 shows the average BDO, 4HB and GBL numbers of the strains, 1889 (see above) and 2471. These results demonstrate that deletion of cytochrome oxidases results in deletion of appBC resulted in a decrease in BDO and 4HB production, although both BDO and 4HB are still produced in good quantities, and these cells are expected to exhibit improved energy efficiency that may be advantageous in scaled up fermentation conditions.

The results disclosed herein demonstrate high yield of desired products such as 4-HB, 4-HBal, 4-HBCoA, BDO or putrescine, in particular BDO. Such modifications have been demonstrated to increase product yield of BDO. Such beneficial modifications, including both increasing and decreasing expression of enzymes, resulted in decreased $CO_2$ loss, decreased by-product formation such as ethanol, acetate, pyruvate, alanine, glutamate and GBL. Additional modifications decreased backflux from desired products such as BDO into pathway intermediates or precursors such as those in the TCA cycle. Additional improvements have been made by identifying enzymes that more efficiently carry out a desired pathway reaction and optionally subjecting the enzyme to evolution to generate variants having improved characteristics such as increased substrate to product conversion, stability, and the like. Such enzymes have included cat2, aldehyde dehydrogenase and aldehyde dehydrogenase, as disclosed herein. In addition, various promoters have been tested to identify promoter variants that provide more efficient transcription of a gene. Additionally, as disclosed herein, various backflux and by-product reactions can decrease the efficiency of product formation in a desired pathway. In some cases, product yield can be increased by decreasing expression of a pathway enzyme if higher expression of the pathway enzyme results in an increase in by-product formation. For example, such a result has been observed with aldehyde dehydrogenas, in which lowere expression reduces ethanol production without lowering BDO production.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, said microbial organism having a 4-hydroxybutyrate pathway and being capable of producing 4-hydroxybutyrate, wherein said microbial organism comprises a genetic modification that decreases expression of an acyl coenzyme A thioesterase.

2. The microbial organism of claim 1, wherein the microbial organism has decreased production of gamma-butyrolactone relative to a parent microbial organism in the absence of said genetic modification.

3. The microbial organism of claim 1, wherein said microbial organism further comprises a 4-hydroxybutyryl-CoA pathway.

4. A method for producing 4-hydroxybutyrate, comprising culturing the non-naturally occurring microbial organism of claim 1 under conditions and for a sufficient period of time to produce 4-hydroxybutyrate.

5. The method of claim 4, wherein the microbial organism has decreased production of gamma-butyrolactone relative to a parent microbial organism in the absence of said genetic modification.

6. The method of claim 4, wherein said non-naturally occurring microbial organism is in a substantially anaerobic culture medium.

7. The microbial organism of claim 1, wherein the microbial organism has a genetic modification comprising at least two genetic modifications that decrease expression of at least two acyl coenzyme A thioesterases.

8. The microbial organism of claim 1, wherein the microbial organism further comprises a genetic modification selected from:
(A) a genetic modification that increases expression of phosphoenolpyruvate carboxylase;
(B) a genetic modification that increases expression of alpha-ketoglutarate dehydrogenase;
(C) a genetic modification that increases expression of a non-phosphotransferase (PTS) glucose uptake system;
(D) a genetic modification that increases expression of a gamma-butyrolactone esterase;
(E) a genetic modification that decreases expression of succinyl-CoA synthetase;
(F) a genetic modification that decreases expression of an alcohol dehydrogenase;
(G) a genetic modification that decreases expression of a non-energy-producing NADH dehydrogenase;
(H) a genetic modification that decreases expression of a cytochrome oxidase; and
(I) a combination of two or more of the genetic modifications of parts (A)-(H).

9. The microbial organism of claim 8, wherein:
(J) the microbial organism of part (A), (B) or (C) has decreased production of ethanol, acetate, pyruvate or alanine, or a combination thereof, relative to a parent microbial organism in the absence of said genetic modification;
(K) the microbial organism of part (B) has decreased production of glutamate relative to a parent microbial organism in the absence of said genetic modification;
(L) the microbial organism of part (C) has a genetic modification comprising increased expression of a permease, glucokinase, or a glucose facilitator, or a combination thereof;
(M) the microbial organism of part (D) has decreased production of gamma-butyrolactone relative to a parent microbial organism in the absence of said genetic modification;
(N) the microbial organism of part (E) has increased production of 4-hydroxybutyrate relative to a parent microbial organism in the absence of said genetic modification;
(O) the microbial organism of part (F) has decreased backflux from a downstream product of the 4-hydroxybutyrate pathway relative to a parent microbial organism in the absence of said genetic modification;
(P) the microbial organism of part (G) has suppressed depletion of the NADH pool or increased energy efficiency in the microbial organism, or a combination thereof, relative to a parent microbial organism in the absence of said genetic modification;
(Q) the microbial organism of part (H) has increased energy efficiency relative to a parent microbial organism in the absence of said genetic modification; or
(R) the microbial organism of part (H) has increased tolerance to a range of oxygen concentrations relative to a parent microbial organism in the absence of said genetic modification.

10. The microbial organism of claim 8, wherein the microbial organism of part (D) further comprises a 4-hydroxybutyryl-CoA pathway.

11. The microbial organism of claim 8, wherein the microbial organism further comprises (A) a genetic modification that increases expression of phosphoenolpyruvate carboxylase.

12. The microbial organism of claim 8, wherein the microbial organism further comprises (B) a genetic modification that increases expression of alpha-ketoglutarate dehydrogenase.

13. The microbial organism of claim 8, wherein the microbial organism further comprises (C) a genetic modification that increases expression of a non-phosphotransferase (PTS) glucose uptake system.

14. The microbial organism of claim 8, wherein the microbial organism further comprises (D) a genetic modification that increases expression of a gamma-butyrolactone esterase.

15. The microbial organism of claim 8, wherein the microbial organism further comprises (E) a genetic modification that decreases expression of succinyl-CoA synthetase.

16. The microbial organism of claim 8, wherein the microbial organism further comprises (F) a genetic modification that decreases expression of an alcohol dehydrogenase.

17. The microbial organism of claim 8, wherein the microbial organism further comprises (G) a genetic modification that decreases expression of a non-energy-producing NADH dehydrogenase.

18. The microbial organism of claim 8, wherein the microbial organism further comprises (H) a genetic modification that decreases expression of a cytochrome oxidase.

19. The microbial organism of claim 8, wherein the microbial organism further comprises (I) a combination of two or more of the genetic modifications of parts (A)-(H).

20. The method of claim 4, wherein the microbial organism has a genetic modification comprising at least two genetic modifications that decrease expression of at least two acyl coenzyme A thioesterases.

21. The method of claim 4, wherein the microbial organism further comprises a genetic modification selected from:
   (A) a genetic modification that increases expression of phosphoenolpyruvate carboxylase;
   (B) a genetic modification that increases expression of alpha-ketoglutarate dehydrogenase;
   (C) a genetic modification that increases expression of a non-phosphotransferase (PTS) glucose uptake system;
   (D) a genetic modification that increases expression of a gamma-butyrolactone esterase;
   (E) a genetic modification that decreases expression of succinyl-CoA synthetase;
   (F) a genetic modification that decreases expression of an alcohol dehydrogenase;
   (G) a genetic modification that decreases expression of a non-energy-producing NADH dehydrogenase;
   (H) a genetic modification that decreases expression of a cytochrome oxidase; and
   (I) a combination of two or more of the genetic modifications of parts (A)-(H).

22. The method of claim 21, wherein the microbial organism of part (D) further comprises a 4-hydroxybutyryl-CoA pathway.

\* \* \* \* \*